(12) United States Patent
Allen et al.

(10) Patent No.: US 10,323,022 B2
(45) Date of Patent: *Jun. 18, 2019

(54) PYRROLIDINYL UREA, PYRROLIDINYL THIOUREA AND PYRROLIDINYL GUANIDINE COMPOUNDS AS TRKA KINASE INHIBITORS

(71) Applicant: Array BioPharma Inc., Boulder, CO (US)

(72) Inventors: Shelley Allen, Boulder, CO (US); Steven W. Andrews, Boulder, CO (US); James F. Blake, Boulder, CO (US); Kevin R. Condroski, San Diego, CA (US); Julia Haas, Boulder, CO (US); Lily Huang, Austin, TX (US); Yutong Jiang, Boulder, CO (US); Timothy Kercher, Boulder, CO (US); Gabrielle R. Kolakowski, Boulder, CO (US); Jeongbeob Seo, Baltimore, MD (US)

(73) Assignee: Array BioPharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/839,706

(22) Filed: Dec. 12, 2017

(65) Prior Publication Data

US 2018/0334450 A1 Nov. 22, 2018

Related U.S. Application Data

(60) Continuation of application No. 15/382,028, filed on Dec. 16, 2016, now Pat. No. 9,878,997, which is a
(Continued)

(51) Int. Cl.
*C07D 403/12* (2006.01)
*A61K 31/4162* (2006.01)
(Continued)

(52) U.S. Cl.
CPC ........ *C07D 403/12* (2013.01); *A61K 31/4155* (2013.01); *A61K 31/4162* (2013.01); *A61K 31/4178* (2013.01); *A61K 31/4192* (2013.01); *A61K 31/4196* (2013.01); *A61K 31/422* (2013.01); *A61K 31/427* (2013.01); *A61K 31/4245* (2013.01); *A61K 31/4375* (2013.01); *A61K 31/4439* (2013.01); *A61K 31/454* (2013.01); *A61K 31/496* (2013.01); *A61K 31/497* (2013.01); *A61K 31/506* (2013.01); *A61K 31/5377* (2013.01); *C07D 401/14* (2013.01); *C07D 403/14* (2013.01);
(Continued)

(58) Field of Classification Search
CPC .............. C07D 403/12; A61K 31/4155; A61K 31/4162

USPC ..................................................... 514/236.5
See application file for complete search history.

(56) References Cited

U.S. PATENT DOCUMENTS 4,997,943 A 3/1991 Iwata et al.
5,849,779 A 12/1998 Hirota et al.
(Continued)

FOREIGN PATENT DOCUMENTS

EP 0761658 A1 12/1997
EP 1043995 B1 11/2006
(Continued)

OTHER PUBLICATIONS

Wadhwa, et al., "Expression of the neurotrophin receptors Trk A and Trk B in adult human astrocytoma and glioblastoma", Journal of Biosciences 28(2), 181-188 (2003).
Wang, et al., "Trk kinase inhibitors as new treatments for cancer and pain", Expert Opinion on Therapeutic Patents, 19(3), 305-319 (2009).
Woolf, et al., "Nerve growth factor contributes to the generation of inflammatory sensory hypersensitivity", Neuroscience 62, 327-331 (1994).
Yilmaz, et al., "Theraputic targeting of Trk supresses tumor proliferation and enhances cisplatin activity in HNSCC", Cancer Biology & Therapy 10(6), 644-653 (2010).
Zahn, et al., "Effect of blockade of nerve growth factor and tumor necrosis factor on pain behaviors after plantar incision", J Pain 5, 157-163 (2004).
(Continued)

*Primary Examiner* — Rita J Desai
(74) *Attorney, Agent, or Firm* — Viksnins Harris Padys Malen LLP; Sarah S. Mastous

(57) ABSTRACT

Compounds of Formula I:

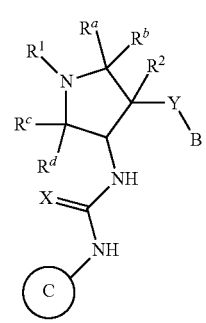

or stereoisomers, tautomers, or pharmaceutically acceptable salts, or solvates or prodrugs thereof, where $R^1$, $R^2$, $R^a$, $R^b$, $R^c$, $R^d$, X, Y, B, and Ring C are as defined herein, and wherein the Y—B moiety and the NH—C(=X)—NH moiety are in the trans configuration, are inhibitors of TrkA kinase and are useful in the treatment of diseases which can be treated with a TrkA kinase inhibitor such as pain, cancer, inflammation, neurodegenerative diseases and certain infectious diseases.

26 Claims, No Drawings

Related U.S. Application Data division of application No. 14/117,615, filed as application No. PCT/US2012/037003 on May 9, 2012, now Pat. No. 9,562,055.

(60) Provisional application No. 61/485,858, filed on May 13, 2011.

(51) Int. Cl.

| | |
|---|---|
| *A61K 31/4155* | (2006.01) |
| *C07D 401/14* | (2006.01) |
| *C07D 403/14* | (2006.01) |
| *C07D 405/14* | (2006.01) |
| *C07D 409/14* | (2006.01) |
| *C07D 413/14* | (2006.01) |
| *C07D 417/14* | (2006.01) |
| *C07D 471/04* | (2006.01) |
| *C07D 487/04* | (2006.01) |
| *C07D 491/04* | (2006.01) |
| *C07D 495/04* | (2006.01) |
| *A61K 31/4178* | (2006.01) |
| *A61K 31/4192* | (2006.01) |
| *A61K 31/4196* | (2006.01) |
| *A61K 31/422* | (2006.01) |
| *A61K 31/4245* | (2006.01) |
| *A61K 31/427* | (2006.01) |
| *A61K 31/4375* | (2006.01) |
| *A61K 31/4439* | (2006.01) |
| *A61K 31/454* | (2006.01) |
| *A61K 31/496* | (2006.01) |
| *A61K 31/497* | (2006.01) |
| *A61K 31/506* | (2006.01) |
| *A61K 31/5377* | (2006.01) |
| *C07D 491/048* | (2006.01) |

(52) U.S. Cl.
CPC ......... *C07D 405/14* (2013.01); *C07D 409/14* (2013.01); *C07D 413/14* (2013.01); *C07D 417/14* (2013.01); *C07D 471/04* (2013.01); *C07D 487/04* (2013.01); *C07D 491/04* (2013.01); *C07D 491/048* (2013.01); *C07D 495/04* (2013.01); *Y02A 50/414* (2018.01)

(56) References Cited

U.S. PATENT DOCUMENTS

| | | | |
|---|---|---|---|
| 5,998,424 | A | 12/1999 | Galemmo, Jr. et al. |
| 6,197,798 | B1 | 3/2001 | Fink et al. |
| 6,410,533 | B1 | 6/2002 | Hirth et al. |
| 7,223,782 | B2 | 5/2007 | Atkinson et al. |
| 7,625,915 | B2 | 12/2009 | Dumas et al. |
| 8,592,454 | B2 | 11/2013 | Shirai et al. |
| 9,163,017 | B2 | 10/2015 | Degoey et al. |
| 9,562,055 | B2 * | 2/2017 | Allen .................. C07D 401/14 |
| 9,878,997 | B2 | 1/2018 | Haas et al. |
| 9,896,435 | B2 * | 2/2018 | Allen .................. C07D 403/12 |
| 2009/0105476 | A1 | 4/2009 | Fairhurs et al. |
| 2009/0163710 | A1 | 6/2009 | Gaul |
| 2018/0179182 | A1 * | 6/2018 | Allen .................. C07D 403/12 |

FOREIGN PATENT DOCUMENTS

| | | |
|---|---|---|
| EP | 2033955 A1 | 3/2009 |
| EP | 1451160 B1 | 1/2010 |
| EP | 2336105 B9 | 9/2014 |
| JP | H0269474 A | 3/1990 |
| JP | H04360866 A | 12/1992 |
| JP | 2005206527 A | 8/2005 |
| JP | 2008509179 A | 3/2008 |
| JP | 2010524880 A | 7/2010 |
| WO | 1992010492 A1 | 6/1992 |
| WO | 1995034559 A1 | 12/1995 |
| WO | 1998004521 A1 | 2/1998 |
| WO | 1999023091 A1 | 5/1999 |
| WO | 1999032110 A1 | 7/1999 |
| WO | 2000039116 A1 | 7/2000 |
| WO | 2000043384 A1 | 7/2000 |
| WO | 2001012188 A1 | 2/2001 |
| WO | 2001028987 A1 | 4/2001 |
| WO | 2002002525 A2 | 1/2002 |
| WO | 2002088101 A2 | 11/2002 |
| WO | 2002090326 A1 | 11/2002 |
| WO | 2003037274 A2 | 5/2003 |
| WO | 2003045920 A1 | 6/2003 |
| WO | 2003051275 A2 | 6/2003 |
| WO | 2004005262 A2 | 1/2004 |
| WO | 2004032827 A2 | 4/2004 |
| WO | 2004032870 A2 | 4/2004 |
| WO | 2004039814 A1 | 5/2004 |
| WO | 2004060305 A2 | 7/2004 |
| WO | 2004060306 A2 | 7/2004 |
| WO | 2004061084 A2 | 7/2004 |
| WO | 2004111009 A1 | 12/2004 |
| WO | 2005024755 A2 | 3/2005 |
| WO | 2005048948 A2 | 6/2005 |
| WO | 2005110994 A2 | 11/2005 |
| WO | 2006014290 A2 | 2/2006 |
| WO | 2006015827 A1 | 2/2006 |
| WO | 2006067401 A1 | 6/2006 |
| WO | 2006068591 A1 | 6/2006 |
| WO | 2006070198 A1 | 7/2006 |
| WO | 2006071940 A2 | 7/2006 |
| WO | 2006081034 A2 | 8/2006 |
| WO | 2006123257 A2 | 11/2006 |
| WO | 2007008917 A2 | 1/2007 |
| WO | 2007059202 A2 | 5/2007 |
| WO | 2007061882 A2 | 5/2007 |
| WO | 2007064872 A2 | 6/2007 |
| WO | 2007089646 A1 | 8/2007 |
| WO | 2008016811 A2 | 2/2008 |
| WO | 2008021859 A1 | 2/2008 |
| WO | 2008033999 A2 | 3/2008 |
| WO | 2008034008 A2 | 3/2008 |
| WO | 2008046003 A2 | 4/2008 |
| WO | 2008071456 A2 | 6/2008 |
| WO | 2008131276 A1 | 10/2008 |
| WO | 2008150899 A1 | 12/2008 |
| WO | 2009007426 A1 | 1/2009 |
| WO | 2009053694 A1 | 4/2009 |
| WO | 2009117080 A1 | 9/2009 |
| WO | 2009140128 A2 | 11/2009 |
| WO | 2009153179 A1 | 12/2009 |
| WO | 2010023480 A1 | 3/2010 |
| WO | 2010032856 A1 | 3/2010 |
| WO | 2010033941 A1 | 3/2010 |
| WO | 2010040663 A1 | 4/2010 |
| WO | 2010048314 A1 | 4/2010 |
| WO | 2010059719 A2 | 5/2010 |
| WO | 2010060703 A1 | 6/2010 |
| WO | 2010075376 A2 | 7/2010 |
| WO | 2010077680 A2 | 7/2010 |
| WO | 2010103334 A1 | 9/2010 |
| WO | 2010104488 A1 | 9/2010 |
| WO | 2010114881 A1 | 10/2010 |
| WO | 2010125799 A1 | 11/2010 |
| WO | 2010141817 A1 | 12/2010 |
| WO | 2011006074 A1 | 1/2011 |
| WO | 2011022473 A1 | 2/2011 |
| WO | 2011032291 A1 | 3/2011 |
| WO | 2011073160 A1 | 6/2011 |
| WO | 2011085886 A1 | 7/2011 |
| WO | 2011146336 A1 | 11/2011 |
| WO | 2011150198 A1 | 12/2011 |
| WO | 2012016001 A1 | 2/2012 |
| WO | 2012036997 A1 | 3/2012 |
| WO | 2012066077 A1 | 5/2012 |
| WO | 2012158413 A2 | 11/2012 |
| WO | 2013063214 A1 | 5/2013 |
| WO | 2013096226 A1 | 6/2013 |

(56) References Cited

FOREIGN PATENT DOCUMENTS

| WO | 2013176970 A1 | 11/2013 |
|---|---|---|
| WO | 2014052563 A1 | 4/2014 |
| WO | 2014052566 A1 | 4/2014 |
| WO | 2014078322 A1 | 5/2014 |
| WO | 2014078323 A1 | 5/2014 |
| WO | 2014078325 A1 | 5/2014 |
| WO | 2014078328 A1 | 5/2014 |
| WO | 2014078331 A1 | 5/2014 |
| WO | 2014078372 A1 | 5/2014 |
| WO | 2014078408 A1 | 5/2014 |
| WO | 2014078417 A1 | 5/2014 |
| WO | 2014078454 A1 | 5/2014 |
| WO | 2015039333 A1 | 3/2015 |
| WO | 2015042085 A2 | 3/2015 |
| WO | 2014078378 A1 | 5/2015 |

OTHER PUBLICATIONS

Wright, et al., "(3R,4S)-4-(2,4,5-Trifluorophenyl)-pyrrolidin-3-ylamine inhibitors of dipeptidyl peptidase IV: Synthesis, in vitro, in vivo, and X-ray crystallographic characterization", Bioorganic & Medicinal Chemistry Letters 17(20), 5638-5642 (2007).

Adriaenssens, et al., "Nerve growth factor is a potential therapeutic target in breast cancer", Cancer Res 68(2), 346-351 (2008).

Asaumi, et al., "Expression of neurotrophins and their receptors (TRK) during fracture healing", Bone 26(6), 625-633 (2000).

Backes, et al., "Pyrrolidine-constrained phenethylamines: The design of potent, selective, and pharmacologically efficacious dipeptidyl peptidase IV (DPP4) inhibitors from a lead-like screening hit", Bioorganic Medicinal Chemistry Letters 17(7), 2005-2012 (2007).

Bardelli, "Mutational analysis of the tyrosine kinome in colorectal cancers", Science 300, 949 (2003).

Baumann, et al., "Synthesis of a Drug-Like Focused Library of Trisubstituted Pyrrolidines Using Integrated Flow Chemistry and Batch Methods", ACS Comb Sci 13(4), 405-413 (2011).

Baumann, et al., "Synthesis of Highly Substituted Nitropyrrolidines, Nitropyrrolizines and Nitropyrroles Via Multicomponent-Multistep Sequences within a Flow Reactor", Heterocycles 82(2), 1297-1316 (2011).

Bouhana, et al., "Comparison of Analgesic Effects of an Allosteric Inhibitor of TrkA to that of an ATP Site Inhibitor of the pan-Trk Axis in a Rodent Model of Inflammatory Pain", Gordon Conference, Salve Regina University, Newport, RI, 1 page, Jun. 7, 2011.

Brodeur, et al., "Neuroblastoma: biological insights into a clinical enigma", Nat Rev Cancer 3, 203-216 (2003).

CAS Registry, "(3S,4R)-4-Phenyl-1-(phenylmethyl)-3-pyrrolidinamine", RN 1279032-19-7; STN entry date Apr. 12, 2011.

Davidson, et al., "Expression and activation of the nerve growth factor receptor TrkA in serous ovarian carcinoma", Clin Cancer Res 9, 2248-2259 (2003).

Davies, et al., "Asymmetric Synthesis of 3, 4-anti- and 3, 4-syn-substituted Aminopyrrolidines via Lithium Amide Conjugate Addition", Organic and Biomolecular Chemistry, vol. 5, 1961-1969 (2007).

De Melo-Jorge, et al., "The Chagas' disease parasite *Trypanosoma cruzi* exploits nerve growth factor receptor TrkA to infect mammalian hosts", Cell Host & Microbe 1(4), 251-261 (2007).

Delafoy, et al., "Role of nerve growth factor in the trinitrobenzene sulfonic acid-induced colonic hypersensitivity", Pain 105, 489-497 (2003).

Di Mola, et al., "Nerve growth factor and Trk high affinity receptor (TrkA) gene expression in inflammatory bowel disease", Gut 46(5), 670-678 (2000).

Dou, et al., "Increased nerve growth factor and its receptors in atopic dermatitis: an immunohistochemical study", Archives of Dermatological Research 298(1), 31-37 (2006).

Du, et al., "Expression of NGF family and their receptors in gastric carcinoma: A cDNA microarray study", World Journal of Gastroenterology 9(7), 1431-1434 (2003).

Eguchi, et al., "Fusion of ETV6 to neurotrophin-3 receptor TRKC in acute myeloid leukemia with t(12;15)(p13;q25)", Blood 93(4), 1355-1363 (1999).

Einsiedel, et al., "Stereocontrolled Dopamine Receptor Binding and Subtype Selectivity of Clebopride Analogues Synthesized from Aspartic Acid", Bioorganic & Medicinal Chemistry Letters 13, 3293-3296 (2003).

Eliav et al., "The kappa opioid agonist GR89 696 blocks hyperalgesia and allodynia in rat models of peripheral neuritis and neuropathy", Pain 79 (2-3), 255-264 (1999).

Euthus, et al., "ETV6-NTRK3—Trk-ing the primary event in human secretory breast cancer", Cancer Cell 2(5), 347-348 (2002).

Freund-Michel, et al., "The nerve growth factor and its receptors in airway inflammatory diseases", Pharmacology & Therapeutics 117(1), 52-76 (2008).

Greco et al., "Rearrangements of NTRK1 gene in papillary thyroid carcinoma", Molecular and Cellular Endocrinology 321(1), 44-49 (2010).

Gruber-Olipitz, et al., "Synthesis, chaperoning, and metabolism of proteins are regulated by NT-3/TrkC signaling in the medulloblastoma cell line DAOY", Journal of Proteome Research 7(5), 1932-1944 (2008).

Gwak, et al., "Attenuation of mechanical hyperalgesia following spinal cord injury by administration of antibodies to serve growth factor in the rat", Neurosci Lett 336, 117-120 (2003).

Herzberg, et al., "NGF involvement in pain induced by chronic constriction injury of the rat sciatic nerve", Neuroreport 8, 1613-1618 (1997).

Hu, et al., "Decrease in bladder overactivity with REN1820 in rats with cyclophosphamide induced cystitis", Journal of Urology 173(3), 1016-1021 (2005).

Jaggar, et al., "Inflammation of the rat urinary bladder is associated with a referred thermal hyperalgesia which is nerve growth factor dependent", Br J Anaesth 83, 442-448 (1999).

Japanese Office Action, dated Nov. 13, 2015 in JP Patent Application No. 2014-510416 and English Translation; 9 pages.

Jin, et al., "TrkC plays an essential role in breast tumor growth and metastasis", Carcinogenesis 31(11), 1939-1947 (2010).

Lamb, et al., "Nerve growth factor and gastric hyperalgesia in the rat", Neurogastroenterol. Motil. 15, 355-361 (2003).

Li, et al., Chinese Journal of Cancer Prevention and Treatment 16(6), 428-430 [with English Abstract] (2009).

Li, et al., "Lumbar 5 ventral root transection-induced upregulation of nerve growth factor in sensory neurons and their target tissues: a mechanism in neuropathic pain", Mol Cell Neurosci 23, 232-250 (2003).

Ma, et al., "The progressive tactile hyperalgesia induced by peripheral inflammation is nerve growth factor dependent", NeuroReport 8, 807-810 (1997).

Mantyh, et al., "Antagonism of Nerve Growth Factor-TrkA Signaling and the Relief of Pain", Anesthesiology vol. 115 (1), 189-204 (2011).

McMahon, et al., "The biological effects of endogenous nerve growth factor on adult sensory neurons revealed by a trkA-IgG fusion molecule", Nat Med 1, 774-780 (1995).

Meyer, et al., "Remarkable leukemogenic potency and quality of a constitutively active neurotrophin receptor, deltaTrkA", Leukemia 21(10), 2171-2180 (2007).

Nakagawara, "Trk receptor tyrosine kinases: a bridge between cancer and neural development", Cancer Letters 169, 107-114 (2001).

Patapoutian, et al., "Trk receptors: mediators of neurotrophin action", Current Opinion in Neurobiology 11, 272-280 (2001).

Pierottia, et al., "Oncogenic rearrangements of the NRTK1/NGF receptor", Cancer Letters 232, 90-98 (2006).

Pinski, et al., "Trk receptor inhibition induces apoptosis of proliferating but not quiescent human osteoblasts", Cancer Research 62, 986-989 (2002).

Ramer, et al., "Adrenergic innervation of rat sensory ganglia following proximal or distal painful sciatic neuropathy: distinct mechanisms revealed by anti-NGF treatment", Eur J Neurosci 11, 837-846 (1999).

(56) References Cited

OTHER PUBLICATIONS

Raychaudhuri, et al., "K252a, a high-affinity nerve growth factor receptor blocker, improves psoriasis: an in vivo study using the severe combined immunodeficient mouse-human skin model", J Investigative Dermatology 122(3), 812-819 (2004).
Ricci, et al., "Neurotrophins and neurotrophin receptors in human lung cancer", American Journal of Respiratory Cell and Molecular Biology 25(4), 439-446 (2001).
Ro, et al., "Effect of NGF and anti-NGF on neuropathic pain in rats following chronic constriction injury of the sciatic nerve", Pain 79(2-3), 265-274 (1999).
Rowbottom, et al., "Identification of 1-(3-(6,7-Dimethoxyquinazolin-4-yloxy)phenyl)-3-(5-(1,1,1-trifluoro-2-methylpropan-2-yl)isoxazol-3-yl)urea Hydrochloride (CEP-32496), a Highly Potent and Orally Efficacious Inhibitor of V-RAF Murine Sarcoma Viral Oncogene Homologue B1 (BR", J Med Chem 55(3), 1082-1105 (2011).
Shelton, et al., "Nerve growth factor mediates hyperalgesia and cachexia in auto-immune arthritis", Pain 116, 8-16 (2005).
Theodosiou, et al., "Hyperalgesia due to nerve damage: role of nerve growth factor", Pain 81, 245-255 (1999).
Truzzi, et al., "Neurotrophins in healthy and diseased skin", Dermato-Endocrinology, 3(1), 32-36 (2011).
Tsuzuki, et al., "Practical Synthesis of (3S,4S)-3-methoxy-4-methylaminopyrrolidine", Tetrahedron: Asymmetry, vol. 12, 2989-2997 (2001).
Vargas-Sanchez, et al., "3-Aminopyrrolidines via Ring Rearrangement of 2-Aminomethylazetidines. Synthesis of (-)-Absouline", Organic Letters 7(26), 5861-5864 (2005).

* cited by examiner

PYRROLIDINYL UREA, PYRROLIDINYL THIOUREA AND PYRROLIDINYL GUANIDINE COMPOUNDS AS TRKA KINASE INHIBITORS

CROSS-REFERENCE TO RELATED APPLICATION(S)

This application is a Continuation of U.S. application Ser. No. 15/382,028, filed Dec. 16, 2016, which is a Divisional of U.S. application Ser. No. 14/117,615, filed Nov. 13, 2013, now U.S. Pat. No. 9,562,055 and claims priority under 35 U.S.C. 119(a) and 35 U.S.C. 365(a) to International Patent Application No. PCT/US2012/037003, filed May 9, 2012; this application also claims priority under 35 U.S.C. 119(e) to U.S. Provisional Application No. 61/485,858 filed May 13, 2011. The entire content of the applications referenced above are hereby incorporated by reference herein.

BACKGROUND OF THE INVENTION

The present invention relates to novel compounds, to pharmaceutical compositions comprising the compounds, to processes for making the compounds and to the use of the compounds in therapy. More particularly, it relates to pyrrolidinyl urea and pyrrolidinyl thiourea compounds which exhibit TrkA kinase inhibition, and which are useful in the treatment of pain, cancer, inflammation, neurodegenerative diseases and certain infectious diseases.

The current treatment regimens for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., *Current Opinion in Neurobiology,* 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C. J. et al. (1994) *Neuroscience* 62, 327-331; Zahn, P. K. et al. (2004)*J. Pain* 5, 157-163; McMahon, S. B. et al., (1995) *Nat. Med.* 1, 774-780; Ma, Q. P. and Woolf, C. J. (1997) *NeuroReport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448) and neuropathic pain animal models (Ramer, M. S. and Bisby, M. A. (1999) *Eur. J. Neurosci.* 11, 837-846; Ro, L. S. et al. (1999); Herzberg, U. et al., *Pain* 79, 265-274 (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. Because TrkA kinase may serve as a mediator of NGF driven biological responses, inhibitors of TrkA and/or other Trk kinases may provide an effective treatment for chronic pain states.

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2008, 3 (1), pp. 32-36), head and neck cancer (Yilmaz, T., et al., *Cancer Biology and Therapy* 2010, 10 (6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), Glioblastoma (Wadhwa, S., et al., *Journal of Biosciences* 2003, 28 (2), pp. 181-188), medulloblastoma (Gruber-Olipitz, M., et al., *Journal of Proteome Research* 2008, 7 (5), pp. 1932-1944), secratory breast cancer (Euthus, D. M., et al., *Cancer Cell* 2002, 2 (5), pp. 347-348), salivary gland cancer (Li, Y.-G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49) and adult myeloid leukemia (Eguchi, M., et al., *Blood* 1999, 93 (4), pp. 1355-1363). In preclinical models of cancer, non-selective small molecule inhibitors of Trk A, B and C were efficacious in both inhibiting tumor growth and stopping tumor metastasis (Nakagawara, A. (2001) *Cancer Letters* 169:107-114; Meyer, J. et al. (2007) *Leukemia,* 1-10; Pierottia, M. A. and Greco A., (2006) *Cancer Letters* 232:90-98; Eric Adriaenssens, E., et al. *Cancer Res* (2008) 68:(2) 346-351).

In addition, inhibition of the neurotrophin/Trk pathway has been shown to be effective in treatment of pre-clinical models of inflammatory diseases with NGF antibodies or non-selective small molecule inhibitors of Trk A. For example, inhibition of the neurotrophin/Trk pathway has been implicated in preclinical models of inflammatory lung diseases including asthma (Freund-Michel, V; Frossard, N., *Pharmacology & Therapeutics* (2008) 117(1), 52-76), interstitial cystitis (Hu Vivian Y; et. al. *The Journal of Urology* (2005), 173(3), 1016-21), inflammatory bowel diseases including ulcerative colitis and Crohn's disease (Di Mola, F. F, et. al., *Gut* (2000) 46(5), 670-678) and inflammatory skin diseases such as atopic dermatitis (Dou, Y.-C., et. al. *Archives of Dermatological Research* (2006) 298(1), 31-37), eczema and psoriasis (Raychaudhuri, S. P., et al., *J. Investigative Dermatology* (2004) 122(3), 812-819).

The TrkA receptor is also thought to be critical to the disease process in the infection of the parasitic infection of *Trypanosoma cruzi* (Chagas disease) in human hosts (de Melo-Jorge, M. et al., *Cell Host & Microbe* (2007) 1(4), 251-261).

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA receptors has been observed in the bone forming area in mouse models of bone fracture (K. Asaumi, et al., *Bone* (2000) 26(6) 625-633). In addition, localization of NGF was observed in almost all bone forming cells (K. Asaumi, et al.). Recently, it was demonstrated that a Trk inhibitor inhibits the tyrosine signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Several classes of small molecule inhibitors of Trk kinases said to be useful for treating pain or cancer are known (*Expert Opin. Ther. Patents* (2009) 19(3), 305-319).

SUMMARY OF THE INVENTION

It has now been found that pyrrolidinyl urea, pyrrolidinyl thiourea and pyrrolidinyl guanidine compounds are inhibitors of TrkA, and may be useful for treating disorders and diseases such as pain, including chronic and acute pain. Compounds of the invention may be useful in the treatment of multiple types of pain including inflammatory pain, neuropathic pain, and pain associated with cancer, surgery, and bone fracture. In addition, compounds of the invention may be useful for treating cancer, inflammation, neurodegenerative diseases and certain infectious diseases.

More specifically, provided herein are compounds of Formula I:

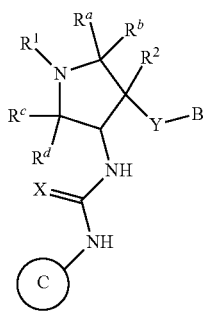

I or stereoisomers, tautomers, or pharmaceutically acceptable salts, solvates or prodrugs thereof, wherein the Y—B moiety and the NH—C(=X)—NH moiety are in the trans configuration and $R^1$, $R^2$, $R^a$, $R^b$, $R^c$, $R^d$, X, Y, B, and Ring C are as defined herein.

In one embodiment, provided herein are compounds of Formula I':

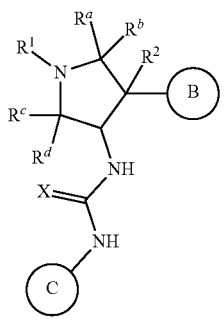

I' or stereoisomers, tautomers, or pharmaceutically acceptable salts, solvates or prodrugs thereof, wherein Ring B and the NH—C(=X)—NH moiety are in the trans configuration and $R^1$, $R^2$, $R^a$, $R^b$, $R^c$, $R^d$, X, Ring B, and Ring C are as defined herein.

Another aspect of the present invention provides methods of preventing or treating a disease or disorder modulated by TrkA, comprising administering to a mammal in need of such treatment an effective amount of a compound of this invention or a stereoisomer, solvate or pharmaceutically acceptable salt thereof. In one embodiment, the disease and disorders include chronic and acute pain, including but not limited to inflammatory pain, neuropathic pain, and pain associated with cancer, surgery, and bone fracture. In another embodiment, the disease and disorders include, but are not limited to, cancer, inflammation, neurodegenerative diseases and certain infectious diseases.

Another aspect of the present invention provides a pharmaceutical composition comprising a compound of the present invention or a pharmaceutically acceptable salt thereof.

Another aspect of the present invention provides the compounds of the present invention for use in therapy.

Another aspect of the present invention provides the compounds of the present invention for use in the treatment of disease and disorders of chronic and acute pain, including but not limited to inflammatory pain, neuropathic pain, and pain associated with cancer, surgery, and bone fracture. Another aspect of the present invention provides the compounds of the present invention for use in the treatment of disease and disorders selected from cancer, inflammation, neurodegenerative diseases and certain infectious diseases.

Another aspect of the present invention provides the use of a compound of this invention in the manufacture of a medicament for the treatment of disease and disorders such as chronic and acute pain including, but not limited to, inflammatory pain, neuropathic pain, and pain associated with cancer, surgery, and bone fracture.

Another aspect of the present invention provides the use of a compound of this invention in the manufacture of a medicament for the treatment of disease and disorders selected from cancer, inflammation, neurodegenerative diseases and certain infectious diseases.

Another aspect of the present invention provides intermediates for preparing compounds of Formula I.

Another aspect of the present invention includes methods of preparing, methods of separation, and methods of purification of the compounds of this invention.

DETAILED DESCRIPTION OF THE INVENTION

Provided herein are compounds, and pharmaceutical formulations thereof, that are potentially useful in the treatment of diseases, conditions and/or disorders modulated by TrkA.

One embodiment provides a compound of Formula I:

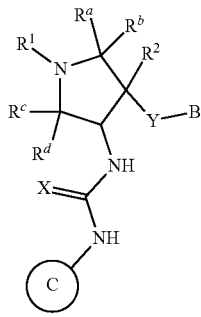

I or stereoisomers, tautomers, or pharmaceutically acceptable salts, solvates or prodrugs thereof, wherein:

the Y—B moiety and the NH—C(=X)—NH moiety are in the trans configuration;

$R^a$, $R^b$, $R^c$ and $R^d$ are independently selected from H and (1-3C)alkyl;

X is O, S or NH;

$R^1$ is (1-3C alkoxy)(1-6C)alkyl, (trifluoromethoxy)(1-6C)alkyl, (1-3C sulfanyl)(1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, cyano(1-6C)alkyl, aminocarbonyl(1-6C)alkyl, hydroxy(1-6C)alkyl, dihydroxy(2-6C)alkyl, (1-6C)alkyl, (1-3Calkylamino)(1-3C)alkyl, (1-4C alkoxycarbonyl)(1-6C)alkyl, amino(1-6C)alkyl, hydroxy(1-3C alkoxy)(1-6C)alkyl, di(1-3C alkoxy)(1-6C)alkyl, (1-3C alkoxy)trifluoro(1-6C)alkyl, hydroxytrifluoro(1-6C)alkyl, (1-4C alkoxycarbonyl)(1-3C alkoxy)(1-6C)alkyl, hydroxycarbonyl(1-3C alkoxy)(1-6C)alkyl, hetAr$^5$(CH$_2$)$_{0-1}$, or Ar$^5$(CH$_2$)$_{0-1}$;

$R^2$ is H, F, or OH;

Y is a bond, —O— or —OCH$_2$—;

B is Ar$^1$, hetAr$^1$, 1-6C alkyl or (1-6C)alkoxy;

Ar$^1$ is phenyl optionally substituted with one or more substituents independently selected from halogen, CF$_3$, CF$_3$O—, (1-4C)alkoxy, hydroxy(1-4C)alkyl, (1-6C)alkyl and CN;

hetAr$^1$ is a 5-6 membered heteroaryl having 1-3 ring heteroatoms independently selected from N, S and O, and optionally substituted with 1-2 groups independently selected form (1-6C)alkyl, halogen, OH, CF$_3$, NH$_2$ and hydroxy(1-2C)alkyl;

Ring C is formula C-1, C-2, or C-3

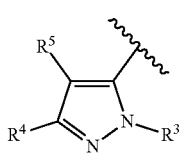

C-1

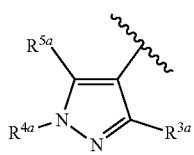

C-2

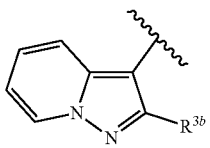

C-3

$R^3$ is H, (1-6C)alkyl, hydroxy(1-6C)alkyl, Ar$^2$, hetCyc$^1$, (3-7C)cycloalkyl, or hetAr$^2$;

Ar$^2$ is phenyl optionally substituted with one or more groups independently selected from halogen, (1-6C)alkyl and hydroxymethyl;

hetCyc$^1$ is a 5-6-membered saturated or partially unsaturated heterocyclic ring having 1-2 ring heteroatoms independently selected from N and O;

hetAr$^2$ is a 5-6 membered heteroaryl ring having 1-3 ring heteroatoms independently selected from N, O and S and optionally substituted with one or more groups independently selected from (1-6C)alkyl and halogen;

$R^4$ is H, OH, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, cyano(1-6C)alkyl, hydroxy (1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr$^3$(1-6C)alkyl, Ar$^3$(1-6C)alkyl, (1-6C)alkoxy, monofluoro(1-6C)alkoxy, difluoro(1-6C)alkoxy trifluoro (1-6C)alkoxy, tetrafluoro(2-6C)alkoxy, pentafluoro(2-6C)alkoxy cyano(1-6C)alkoxy, hydroxy(1-6C)alkoxy, dihydroxy(2-6C)alkoxy, amino(2-6C)alkoxy, aminocarbonyl(1-6C)alkoxy, hydroxyl-carbonyl(1-6C)alkoxy, hetCyc$^2$(1-6C)alkoxy, hetAr$^3$(1-6C)alkoxy, Ar$^3$(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr$^4$, Ar$^4$, hetCyc$^2$(O)CH$_2$—, (1-4C alkoxycarbonyl)(1-6C)alkoxy, hydroxycarbonyl(1-6C)alkoxy, aminocarbonyl(1-6C)alkoxy, hetCyc$^2$C(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)amino-carboxy, hetCyc$^2$C(=O)O—, hydroxydifluoro(1-6C)alkyl, (1-4C alkylcarboxy)(1-6C)alkyl, (1-6C)alkoxycarbonyl, hydroxyl/carbonyl, aminocarbonyl, (1-3C alkoxy)aminocarbonyl, hetCyc$^3$, halogen, CN, trifluoromethylsulfonyl, N-(1-3C alkyl) pyridinonyl, N-(1-3C trifluoroalkyl) pyridinonyl, (1-4C alkylsiloxy)(1-6C)alkoxy, isoindoline-1,3-dionyl(1-6C)alkoxy or N-(1-3C alkyl)oxadiazolonyl;

hetCyc$^2$ is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc$^3$ is a 4-7 membered heterocycle having 1-2 ring heteroatoms independently selected from N and O and optionally substituted with one or more substituents independently selected from F, CN, CF$_3$, (1-6C)alkyl, hydroxy (1-6C)alkyl, (1-3C alkoxy)(1-6C)alkyl, (1-6C) acyl-, (1-6C) alkylsulfonyl, trifluoromethylsulfonyl and (1-4C alkoxy) carbonyl;

hetAr$^3$ is a 5-membered heteroaryl ring having 1-3 ring atoms independently selected from N, O and S and optionally substituted with (1-6C)alkyl;

Ar³ is phenyl optionally substituted with (1-4C)alkoxy;

hetAr⁴ is a 5-6 membered heteroaryl ring having 1-3 ring heteroatoms independently selected from N, S and O and optionally substituted with 1-2 substituents independently selected from (1-6C)alkyl, halogen, CN, hydroxy(1-6C) alkyl, trifluoro(1-6C)alkyl, (3-6C)cycloalkyl, (3-6C cycloalkyl)CH₂—, (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), (1-3C)trifluoroalkyl, and methoxybenzyl; or a 9-10 membered bicyclic heteroaryl having 1-3 ring nitrogen atoms;

Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—;

R⁵ is H, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, phenyl [optionally substituted with one or more groups independently selected from halogen, (1-6C)alkyl and (1-6C)alkoxy], (3-4C)cycloalkyl, amino, aminocarbonyl, or trifluoro(1-3C alky)amido; or R⁴ and R⁵ together with the atoms to which they are attached form a 5-6 membered saturated, partially unsaturated or unsaturated carbocyclic ring optionally substituted with one or more substituents independently selected from (1-6C)alkyl, or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6)acyl, (1-6C)alkyl and oxo, and said sulfur ring atom is optionally oxidized to S(=O) or SO₂;

hetAr⁵ is a 5-6 membered heteroaryl ring having 1-3 ring heteroatoms independently selected from N, O or S, wherein the ring is optionally substituted with one or more substituents independently selected from halogen, (1-6C)alkyl, (1-6C)alkoxy and CF₃;

Ar⁵ is phenyl optionally substituted with one or more groups independently selected from halogen, (1-6C)alkyl, (1-6C)alkoxy, CF₃O—, (1-4C)alkoxycarbonyl and aminocarbonyl;

R³ᵃ is hydrogen, halogen, (1-6C)alkyl, trifluoro(1-6C)alkyl, (3-6C)cycloalkyl, phenyl optionally substituted with one or more substituents independently selected from halogen, (1-6C)alkyl and hydroxymethyl, or a 5-6 membered heteroaryl ring having 1-3 ring heteroatoms independently selected from N, O and S and optionally substituted with one or more groups independently selected from (1-6C)alkyl and halogen;

R³ᵇ is hydrogen, (1-6C)alkyl, trifluoro(1-6C)alkyl, (3-6C)cycloalkyl, phenyl optionally substituted with one or more substituents independently selected from halogen, (1-6C)alkyl and hydroxymethyl, or a 5-6 membered heteroaryl ring having 1-3 ring heteroatoms independently selected from N, O and S and optionally substituted with one or more groups independently selected from (1-6C)alkyl and halogen;

R⁴ᵃ is hydrogen, (1-6C)alkyl, trifluoro(1-6C)alkyl, phenyl [optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH₂—, (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy)(1-3C)trifluoroalkyl, and methoxybenzyl; and R⁵ᵃ is hydrogen, halogen, (1-6C)alkyl, trifluoro(1-6C)alkyl, (3-6C)cycloalkyl, phenyl optionally substituted with one or more substituents independently selected from halogen, (1-6C)alkyl and hydroxymethyl, or a 5-6 membered heteroaryl ring having 1-3 ring heteroatoms independently selected from N, O and S and optionally substituted with one or more groups independently selected from (1-6C)alkyl and halogen.

In one embodiment, compounds of Formula I have the structure I':

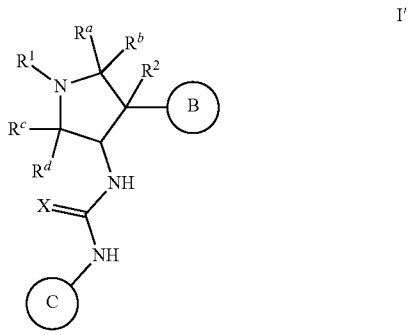

I' or stereoisomers, tautomers, or pharmaceutically acceptable salts, solvates or prodrugs thereof, wherein:

Ring B and the NH—C(=X)—NH moiety are in the trans configuration;

Rᵃ, Rᵇ, Rᶜ and Rᵈ are independently selected from H and (1-3C)alkyl;

X is O or S;

R¹ is (1-3C alkoxy)(1-6C)alkyl, (trifluoromethoxy)(1-6C)alkyl, (1-3C sulfanyl)(1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, cyano(1-6C)alkyl, aminocarbonyl(1-6C)alkyl, hydroxy(1-6C)alkyl, dihydroxy(2-6C)alkyl, (1-6C)alkyl, or (1-3Calkylamino)(1-3C)alkyl;

R² is H, F, or OH;

Ring B is Ar¹ or hetAr¹;

Ar¹ is phenyl optionally substituted with one or more substituents independently selected from halogen, CF₃, CF₃O—, (1-4C)alkoxy, hydroxy(1-4C)alkyl and (1-6C)alkyl;

hetAr¹ is a 5-6 membered heteroaryl having 1-3 ring heteroatoms independently selected from N, S and O, and optionally substituted with 1-2 groups independently selected form (1-6C)alkyl, halogen, OH, CF₃, NH₂ and hydroxy(1-2C)alkyl;

Ring C is

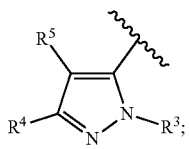

R³ is H, (1-6C)alkyl, hydroxy(1-6C)alkyl, Ar², hetCyc¹, (3-7C)cycloalkyl, or hetAr²;

Ar² is phenyl optionally substituted with one or more groups independently selected from halogen, (1-6C)alkyl and hydroxymethyl;

hetCyc¹ is a 5-6-membered saturated or partially unsaturated heterocyclic ring having 1-2 ring heteroatoms independently selected from N and O;

hetAr² is a 5-6 membered heteroaryl ring having 1-3 ring heteroatoms independently selected from N, O and S and optionally substituted with (1-6C)alkyl;

R⁴ is H, OH, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C) alkylsulfonamido(1-6C)alkyl, sulfamido(1-6C)alkyl, hydroxycarbonyl(1-6C)alkyl, hetAr³(1-6C)alkyl, Ar³(1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy cyano(1-6C)alkoxy, hydroxy(1-6C)alkoxy, dihydroxy(2-6C)alkoxy, amino(2-6C)alkoxy, aminocarbonyl(1-6C)alkoxy, hydroxycarbonyl(1-6C)alkoxy, hetCyc²(1-6C)alkoxy, hetAr³(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl, hetAr⁴, or Ar⁴;

hetCyc² is a 4-6 membered heterocyclic ring having 1-2 ring heteroatoms independently selected from N and O and optionally substituted with 1-2 groups independently selected from (1-6C)alkyl;

hetAr³ is a 5-membered heteroaryl ring having 1-3 ring atoms independently selected from N, O and S and optionally substituted with (1-6C)alkyl;

Ar³ is phenyl optionally substituted with (1-4C)alkoxy;

hetAr⁴ is a 5-6 membered heteroaryl ring having 1-3 ring heteroatoms independently selected from N, S and O and optionally substituted with 1-2 substituents independently selected from (1-6C)alkyl, or a 9-10 membered bicyclic heteroaryl having 1-3 ring nitrogen atoms;

Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl) OC(=O)—; and R⁵ is H, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, or phenyl optionally substituted with one or more groups independently selected from halogen, (1-6C)alkyl and (1-6C)alkoxy; or R⁴ and R⁵ together with the atoms to which they are attached form a 5-6 membered saturated carbocyclic ring optionally substituted with one or more substituents independently selected from (1-6C)alkyl, or R⁴ and R⁵ together with the atoms to which they are attached form a 5-6 membered saturated heterocyclic ring having a ring heteroatom selected from N, O or S, wherein said ring nitrogen atom is optionally substituted with (1-6C alkyl)C(=O)O— or (1-6)acyl, and said sulfur ring atom is optionally oxidized to S(=O) or SO₂.

It is to be understood that in instances where two or more radicals are used in succession to define a substituent attached to a structure, the first named radical is considered to be terminal and the last named radical is considered to be attached to the structure in question. Thus, for example, the radical "alkoxyalkyl" is attached to the structure in question by the alkyl group.

The terms "(1-6C)alkyl", "(1-4C)alkyl" and "(1-3C)alkyl" as used herein refer to saturated linear monovalent hydrocarbon radicals of one to six carbon atoms, one to four carbon atoms, and one to three carbon atoms, respectively, or a branched saturated monovalent hydrocarbon radical of three to six carbon atoms, three to four carbon atoms, or three carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

"(1-4C)Alkoxy", "(1-3C)alkoxy", "(1-6C)alkoxy" and "(2-6C)alkoxy" refer to an —OR radical where $R^c$ is (1-4C)alkyl, (1-3C)alkyl, (1-6C)alkyl, or (2-6C)alkyl, respectively, as defined above. Examples include methoxy, ethoxy, and the like.

"(1-6)Acyl" means a RC(=O)— radical where $R^c$ is a linear saturated monovalent hydrocarbon radical of one to five carbon atoms or a branched saturated monovalent hydrocarbon radical of three to five carbon atoms, e.g., methylcarbonyl, and the like.

"(1-3C Alkoxy)(1-6C)alkyl" and "(1-3C alkoxy)(1-4C)alkyl" mean a linear saturated monovalent hydrocarbon radical of one to six carbon atoms or one to four carbon atoms, or a branched saturated monovalent hydrocarbon radical of three to six carbon atoms or three to four carbon atoms, respectively, wherein one of the carbon atoms is substituted with one (1-3C)alkoxy group as defined herein.

"(1-3C Alkoxy)(1-6C)alkoxy" means a (1-6C)alkoxy group as defined herein, wherein one of the carbon atoms is substituted with a (1-3C)alkoxy group as defined herein. Examples include methoxymethoxy, methoxyethoxy, and the like.

"(1-3C Alkoxy)aminocarbonyl" means a (1-3C alkyl)-O—NH—C(=O)— group.

"(1-6C)Alkoxycarbonyl" and "(1-4C)alkoxycarbonyl" mean a (1-6C)—O—C(=O)— and (1-4C)—O—C(=O)— group, respectively.

(1-4C Alkoxycarbonyl)(1-6C)alkyl means a (1-6C)alkyl group as defined herein, wherein one of the carbons is substituted with a (1-4C alkoxy)carbonyl group as defined herein.

"(1-3C Alkoxy)trifluoro(1-6C)alkyl" means a (1-6C)alkyl group as defined herein, wherein one of the carbons is substituted with three fluoros, and another carbon is substituted with a (1-3C)alkoxy group as defined herein.

"(1-4C Alkoxycarbonyl)(1-6C alkoxy)" means a (1-6C)alkoxy group as defined herein wherein one of the carbon atoms is substituted with one (1-4C alkoxycarbonyl group, i.e., an alkyl-O—C(=O)— group.

"(1-4C Alkoxycarbonyl)(1-3C alkoxy)(1-6C)alkyl" means a (1-3C alkoxy)(1-6C)alkyl group as defined herein wherein one of the carbon atoms is substituted with one (1-4C alkoxycarbonyl group, i.e., an alkyl-O—C(=O)— group.

"(1-3C Alkoxy)hydroxycarbonylalkyl" means a hydroxycarbonylalkyl group as defined herein wherein one of the carbon atoms is substituted with one (1-3C alkoxy) group.

"Amino" means a —NRR' group where R and R' are independently selected from hydrogen or (1-3C)alkyl as defined herein. Examples include $H_2N$—, $CH_3NH$—, $(CH_3)_2N$, and the like.

"Amino(1-6C)alkyl" means a linear saturated monovalent hydrocarbon radical of one to six carbon atoms or a branched saturated monovalent hydrocarbon radical of three to six carbon atoms, wherein one of the carbon atoms is substituted with one —NRR' group where R and R' are independently selected from hydrogen or (1-3C)alkyl as defined herein. Examples include aminomethyl, methylaminoethyl, 2-ethylamino-2-methylethyl, and the like.

"Amino(2-6C)alkoxy" means a (2-6C)alkoxy group as defined herein, wherein one of the carbon atoms is substituted with one —NRR' group where R and R' are independently selected from hydrogen or (1-3C)alkyl as defined herein.

"Aminocarbonyl" means a RR'NCO— radical where R and R' are independently hydrogen or (1-6C)alkyl as defined herein. Examples include $H_2NCO$—, dimethylaminocarbonyl, and the like.

"Aminocarbonyl(1-6C)alkyl" means a linear saturated hydrocarbon radical of one to six carbon atoms or a branched saturated monovalent hydrocarbon radical of three to six carbons wherein one of the carbon atoms is substituted with one aminocarbonyl group as defined herein, e.g., 2-aminocarbonylethyl, 1-, 2-, or 3-dimethylaminocarbonylpropyl, and the like.

"Aminocarbonyl(1-6C)alkoxy" means a (1-6C)alkoxy as defined herein, wherein one of the carbon atoms is substituted with one aminocarbonyl group as defined herein.

"(1-3C)Alkylamido(1-6C)alkoxy" means a (1-6C)alkoxy as defined herein, wherein one of the carbon atoms is substituted with one alkylamino group, i.e., substituted with a (1-3C)C(=O)NH— group.

"(1-4C alkyl)carboxy" means a R'—C(=O)O— group where R' is (1-4C)alkyl.

"(1-4C alkylsiloxy)(1-6C)alkoxy" means a (1-6C)alkoxy group as defined herein wherein one of the carbon atoms is substituted with one (1-4C alkyl)siloxy group, e.g., a (1-4C alkyl)Si—O— group such as a tert-butylsiloxy group.

"(1-3C)Alkylsulfonamido" means a (1-3C)alkyl$SO_2NH$— radical where (1-3C)alkyl is as defined herein "(1-3C Alkylsulfonamido)(1-6C)alkyl" means a linear saturated hydrocarbon radical of one to six carbon atoms or a branched saturated monovalent hydrocarbon radical of three to six carbons substituted with one (1-3C)alkylsulfonamido group as defined herein.

"(1-3C)Alkylsulfonamido(1-6C)alkoxy" means a (1-6C) alkoxy group as defined herein wherein one of the carbon atoms is substituted with one (1-3C)alkylsulfonamido group as defined herein.

"(1-3C)Alkylsulfonyl" means a —$SO_2R$ radical where R is (1-3C)alkyl as defined above, e.g., methylsulfonyl, and the like.

"(1-3C Alkylsulfonyl)(1-6C)alkoxy" means a (1-6C) alkoxy group as defined herein, wherein one of the carbon atoms is substituted with a (1-3C)alkylsulfonyl group.

"Hydroxycarbonyl" means HOC(=O)—.

"(1-4C alkyl)carboxy(1-6C)alkyl" means a (1-6C)alkyl group as defined herein wherein one of the carbon atoms is substituted with a (1-4C alkyl)carboxy group as defined herein.

"Cyano(1-6C)alkyl" means a linear saturated hydrocarbon radical of one to six carbon atoms or a branched saturated monovalent hydrocarbon radical of three to six carbons substituted with a cyano (CN) group.

"(3-6C)Cycloalkyl" means a cyclic saturated monovalent hydrocarbon radical of three to six carbon atoms, e.g., cyclopropyl, cyclobutyl, cyclopentyl, or cyclohexyl.

"Di(1-3C alkoxy)(1-6C)alkyl" means a (1-6C)alkyl group as defined herein, wherein two carbons are each substituted with one (1-3C)alkoxy group as defined herein.

"Dihydroxy(2-6C)alkyl" means a linear saturated hydrocarbon radical of two to six carbon atoms or a branched saturated monovalent hydrocarbon radical of three to six carbons substituted with two hydroxy (OH) groups, provided that two hydroxy groups are not both on the same carbon atom.

"Dihydroxy(2-6C)alkoxy" means a (2-6C)alkoxy group as defined herein, wherein two of the carbon atoms are substituted with a hydroxy group.

"Halogen" as used herein means F, Cl, Br or I.

"Heterocycle" refers to a saturated or partially unsaturated ring system having one or more ring heteroatoms as recited for the specific heterocyclic group, wherein the heterocycle is optionally substituted with substituents as defined for that particular heterocyclic group.

"Heteroaryl" refers to a 5-6 membered unsaturated ring-system having one or more ring heteroatoms as recited for the specific heteroaryl group, wherein the heteroaryl is optionally substituted with substituents as defined for that particular heteroaryl group.

"hetCyc$^2$C(=O)(1-6C)alkoxy" means a (1-6C)alkoxy as defined herein, wherein one of the carbon atoms is substituted with a hetCyc$^2$C(=O) group, wherein hetCyc$^2$ is as defined herein.

"Hydroxy(1-6C)alkyl" and "hydroxy(1-4C)alkyl" means a linear saturated hydrocarbon radical of one to six carbon atoms or one to four carbon atoms, respectively, or a branched saturated monovalent hydrocarbon radical of three to six carbon atoms or three to four carbon atoms, respectively, wherein one of the carbon atoms is substituted with a hydroxy (OH) group.

"Hydroxy(1-6C)alkoxy" means a (1-6C)alkoxy group as defined herein, wherein one of the carbon atoms is substituted with a hydroxy group.

"Hydroxy(1-3C alkoxy)(1-6C)alkyl" means a (1-3C alkoxy)(1-6C)alkyl group as defined herein, wherein one of the carbons is substituted with a hydroxy group.

"Hydroxy(1-3C alkoxy)(1-6C)alkoxy" means a (1-3C alkoxy)(1-6C)alkoxy as defined herein, wherein one of the carbon atoms is substituted with a hydroxy group.

"Hydroxydifluoro(1-6C)alkyl" means a difluoro(1-6C) alkyl group as defined herein, wherein one of the carbon atoms is substituted with a hydroxy group.

"Hydroxytrifluoro(1-6C)alkoxy" means a trifluoro(1-6C) alkoxy group as defined herein, wherein one of the carbon atoms is substituted with a hydroxy group.

"Hydroxycarbonylalkyl" means a linear saturated hydrocarbon radical of one to six carbon atoms or a branched saturated monovalent hydrocarbon radical of three to six carbons substituted with one —COOH group. Examples include 2-hydroxycarbonylethyl, 1-, 2-, or 3-hydroxycarbonylpropyl, and the like.

"Isoindoline-1,3-dionyl(1-6C)alkoxy" means a (1-6C) alkoxy group as defined herein, wherein one of the carbon atoms is substituted with an isoindoline-1,3-dionyl group.

"Monofluoro(1-6C)alkyl", "difluoro(1-6C)alkyl" and "trifluoro(1-6C)alkyl" refer to a (1-6C)alkyl group as defined herein wherein one to three hydrogen atoms, respectively, is replaced by a fluoro group.

"Tetrafluoro(2-6C)alkyl" and "pentafluoro(2-6C)alkyl" refer to a linear saturated monovalent hydrocarbon radical of two to six carbon atoms or a branched saturated monovalent hydrocarbon radical of three to six carbon atoms wherein four to five hydrogen atoms, respectively, is replaced by a fluoro group.

"(Trifluoromethoxy)(1-6C)alkyl" means a linear saturated hydrocarbon radical of one to six carbon atoms or a branched saturated monovalent hydrocarbon radical of three to six carbons substituted with one $CF_3O$— group.

"Trifluoro(1-3C alkyl)amido" means a (1-3C alkyl)C(=O)NH— group wherein one of the carbons is substituted with three fluoros.

"Trifluoro(1-6C)alkoxy" means a (1-6C)alkoxy group as defined herein, wherein one of the carbon atoms is substituted with three fluoros.

"Sulfamido(1-6C)alkyl" means a linear saturated hydrocarbon radical of one to six carbon atoms or a branched saturated monovalent hydrocarbon radical of three to six carbons substituted with one sulfamido ($H_2NSO_2NH$—) group.

It should be noted that compounds of the invention may contain groups that may exist in tautomeric forms, such as heteroatom substituted heteroaryl or heterocyclic groups and the like, which are illustrated in the following general and specific examples:

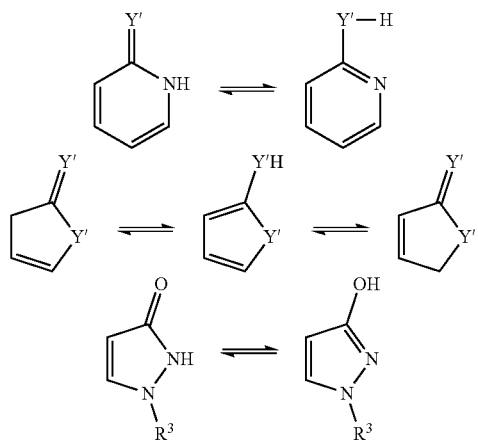

where Y'=O, S, or NR, and though one form is named, described, displayed and/or claimed herein, all the tautomeric forms are intended to be inherently included in such name, description, display and/or claim.

In one embodiment of Formula I, $R^a$, $R^b$, $R^c$ and $R^d$ are independently selected from H and methyl. In one embodiment, $R^a$, $R^b$, $R^c$ and $R^d$ are hydrogen. In one embodiment, $R^a$ is methyl and $R^b$, $R^c$ and $R^d$ are hydrogen. In one embodiment, $R^a$ and $R^b$ are methyl and $R^c$ and $R^d$ are hydrogen. In one embodiment, $R^a$, $R^b$ and $R^c$ are hydrogen and $R^d$ is methyl. In one embodiment, $R^a$ and $R^b$ are hydrogen and $R^c$ and $R^d$ are methyl.

In one embodiment, X is O.
In one embodiment, X is S.
In one embodiment, X is NH.

In one embodiment, $R^1$ is (1-3C alkoxy)(1-6C)alkyl, for example, methoxyethyl, methoxypropyl, ethoxyethyl and 2-methoxypropyl. Particular examples include methoxyethyl and 2-methoxypropyl having the structures:

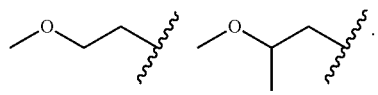

In one embodiment, $R^1$ is (trifluoromethoxy)(1-6C)alkyl, for example, trifluoromethoxyethyl, trifluoromethoxypropyl, and the like. A particular example is trifluoromethoxyethyl.

In one embodiment, $R^1$ is (1-3C sulfanyl)(1-6C)alkyl, for example methyl sulfanylethyl, ethylsulfanylethyl, and the like. A particular example is methylsulfanylethyl.

In one embodiment, $R^1$ is monofluoro(1-6C)alkyl, difluoro(1-6C)alkyl or trifluoro(1-6C)alkyl. Particular examples include 1,3-difluoroprop-2-yl, 2,2-difluoroethyl 2,2,2-trifluoroethyl and 2,2,2-trifluoropropyl having the structures:

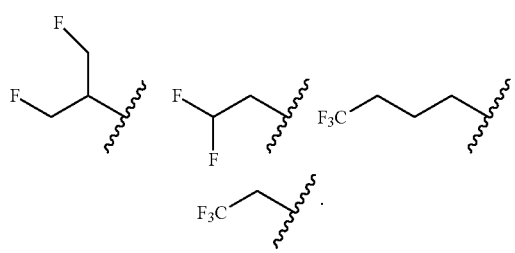

In one embodiment, $R^1$ is tetrafluoro(2-6C)alkyl or pentafluoro(2-6C)alkyl. A particular example is 3,3,4,4,4-pentafluorobutyl.

In one embodiment, $R^1$ is cyano(1-6C)alkyl. A particular example is 2-cyanoethyl.

In one embodiment, $R^1$ is aminocarbonyl(1-6C)alkyl. A particular example is aminocarbonylmethyl. Another example is methylaminocarbonylmethyl having the formula MeNHC(=O)CH$_2$—.

In one embodiment, $R^1$ is hydroxy(1-6C)alkyl. A particular example is 2-hydroxyethyl. Another example is 2-hydroxypropyl.

In one embodiment, $R^1$ is dihydroxy(2-6C)alkyl. A particular example is the structure:

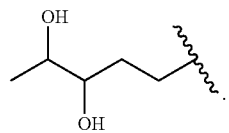 [SMILES: *CCC(O)C(C)O]

In one embodiment, $R^1$ is (1-6C)alkyl. Examples include methyl, ethyl, and propyl.

In one embodiment, $R^1$ is (1-3Calkylamino)(1-3C)alkyl, that is, a (1-3C)alkyl group which is substituted with a (1-3C alkyl)amino group, for example a (1-3Calkyl)NH— group such as methylamino. A particular example is (2-methylamino)ethyl.

In one embodiment, R¹ is (1-4C alkoxycarbonyl)(1-6C) alkyl. A particular example is methoxycarbonylmethyl, having the structure:

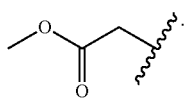 [SMILES: *CC(=O)OC]

In one embodiment, R¹ is amino(1-6C)alkyl, such as methylamino(1-6C)alkyl. A particular example is 2-methylaminoethyl.

In one embodiment, R¹ is hydroxy(1-3C alkoxy)(1-6C) alkyl. Examples include hydroxymethoxy(1-6C)alkyl. Particular examples include the structures:

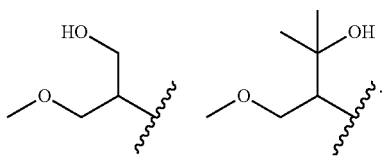

In one embodiment, R¹ is di(1-3C alkoxy)(1-6C)alkyl. Examples include dimethoxy(1-6C)alkyl. A particular example includes 1,3-dimethoxyprop-2-yl having the structure:

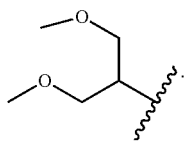

In one embodiment, R¹ is (1-3C alkoxy)trifluoro(1-6C) alkyl. Examples include methoxytrifluoro(1-6C)alkyl. A particular example includes 3,3,3-trifluoro-2-methoxypropyl.

In one embodiment, R¹ is hydroxytrifluoro(1-6C)alkyl. A particular example includes 3,3,3-trifluoro-2-hydroxypropyl.

In one embodiment, R¹ is (1-4C alkoxycarbonyl)(1-3C alkoxy)(1-6C)alkyl. Examples include (methoxycarbonyl)methoxy(1-6C)alkyl. A particular example includes the structure:

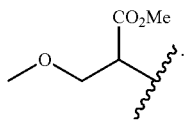

In one embodiment, R¹ is hydroxycarbonyl(1-3C alkoxy)(1-6C)alkyl. Examples include (methoxycarbonyl)hydroxy(1-6C)alkyl. A particular example includes the structure:

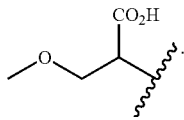

In one embodiment, R¹ is hetAr⁵(CH₂)₀₋₁.

In one embodiment, R¹ is hetAr⁵, where hetAr⁵ is a 5-6 membered heteroaryl ring having 1-3 ring heteroatoms independently selected from N, O or S, wherein the ring is optionally substituted with one or more substituents independently selected from halogen, (1-6C)alkyl, (1-6C)alkoxy and CF₃. Examples include pyrrolyl, pyrazolyl, imidazolyl, furanyl, isoxazolyl, oxazolyl, thiophenyl, thiazolyl, thiadiazolyl, triazolyl, thiadiazolyl, pyridyl, pyrimidyl and pyrazinyl rings, wherein the ring is optionally substituted with one or more substituents independently selected from halogen, (1-6C)alkyl, (1-6C)alkoxy and CF₃.

In one embodiment, R¹ is hetAr⁵, where herAr⁵ is pyrazolyl, pyridyl or pyrazinyl optionally substituted with one or more one or more substituents independently selected from halogen, (1-6C)alkyl, (1-6C)alkoxy and CF₃. In one embodiment, herAr⁵ is substituted with one of said substituents. In one embodiment, R¹ is pyrazolyl, pyridyl or pyrazinyl optionally substituted with methyl, trifluoromethyl, methoxy or ethoxy.

Particular example of R¹ when represented by hetAr⁵ include the structures:

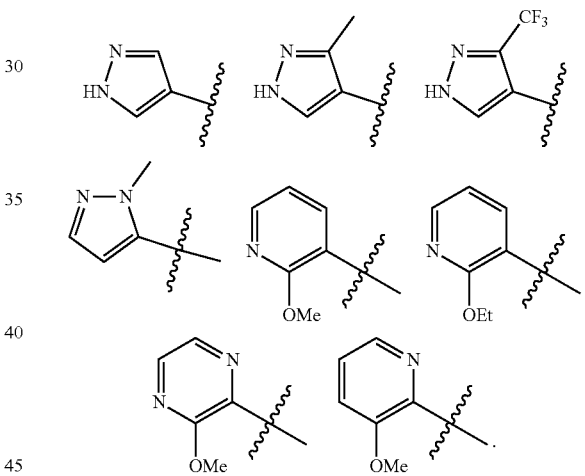

In one embodiment, R¹ is hetAr⁵(CH₂)—, where hetAr⁵ is a 5-6 membered heteroaryl ring having 1-3 ring heteroatoms independently selected from N, O or S, wherein the ring is optionally substituted with one or more substituents independently selected from halogen, (1-6C)alkyl, (1-6C)alkoxy and CF₃. Examples include pyrrolyl, pyrazolyl, imidazolyl, furanyl, isoxazolyl, oxazolyl, thiophenyl, thiazolyl, thiadiazolyl, triazolyl, thiadiazolyl, pyridyl, pyrimidyl and pyrazinyl rings, wherein the ring is optionally substituted with one or more substituents independently selected from halogen, (1-6C)alkyl, (1-6C)alkoxy and CF₃.

In one embodiment, R¹ is hetAr⁵(CH₂)—, where hetAr⁵ is imidazolyl, thiadiazolyl or triazolyl optionally substituted with one or more substituents independently selected from halogen, (1-6C)alkyl, (1-6C)alkoxy and CF₃. In one embodiment, hetAr⁵ is substituted with one or more substituents independently selected from methyl, methoxy, ethoxy, and trifluoromethyl. In one embodiment, hetAr⁵ is substituted with one of said substituents.

Particular example of $R^1$ when represented by hetAr$^5$(CH$_2$)— include the structures:

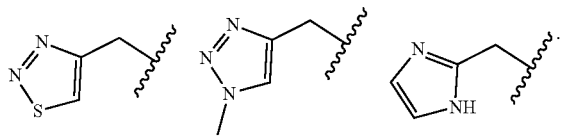

In one embodiment, $R^1$ is Ar$^5$(CH$_2$)$_{0-1}$.

In one embodiment, $R^1$ is Ar$^5$, where Ar$^5$ phenyl optionally substituted with one or more substituents independently selected from halogen, (1-6C)alkyl, (1-6C)alkoxy, CF$_3$O—, (1-4C)alkoxycarbonyl and aminocarbonyl. In one embodiment, Ar$^5$ is phenyl optionally substituted with one or more substituents independently selected from F, Cl, methyl, methoxy, trifluoromethoxy and CH$_3$C(=O)O—.

Examples of $R^1$ when represented by Ar$^5$ include phenyl, 2-methoxyphenyl, 2-fluorophenyl, 2-methylphenyl, 2-chlorophenyl, 2-trifluoromethoxyphenyl, 2-(methoxycarbonyl)phenyl, 4-fluorophenyl, and 2,6-difluorophenyl.

In one embodiment, $R^1$ is selected from (1-3C alkoxy)(1-6C)alkyl, difluoro(1-6C)alkyl and trifluoro(1-6C)alkyl.

In one embodiment, $R^2$ is H.
In one embodiment, $R^2$ is F.
In one embodiment, $R^2$ is OH.

In one embodiment, the Y group of Formula I linking the pyrrolidinyl ring and the B group is a bond.

In one embodiment, the Y group of Formula I linking the pyrrolidinyl ring and the B group is —O—.

In one embodiment, the Y group of Formula I linking the pyrrolidinyl ring and the B group is —OCH$_2$—, where the oxygen of the Y group is coupled to the pyrrolidinyl ring.

In one embodiment, B is represented by Ring B, where Ring B is Ar$^1$ and Ar$^1$ is phenyl optionally substituted with one or more substituents independently selected from halogen, CF$_3$, CF$_3$O—, (1-4C)alkoxy, hydroxy(1-4C)alkyl, (1-6C)alkyl, and CN. Examples include phenyl, fluorophenyl, difluorophenyl, trifluorophenyl, chlorophenyl, trifluoromethylphenyl, methoxyphenyl, cyanophenyl, chlorofluorophenyl, cyanoflurophenyl, and chlorocyanophenyl.

Particular examples of Ring B when represented by Ar$^1$ include phenyl, 2-fluorophenyl, 3-fluorophenyl, 4-fluorophenyl, 3,4-difluorophenyl, 3,5-difluorophenyl, 2,4-difluorophenyl, 2,5-difluorophenyl, 3,4,5-trifluorophenyl, 2-chlorophenyl, 3-chlorophenyl, 4-chlorophenyl, 3-trifluoromethylphenyl 3-methoxyphenyl, 3-chloro-4-fluorophenyl, 4-chloro-3-fluorophenyl, 3-chloro-5-fluorophenyl, 3-cyano-5-fluorophenyl, 2-cyanophenyl, 4-cyanophenyl and 3-cyano-4-fluorophenyl.

In one embodiment, B is represented by Ring B, where Ring B is Ar$^1$, wherein Ar$^1$ is phenyl optionally substituted with one or more substituents independently selected from halogen, CF$_3$, CF$_3$O—, (1-4C)alkoxy, hydroxy(1-4C)alkyl and (1-6C)alkyl. Examples include phenyl, fluorophenyl, difluorophenyl, trifluorophenyl, chlorophenyl, trifluoromethylphenyl, and methoxyphenyl. Particular examples of Ring B when represented by Ar$^1$ include phenyl, 2-fluorophenyl, 3-fluorophenyl, 4-fluorophenyl, 3,4-difluorophenyl, 3,5-difluorophenyl, 2,4-difluorophenyl, 2,5-difluorophenyl, 3,4,5-trifluorophenyl, 2-chlorophenyl, 3-chlorophenyl, 4-chlorophenyl, 3-trifluoromethylphenyl and 3-methoxyphenyl.

In one embodiment, B is represented by Ring B, where Ring B is Ar$^1$, wherein Ar$^1$ is phenyl optionally substituted with one or more halogens.

In one embodiment, B is represented by Ring B, where Ring B is Ar$^1$ as defined for Formula I and Y is a bond.

In one embodiment, B is represented by Ring B, where Ring B is Ar$^1$ as defined for Formula I and Y is —O—. Particular examples include —Y—B groups having the structures:

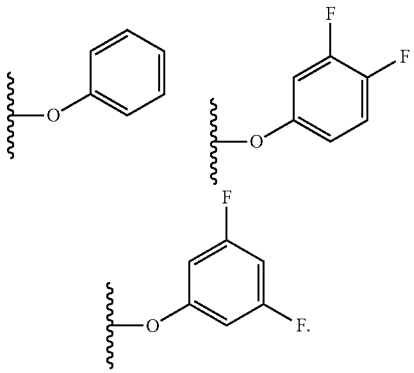

In one embodiment, B is represented by Ring B, where Ring B is Ar$^1$ as defined for Formula I and Y is —OCH$_2$—. A particular example includes a —Y—B group having the structure:

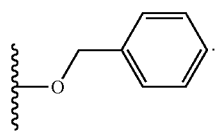 [SMILES: *OCc1ccccc1]

In one embodiment, B is represented by Ring B, where Ring B is hetAr$^1$, and hetAr$^1$ is a 5-6 membered heteroaryl having 1-3 ring heteroatoms independently selected from N, S and O, and is optionally substituted with 1-2 groups independently selected from (1-6C)alkyl, halogen, OH, CF$_3$, NH$_2$ and hydroxy(1-2C)alkyl. In one embodiment, Ring B is hetAr$^1$, wherein hetAr$^1$ is a 5-6 membered heteroaryl having 1-2 ring heteroatoms independently selected from N, S and O, and optionally substituted with 1-2 groups independently selected from (1-6C)alkyl, halogen, OH, CF$_3$, NH$_2$ and hydroxy(1-2C)alkyl. Examples of Ring B include pyridyl, thiophenyl, thiazolyl, oxazolyl, and isoxazolyl rings optionally substituted with 1-2 groups independently selected from (1-6C)alkyl, halogen, OH, CF$_3$, NH$_2$ and hydroxy(1-2C) alkyl. In one embodiment ring B is a pyridyl, thiophenyl, thiazolyl, oxazolyl, or isoxazolyl ring optionally substituted with 1-2 groups independently selected from halogen and (1-6C)alkyl.

Examples of Ring B when represented by hetAr$^1$ include pyrid-4-yl, pyrid-3-yl, pyrid-2-yl, 5-fluoropyrid-3-yl, thien-2-yl, thiazol-2-yl, 2,4-dimethylthiazol-5-yl, oxazol-5-yl, isoxazol-5-yl, thien-2-yl, 5-chloropyrid-3-yl, 5-fluoropyrid-2-yl, 3-fluoropyrid-4-yl, 1-methylpyrazol-4-yl having the structures:

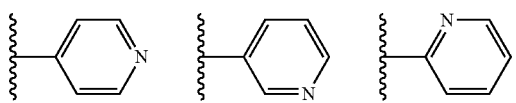

-continued

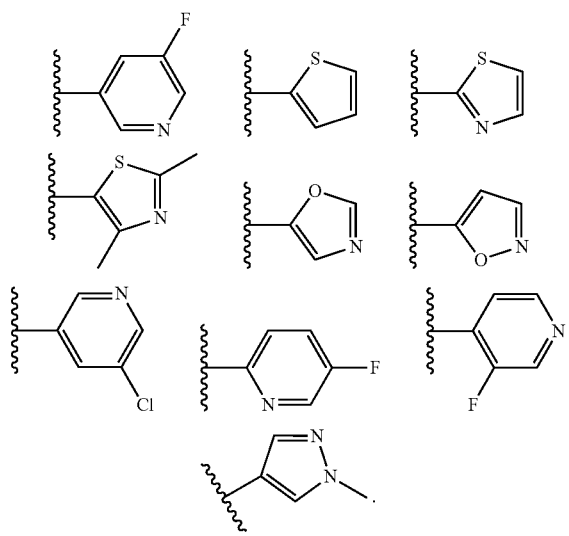

In certain embodiments, examples of Ring B when represented by hetAr¹ include pyrid-4-yl, pyrid-3-yl, pyrid-2-yl, 5-fluoropyrid-3-yl, thien-2-yl, thiazol-2-yl, 2,4-dimethylthiazol-5-yl, oxazol-5-yl and isoxazol-5-yl having the structures:

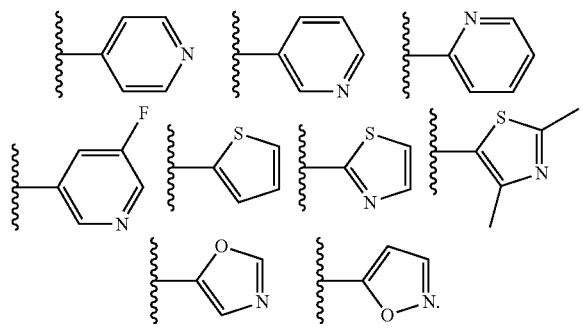

In one embodiment ring B is a pyridyl ring optionally substituted with 1-2 groups independently selected from (1-6C)alkyl and halogen.

In one embodiment, B is represented by Ring B, where Ring B is hetAr¹ as defined for Formula I and Y is a bond.

In one embodiment, B is represented by Ring B, where Ring B is hetAr¹ as defined for Formula I and Y is —O—. A particular example of a —Y—B group is the structure:

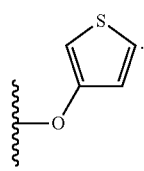 [SMILES: *Oc1ccsc1]

In one embodiment, B is represented by Ring B, where Ring B is hetAr¹ as defined for Formula I and Y is —OCH₂—. A particular example of a —Y—B group is the structure:

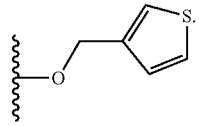 [SMILES: *OCc1ccsc1]

In one embodiment, B is (1-6)alkyl. Examples include methyl, and ethyl, isopropyl.

In one embodiment, B is (1-6C)alkoxy. An example is isopropoxy.

Reference will now be made to Ring C.
In one embodiment, Ring C is formula C-1:

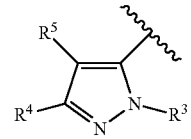

C-1 where $R^3$, $R^4$ and $R^5$ are as defined for Formula I.

In one embodiment, $R^3$ is H.

In one embodiment, $R^3$ is (1-6C)alkyl. Examples of $R^3$ include methyl or ethyl.

In one embodiment, $R^3$ is hydroxy(1-6C)alkyl. An example of $R^3$ is 2-hydroxyethyl.

In one embodiment, $R^3$ is $Ar^2$, where $Ar^2$ is phenyl optionally substituted with one or more groups independently selected from halogen, (1-6C)alkyl and hydroxymethyl. Examples include phenyl, fluorophenyl, methylphenyl and hydroxymethylphenyl.

Examples of $R^3$ when represented by $Ar^2$ include phenyl, 2-fluorophenyl, 3-fluorophenyl, 4-fluorophenyl, 2-methylphenyl, 3-methylphenyl, 4-methylphenyl, 3-(hydroxymethyl)phenyl, 3-chlorophenyl, 3-chloro-4-fluorophenyl and 3-chloro-2-fluorophenyl. Particular examples of $R^3$ when represented by $Ar^2$ include phenyl, 2-fluorophenyl, 3-fluorophenyl, 4-fluorophenyl, 2-methylphenyl, 3-methylphenyl, 4-methylphenyl and 3-(hydroxymethyl)phenyl.

In one embodiment, $R^3$ is hetCyc¹, where hetCyc¹ is a 5-6-membered saturated or partially unsaturated heterocyclic ring having 1-2 ring heteroatoms independently selected from N and O. In one embodiment, $R^3$ is a pyrrolidinyl, tetrahydrofuranyl, imidazolidinyl, piperidinyl, piperazinyl, tetrahydropyranyl, or morpholinyl ring. An example of $R^3$ is tetrahydro-2H-pyran-4-yl.

In one embodiment, $R^3$ is (3-7C)cycloalkyl. In one embodiment $R^3$ is cyclohexyl.

In one embodiment, $R^3$ is hetAr², where hetAr² is 5-6 membered heteroaryl ring having 1-3 ring heteroatoms independently selected from N, O and S and optionally substituted with one or more substituents independently selected from (1-6C)alkyl and halogen. In one embodiment, $R^3$ is a thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl optionally substituted with one or more substituents independently selected from (1-6C)alkyl and halogen. In one embodiment, $R^3$ is pyrazolyl, pyridyl or pyridazinyl optionally substituted with one or more groups independently selected from (1-6C) alkyl and halogen. In one embodiment, $R^3$ is pyrazolyl, pyridyl or pyridazinyl optionally substituted with (1-6C) alkyl or halogen. Examples of $R^3$ when represented by hetAr² include 1-methyl-1H-pyrazol-4-yl, pyrid-2-yl, pyrid-3-yl, pyrid-4-yl, pyridazinyl and 3-chloropyrid-5-yl.

In one embodiment, R³ is hetAr², where hetAr² is a 5-6 membered heteroaryl ring having 1-3 ring heteroatoms independently selected from N, O and S and optionally substituted with (1-6C)alkyl. In one embodiment, R³ is a thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl optionally substituted with (1-6C)alkyl. In one embodiment, R³ is pyrazolyl, pyridyl or pyridazinyl optionally substituted with (1-6C)alkyl. Examples of R³ include 1-methyl-1H-pyrazol-4-yl, pyrid-2-yl, pyrid-3-yl, pyrid-4-yl, and pyridazinyl.

In one embodiment, R³ is selected from H, Ar², hetAr² and (1-6C)alkyl.

In one embodiment, R³ is selected from H, Ar² and (1-6C)alkyl.

In one embodiment, R³ is selected from Ar² and (1-6C)alkyl.

In one embodiment, R³ is selected from Ar², hetAr² and (1-6C)alkyl.

In one embodiment, R⁴ is H.

In one embodiment, R⁴ is OH.

In one embodiment, R⁴ is (1-6C)alkyl. Examples of R⁴ include methyl, ethyl, isopropyl and tert-butyl.

In one embodiment, R⁴ is monofluoro(1-6C)alkyl, difluoro(1-6C)alkyl, trifluoro(1-6C)alkyl, tetrafluoro(2-6C)alkyl or pentafluoro(2-6C)alkyl. Examples of R⁴ include fluoromethyl, 2-fluoroethyl, difluoromethyl and 2,2-difluoroethyl, trifluoromethyl, 2,2,2-trifluoroethyl, 3,3,3-trifluoropropyl, 2,2,3,3-tetrafluoropropyl and 2,2,3,3,3-pentafluoropropyl In one embodiment, R⁴ is trifluoro(1-6C)alkyl. An example of R⁴ includes CF₃.

In one embodiment, R⁴ is cyano(1-6C)alkyl. An example of R⁴ includes cyanomethyl and 2-cyanopropan-2-yl.

In one embodiment, R⁴ is hydroxy(1-6C)alkyl. Examples of R⁴ include hydroxymethyl, 2-hydroxyethyl, 2-hydroxypropyl, 2-hydroxy-2-methylpropyl and 1-hydroxy-2-methylpropan-2-yl.

In one embodiment, R⁴ is dihydroxy(2-6C)alkyl. An example of R⁴ includes 2,3-dihydroxypropyl.

In one embodiment, R⁴ is (1-3C alkoxy)(1-6C)alkyl. Examples of R⁴ include methoxymethyl, 2-methoxyethyl and 3-methoxypropyl.

In one embodiment, R⁴ is amino(1-6C)alkyl. Examples of R⁴ include aminomethyl, 2-aminoethyl and 3-aminopropyl.

In one embodiment, R⁴ is aminocarbonyl(1-6C)alkyl. Examples of R⁴ include aminocarbonylmethyl and 2-(aminocarbonyl)ethyl.

In one embodiment, R⁴ is (1-3C)alkylsulfonamido(1-6C)alkyl. Examples include CH₃SO₂NHCH₂— and CH₃SO₂NHCH₂CH₂—.

In one embodiment, R⁴ is hydroxycarbonyl(1-6C)alkyl. Examples include HOC(=O)CH₂— and HOC(=O)CH₂CH₂—.

In one embodiment, R⁴ is hetAr³(1-6C)alkyl, where hetAr³ is a 5-membered heteroaryl ring having 1-3 ring atoms independently selected from N, S and O and optionally substituted with (1-6C)alkyl. In one embodiment, hetAr³ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. Examples of R⁴ when represented by hetAr³(1-6C)alkyl include (1-methyl-1H-1,2,4-triazol-3-yl)methyl and (5-methyl-1,3,4-oxadiazol-2-yl)methyl.

In one embodiment, R⁴ is Ar³(1-6C)alkyl, where phenyl optionally substituted with (1-4C)alkoxy or hydroxy(1-4C)alkyl. In one embodiment, Ar³ is phenyl or 4-methoxyphenyl. Examples of R⁴ when represented by Ar³(1-6C) alkyl include benzyl and 4-methoxybenzyl.

In one embodiment, R⁴ is (1-6C)alkoxy. Examples include methoxy and ethoxy.

In one embodiment, R⁴ is monofluoro(1-6C)alkoxy, difluoro(1-6C)alkoxy trifluoro(1-6C)alkoxy, tetrafluoro(2-6C)alkoxy or pentafluoro(2-6C)alkoxy. Examples of R⁴ include fluoromethoxy, 2-fluoroethoxy, 2,2-difluoromethoxy, trifluoromethoxy, 2,2,2-trifluoroethoxy and 2,2-difluoroethoxy. In one embodiment, R⁴ is 2-fluoroethoxy.

In one embodiment, R⁴ is cyano(1-6C)alkoxy. An example of R⁴ includes cyanomethoxy and 2-cyanoethoxy.

In one embodiment, R⁴ is hydroxy(1-6C)alkoxy. Examples of R⁴ include 2-hydroxy-2-methylpropoxy, 2-hydroxyethoxy, 2-hydroxypropoxy, 2-hydroxy-2-methylpropoxy and 2-hydroxybutoxy.

In one embodiment, R⁴ is dihydroxy(2-6C)alkoxy. Examples of R⁴ include 2,3-dihydroxypropoxy and 3-hydroxy-2-(hydroxymethyl)propoxy.

In one embodiment, R⁴ is amino(2-6C)alkoxy. An example is H₂NCH₂CH₂O—.

In one embodiment, R⁴ is aminocarbonyl(1-6C)alkoxy. Examples include H₂NC(=O)CH₂O— and H₂NC(=O)CH₂CH₂O—.

In one embodiment, R⁴ is hetCyc²(1-6C)alkoxy, where hetCyc² is a 4-6 membered heterocyclic ring having 1-2 ring heteroatoms independently selected from N and O, wherein hetCyc² is optionally substituted with 1-2 groups independently selected from (1-6C)alkyl, (1-4C alkoxy)carbonyl, and (1-6C)acyl. Examples of hetCyc² include oxetaynyl, tetrahydrofuranyl, tetrahydropyranyl, azetidinyl, pyrrolidinyl, piperidinyl, piperazinyl, morpholinyl, and 1,3-dioxolanyl rings optionally substituted with 1-2 groups independently selected from (1-6C)alkyl, (1-4C alkoxy)carbonyl and (1-6C)acyl. Examples of R⁴ when represented by hetCyc²(1-6C)alkoxy include oxetan-2-ylmethoxy, 2-(oxetan-2-yl)propoxy, (2,2-dimethyl-1,3-dioxolan-4-yl)methoxy, (1,3-dioxolan-4-yl)methoxy, 2-morpholinoethoxy, piperazinylethyoxy and piperidinylethoxy groups optionally substituted with 1-2 groups independently selected from (1-6C) alkyl, (1-4C alkoxy)carbonyl and (1-6C)acyl. Particular examples include the structures:

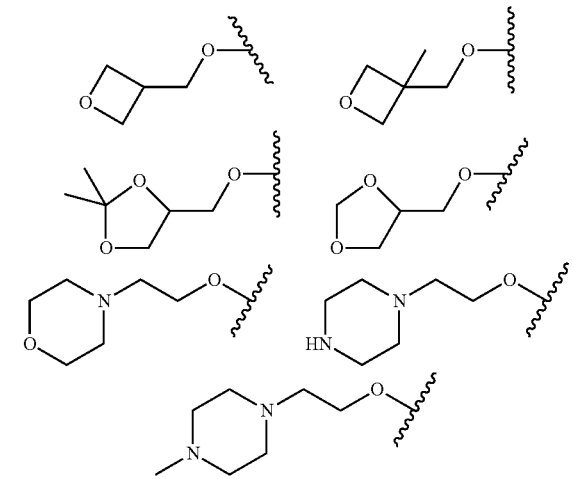

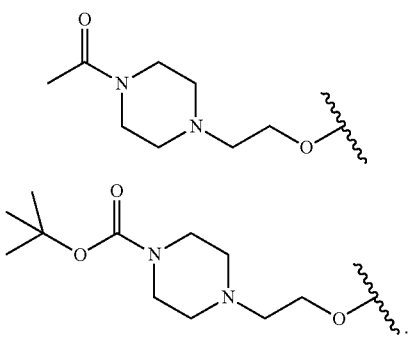

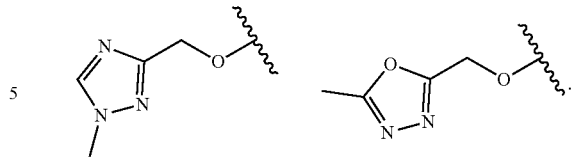

In one embodiment, R⁴ is Ar³(1-6C)alkoxy, where Ar³ is phenyl optionally substituted with (1-4C)alkoxy. Examples include phenylmethoxy and (4-methoxyphenyl)methoxy having the structures:

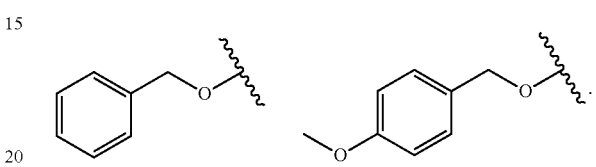

In one embodiment, R⁴ is (1-4C alkoxy)(1-6C)alkoxy. Examples include (2-methoxy)ethoxy having the structure:

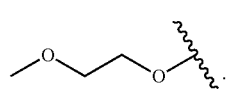

In one embodiment, R⁴ is (1-3Calkylsulfonyl)(1-6C)alkoxy. Examples include (2-methyl sulfonyl)ethoxy having the structure:

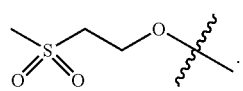 [SMILES: *OCCS(C)(=O)=O]

In one embodiment, R⁴ is (3-6C)cycloalkyl optionally substituted with F, OH, (1-6C alkyl), (1-6C)alkoxy, or (1-3C alkoxy)(1-6C)alkyl. Examples include cyclopropyl, cyclobutyl, cyclopentyl, cyclohexyl, 2-hydroxycyclobutyl. In one embodiment, R⁴ is cyclopropyl or 2-hydroxycyclobutyl. In one embodiment, R⁴ is cyclopropyl.

In one embodiment, R⁴ is (3-6C)cycloalkyl. Examples include cyclopropyl, cyclobutyl, cyclopentyl, cyclohexyl, 2-hydroxycyclobutyl. In one embodiment, R⁴ is cyclopropyl.

In one embodiment, R⁴ is hetAr⁴, where hetAr⁴ is a 5-6 membered heteroaryl ring having 1-3 ring heteroatoms independently selected from N, S and O and optionally substituted with 1-2 substituents independently selected from (1-6C)alkyl, halogen, CN, hydroxy(1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy)(1-3C) trifluoroalkyl, and methoxybenzyl; or a 9-10 membered bicyclic heteroaryl having 1-3 ring nitrogen atoms.

Examples include pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, 1,2,4-oxadiazolyl and imidazo[1,2-a]pyridinyl rings optionally substituted with 1-2 substituents independently selected from (1-6C)alkyl, hydroxy(1-6C)alkyl, trifluoro(1-6C)alkyl, (3-6C)cycloalkyl, In one embodiment, R⁴ is hetCyc²(1-6C)alkoxy, where hetCyc² is a 4-6 membered heterocyclic ring having 1-2 ring heteroatoms independently selected from N and O, wherein hetCyc² is optionally substituted with 1-2 groups independently selected from (1-6C)alky. Examples of heterocyclic rings include oxetaynyl, tetrahydrofuranyl, tetrahydropyranyl, azetidinyl, pyrrolidinyl, piperidinyl, piperazinyl, morpholinyl, and 1,3-dioxolanyl rings optionally substituted with 1-2 groups independently selected from (1-6C)alkyl. Examples of R⁴ when represented by hetCyc²(1-6C)alkoxy include oxetan-2-ylmethoxy, 2-(oxetan-2-yl)propoxy, (2,2-dimethyl-1,3-dioxolan-4-yl)methoxy, (1,3-dioxolan-4-yl)methoxy and 2-morpholinoethoxy, piperazinylethyoxy rings optionally substituted with (1-6C)alkyl, such as:

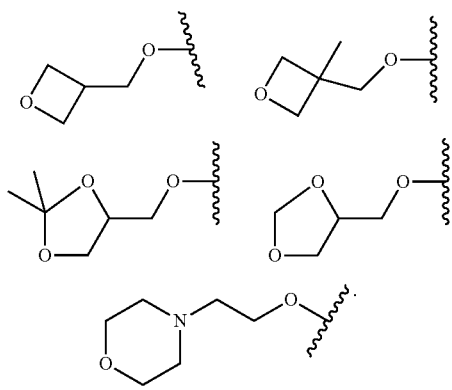

In one embodiment, R⁴ when represented by hetCyc²(1-6C)alkoxy is selected from oxetan-2-ylmethoxy, 2-(oxetan-2-yl)propoxy, (2,2-dimethyl-1,3-dioxolan-4-yl)methoxy, (1,3-dioxolan-4-yl)methoxy and 2-morpholinoethoxy.

In one embodiment, R⁴ is hetAr³(1-6C)alkoxy, where hetAr³ is a 5-membered heteroaryl ring having 1-3 ring atoms independently selected from N, S and O and optionally substituted with (1-6C)alkyl. In one embodiment, hetAr³ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. In one embodiment, hetAr³ is triazolyl or oxadiazolyl ring optionally substituted with a (1-6C)alkyl group such as a methyl group. Examples of R⁴ when represented by hetAr³(1-6C)alkoxy include (1-methyl-1H-1,2,4-triazol-3-yl)methoxy and (5-methyl-1,3,4-oxadiazol-2-yl)methoxy, which can be represented by the structures:

(3-6C cycloalkyl)CH$_2$—, (3-6C cycloalkyl)C(=O)—, (1-3C alkoxy)(1-6C)alkyl, (1-6C)alkoxy, (1-6C)alkylsulfonyl, NH$_2$, (1-6C alkyl)amino, di(1-6C alkyl)amino, (1-3C trifluoroalkoxy)(1-3C)trifluoroalkyl, and methoxybenzyl.

In one embodiment, R$^4$ is hetAr$^4$, where hetAr$^4$ is a pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, 1,2,4-oxadiazolyl or imidazo[1,2-a]pyridinyl ring optionally substituted with 1-2 substituents independently selected from fluoro, methyl, ethyl, isopropyl, cyclopropylmethyl, cyclopropyl, trifluoromethyl, 2,2,2-trifluoroethyl, methoxy, H$_2$N—, (CH$_3$)$_2$N—, 2-hydroxyethyl, 2-methoxyethyl, 1-(2,2,2-trifluoroethoxy)-2,2,2-trifluoroethyl, cyclopropylcarbonyl, methylsulfonyl and 4-methoxybenzyl.

In one embodiment, examples of R$^4$ when represented by hetAr$^4$ include the structures:

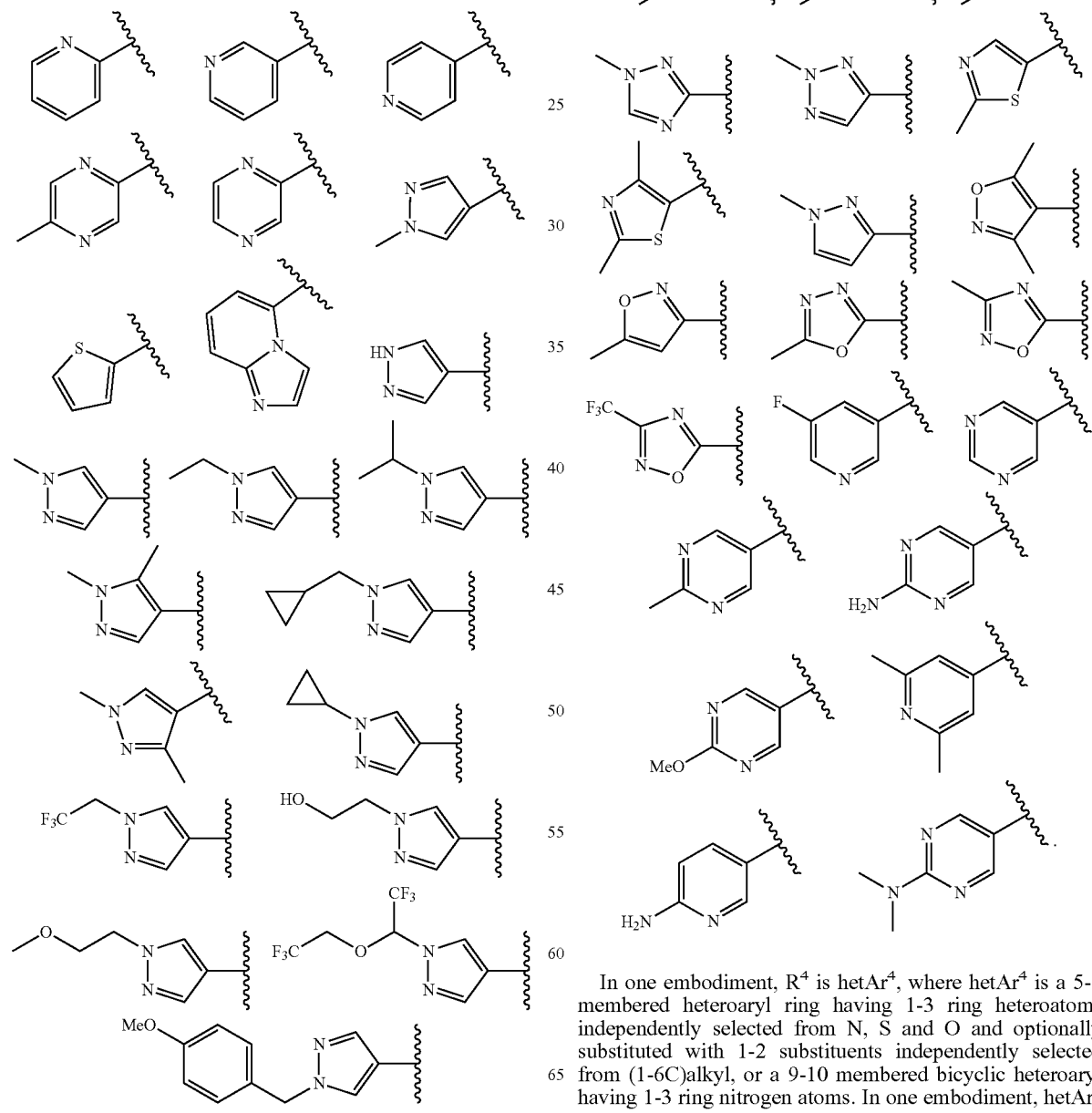

In one embodiment, R$^4$ is hetAr$^4$, where hetAr$^4$ is a 5-6 membered heteroaryl ring having 1-3 ring heteroatoms independently selected from N, S and O and optionally substituted with 1-2 substituents independently selected from (1-6C)alkyl, or a 9-10 membered bicyclic heteroaryl having 1-3 ring nitrogen atoms. In one embodiment, hetAr$^4$ is a 5-6 membered heteroaryl ring having 1-2 ring heteroatoms independently selected from N and S and optionally substituted with 1-2 substituents independently selected from (1-6C)alkyl, or a 9-membered bicyclic heteroaryl having 1-2 ring nitrogen atoms. Examples include pyridyl, pyridazinyl, pyrazolyl, thienyl and imidazo[1,2-a]pyridinyl rings optionally substituted with 1-2 substituents independently selected from (1-6C)alkyl.

In one embodiment, examples of $R^4$ when represented by hetAr$^4$ include pyridn-2-yl, pyridin-3-yl, pyridine-4-yl, 5-methylpyridazin-2-yl, pyridazin-2-yl, 1-methylpyrazol-4-yl, thien-2-yl and imidazo[1,2-a]pyridine-5-yl having the structures:

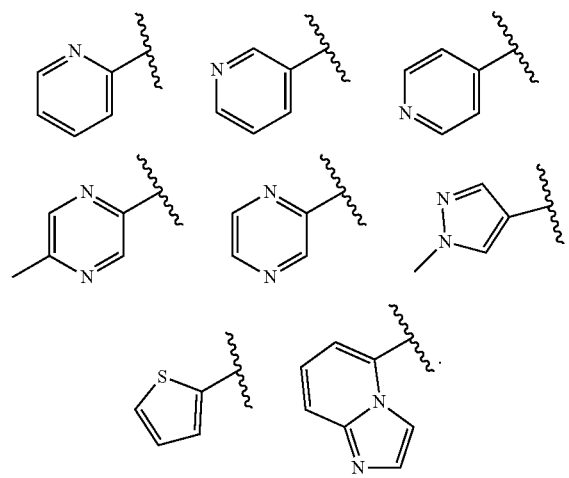

In one embodiment, $R^4$ is Ar$^4$, where Ar$^4$ is phenyl optionally substituted with one or more groups independently selected from (1-6C)alkyl, halogen, CN, CF$_3$, CF$_3$O—, (1-6C)alkoxy, (1-6Calkyl)OC(=O)—, aminocarbonyl, (1-6C)alkylthio, hydroxy(1-6C)alkyl, (1-6C alkyl) SO$_2$—, HOC(=O)— and (1-3C alkoxy)(1-3C alkyl)OC (=O)—. Examples include phenyl optionally substituted with one or more groups independently selected from methyl, F, Cl, CN, methoxy, CH$_3$OC(=O)—, aminocarbonyl, methylaminocarbonyl, dimethylaminocarbonyl, methylthio, hydroxymethyl, CH$_3$SO$_2$—, HOC(=O)— and CH$_3$OCH$_2$CH$_2$OC(=O)—. In certain embodiments, $R^4$ is phenyl optionally substituted with one or two of said substituents. Particular examples include the structures:

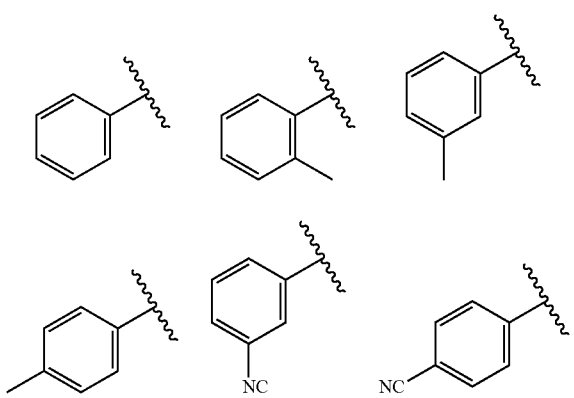

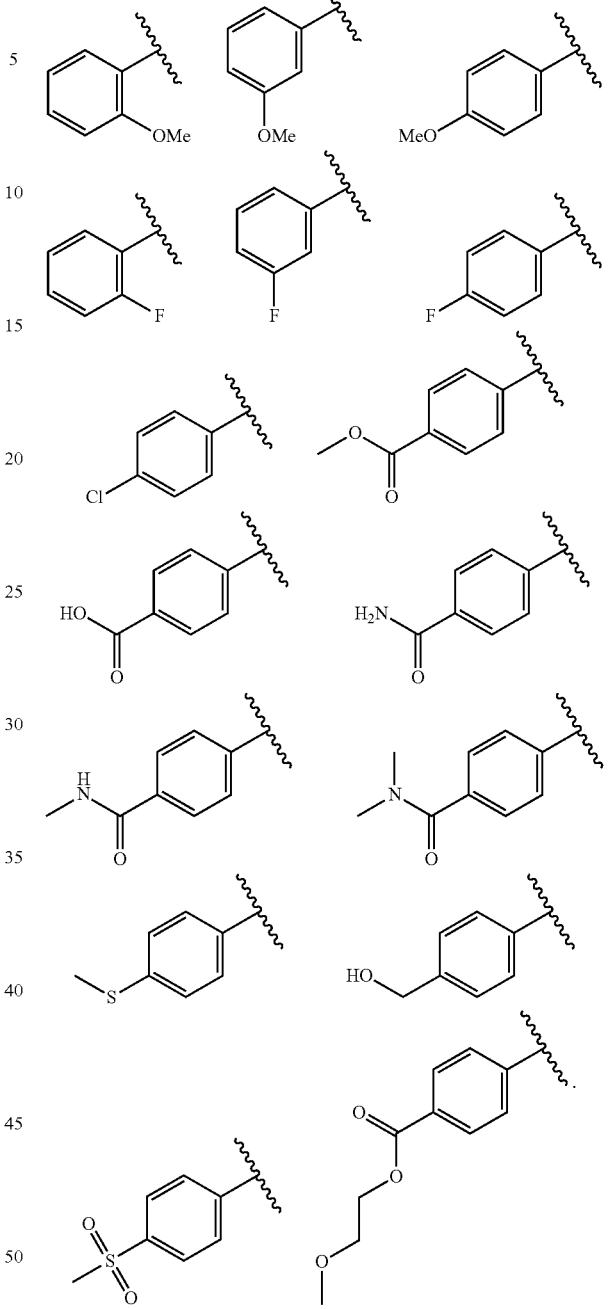

In one embodiment, $R^4$ is hetCyc$^2$(O)CH$_2$, where hetCyc$^2$ is a 4-6 membered heterocyclic ring having 1-2 ring heteroatoms independently selected from N and O, wherein hetCyc$^2$ is optionally substituted with 1-2 groups independently selected from (1-6C)alkyl, (1-4C alkoxy)carbonyl, and (1-6C)acyl. Examples of hetCyc$^2$ include oxetaynyl, tetrahydrofuranyl, tetrahydropyranyl, azetidinyl, pyrrolidinyl, piperidinyl, piperazinyl, morpholinyl, and 1,3-dioxolanyl rings optionally substituted with 1-2 groups independently selected from (1-6C)alkyl, (1-4C alkoxy)carbonyl and (1-6C)acyl. Examples of $R^4$ when represented by hetCyc$^2$(1-6C)alkoxy include piperazinylethyoxy and piperidinylethoxy groups optionally substituted with 1-2 groups independently selected from (1-6C)alkyl, (1-4C alkoxy)carbonyl and (1-6C)acyl. Particular examples include the structures:

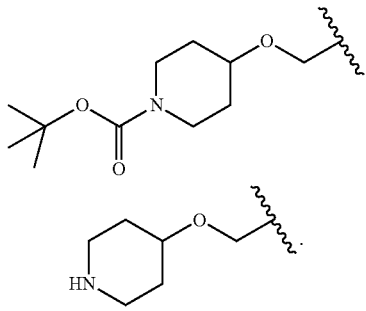

In one embodiment, R⁴ is (1-4C alkoxycarbonyl)(1-6C)alkoxy. Examples include methoxycarbonyl(1-6C)alkoxy and ethylcarbonyl(1-6C)alkoxy. A particular example is ethoxycarbonylmethoxy.

In one embodiment, R⁴ is hydroxycarbonyl(1-6C)alkoxy. A particular example is hydroxycarbonylmethoxy.

In one embodiment, R⁴ is aminocarbonyl(1-6C)alkoxy. Examples include $H_2NC(=O)(1-6C)alkoxy$, $(1-6C\ alkyl)NHC(=O)(1-6C)alkoxy$, and $di(1-6Calkyl)NC(=O)(1-6C)alkoxy$. A particular example is $CH_3CH_2NC(=O)CH_2O-$.

In one embodiment, R⁴ is hetCyc²C(=O)(1-6C)alkoxy, where hetCyc² is a 4-6 membered heterocyclic ring having 1-2 ring heteroatoms independently selected from N and O and optionally substituted with 1-2 groups independently selected from (1-6C)alkyl, (1-4C alkoxy)carbonyl, and (1-6C)acyl. Examples of hetCyc² include oxetaynyl, tetrahydrofuranyl, tetrahydropyranyl, azetidinyl, pyrrolidinyl, piperidinyl, piperazinyl, morpholinyl, and 1,3-dioxolanyl rings optionally substituted with 1-2 groups independently selected from (1-6C)alkyl, (1-4C alkoxy)carbonyl and (1-6C)acyl. In one embodiment, hetCyc² is morpholinyl. A particular example of R⁴ when represented by hetCyc²C(=O)(1-6C)alkoxy is the structure:

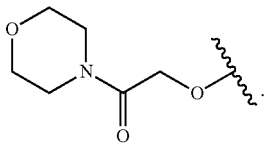 [SMILES: *OCC(=O)N1CCOCC1]

In one embodiment, R⁴ is hydroxy(1-3C alkoxy)(1-6C)alkoxy. A particular example is 2-hydroxy-3-methoxypropoxy, having the structure:

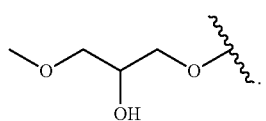 [SMILES: *OCC(O)COC]

In one embodiment, R⁴ is hydroxytrifluoro(1-6C)alkoxy. A particular example is 3,3,3-difluoro-2-hydroxypropoxy having the structure:

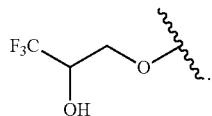 [SMILES: *OCC(O)C(F)(F)F]

In one embodiment, R⁴ is (1-3C)alkylsulfonamido(1-6C)alkoxy. Examples include methanesulfonamido(1-6C)alkoxy. A particular example is 2-methanesulfonamidoethoxy having the structure:

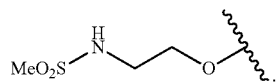

In one embodiment, R⁴ is (1-3C)alkylamido(1-6C)alkoxy. A particular example is 2-(methylamido)ethoxy having the structure:

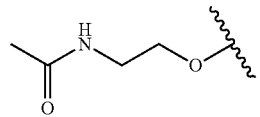 [SMILES: *OCCNC(C)=O]

In one embodiment, R⁴ is di(1-3C alkyl)aminocarboxy. A particular example is dimethylaminocarboxy having the structure:

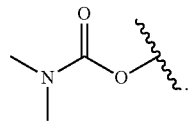

In one embodiment, R⁴ is hetCyc²C(=O)O—, where hetCyc² is a 4-6 membered heterocyclic ring having 1-2 ring heteroatoms independently selected from N and O and optionally substituted with 1-2 groups independently selected from (1-6C)alkyl, (1-4C alkoxy)carbonyl and (1-6C)acyl. Examples of hetCyc² include oxetaynyl, tetrahydrofuranyl, tetrahydropyranyl, azetidinyl, pyrrolidinyl, piperidinyl, piperazinyl, morpholinyl, and 1,3-dioxolanyl rings optionally substituted with 1-2 groups independently selected from (1-6C)alkyl, (1-4C alkoxy)carbonyl and (1-6C)acyl. In one embodiment, hetCyc² is morpholinyl. A particular example of R⁴ when represented by hetCyc²C(=O)O— is the structure:

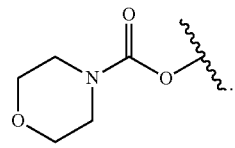 [SMILES: *OC(=O)N1CCOCC1]

In one embodiment, R⁴ is hydroxydifluoro(1-6C)alkyl. An example includes 2,2-difluro-2-hydroxyethyl.

In one embodiment, R⁴ is (1-4C alkylcarboxy)(1-6C)alkyl. Examples include methylcarboxy(1-6C)alkyl. A particular example is 2-(methylcarboxy)ethyl.

In one embodiment, R⁴ is (1-6C)alkoxycarbonyl. Examples include methoxycarbonyl and ethoxycarbonyl.

In one embodiment, R⁴ is hydroxycarbonyl.

In one embodiment, R⁴ is aminocarbonyl, that is, a RR'NCO— radical where R and R' are independently hydrogen or (1-6C)alkyl as defined herein. Examples include aminocarbonyl, methylaminocarbonyl, dimethylaminocarbonyl, ethylcarbonyl and isopropylaminocarbonyl.

In one embodiment, R⁴ is (1-3C alkoxy)aminocarbonyl. An example includes methoxyaminocarbonyl.

In one embodiment, R⁴ is hetCyc³, where is a 4-7 membered heterocycle having 1-2 ring heteroatoms independently selected from N and O and optionally substituted with one or more substituents independently selected from F, CN, CF₃, (1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl. In one embodiment, hetCyc³ is tetrahydropyranyl, piperidinyl, pyrrolidinyl or azetidinyl optionally substituted with one or more substituents independently selected from F, CN, CF₃, (1-6C)alkyl, hydroxy(1-6C)alkyl, (1-3C alkoxy)(1-6C)alkyl, (1-6C) acyl-, (1-6C)alkylsulfonyl, trifluoromethylsulfonyl and (1-4C alkoxy)carbonyl. In one embodiment, hetCyc³ is optionally substituted with one or two of said substituents. In one embodiment, hetCyc³ is tetrahydropyranyl, piperidinyl, pyrrolidinyl or azetidinyl optionally substituted with CN, Me, CH₃C(=O)—, MeSO₂—, CF₃SO₂— or (CH₃)₃COC(=O)—. Particular examples of R⁴ when represented by hetCyc³ include the structures:

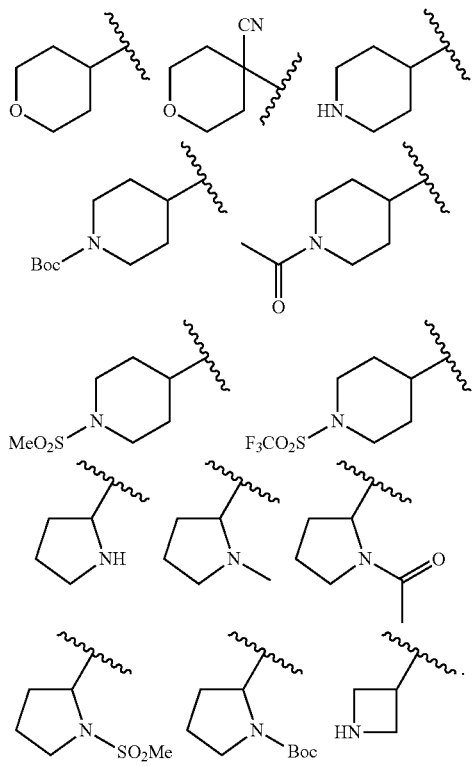

In one embodiment, R⁴ is halogen. In one embodiment, R⁴ is Br.

In one embodiment, R⁴ is CN.

In one embodiment, R⁴ is trifluoromethylsulfonyl.

In one embodiment, R⁴ is N-(1-3C alkyl)pyridinonyl. Examples include N-(1-3C alkyl) substituted pyridin-2(1H)-on-4-yl and N-(1-3C alkyl) substituted pyridin-2(1H)-on-5-yl groups. Particular examples include the structures:

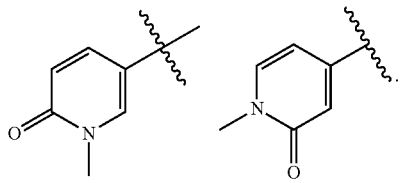

In one embodiment, R⁴ is N-(1-3C trifluoroalkyl)pyridinonyl. Examples include N-(1-3C trifluoroalkyl)-substituted pyridin-2(1H)-on-4-yl and N-(1-3C trifluoroalkyl)-substituted pyridin-2(1H)-on-5-yl groups. A particular example includes the structure:

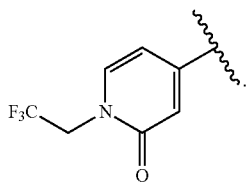 [SMILES: *c1ccn(CC(F)(F)F)c(=O)c1]

In one embodiment, R⁴ is (1-4C alkylsiloxy)(1-6C) alkoxy. Examples include tert-butyl siloxy(1-6C)alkoxy groups. A particular example is 2-(tert-butylsiloxy)propoxy.

In one embodiment, R⁴ is isoindoline-1,3-dionyl(1-6C) alkoxy. A particular example includes the structure:

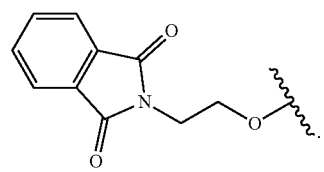 [SMILES: *OCCN1C(=O)c2ccccc2C1=O]

In one embodiment, R⁴ is N-(1-3C alkyl)oxadiazolonyl, Particular examples include the structures:

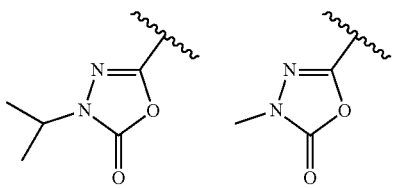

In one embodiment, R⁴ is selected from H, (1-6C)alkyl, trifluoro(1-6C)alkyl, hydroxy(1-6C)alkyl, cyano(1-6C) alkyl, (1-3C alkoxy)(1-6C)alkyl, (1-6C)alkoxy, monofluoro (1-6C)alkoxy, cyano(1-6C)alkoxy, hydroxy(1-6C)alkoxy, dihydroxy(2-6C)alkoxy, hetCyc²(1-6C)alkoxy, Ar³(1-6C) alkoxy, (1-4C alkoxy)(1-6C)alkoxy, (1-3C alkylsulfonyl)(1-6C)alkoxy, (3-6C)cycloalkyl [optionally substituted with F, (1-6C alkyl), (1-6C) alkoxy, or (1-3C alkoxy)(1-6C)alkyl], hetAr⁴, Ar⁴, (1-4C alkoxycarbonyl)(1-6C)alkoxy, hydroxycarbonyl(1-6C)alkoxy, aminocarbonyl(1-6C)alkoxy, hetCyc²C(=O)(1-6C)alkoxy, hydroxy(1-3C alkoxy)(1-6C) alkoxy, hydroxytrifluoro(1-6C)alkoxy, (1-3C)alkylsulfonamido(1-6C)alkoxy, (1-3C)alkylamido(1-6C)alkoxy, di(1-3C alkyl)aminocarboxy, hetCyc$^2$C(═O)O—, hydroxydifluoro (1-6C)alkyl, (1-4C alkylcarboxy)(1-6C)alkyl, (1-6C) alkoxy-carbonyl, hydroxycarbonyl, aminocarbonyl, (1-3C alkoxy)aminocarbonyl, hetCyc$^3$, halogen, CN, trifluoromethylsulfonyl, N-(1-3C alkyl)pyridinonyl, N-(1-3C trifluoroalkyl)pyridinonyl, (1-4C alkylsiloxy)(1-6C)alkoxy, isoindoline-1,3-dionyl(1-6C)alkoxy and N-(1-3C alkyl) oxadiazolonyl.

In one embodiment, $R^4$ is selected from H, (1-6C)alkyl, trifluoro(1-6C)alkyl, hydroxy(1-6C)alkyl, cyano(1-6C) alkyl, (1-3C alkoxy)(1-6C)alkyl, (1-6C)alkoxy, monofluoro (1-6C)alkoxy, cyano(1-6C)alkoxy, hydroxy(1-6C)alkoxy, dihydroxy(2-6C)alkoxy, hetCyc$^2$ (1-6C)alkoxy, Ar$^3$(1-6C) alkoxy, (1-4C alkoxy)(1-6C)alkoxy, (1-3C alkylsulfonyl)(1-6C)alkoxy, (3-6C)cycloalkyl, hetAr$^4$ and Ar$^4$.

In one embodiment, $R^4$ is selected from H, (1-6C)alkyl, trifluoro(1-6C)alkyl, hydroxy(1-6C)alkyl, cyano(1-6C) alkyl, (1-3C alkoxy)(1-6C)alkyl, (1-6C)alkoxy, monofluoro (1-6C)alkoxy, cyano(1-6C)alkoxy, hydroxy(1-6C)alkoxy, dihydroxy(2-6C)alkoxy, hetCyc$^2$(1-6C) alkoxy, Ar$^3$(1-6C) alkoxy, (1-4C alkoxy)(1-6C)alkoxy, (1-3C alkylsulfonyl)(1-6C)alkoxy, (3-6C)cycloalkyl, hetAr$^4$ and Ar$^4$.

In one embodiment, $R^4$ is selected from H, (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C) alkoxy, (1-4C alkoxy)(1-6C)alkoxy, (3-6C)cycloalkyl, hetAr$^4$ and Ar$^4$.

In one embodiment, $R^4$ is selected from (1-6C)alkyl, trifluoro(1-6C)alkyl, cyano(1-6C)alkyl, (1-3C alkoxy)(1-6C)alkyl and (3-6C)cycloalkyl.

In one embodiment, $R^4$ is selected from (1-6C)alkoxy, cyano(1-6C)alkoxy, hydroxy(1-6C)alkoxy and (1-4C alkoxy)(1-6C)alkoxy.

In one embodiment, $R^4$ is selected from hetAr$^4$ and Ar$^4$.
In one embodiment, $R^5$ is H.
In one embodiment, $R^5$ is (1-6C)alkyl. Examples include methyl, ethyl, propyl, isopropyl and butyl.

In one embodiment, $R^5$ is monofluoro(1-6C)alkyl, difluoro(1-6C)alkyl, trifluoro(1-6C)alkyl, tetrafluoro(2-6C) alkyl or pentafluoro(2-6C)alkyl. Examples include fluoromethyl, 2-fluoroethyl, difluoromethyl, 2,2-difluoroethyl, 1,3-difluoroprop-2-yl, trifluoromethyl, 2,2,2-trifluoroethyl, 3,3,3-trifluoropropyl, 1,1,2,2-tetrafluoropropane and 2,2,3,3,3-pentafluoropropyl.

In one embodiment, $R^5$ is halogen. In one embodiment, $R^5$ is F. In one embodiment, $R^5$ is Cl. In one embodiment, $R^5$ is Br.

In one embodiment, $R^5$ is CN.
In one embodiment, $R^5$ is (1-4C)alkoxy. Examples include methoxy and ethoxy.

In one embodiment, $R^5$ is hydroxy(1-4C)alkyl. Examples include hydroxymethyl and 3-hydroxypropyl.

In one embodiment, $R^5$ is (1-4C alkyl)OC(═O)—. Examples include CH$_3$CH$_2$OC(═O)—.

In one embodiment, $R^5$ is (1-6C)alkylthio. An example is methylthio (MeS—).

In one embodiment, $R^5$ is phenyl optionally substituted with one or more groups independently selected from halogen, (1-6C)alkyl and (1-6C)alkoxy. In one embodiment, $R^5$ is phenyl optionally substituted with one or more groups independently selected from F, Cl, methyl, ethyl, methoxy and ethoxy. In one embodiment, $R^5$ is phenyl.

In one embodiment, $R^5$ is (3-4C)cycloalkyl. In one embodiment, $R^5$ is cyclopropyl. In one embodiment, $R^5$ is cyclobutyl.

In one embodiment, $R^5$ is amino. In one embodiment, $R^5$ is NH$_2$.

In one embodiment, $R^5$ is aminocarbonyl. In one embodiment, $R^5$ is H$_2$NC(═O)—.

In one embodiment, $R^5$ is trifluoro(1-3C alky)amido. In one embodiment, $R^5$ is CF$_3$C(═O)NH—.

In one embodiment, $R^5$ is selected from H, halogen, CN, (1-6C)alkyl, (1-4C)alkoxy, hydroxy(1-4C)alkyl, or phenyl optionally substituted with one or more groups independently selected from halogen, (1-6C)alkyl and (1-6C)alkoxy.

In one embodiment, $R^5$ is selected from H, halogen, or (1-6C)alkyl.

In one embodiment, $R^5$ is selected from H, methyl, Cl or Br.

In one embodiment of Formula I, $R^4$ is H, OH, (1-6C) alkyl, monofluoro(1-6C)alkyl, difluoro(1-6C)alkyl, trifluoro (1-6C)alkyl, tetrafluoro(2-6C)alkyl, pentafluoro(2-6C)alkyl, cyano(1-6C)alkyl, hydroxy(1-6C)alkyl, dihydroxy(2-6C) alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxyl-carbonyl(1-6C)alkyl, hetAr$^3$(1-6C)alkyl, Ar$^3$(1-6C)alkyl, (1-6C)alkoxy, monofluoro(1-6C)alkoxy, difluoro(1-6C)alkoxy trifluoro(1-6C) alkoxy, tetrafluoro(2-6C)alkoxy, pentafluoro(2-6C)alkoxy cyano(1-6C)alkoxy, hydroxy(1-6C)alkoxy, dihydroxy(2-6C)alkoxy, amino(2-6C)alkoxy, amino-carbonyl(1-6C) alkoxy, hydroxycarbonyl(1-6C)alkoxy, hetCyc$^2$(1-6C) alkoxy, hetAr$^3$(1-6C)alkoxy, Ar$^3$(1-6C)alkoxy, (1-4C alkoxy)(1-6C)alkoxy, (1-3C alkylsulfonyl)(1-6C)alkoxy, (3-6C)cycloalkyl [optionally substituted with F, (1-6C alkyl), (1-6C) alkoxy, or (1-3C alkoxy)(1-6C)alkyl], hetAr$^4$, Ar$^4$, (1-4C alkoxycarbonyl)(1-6C)alkoxy, hydroxycarbonyl (1-6C)alkoxy, aminocarbonyl(1-6C)alkoxy, hetCyc$^2$C(═O) (1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl) aminocarboxy, hetCyc$^2$C(═O)O—, hydroxydifluoro(1-6C) alkyl, (1-4C alkylcarboxy)(1-6C)alkyl, (1-6C)alkoxycarbonyl, hydroxycarbonyl, aminocarbonyl, (1-3C alkoxy)aminocarbonyl, hetCyc$^3$, halogen, CN, trifluoromethylsulfonyl, N-(1-3C alkyl)pyridinonyl, N-(1-3C trifluoroalkyl) pyridinonyl, (1-4C alkylsiloxy)(1-6C)alkoxy, isoindoline-1,3-dionyl(1-6C)alkoxy or N-(1-3C alkyl)oxadiazolonyl; and $R^5$ is H, (1-6C)alkyl, monofluoro(1-6C)alkyl, difluoro(1-6C) alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC (═O)—, (1-6C)alkylthio, phenyl [optionally substituted with one or more groups independently selected from halogen, (1-6C)alkyl and (1-6C)alkoxy], (3-4C)cycloalkyl, amino, aminocarbonyl, or trifluoro(1-3C alky)amido.

In one embodiment of Formula I, $R^4$ is H, OH, (1-6C) alkyl, monofluoro(1-6C)alkyl, difluoro(1-6C)alkyl, trifluoro (1-6C)alkyl, tetrafluoro(2-6C)alkyl, pentafluoro(2-6C)alkyl, cyano(1-6C)alkyl, hydroxy(1-6C)alkyl, dihydroxy(2-6C) alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxyl-carbonyl(1-6C)alkyl, hetAr$^3$(1-6C)alkyl, Ar$^3$(1-6C) alkyl, (1-6C)alkoxy, monofluoro(1-6C)alkoxy, difluoro(1-6C)alkoxy, trifluoro(1-6C) alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, aminocarbonyl(1-6C) alkoxy, hydroxycarbonyl(1-6C)alkoxy, hetCyc$^2$(1-6C) alkoxy, hetAr$^3$(1-6C)alkoxy, Ar$^3$(1-6C)alkoxy, (1-4C alkoxy)(1-6C)alkoxy, (1-3C alkylsulfonyl)(1-6C)alkoxy, (3-6C)cycloalkyl, hetAr$^4$, or Ar$^4$; and $R^5$ is H, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, or phenyl optionally substituted with one or more groups independently selected from halogen, (1-6C)alkyl and (1-6C)alkoxy.

In one embodiment of Formula I, $R^4$ is selected from H, (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C)alkoxy, (1-4C alkoxy)(1-6C)alkoxy, (3-6C) cycloalkyl, hetAr$^4$ and Ar$^4$, and $R^5$ is selected from H, halogen, CN, (1-6C)alkyl, (1-4C)alkoxy, hydroxy(1-4C) alkyl, (1-6C)alkylthio, or phenyl optionally substituted with one or more groups independently selected from halogen, (1-6C)alkyl and (1-6C)alkoxy.

In one embodiment, $R^4$ and $R^5$ together with the atoms to which they are attached form a 5-6 membered saturated, partially unsaturated or unsaturated carbocyclic ring optionally substituted with one or more substituents independently selected from (1-6C)alkyl; or $R^4$ and $R^5$ together with the atoms to which they are attached form a 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6)acyl, (1-6C)alkyl and oxo, and said sulfur ring atom is optionally oxidized to S(=O) or SO$_2$.

In one embodiment, $R^4$ and $R^5$ together with the atoms to which they are attached form a 5-6 membered saturated, partially unsaturated or unsaturated carbocyclic ring optionally substituted with one or more substituents independently selected from (1-6C)alkyl. Examples of Ring C when $R^4$ and $R^5$ together with the atoms to which they are attached form a 5-6 membered saturated or unsaturated carbocyclic ring include the structures:

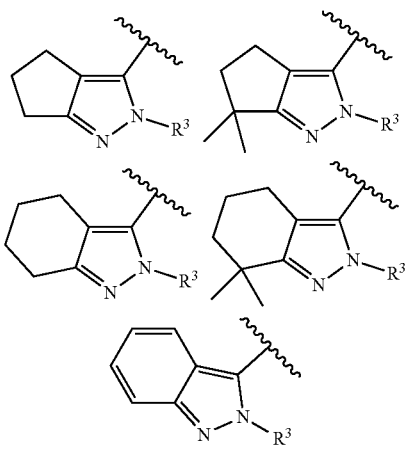

where $R^3$ is as defined for Formula I.

In one embodiment, $R^4$ and $R^5$ together with the atoms to which they are attached form a 5-6 membered saturated carbocyclic ring optionally substituted with one or more substituents independently selected from (1-6C)alkyl, or $R^4$ and $R^5$ together with the atoms to which they are attached form a 5-6 membered saturated heterocyclic ring having a ring heteroatom selected from N, O or S, wherein said ring nitrogen atom is optionally substituted with (1-6C alkyl)C(=O)O— or (1-6)acyl, and said sulfur ring atom is optionally oxidized to S(=O) or SO$_2$.

In one embodiment, $R^4$ and $R^5$ together with the atoms to which they are attached form a 5-6 membered saturated carbocyclic ring optionally substituted with one or more substituents independently selected from (1-6C)alkyl. Examples of Ring C when $R^4$ and $R^5$ together with the atoms to which they are attached form a 5-6 membered saturated carbocyclic ring include the structures:

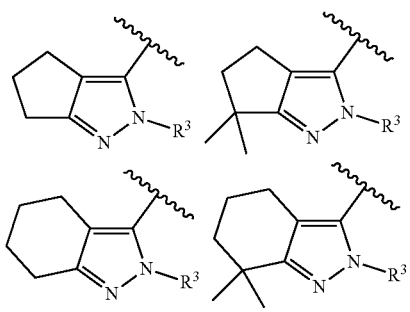

where $R^3$ is as defined for Formula I.

In one embodiment, $R^4$ and $R^5$ together with the atoms to which they are attached form a 5-6 membered saturated, partially unsaturated or unsaturated heterocyclic ring having a ring heteroatom selected from N, O or S, wherein said ring N atom is optionally substituted with (1-6C alkyl)C(=O) O—, (1-6C alkyl)C(=O)—, (1-6C)alkyl or oxo, and said S ring atom is optionally oxidized to S(=O) or SO$_2$. Examples of Ring C when $R^4$ and $R^5$ together with the atoms to which they are attached form a 5-6 membered saturated heterocyclic ring include the structures:

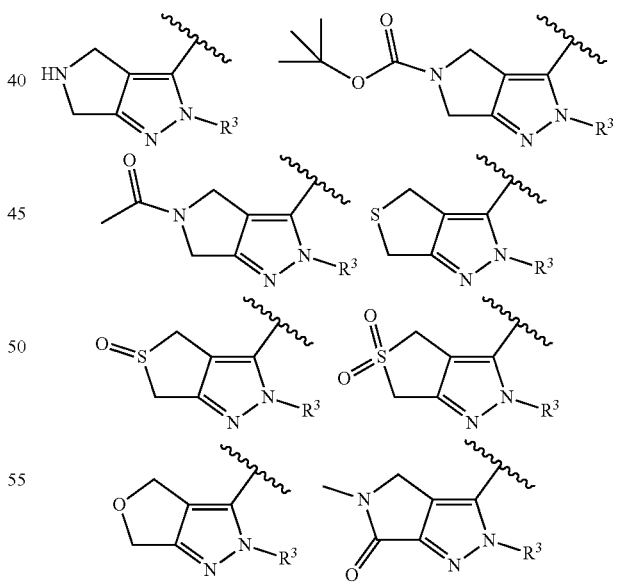

where $R^3$ is as defined for Formula I.

In one embodiment, $R^4$ and $R^5$ together with the atoms to which they are attached form a 5-6 membered saturated heterocyclic ring having a ring heteroatom selected from N, O or S, wherein said ring N atom is optionally substituted with (1-6C alkyl)C(=O)O— or (1-6C alkyl)C(=O)—, and said S ring atom is optionally oxidized to S(=O) or SO$_2$.

Examples of Ring C when $R^4$ and $R^5$ together with the atoms to which they are attached form a 5-6 membered saturated heterocyclic ring include the structures:

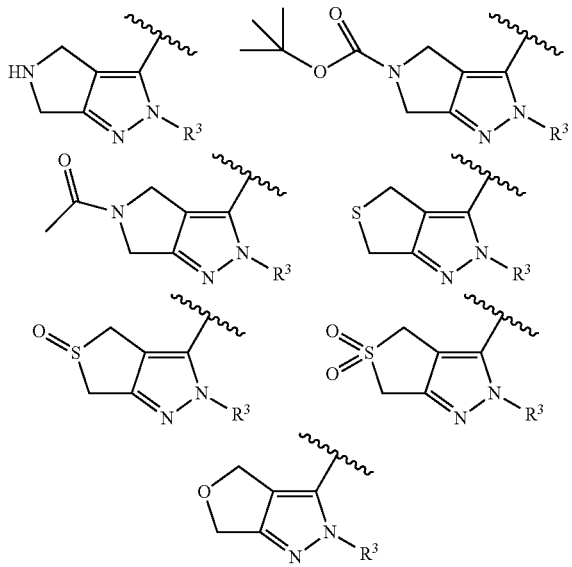

where $R^3$ is as defined for Formula I.

In one embodiment, Ring C is formula C-2

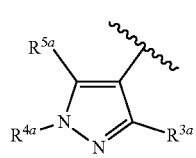

C-2 where $R^{3a}$, $R^{4a}$ and $R^{5a}$ are as defined for Formula I.

In one embodiment, $R^{3a}$ is hydrogen.

In one embodiment, $R^{3a}$ is halogen.

In one embodiment, $R^{3a}$ is (1-6C)alkyl. In one embodiment, $R^{3a}$ is methyl.

In one embodiment, $R^{3a}$ is trifluoro(1-6C)alkyl. In one embodiment, $R^{3a}$ is $CF_3$.

In one embodiment, $R^{3a}$ is (3-6C)cycloalkyl. In one embodiment, $R^{3a}$ is cyclopropyl.

In one embodiment, $R^{3a}$ is phenyl optionally substituted with one or more substituents independently selected from halogen, (1-6C)alkyl and hydroxymethyl. Examples include phenyl, fluorophenyl, methylphenyl and hydroxymethylphenyl, for example include phenyl, 2-fluorophenyl, 3-fluorophenyl, 4-fluorophenyl, 2-methylphenyl, 3-methylphenyl, 4-methylphenyl, 3-(hydroxymethyl)phenyl, 3-chlorophenyl, 3-chloro-4-fluorophenyl and 3-chloro-2-fluorophenyl. In one embedment, $R^{3a}$ is phenyl.

In one embodiment, $R^{3a}$ is a 5-6 membered heteroaryl ring having 1-3 ring heteroatoms independently selected from N, O and S and optionally substituted with one or more groups independently selected from (1-6C)alkyl and halogen. In one embodiment, $R^{3a}$ is a thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl ring optionally substituted with (1-6C)alkyl or halogen. In one embodiment, $R^{3a}$ is pyrazolyl, pyridyl or pyridazinyl optionally substituted with one or more groups independently selected from (1-6C)alkyl and halogen. In one embodiment, $R^{3a}$ is pyrazolyl, pyridyl or pyridazinyl optionally substituted with (1-6C)alkyl or halogen.

In one embodiment, $R^{4a}$ is hydrogen.

In one embodiment, $R^{4a}$ is (1-6C)alkyl. In one embodiment, $R^{4a}$ is methyl, ethyl or isopropyl.

In one embodiment, $R^{4a}$ is trifluoro(1-6C)alkyl. In one embodiment, $R^{4a}$ is 2,2,2-trifluoroethyl.

In one embodiment, $R^{4a}$ is phenyl optionally substituted with one or more groups independently selected from (1-6C)alkyl, halogen, CN, $CF_3$, $CF_3O$—, (1-6C)alkoxy, (1-6Calkyl)OC(=O)—, aminocarbonyl, (1-6C)alkylthio, hydroxy(1-6C)alkyl, (1-6C alkyl)$SO_2$—, HOC(=O)— and (1-3C alkoxy)(1-3C alkyl)OC(=O)—. Examples include phenyl optionally substituted with one or more groups independently selected from methyl, F, Cl, CN, methoxy, $CH_3OC$(=O)—, aminocarbonyl, methylaminocarbonyl, dimethylaminocarbonyl, methylthio, hydroxymethyl, $CH_3SO_2$—, HOC(=O)— and $CH_3OCH_2CH_2OC$(=O)—. In certain embodiments, $R^{4a}$ is phenyl optionally substituted with one or two of said substituents. In one embodiment, $R^{4a}$ is phenyl.

In one embodiment, $R^{4a}$ is a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$— (3-6C cycloalkyl)C(=O)—, (1-3C alkoxy)(1-6C)alkyl, (1-6C)alkoxy, (1-6C)alkylsulfonyl, $NH_2$, (1-6C alkyl)amino, di(1-6C alkyl)amino, (1-3C trifluoroalkoxy)(1-3C)trifluoroalkyl, and methoxybenzyl. Examples include pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, 1,2,4-oxadiazolyl and imidazo[1,2-a]pyridinyl rings optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$— (3-6C cycloalkyl)C(=O)—, (1-3C alkoxy)(1-6C)alkyl, (1-6C)alkoxy, (1-6C)alkylsulfonyl, $NH_2$, (1-6C alkyl)amino, di(1-6C alkyl)amino, (1-3C trifluoroalkoxy)(1-3C)trifluoroalkyl, and methoxybenzyl. In one embodiment, $R^{4a}$ is pyrazinyl.

In one embodiment, $R^{5a}$ is as defined for Formula I.

In one embodiment, $R^{5a}$ is selected from hydrogen, halogen, (1-6C)alkyl and phenyl.

In one embodiment, $R^{5a}$ is hydrogen.

In one embodiment, $R^{5a}$ is halogen.

In one embodiment, $R^{5a}$ is (1-6C)alkyl. In one embodiment, $R^{5a}$ is methyl.

In one embodiment, $R^{5a}$ is phenyl.

In one embodiment, Ring C is formula C-2, in which $R^{3a}$ is (1-6C)alkyl, trifluoro(1-6C)alkyl or phenyl; $R^{4a}$ is (1-6C)alkyl, trifluoro(1-6C)alkyl, phenyl or pyrazinyl; and $R^{5a}$ is hydrogen, (1-6C)alkyl or phenyl.

In one embodiment, Ring C is formula C-3

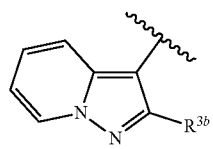

C-3 where $R^{3b}$ is as defined for Formula I.

In one embodiment, $R^{3b}$ is hydrogen.

In one embodiment, $R^{3b}$ is (1-6C)alkyl. In one embodiment, $R^{3b}$ is methyl.

In one embodiment, $R^{3b}$ is trifluoro(1-6C)alkyl. In one embodiment, $R^{3b}$ is $CF_3$.

In one embodiment, $R^{3b}$ is (3-6C)cycloalkyl. In one embodiment, $R^{3b}$ is cyclopropyl.

In one embodiment, $R^{3b}$ is phenyl optionally substituted with one or more substituents independently selected from halogen, (1-6C)alkyl and hydroxymethyl. In one embodiment, $R^{3b}$ is phenyl.

In one embodiment, $R^{3b}$ is a 5-6 membered heteroaryl ring having 1-3 ring heteroatoms independently selected from N, O and S and optionally substituted with one or more groups independently selected from (1-6C)alkyl and halogen. In one embodiment, $R^{3b}$ is a thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl optionally substituted with (1-6C)alkyl or halogen. In one embodiment, $R^{3b}$ is pyrazolyl, pyridyl or pyridazinyl optionally substituted with one or more groups independently selected from (1-6C)alkyl and halogen. In one embodiment, $R^{3b}$ is pyrazolyl, pyridyl or pyridazinyl optionally substituted with (1-6C)alkyl or halogen.

In one embodiment, Ring C is formula C-3 where $R^{3b}$ is hydrogen or phenyl.

In another embodiment of the present invention there is provided a compound according to Formula I, which is designated as Formula I-a, wherein:

X is O;
B is $Ar^1$;
Y is a bond;
Ring C is

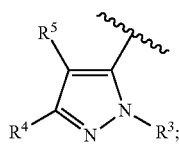

$R^4$ is H, OH, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C) alkylsulfonamido(1-6C)alkyl, sulfamido(1-6C)alkyl, hydroxycarbonyl(1-6C)alkyl, $hetAr^3$(1-6C)alkyl, $Ar^3$(1-6C) alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, aminocarbonyl(1-6C)alkoxy, hydroxycarbonyl (1-6C)lkoxy, $hetCyc^2$(1-6C)alkoxy, $hetAr^3$(1-6C)alkoxy, $Ar^3$(1-6C) alkoxy, (1-4C alkoxy)(1-6C)alkoxy, (1-3C alkylsulfonyl)(1-6C)alkoxy, (3-6C)cycloalkyl, $hetAr^4$, or $Ar^4$;

$R^5$ is H, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, or phenyl optionally substituted with one or more groups independently selected from halogen, (1-6C)alkyl and (1-6C)alkoxy; and $R^a$, $R^b$, $R^c$, $R^d$, $R^1$, $R^2$, $Ar^1$, $R^3$, $hetCyc^2$, $hetAr^3$, $Ar^3$, $hetAr^4$ and $Ar^4$ are as defined for Formula I.

In one embodiment of Formula I-a, $R^a$, $R^b$, $R^c$ and $R^d$ are hydrogen; $R^2$ is hydrogen; and $R^1$, $Ar^1$, $R^3$, $hetCyc^2$, $hetAr^3$, $Ar^3$, $hetAr^4$, and $Ar^4$ are as defined for Formula I.

In one embodiment of Formula I-a, $R^a$, $R^b$, $R^c$ and $R^d$ are hydrogen; $R^2$ is hydrogen; $R^1$ is (1-3C alkoxy)(1-6C)alkyl, difluoro(1-6C)alkyl, or trifluoro(1-6C)alkyl; and $Ar^1$, $R^3$, $hetCyc^2$, $hetAr^3$, $Ar^3$, $hetAr^4$ and $Ar^4$ are as defined for Formula I.

In one embodiment of Formula I-a, $R^a$, $R^b$, $R^c$ and $R^d$ are hydrogen; $R^2$ is hydrogen; $R^1$ is (1-3C alkoxy)(1-6C)alkyl, difluoro(1-6C)alkyl, or trifluoro(1-6C)alkyl; $R^3$ is $Ar^2$, $hetAr^2$ or (1-6C)alkyl; and $Ar^1$, $Ar^2$, $hetAr^2$, $hetCyc^2$, $hetAr^3$, $Ar^3$, $hetAr^4$, and $Ar^4$ are as defined for Formula I.

In one embodiment of Formula I-a, $R^a$, $R^b$, $R^c$ and $R^d$ are hydrogen; $R^2$ is hydrogen; $R^1$ is (1-3C alkoxy)(1-6C)alkyl, difluoro(1-6C)alkyl, or trifluoro(1-6C)alkyl; $R^3$ is $Ar^2$, $hetAr^2$ or (1-6C)alkyl; $R^4$ is H, (1-6C)alkyl, trifluoro(1-6C)alkyl, cyano(1-6C)alkyl, (1-3C alkoxy)(1-6C)alkyl, (1-6C) alkoxy, cyano(1-6C)alkoxy, hydroxy(1-6C)alkoxy, (1-4C alkoxy)(1-6C)alkoxy, (3-6C)cycloalkyl, $hetAr^4$ or $Ar^4$; and $Ar^1$, $Ar^2$, $hetAr^2$, $hetCyc^2$, $hetAr^3$, $Ar^3$, $hetAr^4$, and $Ar^4$ are as defined for Formula I.

In one embodiment of Formula I-a, $R^a$, $R^b$, $R^c$ and $R^d$ are hydrogen; $R^2$ is hydrogen; $R^1$ is (1-3C alkoxy)(1-6C)alkyl, difluoro(1-6C)alkyl, or trifluoro(1-6C)alkyl; $R^3$ is $Ar^2$, $hetAr^2$ or (1-6C)alkyl; $R^4$ is $hetAr^4$ or $Ar^4$; and $Ar^1$, $Ar^2$, $hetAr^2$, $hetCyc^2$, $hetAr^3$, $Ar^3$, $hetAr^4$, and $Ar^4$ are as defined for Formula I.

In one embodiment of Formula I-a, $R^a$, $R^b$, $R^c$ and $R^d$ are hydrogen; $R^2$ is hydrogen; $R^1$ is (1-3C alkoxy)(1-6C)alkyl, difluoro(1-6C)alkyl, or trifluoro(1-6C)alkyl; $R^3$ is $Ar^2$, $hetAr^2$ or (1-6C)alkyl; $R^4$ is H, (1-6C)alkyl, trifluoro(1-6C)alkyl, cyano(1-6C)alkyl, (1-3C alkoxy)(1-6C)alkyl, (1-6C) alkoxy, cyano(1-6C)alkoxy, hydroxy(1-6C)alkoxy, (1-4C alkoxy)(1-6C)alkoxy, (3-6C)cycloalkyl, $hetAr^4$ or $Ar^4$; $R^5$ is H, halogen, CN, (1-6C)alkyl, (1-4C)alkoxy, hydroxy(1-4C) alkyl, or phenyl optionally substituted with one or more groups independently selected from halogen, (1-6C)alkyl and (1-6C)alkoxy; and $Ar^1$, $Ar^2$, $hetAr^2$ $hetCyc^2$, $hetAr^3$, $Ar^3$, $hetAr^4$, and $Ar^4$ are as defined for Formula I.

In one embodiment of Formula I-a, $R^a$, $R^b$, $R^c$ and $R^d$ are hydrogen; $R^2$ is hydrogen; $R^1$ is (1-3C alkoxy)(1-6C)alkyl, difluoro(1-6C)alkyl, or trifluoro(1-6C)alkyl; $R^3$ is $Ar^2$, $hetAr^2$ or (1-6C)alkyl; $R^4$ is H, (1-6C)alkyl, trifluoro(1-6C) alkyl, cyano(1-6C)alkyl, (1-3C alkoxy)(1-6C)alkyl, (1-6C) alkoxy, cyano(1-6C)alkoxy, hydroxy(1-6C)alkoxy, (1-4C alkoxy)(1-6C)alkoxy, (3-6C)cycloalkyl, $hetAr^4$ or $Ar^4$; $R^5$ is H, halogen, or (1-6C)alkyl; and $Ar^1$, $Ar^2$, $hetAr^2$, $hetAr^4$ and $Ar^4$ are as defined for Formula I.

In one embodiment of Formula I-a, $R^a$, $R^b$, $R^c$ and $R^d$ are hydrogen; $R^2$ is hydrogen; $R^1$ is (1-3C alkoxy)(1-6C)alkyl, difluoro(1-6C)alkyl, or trifluoro(1-6C)alkyl; $R^3$ is $Ar^2$, $hetAr^2$ or (1-6C)alkyl; $R^4$ is $hetAr^4$ or $Ar^4$; $R^5$ is H, halogen, or (1-6C)alkyl; and $Ar^1$, $Ar^2$, $hetAr^2$, $hetAr^4$ and $Ar^4$ are as defined for Formula I.

In one embodiment of Formula I-a, $R^4$ is (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C) alkoxy, (1-4C alkoxy)(1-6C)alkoxy, (3-6C)cycloalkyl, $hetAr^4$ or $Ar^4$; and $R^a$, $R^b$, $R^c$, $R^d$, $R^1$, $R^2$, $R^3$, $hetAr^4$ and $Ar^4$ are as defined for Formula I.

In one embodiment of Formula I-a, $R^4$ is (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C) alkoxy, (1-4C alkoxy)(1-6C)alkoxy, (3-6C)cycloalkyl, hetAr⁴ or Ar⁴; R³ is H, (1-6C)alkyl or Ar²; and R^a, R^b, R^c, R^d, R¹, R², hetAr⁴, Ar⁴ and Ar² are as defined for Formula I.

In one embodiment of Formula I-a, R⁴ is (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C)alkoxy, (1-4C alkoxy)(1-6C)alkoxy, (3-6C)cycloalkyl, hetAr⁴ or Ar⁴; R³ is H, (1-6C)alkyl or Ar²; R⁵ is H, (1-6C)alkyl, or halogen; and R^a, R^b, R^c, R^d, R¹, R², hetAr⁴, Ar⁴ and Ar² are as defined for Formula I.

In another embodiment of the present invention there is provided a compound according to Formula I, which is designated as Formula I-b wherein:
X is O;
B is hetAr¹;
Y is a bond;
Ring C is formula C-1:

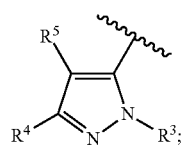

R⁴ is H, OH, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr³(1-6C)alkyl, Ar³(1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, aminocarbonyl(1-6C)alkoxy, hydroxycarbonyl (1-6C)alkoxy, hetCyc²(1-6C)alkoxy, hetAr³(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl, hetAr⁴, or Ar⁴;

R⁵ is H, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, or phenyl optionally substituted with one or more groups independently selected from halogen, (1-6C)alkyl and (1-6C)alkoxy; and R^a, R^b, R^c, R^d, R¹, R², hetAr¹, R³, hetCyc², hetAr³, Ar³, hetAr⁴, and Ar⁴ are as defined for Formula I.

In one embodiment of Formula I-b, R^a, R^b, R^c and R^d are hydrogen; R² is hydrogen; and R¹, hetAr¹, R³, hetCyc², hetAr³, Ar³, hetAr⁴, and Ar⁴ are as defined for Formula I.

In one embodiment of Formula I-b, R^a, R^b, R^c and R^d are hydrogen; R² is hydrogen; R¹ is (1-3C alkoxy)(1-6C)alkyl, difluoro(1-6C)alkyl, or trifluoro(1-6C)alkyl; and hetAr¹, R³, hetCyc², hetAr³, Ar³, hetAr⁴, and Ar⁴ are as defined for Formula I.

In one embodiment of Formula I-b, R^a, R^b, R^c and R^d are hydrogen; R² is hydrogen; R¹ is (1-3C alkoxy)(1-6C)alkyl, difluoro(1-6C)alkyl, or trifluoro(1-6C)alkyl; R³ is Ar², hetAr² or (1-6C)alkyl; and hetAr¹, Ar², hetAr², hetCyc², hetAr³, Ar³, hetAr⁴, and Ar⁴ are as defined for Formula I.

In one embodiment of Formula I-b, R^a, R^b, R^c and R^d are hydrogen; R² is hydrogen; R¹ is (1-3C alkoxy)(1-6C)alkyl, difluoro(1-6C)alkyl, or trifluoro(1-6C)alkyl; R³ is Ar², hetAr² or (1-6C)alkyl; R⁴ is H, (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C)alkoxy, (1-4C alkoxy)(1-6C)alkoxy, (3-6C)cycloalkyl, hetAr⁴ or Ar⁴; and hetAr¹, Ar², hetAr², hetCyc², hetAr³, hetAr⁴ and Ar⁴ are as defined for Formula I.

In one embodiment of Formula I-b, R^a, R^b, R^c and R^d are hydrogen; R² is hydrogen; R¹ is (1-3C alkoxy)(1-6C)alkyl, difluoro(1-6C)alkyl, or trifluoro(1-6C)alkyl; R³ is Ar², hetAr² or (1-6C)alkyl; R⁴ is H, (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C)alkoxy, (1-4C alkoxy)(1-6C)alkoxy, (3-6C)cycloalkyl, hetAr⁴ or Ar⁴; R⁵ is H, halogen, CN, (1-6C)alkyl, (1-4C)alkoxy, hydroxy(1-4C)alkyl, or phenyl optionally substituted with one or more groups independently selected from halogen, (1-6C)alkyl and (1-6C)alkoxy; and hetAr¹, Ar², hetAr², hetCyc², hetAr³, hetAr⁴ and Ar⁴ are as defined for Formula I.

In one embodiment of Formula I-b, R^a, R^b, R^c and R^d are hydrogen; R² is hydrogen; R¹ is (1-3C alkoxy)(1-6C)alkyl, difluoro(1-6C)alkyl, or trifluoro(1-6C)alkyl; R³ is Ar², hetAr² or (1-6C)alkyl; R⁴ is H, (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C)alkoxy, (1-4C alkoxy)(1-6C)alkoxy, (3-6C)cycloalkyl, hetAr⁴ or Ar⁴; R⁵ is H, halogen, or (1-6C)alkyl; and hetAr¹, Ar², hetAr², hetAr³, hetAr⁴ and Ar⁴ are as defined for Formula I.

In one embodiment of Formula I-b, R⁴ is (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C)alkoxy, (1-4C alkoxy)(1-6C)alkoxy, (3-6C)cycloalkyl, hetAr⁴ or Ar⁴; and R^a, R^b, R^c, R^d, R¹, R², R³, hetAr⁴ and Ar⁴ are as defined for Formula I.

In one embodiment of Formula I-b, R⁴ is (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C)alkoxy, (1-4C alkoxy)(1-6C)alkoxy, (3-6C)cycloalkyl, hetAr⁴ or Ar⁴; R³ is H, (1-6C)alkyl or Ar²; and R^a, R^b, R^c, R^d, R¹, R², hetAr⁴, Ar⁴ and Ar² are as defined for Formula I.

In one embodiment of Formula I-b, R⁴ is hetAr⁴ or Ar⁴; R³ is H, (1-6C)alkyl or Ar²; R⁵ is H, (1-6C)alkyl, or halogen; and R^a, R^b, R^c, R^d, R¹, R² hetAr⁴, Ar⁴ and Ar² are as defined for Formula I.

In another embodiment of the present invention there is provided a compound according to Formula I, which is designated as Formula I-c wherein:
X is O;
B is Ar¹;
Y is a bond;
Ring C is formula C-1:

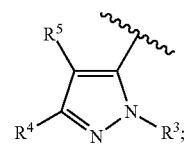

R⁴ and R⁵ together with the atoms to which they are attached form a 5-6 membered saturated, partially unsaturated or saturated carbocyclic ring optionally substituted with one or more substituents independently selected from (1-6C)alkyl, or R⁴ and R⁵ together with the atoms to which they are attached form a 5-6 membered saturated, partially unsaturated or saturated heterocyclic ring having a ring heteroatom selected from N, O or S, wherein said heterocyclic ring is optionally substituted with (1-6C alkyl)C(=O)O—, or (1-6)acyl, and said sulfur ring atom is optionally oxidized to S(=O) or SO$_2$; wherein R$^a$, R$^b$, R$^c$, R$^d$, R$^1$, R$^2$, Ar$^1$ and R$^3$ are as defined for Formula I.

In one embodiment of Formula I-c, R$^4$ and R$^5$ together with the atoms to which they are attached form a 5-6 membered saturated carbocyclic ring optionally substituted with one or more substituents independently selected from (1-6C)alkyl, or R$^4$ and R$^5$ together with the atoms to which they are attached form a 5-6 membered saturated heterocyclic ring having a ring heteroatom selected from N, O or S, wherein said ring nitrogen atom is optionally substituted with (1-6C alkyl)C(=O)O—, or (1-6)acyl, and said sulfur ring atom is optionally oxidized to S(=O) or SO$_2$; wherein R$^a$, R$^b$, R$^c$, R$^d$, R$^1$, R$^2$, Ar$^1$ and R$^3$ are as defined for Formula I.

In one embodiment of Formula I-c, R$^a$, R$^b$, R$^c$, R$^d$ and R$^2$ are hydrogen; and R$^1$, Ar$^1$ and R$^3$ are as defined for Formula I.

In one embodiment of Formula I-c, R$^a$, R$^b$, R$^c$, R$^d$ and R$^2$ are hydrogen; R$^1$ is (1-3C alkoxy)(1-6C)alkyl, (trifluoromethoxy)(1-6C)alkyl, (1-3C sulfanyl)(1-6C)alkyl, trifluoro(1-6C)alkyl, cyano(1-6C)alkyl, or (1-3Calkylamino)(1-3C)alkyl; and Ar$^1$ and R$^3$ are as defined for Formula I.

In one embodiment of Formula I-c, R$^a$, R$^b$, R$^c$, R$^d$ and R$^2$ are hydrogen; R$^1$ is (1-3C alkoxy)(1-6C)alkyl, (trifluoromethoxy)(1-6C)alkyl, (1-3C sulfanyl)(1-6C)alkyl, trifluoro(1-6C)alkyl, cyano(1-6C)alkyl, or (1-3Calkylamino)(1-3C)alkyl; R$^3$ is H, (1-6C)alkyl or phenyl optionally substituted with one or more groups independently selected from halogen, (1-6C)alkyl and hydroxymethyl; and Ar$^1$ is as defined for Formula I.

In one embodiment of Formula I-c, R$^a$, R$^b$, R$^c$, R$^d$ and R$^2$ are hydrogen; R$^1$ is (1-3C alkoxy)(1-6C)alkyl, (trifluoromethoxy)(1-6C)alkyl, (1-3C sulfanyl)(1-6C)alkyl, trifluoro(1-6C)alkyl, cyano(1-6C)alkyl, or (1-3Calkylamino)(1-3C)alkyl; R$^3$ is phenyl optionally substituted with one or more groups independently selected from halogen, (1-6C) alkyl and hydroxymethyl; and Ar$^1$ is as defined for Formula I.

In another embodiment of the present invention there is provided a compound according to Formula I, which is designated as Formula I-d, wherein:
X is O;
B is hetAr$^1$;
Y is a bond;
Ring C is formula C-1:

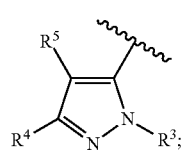

C-1

R$^4$ and R$^5$ together with the atoms to which they are attached form a 5-6 membered saturated, partially unsaturated or saturated carbocyclic ring optionally substituted with one or more substituents independently selected from (1-6C)alkyl, or R$^4$ and R$^5$ together with the atoms to which they are attached form a 5-6 membered saturated, partially unsaturated or saturated heterocyclic ring having a ring heteroatom selected from N, O or S, wherein said heterocyclic ring is optionally substituted with (1-6C alkyl)C(=O)O—, or (1-6)acyl, and said sulfur ring atom is optionally oxidized to S(=O) or SO$_2$; wherein R$^a$, R$^b$, R$^c$, R$^d$, R$^1$, R$^2$, Ar$^1$ and R$^3$ are as defined for Formula I.

In one embodiment of Formula I-d, R$^4$ and R$^5$ together with the atoms to which they are attached form a 5-6 membered saturated carbocyclic ring optionally substituted with one or more substituents independently selected from (1-6C)alkyl, or R$^4$ and R$^5$ together with the atoms to which they are attached form a 5-6 membered saturated heterocyclic ring having a ring heteroatom selected from N, O or S, wherein said ring nitrogen atom is optionally substituted with (1-6C alkyl)C(=O)O—, or (1-6)acyl, and said sulfur ring atom is optionally oxidized to S(=O) or SO$_2$; wherein R$^a$, R$^b$, R$^c$, R$^d$, R$^1$, R$^2$, hetAr$^1$ and R$^3$ are as defined for Formula I.

In one embodiment of Formula I-d, R$^a$, R$^b$, R$^c$, R$^d$ and R$^2$ are hydrogen; and R$^1$, hetAr$^1$ and R$^3$ are as defined for Formula I.

In one embodiment of Formula I-d, R$^a$, R$^b$, R$^c$, R$^d$ and R$^2$ are hydrogen; R$^1$ is (1-3C alkoxy)(1-6C)alkyl, (trifluoromethoxy)(1-6C)alkyl, (1-3C sulfanyl)(1-6C)alkyl, trifluoro(1-6C)alkyl, cyano(1-6C)alkyl, or (1-3Calkylamino)(1-3C)alkyl; and hetAr$^1$ and R$^3$ are as defined for Formula I.

In one embodiment of Formula I-d, R$^a$, R$^b$, R$^c$, R$^d$ and R$^2$ are hydrogen; R$^1$ is (1-3C alkoxy)(1-6C)alkyl, (trifluoromethoxy)(1-6C)alkyl, (1-3C sulfanyl)(1-6C)alkyl, trifluoro(1-6C)alkyl, cyano(1-6C)alkyl, or (1-3Calkylamino)(1-3C)alkyl; R$^3$ is H, (1-6C)alkyl or phenyl optionally substituted with one or more groups independently selected from halogen, (1-6C)alkyl and hydroxymethyl; and hetAr$^1$ is as defined for Formula I.

In one embodiment of Formula I-d, R$^a$, R$^b$, R$^c$, R$^d$ and R$^2$ are hydrogen; R$^1$ is (1-3C alkoxy)(1-6C)alkyl, (trifluoromethoxy)(1-6C)alkyl, (1-3C sulfanyl)(1-6C)alkyl, trifluoro(1-6C)alkyl, cyano(1-6C)alkyl, or (1-3Calkylamino)(1-3C)alkyl; R$^3$ is phenyl optionally substituted with one or more groups independently selected from halogen, (1-6C) alkyl and hydroxymethyl; and hetAr$^1$ is as defined for Formula I.

As noted, the Y—B moiety and the —NH—C(=X)—NH— moiety of Formula I are in trans configuration on the pyrrolidine ring, which relative stereochemistry can be illustrated by either formula A or B:

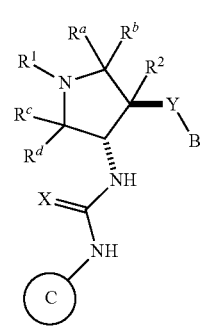

A

-continued

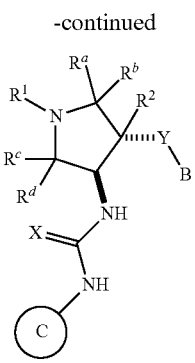

B in which the straight thick bars ( ▬ ) and straight dashed bars ( ⁞⁞⁞ ) indicate relative stereochemistry. In one embodiment of the above Formulas A and B, Y is a bond and B is Ring B, wherein Ring B is Ar¹ or hetAr¹.

In one embodiment of Formula I, the Y—B and the —NH—C(=X)—NH— moieties are trans in the absolute configuration which can be illustrated by formulas C and D:

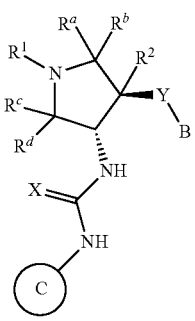

C

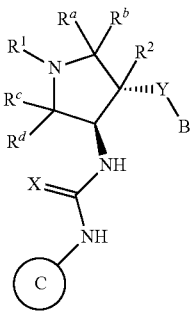

D in which the solid wedges ( ▬ ) and dashed wedges ( ⁞⁞⁞ ) indicate absolute stereochemistry. In one embodiment of the above Formulas C and D, Y is a bond and B is Ring B, wherein Ring B is Ar¹ or hetAr¹.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Particular examples of salts include hydrochloride salts.

The term "pharmaceutically acceptable" indicates that the substance or composition is compatible chemically and/or toxicologically, with the other ingredients comprising a formulation, and/or the mammal being treated therewith.

The present invention also provides a process for the preparation of a compound of Formula I or a salt thereof as defined herein, which comprises:

(a) for a compound of Formula I where X is O, coupling a corresponding compound having the formula II

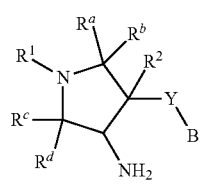

II with a corresponding compound having the formula III

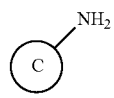

III in the presence carbonyldiimidazole or triphosgene and a base; or (b) for a compound of Formula I where X is S, coupling a corresponding compound having the formula II

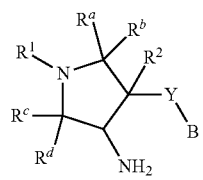

II with a corresponding compound having the formula III

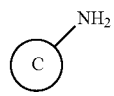

III in the presence di(1H-imidazol-2-yl)methanethione and a base; or (c) for a compound of Formula I where X is O, coupling a corresponding compound having the formula II

II

[structure: pyrrolidine with R¹, N, Rᵃ, Rᵇ, R², Rᶜ, Rᵈ, Y, B, NH₂]

with a corresponding compound having the formula IV

IV

[structure: O=C(L¹)–NH–C(ring)]

where L¹ is a leaving group, in the presence of a base; or (d) for a compound of Formula I where X is O, coupling a corresponding compound having the formula V

V

[structure: pyrrolidine with substituents, NH–C(=O)–L²]

where L² is a leaving group, with a corresponding compound having the formula III

III

[structure: C(ring)–NH₂]

in the presence of a base; or (e) for a compound of Formula I where X is O, activating a corresponding compound having the formula VI

VI

[structure: pyrrolidine with substituents, COOH]

with diphenylphosphoryl azide followed by coupling the activated intermediate with a corresponding compound having the formula III

III

[structure: C(ring)–NH₂]

in the presence a base; or (f) for a compound of Formula I where X is O, coupling a corresponding compound having the formula II

II

[structure: pyrrolidine with R¹, Rᵃ, Rᵇ, R², Rᶜ, Rᵈ, Y, B, NH₂]

with a corresponding compound having the formula VII

VII

[structure: O=C=N–C(ring)]

in the presence of a base; or (g) for a compound of Formula I where R¹ is (trifluoromethoxy)(1-6C)alkyl, (1-3C sulfanyl)(1-6C)alkyl, monofluoro(1-6C)alkyl, difluoro(1-6C)alkyl, trifluoro(1-6C)alkyl, tetrafluoro(2-6C)alkyl, or pentafluoro(2-6C)alkyl, reacting a corresponding compound having the formula VIII

VIII

[structure: pyrrolidine HN, Rᵃ, Rᵇ, R², Rᶜ, Rᵈ, Y, B, NH–C(=O)–NH–C(ring)]

with a corresponding compound having the (trifluoromethoxy)(1-6C)alkyl-L³, (1-3C sulfanyl)(1-6C)alkyl-L³, monofluoro(1-6C)alkyl-L³, difluoro(1-6C)alkyl-L³, trifluoro(1-6C)alkyl-L³, tetrafluoro(2-6C)alkyl-L³, or pentafluoro(2-6C)alkyl-L³, where L³ is a leaving atom or a leaving group, in the presence of a base; or (h) for a compound of Formula I where X is O, R⁴ is CH₃OCH₂— and R⁵ is OHCH₂—, treating a corresponding compound having the general formula IX

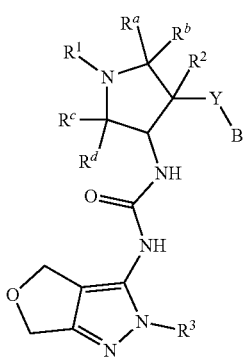

with an inorganic acid; and optionally removing protecting groups and optionally preparing a pharmaceutically acceptable salt thereof.

In the above methods, the term "corresponding" means that the definitions for the "corresponding compound" are as defined for Formula I unless stated otherwise.

In one embodiment of any of the above methods, Y is a bond and B is Ring B, where Ring B is $Ar^1$ or $hetAr^1$ as defined for Formula I.

Referring to method (a), the base may be an amine base, such as triethylamine or diisopropylamine. Suitable solvents include dichloromethane, dichloroethane, THF, DMA and DMF. The reaction is conveniently performed at ambient temperature.

Referring to method (b), the base may be an amine base, such as triethylamine or diisopropylamine. Suitable solvents include dichloromethane, dichloroethane, THF, DMA and DMF. The reaction is conveniently performed at ambient temperature.

Referring to method (c), the leaving group may be, for example, phenoxy or 4-nitrophenoxy. The base may be an amine base, such as triethylamine or diisopropylamine. Suitable solvents include DMA, DMF and DCE. The reaction is conveniently performed at ambient temperature.

Referring to method (d), the leaving group may be, for example, phenoxy or 4-nitrophenoxy. The base may be an amine base, such as triethylamine or diisopropylamine. Suitable solvents include DCE, DMA and DMF. The reaction is conveniently performed at ambient temperature.

Referring to method (e), the base may be an amine base, such as triethylamine or diisopropylamine. Suitable solvents include toluene and DMF. The reaction is conveniently performed at elevated temperatures, for example the reflux temperature of the solvent.

Referring to method (f), the base may be an amine base, such as triethylamine or diisopropylamine. Suitable solvents include DCM, DCE, DMF and THF. The reaction is conveniently performed at temperatures between about 0° C. and ambient temperature.

A compound of Formula VII may be prepared by reacting a compound of Formula III with bis(trichloromethyl) carbonate in the presence of a base, such as an amine base.

Referring to method (g), the base may be an amine base, such as triethylamine or diisopropylamine. Suitable solvents include DMF, DMA and THF. The reaction is conveniently performed at temperatures between ambient temperature and 60° C.

Referring to method (h), the acid may be, for example, hydrochloric acid. Suitable solvents include DCM. The reaction is conveniently performed at ambient temperature.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC), phenoxycarbonyl, and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

The compounds of the formulas II, III, III, IV, V, VI, VII, VIII, and IX are also believed to be novel and are provided as further aspects of the invention.

In one embodiment of the above-described processes (a), (b), (c), and (f), where B is $Ar^1$ and $R^a$, $R^b$, $R^c$, $R^d$ and $R^2$ are hydrogen, a single enantiomer of intermediate II, namely enantiomer 1 of II-A is prepared by chiral crystallization prior to use. Accordingly, in one embodiment, a process for preparing enantiomer 1 of II-A comprises:

preparing racemic trans II-A

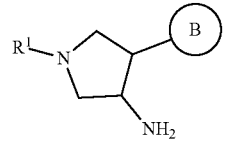

where Ring B and the $NH_2$ group are in the trans configuration; Ring B is Ring B is $Ar^1$ or $hetAr^1$; $Ar^1$ is phenyl optionally substituted with one or more substituents independently selected from halogen, $CF_3$, $CF_3O$—, (1-4C) alkoxy, hydroxy(1-4C)alkyl, (1-6C)alkyl and CN; and $hetAr^1$ is a 5-6 membered heteroaryl having 1-3 ring heteroatoms independently selected from N, S and O, and optionally substituted with 1-2 groups independently selected form (1-6C)alkyl, halogen, OH, $CF_3$, $NH_2$ and hydroxy(1-2C)alkyl; said method comprising:

treating racemic trans II-A with di-p-toluoyl-D-tartaric acid to provide the di-p-toluoyl-D-tartaric acid salt of racemic trans II-A;

recrystallizing the di-p-toluoyl-D-tartaric acid salt of trans II-A to provide the di-p-toluoyl-D-tartaric acid salt of enantiomer 1 of trans II-A; and treating the di-p-toluoyl-D-tartaric acid salt of enantiomer 1 of trans II-A with an inorganic base to provide free base of enantiomer 1 of trans II-A having the absolute configuration as illustrated:

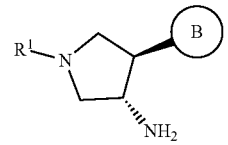

enantiomer 1 of II-A

In one embodiment of racemic trans II-A, $R^1$ is 2-methoxyethoxy and Ring B is 4-fluorophenyl, and racemic trans II-A is prepared by the process comprising:

reacting 4-fluorobenzaldehyde with nitromethane in the presence of acetic acid and ammonium acetate to provide (E)-1-fluoro-4-(2-nitrovinyl)benzene

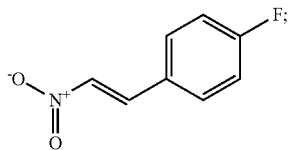

reacting (E)-1-fluoro-4-(2-nitrovinyl)benzene with 2-methoxy-N-(methoxymethyl)-N-((trimethylsilyl)methyl) ethanamine in the presence of a catalytic amount of an acid (such as TFA) to provide trans-3-(4-fluorophenyl)-1-(2-methoxyethyl)-4-nitropyrrolidine

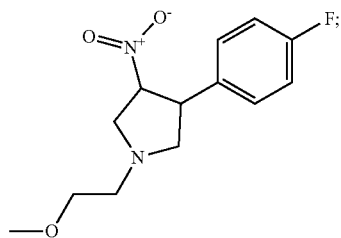 [SMILES: COCCN1CC(c2ccc(F)cc2)C([N+](=O)[O-])C1]

and treating trans-3-(4-fluorophenyl)-1-(2-methoxyethyl)-4-nitropyrrolidine with platinum (IV) oxide or Raney Nickel in a hydrogen atmosphere to provide trans-4-(4-fluorophenyl)-1-(2-methoxyethyl)pyrrolidin-3-amine

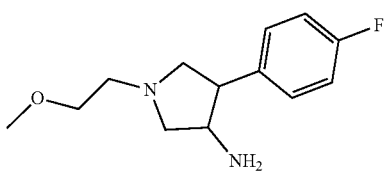 [SMILES: COCCN1CC(N)C(c2ccc(F)cc2)C1]

wherein the 4-fluorophenyl and amino group are in the trans configuration.

In one embodiment, the inorganic base is an alkali metal hydroxide such as sodium hydroxide.

A similar process as above may be used utilizing di-p-toluoyl-L-tartric acid to provide enantiomer 2 of II-A:

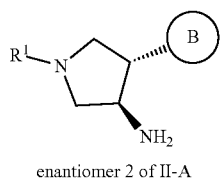

enantiomer 2 of II-A

The ability of compounds of the invention to act as TrkA inhibitors may be demonstrated by the assay described in Example A.

Compounds of Formula I are useful for treating pain, including chronic and acute pain. For example, compounds of Formula I may be useful in the treatment of multiple types of pain including inflammatory pain, neuropathic pain, and pain associated with cancer, surgery, and bone fracture.

In one embodiment, compounds of Formula I are useful for treating acute pain. Acute pain, as defined by the International Association for the Study of Pain, results from disease, inflammation, or injury to tissues. This type of pain generally comes on suddenly, for example, after trauma or surgery, and may be accompanied by anxiety or stress. The cause can usually be diagnosed and treated, and the pain is confined to a given period of time and severity. In some instances, it can become chronic.

In one embodiment, compounds of Formula I are useful for treating chronic pain. Chronic pain, as defined by the International Association for the Study of Pain, is widely believed to represent disease itself. It can be made much worse by environmental and psychological factors. Chronic pain persists over a longer period than acute pain and is resistant to most medical treatments, generally over 3 months or more. It can and often does cause severe problems for patients.

Compounds of Formula I are also useful for treating cancer. Particular examples include neuroblastoma, ovarian, pancreatic, colorectal and prostate cancer.

Compounds of Formula I are also useful for treating inflammation and certain infectious diseases.

In addition, compounds of Formula I may also be used to treat interstitial cystitis (IC), painful bladder syndrome (PBS), urinary incontinence, asthma, anorexia, atopic dermatitis, and psoriasis.

Compounds of Formula I are also useful for treating a neurodegenerative disease in a mammal, comprising administering to said mammal one or more compounds of Formula I or a pharmaceutically acceptable salt thereof in an amount effective to treat or prevent said neurodegenerative disease. In one embodiment, compounds of Formula I may also be used to treat demyelination and dysmyelination by promoting myelination, neuronal survival, and oligodendrocyte differentiation via blocking Sp35-TrkA interaction. In one embodiment, the neurodegenerative disease is multiple sclerosis. In one embodiment, the neurodegenerative disease is Parkinson's disease. In one embodiment, the neurodegenerative disease is Alzheimer's disease.

As used herein, terms "treat" or "treatment" refer to therapeutic or palliative or measures. Beneficial or desired clinical results include, but are not limited to, alleviation, in whole or in part, of symptoms associated with a disorder or condition, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In certain embodiments, compounds of Formula I are useful for preventing diseases and disorders as defined herein. The term "preventing" as used herein means the prevention of the onset, recurrence or spread, in whole or in part, of the disease or condition as described herein, or a symptom thereof.

Accordingly, one embodiment of this invention provides a method of treating pain in a mammal, comprising administering to said mammal one or more compounds of Formula I or a pharmaceutically acceptable salt thereof in an amount effective to treat or prevent said pain. In one embodiment, the pain is chronic pain. In one embodiment, the pain is acute pain. In one embodiment, the pain is inflammatory pain, neuropathic pain, and pain associated with cancer, surgery, and bone fracture.

Another embodiment of this invention provides a method of treating inflammation in a mammal, comprising administering to said mammal one or more compounds of Formula I or a pharmaceutically acceptable salt thereof in an amount effective to treat or prevent said inflammation.

Another embodiment of this invention provides a method of treating a neurodegenerative disease in a mammal, comprising administering to said mammal one or more compounds of Formula I or a pharmaceutically acceptable salt thereof in an amount effective to treat or prevent said neurodegenerative disease.

Another embodiment of this invention provides a method of treating *Trypanosoma cruzi* infection in a mammal, comprising administering to said mammal one or more compounds of Formula I or a pharmaceutically acceptable salt thereof in an amount effective to treat or prevent said *Trypanosoma cruzi* infection.

The phrase "effective amount" means an amount of compound that, when administered to a mammal in need of such treatment, is sufficient to (i) treat or prevent a particular disease, condition, or disorder which can be treated with a compound of Formula I, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional drugs that work by the same or a different mechanism of action. Examples include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone ("PVP") K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, for example a salt such sodium chloride, if desired. The solution is typically filtered, for example using a 0.2 micron filter, to remove impurities and contaminants.

Another formulation may be prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

Accordingly, another aspect of the present invention provides a pharmaceutical composition, which comprises a compound of Formula I or a pharmaceutically acceptable salt thereof, as defined hereinabove, together with a pharmaceutically acceptable diluent or carrier.

According to another embodiment, the present invention provides a compound of Formula I or a pharmaceutically acceptable salt thereof, for use in the treatment of pain in a mammal. In one embodiment, the pain is chronic pain. In one embodiment the pain is acute pain. In one embodiment, the pain is inflammatory pain, neuropathic pain, and pain associated with cancer, surgery, and bone fracture.

In another embodiment, the present invention provides a compound of Formula I or a pharmaceutically acceptable salt thereof, for use in the treatment of inflammation in a mammal.

In another embodiment, the present invention provides a compound of Formula I or a pharmaceutically acceptable salt thereof, for use in the treatment of infectious diseases, for example *Trypanosoma cruzi* infection, in a mammal.

In another embodiment, the present invention provides a compound of Formula I or a pharmaceutically acceptable salt thereof, for use in the treatment of a neurodegenerative disease in a mammal.

According to a further aspect, the present invention provides the use of a compound of Formula I or a pharmaceutically acceptable salt thereof, in the manufacture of a medicament for the treatment of a condition selected from pain, cancer, inflammation, neurodegenerative disease or *Trypanosoma cruzi* infection. In one embodiment, the condition is chronic pain. In one embodiment, the condition is acute pain. In one embodiment, the pain is inflammatory pain, neuropathic pain, and pain associated with cancer, surgery, and bone fracture. In one embodiment, the condition is cancer. In one embodiment, the condition is inflammation. In one embodiment, the condition is a neurodegenerative disease. In one embodiment, the condition is *Trypanosoma cruzi* infection.

Abbreviations used in herein have the following definitions:

| | |
|---|---|
| CDI | Carbonyl diimidazole |
| DCE | Dichloroethane |
| DCM | Dichloromethane |
| DIEA | Diisopropylethylamine |
| DMA | N,N-Dimethylacetamide |
| DMF | N,N-Dimethylformamide |
| DPPA | Diphenylphosphorylazide |
| HATU | (2-(7-Aza-1H-benzotriazole-1-yl)-1,1,3,3-tetramethyluronium hexafluorophosphate) |
| MP-TsOH | Polymer supported p-toluenesulfonic acid (Macroporous Polystyrene resin containing p-toluenesulfonic acid (Purchased from Biotage) |
| MsCl | Methanesulfonyl chloride |
| PS-DMAP | Polystyrene bound dimethyl aminopyridine (Purchased from Biotage) |
| TFA | Trifluoroacetic acid |

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. THF, DCM, toluene, DMF and dioxane were purchased from Aldrich in Sure/Seal™ bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Biological Assay

Example A

TrkA Omnia Assay

Trk enzymatic selectivity was assessed using Omnia™ Kinase Assay reagents from Invitrogen Corp. Enzyme (TrkA from Invitrogen Corp.) and test compound (various concentrations) were incubated for 10 minutes at ambient temperature in a 384-well white polypropylene plate (Nunc catalog#267462). Omnia Tyr Peptide #4, as well as ATP, were then added to the plate. Final concentrations were as follows: 20 nM enzyme, 500 µM of ATP, 10 µM peptide substrate. The assay buffer consisted of 25 mM MOPS pH 7.5, 0.005% (v/v) Triton X-100 and 5 mM $MgCl_2$. The production of phosphorylated peptide was monitored continuously for 70 minutes using a Molecular Devices FlexStation II$^{384}$ microplate reader (excitation=360 nm; emission=485 nm). Initial rates were calculated from progress curves. $IC_{50}$ values were calculated from these rates using either a 4 or 5-parameter logistic curve fit.

Compounds of the invention had an average $IC_{50}$ value below 1000 nM when tested in this assay. Certain compounds had an average $IC_{50}$ value below 100 nM when tested in this assay.

Table A provides averaged $IC_{50}$ values for compounds of the invention when tested in the assay of Example A, where A represents an averaged $IC_{50}$ value <100 nM; B represents an averaged $IC_{50}$ value from 100 to 1,000 nM; and C represents an averaged $IC_{50}$ value from 1,000 to 10,000 nM.

TABLE A

| Ex. # | TrkA Enzyme $IC_{50}$ |
|---|---|
| 1 | A |
| 2 | C |
| 3 | A |
| 4 | A |
| 5 | C |
| 6 | C |
| 7 | C |
| 8 | B |
| 9 | A |
| 10 | A |
| 11 | A |
| 12 | A |
| 13 | A |
| 14 | A |
| 15 | B |
| 16 | C |
| 17 | B |
| 18 | A |
| 19 | B |
| 20 | C |
| 21 | A |
| 22 | A |
| 23 | A |
| 24 | A |
| 25 | B |
| 26 | A |
| 27 | C |
| 28 | B |
| 29 | C |
| 30 | A |
| 31 | B |
| 32 | B |
| 33 | B |
| 34 | C |
| 35 | C |
| 36 | A |
| 37 | A |
| 38 | A |
| 39 | A |
| 40 | A |
| 41 | A |
| 42 | A |
| 43 | B |
| 44 | A |
| 45 | C |
| 46 | C |
| 47 | B |
| 48 | B |
| 49 | C |
| 50 | A |
| 51 | A |
| 52 | A |
| 53 | A |
| 54 | C |
| 55 | B |
| 56 | A |
| 57 | A |
| 58 | A |
| 59 | A |
| 60 | A |
| 61 | A |
| 62 | A |
| 63 | A |
| 64 | A |
| 65 | A |

TABLE A-continued

| Ex. # | TrkA Enzyme IC$_{50}$ |
|---|---|
| 66 | A |
| 67 | B |
| 68 | C |
| 69 | Example 69 omitted |
| 70 | A |
| 71 | A |
| 72 | A |
| 73 | A |
| 74 | A |
| 75 | A |
| 76 | A |
| 77 | A |
| 78 | A |
| 79 | C |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | B |
| 95 | A |
| 96 | A |
| 97 | A |
| 98 | A |
| 99 | A |
| 100 | B |
| 101 | A |
| 102 | A |
| 103 | A |
| 104 | A |
| 105 | A |
| 106 | B |
| 107 | A |
| 108 | A |
| 109 | B |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | B |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | B |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | B |
| 154 | C |
| 155 | A |
| 156 | A |
| 157 | A |
| 158 | C |
| 159 | B |
| 160 | B |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | C |
| 181 | B |
| 182 | A |
| 183 | B |
| 184 | C |
| 185 | B |
| 186 | A |
| 187 | B |
| 188 | B |
| 189 | B |
| 190 | C |
| 191 | B |
| 192 | B |
| 193 | B |
| 194 | A |
| 195 | A |
| 196 | A |
| 197 | A |
| 198 | A |
| 199 | A |
| 200 | B |
| 201 | B |
| 202 | A |
| 203 | B |
| 204 | A |
| 205 | A |
| 206 | B |
| 207 | B |
| 208 | B |
| 209 | B |
| 210 | A |
| 211 | A |
| 212 | C |
| 213 | B |
| 214 | A |
| 215 | A |
| 216 | A |
| 217 | A |
| 218 | A |
| 219 | A |

TABLE A-continued

| Ex. # | TrkA Enzyme IC$_{50}$ |
|---|---|
| 220 | B |
| 221 | A |
| 222 | A |
| 223 | A |
| 224 | A |
| 225 | A |
| 226 | A |
| 227 | A |
| 228 | A |
| 229 | A |
| 230 | B |
| 231 | A |
| 232 | B |
| 233 | B |
| 234 | B |
| 235 | B |
| 236 | B |
| 237 | B |
| 238 | B |
| 239 | B |
| 240 | B |
| 241 | B |
| 242 | A |
| 243 | A |
| 244 | A |
| 245 | B |
| 246 | A |
| 247 | B |
| 248 | A |
| 249 | A |
| 250 | A |
| 251 | A |
| 252 | A |
| 253 | B |
| 254 | A |
| 255 | A |
| 256 | B |
| 257 | B |
| 258 | A |
| 259 | A |
| 260 | A |
| 261 | B |
| 262 | C |
| 263 | A |
| 264 | A |
| 265 | A |
| 266 | A |
| 267 | A |
| 268 | A |
| 269 | A |
| 270 | A |
| 271 | A |
| 272 | A |
| 273 | B |
| 274 | B |
| 275 | B |
| 276 | A |
| 277 | A |
| 278 | A |
| 279 | B |
| 280 | A |
| 281 | A |
| 282 | A |
| 283 | A |
| 284 | A |
| 285 | A |
| 286 | A |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | A |
| 303 | A |
| 304 | A |
| 305 | A |
| 306 | A |
| 307 | A |
| 308 | A |
| 309 | A |
| 310 | B |
| 311 | A |
| 312 | A |
| 313 | A |
| 314 | A |
| 315 | A |
| 316 | A |
| 317 | A |
| 318 | B |
| 319 | A |
| 320 | A |
| 321 | A |
| 322 | A |
| 323 | A |
| 324 | A |
| 325 | A |
| 326 | A |
| 327 | A |
| 328 | A |
| 329 | A |
| 330 | A |
| 331 | A |
| 332 | B |
| 333 | B |
| 334 | A |
| 335 | A |
| 336 | A |
| 337 | A |
| 338 | A |
| 339 | A |
| 340 | B |
| 341 | B |
| 342 | A |
| 343 | A |
| 344 | A |
| 345 | A |
| 346 | A |
| 347 | A |
| 348 | A |
| 349 | A |
| 350 | A |
| 351 | A |
| 352 | A |
| 353 | B |
| 354 | B |
| 355 | A |
| 356 | A |
| 357 | A |
| 358 | A |
| 359 | A |
| 360 | A |
| 361 | A |
| 362 | A |
| 363 | A |
| 364 | A |
| 365 | A |
| 366 | A |
| 367 | A |
| 368 | A |
| 369 | A |
| 370 | A |
| 371 | A |
| 372 | A |
| 373 | A |

TABLE A-continued

| Ex. # | TrkA Enzyme IC$_{50}$ |
|---|---|
| 374 | A |
| 375 | A |
| 376 | A |
| 377 | A |
| 378 | A |
| 379 | A |
| 380 | A |
| 381 | A |
| 382 | A |
| 383 | A |
| 384 | A |
| 385 | A |
| 386 | A |
| 387 | A |
| 388 | A |
| 389 | A |
| 390 | A |
| 391 | A |
| 392 | A |
| 393 | A |
| 394 | B |
| 395 | B |
| 396 | A |
| 397 | A |
| 398 | A |
| 399 | A |
| 400 | B |
| 401 | A |
| 402 | B |
| 403 | A |
| 404 | A |
| 405 | A |
| 406 | A |
| 407 | A |
| 408 | A |
| 409 | A |
| 410 | A |
| 411 | A |
| 412 | A |
| 413 | A |
| 414 | A |
| 415 | A |
| 416 | A |
| 417 | A |
| 418 | A |
| 419 | A |
| 420 | A |
| 421 | A |
| 422 | A |
| 423 | A |
| 424 | A |
| 425 | A |
| 426 | A |
| 427 | A |
| 428 | A |
| 429 | A |
| 430 | A |
| 431 | A |
| 432 | B |
| 433 | A |
| 434 | A |
| 435 | A |
| 436 | A |
| 437 | A |
| 438 | A |
| 439 | A |
| 440 | A |
| 441 | A |
| 442 | A |
| 443 | A |
| 444 | A |
| 445 | A |
| 446 | A |
| 447 | A |
| 448 | A |
| 449 | A |
| 450 | A |

TABLE A-continued

| Ex. # | TrkA Enzyme IC$_{50}$ |
|---|---|
| 451 | A |
| 452 | A |
| 453 | A |
| 454 | A |
| 455 | A |
| 456 | A |
| 457 | A |
| 458 | B |
| 459 | A |
| 460 | A |
| 461 | A |
| 462 | A |
| 463 | A |
| 464 | A |
| 465 | A |
| 466 | A |
| 467 | A |
| 468 | A |
| 469 | C |
| 470 | B |
| 471 | B |
| 472 | B |
| 473 | A |
| 474 | A |
| 475 | A |
| 476 | A |
| 477 | A |
| 478 | A |
| 479 | A |
| 480 | A |
| 481 | A |
| 482 | A |
| 483 | A |
| 484 | A |
| 485 | B |
| 486 | A |
| 487 | A |
| 488 | A |
| 489 | A |
| 490 | A |
| 491 | A |
| 492 | A |
| 493 | A |
| 494 | A |
| 495 | A |
| 496 | B |
| 497 | B |
| 498 | A |
| 499 | A |
| 500 | A |
| 501 | A |
| 502 | A |
| 503 | A |
| 504 | A |
| 505 | A |
| 506 | A |
| 507 | A |
| 508 | A |
| 509 | A |
| 510 | A |
| 511 | A |
| 512 | A |
| 513 | A |
| 514 | A |
| 515 | A |
| 516 | A |
| 517 | A |
| 518 | A |
| 519 | A |
| 520 | A |
| 521 | A |
| 522 | A |
| 523 | A |
| 524 | A |
| 525 | A |
| 526 | A |
| 527 | A |

TABLE A-continued

| Ex. # | TrkA Enzyme IC$_{50}$ |
|---|---|
| 528 | A |
| 529 | A |
| 530 | A |
| 531 | A |
| 532 | A |
| 533 | A |
| 534 | A |
| 535 | A |
| 536 | A |
| 537 | A |
| 538 | A |
| 539 | B |
| 540 | A |
| 541 | A |
| 542 | A |
| 543 | A |
| 544 | A |
| 545 | A |
| 546 | A |
| 547 | A |
| 548 | B |
| 549 | A |
| 550 | A |
| 551 | A |
| 552 | A |
| 553 | B |
| 554 | A |
| 555 | A |
| 556 | A |
| 557 | A |
| 558 | A |
| 559 | A |
| 560 | A |
| 561 | A |
| 562 | A |
| 563 | A |
| 564 | A |
| 565 | A |
| 566 | B |
| 567 | B |
| 568 | A |
| 569 | A |
| 570 | A |
| 571 | A |
| 572 | B |
| 573 | B |
| 574 | A |
| 575 | A |
| 576 | A |
| 577 | A |
| 578 | B |
| 579 | A |
| 580 | B |
| 581 | A |
| 582 | A |
| 583 | A |
| 584 | A |
| 585 | A |
| 586 | A |
| 587 | A |
| 588 | A |
| 589 | B |
| 590 | A |
| 591 | A |
| 592 | A |
| 593 | A |
| 594 | A |
| 595 | A |
| 596 | A |
| 597 | A |
| 598 | A |
| 599 | A |
| 600 | A |
| 601 | A |
| 602 | A |
| 603 | A |
| 604 | A |

TABLE A-continued

| Ex. # | TrkA Enzyme IC$_{50}$ |
|---|---|
| 605 | A |
| 606 | A |
| 607 | A |
| 608 | A |
| 609 | A |
| 610 | A |
| 611 | A |
| 612 | A |
| 613 | A |
| 614 | A |
| 615 | A |
| 616 | A |
| 617 | A |
| 618 | A |
| 619 | A |
| 620 | A |
| 621 | A |
| 622 | A |
| 623 | A |
| 624 | A |
| 625 | A |
| 626 | A |
| 627 | A |
| 628 | A |
| 629 | C |
| 630 | A |
| 631 | A |
| 632 | A |
| 633 | A |
| 634 | A |
| 635 | A |
| 636 | B |
| 637 | A |
| 638 | A |
| 639 | A |
| 640 | A |
| 641 | B |
| 642 | B |
| 643 | A |
| 644 | A |
| 645 | A |
| 646 | B |
| 647 | A |
| 648 | A |
| 649 | B |

Preparation of Synthetic Intermediates

Preparation A

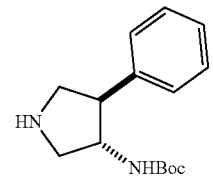

tert-butyl trans-4-phenylpyrrolidin-3-ylcarbamate

Step A: Preparation of trans-1-benzyl-3-nitro-4-phenylpyrrolidine: To a DCM (2 L) solution of (E)-(2-nitrovinyl)benzene (149 g, 1.00 mol) was added TFA (19.5 mL, 0.250 mol), followed by cooling to −15° C. and then slow addition of a DCM (500 mL) solution of N-methoxymethyl-N-(trimethylsilylmethyl)benzylamine (274 g, 1.00 mol) over 3 hours, maintaining the reaction temperature between −15 and −10° C. The reaction was warmed up to ambient temperature and stirred for 18 hours, then washed with 2 N NaOH (500 mL) and treated with 2 N HCl (1 L). The resulting white suspension was stirred for 1 hour before being filtered and washed with DCM. DCM (1 L) and 2 N NaOH (750 mL) were then added to the collected white solid and stirred until all solid dissolved. After phase-separation, the aqueous layer was extracted with DCM (2×1 L). The combined organic layers were dried with $MgSO_4$, filtered and concentrated to afford the title product as an off-white solid (205 g, 73% yield). MS (apci) m/z=283.1 (M+H).

Step B: Preparation of trans-1-benzyl-4-phenylpyrrolidin-3-amine: To a suspension of trans-1-benzyl-3-nitro-4-phenyl-pyrrolidine (93.9 g, 333 mmol) in EtOH (1.20 L) was added concentrated HCl (450 mL), followed by addition of zinc dust (173 g, 2.66 mol) in small portions over 1.5 hours while maintaining the temperature between 55-60 OC. The reaction mixture was stirred at ambient temperature for 18 hours, then cooled in an ice/water bath followed by addition of concentrated $NH_4OH$ (900 mL). The mixture (pH=10-11) was filtered and the collected zinc was washed with $CHCl_3$. The filtrate was then phase-separated, and the aqueous layer was extracted with $CHCl_3$ (2×400 mL). The combined organics was washed with $H_2O$, brine, dried with $MgSO_4$, filtered and concentrated to afford the title compound as an amber oil (85.0 g, 100% yield). MS (apci) m/z=253.2 (M+H).

Step C: Preparation of trans-(1-benzyl-4-phenyl-pyrrolidin-3-yl)-carbamic acid tert-butyl ester: To a mixture of trans-1-benzyl-4-phenylpyrrolidin-3-amine (85.0 g, 333 mmol), THF (750 mL) and triethylamine (69.6 mL, 500 mmol), was slowly added $(Boc)_2O$ (72.7 g, 333 mmol) in portions over 30 minutes. The reaction mixture was stirred at ambient temperature for 16 hours and was concentrated in vacuo. The residue was dissolved in $CHCl_3$ and was washed with aqueous $Na_2CO_3$ and brine. The organic layer was dried with $MgSO_4$, filtered and concentrated to afford the title compound as a pale-yellow solid (116 g, 99% yield). MS (apci) m/z=353.0 (M+H).

Step D: Preparation of tert-butyl trans-4-phenylpyrrolidin-3-ylcarbamate: A 2 gallon Parr reactor was charged with trans-(1-benzyl-4-phenyl-pyrrolidin-3-yl)-carbamic acid tert-butyl ester (114 g, 323 mmol), EtOH (2 L) and 10% Pd/C (50% wet, 11.0 g). The reactor was purged with $N_2$ several times, filled with $H_2$ to 56-57 psi and agitated at 80° C. When the reaction was complete according to HPLC analysis, the reaction mixture was filtered and the filtrate concentrated to provide the crude product as a yellow solid. The crude material was triturated from toluene to afford the title product as a white solid (68.4 g, 78% yield). MS (apci) m/z=262.9 (M+H).

B, 61.9 g, 245 mmol) in DCM (400 mL) was added DIEA (64.1 mL, 368 mmol) and the mixture was cooled in an ice bath. Trifluoroacetic anhydride (38.1 mL, 270 mmol) was added dropwise over 30 minutes under a $N_2$ atmosphere. After the addition, the mixture was stirred for 30 minutes and then concentrated in vacuo. The residue was dissolved in DCM and washed with saturated aqueous $NaHCO_3$ and brine. The solution was dried with $MgSO_4$, filtered and concentrated in vacuo. The crude material was treated with hexanes and the resulting yellow suspension was stirred at ambient temperature for 1 hour. The solid was collected by filtration, washed with hexanes and dried under vacuum to afford the title compound (78.7 g, 92% yield) as a yellow solid. MS (apci) m/z=349.1 (M+H).

Step B: Preparation of trans-tert-butyl-3-phenyl-4-(2,2,2-trifluoroacetamido) pyrrolidine-1-carboxylate: A solution of trans-N-(1-benzyl-4-phenylpyrrolidin-3-yl)-2,2,2-trifluoroacetamide (78.7 g, 226 mmol) in EtOH (400 mL) was purged with $N_2$ and treated with 20% $Pd(OH)_2$ on activated carbon (31.7 g, 45.2 mmol). The mixture was agitated at ambient temperature under 30 psi of $H_2$ in a parr reactor for 7 hours, and then filtered through GF/F paper and concentrated in vacuo. The residue was dissolved in DCM (250 mL), followed by the addition of TEA (49.4 mL, 355 mmol) and cooling in an ice bath. $Boc_2O$ (56.8 g, 260 mmol) was added slowly over 15 minutes and the reaction mixture was warmed to ambient temperature and stirred for 1 hour. The mixture was washed with saturated aqueous $NaHCO_3$ and brine, then dried with $MgSO_4$. The solution was filtered, concentrated and the residue was purified by silica column chromatography eluting with 40% EtOAc/hexanes to provide the title compound as a white solid (63.2 g, 75% yield). $^1$H NMR ($CDCl_3$) δ 7.23-7.39 (m, 5H), 6.36 (br s, 1H), 4.47-4.55 (m, 1H), 3.92-4.00 (m, 1H), 3.78-4.00 (m, 1H), 3.50-3.59 (m, 1H), 3.22-3.45 (m, 2H), 1.49 (s, 9H).

Step C: Preparation of trans-tert-butyl 3-amino-4-phenylpyrrolidine-1-carboxylate: A solution of trans tert-butyl 3-phenyl-4-(2,2,2-trifluoroacetamido)pyrrolidine-1-carboxylate (63.2 g, 176 mmol) in MeOH (200 mL) was cooled in an ice bath and 2 N NaOH (220 mL, 440 mmol) was added. The reaction mixture was allowed to warm to ambient temperature overnight, then concentrated to approximately 200 mL and diluted with $H_2O$ (200 mL). The aqueous mixture was extracted with DCM and the combined extracts were washed with brine and dried over $Na_2SO_4$. The solution was filtered and concentrated to give the title compound as a light yellow oil (46.2 g, 99% yield). MS (apci) m/z=163.0 (M+H-Boc).

Preparation A2

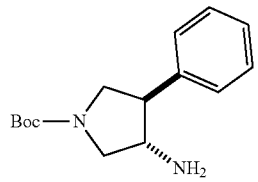

trans-tert-butyl
3-amino-4-phenylpyrrolidine-1-carboxylate

Step A: Preparation of trans-N-(1-benzyl-4-phenylpyrrolidin-3-yl)-2,2,2-trifluoroacetamide: To a solution of trans-1-benzyl-4-phenylpyrrolidin-3-amine (Preparation A, Step Preparation B

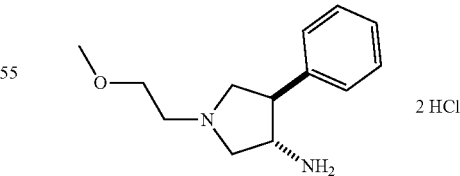

trans-1-(2-methoxyethyl)-4-phenylpyrrolidin-3-amine dihydrochloride

Step A: Preparation of tert-butyl trans-1-(2-methoxyethyl)-4-phenylpyrrolidin-3-ylcarbamate: To a solution of tert-butyl trans-4-phenylpyrrolidin-3-ylcarbamate (Preparation A, 4.82 g, 17.5 mmol) in dry DMF (50 mL) was added sequentially DIEA (9.12 mL, 52.4 mmol) and 1-bromo-2-methoxyethane (1.97 mL, 20.9 mmol). The mixture was stirred at ambient temperature for 46 hours and then poured into H$_2$O (300 mL). The mixture was extracted with EtOAc (3×150 mL) and the combined extracts were washed with brine, dried over MgSO$_4$/activated carbon, filtered through a SiO$_2$ plug capped with packed MgSO$_4$, and eluted with EtOAc. The solution was concentrated and dried in vacuo yielding the product as a white solid (5.15 g, 92% yield). MS (apci) m/z=321.1 (M+H).

Step B: Preparation of trans-1-(2-methoxyethyl)-4-phenylpyrrolidin-3-amine dihydrochloride: To a solution of tert-butyl trans-1-(2-methoxyethyl)-4-phenylpyrrolidin-3-ylcarbamate (5.10 g, 15.9 mmol) in 2:1 EtOAc-MeOH (150 mL) was added 4 N HCl in dioxane (59.7 mL, 239 mmol). The mixture was stirred at ambient temperature for 90 minutes and then concentrated in vacuo. The resulting foam was treated with EtOAc (200 mL), sonicated for 5 minutes and stirred vigorously until a fine white suspension formed. The suspension was filtered, washed with EtOAc and dried under vacuum to afford the title compound as a white powder (5.10 g, 100% yield). MS (apci) m/z=221.1 (M+H).

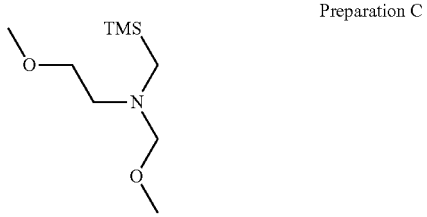

Preparation C 2-methoxy-N-(methoxymethyl)-N-((trimethylsilyl)methyl)ethanamine

Step A: Preparation of 2-methoxy-N-((trimethylsilyl)methyl)ethanamine: To a DMSO solution (15 mL) of 2-methoxyethanamine (14.2 mL, 163 mmol) at 90° C. was added a DMSO (10 mL) solution of (chloromethyl)trimethylsilane (11.4 mL, 81.5 mmol) by addition funnel over 40 minutes. The mixture was heated at 90° C. for 3.5 hours then cooled to ambient temperature. It was then diluted with H$_2$O (150 mL) and extracted with EtOAc (2×150 mL). The combined organic extracts were washed with brine (150 mL), dried with MgSO$_4$, filtered and concentrated to yield the product as a yellow oil (8.14 g, 62% yield). MS (apci) m/z=162.0 (M+H).

Step B: Preparation of 2-methoxy-N-(methoxymethyl)-N-((trimethylsilyl)methyl) ethanamine: A MeOH (2.45 mL) solution of formaldehyde (37% aqueous, 4.91 g, 60.6 mmol) was cooled to 0° C., and treated with a dropwise addition of 2-methoxy-N-((trimethylsilyl) methyl)ethanamine (8.14 g, 50.5 mmol). The biphasic mixture was stirred at 0° C. for 3 hours, then K$_2$CO$_3$ (6.97 g, 50.5 mmol) was added and the mixture was stirred at 0° C. for 1 hour. The yellow oil was decanted onto K$_2$CO$_3$ (2.00 g, 14.4 mmol), and the mixture was stirred at ambient temperature for 2 hours. After the yellow oil was decanted, the solid K$_2$CO$_3$ was washed with Et$_2$O (2×10 mL), and the Et$_2$O washings were combined with the decanted yellow oil and concentrated on a rotary evaporator to yield the product as a yellow oil (9.92 g, 96% yield). $^1$H NMR (CDCl$_3$) δ 4.00 (s, 2H), 3.37-3.43 (m, 2H) 3.29 (s, 3H), 3.19 (s, 3H), 2.77-2.82 (m, 2H), 2.18 (s, 2H), 0.00 (s, 9H).

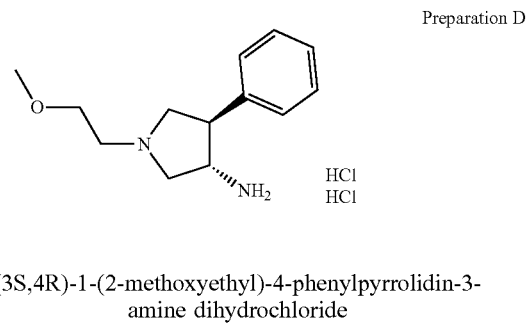

Preparation D (3S,4R)-1-(2-methoxyethyl)-4-phenylpyrrolidin-3-amine dihydrochloride Step A: Preparation of (R)-3-cinnamoyl-4-phenyloxazolidin-2-one: A THF (50 mL) solution of (R)-4-phenyloxazolidin-2-one (5.90 g, 36.2 mmol) was cooled to −78° C. and treated with lithium bis(trimethylsilyl)amide (36.9 mL, 36.9 mmol, 1.0 M in THF) dropwise over 15 minutes. After 15-minute stirring at −78° C., a THF (10 mL) solution of cinnamoyl chloride (6.33 g, 38.0 mmol) was then introduced. The mixture was stirred for 1 hour at −78° C. and 2 hours at ambient temperature before it was quenched with saturated NaHCO$_3$ (50 mL) and stirred for 1 hour. The mixture was diluted with EtOAc (200 mL), washed with water and brine, dried over MgSO$_4$, filtered and concentrated to give the product as a pale yellow solid (10.6 g, 99.9% yield). MS (apci) m/z=293.9 (M+H).

Step B: Preparation of (R)-3-((3S,4R)-1-(2-methoxyethyl)-4-phenylpyrrolidine-3-carbonyl)-4-phenyloxazolidin-2-one: A toluene (500 mL) solution of (R)-3-cinnamoyl-4-phenyloxazolidin-2-one (8.00 g, 27.3 mmol) and TFA (0.210 mL, 2.73 mmol) was first cooled to 5-10° C., followed by dropwise addition of a toluene (30 mL) solution of 2-methoxy-N-(methoxymethyl)-N-((trimethylsilyl)methyl) ethanamine (Preparation C, 8.40 g, 40.9 mmol). The resulting mixture was warmed up to ambient temperature and stirred for 3 hours, then washed with saturated NaHCO$_3$ and water, dried with MgSO$_4$, filtered and concentrated in vacuo. The crude material was purified by silica column chromatography, eluting with 16-20% EtOAc/hexanes, to afford the product (6.5 g, 60% yield). MS (apci) m/z=395.2 (M+H).

Step C: Preparation of (3S,4R)-1-(2-methoxyethyl)-4-phenylpyrrolidine-3-carboxylic acid: To a 1M aqueous solution of LiOH (41.2 mL, 41.2 mmol) at 0° C. was added H$_2$O$_2$ (3.37 mL, 33.0 mmol, 30 wt %). The mixture was then added to solution of (R)-3-((3S,4R)-1-(2-methoxyethyl)-4-phenylpyrrolidine-3-carbonyl)-4-phenyloxazolidin-2-one (6.50 g, 16.5 mmol) in THF (100 mL) over 10 minutes at 0° C. After 1 hour stirring, 2.0 M aqueous Na$_2$SO$_3$ (33.0 mL, 65.9 mmol) was introduced at 0° C. and the reaction mixture was warmed to ambient temperature. After stirring for 10 minutes, the mixture was washed with EtOAc (50 mL). The aqueous layer was acidified with 1 N HCl until pH 3-5, then treated with NaCl (10 g), then extracted with 10% iPrOH/DCM. The organic layer was dried with MgSO$_4$, filtered and concentrated to give the product (4.11 g, 100% yield). MS (apci) m/z=250.1 (M+H).

Step D: Preparation of benzyl (3S,4R)-1-(2-methoxyethyl)-4-phenylpyrrolidin-3-ylcarbamate: To a solution of (3S,4R)-1-(2-methoxyethyl)-4-phenylpyrrolidine-3-carboxylic acid (4.11 g, 16.5 mmol) in toluene (70 mL) was added TEA (5.74 mL, 41.2 mmol) followed by diphenyl phosphoryl azide (4.99 mL, 23.1 mmol). The mixture was stirred at ambient temperature for 1 hour and then heated to reflux for 1 hour. Benzyl alcohol (3.42 mL, 33.0 mmol) was then added and the reaction mixture was refluxed for 15 hours. The reaction mixture was treated with EtOAc, washed with water, dried over MgSO$_4$, filtered and concentrated in vacuo. The crude material was purified by silica column chromatography, eluting with 1% MeOH/DCM to afford the product (2.5 g, 43% yield). MS (apci) m/z=355.2 (M+H).

Step E: Preparation of (3S,4R)-1-(2-methoxyethyl)-4-phenylpyrrolidin-3-amine dihydrochloride: Benzyl (3S,4R)-1-(2-methoxyethyl)-4-phenylpyrrolidin-3-ylcarbamate (0.257 g, 0.725 mmol) and TFA (3.91 mL, 50.8 mmol) were heated at 60° C. for 17 hours. The reaction mixture was concentrated in vacuo, using toluene to azeotrope, then treated with 2 N HCl in Et$_2$O and concentrated again to give the title compound (0.21 g, 100% yield) as an off-white solid. MS (apci) m/z=221.2 (M+H).

Preparation E

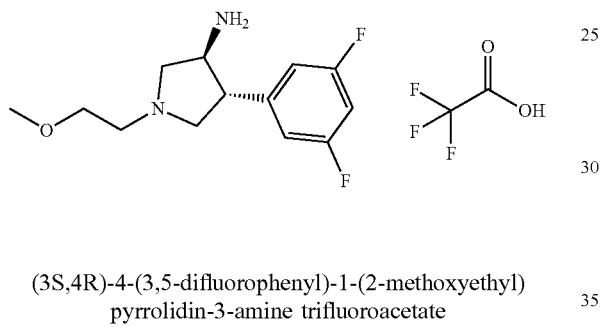

(3S,4R)-4-(3,5-difluorophenyl)-1-(2-methoxyethyl)pyrrolidin-3-amine trifluoroacetate Step A: Preparation of (R,E)-3-(3-(3,5-difluorophenyl)acryloyl)-4-phenyloxazolidin-2-one: To a solution of (E)-3-(3,5-difluorophenyl)acrylic acid (10.0 g, 54.3 mmol) in Et$_2$O (150 mL) at 0° C. was added DIEA (9.48 mL, 54.3 mmol) followed by pivaloyl chloride (6.69 mL, 54.3 mmol). The mixture was stirred at 0° C. for 1 hour and cooled to −78° C. Meanwhile (R)-4-phenyloxazolidin-2-one (8.86 g, 54.3 mmol) in THF (200 mL) was cooled to −78° C. and butyllithium (21.7 mL, 2.5 M, 54.3 mmol) was added slowly. The mixture was stirred for 20 minutes at −78° C. and transferred by cannula to the solution of mixed anhydride. The combined mixture was stirred at −78° C. for 15 min, allowed to warm to 0° C. and stirred for an additional 30 minutes. The reaction mixture was quenched with saturated NH$_4$Cl (25 mL), diluted with EtOAc (600 mL), washed with water, NaHCO$_3$, and brine, dried over MgSO$_4$, and concentrated in vacuo. The crude material was purified by silica column chromatography, eluting with 10-20% Ethyl acetate/Hexanes to afford the product (11.0 g, 61.5% yield).

Step B: Preparation of (3S,4R)-4-(3,5-difluorophenyl)-1-(2-methoxyethyl)pyrrolidin-3-amine trifluoroacetic acid salt: Prepared by the methods described in Preparation D, Steps B through E, replacing (R)-3-cinnamoyl-4-phenyloxazolidin-2-one with (R,E)-3-(3-(3,5-difluorophenyl)acryloyl)-4-phenyloxazolidin-2-one to afford the title compound (1.70 g, 102% yield). MS (apci) m/z=257.2 (M+H).

Preparation F

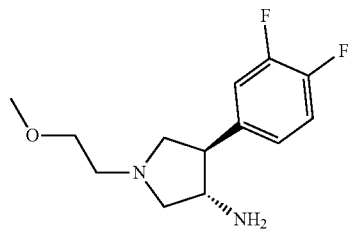

(3S,4R)-4-(3,4-difluorophenyl)-1-(2-methoxyethyl)pyrrolidin-3-amine

Prepared according to the method described in Preparation D, replacing cinnamoyl chloride with (E)-3-(3,4-difluorophenyl)acryloyl chloride. MS (apci) m/z=257.1 (M+H).

Preparation G

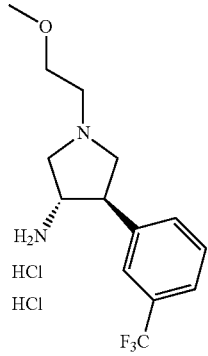

(3S,4R)-1-(2-methoxyethyl)-4-(3-(trifluoromethyl)phenyl)pyrrolidin-3-amine dihydrochloride Step A: Preparation of tert-butyl (3S,4R)-1-(2-methoxyethyl)-4-(3-(trifluoromethyl)-phenyl)pyrrolidin-3-ylcarbamate: A solution of tert-butyl (3S,4R)-4-(3-(trifluoromethyl)phenyl)-pyrrolidin-3-ylcarbamate (100 mg, 0.303 mmol, commercially available), N,N-diethylpropan-2-amine (0.145 mL, 0.908 mmol) and 1-bromo-2-methoxyethane (0.0361 mL, 0.363 mmol) in DMF (1 mL) was stirred at ambient temperature for 2 hours, then heated to 60° C. for 4 hours, then cooled to ambient temperature overnight. After partitioning between EtOAc and saturated NaHCO$_3$ (10 mL each), the organic layer was washed with water and brine (2×10 mL each), dried over Na$_2$SO$_4$, filtered and concentrated to yield the crude product as white solid (80 mg, 68% yield). LCMS (apci) m/z=389.1 (M+H).

Step B: Preparation of (3S,4R)-1-(2-methoxyethyl)-4-(3-(trifluoromethyl)phenyl)-pyrrolidin-3-amine dihydrochloride: A solution of tert-butyl (3S,4R)-1-(2-methoxyethyl)-4-(3-(trifluoromethyl)phenyl)pyrrolidin-3-ylcarbamate (80.0 mg, 0.206 mmol) in 5-6 N HCl in IPA (4.12 mL, 20.6 mmol) was stirred at ambient temperature for 1 hour, followed by concentrating in vacuo and triturating with Et$_2$O to afford the product as beige solid (74 mg, 99.5% yield). LCMS (apci) m/z=289.1 (M+H).

Preparation H

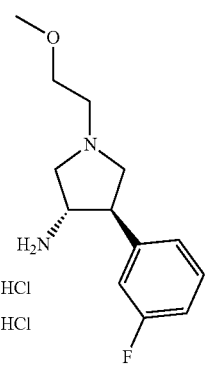

(3S,4R)-4-(3-fluorophenyl)-1-(2-methoxyethyl)pyrrolidin-3-amine dihydrochloride

Prepared according to the method of Preparation G, replacing tert-butyl (3S,4R)-4-(3-(trifluoromethyl)phenyl)-pyrrolidin-3-ylcarbamate with tert-butyl (3S,4R)-4-(3-fluorophenyl) pyrrolidin-3-ylcarbamate to afford the title compound. LCMS (apci) m/z=239.1 (M+H).

Preparation I

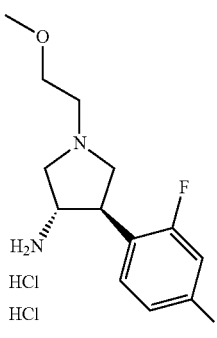

(3S,4R)-4-(2,4-difluorophenyl)-1-(2-methoxyethyl) pyrrolidin-3-amine dihydrochloride Prepared according to the method of Preparation G, replacing tert-butyl (3S,4R)-4-(3-(trifluoromethyl)phenyl)-pyrrolidin-3-ylcarbamate with tert-butyl (3S,4R)-4-(2,4 di-fluoro-phenyl)pyrrolidin-3-ylcarbamate to afford the title compound. LCMS (apci) m/z=257.1 (M+H).

Preparation J

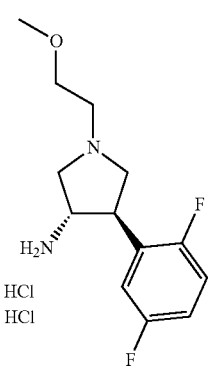

(3S,4R)-4-(2,5-difluorophenyl)-1-(2-methoxyethyl) pyrrolidin-3-amine dihydrochloride Prepared according to the method of Preparation G, replacing tert-butyl (3S,4R)-4-(3-(trifluoromethyl)phenyl)-pyrrolidin-3-ylcarbamate with tert-butyl (3S,4R)-4-(2,5 di-fluoro-phenyl)pyrrolidin-3-ylcarbamate to afford the title compound. LCMS (apci) m/z=257.1 (M+H).

Preparation K

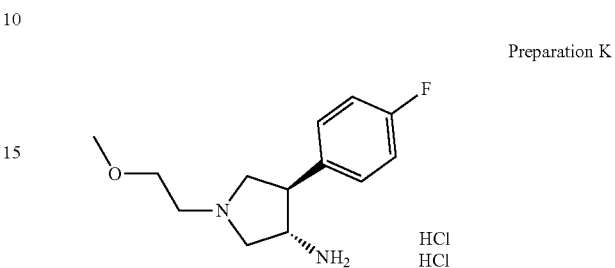

(3S,4R)-4-(4-fluorophenyl)-1-(2-methoxyethyl)pyrrolidin-3-amine dihydrochloride

Prepared according to the method described in Preparation D, replacing cinnamoyl chloride with (E)-3-(4-fluorophenyl)acryloyl chloride. MS (apci) m/z=239.1 (M+H).

Preparation L1

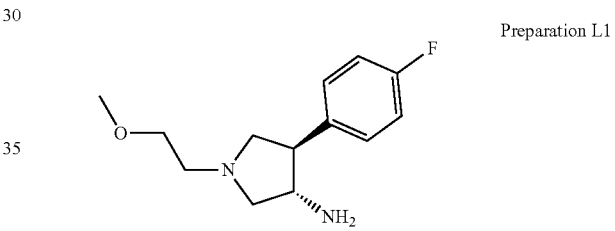

(3S,4R)-4-(4-fluorophenyl)-1-(2-methoxyethyl)pyrrolidin-3-amine

Step A: Preparation of (E)-1-fluoro-4-(2-nitrovinyl)benzene: Acetic acid (2.0 L, 35.5 mol) and ammonium acetate (310.5 g, 4.03 mol) were stirred at ambient temperature for 1 hour, then nitromethane (611 mL, 11.3 mol) and 4-fluorobenzaldehyde (200 g, 1.61 mol) were added and the reaction mixture was heated to 90° C. for 3 hours. The reaction was allowed to cool to ambient temperature, then H$_2$O (4 L) was added over 2 hours with mechanical stirring. The suspension was stirred 1 hour, then filtered and washed with 2:1 water/acetic acid (500 mL). The solids were dried in a vacuum oven (50° C.) to afford the title product as a pale yellow solid (238 g, 1.42 mol, 88% yield). $^1$H NMR (CDCl$_3$) δ 7.98 (1H), 7.55 (3H), 7.16 (2H).

Step B: Preparation of trans-3-(4-fluorophenyl)-1-(2-methoxyethyl)-4-nitro-pyrrolidine: To a suspension of (E)-1-fluoro-4-(2-nitrovinyl)benzene (201 g, 1.20 mol) in DCM (1.09 L) and TFA (9.3 mL, 120 mmol) was added dropwise over 30 minutes 2-methoxy-N-(methoxymethyl)-N-((trimethylsilyl)methyl)ethanamine (Preparation C; 383 g, 1.86 mol) and the internal reaction temperature was maintained between 23-36° C. by cooling in an ice bath. The reaction mixture was poured into aqueous phosphate buffer solution (pH 7, 500 mL) and diluted with DCM (300 mL). The phases were separated and the aqueous phase was extracted with DCM (400 mL). The organic phases were combined, washed with brine (300 mL), dried (MgSO$_4$), filtered and concentrated under reduced pressure. The crude oil was purified by silica column chromatography eluting with 40% EtOAc/heptane to afford the title compound as a yellow oil (245 g, 76% yield). MS (apci) m/z=269.1 (M+H).

Step C: Preparation of trans-4-(4-fluorophenyl)-1-(2-methoxyethyl)pyrrolidin-3-amine: To a solution of trans-3-(4-fluorophenyl)-1-(2-methoxyethyl)-4-nitropyrrolidine (289 g, 1.08 mol) in EtOH (1 L) was added platinum(IV) oxide (24.5 g, 108 mmol) in a Parr vessel and installed into a Parr shaker. The vessel was evacuated and backfilled with nitrogen (3×), then evacuated and backfilled with hydrogen (60 psi). The vessel was recharged with hydrogen as needed until the reaction was complete. The reaction mixture was filtered through Celite® and rinsed with MeOH (50 mL), then concentrated under reduced pressure to afford the title compound as a yellow oil (243 g, 95% yield). MS (apci) m/z=239.1 (M+H).

Step D: Preparation of (3S,4R)-4-(4-fluorophenyl)-1-(2-methoxyethyl)pyrrolidin-3-amine (2S,3S)-2,3-bis(4-methylbenzoyloxy)succinate: To a solution of (3 S,4R)-4-(4-fluorophenyl)-1-(2-methoxyethyl)pyrrolidin-3-amine (120 g, 504 mmol) in THF (3.0 L) and H$_2$O (333 mL) was added di-p-toluoyl-D-tartaric acid (195 g, 504 mmol). Stirred at ambient temperature for 1 hour, then placed in a freezer (−11° C.) for 18 hours. The mixture was stirred to give a slurry, filtered, and rinsed with Et$_2$O (4×100 mL). The solid was dried in vacuum oven (40° C.) for 4 hours, then recrystallized twice by the following procedure: the solid was dissolved in THF (1.06 mL) and H$_2$O (118 mL) with heating to 45° C., then allowing to cool to ambient temperature over 2 hours, then placed in a freezer (−11° C.) for 18 hours; the mixture was stirred to give a slurry, filtered, and rinsed with Et$_2$O (4×100 mL). After two recrystallizations, the solid was dried in vacuum oven (40° C.) for 18 hours to afford the title compound as a white crystalline solid (96 g, 31% yield). MS (apci) m/z=239.2 (M+H).

Step E: Preparation of (3S,4R)-4-(4-fluorophenyl)-1-(2-methoxyethyl)pyrrolidin-3-amine: (3 S,4R)-4-(4-fluorophenyl)-1-(2-methoxyethyl)pyrrolidin-3-amine (2S,3 S)-2,3-bis(4-methylbenzoyloxy)succinate (20 g, 32.0 mmol) was dissolved in DCM (300 mL) and washed with 1M NaOH (2×200 mL). The combined aqueous phases were extracted with DCM (200 mL). The combined organic extracts were washed with brine (200 mL), dried (MgSO$_4$), filtered and concentrated, then dried under vacuum to afford the title compound as a yellow oil (6.17 g, 81%, >99% ee). MS (apci) m/z=239.1 (M+H).

The following pyrrolidine intermediates were made according to the method of Preparation L1, using the appropriate benzaldehyde in Step A and replacing EtOH and platinum(IV) oxide with MeOH and Raney nickel respectively in Step C. For preparation L3, the 90% THF/H$_2$O in Step D was replaced with 85% MeOH/H$_2$O.

| Preparation # | Structure | Name | Data |
| --- | --- | --- | --- |
| L2 | 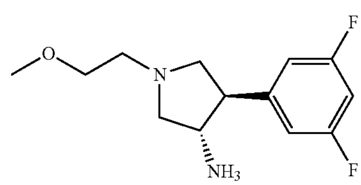 [SMILES: COCCN1C[C@@H](N)[C@H](c2cc(F)cc(F)c2)C1] | (3S,4R)-4-(3,5-difluorophenyl)-1-(2-methoxyethyl)pyrrolidin-3-amine | MS (apci) m/z = 257.1 (M + H) |
| L3 | 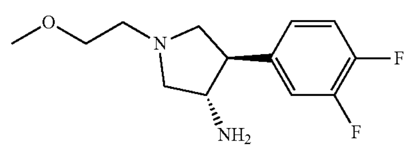 | (3S,4R)-4-(3,4-difluorophenyl)-1-(2-methoxyethyl)pyrrolidin-3-amine (2S,3S)-2,3-bis(4-methylbenzoyloxy)succinate | MS (apci) m/z = 257.1 (M + H) |
| L4 | 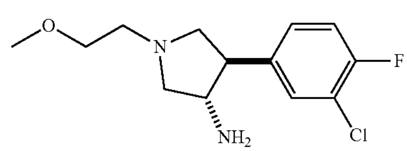 [SMILES: COCCN1C[C@@H](N)[C@H](c2ccc(F)c(Cl)c2)C1] | trans-4-(3-chloro-4-fluorophenyl)-1-(2-methoxyethyl)pyrrolidin-3-amine | MS (apci) m/z = 273.1 (M + H) |
| L5 | 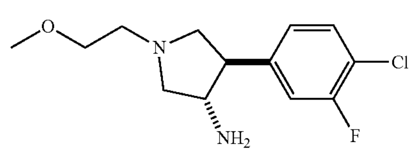 [SMILES: COCCN1C[C@@H](N)[C@H](c2ccc(Cl)c(F)c2)C1] | trans-4-(4-chloro-3-fluorophenyl)-1-(2-methoxyethyl)pyrrolidin-3-amine | MS (apci) m/z = 273.1 (M + H) |
| L6 | 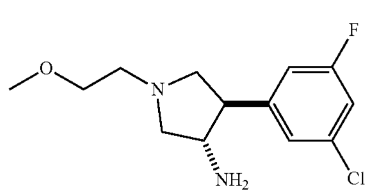 [SMILES: COCCN1C[C@@H](N)[C@H](c2cc(F)cc(Cl)c2)C1] | trans-4-(3-chloro-5-fluorophenyl)-1-(2-methoxyethyl)pyrrolidin-3-amine | MS (apci) m/z = 273.1 (M + H) |

-continued

| Preparation # | Structure | Name | Data |
|---|---|---|---|
| L7 | 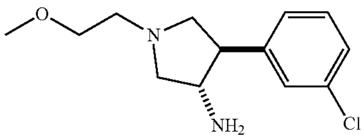 [SMILES: COCCN1C[C@@H](N)[C@H](c2cccc(Cl)c2)C1] | trans-4-(3-chlorophenyl)-1-(2-methoxyethyl)pyrrolidin-3-amine | MS (apci) m/z = 255.1 (M + H) |
| L8 | 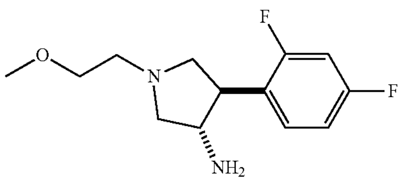 [SMILES: COCCN1C[C@@H](N)[C@H](c2ccc(F)cc2F)C1] | trans-4-(2,4-difluorophenyl)-1-(2-methoxyethyl)pyrrolidin-3-amine | MS (apci) m/z = 256.1 (M + H) |
| L9 | 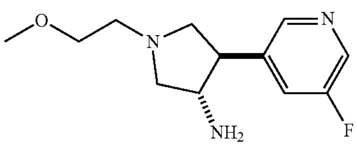 [SMILES: COCCN1C[C@@H](N)[C@H](c2cncc(F)c2)C1] | trans-4-(5-fluoropyridin-3-yl)-1-(2-methoxyethyl)pyrrolidin-3-amine | MS (apci) m/z = 240.1 (M + H) |
| L10 | 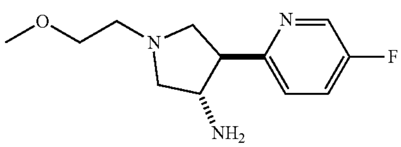 [SMILES: COCCN1C[C@@H](N)[C@H](c2ccc(F)cn2)C1] | trans-4-(5-fluoropyridin-2-yl)-1-(2-methoxyethyl)pyrrolidin-3-amine | $^1$H NMR consistent with expected product |
| L11 | 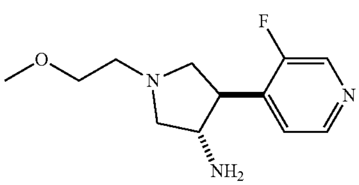 [SMILES: COCCN1C[C@@H](N)[C@H](c2ccncc2F)C1] | trans-4-(3-fluoropyridin-4-yl)-1-(2-methoxyethyl)pyrrolidin-3-amine | Not available |
| L12 | 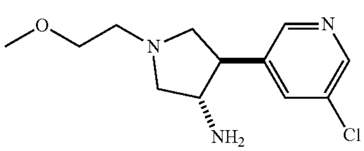 [SMILES: COCCN1C[C@@H](N)[C@H](c2cncc(Cl)c2)C1] | trans-4-(5-chloropyridin-3-yl)-1-(2-methoxyethyl)pyrrolidin-3-amine | MS (apci) m/z = 256.1 (M + H) |
| L13 | 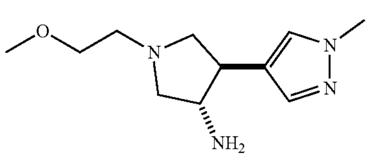 | trans-1-(2-methoxyethyl)-4-(1-methyl-1H-pyrazol-4-yl)pyrrolidin-3-amine | $^1$H NMR consistent with expected product |
| L14 | 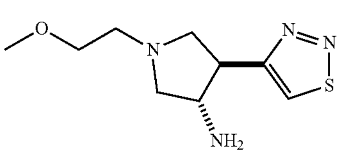 | trans-1-(2-methoxyethyl)-4-(1,2,3-thiadiazol-4-yl)pyrrolidin-3-amine | Not available |

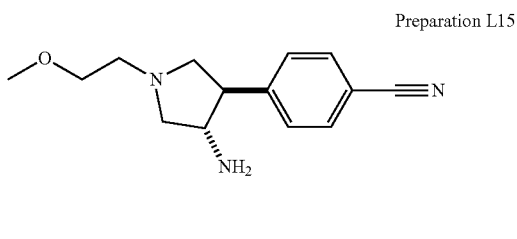

4-(trans-4-amino-1-(2-methoxyethyl)pyrrolidin-3-yl)benzonitrile

Prepared according to the method described in Preparation L1, Steps A to C, replacing 4-fluorobenzaldehyde with 4-formylbenzonitrile in Step A and replacing EtOH and platinum(IV) oxide with MeOH, Zn (dust) and saturated NH$_4$Cl, respectively in Step C. MS (apci) m/z=246.1 (M+H).

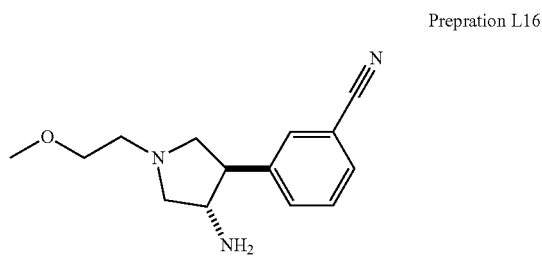

3-(trans-4-amino-1-(2-methoxyethyl)pyrrolidin-3-yl)benzonitrile

Prepared according to the method described in Preparation L1, Steps A to C, replacing 4-fluorobenzaldehyde with 3-formylbenzonitrile in Step A, and replacing EtOH and platinum(IV) oxide with MeOH, Zn (dust) and saturated NH$_4$Cl, respectively, in Step C. MS (apci) m/z=246.2 (M+H).

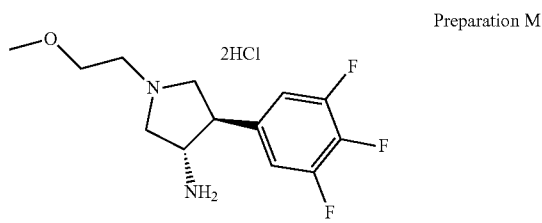 [SMILES: COCCN1C[C@@H](N)[C@H](c2cc(F)c(F)c(F)c2)C1]

(3S,4R)-1-(2-methoxyethyl)-4-(3,4,5-trifluorophenyl)pyrrolidin-3-amine dihydrochloride Prepared according to the method described in Preparation D, replacing cinnamoyl chloride with (E)-3-(3,4,5-trifluorophenyl)acryloyl chloride. $^1$H NMR (D$_2$O) δ 7.06-7.10 (m, 2H), 4.13-4.20 (m, 1H), 3.92-3.99 (m, 2H), 3.71-3.74 (m, 1H), 3.57-3.63 (m, 3H), 3.41-3.49 (m, 3H), 3.25 (s, 3H).

Trans-5-(4-amino-1-(2-methoxyethyl)pyrrolidin-3-yl)-2-fluorobenzonitrile

Step A: (E)-2-fluoro-5-(2-nitrovinyl)benzonitrile: To a solution of 2-fluoro-5-formylbenzonitrile (3.84 g, 25.0 mmol) in 3:1 CH$_3$NO$_2$/CH$_3$CN (25 mL) was added DMAP (0.305 g, 2.50 mmol) and the mixture stirred at ambient temperature for 23 hours. The mixture was cooled on an ice bath and Ac$_2$O (3.54 mL, 37.5 mmol) was added. The mixture was stirred for 5 minutes, allowed to reach ambient temperature and stirred for 1 hour. The mixture was concentrated to a yellow solid. The solid was suspended in iPrOH (70 mL) and stirred for 10 minutes. The suspension was collected via vacuum filtration, the cake washed with iPrOH and dried in vacuum to afford the title compound as a light tan powder (3.36 g, 70%). $^1$H NMR (CDCl$_3$) δ 7.96 (d, 1H), 7.79-7.88 (m, 2H), 7.57 (d, 1H), 7.36 (t, 1H).

Step B: Trans-2-fluoro-5-(1-(2-methoxyethyl)-4-nitropyrrolidin-3-yl)benzonitrile: Using (E)-2-fluoro-5-(2-nitrovinyl)benzonitrile in Step B of the procedure describe in Preparation L1, the title compound was prepared as light gold syrup (1.56 g, 53%). MS (apci) m/z=294.1 (M+H).

Step C: Trans-5-(4-amino-1-(2-methoxyethyl)pyrrolidin-3-yl)-2-fluorobenzonitrile: A solution of trans-2-fluoro-5-(1-(2-methoxyethyl)-4-nitropyrrolidin-3-yl)benzonitrile (450 mg, 1.53 mmol) in MeOH (6.0 mL) was cooled to 0°. Zn dust (1.00 mg, 15.3 mmol) and saturated aqueous NH$_4$Cl (1.0 mL) were added sequentially and the mixture was stirred for 5 minutes. The mixture was allowed to reach ambient temperature and stirred until complete by LCMS analysis. The mixture was filtered through packed Celite® using MeOH for rinsing and elution and the filtrate was concentrated to a colorless syrup. The syrup was treated with 1M K$_2$CO$_3$ (15 mL), mixed and extracted with CH$_2$Cl$_2$ (3×). The combined CH$_2$Cl$_2$ extracts were dried over Na$_2$SO$_4$, filtered and concentrated to provide the title compound as a colorless syrup (412 mg, 100%). MS (apci) m/z=264.1 (M+H).

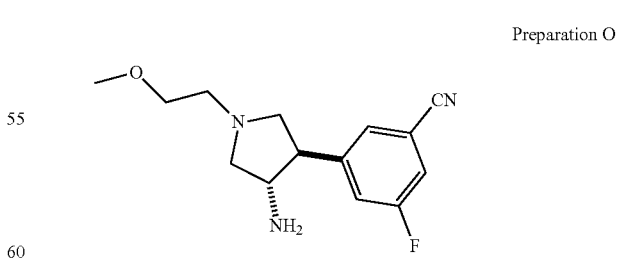

Trans-3-(4-amino-1-(2-methoxyethyl)pyrrolidin-3-yl)-5-fluorobenzonitrile

Step A: 3-fluoro-5-formylbenzonitrile: A solution of 3-bromo-5-fluorobenzonitrile (5.00 g, 25.0 mmol) in dry THF (25 mL) was cooled to 0° C. and 2M iPrMgCl (15.0 mL, 30.0 mmol) in THF was added dropwise over 5 minutes. The mixture was stirred at 0° C. for 15 minutes then at ambient temperature for 1 hour. The mixture was cooled to 0° C. and dry DMF (5.81 mL, 75.0 mmol) was added. The mixture was stirred for 17 hours during which time the temperature reached ambient temperature after 2 hours. The mixture was added to ice water (150 mL) and Et$_2$O (100 mL). The biphasic mixture was stirred and treated with 6M HCl to aqueous pH=3. The organic layer was removed and the aqueous layer extracted with Et$_2$O (2×). The combined Et$_2$O fractions were washed with saturated NaCl and dried over MgSO$_4$/activated carbon. The dried solution was filtered through a SiO$_2$ plug eluting with Et$_2$O. The filtrate was concentrated to give the title compound as a yellow solid that was dried in vacuum (3.68 g, 99%). $^1$H NMR (CDCl$_3$) δ 10.0 (s, 1H), 8.00 (s, 1H), 7.81-7.86 (m, 1H), 7.62-7.67 (m, 1H).

Step B: Trans-3-(4-amino-1-(2-methoxyethyl)pyrrolidin-3-yl)-5-fluorobenzonitrile: The tile compound was prepared using 3-fluoro-5-formylbenzonitrile in the procedure described for the preparation of trans-5-(4-amino-1-(2-methoxyethyl)pyrrolidin-3-yl)-2-fluorobenzonitrile (Preparation N). The compound was isolated as a colorless syrup (542 mg, 93%). MS (apci) m/z=264.1 (M+H).

Preparation P

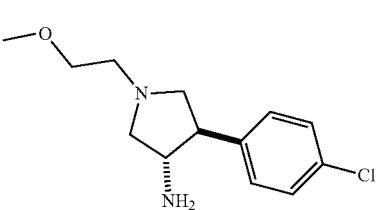

Trans-1-(2-methoxyethyl)-4-(4-chlorophenyl)pyrrolidin-3-amine

Step A: Trans-3-(4-chlorophenyl)-1-(2-methoxyethyl)-4-nitropyrrolidine: Using (E)-1-chloro-4-(2-nitrovinyl)benzene in Step B of the procedure describe in Preparation L1, the title compound was prepared as viscous colorless oil (5.10 g, 64%). MS (apci) m/z=285.0 (M+H).

Step B: Trans-1-(2-methoxyethyl)-4-(4-chlorophenyl)pyrrolidin-3-amine: To a suspension of 2800 Raney Nickel (50 wt % in H$_2$O, 0.873 g, 5.10 mmol) in MeOH (25 mL) was added trans-3-(4-chlorophenyl)-1-(2-methoxyethyl)-4-nitropyrrolidine (2.90 g, 10.2 mmol) in MeOH (25 mL). The mixture was flushed with H$_2$ gas and stirred under a balloon atmosphere of H$_2$ for 16 hours. The mixture was purged with N$_2$ gas and filtered through packed Celite® using MeOH for rinsing and elution. The filtrate was concentrated to a cloudy oil. The oil was dissolved in CH$_2$Cl$_2$ and dried over Na$_2$SO$_4$/activated carbon. The solution was filtered and concentrated to provide the title compound as a light gold oil that was dried in vacuum (2.46 g, 95%). MS (apci) m/z=255.1 (M+H).

Table 1 provides a list of commercially available pyrazole intermediates which were used in the synthesis of compounds described in the Examples.

TABLE 1

| Pyrazole | Vendor/Catalog# | CAS# |
| --- | --- | --- |
| 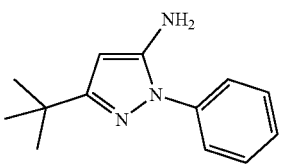 [SMILES: CC(C)(C)c1cc(N)n(-c2ccccc2)n1] | Oakwood, 021512 | 126208-61-5 |
| 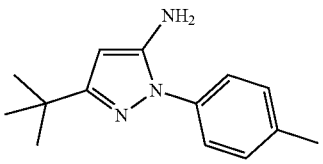 [SMILES: Cc1ccc(-n2nc(C(C)(C)C)cc2N)cc1] | Array BioPharma, A1075-0 | N/A |
| 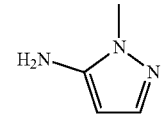 | Maybridge, GK03066 | 1192-21-8 |
| 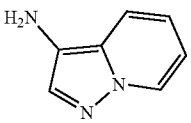 | J & W PharmaLab, 68-0257S | N/A |

TABLE 1-continued
| Pyrazole | Vendor/Catalog# | CAS# |
|---|---|---|
| 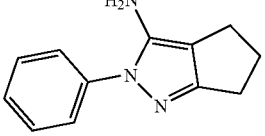 | Ryan Scientific, EN300-14400 | 89399-92-8 |
|  | Oakwood, 021516 | N/A |
| 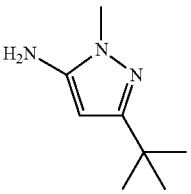 | Alfa Aesar, AAB20095-06 | 118430-73-2 |
| 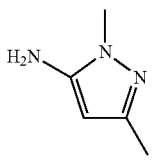 | Aldrich, 532223 | 3524-32-1 |
| 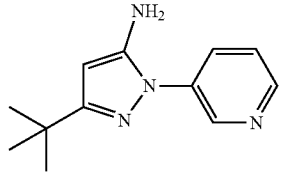 [SMILES: CC(C)(C)c1cc(N)n(-c2cccnc2)n1] | Accela ChemBio Chem Co, SY003755 | 876299-97-7 |
| 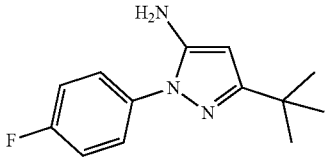 [SMILES: CC(C)(C)c1cc(N)n(-c2ccc(F)cc2)n1] | ChemImpex, 18122 | 778611-16-8 |
| 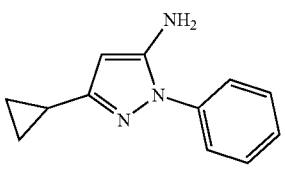 [SMILES: Nc1cc(C2CC2)nn1-c1ccccc1] | Oakwood, 017105 | 175137-45-8 |
| 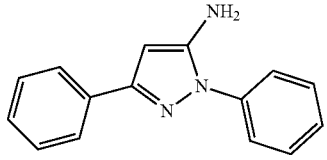 [SMILES: Nc1cc(-c2ccccc2)nn1-c1ccccc1] | Alfa Aesar, AAB20464-06 | 5356-71-8 |
| 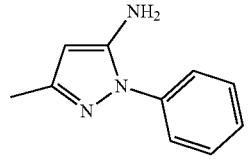 | Aldrich, 541001 | 1131-18-6 |

TABLE 1-continued
| Pyrazole | Vendor/Catalog# | CAS# |
|---|---|---|
| 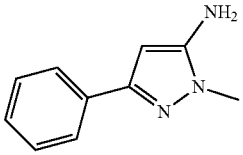 | Alfa Aesar, AAA15754-06 | 10199-50-5 |
| 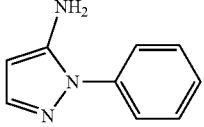 [SMILES: Nc1ccnn1-c1ccccc1] | TCI America, A0174 | 826-85-7 |
| 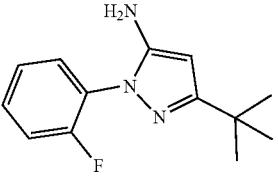 [SMILES: CC(C)(C)c1cc(N)n(-c2ccccc2F)n1] | Oakwood, 023890 | N/A |
| 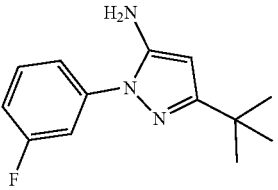 [SMILES: CC(C)(C)c1cc(N)n(-c2cccc(F)c2)n1] | J & W Pharmalab, 68-0035S | 1187931-80-1 |
| 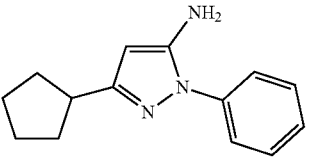 [SMILES: Nc1cc(C2CCCC2)nn1-c1ccccc1] | VWR, EN300-09508 | N/A |
| 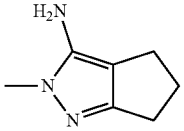 | ChemBridge, 4019184 | 885529-68-0 |
| 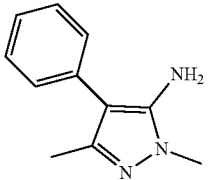 | ChemBridge, 4001950 | N/A |
| 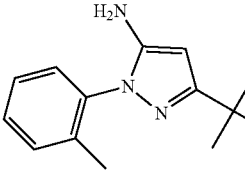 | ChemImpex, 19156 | 337533-96-7 |
| 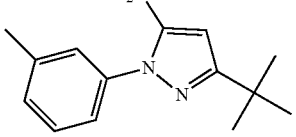 | ChemImpex, 19155 | 898537-77-4 |

TABLE 1-continued
| Pyrazole | Vendor/Catalog# | CAS# |
|---|---|---|
| 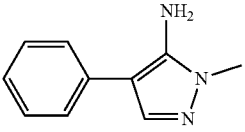 | ChemBridge, 4006072 | N/A |
| 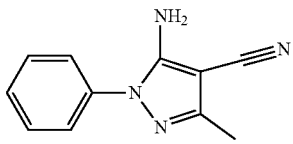 | Oakwood, 005982 | 5346-56-5 |
| 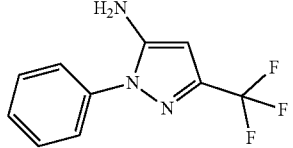 [SMILES: Nc1cc(C(F)(F)F)nn1-c1ccccc1] | ChemImpex, 18771 | 182923-55-3 |
| 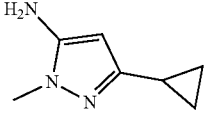 | Maybridge, KM00278 | 118430-74-3 |
| 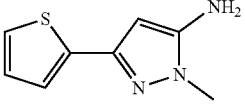 | Maybridge, KM00835 | 118430-78-7 |
| 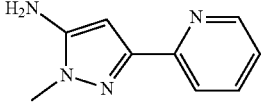 | ChemBridge, 4015288 | N/A |
| 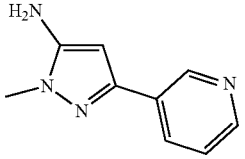 | ChemBridge, 4015289 | N/A |
| 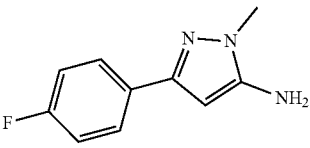 | Matrix, 020274 | N/A |
| 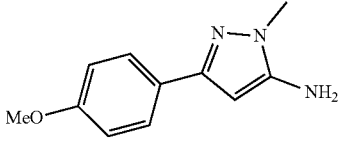 | Matrix, 019183 | N/A |
| 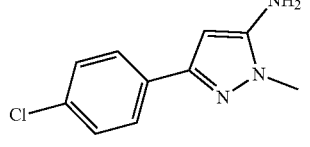 | Maybridge, KM 04038 | 126417-82-1 |

TABLE 1-continued

| Pyrazole | Vendor/Catalog# | CAS# |
|---|---|---|
| (structure: 5-amino-1,3-dimethyl-4-phenylpyrazole) | ChemBridge, 4001950 | N/A |
| (structure: 5-amino-4-cyano-1-phenyl-3-(cyanomethyl)pyrazole) | Lancaster, AAA17470-06 | 7152-40-1 |
| (structure: 5-amino-3-ethyl-4-methyl-1-phenylpyrazole) | ChemBridge, 4010196 | 91642-97-6 |
| (structure: ethyl 5-amino-1-phenyl-1H-pyrazole-4-carboxylate) | VWR, AAA13296-14 | 16078-71-0 |

N/A = Not available

Intermediate P1

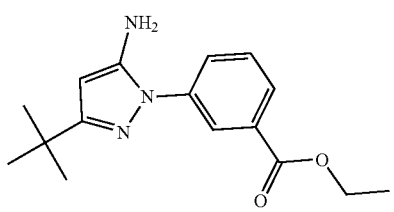

Ethyl 3-(5-amino-3-tert-butyl-1H-pyrazol-1-yl)benzoate

To a suspension of ethyl 3-hydrazinylbenzoate hydrochloride (500 mg, 2.31 mmol) in EtOH (20 mL) was added 4,4-dimethyl-3-oxopentanenitrile (318 mg, 2.54 mmol). The reaction mixture was heated to reflux for 18 hours, then cooled to ambient temperature and concentrated in vacuo. The crude product was purified by silica column chromatography, eluting with 0-5% MeOH/DCM to yield the product as a yellow oil (154 mg, 23% yield). MS (apci) m/z=288.2 (M+H).

The compounds in Table 2 were prepared by the method as described for Intermediate P1, substituting 4,4-dimethyl-3-oxopentanenitrile with the appropriate cyanoketone and ethyl 3-hydrazinylbenzoate hydrochloride with the appropriate hydrazine.

TABLE 2

| Intermediate # | Structure | Data |
|---|---|---|
| P2 | (3,4-dimethyl-1-phenyl-1H-pyrazol-5-amine) | MS (apci) m/z = 188.2 (M + H) |

TABLE 2-continued
| Intermediate # | Structure | Data |
|---|---|---|
| P3 | 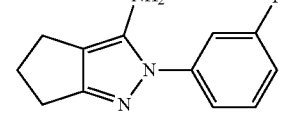 | MS (apci) m/z = 218.1 (M + H) |
| P4 | 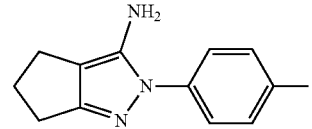 | MS (apci) m/z = 218.2 (M + H) |
| P5 | 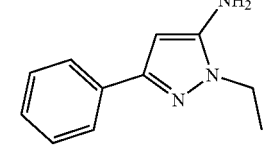 | MS (apci) m/z = 188.2 (M + H) |
| P6 | 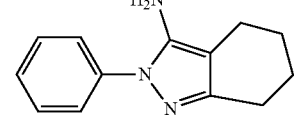 | MS (apci) m/z = 214.2 (M + H) |
| P7 | 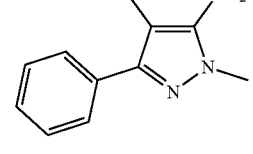 | MS (apci) m/z = 188.2 (M + H) |
| P8 | 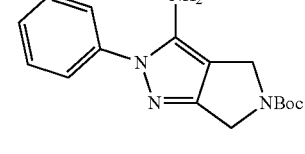 | MS (apci) m/z = 301.0 (M + H) |
| P9 | 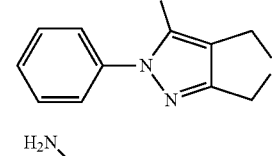 | MS (apci) m/z = 218.1 (M + H) |
| P10 | 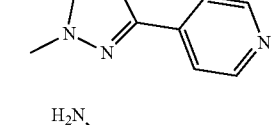 | MS (apci) m/z = 175.2 (M + H) |
| P11 | 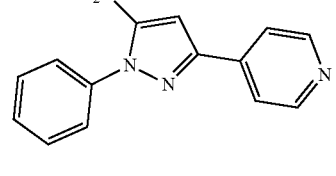 | MS (apci) m/z = 237.3 (M + H) |
| P12 | 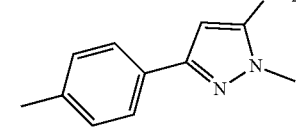 | MS (apci) m/z = 188.2 (M + H) |

TABLE 2-continued

| Intermediate # | Structure | Data |
| --- | --- | --- |
| P13 | 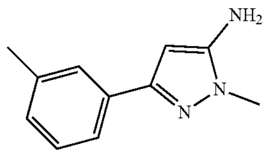 | MS (apci) m/z = 188.2 (M + H) |
| P14 | 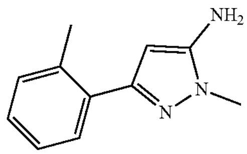 | MS (apci) m/z = 188.2 (M + H) |
| P15 | 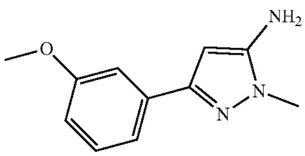 | MS (apci) m/z = 204.2 (M + H) |
| P16 | 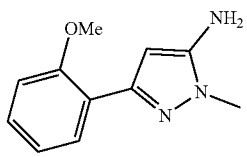 | MS (apci) m/z = 204.2 (M + H) |
| P17 | 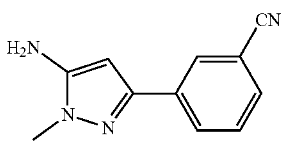 | MS (apci) m/z = 199.0 (M + H) |
| P18 | 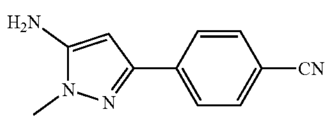 | MS (apci) m/z = 199.1 (M + H) |
| P19 | 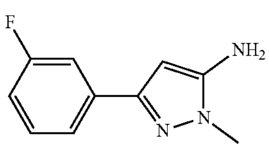 | MS (apci) m/z = 192.2 (M + H) |
| P20 | 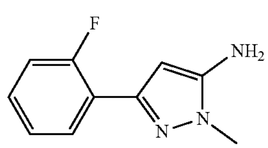 | MS (apci) m/z = 192.2 (M + H) |
| P21 | 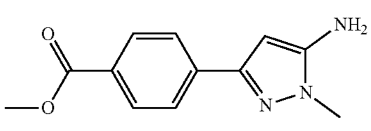 | MS (apci) m/z = 232.2 (M + H) |
| P22 | 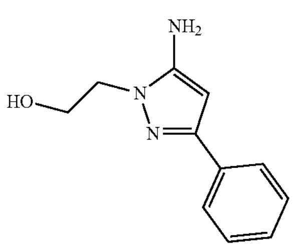 [SMILES: Nc1cc(-c2ccccc2)nn1CCO] | MS (apci) m/z = 204.2 (M + H) |

TABLE 2-continued

| Intermediate # | Structure | Data |
|---|---|---|
| P23 | 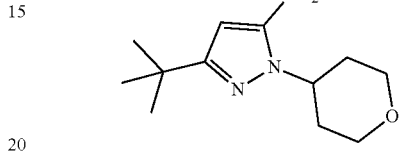 | MS (apci) m/z = 206.1 (M + H) |

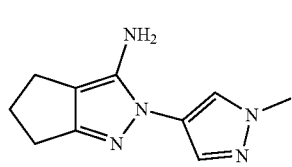

Intermediate P101

2-(1-methyl-1H-pyrazol-4-yl)-2,4,5,6-tetrahydrocyclopenta-[c]pyrazol-3-amine

Step A: Preparation of di-tert-butyl 1-(1-methyl-1H-pyrazol-4-yl)hydrazine-1,2-dicarboxylate: To a solution of 4-bromo-1-methyl-1H-pyrazole (1.93 mL, 18.6 mmol) in ether (37.3 mL) cooled to −78° C. was added nBuLi (23.3 mL, 37.3 mmol). After stirring at −78° C. for 30 minutes, a solution of di-t-butyl azodicarboxylate (4.29 g, 18.6 mmol) in Et$_2$O (37.3 mL, 18.6 mmol) was added dropwise. After 1 hour, the reaction mixture was warmed up to −20° C. and quenched with ice. After warming to ambient temperature, the mixture was filtered and rinsed with Et$_2$O. The resulting solid was taken up in a mixture of DCM and water, and the mixture was phase separated. The organic layer was dried with MgSO$_4$, filtered and concentrated in vacuo to afford the first batch of product as a white solid (1.64 g, 28% yield). A second batch of product was recovered from the filtrate by silica column chromatography, eluting with 40-60% hexanes/EtOAc (0.51 g, 8.8% yield). MS (apci) m/z=313.0 (M+H).

Step B: Preparation of 2-(1-methyl-1H-pyrazol-4-yl)-2,4,5,6-tetrahydrocyclopenta-[c]pyrazol-3-amine: To a solution of di-tert-butyl 1-(1-methyl-1H-pyrazol-4-yl)hydrazine-1,2-dicarboxylate (103 mg, 0.330 mmol) in EtOH (1.65 mL, 0.330 mmol) was added concentrated HCl (137 µL, 1.65 mmol). The mixture was stirred at ambient temperature for 5 minutes, then cooled in an ice bath followed by addition of 2-oxocyclopentanecarbonitrile (36.0 mg, 0.330 mmol). After stirring for 5 minutes, the reaction mixture was warmed to ambient temperature overnight. The reaction mixture was concentrated and partitioned in water and DCM. After phase-separation, the aqueous layer was basified (pH 10) and then extracted with DCM (3×10 mL). The combined organic extracts were dried with MgSO$_4$, filtered and concentrated in vacuo. The crude material was purified by reverse-phase column chromatography, eluting with 0-100% acetonitrile/water to afford the product as a yellow solid (4.5 mg, 6.7% yield). MS (apci) m/z=204.1 (M+H).

Intermediate P102

3-tert-butyl-1-(tetrahydro-2H-pyran-4-yl)-1H-pyrazol-5-amine

Step A: Preparation of (tetrahydro-2H-pyran-4-yl)hydrazine hydrochloride: A suspension of dihydro-2H-pyran-4(3H)-one (2.00 g, 20.0 mmol) and tert-butyl hydrazinecarboxylate (2.64 g, 20.0 mmol) in hexanes (20.0 mL) was refluxed for 2 hours. After cooling, BH$_3$-THF complex (20.0 mL, 20.0 mmol) was added and the reaction mixture was stirred for 1 hour. The mixture was then treated with 4 N HCl in dioxane (20.0 mL, 79.9 mmol), followed by 3 drops of water. After stirring at ambient temperature for 1 hour, the reaction mixture was filtered and rinsed with EtOAc to afford the product as a solid (2.39 g, 78.4% yield). MS (apci) m/z=117.0 (M+H).

Step B: Preparation of 3-tert-butyl-1-(tetrahydro-2H-pyran-4-yl)-1H-pyrazol-5-amine: Prepared by the method as described in for the preparation of Intermediate P1, substituting (tetrahydro-2H-pyran-4-yl)hydrazine dihydrochloride for ethyl 3-hydrazinylbenzoate hydrochloride to yield the product as a yellow oil (0.472 g, 99.9% yield). MS (apci) m/z=224.1 (M+H).

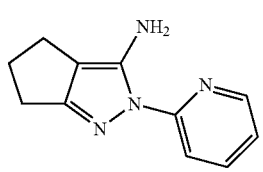

Intermediate P103

2-(pyridin-2-yl)-2,4,5,6-tetrahydrocyclopenta[c]pyrazol-3-amine

Step A: Preparation of 2-(2-(pyridin-2-yl)hydrazono)cyclopentane-carbonitrile: A solution of 2-hydrazinylpyridine (0.200 g, 1.83 mmol) and 2-oxocyclopentanecarbonitrile (0.200 g, 1.83 mmol) in MeOH (9.16 mL) was treated with concentrated HCl (0.764 mL, 9.16 mmol) and refluxed for 16 hours. The reaction mixture was concentrated in vacuo, and then partitioned in water and DCM. After phase-separation, the aqueous layer was washed with DCM, basified (saturated NaHCO$_3$, pH 10), and extracted with DCM. The combined organic layers were dried with MgSO₄, filtered and concentrated. The crude material was purified by silica column chromatography, eluting with 100% EtOAc to afford the product (0.289 g, 78.6% yield). MS (apci) m/z=201.2 (M+H).

Step B: Preparation of 2-(pyridin-2-yl)-2,4,5,6-tetrahydrocyclopenta[c]pyrazol-3-amine: A solution of 2-(2-(pyridin-2-yl)hydrazono)cyclopentanecarbonitrile (0.243 g, 1.21 mmol) in EtOH (6.06 mL, 1.21 mmol) was treated with 6 M HCl (0.202 mL, 1.21 mmol) and refluxed for 3 days. After removal of the solvent, the crude residue was diluted in water, basified (saturated NaHCO₃, pH 10) and extracted with DCM. The combined organic layers were dried with MgSO₄, filtered and concentrated. The crude material was purified by silica column chromatography, eluting with 50% EtOAc/hexanes to afford the product (0.198 g, 81.6% yield). MS (apci) m/z=201.2 (M+H).

Intermediate P104

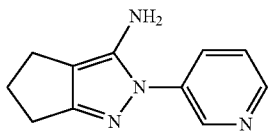

2-(pyridin-3-yl)-2,4,5,6-tetrahydrocyclopenta[c]pyrazol-3-amine

Prepared by the method described above for Intermediate P103, substituting 3-hydrazinylpyridine for 2-hydrazinyl pyridine to afford the title product. MS (apci) m/z=201.1 (M+H).

Intermediate P105

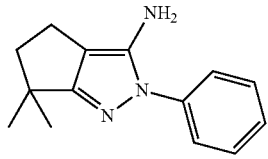

6,6-dimethyl-2-phenyl-2,4,5,6-tetrahydrocyclopenta[c]pyrazol-3-amine

Step A: Preparation of 5-chloro-2,2-dimethylpentanenitrile: Isobutyronitrile (1.38 g, 20.0 mmol) and 1-bromo-3-chloropropane (3.46 g, 22.0 mmol) were sequentially added to a 1 M solution of lithium bis(trimethylsilyl)amide (20.0 mL, 20.0 mmol) while stirring. After stirring at 70° C. for 16 hours, the reaction mixture was quenched with water then extracted with DCM. The combined organic layers were dried with MgSO₄, filtered and concentrated in vacuo to afford 5-chloro-2,2-dimethylpentanenitrile (2.91 g, 100% yield). ¹H NMR (CDCl₃) δ 3.57-3.61 (m, 2H), 1.94-2.02 (m, 2H), 1.67-1.72 (m, 2H), 1.37 (s, 6H).

Step B: Preparation of 2,2-dimethylhexanedinitrile: A suspension of 5-chloro-2,2-dimethylpentanenitrile (2.91 g, 20.0 mmol) and NaCN (1.57 g, 32.0 mmol) in DMF (20.0 mL) and water (1 mL) was heated at 100° C. for 16 hours. After cooling, the reaction mixture was diluted with water and refluxed for 30 minutes, then cooled, poured into water and stirred for 3 hours. The solution was then extracted with Et₂O. The combined Et₂O extracts were washed with H₂O, dried with MgSO₄, filtered and concentrated in vacuo to afford the product (2.20 g, 80.7% yield). ¹H NMR (CDCl₃) δ 2.42-2.47 (m, 2H), 1.83-1.92 (m, 2H), 1.67-1.72 (m, 2H), 1.39 (s, 6H).

Step C: Preparation of 3,3-dimethyl-2-oxocyclopentanecarbonitrile: A suspension of KOtBu (0.511 g, 4.55 mmol) in toluene (18.4 mL) was treated a toluene (2.0 mL) solution of 2,2-dimethylhexanedinitrile (1.00 g, 7.34 mmol) and heated at 80° C. for 2 hours. The reaction mixture was then cooled to ambient temperature and quenched with water. The mixture was separated and the organic layer was stirred in 2 N HCl (20 mL) for 16 hours. The mixture was separated and the organic layer dried with MgSO₄, filtered and concentrated in vacuo to a yellow-white solid. The crude solid was purified by silica column chromatography, eluting with 10-40% EtOAc/hexanes, to afford the product (0.250 g, 24.8% yield). ¹H NMR (CDCl₃) δ 3.20-3.26 (m, 1H), 2.38-2.47 (m, 1H), 2.14-2.25 (m, 1H), 1.97-2.05 (m, 1H), 1.74-1.83 (m, 1H), 1.14 (s, 6H).

Step D: Preparation of 6,6-dimethyl-2-phenyl-2,4,5,6-tetrahydrocyclopenta[c]pyrazol-3-amine: Prepared by the method as described for Intermediate P1, substituting phenylhydrazine for ethyl 3-hydrazinylbenzoate hydrochloride and 3,3-dimethyl-2-oxocyclopentanecarbonitrile for 4,4-dimethyl-3-oxopentanenitrile to afford the product (0.192 g, 46.2% yield) as a yellow solid. MS (apci) m/z=228.2 (M+H).

Intermediate P106

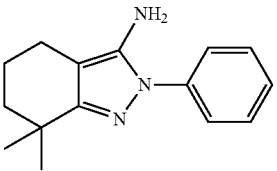

7,7-dimethyl-2-phenyl-4,5,6,7-tetrahydro-2H-indazol-3-amine

Step A: Preparation of 2,2-dimethylheptanedinitrile: Prepared by the method as described for Intermediate P105, Steps A and B, substituting 1-bromo-4-chlorobutane for 1-bromo-3-chloropropane to yield the product (2.21 g, 73.7% yield). ¹H NMR (CDCl₃) δ 2.37-2.42 (m, 2H), 1.53-1.77 (m, 6H), 1.36 (s, 6H).

Step B: Preparation of 3,3-dimethyl-2-oxocyclohexanecarbonitrile: A suspension of KOtBu (0.463 g, 4.13 mmol) in toluene (16.6 mL) was treated with a solution of 2,2-dimethylheptanedinitrile (1.00 g, 6.66 mmol) in toluene (2.0 mL) and heated at 80° C. for 48 hours. After cooling to ambient temperature, the reaction mixture was quenched with water and phase-separated, and the organic layer was stirred with 2 N HCl (20 mL) for 16 hours. After phase-separation, the organic layer was dried with MgSO₄, filtered and concentrated in vacuo. The crude material was purified by silica column chromatography, eluting with 10-20% EtOAc/hexanes to afford the product (0.374 g, 37.2% yield). ¹H NMR (CDCl₃) δ 3.72-3.78 (m, 1H), 2.42-2.50 (m. 1H), 1.78-2.04 (m, 4H), 1.60-1.70 (m, 1H), 1.21 (s, 3H), 1.16 (s, 3H).

Step C: Preparation of 7,7-dimethyl-2-phenyl-4,5,6,7-tetrahydro-2H-indazol-3-amine: Prepared by the method as described for Intermediate P1, substituting phenylhydrazine for ethyl 3-hydrazinylbenzoate hydrochloride and 3,3-dimethyl-2-oxocyclohexanecarbonitrile for 4,4-dimethyl-3-oxopentanenitrile to yield the product as an off-white solid (0.490 g, 54.2% yield, 66% purity). MS (apci) m/z=242.2 (M+H).

Intermediate P107

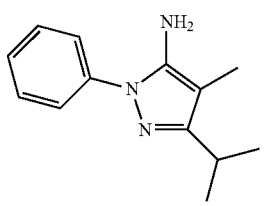

3-isopropyl-4-methyl-1-phenyl-1H-pyrazol-5-amine

Step A: Preparation of 2,4-dimethyl-3-oxopentanenitrile: To a solution of propiononitrile (518 mg, 9.40 mmol) in THF (50 mL, 7.83 mmol) at −78° C. under $N_2$ was slowly added lithium bis(trimethylsilyl)amide (1M in THF) (7.83 mL, 7.83 mmol). After 30 minutes, methyl isobutyrate (0.898 mL, 7.83 mmol) was added dropwise, and the reaction mixture was warmed to 0° C. A yellow precipitate formed, the reaction mixture was stirred for 1 hour, then diluted with $H_2O$ (50 mL) to dissolve the solids. The mixture was extracted with $Et_2O$ (25 mL), and the basic aqueous phase was acidified with 2M HCl (5 mL) and extracted with $Et_2O$ (2×50 mL). The combined organic phases were washed with brine (50 mL), dried with $MgSO_4$, filtered, and concentrated to afford the product (421 mg, 42.9% yield)

Step B: Preparation of 3-isopropyl-4-methyl-1-phenyl-1H-pyrazol-5-amine: Prepared by the method as described for Intermediate P1, substituting phenyl hydrazine for ethyl 3-hydrazinylbenzoate hydrochloride and 4,4-dimethyl-3-oxopentanenitrile with 2,4-dimethyl-3-oxopentanenitrile to yield the product as a yellow syrup (0.587 g, 81.1% yield). MS (apci) m/z=216.2 (M+H).

Intermediate P108

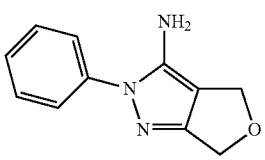

2-phenyl-4,6-dihydro-2H-furo[3,4-c]pyrazol-3-amine

Step A: Preparation of 4-oxotetrahydrofuran-3-carbonitrile: To a suspension of KOtBu (996.6 mg, 8.881 mmol) in THF (640.4 mg, 8.881 mmol) cooled to 0° C. was added dropwise methyl 2-hydroxyacetate (675.7 µL, 8.881 mmol) and stirred for 10 minutes. The acrylonitrile (589.1 µL, 8.881 mmol) was then added and the reaction stirred at ambient temperature. After 3 hours, the reaction was diluted with $H_2O$ (50 mL), then extracted with $Et_2O$ (25 mL) to remove any starting ester. The basic aqueous phase was acidified with 2M HCl (5 mL), then extracted with $Et_2O$ (2×50 mL). The combined organic phases were dried with $MgSO_4$, filtered, and concentrated to afford a light brown oil (446 mg, 45.2% yield). $^1$H NMR (CDCl$_3$) δ 4.63 (t, 1H), 4.24 (t, 1H), 4.14 (d, 1H), 4.02 (d, 1H), 3.57 (t, 1H).

Step B: Preparation of 2-phenyl-4,6-dihydro-2H-furo[3,4-c]pyrazol-3-amine:

Prepared by the method as described for Intermediate P1, substituting phenyl hydrazine for ethyl 3-hydrazinylbenzoate hydrochloride and 4,4-dimethyl-3-oxopentanenitrile with 4-oxotetrahydrofuran-3-carbonitrile to yield the product as a reddish-brown syrup (182 mg, 22.5% yield). MS (apci) m/z=202.1 (M+H).

Intermediate P109

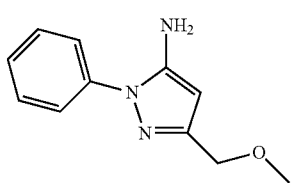

3-(methoxymethyl)-1-phenyl-1H-pyrazol-5-amine

Step A: Preparation of 4-methoxy-3-oxobutanenitrile: To a solution of methyl 2-methoxyacetate (0.4753 mL, 4.803 mmol) in THF (20 mL, 4.803 mmol) at −78° C. under $N_2$ was added acetonitrile (0.3033 mL, 5.763 mmol), followed by lithium bis(trimethylsilyl)amide (1M in THF) (4.803 mL, 4.803 mmol). After stirring 1 hour, the reaction mixture was warmed to 0° C. and stirred for 1 hour. The reaction mixture was then diluted with $H_2O$ (25 mL), washed with $Et_2O$ (25 mL), then neutralized with 2 M HCl (1.5 mL). This was extracted with $Et_2O$ (2×25 mL) and the combined organic phases were washed with brine (25 mL), dried with $MgSO_4$, filtered, and concentrated to afford the product (169 mg, 31.1% yield). $^1$H NMR (CDCl$_3$) δ 4.09 (s, 2H), 3.66 (s, 2H), 3.46 (s, 3H)

Step B: Preparation of 3-(methoxymethyl)-1-phenyl-1H-pyrazol-5-amine: Prepared by the method as described for Intermediate P1, substituting phenyl hydrazine for ethyl 3-hydrazinylbenzoate hydrochloride and 4,4-dimethyl-3-oxopentanenitrile with 4-methoxy-3-oxobutanenitrile to yield the product as a pale yellow residue (6.0 mg, 2.0% yield). MS (apci) m/z=204.0 (M+H).

Intermediate P110

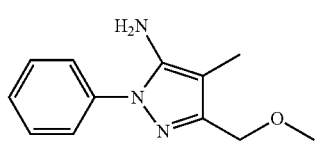

3-(methoxymethyl)-4-methyl-1-phenyl-1H-pyrazol-5-amine

Prepared according to the method as described for Intermediate P109, replacing acetonitrile with propionitrile to afford the product as an orange residue. MS (apci) m/z=218.0 (M+H).

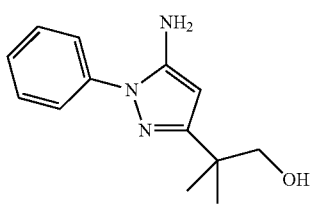

Intermediate P111

2-(5-amino-1-phenyl-1H-pyrazol-3-yl)-2-methylpropan-1-ol

Step A: Preparation of methyl 3-(tert-butyldimethylsilyloxy)-2,2-dimethyl-propanoate: Methyl 3-hydroxy-2,2-dimethylpropanoate (1.000 g, 7.567 mmol), TBDMS-Cl (1.140 g, 7.567 mmol) and imidazole (0.5666 g, 8.323 mmol) were dissolved in DMF (5 mL, 7.567 mmol) and stirred at ambient temperature overnight. The reaction mixture was diluted with $H_2O$ (25 mL) and extracted with EtOAc (2×25 mL). The combined organic phases were washed with brine (25 mL), dried with $MgSO_4$, filtered and concentrated to afford the product (1.92 g, 103% yield). $^1$H NMR ($CDCl_3$) δ 3.66 (s, 3H), 3.57 (s, 2H), 1.15 (s, 6H), 0.87 (s, 9H), 0.02 (s, 6H).

Step B: Preparation of 5-(tert-butyldimethylsilyloxy)-4,4-dimethyl-3-oxopentanenitrile: Prepared according to the method described for Intermediate P109, replacing methyl 2-methoxyacetate with methyl 3-(tert-butyldimethylsilyloxy)-2,2-dimethylpropanoate to afford the product as a pale yellow residue. $^1$H NMR ($CDCl_3$) δ 3.70 (s, 2H), 3.55 (s, 2H), 1.15 (s, 6H), 0.89 (s, 9H), 0.06 (s, 6H).

Step C: Preparation of 2-(5-amino-1-phenyl-1H-pyrazol-3-yl)-2-methylpropan-1-ol: Prepared by the method as described for Intermediate P1, substituting phenyl hydrazine for ethyl 3-hydrazinylbenzoate hydrochloride and 4,4-dimethyl-3-oxopentanenitrile with methyl 3-(tert-butyldimethylsilyloxy)-2,2-dimethylpropanoate to yield the product as yellow syrup (74 mg, 66% yield). MS (apci) m/z=232.2 (M+H).

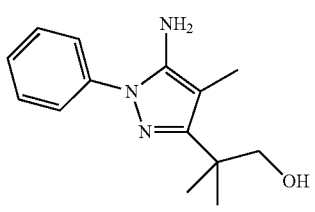

Intermediate P112

2-(5-amino-4-methyl-1-phenyl-1H-pyrazol-3-yl)-2-methylpropan-1-ol

Prepared according to the method described for Intermediate P111, replacing acetonitrile with propionitrile to afford the product as a yellow residue. MS (apci) m/z=246.2 (M+H).

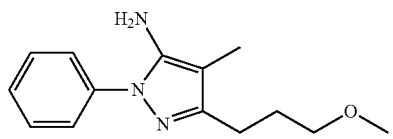

Intermediate P113

3-(3-methoxypropyl)-4-methyl-1-phenyl-1H-pyrazol-5-amine

Prepared according to the method described for Intermediate P109, replacing methyl 2-methoxyacetate with methyl 4-methoxybutanoate and replacing acetonitrile with propionitrile in Step A to afford the product as an orange-brown syrup. MS (apci) m/z=246.1 (M+H).

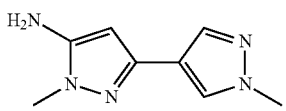

Intermediate P114

1,1'-dimethyl-1H, 1'H-3,4'-bipyrazol-5-amine

Step A: Preparation of 3-(1-methyl-1H-pyrazol-4-yl)-3-oxopropanenitrile: A solution of ethyl 1-methyl-1H-pyrazole-4-carboxylate (500 mg, 3.24 mmol), toluene (7.50 mL, 70.4 mmol), and acetonitrile (346 μL, 6.49 mmol) was treated in one portion with KOtBu (1092 mg, 9.73 mmol) to give a hazy solution. The reaction was allowed to stir at ambient temperature for one hour, and was determined to be complete by HPLC analysis. The mixture was treated with water (7.5 mL) and stirred for 1 minute, then acidified with 3M HCl (3027 μL, 9.08 mmol) to pH 5.5-6. The aqueous layer was extracted with ethyl acetate (3×5 mL) and the combined organic extracts were concentrated in vacuo to give a yellow viscous oil, which completely solidified upon placing under high vacuum to afford the product (102 mg, 21.1% yield). $^1$H NMR ($CDCl_3$) δ 8.02 (s, 1H), 7.94 (s, 1H), 3.98 (s, 3H), 3.82 (s, 2H)

Step B: Preparation of 1,1'-dimethyl-1H,1'H-3,4'-bipyrazol-5-amine: Prepared by the method as described for Intermediate P1, substituting methyl hydrazine for ethyl 3-hydrazinylbenzoate hydrochloride and replacing 4,4-dimethyl-3-oxopentanenitrile with 3-(1-methyl-1H-pyrazol-4-yl)-3-oxopropanenitrile to yield the product as an ivory white solid (45 mg, 44.6% yield). MS (apci) m/z=178.1 (M+H).

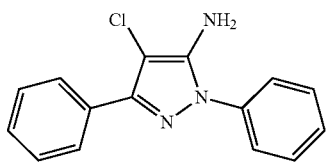

Intermediate P115

4-chloro-1,3-diphenyl-1H-pyrazol-5-amine

To a solution of 1,3-diphenyl-1H-pyrazol-5-amine (Table 1; 0.100 g, 0.425 mmol) in acetonitrile (2 mL) was added N-chlorosuccinimide (0.0568 g, 0.425 mmol). The pale yellow solution was stirred at ambient temperature for 3 hours, then concentrated in vacuo and purified by silica column chromatography eluting with 20% EtOAc/Hexanes to afford the product as a light brown oil (0.10 g, 87% yield). MS (apci) m/z=270.0 (M+H).

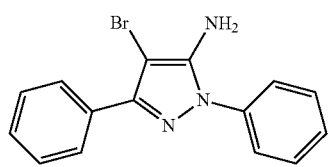

Intermediate P116

4-bromo-1,3-diphenyl-1H-pyrazol-5-amine

Prepared according to the procedure described for Intermediate P115, substituting N-chloro succinimide with N-bromo-succinimide. MS (apci) m/z=313.9 (M+H).

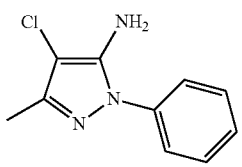

Intermediate P117

4-chloro-3-methyl-1-phenyl-1H-pyrazol-5-amine

Prepared according to the procedure described for Intermediate P115, substituting 1,3-diphenyl-1H-pyrazol-5-amine with 3-methyl-1-phenyl-1H-pyrazol-5-amine. MS (apci) m/z=207.9 (M+H).

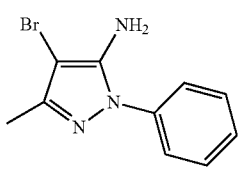

Intermediate P118

4-bromo-3-methyl-1-phenyl-1H-pyrazol-5-amine

Prepared according to the procedure described for Intermediate P117, substituting N-chloro succinimide with N-bromo-succinimide. MS (apci) m/z=251.9 (M+H).

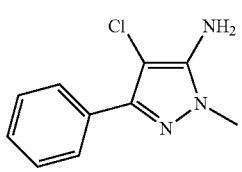

Intermediate P119

4-chloro-1-methyl-3-phenyl-1H-pyrazol-5-amine

Prepared according to the procedure described for Intermediate P115, substituting 1,3-diphenyl-1H-pyrazol-5-amine with 1-methyl-3-phenyl-1H-pyrazol-5-amine (Table 1). MS (apci) m/z=208.0 (M+H).

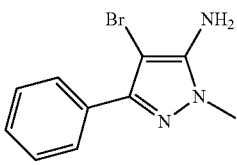

Intermediate P120

4-bromo-1-methyl-3-phenyl-1H-pyrazol-5-amine

Prepared according to the procedure described for Intermediate P119, substituting N-chloro succinimide with N-bromo-succinimide. MS (apci) m/z=251.9 (M+H).

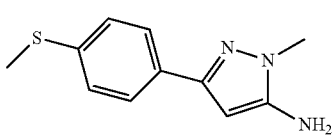

Intermediate P121

1-methyl-3-(4-(methylthio)phenyl)-1H-pyrazol-5-amine

Step A: Preparation of 3-(4-(methylthio)phenyl)-3-oxopropanenitrile: To a suspension of NaH (60% in mineral oil) (154 mg, 3.84 mmol) in dioxane (25.0 mL, 2.74 mmol) was added acetonitrile (0.217 mL, 4.12 mmol). The reaction mixture was stirred at ambient temperature for 30 minutes, then treated with methyl 4-(methylthio)benzoate (500 mg, 2.74 mmol) and heated to reflux for 15 hours. The suspension was cooled, then diluted with water (25 mL) and washed with Et$_2$O (25 mL). The aqueous layer was neutralized with 2M HCl (1.8 mL) and extracted with Et$_2$O (2×25 mL). The combined organic phases were washed with brine (25 mL), dried with MgSO$_4$, filtered and concentrated in vacuo. The resultant residue was purified by silica column chromatography eluting with 0-5% MeOH/DCM to afford the product (317 mg, 60.4% yield). $^1$H NMR (CDCl$_3$) δ 7.82 (d, 2H), 7.30 (d, 2H), 4.02 (s, 2H), 2.54 (s, 3H).

Step B: Preparation of 1-methyl-3-(4-(methylthio)phenyl)-1H-pyrazol-5-amine: Prepared by the method as described in Intermediate P1, substituting methylhydrazine for ethyl 3-hydrazinylbenzoate hydrochloride and substituting 3-(4-(methylthio)phenyl)-3-oxopropanenitrile for 4,4-dimethyl-3-oxopentanenitrile to yield the product as a yellow solid (0.307 g, 96.7% yield). MS (apci) m/z=220.0 (M+H).

Intermeidate P122

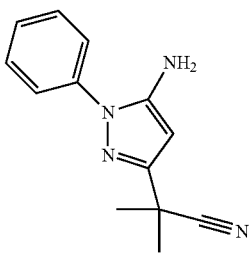

2-(5-amino-1-phenyl-1H-pyrazol-3-yl)-2-methylpropanenitrile

Prepared according to the procedure for Intermediate P121, substituting methyl 4-(methylthio)benzoate with ethyl 2-cyano-2-methylpropanoate in Step A and phenyl hydrazine hydrochloride for methyl hydrazine in Step B. MS (apci) m/z=227.1 (M+H).

Intermediate P123

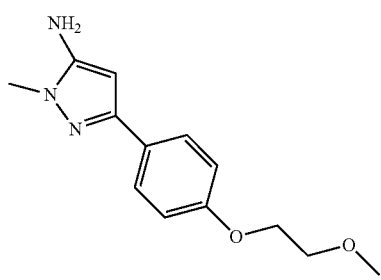

3-(4-(2-methoxyethoxy)phenyl)-1-methyl-1H-pyrazol-5-amine

Step A: Preparation of 3-(4-(benzyloxy)phenyl)-3-oxopropanenitrile: Prepared according to the procedure described for Intermediate P121, substituting methyl 4-(methylthio)benzoate with methyl 4-(benzyloxy)benzoate in Step A. $^1$H NMR (CDCl$_3$) δ 7.90 (d, 2H), 7.42 (m, 4H), 7.37 (m, 1H), 7.05 (d, 2H), 5.16 (s, 2H), 4.00 (s, 2H).
Step B: Preparation of 3-(4-(benzyloxy)phenyl)-1-methyl-1H-pyrazol-5-amine: Prepared by the method as described for Intermediate P1, substituting methylhydrazine for ethyl 3-hydrazinylbenzoate hydrochloride and 3-(4-(benzyloxy)phenyl)-3-oxopropanenitrile for 4,4-dimethyl-3-oxopentanenitrile to yield the product as a yellow solid. MS (apci) m/z=280.1 (M+H).
Step C: Preparation of 4-(5-amino-1-methyl-1H-pyrazol-3-yl)phenol: To a solution of 3-(4-(benzyloxy)phenyl)-1-methyl-1H-pyrazol-5-amine (47 mg, 0.17 mmol) in EtOH (5.0 mL) was added 5% Pd/C (9.0 mg, 0.0084 mmol) and stirred under a H$_2$ balloon for 17 hours. The reaction mixture was filtered through Celite®, rinsed with EtOH and concentrated in vacuo to afford the product (28 mg, 88% yield). MS (apci) m/z=190.1 (M+H).
Step D: Preparation of 3-(4-(2-methoxyethoxy)phenyl)-1-methyl-1H-pyrazol-5-amine: To a solution of 4-(5-amino-1-methyl-1H-pyrazol-3-yl)phenol (14 mg, 0.074 mmol) in DMSO (0.50 mL, 7.0 mmol) was added Cs$_2$CO$_3$ (48 mg, 0.15 mmol) and 1-bromo-2-methoxyethane (9.7 µL, 0.10 mmol). The reaction mixture was stirred for 16 hours, then diluted with water (10 mL) and extracted with DCM (3×10 mL). The combined organic extracts were washed with brine (10 mL), dried with MgSO$_4$, filtered and concentrated to afford the crude product (22 mg, 120% yield). The crude product was used without purification in subsequent steps. MS (apci) m/z=248.0 (M+H).

Intermediate P124

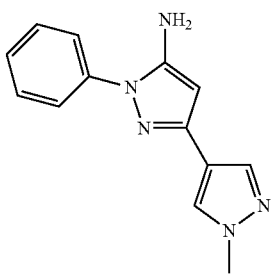

1'-methyl-1-phenyl-1H,1'H-3,4'-bipyrazol-5-amine

Prepared according to the procedure described for Intermediate P114, substituting methylhydrazine with phenylhydrazine in Step B. MS (apci) m/z=240.0 (M+H).

Intermediate P125

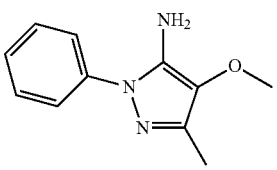

4-methoxy-3-methyl-1-phenyl-1H-pyrazol-5-amine

Prepared according to the procedure for Intermediate P121, substituting methyl 4-(methylthio)benzoate with ethyl acetate and substituting acetonitrile with 2-methoxyacetonitrile in Step A and phenyl hydrazine hydrochloride for methyl hydrazine in Step B. MS (apci) m/z=204.0 (M+H).

Intermediate P126

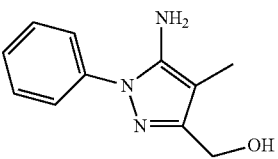

(5-amino-4-methyl-1-phenyl-1H-pyrazol-3-yl)methanol

Prepared according to the procedure for Intermediate P112, substituting methyl 3-hydroxy-2,2-dimethylpropanoate with ethyl 2-hydroxyacetate in Step A. MS (apci) m/z=204.1 (M+H).

Intermediate P127

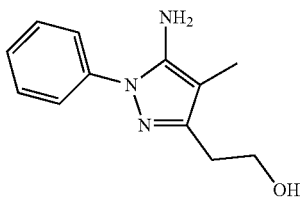

2-(5-amino-4-methyl-1-phenyl-1H-pyrazol-3-yl)ethanol

Prepared according to the procedure for Intermediate P112, substituting methyl 3-hydroxy-2,2-dimethylpropanoate with methyl 3-hydroxypropanoate in Step A. MS (apci) m/z=218.0 (M+H).

Intermediate P128

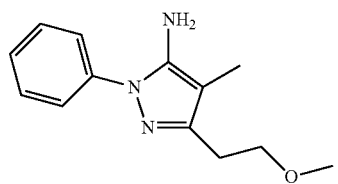

3-(2-methoxyethyl)-4-methyl-1-phenyl-1H-pyrazol-5-amine

Step A: Preparation of 5-methoxy-2-methyl-3-oxopentanenitrile: To a suspension of NaNH$_2$ (50 wt % suspension in toluene) (330 mg, 4.23 mmol) in THF (25 mL, 4.23 mmol) under N$_2$ at −78° C. was added propiononitrile (0.448 mL, 6.35 mmol), and the reaction mixture was stirred for 30 minutes. Methyl 3-methoxypropanoate (0.495 mL, 4.23 mmol) was added and the reaction mixture was stirred at −78° C. for 1 hour, then at 0° C. for 2.5 hours. The reaction mixture was diluted with H$_2$O (25 mL) and washed with Et$_2$O (25 mL). The basic aqueous phase was neutralized with 2M HCl (1.6 mL), then extracted with Et$_2$O (3×25 mL). The combined organic phases were washed with brine (25 mL), dried with MgSO$_4$, filtered, and concentrated to afford the crude product as a pale greenish oil (171 mg). The crude mixture was taken directly to the next step.

Step B: Preparation of 3-(2-methoxyethyl)-4-methyl-1-phenyl-1H-pyrazol-5-amine: Prepared by the method as described for Intermediate P1, substituting 5-methoxy-2-methyl-3-oxopentanenitrile for 4,4-dimethyl-3-oxopentanenitrile and substituting phenylhydrazine hydrochloride for ethyl 3-hydrazinylbenzoate hydrochloride to yield the product as a yellow solid (56 mg, 20% yield). MS (apci) m/z=232.0 (M+H).

Intermediate P129

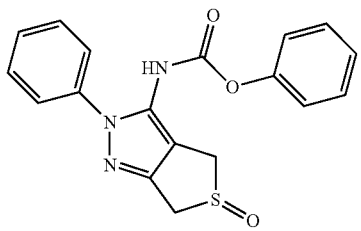

Phenyl (5-oxido-2-phenyl-4,6-dihydro-2H-thieno[3,4-c]pyrazol-3-yl)carbamate

A THF (4 mL) solution of phenyl 2-phenyl-4,6-dihydro-2H-thieno[3,4-c]pyrazol-3-ylcarbamate (Intermediate P130, Step B; 50 mg, 0.15 mmol) was cooled to −50° C. with an external dry-ice/MeCN bath and treated with a THF (2 mL) solution of 3-chlorobenzoperoxoic acid (33 mg, 0.13 mmol). After stirring for 1 hour, the mixture was quenched with Na$_2$S$_2$O$_3$ and water, extracted with EtOAc, washed with NaHCO$_3$ and brine, dried with MgSO$_4$, filtered, and concentrated to give the product which was directly used in next step without further purification. MS (apci) m/z=354.1 (M+H).

Intermediate P130

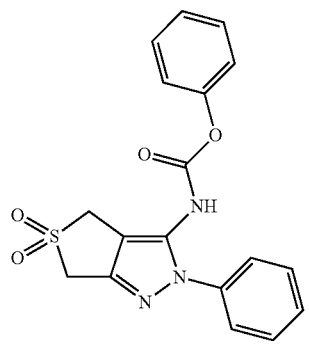

Phenyl (5,5-dioxido-2-phenyl-4,6-dihydro-2H-thieno[3,4-c]pyrazol-3-yl)carbamate

Step A: Preparation of 2-phenyl-4,6-dihydro-2H-thieno[3,4-c]pyrazol-3-amine: A suspension of 4-oxotetrahydrothiophene-3-carbonitrile (1.00 g, 7.86 mmol) and phenylhydrazine hydrochloride (1.25 g, 8.65 mmol) in absolute EtOH (40 mL) was refluxed for 2 hours. After removal of solvent under reduced pressure, the white solid residue was triturated with 1 N NaOH (40 mL). The solid was collected by filtration, washed with 0.1 N NaOH, water, and hexanes (approx. 10 mL each) then dried on high vacuum to yield the product as white solid (1.6 g, 95% yield). MS (apci pos) m/z=218.1 (M+H).

Step B: Preparation of phenyl 2-phenyl-4,6-dihydro-2H-thieno[3,4-c]pyrazol-3-ylcarbamate To a suspension of 2-phenyl-4,6-dihydro-2H-thieno[3,4-c]pyrazol-3-amine (500 mg, 2.30 mmol) in EtOAc (10 mL) was added NaOH (2M aq, 2.3 mL, 4.60 mmol), followed by dropwise addition of phenyl carbonochloridate (0.400 mL, 3.22 mmol). After stirring at ambient temperature for 2 hours, another portion of phenyl carbonochloridate (0.16 mL, 1.3 mmol) was added dropwise, and the reaction was stirred at ambient temperature for 15 hours. The reaction mixture was diluted with EtOAc (20 mL) and phase-separated. The organic phase was washed with H$_2$O, brine (25 mL each), then dried with Na$_2$SO$_4$, filtered and concentrated. The crude material was purified by reverse-phase column chromatography, eluting with 5-70% acetonitrile/water to yield the product as white solid (0.5 g, 64% yield). MS (apci pos) m/z=338.1 (M+H).

Step C: Preparation of phenyl (5,5-dioxido-2-phenyl-4,6-dihydro-2H-thieno[3,4-c]pyrazol-3-yl)carbamate. To a turbid solution of phenyl 2-phenyl-4,6-dihydro-2H-thieno[3,4-c]pyrazol-3-ylcarbamate (50 mg, 0.15 mmol) in DCM (1.5 mL) at 0° C. was added MCPBA (91 mg, 0.37 mmol, 70-75% water complex), and the mixture was stirred at ambient temperature for 10 min. The mixture was then diluted with DCM (3 mL) and washed with saturated aqueous NaHCO$_3$ (3×2 mL) and saturated aqueous Na$_2$S$_2$O$_3$ (3×2 mL). The organic layer was dried with MgSO$_4$, filtered and concentrated under reduced pressure to yield the title product as light yellowish foamy solid (31 mg, 57% yield, 95% pure). MS (apci pos) m/z=371.0 (M+H).

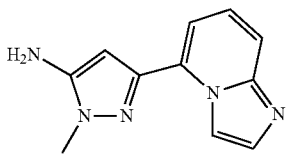

Intermediate P131

3-(imidazo[1,2-a]pyridin-5-yl)-1-methyl-1H-pyrazol-5-amine

Step A: Methyl imidazo[1,2-a]pyridine-5-carboxylate: To a suspension of methyl 6-aminopicolinate (1.52 g, 10.0 mmol) in iPrOH (10 mL) was added 2-chloroacetaldehyde (2.57 mL, 20.0 mmol) and the mixture was stirred at ambient temperature for 30 minutes. The resulting solution was heated at 70° C. for 16 hours, then cooled to ambient temperature and concentrated in vacuo. The residue was diluted with H$_2$O (40 mL) and treated with 1M K$_2$CO$_3$ until pH=10. The mixture was extracted with EtOAc (3×) and the combined extracts were washed with saturated NaCl and dried over MgSO$_4$/activated carbon. The dried solution was eluted through a SiO$_2$ plug capped with MgSO$_4$ layer using EtOAc for elution. The solution was concentrated to provide the title compound as a cream-white solid (1.73 g, 98.2% yield). MS (apci) m/z=177.0 (M+H).

Step B: 3-(imidazo[1,2-a]pyridin-5-yl)-3-oxopropanenitrile: A 1M solution of LiHMDS (3.15 mL, 3.15 mmol) in dry THF was cooled to −78° C. and acetonitrile (0.172 mL, 3.30 mmol) was added dropwise over 1 minute. The mixture was stirred at −78° C. for 1 hour and a solution of methyl imidazo[1,2-a]pyridine-5-carboxylate (0.529 g, 3.00 mmol) in dry THF (2.0 mL) was added. The mixture was allowed to reach ambient temperature and was stirred for 2.5 hours. The mixture was poured into chilled H$_2$O (30 mL) and the resulting aqueous solution was extracted with Et$_2$O (3×). The aqueous portion was cooled to 0° C. and 6M HCl was added slowly until pH=6. The resulting yellow suspension was filtered and the collected solid was washed with H$_2$O and EtOAc. The solid was dried in vacuum to provide the title compound as a yellow solid (317 mg, 57.1% yield). MS (apci) m/z=186.0 (M+H).

Step C: 3-(imidazo[1,2-a]pyridin-5-yl)-1-methyl-1H-pyrazol-5-amine: To a fine suspension of 3-(imidazo[1,2-a]pyridin-5-yl)-3-oxopropanenitrile (229 mg, 1.24 mmol) in absolute EtOH (4 mL) was added methylhydrazine (78.1 µL, 1.45 mmol) and the resulting solution was stirred at ambient temperature for 2 hours. The reaction mixture was heated at reflux for 5 hours and additional methylhydrazine (200 µL) was added. The mixture was heated at reflux for 15 hours, cooled to ambient temperature and concentrated. The residual tan solid was dissolved in 5% MeOH/CH$_2$Cl$_2$ and eluted through a SiO$_2$ plug eluting with 5% MeOH/CH$_2$Cl$_2$. The eluent was concentrated and the residual yellow solid was washed with MTBE and dried in vacuum to afford the title compound as a light yellow powder (150 mg, 56.9% yield). MS (apci) m/z=214.0 (M+H).

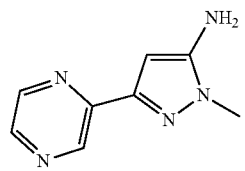

Intermediate P132

1-methyl-3-(pyrazin-2-yl)-1H-pyrazol-5-amine

Step A: Preparation of 3-oxo-3-(pyrazin-2-yl)propanenitrile: To a suspension of NaH (60% in mineral oil, 81.1 mg, 2.03 mmol) in dioxane (15 mL) was added acetonitrile (0.114 mL, 2.17 mmol), followed by methyl pyrazine-2-carboxylate (200 mg, 1.45 mmol) and the reaction heated to reflux for 2.5 hours. The reaction mixture was cooled to ambient temperature and diluted with H$_2$O (25 mL) and extracted with Et$_2$O (25 mL). The aqueous phase was neutralized with 2M aqueous HCl (0.7 mL), then extracted with 10% MeOH/DCM (3×25 mL). The combined organic phases were washed with brine (25 mL), dried with MgSO$_4$, filtered, and concentrated to yield the crude product as an orange syrup (134 mg, 62.9% yield). $^1$H NMR (CDCl$_3$) δ 9.32 (d, 1H), 8.87 (d, 1H), 8.68 (dd, 1H), 4.34 (s, 2H).

Step B: Preparation of 1-methyl-3-(pyrazin-2-yl)-1H-pyrazol-5-amine: To a suspension of 3-oxo-3-(pyrazin-2-yl)propanenitrile (67.0 mg, 0.455 mmol) in EtOH (5 mL) was added methylhydrazine (0.024 mL, 0.455 mmol). The reaction mixture was refluxed for 15 hours, then concentrated in vacuo. The crude product was purified by silica column chromatography, eluting with 0-5% MeOH/DCM to yield the product as a brown residue (33 mg, 41% yield). MS (apci) m/z=176.2 (M+H).

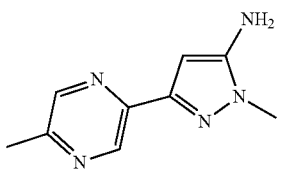

Intermediate P133

1-methyl-3-(5-methylpyrazin-2-yl)-1H-pyrazol-5-amine

Prepared by the method as described for Intermediate P107, substituting methyl isobutyrate in Step A with methyl 5-methylpyrazine-2-carboxylate and propionitrile with acetonitrile to afford 3-(5-methylpyrazin-2-yl)-3-oxopropanenitrile. In Step B, phenylhydrazine was replaced by methylhydrazine to afford the title pyrazole. MS (apci) m/z=190.2 (M+H).

Intermediate P134

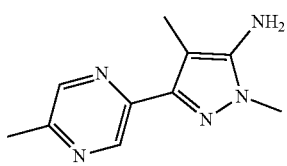

1,4-dimethyl-3-(5-methylpyrazin-2-yl)-1H-pyrazol-5-amine

Prepared by the method as described for Intermediate P107, substituting methyl isobutyrate in Step A with methyl 5-methylpyrazine-2-carboxylate to afford 2-methyl-3-(5-methylpyrazin-2-yl)-3-oxopropanenitrile. In Step B, phenylhydrazine was replaced by methylhydrazine to afford the title compound. MS (apci) m/z=204.1 (M+H).

Intermediate P135

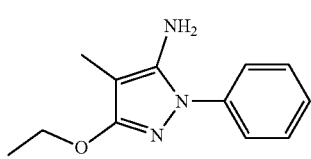

3-ethoxy-4-methyl-1-phenyl-1H-pyrazol-5-amine

Step A: Preparation of 5-amino-4-methyl-1-phenyl-1H-pyrazol-3 (2H)-one: A mixture of ethyl 2-cyanopropanoate (5.0 g, 46 mmol) and phenylhydrazine (5.9 g, 46 mmol) in dioxane (10 mL) was heated at 110° C. for 17 hours. The crude material was cooled to ambient temperature, concentrated, and triturated with cold EtOH and $Et_2O$. The resultant solid was filtered, washed with $Et_2O$, and dried under vacuum to give the product as a white solid (3.4 g, 39% yield). MS (apci) m/z=190.0 (M−H).

Step B: Preparation of 3-ethoxy-4-methyl-1-phenyl-1H-pyrazol-5-amine: To a suspension of 5-amino-4-methyl-1-phenyl-1H-pyrazol-3(2H)-one (10.0 g, 52.9 mmol) in DMF (100 mL) was added $K_2CO_3$ (14.6 g, 106 mmol) and bromoethane (4.34 mL, 58.1) at ambient temperature. After stirring for 17 hours, the reaction mixture was treated with EtOAc and washed with water (3×, to obtain the N-alkylation product) and brine, dried with $MgSO_4$, filtered, and concentrated to give the product (5.35 g, 47% yield). MS (apci) m/z=218.1 (M+H).

The compounds in Table 3 were prepared by the method as described for Intermediate P135, substituting bromoethane with the appropriate alkyl halide or alkyl methanesulfonate.

TABLE 3

| Intermediate # | Structure | Data |
|---|---|---|
| P200 | 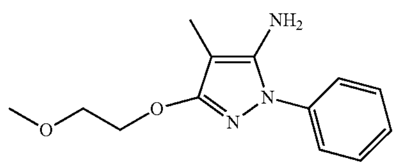 [SMILES: COCCOc1nn(-c2ccccc2)c(N)c1C] | MS (apci) m/z = 248.1 (M + H) |
| P201 | 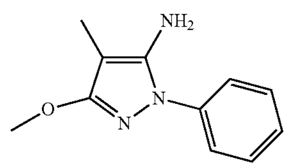 | MS (apci) m/z = 204.1 (M + H) |
| P202 | 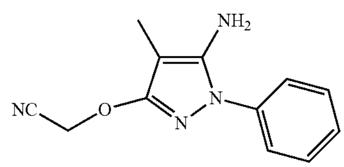 [SMILES: Cc1c(OCC#N)nn(-c2ccccc2)c1N] | MS (apci) m/z = 229.0 (M + H) |
| P203 | 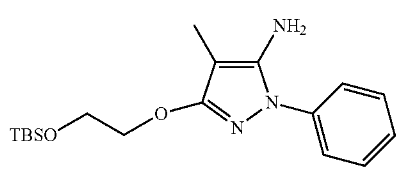 [SMILES: Cc1c(OCCO[Si](C)(C)C(C)(C)C)nn(-c2ccccc2)c1N] | MS (apci) m/z = 348.1 (M + H) |

TABLE 3-continued

| Intermediate # | Structure | Data |
|---|---|---|
| P204 | 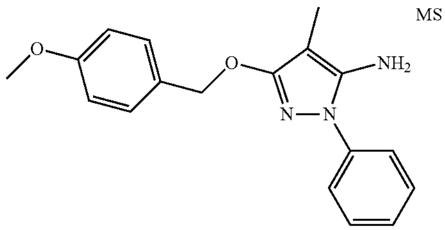 | MS (apci) m/z = 310.0 (M + H) |
| P205 | 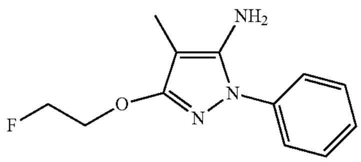 [SMILES: Cc1c(OCCF)nn(-c2ccccc2)c1N] | MS (apci) m/z = 236.1 (M + H) |
| P206 | 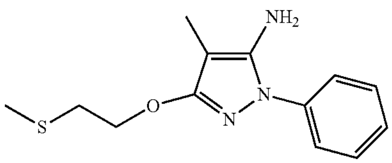 [SMILES: CSCCOc1nn(-c2ccccc2)c(N)c1C] | MS (apci) m/z = 264.0 (M + H) |
| P207 | 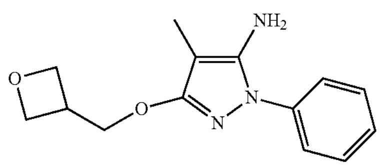 [SMILES: Cc1c(OCC2COC2)nn(-c2ccccc2)c1N] | MS (apci) m/z = 260.1 (M + H) |
| P208 | 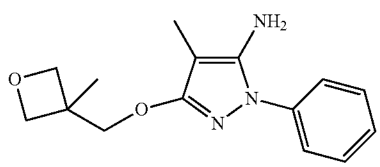 [SMILES: Cc1c(OCC2(C)COC2)nn(-c2ccccc2)c1N] | MS (apci) m/z = 274.1 (M + H) |
| P209 | 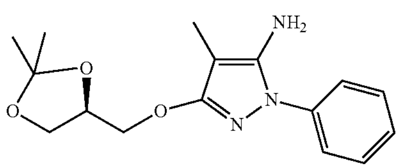 [SMILES: Cc1c(OC[C@H]2COC(C)(C)O2)nn(-c2ccccc2)c1N] | MS (apci) m/z = 304.1 (M + H) |
| P210 | 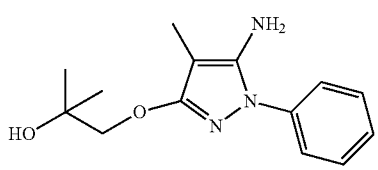 [SMILES: Cc1c(OCC(C)(C)O)nn(-c2ccccc2)c1N] | MS (apci) m/z = 262.1 (M + H) |
| P211 | 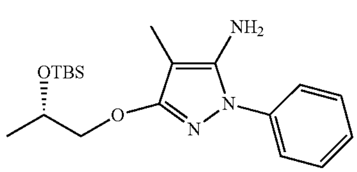 [SMILES: Cc1c(OC[C@H](C)O[Si](C)(C)C(C)(C)C)nn(-c2ccccc2)c1N] | MS (apci) m/z = 362.0 (M + H) |
| P212 | 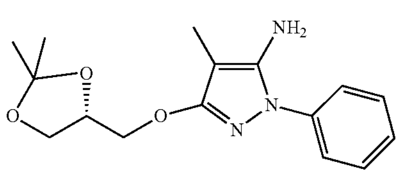 [SMILES: Cc1c(OC[C@@H]2COC(C)(C)O2)nn(-c2ccccc2)c1N] | MS (apci) m/z = 304.1 (M + H) |

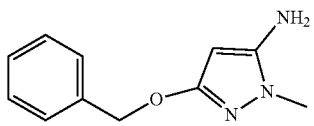

Intermediate P136

3-(benzyloxy)-1-methyl-1H-pyrazol-5-amine

Step A: Preparation of 5-amino-1-methyl-4-phenyl-1H-pyrazol-3(2H)-one: To a suspension of ethyl 2-cyano-2-phenylacetate (2.56 g, 13.3 mmol) in EtOH (10 mL) was added dropwise methylhydrazine (1.09 mL, 19.9 mmol). The reaction was heated at 85° C. for 15 hours. The reaction mixture was cooled to 0° C. and filtered. The resultant solid was washed with cold EtOH (20 mL) and Et$_2$O (20 mL) to give the desired product (2.10 g, 83.7% yield). MS (apci) m/z=190.2 (M+H)

Step B: Preparation of 3-(benzyloxy)-1-methyl-1H-pyrazol-5-amine: A suspension of 5-amino-1-methyl-1H-pyrazol-3(2H)-one (0.35 g, 3.1 mmol), Benzyl chloride (0.43 g, 3.4 mmol), and K$_2$CO$_3$ (1.3 g, 9.3 mmol) in DMF (4 mL) was heated at 70° C. for 17 hours. After cooling, the reaction mixture was treated with EtOAc, washed with water and brine, dried with MgSO$_4$, and concentrated in vacuo. The crude product was purified by silica column chromatography eluting with 2-6% MeOH/DCM to afford the title compound (0.16 g, 25% yield). MS (apci) m/z=204.0 (M+H).

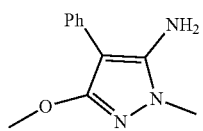

Intermediate P137

3-methoxy-1-methyl-4-phenyl-1H-pyrazol-5-amine

To a suspension of 5-amino-1-methyl-4-phenyl-1H-pyrazol-3(2H)-one (Step A of the preparation of Intermediate P136; 208 mg, 1.10 mmol) and K$_2$CO$_3$ (456 mg, 3.30 mmol) in DMF (5 mL) was added dropwise iodomethane (172 mg, 1.21 mmol). The reaction mixture was stirred for 15 hours. The solvent was removed under reduced pressure and the residue was purified by silica column chromatography eluting with 33% EtOAc/Hexanes to give the title pyrazole (66.0 mg, 30.4% yield). MS (apci) m/z=204.1 (M+H).

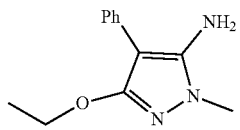

Intermediate P138

3-ethoxy-1-methyl-4-phenyl-1H-pyrazol-5-amine

Prepared as described in Intermediate P137, replacing iodomethane with iodoethane in Step B to afford the title compound. MS (apci) m/z=218.2 (M+H).

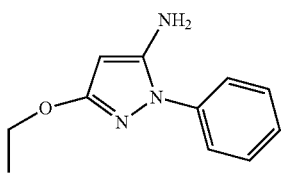

Intermediate P139

3-ethoxy-1-phenyl-1H-pyrazol-5-amine

Prepared according to the procedure described for Intermediate 135, substituting ethyl-2-cyanopropanoate with ethyl-2-cyanoacetate in Step A. MS (apci) m/z=204.0 (M+H).

The compounds in the following Table were prepared by the method as described for Intermediate P135, substituting bromoethane with the appropriate alkyl halide, alkyl methanesulfonate or epoxide.

| Intermediate # | Structure | MS (apci) m/z |
| --- | --- | --- |
| P140 | 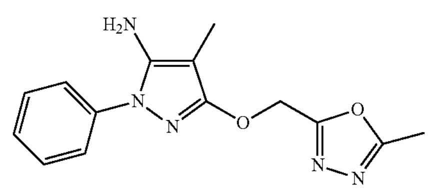 [SMILES: Cc1nnc(COc2nn(-c3ccccc3)c(N)c2C)o1] | 286.1 (M + H) |
| P141 | 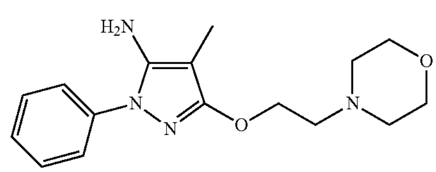 [SMILES: Cc1c(OCCN2CCOCC2)nn(-c2ccccc2)c1N] | 303.1 (M + H) |

-continued

| Intermediate # | Structure | MS (apci) m/z |
|---|---|---|
| P142 | 5-amino-4-methyl-1-phenyl-3-[(2S)-2-hydroxybutoxy]pyrazole | 262.1 (M + H) |
| P143 | 5-amino-4-methyl-1-phenyl-3-[2-(4-Boc-piperazin-1-yl)ethoxy]pyrazole | 402.2 (M + H) |
| P144 | 5-amino-4-methyl-1-phenyl-3-(ethoxycarbonylmethoxy)pyrazole | 276.1 (M + H) |
| P145 | 5-amino-4-methyl-1-phenyl-3-[2-(phthalimido)ethoxy]pyrazole | 363.1 (M + H) |
| P146 | 5-amino-4-methyl-1-phenyl-3-[(2S)-2-hydroxypropoxy]pyrazole | 248.1 (M + H) |
| P147 | 5-amino-4-methyl-1-phenyl-3-[(2R)-2-hydroxypropoxy]pyrazole | 248.1 (M + H) |
| P148 | 5-amino-4-methyl-1-phenyl-3-[(2S)-3,3,3-trifluoro-2-hydroxypropoxy]pyrazole | 302.1 (M + H) |
| P149 | 5-amino-4-methyl-1-phenyl-3-[(2R)-3,3,3-trifluoro-2-hydroxypropoxy]pyrazole | 302.1 (M + H) |
| P150 | 5-amino-4-methyl-1-phenyl-3-[(2R)-2-hydroxybutoxy]pyrazole | 262.1 (M + H) |

Intermediate 151

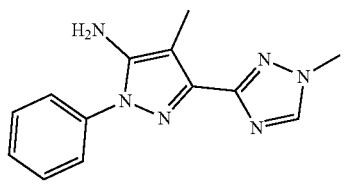

1'-(2-methoxyethyl)-1-phenyl-1H, 1'H-[3,4'-bipyrazol]-5-amine

Step A: Preparation of methyl 1-methyl-1H-1,2,4-triazole-3-carboxylate: To a stirred suspension of NaH (60% oil dispersion, 0.346 g, 8.66 mmol) in DMF (20 mL) was added dropwise a solution of methyl 1H-1,2,4-triazole-3-carboxylate (1.00 g, 7.87 mmol) in DMF (20 mL) at 0° C. under nitrogen. The reaction mixture was stirred at 0° C. for 1 hour. MeI (0.982 mL, 15.7 mmol) was added dropwise. The reaction mixture was stirred at ambient temperature overnight. The reaction was poured into cold water and extracted with EtOAc. The combined organic layers were washed with brine, dried and concentrated. The residue was purified by column chromatography (3:1 hexanes/EtOAc) to give the title compound (0.380 g, 34% yield) as a white solid. MS (apci) m/z=142.1 (M+H).

Step B: Preparation of 1'-(2-methoxyethyl)-1-phenyl-1H, 1'H-[3,4'-bipyrazol]-5-amine: Prepared according to the method described for Intermediate P109, using methyl 1-methyl-1H-1,2,4-triazole-3-carboxylate as a replacement for methyl 2-methoxyacetate, and substituting propionitrile for acetonitrile in Step A. MS (apci) m/z=255.1 (M+H).

Intermediate 152

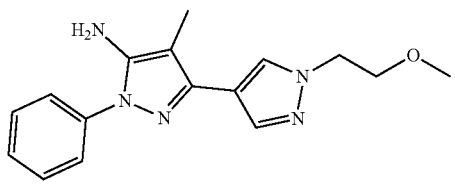

1'-(2-methoxyethyl)-4-methyl-1-phenyl-1H, 1'H-r[3,4'-bipyrazol]-5-amine

Prepared according to the method described for Intermediate P109, using ethyl 1-(2-methoxyethyl)-1H-pyrazole-4-carboxylate as a replacement for methyl 2-methoxyacetate, and substituting propionitrile for acetonitrile in Step A.

Intermediate 153

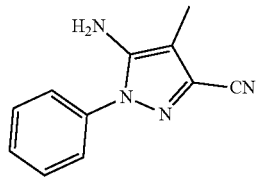

5-amino-4-methyl-1-phenyl-1H-pyrazole-3-carbonitrile

To a stirred solution of aniline (2.02 g, 21.7 mmol) in 6 N HCl (22 mL) was added dropwise a solution of NaNO₂ (1.50 g, 21.7 mmol) in water (20 mL) at 0-5° C. The reaction mixture was stirred at 0° C. for 15 minutes. Acetic acid (10 mL) was added. This solution was added dropwise to a stirred solution of ethyl 2,3-dicyanobutanoate (Prepared according to the procedure described in *Bioorganic & Medicinal Chemistry*, 2004, 12, 3345-3356, 3.60 g, 21.7 mmol) in acetic acid (12 mL) and water (18 mL) at 0° C. After stirring for 1 hour, concentrated ammonium hydroxide (50 mL) was added dropwise followed by THF (50 mL). The reaction was stirred at ambient temperature overnight. The organic layer was separated. The aqueous layer was extracted with EtOAc. The combined organic layers were washed with brine, dried and concentrated. The residue was purified by flash chromatography on silica gel (3:1 hexanes/EtOAc) to give the title compound (2.95 g, 69% yield). MS (apci) m/z=198.9 (M+H).

Intermediate 154

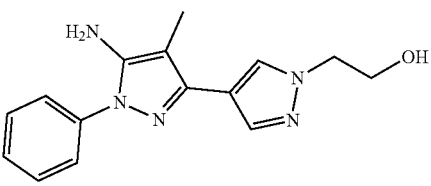

2-(5-amino-4-methyl-1-phenyl-1H, 1'H-3,4'-bipyrazol-1'-yl)ethanol

Step A: Preparation of ethyl 1-(2-((tert-butyldimethylsilyl)oxy)ethyl)-1H-pyrazole-4-carboxylate: Prepared according to the method described for Example 556, replacing 1-bromo-2-methoxyethane with (2-bromoethoxy)(tert-butyl)dimethylsilane in Step A. MS (apci) m/z=298.9 (M+H).

Step B: Preparation of 2-(5-amino-4-methyl-1-phenyl-1H, 1'H-3,4'-bipyrazol-1'-yl)ethanol: Prepared according to the method described for Intermediate P109 using ethyl 1-(2-((tert-butyldimethylsilyl)oxy)ethyl)-1H-pyrazole-4-carboxylate as a replacement for methyl 2-methoxyacetate, and substituting propionitrile for acetonitrile in Step A. MS (apci) m/z=283.9 (M+H).

Intermediate 155

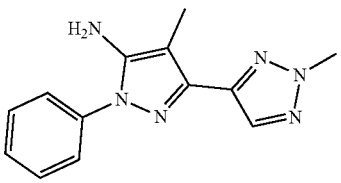

4-methyl-3-(2-methyl-2H-1,2,3-triazol-4-yl)-1-phenyl-1H-pyrazol-5-amine

Step A: Preparation of ethyl 2-methyl-2H-1,2,3-triazole-4-carboxylate: A mixture of ethyl 2H-1,2,3-triazole-4-carboxylate (2.00 g, 14.2 mmol), K₂CO₃ (3.53 g, 25.5 mmol)

and methyl iodide (3.54 mL, 56.7 mmol) in acetonitrile (40 mL) was stirred at 50° C. under nitrogen overnight. After cooling to ambient temperature, the mixture was filtered through Celite®. The filtrate was concentrated in vacuo. The residue was purified by flash chromatography on silica gel (4:1 hexane/EtOAc) to give the title compound (0.780 g, 35% yield). MS (apci) m/z=156.0 (M+H).

Step B: Preparation of 4-methyl-3-(2-methyl-2H-1,2,3-triazol-4-yl)-1-phenyl-1H-pyrazol-5-amine: Prepared according to the method described for Intermediate P109 using ethyl 2-methyl-2H-1,2,3-triazole-4-carboxylate as a replacement for methyl 2-methoxyacetate, and substituting propionitrile for acetonitrile in Step A. MS (apci) m/z=254.9 (M+H).

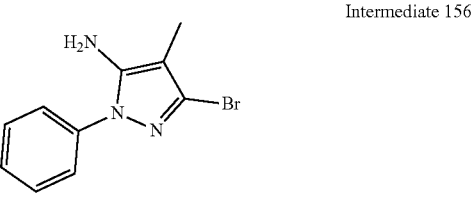

Intermediate 156

3-bromo-4-methyl-1-phenyl-1H-pyrazol-5-amine

To a stirred solution of 5-amino-4-methyl-1-phenyl-1H-pyrazol-3(2H)-one (Intermediate P135, Step A, 1.00 g, 5.29 mmol) in MeCN (20 mL) was added POBr$_3$ (2.27 g, 7.93 mmol). The reaction mixture was heated at reflux for 3 hours. The reaction was concentrate in vacuo. The residue was taken up in DCM. Saturated aqueous NaHCO$_3$ solution was carefully added. The aqueous layer was extracted with DCM. The combined organic layers were washed with brine, dried and concentrated. The residue was purified by flash chromatography on silica gel (1:2 hexane/EtOAc to give the title compound (0.23 g, 17% yield). MS (apci) m/z=251.8 (M+H).

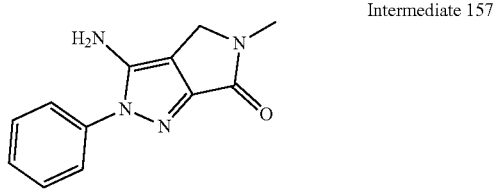 [SMILES: CN1Cc2c(nn(-c3ccccc3)c2N)C1=O]

Intermediate 157

3-amino-5-methyl-2-phenyl-4,5-dihydropyrrolo[3,4-c]pyrazol-6(2H)-one

Step A: Preparation of ethyl 5-amino-4-((methylamino)methyl)-1-phenyl-1H-pyrazole-3-carboxylate: To a stirred solution of ethyl 5-amino-4-formyl-1-phenyl-1H-pyrazole-3-carboxylate (Prepared according to the procedure described in *J. Heterocyclic Chemistry*, 2010, 47, p. 287-291, 142 mg, 0.548 mmol) in DCM (3 mL) was added 2.0 M MeNH$_2$ in THF (0.822 mL, 1.64 mmol). Two drops of acetic acid was added. The reaction mixture was stirred at ambient temperature overnight. MeOH (0.4 mL) was added followed by NaBH$_4$ (31 mg, 0.82 mmol) portionwise. The reaction was quenched by the slow addition of water. The mixture was extracted with DCM. The combined organic layers were washed with brine, dried and concentrated. The crude was used in the next step without further purification. MS (apci) m/z=275.0 (M+H).

Step B: Preparation of 3-amino-5-methyl-2-phenyl-4,5-dihydropyrrolo[3,4-c]pyrazol-6(2H)-one: To a stirred solution of ethyl 5-amino-4-((methylamino)methyl)-1-phenyl-1H-pyrazole-3-carboxylate (crude, 65 mg, 0.24 mmol) in MeOH (0.5 mL) and THF (0.5 mL) was added 2 N NaOH (0.24 mL, 0.47 mmol). The reaction mixture was stirred at ambient temperature for 4 hours and then concentrated in vacuo. To the residue was added water. The pH was adjusted to 4-5 using 1 N HCl. Water was evaporated under reduced pressure. The crude acid (58 mg) was dissolved in DMF (3 mL). Et$_3$N (66 µL, 0.47 mmol) was added followed by EDCI (90 mg, 0.47 mmol) and HOBt (32 mg, 0.24 mmol). The reaction mixture was stirred at ambient temperature overnight and then partitioned between EtOAc and water. The aqueous layer was extracted with EtOAc. The combined organic layers were washed with water and brine, dried and concentrated. The residue was purified by flash chromatography on silica gel (2% MeOH in DCM) to give the title compound (15 mg, 28%) as a white solid. MS (apci) m/z=228.9 (M+H).

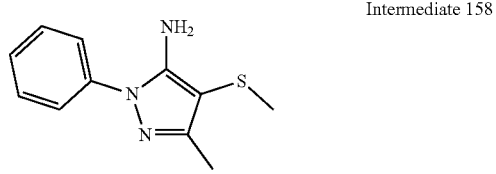

Intermediate 158

3-methyl-4-(methylthio)-1-phenyl-1H-pyrazol-5-amine

Prepared according to the method described for Intermediate P109, replacing methyl 2-methoxyacetate with ethyl acetate and replacing acetonitrile with 2-(methylthio)acetonitrile in Step A to afford the product as a brown oil. MS (apci) m/z=220.1 (M+H).

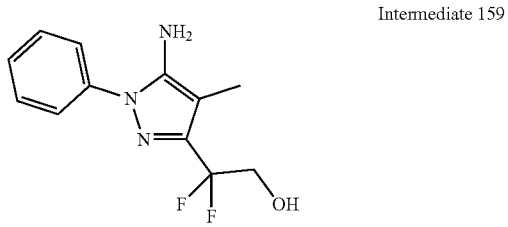 [SMILES: Cc1c(C(F)(F)CO)nn(-c2ccccc2)c1N]

Intermediate 159

2-(5-amino-4-methyl-1-phenyl-1H-pyrazol-3-yl)-2,2-difluoroethanol

Prepared according to the method described for Intermediate P111, replacing acetonitrile with propionitrile and replacing methyl 3-hydroxy-2,2-dimethylpropanoate with ethyl 2,2-difluoro-3-hydroxypropanoate to afford the product as a pale yellow solid. MS (apci) m/z=254.1 (M+H).

Intermediate 160

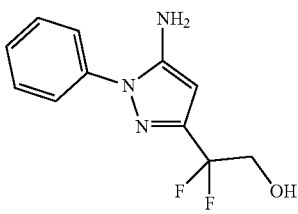

2-(5-amino-1-phenyl-1H-pyrazol-3-yl)-2,2-difluoroethanol

Prepared according to the method described for Intermediate P111, replacing methyl 3-hydroxy-2,2-dimethylpropanoate with ethyl 2,2-difluoro-3-hydroxypropanoate to afford the product as a pale yellow solid. MS (apci) m/z=240.0 (M+H).

Intermediate 161


2-(5-amino-1-phenyl-1H-pyrazol-3-yl)ethanol

Prepared according to the method described in Intermediate P111, replacing methyl 3-hydroxy-2,2-dimethylpropanoate with methyl 3-hydroxypropanoate in Step A. MS (apci) m/z=204.1 (M+H).

Intermediate 162


1-(5-amino-4-methyl-1-phenyl-1H-pyrazol-3-yl)-2-methylpropan-2-ol

Step A: Preparation of ethyl 3-hydroxy-3-methylbutanoate: To a solution of lithium bis(trimethylsilyl)amide (1M in THF) (100 mL, 100 mmol) in THF (100 mL) under $N_2$ and cooled to −78° C. was added ethyl acetate (9.74 mL, 100 mmol). The reaction mixture was stirred for 30 minutes, and then acetone (8.81 mL, 120 mmol) was added. The reaction mixture was stirred for 10 minutes, and then quenched with HCl (2M aqueous, 70 mL, 140 mmol) and allowed to warm to ambient temperature. The reaction mixture was extracted with EtOAc (2×150 mL). The organic phases were combined and washed with saturated aqueous $NaHCO_3$ (2×50 mL), dried ($MgSO_4$), filtered and concentrated to afford the product as a yellow oil (12.8 g, 88% yield). $^1$H NMR ($CDCl_3$) δ 4.18 (q, 3H), 2.49 (s, 2H), 1.29 (m, 9H).

Step B: Preparation of 5-hydroxy-5-methyl-3-oxohexanenitrile: To a solution of propionitrile (1.77 mL, 30.5 mmol) in THF (100 mL) under $N_2$ at −78° C. was added lithium bis(trimethylsilyl)amide (1M in THF) (27.9 mL, 27.9 mmol). Stirred 1 hour, then ethyl 3-hydroxy-3-methylbutanoate (1.86 g, 12.7 mmol) was added. The reaction mixture was stirred at −78° C. for 1 hour, then stirred at 0° C. for 1.5 hours, then diluted with $H_2O$ (100 mL) and extracted with $Et_2O$ (50 mL). The phases were separated and the basic aqueous phase was neutralized with HCl (6M aqueous, 4.5 mL), then extracted with $Et_2O$ (3×75 mL). The combined organic phases were washed with brine (75 mL), dried ($MgSO_4$), filtered, and concentrated to afford the product as a pale yellow oil (1.24 g, 63% yield). $^1$H NMR ($CDCl_3$) δ 3.54 (m, 1H), 2.89 (s, 2H), 1.50 (d, 3H), 1.32 (s, 3H), 1.31 (s, 3H).

Step C: Preparation of 1-(5-amino-4-methyl-1-phenyl-1H-pyrazol-3-yl)-2-methylpropan-2-ol: To a suspension of phenylhydrazine (0.793 mL, 7.99 mmol) and HCl (5-6M in iPrOH, 1.60 mL, 7.99 mmol) in EtOH (25 mL) was added a solution of 5-hydroxy-2,5-dimethyl-3-oxohexanenitrile (1.24 g, 7.99 mmol) in EtOH (25 mL). The reaction mixture was refluxed for 17 hours, then cooled to ambient temperature, diluted with saturated aqueous $NaHCO_3$ (10 mL), extracted 10:90 MeOH/DCM (3×25 mL), and the combined organic phases were dried ($MgSO_4$), filtered and concentrated. Purified by silica column chromatography eluting with 0-75% acetone/hexanes to afford the title compound as an orange oil (1.13 g, 58% yield). MS (apci) m/z=246.1 (M+H).

The following pyrazole intermediates were prepared according to the method used for the preparation of Intermediate 162, Steps B and C, using the appropriate starting material. For the preparation of Intermediates 168 and 169, the starting material (purchased from Oakwood) was a mixture of cis and trans diastereomers.

| Intermediate # | Structure | Name | MS (apci) m/z |
|---|---|---|---|
| 163 | 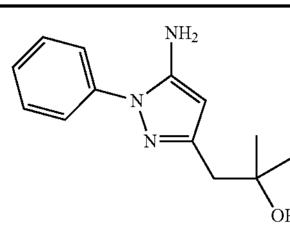 | 1-(5-amino-1-phenyl-1H-pyrazol-3-yl)-2-methylpropan-2-ol | 232.1 (M + H) |

-continued

| Intermediate # | Structure | Name | MS (apci) m/z |
|---|---|---|---|
| 164 | 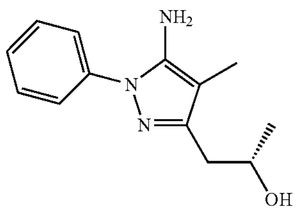 [SMILES: Cc1c(C[C@H](C)O)nn(-c2ccccc2)c1N] | (S)-1-(5-amino-4-methyl-1-phenyl-1H-pyrazol-3-yl)propan-2-ol | 232.1 (M + H) |
| 165 | 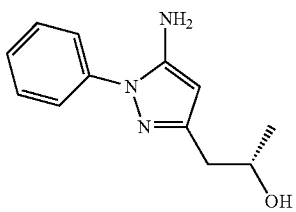 [SMILES: C[C@H](O)Cc1cc(N)n(-c2ccccc2)n1] | (S)-1-(5-amino-1-phenyl-1H-pyrazol-3-yl)propan-2-ol | 218.1 (M + H) |
| 166 | 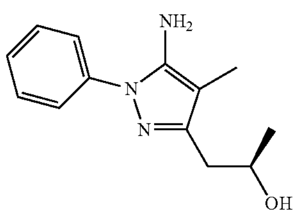 [SMILES: Cc1c(C[C@@H](C)O)nn(-c2ccccc2)c1N] | (R)-1-(5-amino-4-methyl-1-phenyl-1H-pyrazol-3-yl)propan-2-ol | 232.1 (M + H) |
| 167 | 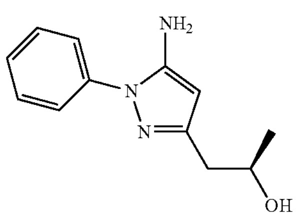 [SMILES: C[C@@H](O)Cc1cc(N)n(-c2ccccc2)n1] | (R)-1-(5-amino-1-phenyl-1H-pyrazol-3-yl)propan-2-ol | 218.1 (M + H) |
| 168 | 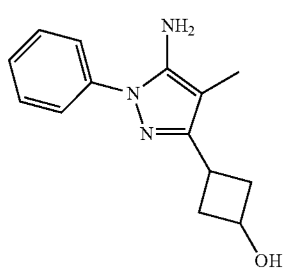 [SMILES: Cc1c(C2CC(O)C2)nn(-c2ccccc2)c1N] | 3-(5-amino-4-methyl-1-phenyl-1H-pyrazol-3-yl)cyclobutanol | 244.1 (M + H) |
| 169 | 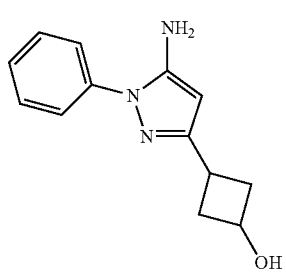 [SMILES: Nc1cc(C2CC(O)C2)nn1-c1ccccc1] | 3-(5-amino-1-phenyl-1H-pyrazol-3-yl)cyclobutanol | 230.1 (M + H) |

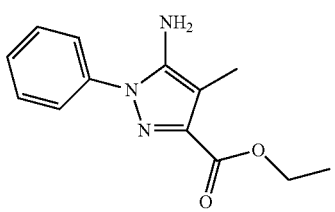

Intermediate 170 ethyl 5-amino-4-methyl-1-phenyl-1H-pyrazole-3-carboxylate

Prepared according to the method described for Intermediate P109, replacing methyl 2-methoxyacetate with diethyl oxalate and replacing acetonitrile with propionitrile in Step A to afford the product as a yellow solid. MS (apci) m/z=246.1 (M+H).

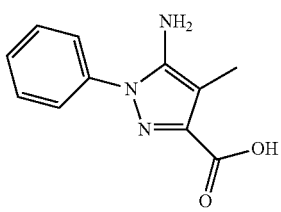

Intermediate 171

5-amino-4-methyl-1-phenyl-1H-pyrazole-3-carboxylic acid

To a solution of ethyl 5-amino-4-methyl-1-phenyl-1H-pyrazole-3-carboxylate (Intermediate 170, 1.52 mg, 6.21 mmol) in THF (12 mL) and MeOH (6 mL) was added LiOH (2M aq, 9.31 mL, 18.6 mmol). The reaction mixture was stirred at ambient temperature for 19 hours, then partially concentrated under reduced pressure, then neutralized with 6M HCl (3.2 mL), extracted with 10:90 MeOH/DCM (3×25 mL), and the combined organic extracts were washed with brine (50 mL), dried ($MgSO_4$), filtered and concentrated to give the title compound as a yellow solid (1.3 g, 96% yield) MS (apci) m/z=218.1 (M+H).

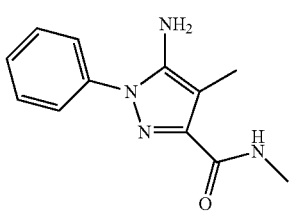

Intermediate 172

5-amino-N,4-dimethyl-1-phenyl-1H-pyrazole-3-carboxamide

To a solution of 5-amino-4-methyl-1-phenyl-1H-pyrazole-3-carboxylic acid (Intermediate 171, 223 mg, 1.02 mmol) in acetonitrile (10 mL) were added DIEA (0.71 mL, 4.10 mmol), methanamine hydrochloride (138 mg, 2.05 mmol), DMF (2 mL), and then HATU (428 mg, 1.13 mmol). The reaction mixture was stirred at ambient temperature for 19 hours and then partially concentrated under reduced pressure. The mixture was purified by reverse-phase column chromatography, eluting with 5-60% acetonitrile/water to afford the title compound as a pale yellow solid (182 mg, 77% yield). MS (apci) m/z=231.1 (M+H).

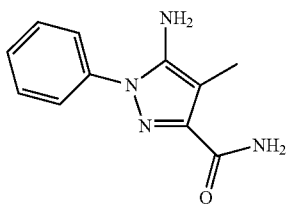

Intermediate 173

5-amino-4-methyl-1-phenyl-1H-pyrazole-3-carboxamide

A solution of 5-amino-4-methyl-1-phenyl-1H-pyrazole-3-carbonitrile (150 mg, 0.757 mmol) in concentrated $H_2SO_4$ (0.5 mL) was stirred at ambient temperature for 17 hours. The reaction mixture was cooled and neutralized by the addition of aqueous NaOH (2M, 11 mL), then extracted 10% MeOH/DCM (5×10 mL), and the combined organic extracts were washed with brine, dried ($MgSO_4$), filtered and concentrated under reduced pressure to afford the title compound as a white solid (151 mg, 95% yield). MS (apci) m/z=239.1 (M+Na).

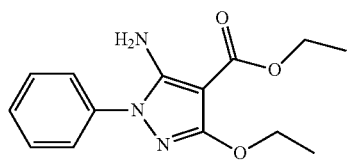

Intermediate 174 ethyl 5-amino-3-ethoxy-1-phenyl-1H-pyrazole-4-carboxylate

Step A: Preparation of diethyl 2-cyanomalonate: To a suspension of NaH (60 wt in mineral oil, 499 mg, 12.49 mmol) in THF (100 mL) under $N_2$ at 0° C. was added diethyl malonate (1.90 mL, 12.49 mmol). The ice bath was removed and the reaction mixture was stirred at ambient temperature for 30 minutes, then cooled to 0° C. and cyanic bromide (5M in MeCN, 2.5 mL, 12.49 mmol) was added. The reaction mixture was stirred at ambient temperature for 19 hours, then diluted with $H_2O$ (50 mL), extracted with $Et_2O$ (50 mL). The aqueous phase was neutralized with HCl (2M aq, 3 mL) then extracted with DCM (2×50 mL). The combined DCM extracts were dried ($MgSO_4$), filtered, and concentrated to afford the product as a yellow oil (837 mg, 36% yield). 1H NMR ($CDCl_3$) δ 4.46 (s, 1H), 4.35 (q, 4H), 1.35 (t, 6H).

Step B: Preparation of ethyl 5-amino-3-ethoxy-1-phenyl-1H-pyrazole-4-carboxylate: Prepared according to the method described for Intermediate P135, replacing ethyl 2-cyanopropanoate with diethyl 2-cyanomalonate in Step A to afford the product as a brown syrup (400 mg, 32% yield). MS (apci) m/z=276.1 (M+H).

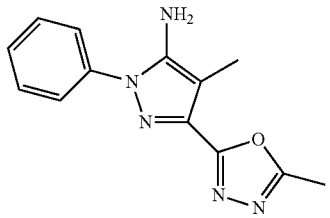

Intermediate 175

4-methyl-3-(5-methyl-1,3,4-oxadiazol-2-yl)-1-phenyl-1H-pyrazol-5-amine

Step A: Preparation of N'-acetyl-5-amino-4-methyl-1-phenyl-1H-pyrazole-3-carbohydrazide: To a solution of 5-amino-4-methyl-1-phenyl-1H-pyrazole-3-carboxylic acid (Intermediate 171, 93 mg, 0.428 mmol) in DCM (5 mL) and DIEA (0.149 mL, 0.856 mmol) was added isobutyl carbonochloridate (0.061 mL, 0.471 mmol). The reaction mixture was stirred at ambient temperature for 1 hour, then acetohydrazide (48 mg, 0.642 mmol) was added. The reaction mixture was stirred at ambient temperature for 18 hours, then diluted with H$_2$O (10 mL), extracted DCM (2×10 mL), dried (MgSO$_4$), filtered and concentrated under reduced pressure to afford the product as a pale yellow solid (119 mg, 101% yield). MS (apci) m/z=274.1 (M+H).

Step B: Preparation of 4-methyl-3-(5-methyl-1,3,4-oxadiazol-2-yl)-1-phenyl-1H-pyrazol-5-amine: A mixture of N'-acetyl-5-amino-4-methyl-1-phenyl-1H-pyrazole-3-carbohydrazide (117 mg, 0.428 mmol) and POCl$_3$ (0.5 mL) was heated in a pressure tube to 90° C. for 1 hour. The reaction mixture was transferred to a separatory funnel with EtOAc (5 mL), then diluted with saturated aqueous NaHCO$_3$ (20 mL), extracted with EtOAc (2×15 mL), dried (MgSO$_4$), filtered and concentrated. The residue was purified by silica column chromatography eluting with 0-75% acetone/hexanes to afford the title compound as a yellow solid (19.6 mg, 18% yield). MS (apci) m/z=256.1 (M+H).

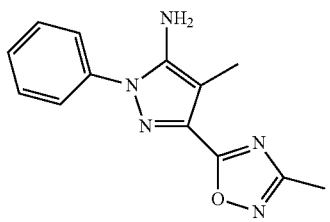

Intermediate 176

4-methyl-3-(3-methyl-1,2,4-oxadiazol-5-yl)-1-phenyl-1H-pyrazol-5-amine

To a suspension of NaH (60% in mineral oil, 36 mg, 0.897 mmol) in THF (5 mL) under N$_2$ was added N-hydroxyacetimidamide (66 mg, 0.897 mmol). The reaction mixture was heated to reflux for 1 hour, then cooled to ambient temperature and ethyl 5-amino-4-methyl-1-phenyl-1H-pyrazole-3-carboxylate (Intermediate 170, 200 mg, 0.815 mmol) was added. The reaction mixture was heated to reflux for 18 hours, then cooled to ambient temperature and additional NaH (60% in mineral oil, 18 mg, 0.449 mmol) was added. The reaction mixture was heated to reflux for 4 hours, then diluted with H$_2$O (10 mL), extracted DCM (2×15 mL), and the combined organic extracts were dried (MgSO$_4$), filtered and concentrated under reduced pressure. The residue was purified by silica column chromatography eluting with 0-50% acetone/hexanes to afford the title compound as an orange solid (84 mg, 40% yield). MS (apci) m/z=256.1 (M+H).

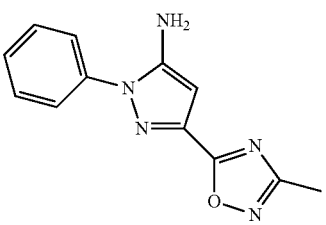

Intermediate 177

3-(3-methyl-1,2,4-oxadiazol-5-yl)-1-phenyl-1H-pyrazol-5-amine

Prepared according to the method described in Intermediate 176, replacing ethyl 5-amino-4-methyl-1-phenyl-1H-pyrazole-3-carboxylate with ethyl 5-amino-1-phenyl-1H-pyrazole-3-carboxylate (Nanjing Chemlin Chemical Co.) to afford the product as a tan solid (83 mg, 53% yield). MS (apci) m/z=242.1 (M+H).

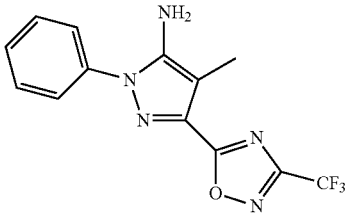

Intermediate 178

4-methyl-1-phenyl-3-(3-(trifluoromethyl)-1,2,4-oxadiazol-5-yl)-1H-pyrazol-5-amine Step A: Preparation of 2,2,2-trifluoro-N'-hydroxyacetimidamide: To a suspension of hydroxylamine hydrochloride (5.45 g, 78.4 mmol) in MeOH (100 mL) was added NaOMe (25 wt % solution in MeOH, 17.9 mL, 78.4 mmol) and the mixture stirred at ambient temperature for 10 minutes, then filtered and the solid was washed with MeOH. The filtrate was cooled to 0° C. and then 2,2,2-trifluoroacetonitrile (7.45 g, 78.4 mmol) gas was bubbled into the solution over 30 minutes. The reaction mixture was then allowed to warm to ambient temperature for 19 hours. The solution was concentrated under reduced pressure to 50 mL and the solids were filtered. The filtrate was concentrated, re-suspended in cold MeOH, and filtered. The filtrate was concentrated, again re-suspended in cold MeOH, and filtered. The filtrate was concentrated to give the product as a waxy white solid (6.7 g, 67% yield). $^1$H NMR (CD$_3$CN) δ 8.32 (s, 1H), 5.25 (br s, 2H). $^{19}$F NMR (CD$_3$CN) δ −71.8 (s).

Step B: Preparation of 4-methyl-1-phenyl-3-(3-(trifluoromethyl)-1,2,4-oxadiazol-5-yl)-1H-pyrazol-5-amine: To a suspension of NaH (60% in mineral oil, 356 mg, 0.897 mmol) in THF (5 mL, 0.815 mmol) under N₂ was added 2,2,2-trifluoro-N'-hydroxyacetimidamide (115 mg, 0.897 mmol). The reaction mixture was heated to reflux for 1 hour, then cooled to ambient temperature and powdered 4 Å molecular sieves (200 mg) and ethyl 5-amino-4-methyl-1-phenyl-1H-pyrazole-3-carboxylate (Intermediate 170; 200 mg, 0.815 mmol) were added and heated to reflux. The reaction mixture was heated to reflux for 18 hours, then filtered, diluted with H₂O (15 mL), extracted DCM (2×25 mL), and the combined organic extracts were washed with brine (25 mL), dried (MgSO₄), filtered and concentrated under reduced pressure. The residue was purified by silica column chromatography eluting with 0-50% acetone/hexanes to afford the title compound as a white solid (44 mg, 17% yield). MS (apci) m/z=310.1 (M+H).

Intermediate 179

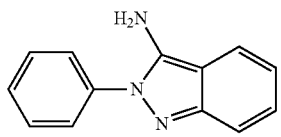

2-phenyl-2H-indazol-3-amine

Step A: Preparation of 1-(2-iodophenyl)-2-phenyldiazene: To a solution of 2-iodoaniline (1.00 g, 4.57 mmol) in acetic acid (46 mL) was added nitrosobenzene (0.880 g, 8.22 mmol) and the mixture was heated at 85° C. for 16 hours. The mixture was cooled to ambient temperature, poured into water and slowly treated with saturated NaHCO₃ until basic. The mixture was extracted with EtOAc (3×) and the combined extracts were washed with water, saturated NaCl and dried over MgSO₄. The solution was filtered, concentrated and the residue purified by reverse phase chromatography to provide the title compound as a red solid (0.880 g, 63% yield). ¹H NMR (CDCl₃) δ 7.23-7.39 (m, 3H), 7.64 (d, 1H), 7.56-7.51 (m, 3H), 7.45 (t, 1H), 7.1 (t, 1H).

Step B: 2-(phenyldiazenyl)benzonitrile: To a solution of 1-(2-iodophenyl)-2-phenyldiazene (0.44 g, 1.4 mmol) in 1-propanol (14 mL) was added CuCN (0.900 g, 10.0 mmol) and the reaction was heated at reflux for 16 hours. The mixture was cooled to ambient temperature, filtered and the collected solid washed with CH₂Cl₂. The combined filtrate and washes were concentrated to provide the title compound as red-orange solid that was dried in vacuum (0.280 g, 95% yield). ¹H NMR (CDCl₃) δ 8.03-8.06 (m, 2H), 7.88 (dd, 2H), 7.71 (t, 1H), 7.54-7.58 (m, 4H).

Step C: 2-phenyl-2H-indazol-3-amine: A mixture of 2-(phenyldiazenyl)benzonitrile (0.28 g, 1.35 mmol) and SnCl₂ dihydrate (0.562 mL, 6.76 mmol) in EtOH (14 mL) was heated at reflux for 16 hours. The mixture was cooled to ambient temperature and concentrated. The residue was diluted with EtOAc and water and filtered. The aqueous layer was removed and the EtOAc layer was washed with water. The combined aqueous fractions were basified with saturated NaHCO₃ and extracted with CH₂Cl₂ (2×). The combined organic layers were dried over MgSO₄, filtered and concentrated to provide the title compound as a light purple solid that was dried in vacuum (0.241 g, 85% yield). ¹H NMR (CDCl₃) δ 7.69 (d, 2H), 7.52-7.58 (m, 3H), 7.47 (d, 2H), 7.26 (t, 1H), 6.90 (t, 1H), 4.28 (br s, 2H).

Intermediate 180

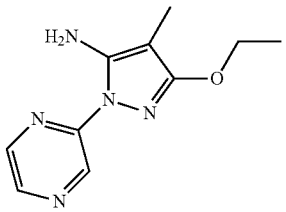

3-ethoxy-4-methyl-1-(pyrazin-2-yl)-1H-pyrazol-5-amine

Step A: 5-amino-4-methyl-1-(pyrazin-2-yl)-1H-pyrazol-3(2H)-one: To a mixture of 2-hydrazinylpyrazine (0.551 g, 5.00 mmol) and ethyl 2-cyanopropanoate (0.669 g, 5.00 mmol) in abs. EtOH (10 mL) was added 3M NaOEt in EtOH (0.167 mL, 0.501 mmol) and the mixture was heated at reflux for 64 hours. The mixture was concentrated and the residual yellow-brown solid was treated with EtOAc (30 mL) and sonicated. The resulting tan suspension was stirred vigorously for 8 hours. The solid was collected via vacuum filtration, washed with EtOAc and dried in vacuum to afford the title compound as a light tan powder (682 mg, 71%). ¹H NMR (DMSO d₆) δ 10.3 (br s, 1H), 8.82 (s, 1H), 8.30 (d, 2H), 6.55 (s, 2H), 1.71 (s, 3H).

Step B: 3-ethoxy-4-methyl-1-(pyrazin-2-yl)-1H-pyrazol-5-amine: A mixture of 5-amino-4-methyl-1-(pyrazin-2-yl)-1H-pyrazol-3(2H)-one (382 mg, 2.00 mmol) and powdered K₂CO₃ (552 mg, 4.00 mmol) in dry DMF (3.0 mL) was stirred at ambient temperature for 10 minutes. The mixture was cooled to 0° C. and bromoethane (229 mg, 2.10 mmol) was added. The mixture was allowed to reach ambient temperature and was stirred 24 hours. The reaction mixture poured into cold H₂O (12 mL), allowed to reach ambient temperature and was extracted with EtOAc (3×). The combined extracts were washed with saturated NaCl (2×), dried over MgSO₄ and activated carbon. The dried solution was diluted with and equal volume of hexanes and filtered through a SiO₂ plug capped with a MgSO₄ layer eluting with 50% EtOAc-hexanes. The filtrate was concentrated and the residual yellow solid was washed with hexanes (3×) and dried in vacuum to afford the title compound as a light yellow crystalline solid (195 mg, 45%). ¹H NMR (CDCl₃) δ 9.10 (s, 1H), 8.23 (s, 1H), 8.14 (s, 1H), 5.50 (br s, 2H), 4.33 (q, 2H), 1.80 (s, 3H), 1.42 (t, 3H).

Intermediate 181

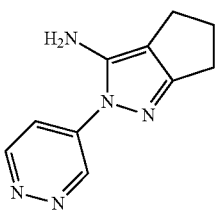

2-(pyridazin-4-yl)-2,4,5,6-tetrahydrocyclopenta[c]pyrazol-3-amine

A suspension of 4-hydrazinylpyridazine hydrobromide (0.368 g, 1.93 mmol) in absolute EtOH (5 mL) was treated with 2-oxocyclopentanecarbonitrile (0.191 g, 1.75 mmol)

and the mixture was heated at reflux for 22 hours. The mixture was cooled to ambient temperature and was concentrated to an orange solid. The solid was suspended in 1M NaOH and stirred for 10 minutes. The solid was collected, washed thoroughly with $H_2O$ and $Et_2O$ and dried in vacuum to furnish title compound as a tan powder (0.323 g, 92%). MS (apci) m/z=202.1 (M+H).

Intermediate 182

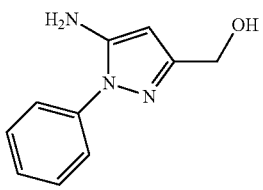

(5-amino-1-phenyl-1H-pyrazol-3-yl)methanol

Step A: Ethyl 2-(tert-butyldimethylsilyloxy)acetate: A mixture of ethyl 2-hydroxyacetate (3.00 g, 28.8 mmol), TBDMS-Cl (5.21 g, 34.6 mmol) and imidazole (2.55 g, 37.5 mmol) was stirred at ambient temperature for 60 hours. The mixture was concentrated and the residue was purified by $SiO_2$ chromatography eluting with 10% EtOAc-hexanes to provide the title compound as a colorless oil (4.12 g, 65%). $^1$H NMR (CDCl$_3$) δ 4.12 (s, 2H), 4.09 (q, 2H), 1.17 (t, 3H), 0.18 (s, 9H), 0.00 (s, 6H).

Step B: (5-amino-1-phenyl-1H-pyrazol-3-yl)methanol: A solution of acetonitrile (0.526 mL, 10.1 mmol) in dry THF (20.4 mL, 9.16 mmol) was cooled to −78° C. and 2.5M nBuLi in hexanes (4.21 mL, 10.5 mmol) was added dropwise. The reaction mixture was stirred for 15 minutes and ethyl 2-(tert-butyldimethylsilyloxy)acetate (2.00 g, 9.16 mmol) was added. The reaction mixture was allowed to warm to ambient temperature and was stirred for 2 hours. The reaction mixture was diluted with ice water and was concentrated. The residual aqueous mixture was acidified to pH=5 and extracted with EtOAc (3×). The combined organics were washed with brine, dried over $MgSO_4$, filtered and concentrated. The residual brown oil was dissolved in MeOH (23 mL) and phenyl hydrazine (0.907 mL, 9.14 mmol) was added. The mixture was treated with concentrated HCl (3.81 mL, 45.7 mmol) and heated at reflux for 18 hours. Upon cooling, the mixture was concentrated and the residue was partitioned into in $H_2O$ and $CH_2Cl_2$. The mixture was filtered and the organic layer was removed from the filtrate. The aqueous portion was washed with $CH_2Cl_2$ and was treated with saturated $NaHCO_3$ until basic. The aqueous mixture was extracted with $CH_2Cl_2$ (3×) and the combined organic fractions were dried over $MgSO_4$, filtered and concentrated. The residue was purified by silica column chromatography using 70-100% EtOAc/hexanes gradient elution followed by 0-5% MeOH/EtOAc. The product pools were combined and concentrated to give the title compound as a yellow foam (0.760 g, 44% yield). MS (apci) m/z=190.1 (M+H).

Intermediate 183

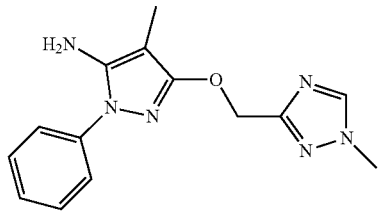

4-methyl-3-((1-methyl-1H-1,2,4-triazol-3-yl)methoxy)-1-phenyl-1H-pyrazol-5-amine The title compound was prepared by the method as described for Intermediate P135, substituting bromoethane with 3-(chloromethyl)-1-methyl-1H-1,2,4-triazole hydrochloride. The product was isolated as a gold syrup (110 mg, 27%). MS (apci) m/z=285.1 (M+H).

Intermediate 184

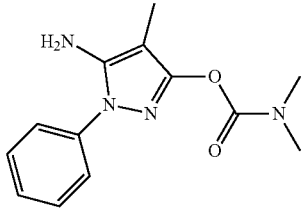

5-amino-4-methyl-1-phenyl-1H-pyrazol-3-yl dimethylcarbamate

A mixture of 5-amino-4-methyl-1-phenyl-1H-pyrazol-3(2H)-one (Intermediate P135 Step A, 0.378 g, 2.00 mmol) and powdered $K_2CO_3$ (0.553 g, 4.00 mmol) in dry DMF (4 mL) was stirred at ambient temperature for 5 minutes. Dimethylcarbamoyl chloride (0.206 mL, 2.20 mmol) was added and the mixture was stirred for 6 hours. The mixture was poured into chilled $H_2O$ (40 mL) and was extracted with EtOAc (3×). The combined extracts were washed with saturated NaCl (2×), dried over $MgSO_4$ and filtered through a $SiO_2$ plug capped with a $MgSO_4$ layer (EtOAc elution). The filtrate was concentrated and the residue dried in vacuum to give the title compound as a light gold syrup (0.507 g, 97%). MS (apci) m/z=261.1 (M+H).

Intermediate 185

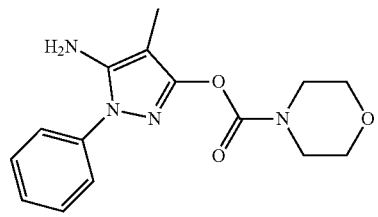

5-amino-4-methyl-1-phenyl-1H-pyrazol-3-yl morpholine-4-carboxylate

The title compound was prepared using morpholine-4-carbonyl chloride in the procedure outlined for 5-amino-4- methyl-1-phenyl-1H-pyrazol-3-yl dimethylcarbamate (Intermediate 184). The compound was isolated as a light yellow wax (0.285 g, 47%). ¹H NMR (CDCl₃) δ 7.54 (d, 2H), 7.43 (t, 2H), 7.31 (t, 1H), 3.66-3.78 (m, 8H), 3.57 (br s, 2H), 1.85 (s, 3H).

Intermediate 186

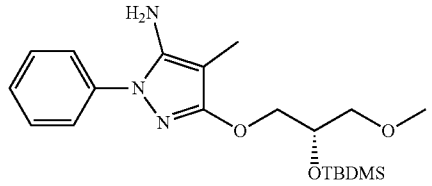

(S)-3-(2-((tert-butyldimethylsilyl)oxy)-3-methoxypropoxy)-4-methyl-1-phenyl-1H-pyrazol-5-amine Step A: (S)-1-(5-amino-4-methyl-1-phenyl-1H-pyrazol-3-yloxy)-3-methoxypropan-2-ol: A mixture of 5-amino-4-methyl-1-phenyl-1H-pyrazol-3(2H)-one (P135 Step A, 1.21 g, 6.40 mmol) and powdered K₂CO₃ (1.77 g, 12.8 mmol) in dry DMF (12 mL) was stirred at ambient temperature for 10 minutes. (S)-2-(methoxymethyl)oxirane (0.622 mL, 6.72 mmol) was added and the mixture was stirred at 80° C. for 6 hours. The mixture was cooled to ambient temperature, poured into chilled H₂O (25 mL) and extracted with EtOAc (3×). The combined extracts were washed with saturated NaCl (2×), dried over MgSO₄ and filtered through a SiO₂ plug capped with a layer of MgSO₄ eluting with EtOAc. The filtrate was concentrated to give the title compound as a colorless, viscous oil (701 mg, 40%). MS (apci) m/z=278.1 (M+H).

Step B: (S)-3-(2-((tert-butyldimethylsilyl)oxy)-3-methoxypropoxy)-4-methyl-1-phenyl-1H-pyrazol-5-amine: To a solution of TBDMS-Cl (725 mg, 4.81 mmol) and imidazole (390 mg, 5.72 mmol) in dry DMF (7.0 mL) was added (S)-1-(5-amino-4-methyl-1-phenyl-1H-pyrazol-3-yloxy)-3-methoxypropan-2-ol (635 mg, 2.29 mmol) in dry DMF (2 mL). The mixture stirred at ambient temperature for 2.5 hours. The mixture added to H₂O (70 mL), mixed for 5 minutes and extracted with Et₂O (3×). The combined extracts were washed with saturated NaCl (2×) and dried over MgSO₄. The dried solution was filtered through a SiO₂ plug capped with a layer of MgSO₄ (Et₂O elution). The filtrate was concentrated to give the title compound as a colorless oil that was dried in vacuum (940 mg, 105%). MS (apci) m/z=392.2 (M+H). ¹H NMR (CDCl₃) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 187

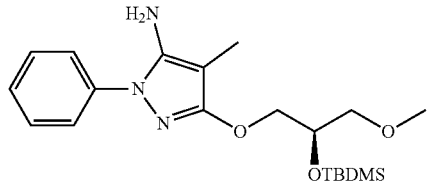

(R)-3-(2-((tert-butyldimethylsilyl)oxy)-3-methoxypropoxy)-4-methyl-1-phenyl-1H-pyrazol-5-amine The title compound was prepared using the procedure described for (S)-3-(2-((tert-butyldimethyl silyl)oxy)-3-methoxypropoxy)-4-methyl-1-phenyl-1H-pyrazol-5-amine (Intermediate 186) substituting (S)-2-(methoxymethyl)oxirane with (R)-2-(methoxymethyl)oxirane in Step A. The product was obtained as a colorless syrup (921 mg, 38% over 2 steps). MS (apci) m/z=392.2 (M+H). ¹H NMR (CDCl₃) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 188

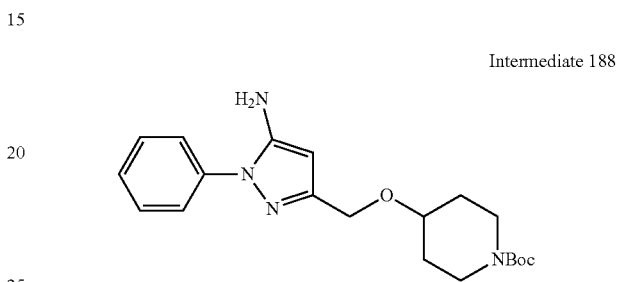

tert-butyl 4-((5-amino-1-phenyl-1H-pyrazol-3-yl)methoxy)piperidine-1-carboxylate Step A: tert-butyl 4-(2-ethoxy-2-oxoethoxy)piperidine-1-carboxylate: A solution of tert-butyl 4-hydroxypiperidine-1-carboxylate (2.00 g, 9.94 mmol) in dry THF (25 mL) was cooled to 0° C. and KOtBu (1.12 g, 9.94 mmol) was added. The mixture was allowed to reach ambient temperature and was stirred for 10 minutes. The mixture was cooled to 0° C. and ethyl 2-bromoacetate (1.65 mL, 14.9 mmol) was added dropwise. The reaction was allowed to reach ambient temperature and was stirred for 17 hours. The mixture was partitioned into in H₂O and EtOAc, mixed and the organic layer was removed. The organic layer was dried over MgSO₄, filtered and concentrated. The residual thick yellow oil was purified by silica chromatography using a 10-25% EtOAc/hexanes gradient elution to afford the title compound as a colorless oil (0.967 g, 34% yield). ¹H NMR (CDCl₃) δ 4.22 (q, 2H), 4.12 (s, 2H), 3.67-3.84 (m, 2H), 3.52-3.63 (m, 1H), 3.05-3.11 (m, 2H), 1.81-1.90 (m, 2H), 1.53-1.62 (m, 2H), 1.45 (s, 9H), 1.29 (t, 3H).

Step B: tert-butyl 4-((5-amino-1-phenyl-1H-pyrazol-3-yl)methoxy)piperidine-1-carboxylate: A solution of diisopropylamine (1.08 mL, 7.74 mmol) in dry THF (5 mL) was cooled to 0° C. and 2.5M nBuLi in hexanes (2.96 mL, 7.41 mmol) was slowly added. The mixture was stirred at 0° C. for 10 minutes and was cooled to −78° C. Acetonitrile (0.404 mL, 7.74 mmol) was added and the mixture was stirred for 15 minutes. A solution of tert-butyl 4-(2-ethoxy-2-oxoethoxy)piperidine-1-carboxylate (0.967 g, 3.37 mmol) in THF (2.5 mL) was added and the mixture was stirred at −78° C. for 1 hour. The mixture was allowed to reach ambient temperature, was quenched with ice water and concentrated. The residual aqueous mixture was neutralized with 2M HCl and was extracted with CH₂Cl₂ (3×). The combined organic fractions were dried over MgSO₄, filtered and concentrated to provide the crude cyano-ketone as a yellow oil that was used immediately in the next step.

Step C: tert-butyl 4-((5-amino-1-phenyl-1H-pyrazol-3-yl)methoxy)piperidine-1-carboxylate: The crude oil obtained in Step B was dissolved in EtOH (17 mL) and phenylhydrazine (0.396 mL, 3.99 mmol) was added. The mixture was heated at 60° C. for 60 hours, was cooled to ambient temperature and was concentrated. The residue was partitioned into EtOAc and water, mixed and the organic layer removed. The aqueous layer was extracted with EtOAc (2×) and the combined EtOAc portions were dried over $MgSO_4$, filtered and concentrated. The residual orange oil was purified by silica chromatography using a 10-100% EtOAc/hexanes gradient elution. The pooled product fractions were concentrated and the residual yellow-orange oil was re-purified by reverse phase HPLC using a 0-100% acetonitrile/water gradient to provide the title compound as an orange foam (0.264 g, 21% yield). MS (apci) m/z=373.2 (M+H).

Intermediate 189

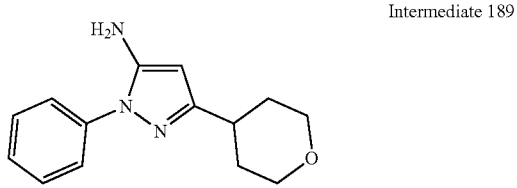 [SMILES: Nc1cc(C2CCOCC2)nn1-c1ccccc1]

1-phenyl-3-(tetrahydro-2H-pyran-4-yl)-1H-pyrazol-5-amine

Step A: 3-oxo-3-(tetrahydro-2H-pyran-4-yl)propanenitrile: A 1M solution of LHMDS in dry THF (26.3 mL, 26.3 mmol) was cooled to −78° C. and acetonitrile (1.43 mL, 27.5 mmol) was added dropwise over 2 minutes. The mixture was stirred at −78° C. for 1 hour and a solution of methyl tetrahydro-2H-pyran-4-carboxylate (3.41 mL, 25.0 mmol) in dry THF (12 mL) was added. The mixture was stirred for 1 hour, the dry ice bath was removed and the mixture allowed to reach ambient temperature. The mixture was poured into chilled $H_2O$ (250 mL) and was extracted with $Et_2O$ (3×). The aqueous portion was cooled to 0° C. and 6M HCl was added dropwise to pH=3 (starting pH=12). The mixture was extracted with EtOAc (3×) and the combined extracts were dried over $MgSO_4$. The solution eluted through a $SiO_2$ plug eluting with EtOAc. The filtrate was concentrated to give the title compound as a colorless oil (2.52 g, 66%). $^1$H NMR (CDCl$_3$) δ 3.99-4.06 (m, 2H), 3.54 (s, 2H), 3.46 (t, 2H), 2.76-2.86 (m, 1H), 1.70-1.86 (m, 4H).

Step B: 1-phenyl-3-(tetrahydro-2H-pyran-4-yl)-1H-pyrazol-5-amine: To a solution of 3-oxo-3-(tetrahydro-2H-pyran-4-yl)propanenitrile (2.30 g, 12.8 mmol) in absolute EtOH (35 mL) was added phenylhydrazine hydrochloride (2.21 g, 15.3 mmol) and the mixture was heated at reflux until complete by TLC (5 hours). The mixture was cooled to ambient temperature and was concentrated. The residue was partitioned in $H_2O$ (75 mL) and EtOAc (40 mL). 2M NaOH was added to pH=5 with vigorous mixing, the organic layer was removed and the aqueous was extracted with EtOAc (2×). The combined EtOAc fractions were washed with $H_2O$ and saturated NaCl. The solution was diluted with an equal volume of hexanes, dried over $MgSO_4$/activated carbon and eluted through a $SiO_2$ plug eluting with 50% EtOAc-hexanes. The filtrate was concentrated to give a gold syrup. The syrup was treated with $Et_2O$ and stirred until a fine, granular suspension formed. The solid was collected, washed with $Et_2O$ and dried in vacuum to furnish the title compound as a white solid (2.01 g, 65%). $^1$H NMR (CDCl$_3$) δ 7.55 (d, 2H), 7.46 (t, 2H), 7.32 (t, 1H), 5.49 (s, 1H), 4.00-4.08 (m, 2H), 3.97 (br s, 2H), 3.52 (dt, 2H), 2.86 (m, 1H) 1.73-1.93 (m, 4H).

The following compounds were prepared according to the method used for the preparation of 1-phenyl-3-(tetrahydro-2H-pyran-4-yl)-1H-pyrazol-5-amine (Intermediate 189) using either acetonitrile or propiononitrile in Step A in conjunction with the appropriate ester.

| Intermediate # | Structure | Data |
| --- | --- | --- |
| 190 | ![structure] | MS (apci) m/z = 343.1 (M + H) |
| 191 | ![structure] | MS (apci) m/z = 258.0 (M + H) |
| 192 | ![structure] | $^1$H NMR (CDCl$_3$) δ 7.62 (d, 2H), 7.50 (t, 2H), 7.37 (t, 1H), 5.72 (s, 1H), 3.91 (br s, 2H), 2.58 (s, 3H), 2.44 (s, 3H). |

-continued

| Intermediate # | Structure | Data |
|---|---|---|
| 193 | 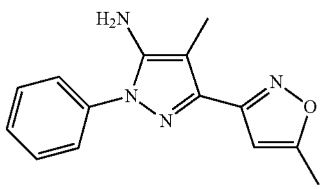 [SMILES: Cc1cc(-c2nn(-c3ccccc3)c(N)c2C)no1] | $^1$H NMR (CDCl$_3$) δ 7.60 (d, 2H), 7.49 (t, 2H), 7.37 (t, 1H), 6.45 (s, 1H), 3.67 (br s, 2H), 2.45 (s, 3H), 2.24 (s, 3H). |
| 194 | 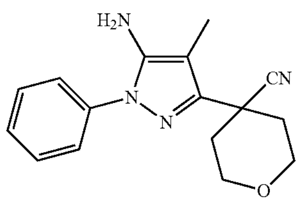 [SMILES: Cc1c(C2(C#N)CCOCC2)nn(-c2ccccc2)c1N] | $^1$H NMR (CDCl$_3$) δ 7.45-7.56 (m, 4H), 7.35 (t, 1H), 4.00-4.06 (m, 2H), 3.88 (dt, 2H), 3.62 (br s, 2H), 2.18-2.34 (m, 4H), 2.11 (s, 3H). |
| 195 | 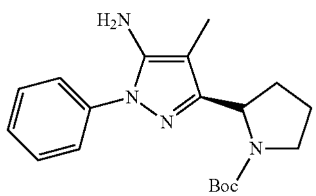 | MS (apci) m/z = 343.2 (M + H) |
| 196 | 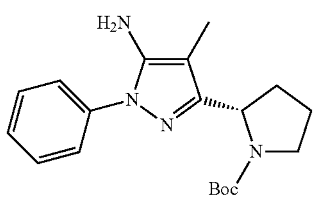 [SMILES: Cc1c([C@@H]2CCCN2C(=O)OC(C)(C)C)nn(-c2ccccc2)c1N] | MS (apci) m/z = 343.2 (M + H) |
| 197 | 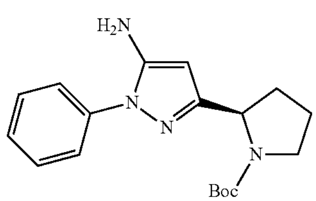 [SMILES: CC(C)(C)OC(=O)N1CCC[C@@H]1c1cc(N)n(-c2ccccc2)n1] | MS (apci) m/z = 329.2 (M + H) |
| 198 | 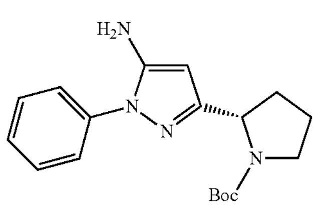 [SMILES: CC(C)(C)OC(=O)N1CCC[C@H]1c1cc(N)n(-c2ccccc2)n1] | MS (apci) m/z = 329.2 (M + H) |

Intermediate 199

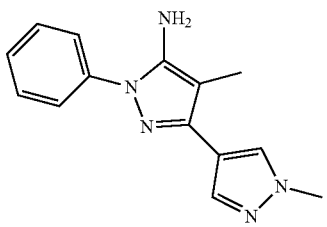

Phenyl 1',4-dimethyl-1-phenyl-1H, 1'H-3,4'-bipyrazol-5-ylcarbamate

Step A: ethyl 1-methyl-1H-pyrazole-4-carboxylate: To a 3000-mL three-necked flask was added ethyl 2-formyl-3-oxopropanoate (100 g, 694 mmol), followed by anhydrous 200-proof EtOH (694 mL) to obtain a clear yellowish solution. The reaction was cooled in an ice bath to 5° C., and then methylhydrazine (35.8 mL, 680 mmol) was added dropwise. A vigorous exotherm was observed during hydrazine addition and the temperature was kept below 12° C. by controlling the addition rate. After the hydrazine addition was complete, the ice bath was removed, and the reaction was allowed to stir at ambient temperature overnight. The reaction was concentrated on a rotary evaporator to a crude orange oil. The crude was taken up in DCM and re-concentrated, then on high vacuum for 2 days to yield tan orange oil. LC/MS and $^1$H NMR showed essentially pure ethyl 1-methyl-1H-pyrazole-4-carboxylate (106 g, 99.1%).

Step B: 2-methyl-3-(1-methyl-1H-pyrazol-4-yl)-3-oxopropanenitrile: To a four-necked 5-liter round bottomed flask fitted with an overhead stirrer and addition funnel was charged LHMDS (1444 mL, 1444 mmol) (1.0M in THF). The solution was cooled in an acetone/dry ice bath first (internal temperature of −79° C.) under nitrogen, followed by slow addition of propiononitrile (103 mL, 1444 mmol) via dropping funnel. The mixture was stirred at −80° C. for 90 minutes. A solution of ethyl 1-methyl-1H-pyrazole-4-carboxylate (106 g, 688 mmol) in anhydrous THF (500 mL) was then introduced dropwise via an addition funnel (addition time: about 45 minutes; internal temperature during addition remained below −76° C.). After the addition was complete, the reaction was allowed to slowly warm to ambient temperature and stirred overnight. An orange glass deposited on the bottom of the flask. The organics were decanted and the glass was dissolved in warm water. The mixture was washed with ether (3×1000 mL). The aqueous phase was then pH-adjusted to 5 (pH paper) using concentrated HCl and saturated bicarbarbonate solution The aqueous layer was extracted with DCM (3×1000 mL). The combined organic extracts were dried over MgSO$_4$ filtered and concentrated to yield the 2-methyl-3-(1-methyl-1H-pyrazol-4-yl)-3-oxopropanenitrile as an amber oil (92 g, 82%). MS (apci) m/z=162.1 (M−H).

Step C: 1',4-dimethyl-1-phenyl-1H,1'H-3,4'-bipyrazol-5-amine: A 3 , 3 necked round bottomed flask was charged with 2-methyl-3-(1-methyl-1H-pyrazol-4-yl)-3-oxopropanenitrile (60 g, 368 mmol) absolute anhydrous ethanol (1000 mL) and phenylhydrazine hydrochloride (58 g, 404 mmol) at ambient temperature to form a yellowish suspension. The reaction vessel was equipped with a water condenser and refluxed (using a heating mantle) overnight. The reaction was concentrated and 1M NaOH (1 L) was added and the solid was broken up and collected. The solid was washed with water and hexanes. A second crop crashed out in the filtrate and was collected. The combined solids were crushed and triturated with ether (500 mL). The solid was collected filtration, washed with hexanes and air dried under vacuum to provide 1',4-dimethyl-1-phenyl-1H, 1'H-3,4'-bipyrazol-5-amine (93 g, 100%).

Step D: phenyl 1',4-dimethyl-1-phenyl-1H, 1'H-3,4'-bipyrazol-5-ylcarbamate: In a 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (both the aqueous and organic layers were clear but a precipitate was observed in between the two layers). After 3 minutes, phenyl carbonochloridate (74.29 mL, 592.2 mmol) was added slowly at ambient temperature exotherm to 33° C. The reaction stirred at ambient temperature for 2 hours. Additional phenyl carbonochloridate (10 mL) was added. After 30 minutes the organics were separated, washed with brine and concentrated in vacuo. The product was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4%).

Intermediate 200

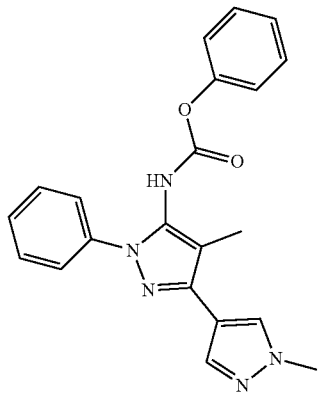

phenyl 1',4-dimethyl-1-phenyl-1H, 1'H-3,4'-bipyrazol-5-ylcarbamate

A 3 , round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (the aqueous and organic layers were clear, but a precipitate was observed in between the two layers). After 3 minutes, phenyl carbonochloridate (74.29 mL, 592.2 mmol) was added slowly at ambient temperature (the temperature of the reaction mixture increased to 33° C. during the addition). The reaction stirred at ambient temperature for 2 hours. Additional phenyl carbonochloridate (10 mL) was added. After 30 minutes the organics layers were separated, washed with brine and concentrated in vacuo. The residue was purified by silica gel chromatography (eluting with 75% ethyl acetate in hexanes) to provide phenyl 1',4-dimethyl-1-phenyl-1H, 1'H-3,4'-bipyrazol-5-ylcarbamate (60 g, 81.4%).

Intermediate 201

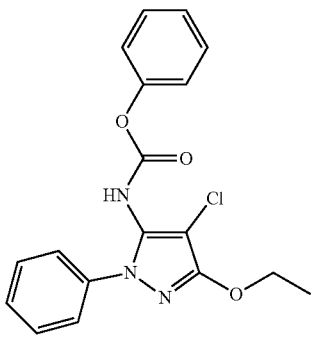

phenyl (4-chloro-3-ethoxy-1-phenyl-1H-pyrazol-5-yl)carbamate

Step A: Preparation of phenyl (3-ethoxy-1-phenyl-1H-pyrazol-5-yl)carbamate: To a suspension of 3-ethoxy-1-phenyl-1H-pyrazol-5-amine (Intermediate P139, 169 mg, 0.832 mmol) in EtOAc (5 mL) at 0° C. was added 2.0 M aqueous NaOH solution (1.25 mL, 2.50 mmol), followed by dropwise addition of phenyl carbonochloridate (0.178 mL, 1.41 mmol). The reaction was stirred at ambient temperature for 15 hours. The reaction mixture was diluted with EtOAc and phase-separated. The organic layer was washed with water and brine, dried over MgSO$_4$, and concentrated. The residue was purified by flash chromatography on silica gel (6:1 hexanes:EtOAc) to give the title compound (219 mg, 81% yield). MS (apci) m/z=324.1 (M+H).

Step B: Preparation of phenyl (4-chloro-3-ethoxy-1-phenyl-1H-pyrazol-5-yl)carbamate: To a solution of phenyl 3-ethoxy-1-phenyl-1H-pyrazol-5-ylcarbamate (92 mg, 0.28 mmol) and pyridinium 4-methylbenzenesulfonate (7.2 mg, 0.028 mmol) in DCM (2 mL) was added N-chlorosuccinimide (42 mg, 0.31 mmol) at ambient temperature. The mixture was stirred at ambient temperature for 2 days and then concentrated under reduced pressure. The residue was purified by flash chromatography on silica gel (9:1, hexanes/EtOAc) to give the title compound (76 mg, 75% yield). MS (apci) m/z=358.1 (M+H).

Intermediate 202

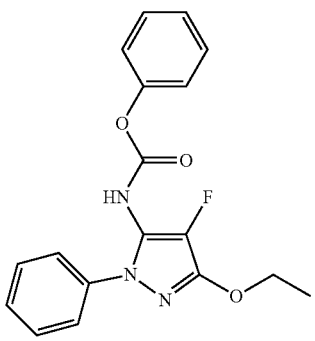

Phenyl (3-ethoxy-4-fluoro-1-phenyl-1H-pyrazol-5-yl)carbamate

Prepared according to the procedure described in Example 167, step B using phenyl 3-ethoxy-1-phenyl-1H-pyrazol-5-ylcarbamate as a replacement for phenyl 3-methyl-1-phenyl-1H-pyrazol-5-ylcarbamate.

Intermediate 203

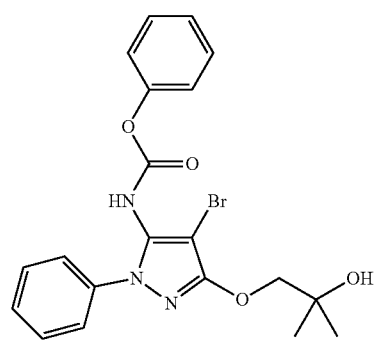

Phenyl (4-bromo-3-(2-hydroxy-2-methylpropoxy)-1-phenyl-1H-pyrazol-5-yl)carbamate Step A: Preparation of 5-amino-1-phenyl-H-pyrazol-3(2H)-one: Prepared according to the method described for Intermediate P1, replacing 4,4-dimethyl-3-oxopentanenitrile with ethyl 2-cyanoacetate, and substituting phenylhydrazine for ethyl 3-hydrazinylbenzoate hydrochloride. MS (apci) m/z=176.0 (M+H).

Step B: Preparation of 1-((5-amino-1-phenyl-1H-pyrazol-3-yl)oxy)-2-methylpropan-2-ol: A mixture of 5-amino-1-phenyl-1H-pyrazol-3(2H)-one (0.330 g, 1.88 mmol), 2,2-dimethyloxirane (0.143 g, 1.98 mmol) and K$_2$CO$_3$ (0.521 g, 3.77 mmol) in DMA (5 mL) was heated at 80° C. for 3 days. After cooling, the reaction mixture was diluted with EtOAc, washed with water and brine and dried over MgSO$_4$. The mixture was filtered through a pad of SiO$_2$ eluting with EtOAc to yield the title compound. MS (apci) m/z=248.1 (M+H).

Step C: Preparation of phenyl (3-(2-hydroxy-2-methylpropoxy)-1-phenyl-H-pyrazol-5-yl)carbamate: Prepared according to the method described for Intermediate 201. Step A using 1-((5-amino-1-phenyl-1H-pyrazol-3-yl)oxy)-2-methylpropan-2-ol as a replacement for 3-ethoxy-1-phenyl-1H-pyrazol-5-amine. MS (apci) m/z=368.1 (M+H).

Step D: Preparation of phenyl (4-bromo-3-(2-hydroxy-2-methylpropoxy)-1-phenyl-1H-pyrazol-5-yl)carbamate: Prepared according to the method described for Intermediate 201, Step B using N-bromosuccinimide as a replacement for N-chlorosuccinimide, and substituting phenyl (3-(2-hydroxy-2-methylpropoxy)-1-phenyl-1H-pyrazol-5-yl)carbamate for phenyl 3-ethoxy-1-phenyl-1H-pyrazol-5-ylcarbamate. MS (apci) m/z=446.1 (M+H).

The following compounds prepared according to the method describe for the preparation of Intermediate 200, using the appropriate amino pyrazole intermediate:

| Intermediate # | Structure | Name | Data |
|---|---|---|---|
| 204 | 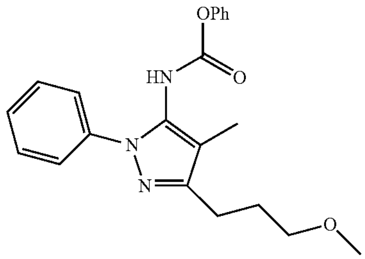 [SMILES: COCCCc1nn(-c2ccccc2)c(NC(=O)Oc2ccccc2)c1C] | phenyl 3-(3-methoxypropyl)-4-methyl-1-phenyl-1H-pyrazol-5-ylcarbamate | MS (apci) m/z = 366.1 (M + H). |
| 205 | 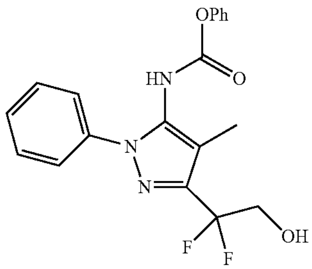 [SMILES: Cc1c(C(F)(F)CO)nn(-c2ccccc2)c1NC(=O)Oc1ccccc1] | phenyl 3-(1,1-difluoro-2-hydroxyethyl)-4-methyl-1-phenyl-1H-pyrazol-5-ylcarbamate | MS (apci) m/z = 374.1 (M + H). |
| 206 | 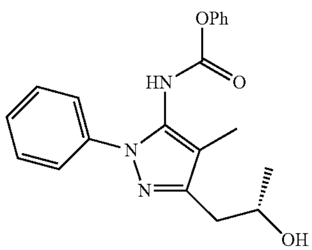 [SMILES: Cc1c(C[C@H](C)O)nn(-c2ccccc2)c1NC(=O)Oc1ccccc1] | (S)-phenyl 3-(2-hydroxypropyl)-4-methyl-1-phenyl-1H-pyrazol-5-ylcarbamate | MS (apci) m/z = 352.1 (M + H). |
| 207 | 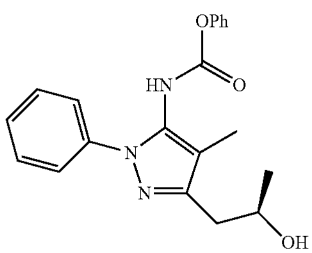 [SMILES: Cc1c(C[C@@H](C)O)nn(-c2ccccc2)c1NC(=O)Oc1ccccc1] | (R)-phenyl 3-(2-hydroxypropyl)-4-methyl-1-phenyl-1H-pyrazol-5-ylcarbamate | MS (apci) m/z = 352.1 (M + H). |
| 208 | 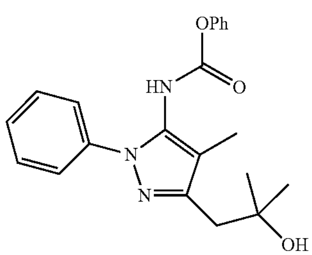 [SMILES: Cc1c(CC(C)(C)O)nn(-c2ccccc2)c1NC(=O)Oc1ccccc1] | phenyl 3-(2-hydroxy-2-methylpropyl)-4-methyl-1-phenyl-1H-pyrazol-5-ylcarbamate | MS (apci) m/z = 366.2 (M + H). |
| 209 | 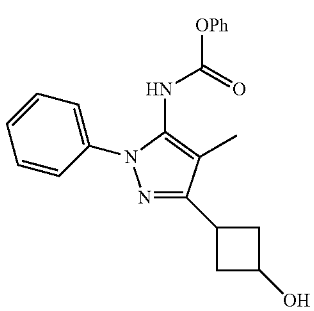 [SMILES: Cc1c(C2CC(O)C2)nn(-c2ccccc2)c1NC(=O)Oc1ccccc1] | phenyl 3-(3-hydroxycyclobutyl)-4-methyl-1-phenyl-1H-pyrazol-5-ylcarbamate | MS (apci) m/z = 364.2 (M + H). |

-continued

| Intermediate # | Structure | Name | Data |
|---|---|---|---|
| 210 | 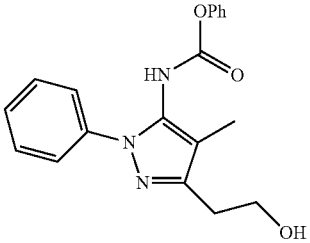 [SMILES: Cc1c(CCO)nn(-c2ccccc2)c1NC(=O)Oc1ccccc1] | phenyl 3-(2-hydroxyethyl)-4-methyl-1-phenyl-1H-pyrazol-5-ylcarbamate | MS (apci) m/z = 338.1 (M + H). |
| 211 | 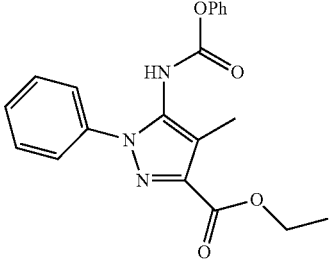 [SMILES: CCOC(=O)c1nn(-c2ccccc2)c(NC(=O)Oc2ccccc2)c1C] | ethyl 4-methyl-5-(phenoxycarbonyl-amino)-1-phenyl-1H-pyrazole-3-carboxylate | MS (apci) m/z = 366.1 (M + H). |
| 212 | 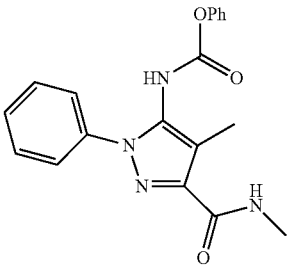 [SMILES: CNC(=O)c1nn(-c2ccccc2)c(NC(=O)Oc2ccccc2)c1C] | phenyl 4-methyl-3-(methylcarbamoyl)-1-phenyl-1H-pyrazol-5-ylcarbamate | MS (apci) m/z = 351.1 (M + H). |
| 213 | 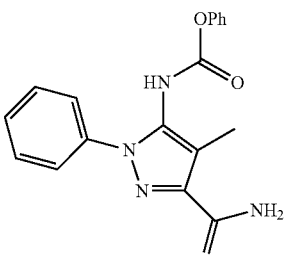 | phenyl 3-carbamoyl-4-methyl-1-phenyl-1H-pyrazol-5-ylcarbamate | MS (apci) m/z = 337.1 (M + H). |
| 214 | 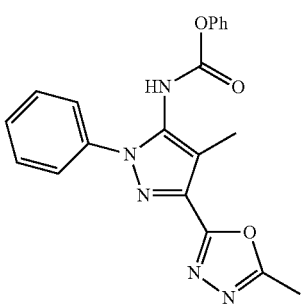 [SMILES: Cc1nnc(-c2nn(-c3ccccc3)c(NC(=O)Oc3ccccc3)c2C)o1] | phenyl (4-methyl-3-(5-methyl-1,3,4-oxadiazol-2-yl)-1-phenyl-1H-pyrazol-5-yl)carbamate | MS (apci) m/z = 376.1 (M + H). |

-continued

| Intermediate # | Structure | Name | Data |
|---|---|---|---|
| 215 | 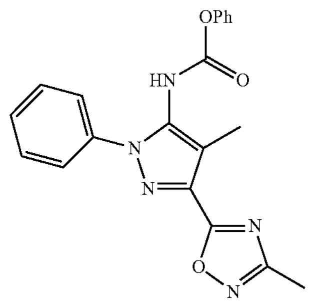 [SMILES: Cc1noc(-c2nn(-c3ccccc3)c(NC(=O)Oc3ccccc3)c2C)n1] | phenyl 4-methyl-3-(3-methyl-1,2,4-oxadiazol-5-yl)-1-phenyl-1H-pyrazol-5-ylcarbamate | MS (apci) m/z = 376.1 (M + H). |
| 216 | 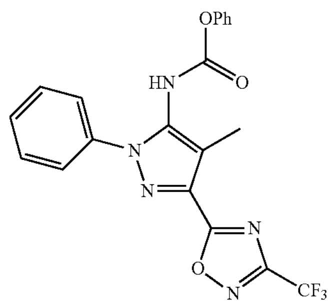 [SMILES: Cc1c(-c2nc(C(F)(F)F)no2)nn(-c2ccccc2)c1NC(=O)Oc1ccccc1] | phenyl 4-methyl-1-phenyl-3-(3-(trifluoromethyl)-1,2,4-oxadiazol-5-yl)-1H-pyrazol-5-ylcarbamate | MS (apci) m/z = 430.1 (M + H). |
| 217 | 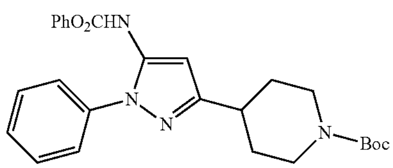 | tert-butyl 4-(5-((phenoxycarbonyl)amino)-1-phenyl-1H-pyrazol-3-yl)piperidine-1-carboxylate | MS (apci) m/z = 463.3 (M + H) |
| 218 | 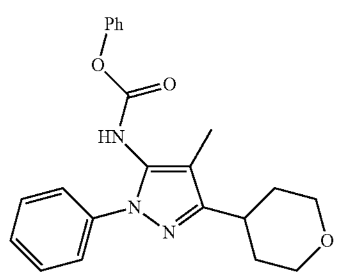 [SMILES: Cc1c(C2CCOCC2)nn(-c2ccccc2)c1NC(=O)Oc1ccccc1] | phenyl (4-methyl-1-phenyl-3-(tetrahydro-2H-pyran-4-yl)-1H-pyrazol-5-yl)carbamate | MS (apci) m/z = 378.2 (M + H) |
| 219 | 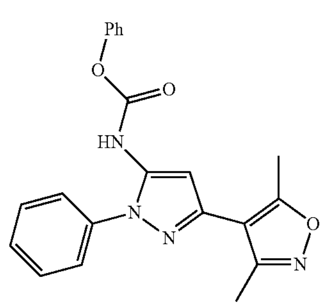 [SMILES: Cc1noc(C)c1-c1cc(NC(=O)Oc2ccccc2)n(-c2ccccc2)n1] | phenyl (3-(3,5-dimethylisoxazol-4-yl)-1-phenyl-1H-pyrazol-5-yl)carbamate | $^1$H NMR (CDCl$_3$) δ 7.56-7.64 (m, 4H), 7.48-7.52 (m, 1H), 7.40 (t, 2H), 7.26 (t, 2H), 7.16 (br s, 2H), 6.71 (br s, 1H), 2.60 (s, 3H) 2.46 (s, 3H) |

-continued

| Intermediate # | Structure | Name | Data |
|---|---|---|---|
| 220 | 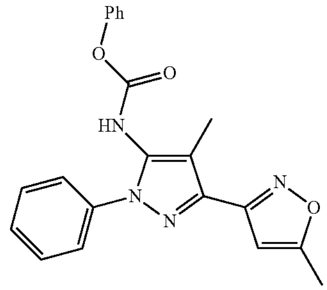 [SMILES: Cc1cc(-c2nn(-c3ccccc3)c(NC(=O)Oc3ccccc3)c2C)no1] | phenyl (4-methyl-3-(5-methylisoxazol-3-yl)-1-phenyl-1H-pyrazol-5-yl)carbamate | $^1$H NMR (CDCl$_3$) δ 7.54 (d, 2H), 7.49 (t, 2H), 7.41 (t, 1H), 7.33 (br s, 2H), 7.20 (br s, 1H), 7.08 (br s, 1H), 6.74 (br s, 1H), 6.66 (br s, 1H), 6.48 (s, 1H), 2.45 (s, 3H) 2.34 (s, 3H) |
| 221 | 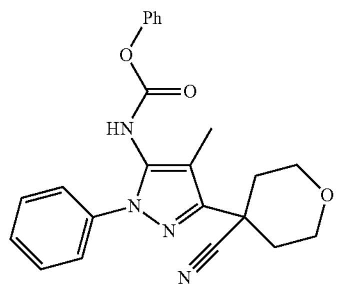 [SMILES: Cc1c(C2(C#N)CCOCC2)nn(-c2ccccc2)c1NC(=O)Oc1ccccc1] | phenyl (3-(4-cyanotetrahydro-2H-pyran-4-yl)-4-methyl-1-phenyl-1H-pyrazol-5-yl)carbamate | $^1$H NMR (CDCl$_3$) δ 7.06-7.56 (m, 9H), 6.75 (br s, 1H), 6.51 (s, 1H), 4.04 (d, 2H) 3.89 (t, 2H), 2.20-2.39 (m, 4H), 2.28 (s, 3H) |
| 222 | 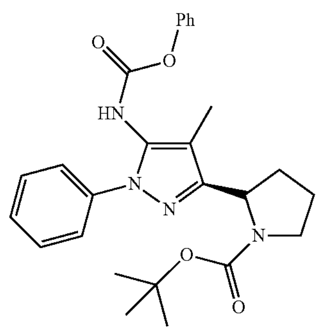 | (R)-tert-butyl 2-(4-methyl-5-((phenoxy-carbonyl)amino)-1-phenyl-1H-pyrazol-3-yl)pyrrolidine-1-carboxylate | MS (apci) m/z = 463.2 (M + H) |
| 223 | 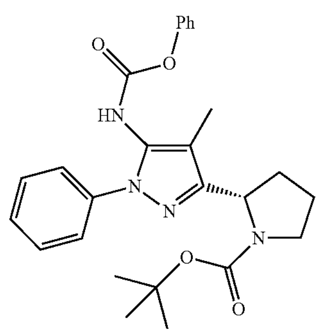 [SMILES: Cc1c([C@@H]2CCCN2C(=O)OC(C)(C)C)nn(-c2ccccc2)c1NC(=O)Oc1ccccc1] | (S)-tert-butyl 2-(4-methyl-5-((phenoxy-carbonyl)amino)-1-phenyl-1H-pyrazol-3-yl)pyrrolidine-1-carboxylate | MS (apci) m/z = 463.2 (M + H) |
| 224 | 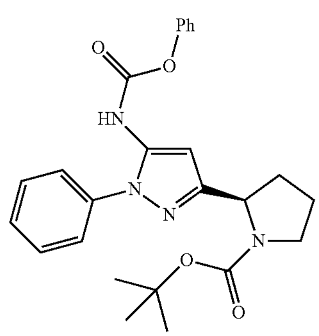 [SMILES: CC(C)(C)OC(=O)N1CCC[C@@H]1c1cc(NC(=O)Oc2ccccc2)n(-c2ccccc2)n1] | (R)-tert-butyl 2-(5-((phenoxycarbonyl)amino)-1-phenyl-1H-pyrazol-3-yl)pyrrolidine-1-carboxylate | MS (apci) m/z = 449.2 (M + H) |

| Intermediate # | Structure | Name | Data |
|---|---|---|---|
| 225 | 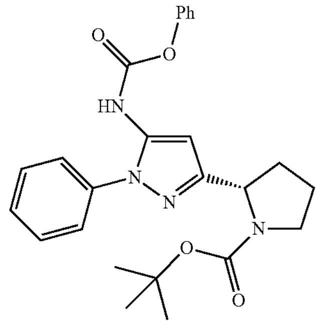 [SMILES: CC(C)(C)OC(=O)N1CCC[C@H]1c1cc(NC(=O)Oc2ccccc2)n(-c2ccccc2)n1] | (S)-tert-butyl 2-(5-((phenoxycarbonyl)amino)-1-phenyl-1H-pyrazol-3-yl)pyrrolidine-1-carboxylate | MS (apci) m/z = 449.2 (M + H) |
| 226 | 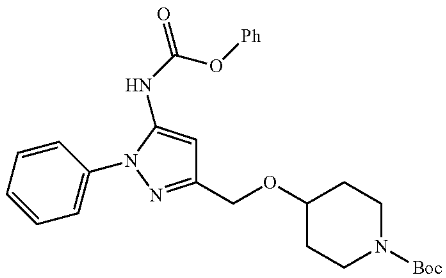 [SMILES: CC(C)(C)OC(=O)N1CCC(OCc2cc(NC(=O)Oc3ccccc3)n(-c3ccccc3)n2)CC1] | tert-butyl 4-((5-((phenoxycarbonyl)amino)-1-phenyl-1H-pyrazol-3-yl)methoxy)piperidine-1-carboxylate | MS (apci) m/z = 493.2 (M + H) |
| 227 | 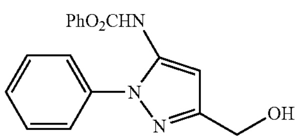 | phenyl (3-(hydroxymethyl)-1-phenyl-1H-pyrazol-5-yl)carbamate | MS (apci) m/z = 310.1 (M + H) |

Intermediate 228

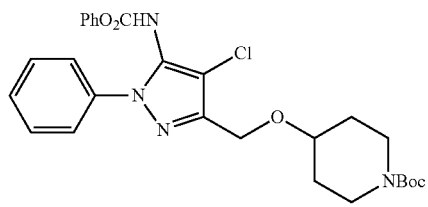

tert-butyl 4-((4-chloro-5-((phenoxycarbonyl)amino)-1-phenyl-1H-pyrazol-3-yl)methoxy)piperidine-1-carboxylate To a suspension of tert-butyl 4-((5-(phenoxycarbonylamino)-1-phenyl-1H-pyrazol-3-yl)methoxy)piperidine-1-carboxylate (Intermediate 226), 98.5 mg, 0.200 mmol) in DCM (2.0 mL) was added pyridinium 4-methylbenzenesulfonate (PPTS) (5.03 mg, 0.020 mmol) and N-chlorosuccinimide (40.1 mg, 0.300 mmol). The resulting solution was stirred at ambient temperature for 8 days. The mixture was diluted with water and CH₂Cl₂, the organic layer was separated and the aqueous was extracted with CH₂Cl₂ (2×). The combined organic fractions were dried over MgSO₄, filtered and concentrated. The residue was purified by silica chromatography using 30-40% EtOAc/hexanes gradient elution to afford the title compound as an orange oil (73.5 mg, 70% yield). MS (apci) m/z=527.2 (M+H).

Intermediate 229

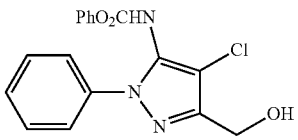

Phenyl (4-chloro-3-(hydroxymethyl)-1-phenyl-1H-pyrazol-5-yl)carbamate

Prepared from phenyl 3-(hydroxymethyl)-1-phenyl-1H-pyrazol-5-ylcarbamate (Intermediate 227) using the procedure outlined for the preparation of tert-butyl 4-((4-chloro-5-((phenoxycarbonyl)amino)-1-phenyl-1H-pyrazol-3-yl)methoxy)piperidine-1-carboxylate (Intermediate 228). In this instance, the compound was isolated a white solid (108 mg, 28%). MS (apci) m/z=344.0 (M+H).

Intermediate 230

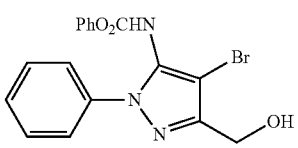

Phenyl (4-bromo-3-(hydroxymethyl)-1-phenyl-1H-pyrazol-5-yl)carbamate

To a suspension of phenyl 3-(hydroxymethyl)-1-phenyl-1H-pyrazol-5-ylcarbamate (Intermediate 227, 100 mg, 0.323 mmol) in $CH_2Cl_2$ (1.6 mL) was added pyridinium 4-methylbenzenesulfonate (PPTS) (8.12 mg, 0.0323 mmol) and N-bromosuccinimide (86.3 mg, 0.485 mmol). The reaction mixture was stirred for 16 hours at ambient temperature. The resulting suspension was filtered and the collected solid washed briefly with $CH_2Cl_2$ and dried in vacuum to afford the title compound a white solid (48.5 mg, 39%). MS (apci) m/z=388.0 (M+H).

The following pyrazole intermediates were made according to the methods described for the preparation of Intermediate 228, 229 or 230.

| Intermediate | Structure | Name | MS (apci) m/z |
|---|---|---|---|
| 231 | 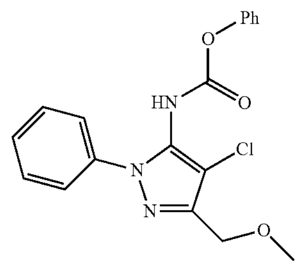 [SMILES: COCc1nn(-c2ccccc2)c(NC(=O)Oc2ccccc2)c1Cl] | phenyl (4-chloro-3-(methoxymethyl)-1-phenyl-1H-pyrazol-5-yl)carbamate | 358.1 (M + H) |
| 232 | 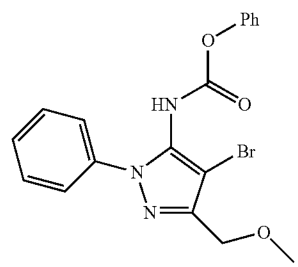 [SMILES: COCc1nn(-c2ccccc2)c(NC(=O)Oc2ccccc2)c1Br] | phenyl (4-bromo-3-(methoxymethyl)-1-phenyl-1H-pyrazol-5-yl)carbamate | 402.2 (M + H) |
| 233 | 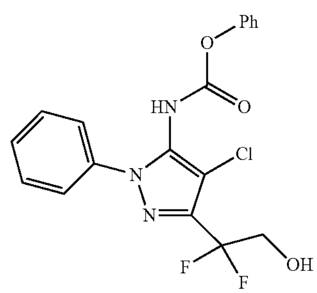 [SMILES: O=C(Nc1c(Cl)c(C(F)(F)CO)nn1-c1ccccc1)Oc1ccccc1] | phenyl (4-chloro-3-(1,1-difluoro-2-hydroxyethyl)-1-phenyl-1H-pyrazol-5-yl)carbamate | 394.1 (M + H) |
| 234 | 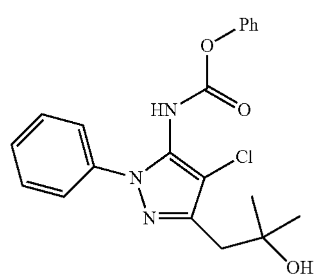 [SMILES: CC(C)(O)Cc1nn(-c2ccccc2)c(NC(=O)Oc2ccccc2)c1Cl] | phenyl (4-chloro-3-(2-hydroxy-2-methylpropyl)-1-phenyl-1H-pyrazol-5-yl)carbamate | 386.1 (M + H) |
| 235 | 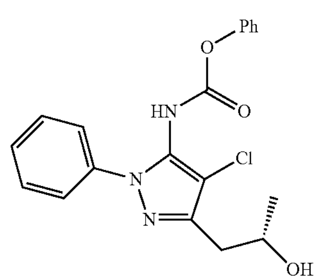 [SMILES: C[C@H](O)Cc1nn(-c2ccccc2)c(NC(=O)Oc2ccccc2)c1Cl] | (S)-phenyl (4-chloro-3-(2-hydroxypropyl)-1-phenyl-1H-pyrazol-5-yl)carbamate | 372.1 (M + H) |

-continued

| Intermediate | Structure | Name | MS (apci) m/z |
|---|---|---|---|
| 236 | 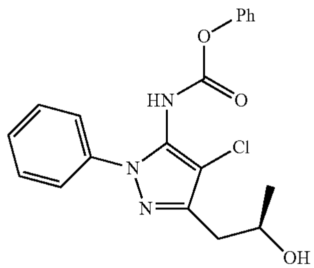 [SMILES: C[C@@H](O)Cc1nn(-c2ccccc2)c(NC(=O)Oc2ccccc2)c1Cl] | (R)-phenyl (4-chloro-3-(2-hydroxypropyl)-1-phenyl-1H-pyrazol-5-yl)carbamate | 372.1 (M + H) |
| 237 | 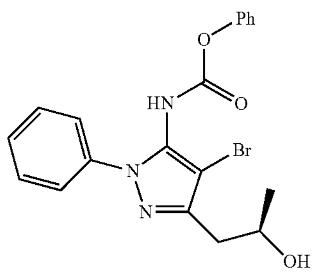 [SMILES: C[C@@H](O)Cc1nn(-c2ccccc2)c(NC(=O)Oc2ccccc2)c1Br] | (R)-phenyl (4-bromo-3-(2-hydroxypropyl)-1-phenyl-1H-pyrazol-5-yl)carbamate | 416.0 (M + H) |
| 238 | 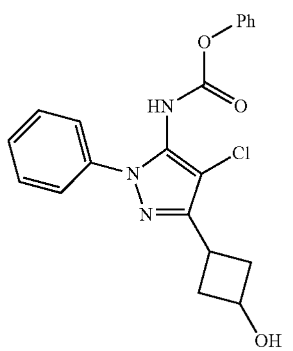 [SMILES: O=C(Nc1c(Cl)c(C2CC(O)C2)nn1-c1ccccc1)Oc1ccccc1] | phenyl (4-chloro-3-(3-hydroxycyclobutyl)-1-phenyl-1H-pyrazol-5-yl)carbamate | 384.1 (M + H) |
| 239 | 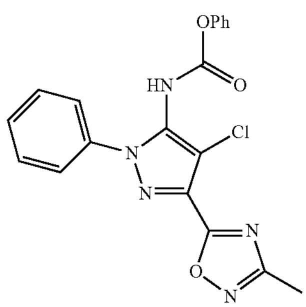 [SMILES: Cc1noc(-c2nn(-c3ccccc3)c(NC(=O)Oc3ccccc3)c2Cl)n1] | phenyl 4-chloro-3-(3-methyl-1,2,4-oxadiazol-5-yl)-1-phenyl-1H-pyrazol-5-ylcarbamate | 396.0 (M + H) |
| 240 | 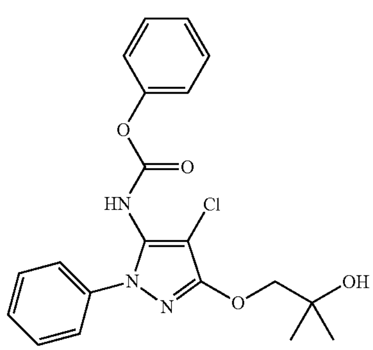 | phenyl (4-chloro-3-(2-hydroxy-2-methylpropoxy)-1-phenyl-1H-pyrazol-5-yl)carbamate | 446.1 (M + H) |

| Intermediate | Structure | Name | MS (apci) m/z |
|---|---|---|---|
| 241 | 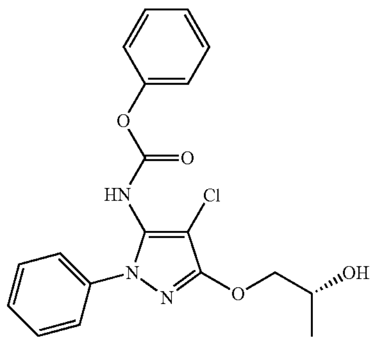 [SMILES: C[C@@H](O)COc1nn(-c2ccccc2)c(NC(=O)Oc2ccccc2)c1Cl] | phenyl (4-chloro-3-(2-hydroxy-2-methylpropoxy)-1-phenyl-1H-pyrazol-5-yl)carbamate | 388.1 (M + H) |
| 242 | 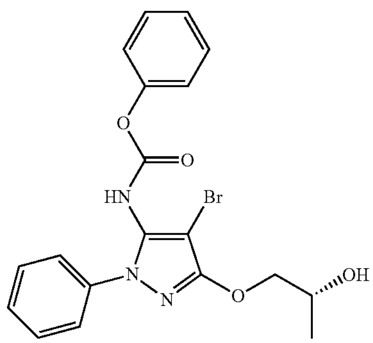 [SMILES: C[C@@H](O)COc1nn(-c2ccccc2)c(NC(=O)Oc2ccccc2)c1Br] | phenyl (4-bromo-3-(2-hydroxy-1-methylpropoxy)-1-phenyl-1H-pyrazol-5-yl)carbamate | 433.0 (M + H) |
| 243 | 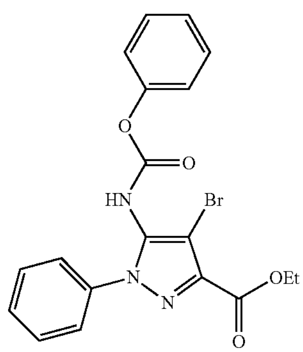 [SMILES: CCOC(=O)c1nn(-c2ccccc2)c(NC(=O)Oc2ccccc2)c1Br] | ethyl 4-bromo-5-((phenoxycarbonyl)amino)-1-phenyl-1H-pyrazole-3-carboxylate | 430.0 (M + H) |

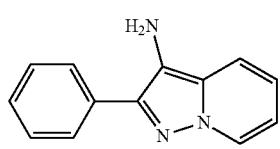

Intermediate 244

2-phenylpyrazolo[1,5-a]pyridin-3-amine

Step A: Ethyl 2-phenylpyrazolo[1,5-a]pyridine-3-carboxylate: To a solution of 1-aminopyridinium iodide (2.22 g, 10.0 mmol) in DMF (20 mL) was added $K_2CO_3$ (1.93 g, 14.0 mmol) and ethyl 3-phenylpropiolate (3.30 mL, 20.0 mmol). The mixture was stirred at ambient temperature for 18 hours and was poured chilled water (100 mL). The mixture was stirred for 30 minutes and was filtered through packed Celite®, rinsing with EtOAc and $H_2O$. The organic layer was removed and was washed with $H_2O$ (4×), dried with over $MgSO_4$, filtered and concentrated. The residual dark red-orange oil was purified by silica chromatography using a 10-50% EtOAc/hexanes gradient elution to furnish the title compound as a yellow solid (1.75 g, 65.7% yield). MS (apci) m/z=267.0 (M+H).

Step B: 2-phenylpyrazolo[1,5-a]pyridine-3-carboxylic acid hydrochloride: To solution of ethyl 2-phenylpyrazolo[1,5-a]pyridine-3-carboxylate (1.72 g, 6.46 mmol) in EtOH (10 mL) was added 2M NaOH (16.1 mL, 32.3 mmol) and the reaction mixture was heated at reflux for 7 hours. The reaction mixture was cooled to ambient temperature and was cooled in an ice bath. The mixture was acidified with concentrated HCl and the resulting suspension was collected via vacuum filtration. The product cake was washed with water and dried in vacuum to afford the title compound as a gold solid (1.69 g, 95.2% yield). MS (apci) m/z=195.2 ((M+H)—$CO_2$).

Step C: 2-phenylpyrazolo[1,5-a]pyridine: A mixture of 2-phenylpyrazolo[1,5-a]pyridine-3-carboxylic acid hydrochloride (1.00 g, 3.64 mmol) in polyphosphoric acid (41.6 m, 364 mmol) was heated at 80° C. for 17 hours. The resulting gelatinous mixture was cooled to ambient temperature and ice water was added (150 mL). The mixture was stirred until a granular suspension began to form. The suspension was transferred to water (350 mL) and the mixture stirred until a fine granular suspension resulted. The solid was collected via vacuum filtration, washed with water and dried in vacuum to afford the title compound as an orange solid (0.84 g, 118%) that was used directly in the next step. MS (apci) m/z=195.2 (M+H).

Step D: 3-nitroso-2-phenylpyrazolo[1,5-a]pyridine: To a solution of 2-phenylpyrazolo[1,5-a]pyridine (0.84 g, 2.85 mmol) in acetic acid (2.85 mL, 51.4 mmol) was added $NaNO_2$ (0.295 g, 4.28 mmol) in water (1.43 mL) dropwise over 10 minutes (vigorous bubbling observed). The mixture was stirred for 20 minutes and was quenched with ice. The resulting suspension was warmed to ambient temperature and the solid collected via vacuum filtration. The collected solid was washed with water and dried in vacuum to provide the title compound as a dark green solid (0.380 g, 59.6%). MS (apci) m/z=224.1 (M+H).

Step E: 2-phenylpyrazolo[1,5-a]pyridin-3-amine: To a mixture of 3-nitroso-2-phenylpyrazolo[1,5-a]pyridine (0.380 g, 1.70 mmol) and Zn dust (0.557 g, 8.51 mmol) in EtOH (3.81 mL) was added concentrated HCl (0.156 mL, 1.87 mmol). The mixture was heated at reflux for 3 hours and was cooled to ambient temperature. The mixture was diluted with MeOH, filtered and the Zn cake washed with MeOH. The combined filtrate and washes were concentrated and the residue was partitioned into in water and DCM. The organic layer was removed and the aqueous portion was treated with saturated $NaHCO_3$ to achieve pH=10. The mixture was extracted with DCM (3×) and the combined extracts were washed with saturated NaCl, dried over $MgSO_4$, filtered and concentrated. The residue was dried in vacuum to furnish the title compound as brown solid (0.304 g, 85.5% yield). MS (apci) m/z=210.1 (M+H). $^1$H NMR ($CDCl_3$) δ 8.31 (d, 1H), 7.91 (d, 2H), 7.49 (t, 2H), 7.38 (t, 2H), 6.96 (dd, 1H), 6.64 (t, 1H), 3.21 (br s, 2H).

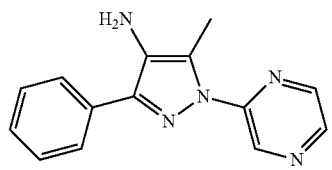

Intermediate 245

5-methyl-3-phenyl-1-(pyrazin-2-yl)-1H-pyrazol-4-amine

Step A: 2-(5-methyl-4-nitroso-3-phenyl-1H-pyrazol-1-yl)pyrazine To a solution of 2-hydrazinylpyrazine (0.485 g, 4.40 mmol) in HOAc (6 mL) was added (2-(hydroxyimino)-1-phenylbutane-1,3-dione (0.765 g, 4.00 mmol) in small portions over 2 minutes. The mixture was stirred for 5 minutes and the resulting light orange suspension was stirred at 60° C. for 6 hours. EtOH (1 mL) was added and the mixture was heated at 60° C. for an additional 6 hours. The resulting dark green suspension was cooled to ambient temperature and the mixture was diluted with $H_2O$ (30 mL). The green suspension was stirred for 1 hour and the solid was collected via vacuum filtration. The collected solid was washed with $H_2O$ and dried in vacuum. The solid was suspended in EtOH (25 mL) and concentrated HCl (500 µL) was added. The mixture was heated at reflux for 20 hours, cooled to ambient temperature and diluted with chilled $H_2O$ (75 mL). The mixture was treated with 1M NaOH to pH=7 and was extracted with $Et_2O$ (3×). The combined extracts were washed with saturated NaCl and dried over $MgSO_4$. The dried solution was filtered through packed Celite® and concentrated. The residual green-yellow solid was purified on a $SiO_2$ column using step gradient elution (25% $CH_2Cl_2$, 50% EtOAc/hexanes) to furnish the title compound as a turquoise solid (325 mg, 31%). MS (apci) m/z=266.1 (M+H).

Step B: 5-methyl-3-phenyl-1-(pyrazin-2-yl)-1H-pyrazol-4-amine: To a mixture of 2-(5-methyl-4-nitroso-3-phenyl-1H-pyrazol-1-yl)pyrazine (325 mg, 1.04 mmol) and Zn dust (340 mg, 5.21 mmol) in EtOH (10 mL) was added concentrated HCl (95.5 µL, 1.15 mmol). The mixture was stirred at ambient temperature for 17 hours, then at 65° C. for 3 hours. The mixture was cooled to ambient temperature and was filtered through packed Celite® eluting with MeOH. The eluent was concentrated, and the residue was treated with $H_2O$ and mixed. The resulting orange suspension treated with 2M HCl to pH=1 and the mixture was extracted with $Et_2O$ (3×). The aqueous portion was treated with 2M NaOH to pH=8 and extracted with EtOAc (3×). The combined EtOAc extracts were washed with saturated NaCl and dried over $MgSO_4$/activated carbon. The solution was eluted through a $SiO_2$ plug eluting with EtOAc. The eluent was concentrated to give the title compound as a light yellow wax (33 mg, 13%). MS (esi) m/z=252.2 (M+H).

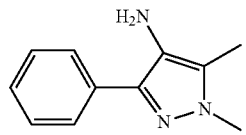

Intermediate 246

1,5-dimethyl-3-phenyl-1H-pyrazol-4-amine

Step A: 1,5-dimethyl-4-nitroso-3-phenyl-1H-pyrazole: To a solution of methylhydrazine (0.484 g, 10.5 mmol) in HOAc (10 mL) was added 2-(hydroxyimino)-1-phenylbutane-1,3-dione (2.01 g, 10.5 mmol) in small portions over 5 minutes. The reaction mixture was heated at 60° C. for 1 hour and was cooled to ambient temperature. $Et_2O$ (50 mL) and $H_2O$ (10 mL) were added to the mixture followed by slow addition of saturated $Na_2CO_3$ until pH=8 was obtained. The organic layer was removed and the aqueous layer was extracted with $Et_2O$ (2×). The combined organic fractions were dried over $Na_2SO_4$, filtered and concentrated. The residue was purified by silica gel chromatography (1:5 EtOAc/hexanes) to give the title compound as a green solid (1.32 g, 63%). MS (apci) m/z=202.1 (M+H).

Step B: 1,5-dimethyl-3-phenyl-1H-pyrazol-4-amine: To a solution of 1,5-dimethyl-4-nitroso-3-phenyl-1H-pyrazole (1.32 g, 6.60 mmol) in MeOH (50 mL) was added $Pd(OH)_2$ on carbon (200 mg, 20 wt %, 0.286 mmol) and the reaction mixture was shaken under 50 psi of $H_2$ for 3 hours at ambient temperature. The reaction mixture was evacuated, purged with $N_2$ filtered through a pad of Celite® with MeOH elution. The eluent was concentrated and the residue dried in vacuum to provide the title compound as a tan solid (1.23 g, 100%). MS (apci) m/z=188.1 (M+H).

Intermediate 247

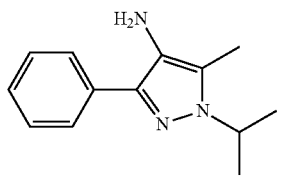

1-isopropyl-5-methyl-3-phenyl-1H-pyrazol-4-amine

The title compound was prepared according to the method described for Intermediate 246, using isopropylhydrazine hydrochloride in place of methylhydrazine in Step A to provide 620 mg (57%) of the title compound over 2 steps. MS (apci) m/z=216.1 (M+H).

Intermediate 248

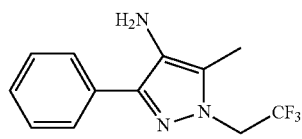

5-methyl-3-phenyl-1-(2,2,2-trifluoroethyl)-1H-pyrazol-4-amine

Step A: 5-methyl-4-nitroso-3-phenyl-1-(2,2,2-trifluoroethyl)-1H-pyrazole: The title compound was prepared using (2,2,2-trifluoroethyl)hydrazine in place of methylhydrazine in Step A of the procedure described for the preparation of 1,5-dimethyl-3-phenyl-1H-pyrazol-4-amine (Intermediate 246). The compound was isolated as a green solid (999 mg, 71%). $^1$H NMR (CDCl$_3$) δ 7.60-7.73 (m, 5H), 4.70 (q, 2H), 2.27 (t, 3H).

Step B: 5-methyl-3-phenyl-1-(2,2,2-trifluoroethyl)-1H-pyrazol-4-amine: To a mixture of 5-methyl-4-nitroso-3-phenyl-1-(2,2,2-trifluoroethyl)-1H-pyrazole (50 mg, 0.186 mmol) and Zn dust (60.7 mg, 0.929 mmol) in EtOH (0.4 mL) was added concentrated HCl (17.0 µL, 0.204 mmol) and the mixture was heated at reflux for 3 hours. The mixture was cooled to ambient temperature and was diluted with MeOH and filtered. The filtrate was concentrated and the residue was diluted in water. The aqueous mixture was treated with saturated NaHCO$_3$ until pH=10 was achieved. The mixture was extracted with DCM (3×) and the combined extracts were dried over Na$_2$SO$_4$, filtered and concentrated afford the title compound as a yellow oil (47.1 mg, 99.4% yield). MS (apci) m/z=256.1 (M+H).

Intermediate 249

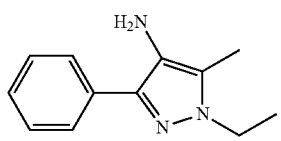

1-ethyl-5-methyl-3-phenyl-1H-pyrazol-4-amine

Step A: 1-ethyl-5-methyl-4-nitroso-3-phenyl-1H-pyrazole: The title compound was prepared according to the procedure described for the preparation of Intermediate 246, using ethylhydrazine oxalate in place of methylhydrazine in Step A. 1-Ethyl-5-methyl-4-nitroso-3-phenyl-1H-pyrazole was isolated as a green oil (288 mg, 26%). $^1$H NMR (CDCl$_3$) δ 8.19 (d, 2H), 7.46-7.50 (m, 3H), 4.15 (q, 2H), 2.43 (s, 3H), 1.50 (t, 3H). The minor regioisomer, 1-ethyl-3-methyl-4-nitroso-5-phenyl-1H-pyrazole, was also obtained as a blue-green solid (165 mg, 15%). $^1$H NMR (CDCl$_3$) δ 7.71 (dd, 2H), 7.59 (m, 3H), 4.17 (q, 2H), 2.28 (s, 3H), 1.51 (t, 3H).

Step B: 1-ethyl-5-methyl-3-phenyl-1H-pyrazol-4-amine: Prepared according to the procedure described for the preparation of Intermediate 248, using 1-ethyl-5-methyl-4-nitroso-3-phenyl-1H-pyrazole in Step B. the title compound was isolated as a light purple solid (281 mg, 104%). MS (apci) m/z=202.1 (M+H).

Intermediate 250

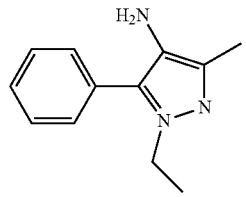

1-ethyl-3-methyl-5-phenyl-1H-pyrazol-4-amine

Prepared according to the procedure described for the preparation of Intermediate 249, using 1-ethyl-3-methyl-4-nitroso-5-phenyl-1H-pyrazole in Step A. The title compound was prepared according to Step B. The compound was isolated as a colorless oil (82.4 mg, 52.5%) after purification by reverse-phase chromatography. MS (apci) m/z=202.1 (M+H).

Intermediate 251

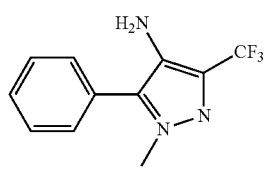

1-methyl-5-phenyl-3-(trifluoromethyl)-1H-pyrazol-4-amine

Step A: 4,4,4-trifluoro-2-(hydroxyimino)-1-phenylbutane-1,3-dione: A solution of 4,4,4-trifluoro-1-phenylbutane-1,3-dione (5.00 g, 23.1 mmol) in HOAc (46.3 mL) was chilled to 10° C. and sodium nitrite (1.84 g, 26.6 mmol) in water (6.0 mL) was added. The mixture was stirred at ambient temperature for 90 minutes and was diluted with H$_2$O (150 mL). The mixture was extracted with Et$_2$O (3×) and the combined organic fractions were carefully washed with saturated NaHCO$_3$ until pH=9. The Et$_2$O solution was washed with H$_2$O and saturated NaCl and was dried over MgSO$_4$. The dried solution was filtered and concentrated to afford the title compound as a yellow foam (4.21 g, 74.2% yield). MS (apci) m/z=244.1 (M−H).

Step B: 4-nitroso-3-phenyl-5-(trifluoromethyl)-1H-pyrazole: A solution of hydrazine monohydrate (0.204 g, 4.08 mmol) in EtOH (5 mL) was cooled to 0° C. and 4,4,4-trifluoro-2-(hydroxyimino)-1-phenylbutane-1,3-dione (1.00 g, 4.08 mmol) in EtOH (15 mL) was added. The reaction mixture was stirred at ambient temperature for 3 hours, excess powdered MgSO$_4$ was added and the mixture was heated at 60° C. for 16 hours. The mixture was cooled to ambient temperature, filtered and concentrated to afford the crude title compound as a green solid (78.7 mg, 8.0%) that was taken directly to the next step. MS (apci) m/z=240.0 (M−H).

Step C: 1-methyl-5-phenyl-3-(trifluoromethyl)-1H-pyrazol-4-amine: To a solution of 4-nitroso-3-phenyl-5-(trifluoromethyl)-1H-pyrazole (78.7 mg, 0.326 mmol) in DMF (1.6 mL) was added NaH (14.4 mg, 0.359 mmol) and the mixture was stirred at ambient temperature for 30 minutes. The mixture was treated with methyl iodide (40.6 µL, 0.653 mmol) and stirred for 17 hours. The reaction mixture was directly purified by reverse phase HPLC using 20-100% acetonitrile/water gradient elution to provide a light blue solid (40.2 mg). The solid was dissolved in EtOH (0.35 mL) and was subjected to the reduction procedure described in Step B of the preparation of 5-methyl-3-phenyl-1-(2,2,2-trifluoroethyl)-1H-pyrazol-4-amine (Intermediate 248). The title compound was obtained as white solid (25.1 mg, 66.1%).

Intermediate 252

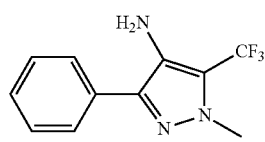

1-methyl-3-phenyl-5-(trifluoromethyl)-1H-pyrazol-4-amine

Step A: 1-methyl-4-nitroso-3-phenyl-5-(trifluoromethyl)-1H-pyrazole: To a solution of methylhydrazine (0.214 mL, 4.08 mmol) in EtOH (20 mL) was added 4,4,4-trifluoro-2-(hydroxyimino)-1-phenylbutane-1,3-dione (Intermediate 251, Step A; 1.00 g, 4.079 mmol). The reaction mixture was stirred at ambient temperature for 1 hour and excess MgSO$_4$ was added. The mixture was stirred at 60° C. for 48 hours and was cooled to ambient temperature. The mixture was filtered and the filtrate concentrated to a green residue. The residue was purified by silica gel chromatography using a 10-30% EtOAc/hexanes gradient for elution to provide the title compound as a green solid (482 mg, 46%). $^1$H NMR (CDCl$_3$) δ 7.89 (d, 2H), 7.45-7.52 (m, 3H), 4.15 (s, 3H).

Step B: 1-methyl-3-phenyl-5-(trifluoromethyl)-1H-pyrazol-4-amine: Prepared from 1-methyl-4-nitroso-3-phenyl-5-(trifluoromethyl)-1H-pyrazole according to the method described for the preparation of Intermediate 248, Step B. The title compound was obtained as white solid (309 mg, 68%). $^1$H NMR (CDCl$_3$) δ 7.65 (d, 2H), 7.45 (t, 2H), 7.35 (t, 1H), 3.93 (s, 3H), 3.52 (br s, 2H).

Preparation U-1

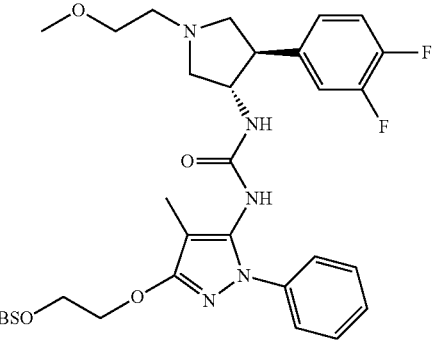

1-(3-(2-(tert-butyldimethylsilyloxy)ethoxy)-4-methyl-1-phenyl-1H-pyrazol-5-yl)-3-((3S,4R)-4-(3,4-difluorophenyl)-1-(2-methoxyethyl)pyrrolidin-3-yl)urea Prepared according to the method of Example 1, replacing trans-1-(2-methoxyethyl)-4-phenylpyrrolidin-3-amine dihydrochloride (Preparation B) with (3S,4R)-4-(3,4-difluorophenyl)-1-(2-methoxyethyl)pyrrolidin-3-amine (Preparation F) and using the Intermediate P203. MS (apci) m/z=630.1 (M+H).

Preparation U-2

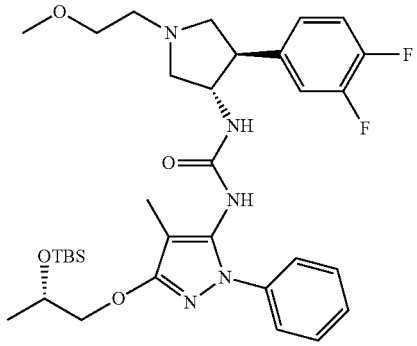

1-(3-((S)-2-(tert-butyldimethylsilyloxy)propoxy)-4-methyl-1-phenyl-1H-pyrazol-5-yl)-3-((3S,4R)-4-(3,4-difluorophenyl)-1-(2-methoxyethyl)pyrrolidin-3-yl)urea Prepared according to the method of Example 1, replacing trans-1-(2-methoxyethyl)-4-phenylpyrrolidin-3-amine dihydrochloride (Preparation B) with (3S,4R)-4-(3,4-difluorophenyl)-1-(2-methoxyethyl)pyrrolidin-3-amine (Preparation F) and using Intermediate P211. MS (apci) m/z=644.4 (M+H).

SYNTHETIC EXAMPLES

Example 1

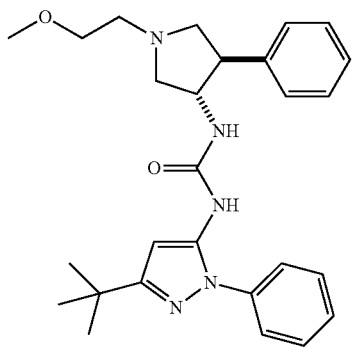 [SMILES: COCCN1C[C@@H](NC(=O)Nc2cc(C(C)(C)C)nn2-c2ccccc2)[C@H](c2ccccc2)C1]

1-(3-tert-butyl-1-phenyl-H-pyrazol-5-yl)-3-(trans-1-(2-methoxyethyl)-4-phenylpyrrolidin-3-yl)urea Step A: Preparation of phenyl 3-tert-butyl-1-phenyl-1H-pyrazol-5-ylcarbamate: To a solution of 3-tert-butyl-1-phenyl-1H-pyrazol-5-amine (Table 1; 200.0 mg, 0.9290 mmol) in EtOAc (10 mL) was added 2 M aqueous NaOH (0.9290 mL, 1.858 mmol) followed by phenyl chloroformate (0.1632 mL, 1.301 mmol). The reaction was stirred at ambient temperature for 1 hour and then the phases were separated. The organic phase was washed with $H_2O$ (10 mL), brine (10 mL), dried with $MgSO_4$, filtered and concentrated to yield the product as a brown crystalline solid (320 mg, 103% yield). MS (apci) m/z=336.1 (M+H).

Step B: Preparation of 1-(3-tert-butyl-1-phenyl-1H-pyrazol-5-yl)-3-(trans-1-(2-methoxyethyl)-4-phenylpyrrolidin-3-yl)urea: To a solution of trans-1-(2-methoxyethyl)-4-phenylpyrrolidin-3-amine dihydrochloride (Preparation B, 30.0 mg, 0.102 mmol) and DIEA (0.0535 mL, 0.307 mmol) in DMA (1 mL) was added phenyl 3-tert-butyl-1-phenyl-1H-pyrazol-5-ylcarbamate (34.3 mg, 0.102 mmol), and the reaction mixture as stirred at ambient temperature for 1 hour. The reaction mixture was directly purified by reverse-phase column chromatography, eluting with 5-60% acetonitrile/water to yield the product as a tan solid (38 mg, 81% yield). MS (apci) m/z=462.2 (M+H).

The compounds of Table 4 were prepared according to the method of Example 1 using the appropriate starting materials.

TABLE 4

| Ex. # | Structure | Name | Data |
|---|---|---|---|
| 2 | 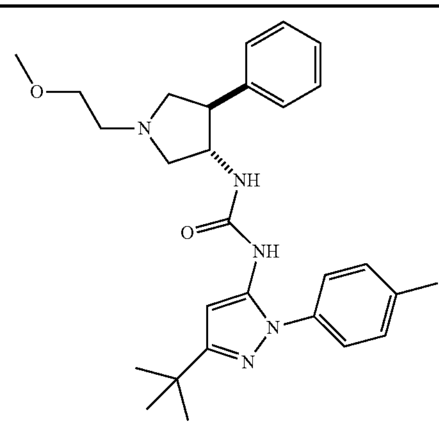 | 1-(3-tert-butyl-1-p-tolyl-1H-pyrazol-5-yl)-3-(trans-1-(2-methoxyethyl)-4-phenylpyrrolidin-3-yl)urea hydrochloride | MS (apci) m/z = 476.3 (M + H). |
| 3 | 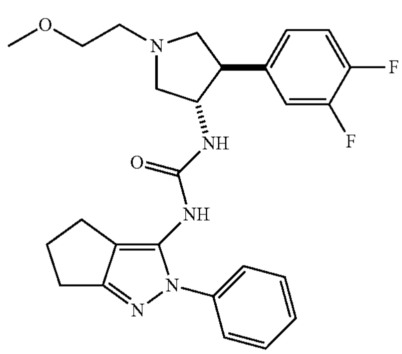 [SMILES: COCCN1C[C@@H](NC(=O)Nc2c3c(nn2-c2ccccc2)CCC3)[C@H](c2ccc(F)c(F)c2)C1] | trans-1-(4-(3,4-difluorophenyl)-1-(2-methoxyethyl)pyrrolidin-3-yl)-3-(2-phenyl-2,4,5,6-tetrahydrocyclopenta[c]pyrazol-3-yl)urea | MS (apci) m/z = 482.4 (M + H). |

| Ex. # | Structure | Name | Data |
|---|---|---|---|
| 4 | 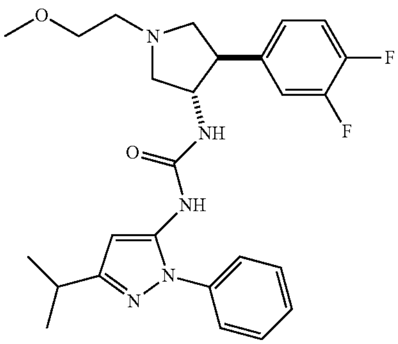 [SMILES: COCCN1C[C@@H](NC(=O)Nc2cc(C(C)C)nn2-c2ccccc2)[C@H](c2ccc(F)c(F)c2)C1] | trans-1-(4-(3,4-difluorophenyl)-1-(2-methoxyethyl)pyrrolidin-3-yl)-3-(3-isopropyl-1-phenyl-1H-pyrazol-5-yl)urea | MS (apci) m/z = 484.7 (M + H). |
| 5 | 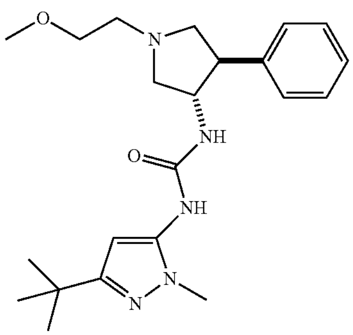 [SMILES: COCCN1C[C@@H](NC(=O)Nc2cc(C(C)(C)C)nn2C)[C@H](c2ccccc2)C1] | 1-(3-tert-butyl-1-methyl-1H-pyrazol-5-yl)-3-(trans-1-(2-methoxyethyl)-4-phenylpyrrolidin-3-yl)urea | MS (apci) m/z = 400.2 (M + H). |
| 6 | 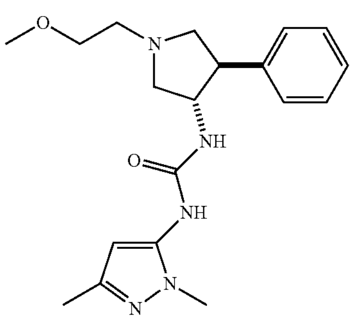 [SMILES: COCCN1C[C@@H](NC(=O)Nc2cc(C)nn2C)[C@H](c2ccccc2)C1] | 1-(1,3-dimethyl-1H-pyrazol-5-yl)-3-(trans-1-(2-methoxyethyl)-4-phenylpyrrolidin-3-yl)urea | MS (apci) m/z = 358.1 (M + H). |
| 7 | 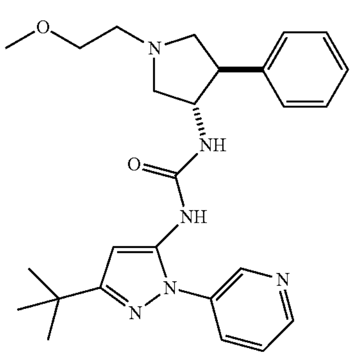 [SMILES: COCCN1C[C@@H](NC(=O)Nc2cc(C(C)(C)C)nn2-c2cccnc2)[C@H](c2ccccc2)C1] | 1-(3-tert-butyl-1-(pyridin-3-yl)-1H-pyrazol-5-yl)-3-(trans-1-(2-methoxyethyl)-4-phenylpyrrolidin-3-yl)urea | MS (apci) m/z = 463.2 (M + H). |

TABLE 4-continued

| Ex. # | Structure | Name | Data |
|---|---|---|---|
| 8 | 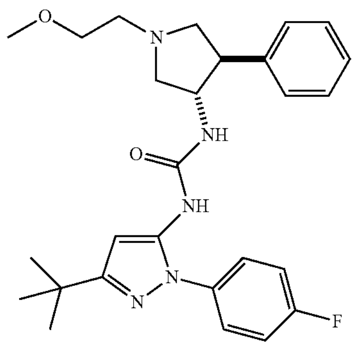 [SMILES: COCCN1C[C@@H](NC(=O)Nc2cc(C(C)(C)C)nn2-c2ccc(F)cc2)[C@H](c2ccccc2)C1] | 1-(3-tert-butyl-1-(4-fluorophenyl)-1H-pyrazol-5-yl)-3-(trans-1-(2-methoxyethyl)-4-phenyl-pyrrolidin-3-yl)urea | MS (apci) m/z = 480.2 (M + H). |
| 9 | 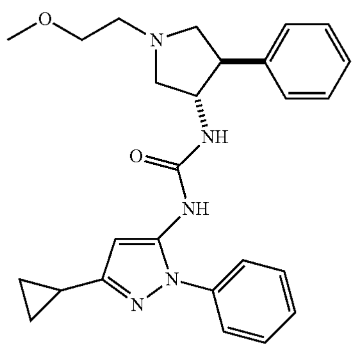 [SMILES: COCCN1C[C@@H](NC(=O)Nc2cc(C3CC3)nn2-c2ccccc2)[C@H](c2ccccc2)C1] | 1-(3-cyclopropyl-1-phenyl-1H-pyrazol-5-yl)-3-(trans-1-(2-methoxyethyl)-4-phenylpyrrolidin-3-yl)urea | MS (apci) m/z = 446.2 (M + H). |
| 10 | 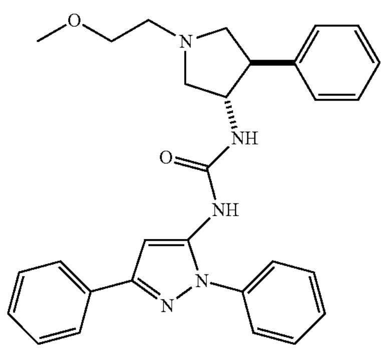 [SMILES: COCCN1C[C@@H](NC(=O)Nc2cc(-c3ccccc3)nn2-c2ccccc2)[C@H](c2ccccc2)C1] | 1-(1,3-diphenyl-1H-pyrazol-5-yl)-3-(trans-1-(2-methoxyethyl)-4-phenylpyrrolidin-3-yl)urea | MS (apci) m/z = 482.2 (M + H). |
| 11 | 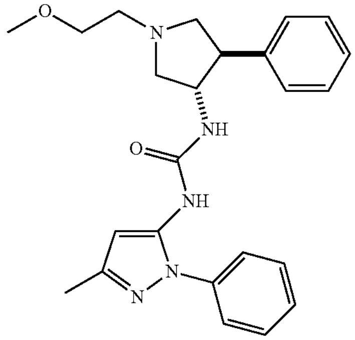 [SMILES: COCCN1C[C@@H](NC(=O)Nc2cc(C)nn2-c2ccccc2)[C@H](c2ccccc2)C1] | 1-(trans-1-(2-methoxyethyl)-4-phenylpyrrolidin-3-yl)-3-(3-methyl-1-phenyl-1H-pyrazol-5-yl)urea | MS (apci) m/z = 420.1 (M + H). |

TABLE 4-continued

| Ex. # | Structure | Name | Data |
|---|---|---|---|
| 12 | 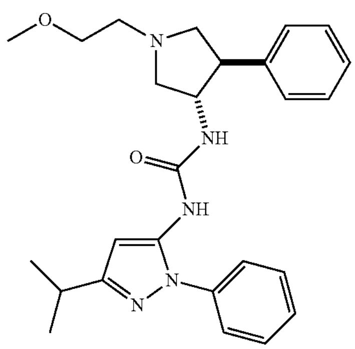 [SMILES: COCCN1C[C@@H](NC(=O)Nc2cc(C(C)C)nn2-c2ccccc2)[C@H](c2ccccc2)C1] | 1-(3-isopropyl-1-phenyl-1H-pyrazol-5-yl)-3-(trans-1-(2-methoxyethyl)-4-phenylpyrrolidin-3-yl)urea | MS (apci) m/z = 448.2 (M + H). |
| 13 | 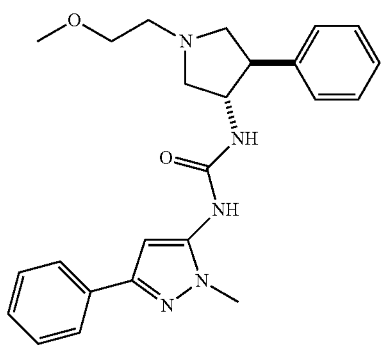 [SMILES: COCCN1C[C@@H](NC(=O)Nc2cc(-c3ccccc3)nn2C)[C@H](c2ccccc2)C1] | 1-(trans-1-(2-methoxyethyl)-4-phenylpyrrolidin-3-yl)-3-(1-methyl-3-phenyl-1H-pyrazol-5-yl)urea | MS (apci) m/z = 420.1 (M + H). |
| 14 | 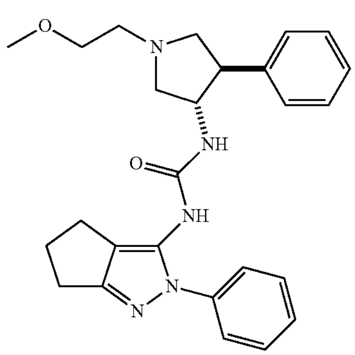 [SMILES: COCCN1C[C@@H](NC(=O)Nc2c3c(nn2-c2ccccc2)CCC3)[C@H](c2ccccc2)C1] | 1-(trans-1-(2-methoxyethyl)-4-phenylpyrrolidin-3-yl)-3-(2-phenyl-2,4,5,6-tetrahydrocyclopenta[c]pyrazol-3-yl)urea | MS (apci) m/z = 446.2 (M + H). |
| 15 | 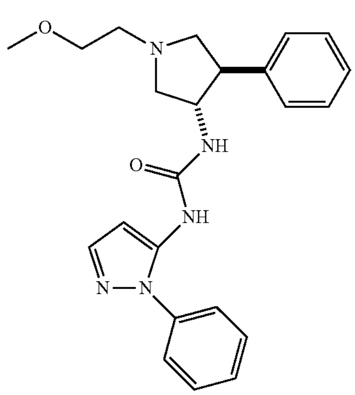 [SMILES: COCCN1C[C@@H](NC(=O)Nc2ccnn2-c2ccccc2)[C@H](c2ccccc2)C1] | 1-(trans-1-(2-methoxyethyl)-4-phenylpyrrolidin-3-yl)-3-(1-phenyl-1H-pyrazol-5-yl)urea | MS (apci) m/z = 406.1 (M + H). |

TABLE 4-continued

| Ex. # | Structure | Name | Data |
| --- | --- | --- | --- |
| 16 | 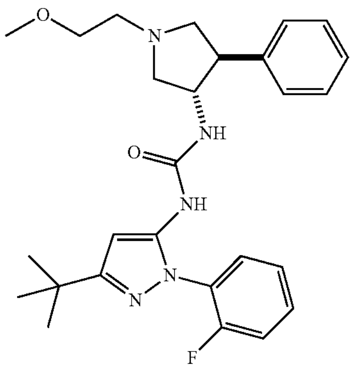 [SMILES: COCCN1C[C@@H](NC(=O)Nc2cc(C(C)(C)C)nn2-c2ccccc2F)[C@H](c2ccccc2)C1] | 1-(3-tert-butyl-1-(2-fluorophenyl)-1H-pyrazol-5-yl)-3-(trans-1-(2-methoxyethyl)-4-phenylpyrrolidin-3-yl)urea | MS (apci) m/z = 480.1 (M + H). |
| 17 | 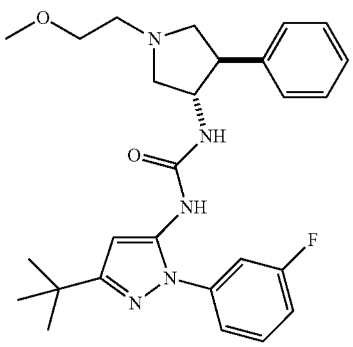 [SMILES: COCCN1C[C@@H](NC(=O)Nc2cc(C(C)(C)C)nn2-c2cccc(F)c2)[C@H](c2ccccc2)C1] | 1-(3-tert-butyl-1-(3-fluorophenyl)-1H-pyrazol-5-yl)-3-(trans-1-(2-methoxyethyl)-4-phenylpyrrolidin-3-yl)urea | MS (apci) m/z = 480.1 (M + H). |
| 18 | 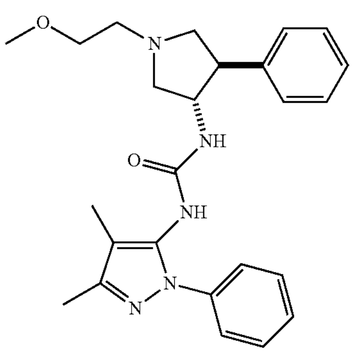 [SMILES: COCCN1C[C@@H](NC(=O)Nc2c(C)c(C)nn2-c2ccccc2)[C@H](c2ccccc2)C1] | 1-(3,4-dimethyl-1-phenyl-1H-pyrazol-5-yl)-3-(trans-1-(2-methoxyethyl)-4-phenylpyrrolidin-3-yl)urea | MS (apci) m/z = 434.2 (M + H). |
| 19 | 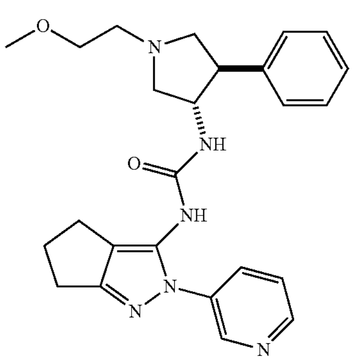 [SMILES: COCCN1C[C@@H](NC(=O)Nc2c3c(nn2-c2cccnc2)CCC3)[C@H](c2ccccc2)C1] | 1-(trans-1-(2-methoxyethyl)-4-phenylpyrrolidin-3-yl)-3-(2-(pyridin-3-yl)-2,4,5,6-tetrahydrocyclopenta[c]pyrazol-3-yl)urea | MS (apci) m/z = 447.2 (M + H). |

Example 20

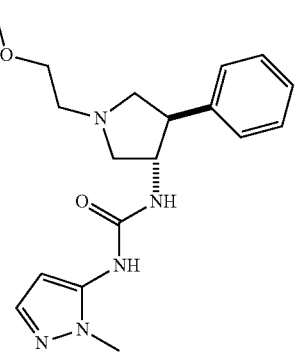

1-(trans-1-(2-methoxyethyl)-4-phenylpyrrolidin-3-yl)-3-(1-methyl-1H-pyrazol-5-yl)urea Step A: Preparation of 4-nitrophenyl trans-1-(2-methoxyethyl)-4-phenylpyrrolidin-3-ylcarbamate: To a suspension of trans-1-(2-methoxyethyl)-4-phenylpyrrolidin-3-amine dihydrochloride (Preparation B; 0.180 g, 0.614 mmol) in DCM (3 mL) at 0° C. was added triethylamine (0.428 mL, 3.07 mmol) followed by dropwise addition of a solution of 4-nitrophenyl carbonochloridate (0.136 g, 0.675 mmol) in DCM (0.5 mL). The ice bath was removed and the reaction mixture stirred at ambient temperature for 1 hour. The mixture was diluted in saturated NaHCO₃ (30 mL) and extracted with DCM (3×20 mL). The combined organic layers were washed with brine (20 mL), dried with MgSO₄, filtered and concentrated in vacuo to yield the crude intermediate, which was used in the next step without purification. MS (apci) m/z=386.2 (M+H).

Step B: Preparation of 1-(trans-1-(2-methoxyethyl)-4-phenylpyrrolidin-3-yl)-3-(1-methyl-1H-pyrazol-5-yl)urea: To a solution of 4-nitrophenyl trans-1-(2-methoxyethyl)-4-phenylpyrrolidin-3-ylcarbamate (80 mg, 0.21 mmol) in DCE (1 mL) was added 1-methyl-1H-pyrazol-5-amine (Table 1; 24 mg, 0.25 mmol) followed by DIEA (0.15 mL, 0.83 mmol). The mixture was heated at 55° C. for 18 hours, then diluted with 1 mL of DCM, washed with saturated bicarbonate (2×1 mL) and concentrated in vacuo. The crude residue was purified by reverse-phase column chromatography eluting with 5-45% acetonitrile/water to afford the title product (10 mg, 14% yield). MS (apci) m/z=344.2 (M+H).

Example 21

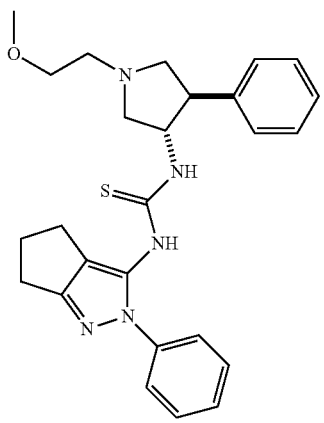 [SMILES: COCCN1C[C@@H](NC(=S)Nc2c3c(nn2-c2ccccc2)CCC3)[C@H](c2ccccc2)C1]

1-(trans-1-(2-methoxyethyl)-4-phenylpyrrolidin-3-yl)-3-(2-phenyl-2,4,5,6-tetrahydrocyclopenta[c]pyrazol-3-yl)thiourea To a CHCl₃ (0.5 mL) suspension of 2-phenyl-2,4,5,6-tetrahydrocyclopenta[c]pyrazol-3-amine (Table 1; 45.2 mg, 0.227 mmol) was added di(1H-imidazol-1-yl)methanethione (40.4 mg, 0.227 mmol) followed by DIEA (0.158 mL, 0.908 mmol). After stirring at ambient temperature for 16 hours, trans-1-(2-methoxyethyl)-4-phenylpyrrolidin-3-amine (Preparation B, 50.0 mg, 0.227 mmol) was added to the reaction mixture in one portion. After 2 hours, the reaction was directly purified by reverse-phase column chromatography, eluting with 5-68% acetonitrile/water to yield the title product as white solid (70 mg, 67% yield). MS (apci) m/z=462.1 (M+H).

Example 22

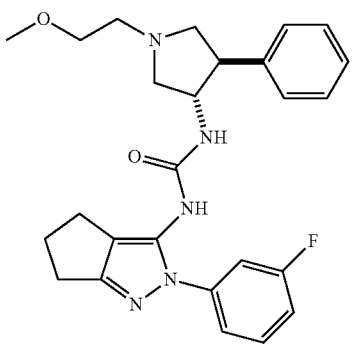 [SMILES: COCCN1C[C@@H](NC(=O)Nc2c3c(nn2-c2cccc(F)c2)CCC3)[C@H](c2ccccc2)C1]

1-(2-(3-fluorophenyl)-2,4,5,6-tetrahydrocyclopenta[c]pyrazol-3-yl)-3-(trans-1-(2-methoxyethyl)-4-phenylpyrrolidin-3-yl)urea A solution of 2-(3-fluorophenyl)-2,4,5,6-tetrahydrocyclopenta[c]pyrazol-3-amine (Intermediate P3; 25.0 mg, 0.115 mmol) in DCM (575 µL, 0.115 mmol) was treated with 1,1'-carbonyldiimidazole (18.7 mg, 0.115 mmol) and TEA (32.1 µL, 0.230 mmol). After stirring at ambient temperature for 3 hours, trans-1-(2-methoxyethyl)-4-phenylpyrrolidin-3-amine dihydrochloride (Preparation B, 33.7 mg, 0.115 mmol) was added, followed by TEA (64.2 µL, 0.460 mmol). After stirring at ambient temperature for 30 minutes, the crude reaction mixture was directly purified by reverse-phase column chromatography, eluting with 0-100% acetonitrile/water, to afford the title compound as a clear oil (17.6 mg, 33.0% yield). MS (apci) m/z=464.1 (M+H).

The compounds of Table 5 were prepared according to the method of Example 22 using the appropriate starting materials. Conversion time to the activated intermediate with 1,1'-carbonyldiimidazole varied, and was monitored by taking an aliquot and quenching in MeOH. LCMS analysis was used to monitor complete conversion to the methyl carbamate (30 minutes to 16 hours).

TABLE 5

| Ex. # | Structure | Name | Data |
| --- | --- | --- | --- |
| 23 | 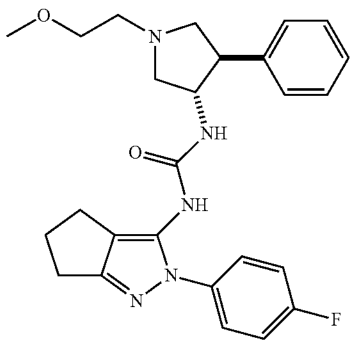 [SMILES: COCCN1C[C@@H](NC(=O)Nc2c3c(nn2-c2ccc(F)cc2)CCC3)[C@H](c2ccccc2)C1] | 1-(2-(4-fluorophenyl)-2,4,5,6-tetrahydrocyclopenta[c]pyrazol-3-yl)-3-(trans-1-(2-methoxyethyl)-4-phenylpyrrolidin-3-yl)urea | MS (apci) m/z = 464.0 (M + H). |
| 24 | 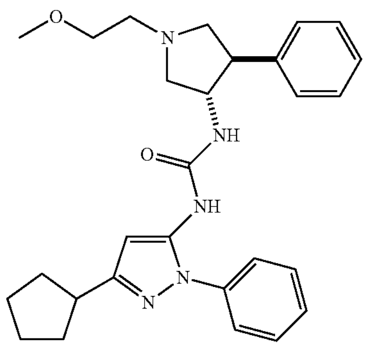 [SMILES: COCCN1C[C@@H](NC(=O)Nc2cc(C3CCCC3)nn2-c2ccccc2)[C@H](c2ccccc2)C1] | 1-(3-cyclopentyl-1-phenyl-1H-pyrazol-5-yl)-3-(trans-1-(2-methoxyethyl)-4-phenylpyrrolidin-3-yl)urea | MS (apci) m/z = 474.2 (M + H). |
| 25 | 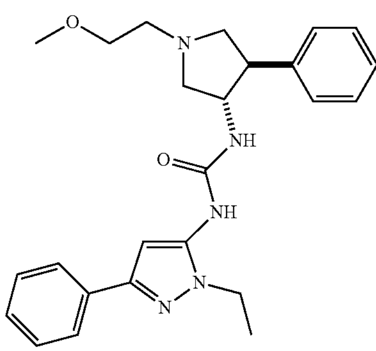 [SMILES: CCn1nc(-c2ccccc2)cc1NC(=O)N[C@@H]1CN(CCOC)C[C@H]1c1ccccc1] | 1-(1-ethyl-3-phenyl-1H-pyrazol-5-yl)-3-(trans-1-(2-methoxyethyl)-4-phenylpyrrolidin-3-yl)urea | MS (apci) m/z = 434.2 (M + H). |
| 26 | 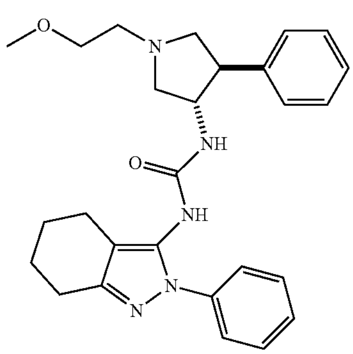 [SMILES: COCCN1C[C@@H](NC(=O)Nc2c3c(nn2-c2ccccc2)CCCC3)[C@H](c2ccccc2)C1] | 1-(trans-1-(2-methoxyethyl)-4-phenylpyrrolidin-3-yl)-3-(2-phenyl-4,5,6,7-tetrahydro-2H-indazol-3-yl)urea | MS (apci) m/z = 460.2 (M + H). |

TABLE 5-continued

| Ex. # | Structure | Name | Data |
|---|---|---|---|
| 27 | 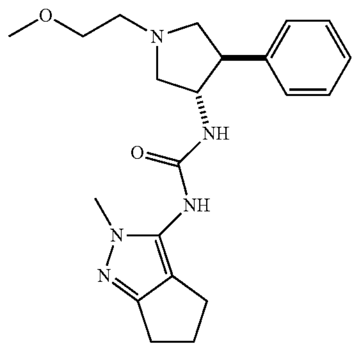 [SMILES: COCCN1C[C@@H](NC(=O)Nc2c3c(nn2C)CCC3)[C@H](c2ccccc2)C1] | 1-(trans-1-(2-methoxyethyl)-4-phenylpyrrolidin-3-yl)-3-(2-methyl-2,4,5,6-tetrahydrocyclopenta[c]pyrazol-3-yl)urea | MS (apci) m/z = 384.2 (M + H). |
| 28 | 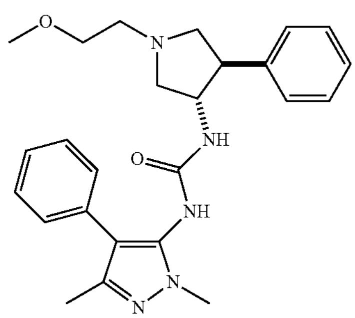 [SMILES: COCCN1C[C@@H](NC(=O)Nc2c(-c3ccccc3)c(C)nn2C)[C@H](c2ccccc2)C1] | 1-(1,3-dimethyl-4-phenyl-1H-pyrazol-5-yl)-3-(trans-1-(2-methoxyethyl)-4-phenylpyrrolidin-3-yl)urea | MS (apci) m/z = 434.2 (M + H). |
| 29 | 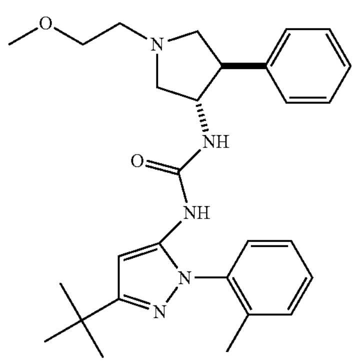 [SMILES: COCCN1C[C@@H](NC(=O)Nc2cc(C(C)(C)C)nn2-c2ccccc2C)[C@H](c2ccccc2)C1] | 1-(3-tert-butyl-1-o-tolyl-1H-pyrazol-5-yl)-3-(trans-1-(2-methoxyethyl)-4-phenylpyrrolidin-3-yl)urea | MS (apci) m/z = 476.1 (M + H). |
| 30 | 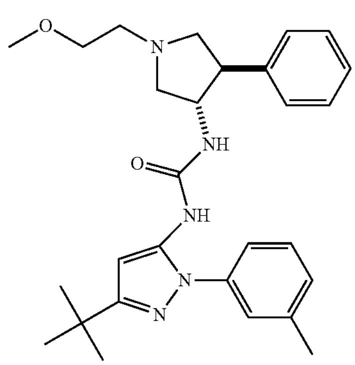 [SMILES: COCCN1C[C@@H](NC(=O)Nc2cc(C(C)(C)C)nn2-c2cccc(C)c2)[C@H](c2ccccc2)C1] | 1-(3-tert-butyl-1-m-tolyl-1H-pyrazol-5-yl)-3-(trans-1-(2-methoxyethyl)-4-phenylpyrrolidin-3-yl)urea | MS (apci) m/z = 476.2 (M + H). |

TABLE 5-continued

| Ex. # | Structure | Name | Data |
|---|---|---|---|
| 31 | 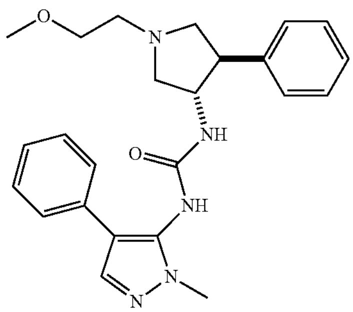 [SMILES: COCCN1C[C@@H](NC(=O)Nc2c(-c3ccccc3)cnn2C)[C@H](c2ccccc2)C1] | 1-(trans-1-(2-methoxyethyl)-4-phenylpyrrolidin-3-yl)-3-(1-methyl-4-phenyl-1H-pyrazol-5-yl)urea | MS (apci) m/z = 420.2 (M + H). |
| 32 | 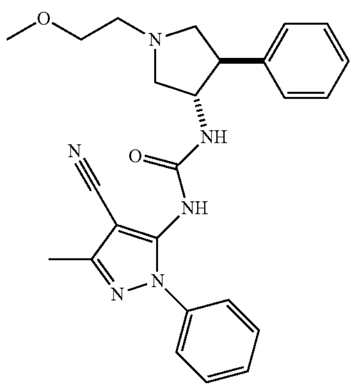 [SMILES: COCCN1C[C@@H](NC(=O)Nc2c(C#N)c(C)nn2-c2ccccc2)[C@H](c2ccccc2)C1] | 1-(4-cyano-3-methyl-1-phenyl-1H-pyrazol-5-yl)-3-(trans-1-(2-methoxyethyl)-4-phenylpyrrolidin-3-yl)urea | MS (apci) m/z = 445.1 (M + H). |
| 33 | 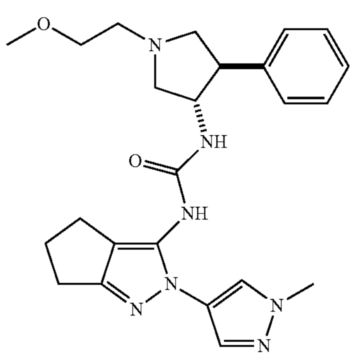 [SMILES: COCCN1C[C@@H](NC(=O)Nc2c3c(nn2-c2cnn(C)c2)CCC3)[C@H](c2ccccc2)C1] | 1-(trans-1-(2-methoxyethyl)-4-phenylpyrrolidin-3-yl)-3-(2-(1-methyl-1H-pyrazol-4-yl)-2,4,5,6-tetrahydrocyclopenta[c]pyrazol-3-yl)urea | MS (apci) m/z = 450.1 (M + H). |
| 34 | 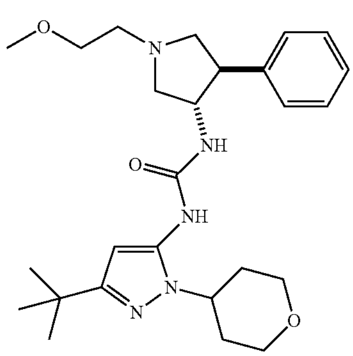 [SMILES: COCCN1C[C@@H](NC(=O)Nc2cc(C(C)(C)C)nn2C2CCOCC2)[C@H](c2ccccc2)C1] | 1-(3-tert-butyl-1-(tetrahyro-2H-pyran-4-yl)-1H-pyrazol-5-yl)-3-(trans-1-(2-methoxyethyl)-4-phenylpyrrolidin-3-yl)urea | MS (apci) m/z = 470.2 (M + H). |

TABLE 5-continued

| Ex. # | Structure | Name | Data |
|---|---|---|---|
| 35 | 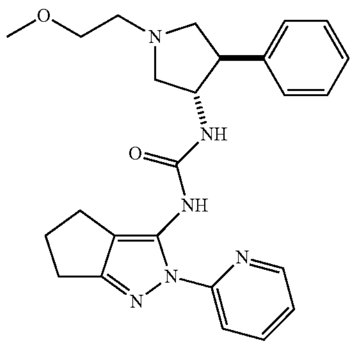 [SMILES: COCCN1C[C@@H](NC(=O)Nc2c3c(nn2-c2ccccn2)CCC3)[C@H](c2ccccc2)C1] | 1-(trans-1-(2-methoxyethyl)-4-phenylpyrrolidin-3-yl)-3-(2-(pyridin-2-yl)-2,4,5,6-tetrahydrocyclopenta[c]pyrazol-3-yl)urea | MS (apci) m/z = 447.0 (M + H). |
| 36 | 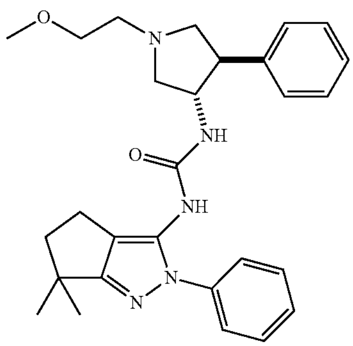 [SMILES: COCCN1C[C@@H](NC(=O)Nc2c3c(nn2-c2ccccc2)C(C)(C)CC3)[C@H](c2ccccc2)C1] | 1-(6,6-dimethyl-2-phenyl-2,4,5,6-tetrahydro-yclopenta[c]pyrazol-3-yl)-3-(trans-1-(2-methoxyethyl)-4-phenyl-pyrrolidin-3-yl)urea | MS (apci) m/z = 474.0 (M + H). |
| 37 | 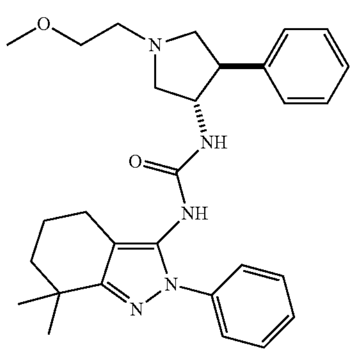 [SMILES: COCCN1C[C@@H](NC(=O)Nc2c3c(nn2-c2ccccc2)C(C)(C)CCC3)[C@H](c2ccccc2)C1] | 1-(7,7-dimethyl-2-phenyl-4,5,6,7-tetrahydro-2H-indazol-3-yl)-3-(trans-1-(2-methoxyethyl)-4-phenylpyrrolidin-3-yl)urea | MS (apci) m/z = 488.2 (M + H). |

Example 38

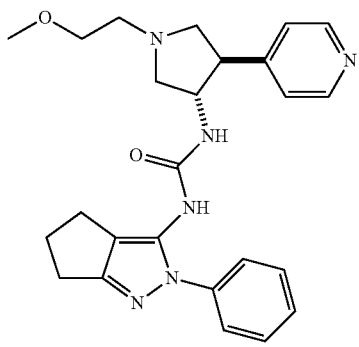 [SMILES: COCCN1C[C@@H](NC(=O)Nc2c3c(nn2-c2ccccc2)CCC3)[C@H](c2ccncc2)C1]

1-(trans-1-(2-methoxyethyl)-4-(pyridin-4-yl)pyrrolidin-3-yl)-3-(2-phenyl-2,4,5,6-tetrahydrocyclopenta[c]pyrazol-3-yl)urea Step A: Preparation of trans-ethyl 1-(2-methoxyethyl)-4-(pyridin-4-yl)pyrrolidine-3-carboxylate: To a solution of (E)-ethyl 3-(pyridin-4-yl)acrylate (200 mg, 1.13 mmol) in DCM (10 mL) cooled to 0° C. were sequentially added TFA (0.017 mL, 0.226 mmol) in one portion followed by dropwise addition of 2-methoxy-N-(methoxymethyl)-N-((trimethylsilyl) methyl)ethanamine (Preparation C, 278 mg, 1.35 mmol). The reaction was stirred at ambient temperature for 3 hours. It was quenched with saturated NaHCO₃ (10 mL), the phases were separated and the aqueous layer was extracted with DCM (15 mL). The combined organic phases were dried with MgSO₄, filtered and concentrated in vacuo. The crude product was purified by silica column chromatography, eluting with 0 to 5% MeOH/DCM to yield the product as a colorless oil (276 mg, 88% yield). MS (apci) m/z=279.2 (M+H).

Step B: Preparation of lithium trans-1-(2-methoxyethyl)-4-(pyridin-4-yl)pyrrolidine-3-carboxylate: To a solution of trans-ethyl 1-(2-methoxyethyl)-4-(pyridin-4-yl)pyrrolidine-3-carboxylate (276 mg, 0.992 mmol) in THF (6 mL) and MeOH (3 mL) was added 2M aqueous LiOH (0.496 mL, 0.992 mmol). The reaction mixture was stirred at ambient temperature for 2 hours, and the resulting white precipitate was collected by vacuum filtration, rinsed with Et$_2$O, and air dried. The filtrate was concentrated to a yellow solid, triturated with MeOH (1 mL), filtered, and the white solid rinsed with Et$_2$O and air dried. The two crops of solids were combined to give the product as a white solid (197 mg, 88% yield). $^1$H NMR (d$_6$-DMSO) δ 8.37-8.39 (m, 2H), 7.26-7.28 (m, 2H), 3.36-3.43 (m, 3H), 3.24 (s, 3H), 2.75-2.86 (m, 1H), 2.41-2.68 (m, 6H).

Step C: Preparation of benzyl trans-1-(2-methoxyethyl)-4-(pyridin-4-yl)pyrrolidin-3-ylcarbamate: To a suspension of lithium trans-1-(2-methoxyethyl)-4-(pyridin-4-yl)pyrrolidine-3-carboxylate (25 mg, 0.098 mmol) in toluene (1.8 mL) and DMF (0.2 mL) were sequentially added DIEA (0.034 mL, 0.20 mmol) and diphenylphosphoryl azide (0.029 mL, 0.14 mmol). The reaction mixture was stirred at ambient temperature for 20 minutes then refluxed for 10 minutes. Benzyl alcohol (100 mg, 0.98 mmol) was introduced, and the reaction mixture was refluxed for 17 hours. The reaction mixture was directly purified by silica column chromatography, eluting with 0-10% MeOH/DCM to yield the product as a yellow oil (11 mg, 32% yield). MS (apci) m/z=356.1 (M+H).

Step D: Preparation of trans-1-(2-methoxyethyl)-4-(pyridin-4-yl)pyrrolidin-3-amine bis(2,2,2-trifluoroacetate): A solution of benzyl trans-1-(2-methoxyethyl)-4-(pyridin-4-yl)pyrrolidin-3-ylcarbamate (11 mg, 0.031 mmol) in TFA (1 mL) was heated in a sealed tube at 60° C. for 18 hours. The reaction mixture was transferred with EtOH (5 mL) and concentrated to give the crude product as a brown oil, which was used directly in Step F, assuming quantitative yield. MS (apci) m/z=222.1 (M+H).

Step E: Preparation of phenyl 2-phenyl-2,4,5,6-tetrahydrocyclopenta[c]pyrazol-3-ylcarbamate: A suspension of 2-phenyl-2,4,5,6-tetrahydrocyclopenta[c]pyrazol-3-amine (Table 1; 100 mg, 0.50 mmol) in EtOAc (2.0 mL) and 2 M aqueous NaOH (0.50 mL, 1.0 mmol) was treated with phenyl carbonochloridate (0.088 mL, 0.70 mmol) dropwise and stirred for 16 hours at ambient temperature. The reaction mixture was then phase-separated and the organic phase was washed with water (5 mL) and brine (5 mL), dried over Na$_2$SO$_4$, filtered and concentrated in vacuo to afford the product (160 mg, 100% yield). MS (apci) m/z=320.1 (M+H).

Step F: Preparation of 1-(trans-1-(2-methoxyethyl)-4-(pyridin-4-yl)pyrrolidin-3-yl)-3-(2-phenyl-2,4,5,6-tetrahydrocyclopenta[c]pyrazol-3-yl)urea: Prepared by the method as described in Example 1, substituting phenyl 3-tert-butyl-1-phenyl-1H-pyrazol-5-ylcarbamate in Step B with phenyl 2-phenyl-2,4,5,6-tetrahydrocyclopenta[c]pyrazol-3-ylcarbamate and substituting trans-1-(2-methoxyethyl)-4-phenylpyrrolidin-3-amine dihydrochloride in Step B with trans-1-(2-methoxyethyl)-4-(pyridin-4-yl)pyrrolidin-3-amine bis(2,2,2-trifluoroacetate) to provide the final product as a white solid (6.0 mg, 42% yield). MS (apci) m/z=447.2 (M+H).

Example 39

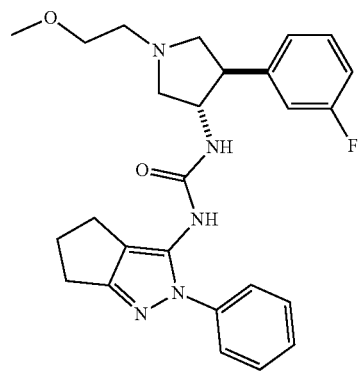

trans-1-(4-(3-fluorophenyl)-1-(2-methoxyethyl)pyrrolidin-3-yl)-3-(2-phenyl-2,4,5,6-tetrahydrocyclopenta[c]pyrazol-3-yl)urea Step A: Preparation of trans-tert-butyl 3-(3-fluorophenyl)-4-(3-(2-phenyl-2,4,5,6-tetrahydrocyclopenta[c]pyrazol-3-yl)ureido)pyrrolidine-1-carboxylate: To a suspension of trans-1-(tert-butoxycarbonyl)-4-(3-fluorophenyl)pyrrolidine-3-carboxylic acid (purchased from ChemImpex; 100 mg, 0.32 mmol) in anhydrous toluene (2 mL) was added triethylamine (180 µL, 1.29 mmol) followed by diphenylphosphoryl azide (98 µL, 0.45 mmol). The resulting solution was stirred at ambient temperature for 1 hour and then at reflux for 1 hour. After cooling, the reaction mixture was treated with 2-phenyl-2,4,5,6-tetrahydrocyclopenta[c]pyrazol-3-amine (Table 1; 193 mg, 0.97 mmol) and stirred at reflux for 15 hours. The cooled mixture was partitioned between saturated NaHCO$_3$ (20 mL) and EtOAc (20 mL) and the aqueous layer was extracted with EtOAc (2×10 mL). The combined organic phases were washed with brine (10 mL), dried over Na$_2$SO$_4$ and concentrated in vacuo. The crude material was purified by silica column chromatography, eluting with 1% MeOH/DCM followed by 5% MeOH/DCM to afford the product as a brown gum. LCMS analysis of the gum indicated this to be about a 2:1 mixture of desired product and the symmetrical urea of the 2-phenyl-2,4,5,6-tetrahydrocyclopenta[c]pyrazol-3-amine starting material (by LCMS). The mixture was taken directly into the next step. MS (apci) m/z=506.2 (M+H).

Step B: Preparation of 1-(trans-4-(3-fluorophenyl)pyrrolidin-3-yl)-3-(2-phenyl-2,4,5,6-tetrahydrocyclopenta[c]pyrazol-3-yl)urea: To the mixture isolated in Step A (90 mg, 0.18 mmol) in CH$_2$Cl$_2$ (8 mL) was added TFA (2 mL). The solution was stirred at ambient temperature for 2 hours and then concentrated, and the residue was partitioned between 1N NaOH (20 mL) and CH$_2$Cl$_2$ (20 mL). The aqueous layer was extracted with CH$_2$Cl$_2$ (2×10 mL), and the combined organic phases were washed with brine (10 mL), dried over Na$_2$SO$_4$ and concentrated to afford a brown gum. Purification by silica column chromatography eluting with 2% MeOH/DCM to 10% MeOH/CH$_2$Cl$_2$/0.1% 7N NH$_3$/MeOH afforded the product as a pale yellow solid (31 mg, 43% yield). MS (apci) m/z=406.1 (M+H).

Step C: Preparation of trans-1-(4-(3-fluorophenyl)-1-(2-methoxyethyl)pyrrolidin-3-yl)-3-(2-phenyl-2,4,5,6-tetrahydrocyclopenta[c]pyrazol-3-yl)urea: To a solution of 1-(trans-4-(3-fluorophenyl)pyrrolidin-3-yl)-3-(2-phenyl-2, 4,5,6-tetrahydrocyclopenta[c]pyrazol-3-yl)urea (31 mg, 0.076 mmol) in anhydrous. DMF (1 mL) was added 1-bromo-2-methoxyethane (9.1 µL, 0.09 mmol) followed by DIEA (40 µL, 0.23 mmol). The mixture was warmed to 60° C. and stirred for 15 hours. The cooled mixture was partitioned between saturated. NaHCO$_3$ (20 mL) and EtOAc (10 mL) and the aqueous layer was extracted with EtOAc (2×10 mL). The combined organic phases were washed with water (5×10 mL) and brine (10 mL) then dried over Na$_2$SO$_4$ and concentrated. The crude material was purified by silica column chromatography, eluting with 2.5% MeOH/CH$_2$Cl$_2$ to afford the product as a colorless glass (14 mg, 40% yield). MS (apci) m/z=464.1 (M+H).

Example 40

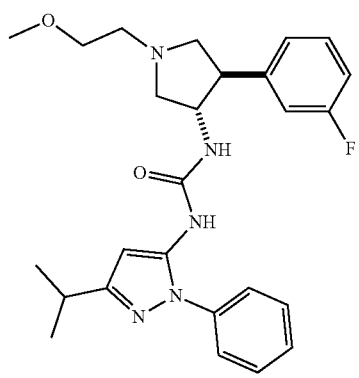

trans-1-(-4-(3-fluorophenyl)-1-(2-methoxyethyl) pyrrolidin-3-yl)-3-(3-isopropyl-1-phenyl-1H-pyrazol-5-yl)urea Prepared using the procedure as described for Example 39, substituting 3-isopropyl-1-phenyl-1H-pyrazol-5-amine (Table 1) for 2-phenyl-2,4,5,6-tetrahydrocyclopenta[c]pyrazol-3-amine in Step A. MS (apci) m/z=466.2 (M+H).

Example 41

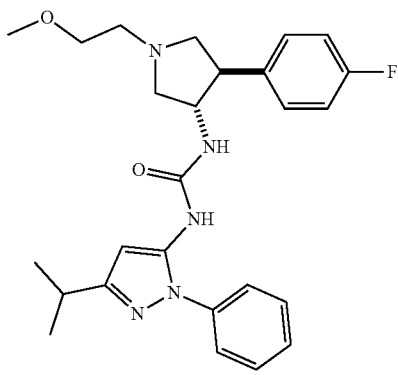

trans-1-(4-(4-fluorophenyl)-1-(2-methoxyethyl)pyrrolidin-3-yl)-3-(3-isopropyl-1-phenyl-1H-pyrazol-5-yl)urea Prepared according to the procedures described for Example 39, substituting trans-1-(tert-butoxycarbonyl)-4-(4-fluorophenyl)pyrrolidine-3-carboxylic acid for trans-1-(tert-butoxycarbonyl)-4-(3-fluorophenyl)pyrrolidine-3-carboxylic acid in Step A. MS (apci) m/z=466.2 (M+H).

Example 42

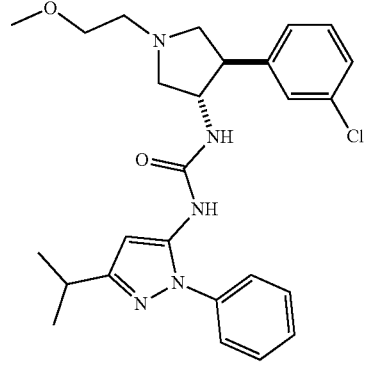

trans-1-(4-(3-chlorophenyl)-1-(2-methoxyethyl)pyrrolidin-3-yl)-3-(3-isopropyl-1-phenyl-1H-pyrazol-5-yl)urea Prepared according to the procedures described for Example 40, substituting trans-1-(tert-butoxycarbonyl)-4-(3-chlorophenyl)pyrrolidine-3-carboxylic acid for trans-1-(tert-butoxy-carbonyl)-4-(3-fluorophenyl)pyrrolidine-3-carboxylic acid in Step A. MS (apci) m/z=482.1 (M+H).

Example 43

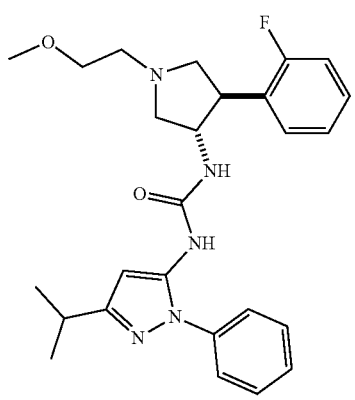

trans-1-(4-(2-fluorophenyl)-1-(2-methoxyethyl)pyrrolidin-3-yl)-3-(3-isopropyl-1-phenyl-1H-pyrazol-5-yl)urea Prepared according to the procedures described for Example 40, substituting trans-1-(tert-butoxycarbonyl)-4-(2-fluorophenyl)pyrrolidine-3-carboxylic acid for trans-1-(tert-butoxycarbonyl)-4-(3-fluorophenyl)pyrrolidine-3-carboxylic acid in Step A. MS (apci) m/z=466.2 (M+H).

Example 44

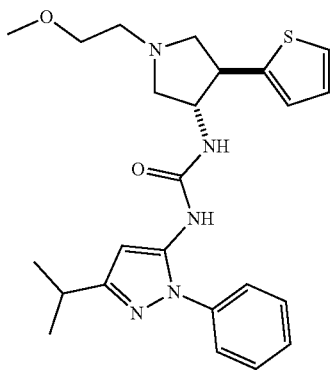

trans-1-(3-isopropyl-1-phenyl-1H-pyrazol-5-yl)-3-(1-(2-methoxyethyl)-4-(thiophen-2-yl)pyrrolidin-3-yl)urea Prepared according to the procedures described for Example 40, substituting trans-1-(tert-butoxycarbonyl)-4-(thiophen-2-yl)pyrrolidine-3-carboxylic acid for trans-1-(tert-butoxycarbonyl)-4-(3-fluorophenyl)pyrrolidine-3-carboxylic acid in Step A. MS (apci) m/z=454.1 (M+H).

Example 45

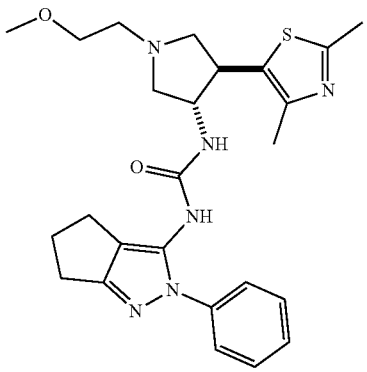

1-((3,4-trans)-4-(2,4-dimethylthiazol-5-yl)-1-(2-methoxyethyl)pyrrolidin-3-yl)-3-(2-phenyl-2,4,5,6-tetrahydrocyclopenta[c]pyrazol-3-yl)urea Step A: Preparation of (E)-methyl 3-(2,4-dimethylthiazol-5-yl)acrylate: A solution of methyl (triphenyl-phosphoranylidene)acetate (2.61 g, 7.80 mmol) in CH$_2$Cl$_2$ (10 mL) was cooled to 0° C., and then a solution of 4-methyl thiazole 4-carboxaldehyde (purchased from Maybridge, 1.00 g, 7.08 mmol) in dry CH$_2$Cl$_2$ (10 mL) was added dropwise over a period of 15 minutes. The reaction was warmed up to ambient temperature and stirred for 24 hours. After removal of solvent under reduced pressure, the yellowish solid residue obtained was dissolved in CH$_2$Cl$_2$ and purified by silica gel flash chromatography, eluting with 15% EtOAc/hexanes, to provide the product as a white powder (1.32 g, 94.5% yield). $^1$H-NMR (400 MHz, DMSO-d$^6$) δ 7.73 (d, J=15.62 Hz, 1H), 6.07 (d, J=15.62 Hz, 1H), 3.71 (s, 3H, OCH$_3$), 2.63 (s, 3H, CH$_3$), 2.42 (s, 3H, CH$_3$). MS (apci) m/z=198 (M+H).

Step B: Preparation of (3,4-trans)-methyl 4-(2,4-dimethylthiazol-5-yl)-1-(2-methoxyethyl)pyrrolidine-3-carboxylate: A solution of (E)-methyl 3-(2,4-dimethylthiazol-5-yl)acrylate (200 mg, 1.01 mmol) and TFA (7.81 μL, 0.101 mmol) in toluene (15 mL) was cooled in an ice bath, followed by dropwise addition of a solution of 2-methoxy-N-(methoxymethyl)-N-((trimethylsilyl)methyl)ethanamine (312 mg, 1.52 mmol) in toluene (5 mL). The reaction was warmed up to ambient temperature and stirred for 3 days. The reaction mixture was washed with saturated NaHCO$_3$ (25 mL) and water (2×25 mL), dried with Na$_2$SO$_4$, filtered and concentrated in vacuo. The crude material was purified by reverse-phase column chromatography, eluting with 5-50% acetonitrile/water to yield the product as clear oil (43 mg, 14% yield). MS (apci) m/z=299.1 (M+H).

Step C: Preparation of (3,4-trans)-4-(2,4-dimethylthiazol-5-yl)-1-(2-methoxyethyl)pyrrolidine-3-carboxylic acid: To a solution of (3,4-trans)-methyl 4-(2,4-dimethylthiazol-5-yl)-1-(2-methoxyethyl)pyrrolidine-3-carboxylate (41 mg, 0.14 mmol) in a mixed solvent system of 2:2:1 THF/MeOH/water (0.7 mL) was added LiOH—H$_2$O (17 mg, 0.41 mmol), and the mixture was stirred at ambient temperature overnight. After removal of solvent, the solid residue was taken up in water (0.2 mL) and acidified with 1 N HCl, until pH 4-5. The mixture was directly purified by reverse-phase chromatography, eluting with 5 to 33% acetonitrile/water to yield the product as clear oil (30 mg, 77% yield). MS (apci) m/z=285.1 (M+H).

Step D: Preparation of benzyl (3,4-trans)-4-(2,4-dimethylthiazol-5-yl)-1-(2-methoxyethyl)pyrrolidin-3-ylcarbamate: To a turbid solution of (3,4-trans)-4-(2,4-dimethylthiazol-5-yl)-1-(2-methoxyethyl)pyrrolidine-3-carboxylic acid (25.6 mg, 0.09 mmol) in toluene (0.9 mL) was added TEA (31 μL, 0.22 mmol) followed by diphenyl phosphorazidate (27 μL, 0.13 mmol). The mixture was stirred at ambient temperature for 1 hour and then at 100° C. for 1 hour. Benzyl alcohol (19 μL, 0.18 mmol) was added and the mixture was heated at 100° C. for 18 hours. After cooling, the mixture was diluted with EtOAc (2 mL), washed with water (2×1 mL), dried with MgSO$_4$, filtered and concentrated. The crude residue was purified by reverse-phase column chromatography, eluting with 5 to 60% acetonitrile/water to yield the product as yellowish oil (18 mg, 51% yield). MS (apci) m/z=390.1 (M+H).

Step E: Preparation of (3,4-trans)-4-(2,4-dimethylthiazol-5-yl)-1-(2-methoxyethyl)pyrrolidin-3-amine bis(2,2,2-trifluoroacetate): A solution of benzyl (3,4-trans)-4-(2,4-dimethylthiazol-5-yl)-1-(2-methoxyethyl)pyrrolidin-3-ylcarbamate (18.0 mg, 0.0462 mmol) in TFA (178 μL, 2.31 mmol) was heated at 60° C. for 18 hours. The reaction mixture was diluted with toluene/EtOH and concentrated. The crude material was purified by reverse-phase column chromatography eluting with 5-38% acetonitrile/water to yield the product as colorless glassy solid (14 mg, 63% yield). MS (apci) m/z=256.1 (M+H).

Step F: Preparation of 1-((3,4-trans)-4-(2,4-dimethylthiazol-5-yl)-1-(2-methoxyethyl)pyrrolidin-3-yl)-3-(2-phenyl-2,4,5,6-tetrahydrocyclopenta[c]pyrazol-3-yl)urea: To a clear solution of (3,4-trans)-4-(2,4-dimethylthiazol-5-yl)-1-(2-methoxyethyl)pyrrolidin-3-amine bis(2,2,2-trifluoroacetate) (14 mg, 0.029 mmol) in DMA (0.3 mL) was added phenyl 2-phenyl-2,4,5,6-tetrahydrocyclopenta[c]pyrazol-3-ylcarbamate (11 mg, 0.035 mmol). The mixture was cooled in an ice bath, and DIEA (0.020 mL, 0.12 mmol) was added. The reaction was warmed up to ambient temperature and stirred for 5 minutes, then directly purified by reverse-phase chromatography, eluting with 5 to 50% acetonitrile/water to yield the title product as white solid (10 mg, 72% yield). MS (apci) m/z=481.2 (M+H).

Example 46

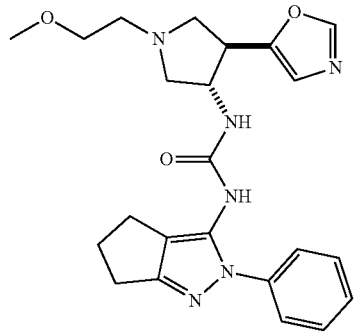

1-(trans-1-(2-methoxyethyl)-4-(oxazol-5-yl)pyrrolidin-3-yl)-3-(2-phenyl-2,4,5,6-tetrahydrocyclopenta[c]pyrazol-3-yl)urea Step A: Preparation of (E)-ethyl 3-(oxazol-5-yl)acrylate: To a suspension of NaH (60% in mineral oil, 227 mg, 5.67 mmol) in THF (40 mL) under $N_2$ at 0° C. was added dropwise ethyl 2-(diethoxyphosphoryl)acetate (1.12 mL, 5.67 mmol). The mixture was stirred at 0° C. for 30 minutes, and then a solution of oxazole-5-carbaldehyde (500 mg, 5.15 mmol) in THF (5 mL) was added. The ice bath was removed, and the reaction was stirred at ambient temperature for 18 hours. The reaction was diluted with $H_2O$ (30 mL) and extracted with EtOAc (50 mL). The organic phase was washed with brine (50 mL), dried with $MgSO_4$, filtered and concentrated in vacuo. The crude product was purified by silica column chromatography, eluting with 0 to 1% MeOH/DCM to yield the product as a pale yellow oil (354 mg, 41.1% yield). $^1$H NMR (CDCl$_3$) δ 7.92 (s, 1H), 7.48 (d, 1H), 7.29 (s, 1H), 6.40 (d, 1H), 4.27 (q, 2H), 1.29 (t, 3H).

Step B: Preparation of trans-ethyl 1-(2-methoxyethyl)-4-(oxazol-5-yl)pyrrolidine-3-carboxylate: To a solution of (E)-ethyl 3-(oxazol-5-yl)acrylate (354 mg, 2.12 mmol) in DCM (20 mL) at 0° C. were added TFA (0.033 mL, 0.42 mmol), then dropwise 2-methoxy-N-(methoxymethyl)-N-((trimethylsilyl)methyl)ethanamine (Preparation C, 522 mg, 2.54 mmol). The ice bath was removed and the reaction stirred at ambient temperature for 18 hours, then the reaction mixture diluted with saturated aqueous NaHCO$_3$ (20 mL), separated and the aqueous phase extracted with DCM (20 mL). The combined organic phases were dried with MgSO$_4$, filtered and concentrated in vacuo. The crude product was purified by silica column chromatography, eluting with 0-3% MeOH/DCM to yield the product as a pale yellow oil (321 mg, 56.5% yield). MS (apci) m/z=269.2 (M+H).

Step C: Preparation of lithium trans-1-(2-methoxyethyl)-4-(oxazol-5-yl)pyrrolidine-3-carboxylate: To a solution of trans-ethyl 1-(2-methoxyethyl)-4-(oxazol-5-yl)pyrrolidine-3-carboxylate (321 mg, 1.20 mmol) in THF (6 mL) and MeOH (3 mL) was added 2M aqueous LiOH (0.837 mL, 1.67 mmol). The reaction was stirred at ambient temperature for 1.5 hours and then concentrated to a yellow sticky solid. The crude product was dissolved in MeOH (10 mL) and concentrated to yield the product as a yellow foam (234 mg, 79.4% yield). MS (apci neg) m/z=239.2 (M-Li).

Step D: Preparation of benzyl trans-1-(2-methoxyethyl)-4-(oxazol-5-yl)pyrrolidin-3-ylcarbamate: To a solution trans-ethyl 1-(2-methoxyethyl)-4-(oxazol-5-yl)pyrrolidine-3-carboxylate (234 mg, 0.872 mmol) in DMF (0.8 mL) were added DIEA (0.304 mL, 1.74 mmol) then toluene (10 mL). Diphenylphosphoryl azide (0.263 mL, 1.22 mmol) was added and the reaction was stirred at ambient temperature for 1 hour, then at reflux for 1 hour. Benzyl alcohol (0.903 mL, 8.72 mmol) was added and the reaction refluxed for 17 hours. The mixture was cooled and diluted with $H_2O$ (25 mL) and extracted with DCM (3×20 mL), and the combined organic phases were washed with brine (25 mL), dried with MgSO$_4$, filtered, concentrated. The crude product was purified by reverse-phase column chromatography, eluting with 5-70% acetonitrile/water to yield the product as a pale yellow syrup (55 mg, 18% yield). MS (apci) m/z=346.1 (M+H).

Step E: Preparation of trans-1-(2-methoxyethyl)-4-(oxazol-5-yl)pyrrolidin-3-amine bis(2,2,2-trifluoroacetate): A solution of benzyl trans-1-(2-methoxyethyl)-4-(oxazol-5-yl)pyrrolidin-3-ylcarbamate (55 mg, 0.16 mmol) in TFA (2 mL) was heated in a sealed tube at 60° C. for 16 hours. The reaction mixture was transferred to a flask containing EtOH (10 mL) and concentrated in vacuo. The crude product was dissolved in toluene (15 mL) and azeotroped three times to yield the crude product as a brown syrup (130 mg, 186% yield). MS (apci) m/z=212.1 (M+H).

Step F: Preparation of 1-(trans-1-(2-methoxyethyl)-4-(oxazol-5-yl)pyrrolidin-3-yl)-3-(2-phenyl-2,4,5,6-tetrahydrocyclopenta[c]pyrazol-3-yl)urea: Prepared by the method as described in Example 45, Step F using trans-1-(2-methoxyethyl)-4-(oxazol-5-yl)pyrrolidin-3-amine bis(2,2,2-trifluoroacetate) to give the product as a colorless residue (5.0 mg, 18% yield). MS (apci) m/z=437.3 (M+H).

Example 47

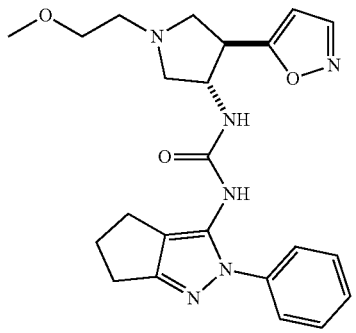

1-(trans-4-(isoxazol-5-yl)-1-(2-methoxyethyl)pyrrolidin-3-yl)-3-(2-phenyl-2,4,5,6-tetrahydrocyclopenta[c]pyrazol-3-yl)urea Prepared by the method as described in Example 46, substituting oxazole-5-carbaldehyde in Step A with isoxazole-5-carbaldehyde. MS (apci) m/z=437.0 (M+H).

Example 48

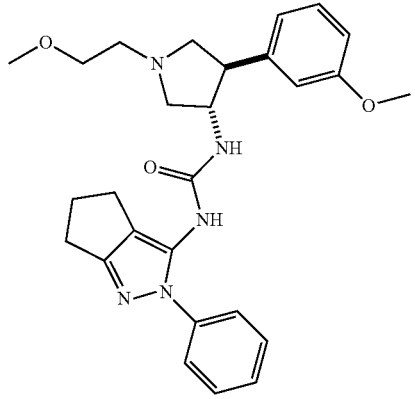

1-((3,4-trans)-1-(2-methoxyethyl)-4-(3-methoxyphenyl)pyrrolidin-3-yl)-3-(2-phenyl-2,4,5,6-tetrahydrocyclopenta[c]pyrazol-3-yl)urea Step A: Preparation of (3,4-trans)-tert-butyl 3-(3-methoxyphenyl)-4-(3-(2-phenyl-2,4,5,6-tetrahydrocyclopenta[c]pyrazol-3-yl)ureido)pyrrolidine-1-carboxylate: To a mixture of (3,4-trans)-tert-butyl 3-amino-4-(3-methoxyphenyl)pyrrolidine-1-carboxylate (30 mg, 0.095 mmol, purchased from BroadPharm) and phenyl 2-phenyl-2,4,5,6-tetrahydrocyclopenta[c]pyrazol-3-ylcarbamate (37 mg, 0.11 mmol) was added DMA (0.5 mL), cooled in an ice bath, then added DIEA (0.050 mL, 0.29 mmol). The ice bath was removed and the reaction was stirred at ambient temperature for 2 hours. The reaction mixture was then directly purified by reverse-phase chromatography eluting with 5-75% acetonitrile/water 5 to 75% to yield the product as white solid (15 mg, 30% yield). MS (apci) m/z=518.0 (M+H).

Step B: Preparation of 1-((3,4-trans)-4-(3-methoxyphenyl)pyrrolidin-3-yl)-3-(2-phenyl-2,4,5,6-tetrahydrocyclopenta[c]pyrazol-3-yl)urea hydrochloride: A solution of (3,4-trans)-tert-butyl 3-(3-methoxyphenyl)-4-(3-(2-phenyl-2,4,5,6-tetrahydrocyclopenta[c] pyrazol-3-yl)ureido)pyrrolidine-1-carboxylate (15 mg, 0.029 mmol) in 5-6 N HCl in IPA (58 µL, 0.29 mmol) was stirred at ambient temperature for 3 hours, then concentrated in vacuo, treated with ether, and dried on high vacuum, yielding the crude product as an off-white solid. The solid was directly used in the next step without further purification. MS (apci) m/z=418.1 (M+H).

Step C: Preparation of 1-((3,4-trans)-1-(2-methoxyethyl)-4-(3-methoxyphenyl)pyrrolidin-3-yl)-3-(2-phenyl-2,4,5,6-tetrahydrocyclopenta[c]pyrazol-3-yl)urea: To a DMF (0.3 mL) solution of 1-((3,4-trans)-4-(3-methoxyphenyl)pyrrolidin-3-yl)-3-(2-phenyl-2,4,5,6-tetrahydrocyclopenta[c]pyrazol-3-yl)urea hydrochloride (13 mg, 0.029 mmol) was added N-ethyl-N-isopropylpropan-2-amine (16 µL, 0.086 mmol) and 1-bromo-2-methoxyethane (4.8 mg, 0.034 mmol), and the reaction was stirred at ambient temperature for 3 days. The reaction was directly purified by reverse-phase column chromatography eluting with 5-55% acetonitrile/water, yielding the title product as white solid (10 mg, 73% yield). MS (apci) m/z=476.2 (M+H).

Example 49

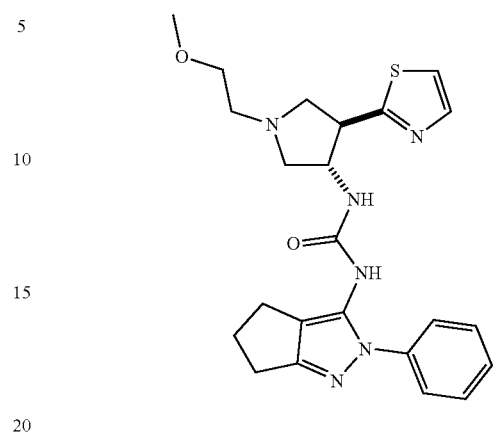

1-(1-(2-methoxyethyl)-4-(thiazol-2-yl)pyrrolidin-3-yl)-3-(2-phenyl-2,4,5,6-tetrahydrocyclopenta[c]pyrazol-3-yl)urea Step A: Preparation of trans-(1-(2-methoxyethyl)-4-nitropyrrolidin-3-yl)thiazole: PS-DMAP (3.52 g, 5.00 mmol) was added in small portions to a solution of thiazole-2-carbaldehyde (2.83 g, 25.0 mmol) in acetonitrile (5 mL) and nitromethane (5 mL). The reaction was stirred at ambient temperature for 4 hours and acetonitrile (50 mL) was added followed by acetic anhydride (2.59 mL, 27.5 mmol). The reaction was stirred for 1 hour, filtered and concentrated in vacuo to afford (E)-2-(2-nitrovinyl)thiazole (3.99 g). A portion of (E)-2-(2-nitrovinyl)thiazole (1.00 g, 6.40 mmol) was dissolved in DCM (5 mL), cooled to 0° C. and treated with TFA (0.0987 mL, 1.28 mmol) followed by 2-methoxy-N-(methoxymethyl)-N-((trimethylsilyl) methyl)ethanamine (1.32 g, 6.40 mmol) dropwise. The reaction was allowed to warm to ambient temperature overnight. 1N NaOH (5 mL) was added and the reaction was extracted with several portions of DCM in a phase separator frit. The combined DCM extracts were concentrated to afford the crude title compound (1.61 g, 94.1% yield). MS (apci) m/z=258.0 (M+H).

Step B: Preparation of trans-1-(2-methoxyethyl)-4-(thiazol-2-yl)pyrrolidin-3-amine: trans-1-(2-Methoxyethyl)-4-nitropyrrolidin-3-yl)thiazole (80 mg, 0.31 mmol) was dissolved in 1 mL of MeOH and treated with 10% Pd/C (33 mg, 0.031 mmol). The reaction mixture was stirred under a hydrogen balloon overnight, filtered through Celite® and concentrated to afford the crude title compound (68 mg, 96% yield). MS (apci) m/z=228.1 (M+H).

Step C: Preparation of 1-(trans-1-(2-methoxyethyl)-4-(thiazol-2-yl)pyrrolidin-3-yl)-3-(2-phenyl-2,4,5,6-tetrahydrocyclopenta[c]pyrazol-3-yl)urea: trans-1-(2-Methoxyethyl)-4-(thiazol-2-yl)pyrrolidin-3-amine (15.0 mg, 0.0660 mmol) was dissolved in 1 mL of DCM and treated with DIEA (23.0 µL, 0.132 mmol) followed by phenyl 2-(cyclohexa-1,3-dienyl)-2,4,5,6-tetrahydrocyclopenta[c]pyrazol-3-ylcarbamate (25.4 mg, 0.0792 mmol). The reaction mixture was stirred at ambient temperature for 18 hours, concentrated and purified by reverse-phase column chromatography, eluting with 0-50% acetonitrile/water, to afford the title compound (3.2 mg, 10.7% yield). MS (apci) m/z=453.1 (M+H).

Example 50

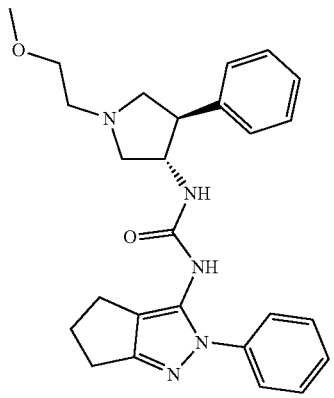 [SMILES: COCCN1C[C@@H](NC(=O)Nc2c3c(nn2-c2ccccc2)CCC3)[C@H](c2ccccc2)C1]

1-((3S,4R)-1-(2-methoxyethyl)-4-phenylpyrrolidin-3-yl)-3-(2-phenyl-2,4,5,6-tetrahydrocyclopenta[c]pyrazol-3-yl)urea To a DCM (5 mL) solution of (3S,4R)-1-(2-methoxyethyl)-4-phenylpyrrolidin-3-amine dihydrochloride (Preparation D; 0.10 g, 0.34 mmol) in DCM (5 mL) at 0° C. was sequentially added phenyl 2-phenyl-2,4,5,6-tetrahydrocyclopenta[c]pyrazol-3-ylcarbamate (Example 38, Step C; 0.13 g, 0.41 mmol) and TEA (0.14 mL, 1.0 mmol). The resulting mixture was allowed to warmed up to ambient temperature and stirred for 2 hours. It was then treated with EtOAc, washed with saturated $NH_4Cl$, saturated $NaHCO_3$, and brine. The combined organic layers were dried with $MgSO_4$, filtered and concentrated. The crude material was purified by silica column chromatography, eluting with 2-2.5% MeOH/DCM to yield the product (0.11 g, 72% yield). MS (apci) m/z=446.2 (M+H).

Example 51

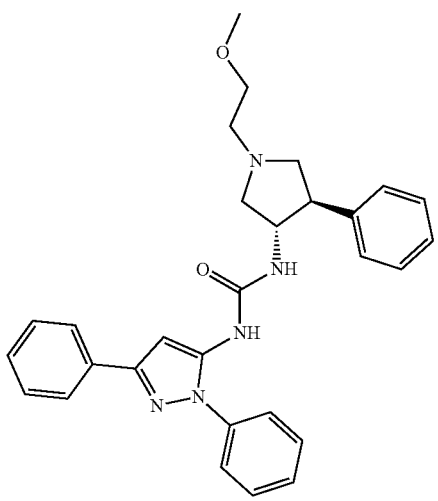 [SMILES: COCCN1C[C@@H](NC(=O)Nc2cc(-c3ccccc3)nn2-c2ccccc2)[C@H](c2ccccc2)C1]

1-(1,3-diphenyl-1H-pyrazol-5-yl)-3-((3S,4R)-1-(2-methoxyethyl)-4-phenylpyrrolidin-3-yl)urea 1,3-Diphenyl-1H-pyrazol-5-amine (Table 1; 32.0 mg, 0.136 mmol), DIEA (35.6 µL, 0.204 mmol) and 1,1'-carbonyldiimidazole (19.3 mg, 0.119 mmol) were combined in $CHCl_3$ (0.5 mL) in a sealed vessel and heated at 60° C. for 4 hours. The mixture was cooled to ambient temperature and (3S,4R)-1-(2-methoxyethyl)-4-phenylpyrrolidin-3-amine dihydrochloride (Preparation D; 15.0 mg, 0.0681 mmol) was added. After heating at 100° C. for 15 hours, the reaction mixture was concentrated and directly purified by reverse-phase column chromatography, eluting with 0-70% acetonitrile/water to afford the title compound (5.6 mg, 17% yield). MS (apci) m/z=482.2 (M+H).

Example 52

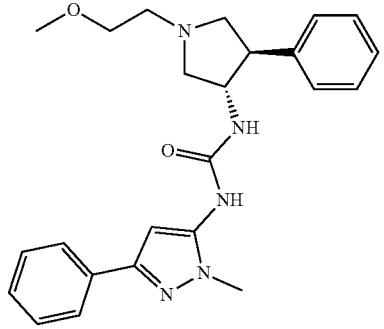 [SMILES: COCCN1C[C@@H](NC(=O)Nc2cc(-c3ccccc3)nn2C)[C@H](c2ccccc2)C1]

1-((3S,4R)-1-(2-methoxyethyl)-4-phenylpyrrolidin-3-yl)-3-(1-methyl-3-phenyl-1H-pyrazol-5-yl)urea To a solution of 1-methyl-3-phenyl-1H-pyrazol-5-amine (Table 1; 49 mg, 0.28 mmol) in DCM (2 mL) was added CDI (46 mg, 0.28 mmol) followed by DIEA (200 µL, 1.1 mmol). After 2 hours at ambient temperature, a solution of (3S,4R)-1-(2-methoxyethyl)-4-phenylpyrrolidin-3-amine dihydrochloride (Preparation D, 83 mg, 0.28 mmol) in DCM (0.6 mL) was added. The reaction was stirred 15 minutes, then purified directly by reverse-phase column chromatography, eluting with 5-50% acetonitrile/water to afford the title product as a white solid (45 mg, 38% yield). MS (apci) m/z=420.1 (M+H).

The compounds of Table 6 were prepared according to the method of Example 52 using the appropriate starting materials. Conversion time to the activated intermediate with CDI varied, and was monitored by taking an aliquot and quenching in MeOH. LCMS analysis was used to monitor complete conversion to the methyl carbamate (30 minutes to 16 hours).

TABLE 6

| Ex. # | Structure | Name | Data |
|---|---|---|---|
| 53 | 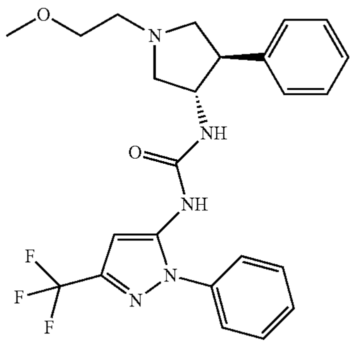 [SMILES: COCCN1C[C@@H](NC(=O)Nc2cc(C(F)(F)F)nn2-c2ccccc2)[C@H](c2ccccc2)C1] | 1-((3S,4R)-1-(2-methoxyethyl)-4-phenylpyrrolidin-3-yl)-3-(1-phenyl-3-(trifluoromethyl)-1H-pyrazol-5-yl)urea | MS (apci) m/z = 474.2 (M + H). |
| 54 | 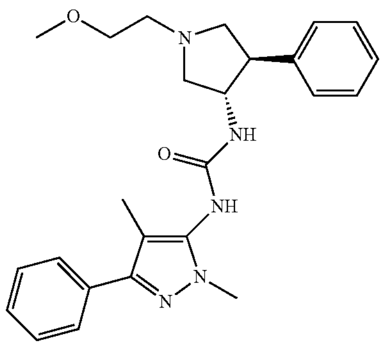 [SMILES: COCCN1C[C@@H](NC(=O)Nc2c(C)c(-c3ccccc3)nn2C)[C@H](c2ccccc2)C1] | 1-(1,4-dimethyl-3-phenyl-1H-pyrazol-5-yl)-3-((3S,4R)-1-(2-methoxyethyl)-4-phenylpyrrolidin-3-yl)urea | MS (apci) m/z = 434.1 (M + H). |
| 55 | 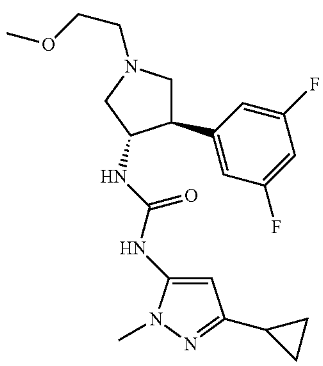 [SMILES: COCCN1C[C@@H](NC(=O)Nc2cc(C3CC3)nn2C)[C@H](c2cc(F)cc(F)c2)C1] | 1-(3-cyclopropyl-1-methyl-1H-pyrazol-5-yl)-3-((3S,4R)-4-(3,5-difluorophenyl)-1-(2-methoxyethyl)pyrrolidin-3-yl)urea | MS (apci) m/z = 420.1 (M + H). |
| 56 | 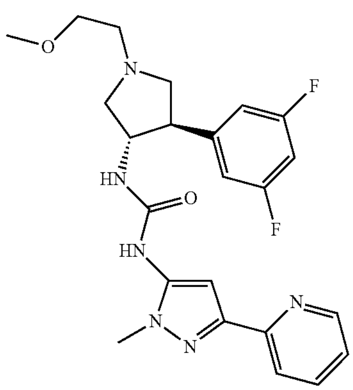 [SMILES: COCCN1C[C@@H](NC(=O)Nc2cc(-c3ccccn3)nn2C)[C@H](c2cc(F)cc(F)c2)C1] | 1-((3S,4R)-4-(3,5-difluorophenyl)-1-(2-methoxyethyl)pyrrolidin-3-yl)-3-(1-methyl-3-(pyridin-2-yl)-1H-pyrazol-5-yl)urea | MS (apci) m/z = 457.1 (M + H). |

TABLE 6-continued

| Ex. # | Structure | Name | Data |
| --- | --- | --- | --- |
| 57 | 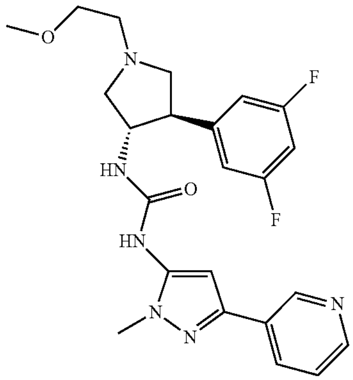 [SMILES: COCCN1C[C@@H](NC(=O)Nc2cc(-c3cccnc3)nn2C)[C@H](c2cc(F)cc(F)c2)C1] | 1-((3S,4R)-4-(3,5-difluorophenyl)-1-(2-methoxyethyl)pyrrolidin-3-yl)-3-(1-methyl-3-(pyridin-3-yl)-1H-pyrazol-5-yl)urea | MS (apci) m/z = 457.1 (M + H). |
| 58 | 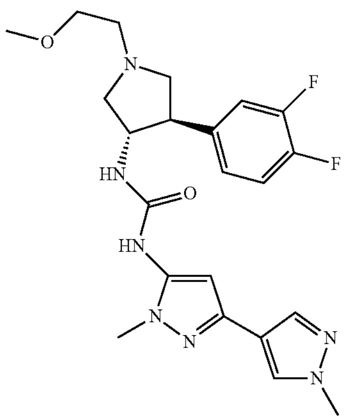 | 1-((3S,4R)-4-(3,4-difluorophenyl)-1-(2-methoxyethyl)pyrrolidin-3-yl)-3-(1,1'-dimethyl-1H,1'H-3,4'-bipyrazol-5-yl)urea | MS (apci) m/z = 460.1 (M + H). |
| 59 | 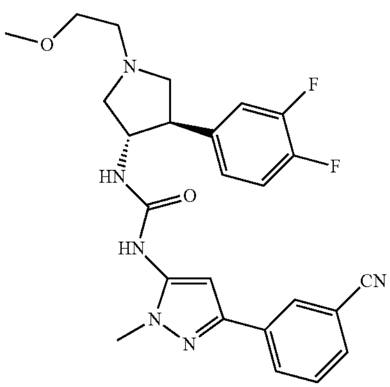 [SMILES: COCCN1C[C@@H](NC(=O)Nc2cc(-c3cccc(C#N)c3)nn2C)[C@H](c2ccc(F)c(F)c2)C1] | 1-(3-(3-cyanophenyl)-1-methyl-1H-pyrazol-5-yl)-3-((3S,4R)-4-(3,4-difluorophenyl)-1-(2-methoxyethyl)pyrrolidin-3-yl)urea | MS (apci) m/z = 481.1 (M + H). |
| 60 | 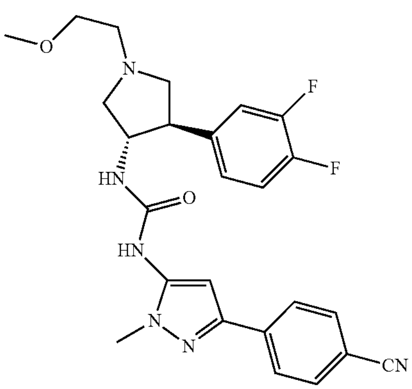 [SMILES: COCCN1C[C@@H](NC(=O)Nc2cc(-c3ccc(C#N)cc3)nn2C)[C@H](c2ccc(F)c(F)c2)C1] | 1-(3-(4-cyanophenyl)-1-methyl-1H-pyrazol-5-yl)-3-((3S,4R)-4-(3,4-difluorophenyl)-1-(2-methoxyethyl)pyrrolidin-3-yl)urea | MS (apci) m/z = 481.1 (M + H). |

TABLE 6-continued

| Ex. # | Structure | Name | Data |
|---|---|---|---|
| 61 | 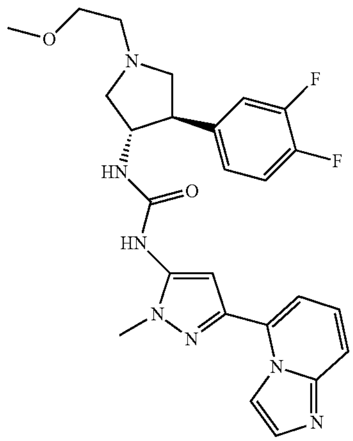 [SMILES: COCCN1C[C@@H](NC(=O)Nc2cc(-c3cccc4nccn34)nn2C)[C@H](c2ccc(F)c(F)c2)C1] | 1-((3S,4R)-4-(3,4-difluorophenyl)-1-(2-methoxyethyl)pyrrolidin-3-yl)-3-(3-(imidazo[1,2-a]pyridin-5-yl)-1-methyl-1H-pyrazol-5-yl)urea | MS (apci) m/z = 496.1 (M + H). |
| 62 | 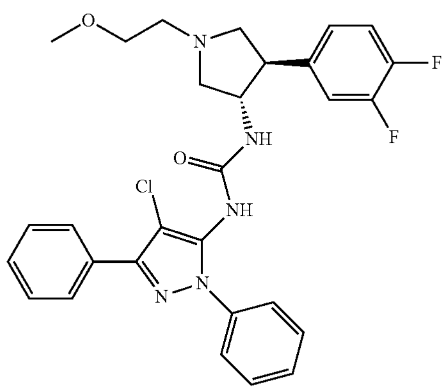 [SMILES: COCCN1C[C@@H](NC(=O)Nc2c(Cl)c(-c3ccccc3)nn2-c2ccccc2)[C@H](c2ccc(F)c(F)c2)C1] | 1-(4-chloro-1,3-diphenyl-1H-pyrazol-5-yl)-3-((3S,4R)-4-(3,4-difluorophenyl)-1-(2-methoxyethyl)pyrrolidin-3-yl)urea | MS (apci) m/z = 552.0 (M + H). |
| 63 | 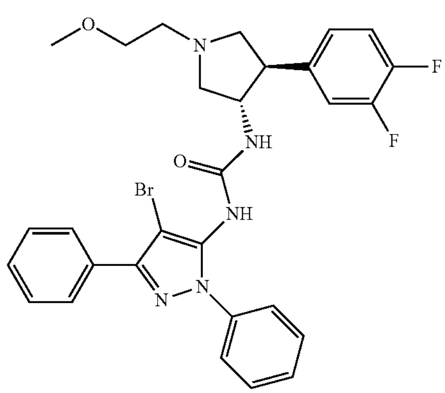 [SMILES: COCCN1C[C@@H](NC(=O)Nc2c(Br)c(-c3ccccc3)nn2-c2ccccc2)[C@H](c2ccc(F)c(F)c2)C1] | 1-(4-bromo-1,3-diphenyl-1H-pyrazol-5-yl)-3-((3S,4R)-4-(3,4-difluorophenyl)-1-(2-methoxyethyl)pyrrolidin-3-yl)urea | MS (apci) m/z = 596.0 (M + H). |
| 64 | 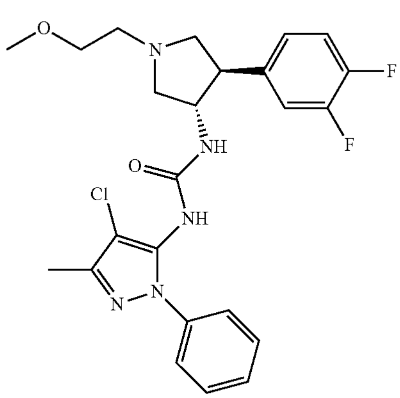 [SMILES: COCCN1C[C@@H](NC(=O)Nc2c(Cl)c(C)nn2-c2ccccc2)[C@H](c2ccc(F)c(F)c2)C1] | 1-(4-chloro-3-methyl-1-phenyl-1H-pyrazol-5-yl)-3-((3S,4R)-4-(3,4-difluorophenyl)-1-(2-methoxyethyl)pyrrolidin-3-yl)urea | MS (apci) m/z = 490.0 (M + H). |

TABLE 6-continued

| Ex. # | Structure | Name | Data |
|---|---|---|---|
| 65 | 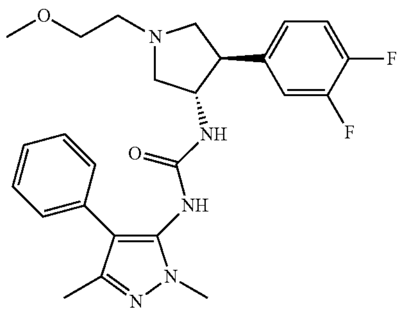 [SMILES: COCCN1C[C@@H](NC(=O)Nc2c(-c3ccccc3)c(C)nn2C)[C@H](c2ccc(F)c(F)c2)C1] | 1-((3S,4R)-4-(3,4-difluorophenyl)-1-(2-methoxyethyl)pyrrolidin-3-yl)-3-(1,3-dimethyl-4-phenyl-1H-pyrazol-5-yl)urea | MS (apci) m/z = 470.1 (M + H). |
| 66 | 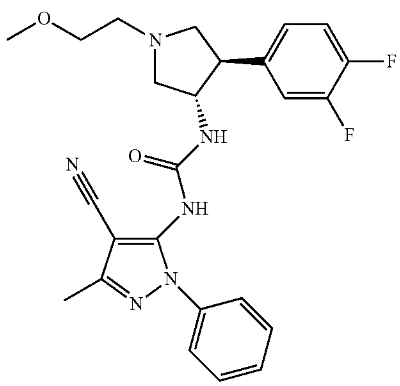 [SMILES: COCCN1C[C@@H](NC(=O)Nc2c(C#N)c(C)nn2-c2ccccc2)[C@H](c2ccc(F)c(F)c2)C1] | 1-(4-cyano-3-methyl-1-phenyl-1H-pyrazol-5-yl)-3-((3S,4R)-4-(3,4-difluorophenyl)-1-(2-methoxyethyl)pyrrolidin-3-yl)urea | MS (apci) m/z = 481.1 (M + H). |
| 67 | 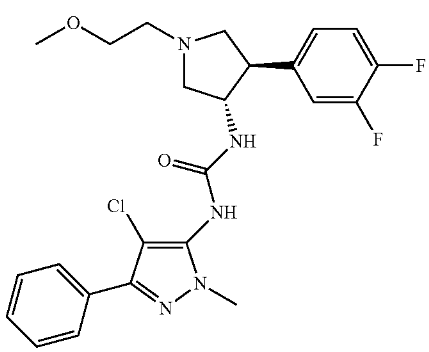 [SMILES: COCCN1C[C@@H](NC(=O)Nc2c(Cl)c(-c3ccccc3)nn2C)[C@H](c2ccc(F)c(F)c2)C1] | 1-(4-chloro-1-methyl-3-phenyl-1H-pyrazol-5-yl)-3-((3S,4R)-4-(3,4-difluorophenyl)-1-(2-methoxyethyl)pyrrolidin-3-yl)urea | MS (apci) m/z = 490.0 (M + H). |
| 68 | 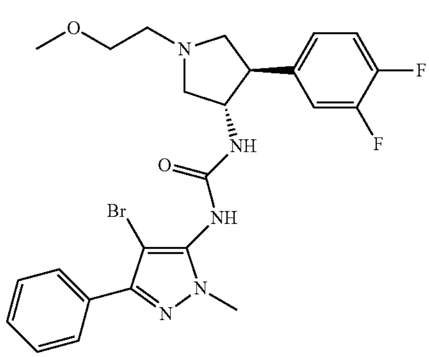 [SMILES: COCCN1C[C@@H](NC(=O)Nc2c(Br)c(-c3ccccc3)nn2C)[C@H](c2ccc(F)c(F)c2)C1] | 1-(4-bromo-1-methyl-3-phenyl-1H-pyrazol-5-yl)-3-((3S,4R)-4-(3,4-difluorophenyl)-1-(2-methoxyethyl)pyrrolidin-3-yl)urea | MS (apci) m/z = 534.0 (M + H). |
| 69 | Example 69 intentionally omitted | | |

TABLE 6-continued

| Ex. # | Structure | Name | Data |
|---|---|---|---|
| 70 | 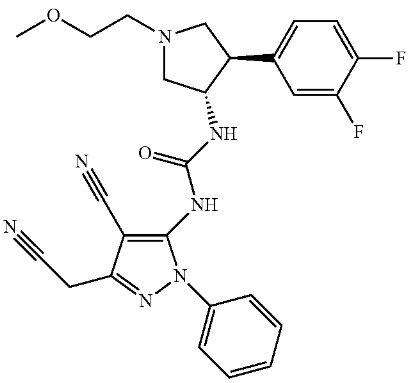 [SMILES: COCCN1C[C@@H](NC(=O)Nc2c(C#N)c(CC#N)nn2-c2ccccc2)[C@H](c2ccc(F)c(F)c2)C1] | 1-(4-cyano-3-(cyanomethyl)-1-phenyl-1H-pyrazol-5-yl)-3-((3S,4R)-4-(3,4-difluorophenyl)-1-(2-methoxyethyl)pyrrolidin-3-yl)urea | MS (apci) m/z = 506.0 (M + H). |
| 71 | 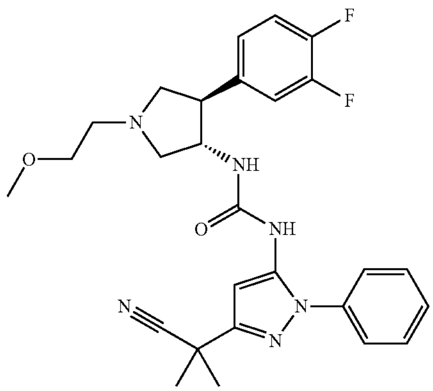 [SMILES: COCCN1C[C@@H](NC(=O)Nc2cc(C(C)(C)C#N)nn2-c2ccccc2)[C@H](c2ccc(F)c(F)c2)C1] | 1-(3-(2-cyanopropan-2-yl)-1-phenyl-1H-pyrazol-5-yl)-3-((3S,4R)-4-(3,4-difluorophenyl)-1-(2-methoxyethyl)pyrrolidin-3-yl)urea | MS (apci) m/z = 509.1 (M + H). |
| 72 | 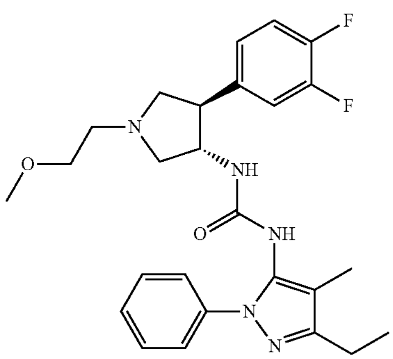 [SMILES: CCc1nn(-c2ccccc2)c(NC(=O)N[C@@H]2CN(CCOC)C[C@H]2c2ccc(F)c(F)c2)c1C] | 1-((3S,4R)-4-(3,4-difluorophenyl)-1-(2-methoxyethyl)pyrrolidin-3-yl)-3-(3-ethyl-4-methyl-1-phenyl-1H-pyrazol-5-yl)urea | MS (apci) m/z = 484.1 (M + H). |
| 73 | 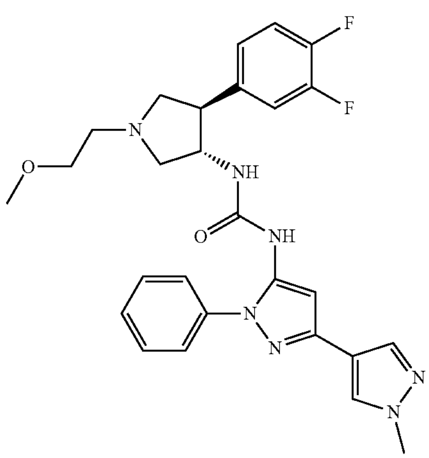 [SMILES: COCCN1C[C@@H](NC(=O)Nc2cc(-c3cnn(C)c3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(1'-methyl-1-phenyl-1H,1'H-3,4'-bipyrazol-5-yl)urea | MS (apci) m/z = 522.1 (M + H). |

TABLE 6-continued

| Ex. # | Structure | Name | Data |
|---|---|---|---|
| 74 | 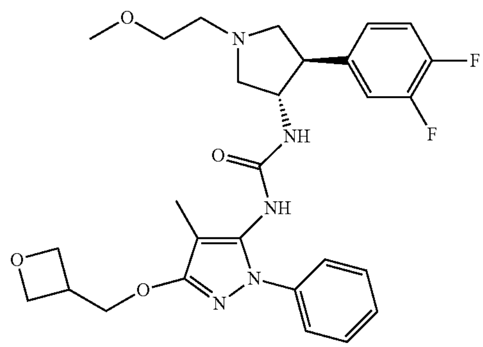 [SMILES: COCCN1C[C@@H](NC(=O)Nc2c(C)c(OCC3COC3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-3-(oxetan-3-ylmethoxy)-1-phenyl-1H-pyrazol-5-yl)urea | MS (apci) m/z = 542.1 (M + H). |
| 75 | 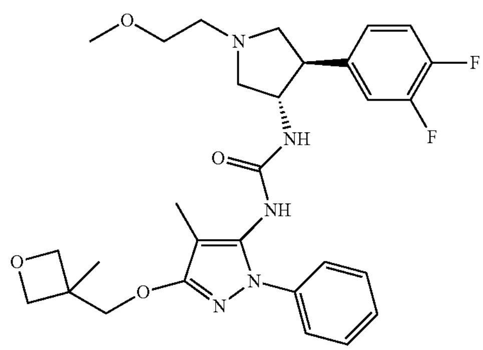 [SMILES: COCCN1C[C@@H](NC(=O)Nc2c(C)c(OCC3(C)COC3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-3-((3-methyloxetan-3-yl)methoxy)-1-phenyl-1H-pyrazol-5-yl)urea | MS (apci) m/z = 556.1 (M + H). |
| 76 | 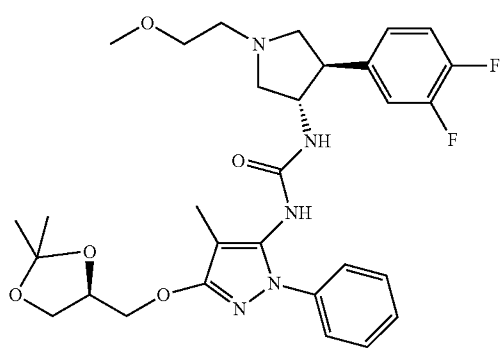 [SMILES: COCCN1C[C@@H](NC(=O)Nc2c(C)c(OC[C@H]3COC(C)(C)O3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(((S)-2,2-dimethyl-1,3-dioxolan-4-yl)methoxy)-4-methyl-1-phenyl-1H-pyrazol-5-yl)urea | MS (apci) m/z = 586.1 (M + H). |
| 77 | 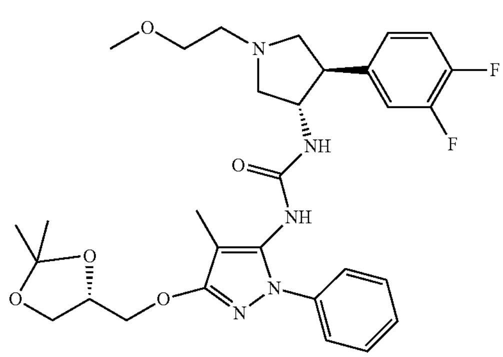 [SMILES: COCCN1C[C@@H](NC(=O)Nc2c(C)c(OC[C@@H]3COC(C)(C)O3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(((R)-2,2-dimethyl-1,3-dioxolan-4-yl)methoxy)-4-methyl-1-phenyl-1H-pyrazol-5-yl)urea | MS (apci) m/z = 586.2 (M + H). |

The compounds of Table 7 were prepared according to the method of Example 1 replacing the compound of Preparation B with the compound of Preparation D, E, F, G, H, J or K and using the appropriate pyrazole intermediate.

TABLE 7

| Ex. # | Structure | Name | Data |
|---|---|---|---|
| 78 | 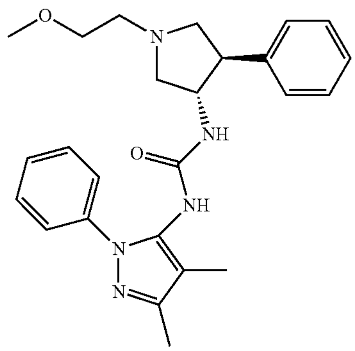 [SMILES: COCCN1C[C@@H](NC(=O)Nc2c(C)c(C)nn2-c2ccccc2)[C@H](c2ccccc2)C1] | 1-(3,4-dimethyl-1-phenyl-1H-pyrazol-5-yl)-3-((3S,4R)-1-(2-methoxyethyl)-4-phenylpyrrolidin-3-yl)urea | MS (apci) m/z = 434.1 (M + H). |
| 79 | 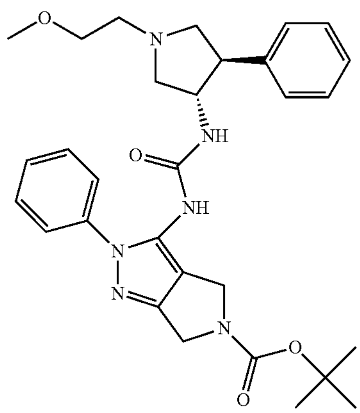 [SMILES: COCCN1C[C@@H](NC(=O)Nc2c3c(nn2-c2ccccc2)CN(C(=O)OC(C)(C)C)C3)[C@H](c2ccccc2)C1] | tert-butyl 3-(3-((3S,4R)-1-(2-methoxyethyl)-4-phenylpyrrolidin-3-yl)ureido)-2-phenyl-4,6-dihydropyrrolo[3,4-c]pyrazole-5(2H)-carboxylate | MS (apci) m/z = 547.1 (M + H). |
| 80 | 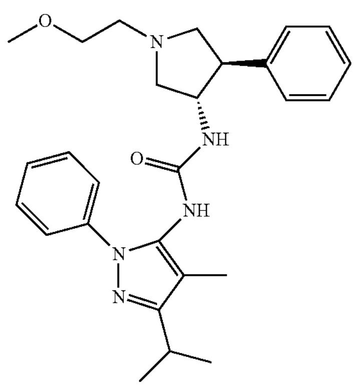 [SMILES: COCCN1C[C@@H](NC(=O)Nc2c(C)c(C(C)C)nn2-c2ccccc2)[C@H](c2ccccc2)C1] | 1-(3-isopropyl-4-methyl-1-phenyl-1H-pyrazol-5-yl)-3-((3S,4R)-1-(2-methoxyethyl)-4-phenylpyrrolidin-3-yl)urea | MS (apci) m/z = 462.3 (M + H). |
| 81 | 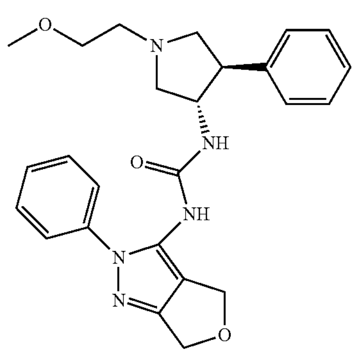 [SMILES: COCCN1C[C@@H](NC(=O)Nc2c3c(nn2-c2ccccc2)COC3)[C@H](c2ccccc2)C1] | 1-((3S,4R)-1-(2-methoxyethyl)-4-phenylpyrrolidin-3-yl)-3-(2-phenyl-4,6-dihydro-2H-furo[3,4-c]pyrazol-3-yl)urea | MS (apci) m/z = 448.2 (M + H). |

TABLE 7-continued
| Ex. # | Structure | Name | Data |
|---|---|---|---|
| 82 | 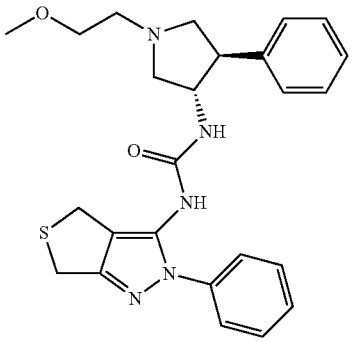 [SMILES: COCCN1C[C@@H](NC(=O)Nc2c3c(nn2-c2ccccc2)CSC3)[C@H](c2ccccc2)C1] | 1-((3S,4R)-1-(2-methoxy-ethyl)-4-phenylpyrrolidin-3-yl)-3-(2-phenyl-4,6-dihydro-2H-thieno[3,4-c]pyrazol-3-yl)urea | MS (apci) m/z = 464.2 (M + H). |
| 83 | 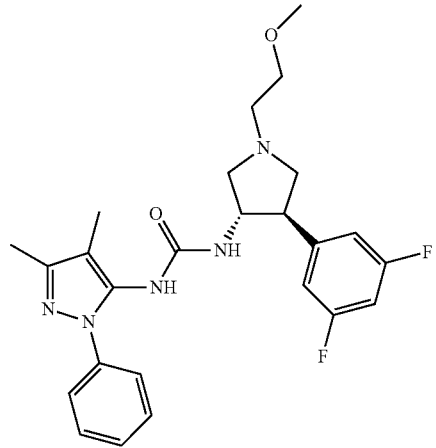 [SMILES: COCCN1C[C@@H](NC(=O)Nc2c(C)c(C)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(3,4-dimethyl-1-phenyl-1H-pyrazol-5-yl)urea | MS (apci) m/z = 470.2 (M + H). |
| 84 | 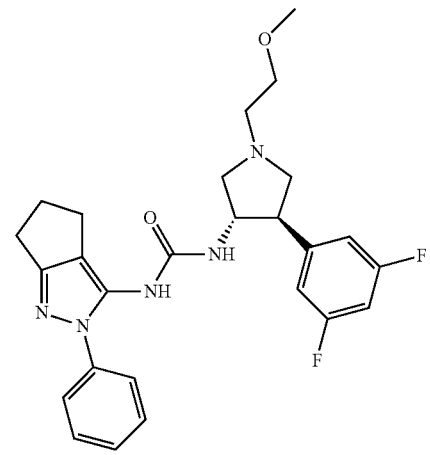 | 1-((3S,4R)-4-(3,5-difluorophenyl)-1-(2-methoxyethyl)pyrrolidin-3-yl)-3-(2-phenyl-2,4,5,6-tetrahydrocyclopenta[c]pyrazol-3-yl)urea | MS (apci) m/z = 482.2 (M + H). |

TABLE 7-continued

| Ex. # | Structure | Name | Data |
|---|---|---|---|
| 85 | 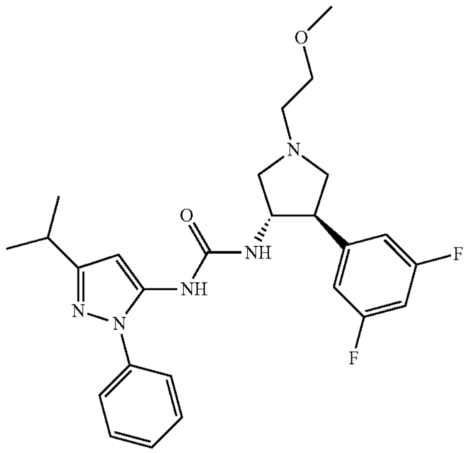 [SMILES: COCCN1C[C@@H](NC(=O)Nc2cc(C(C)C)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(3-isopropyl-1-phenyl-1H-pyrazol-5-yl)urea | MS (apci) m/z = 484.2 (M + H). |
| 86 | 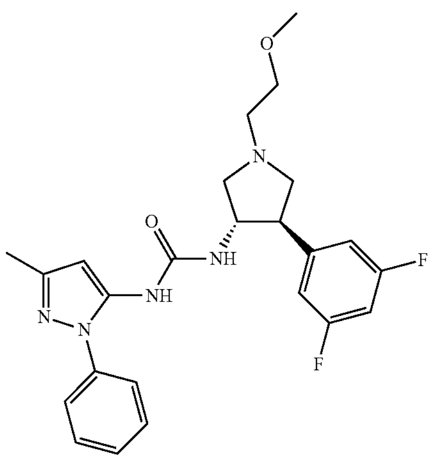 [SMILES: COCCN1C[C@@H](NC(=O)Nc2cc(C)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(3-methyl-1-phenyl-1H-pyrazol-5-yl)urea | MS (apci) m/z = 456.1 (M + H). |
| 87 | 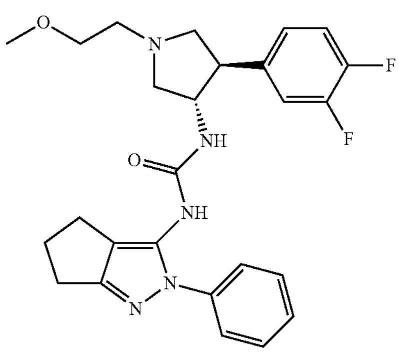 [SMILES: COCCN1C[C@@H](NC(=O)Nc2c3c(nn2-c2ccccc2)CCC3)[C@H](c2ccc(F)c(F)c2)C1] | 1-((3S,4R)-4-(3,4-difluorophenyl)-1-(2-methoxyethyl)pyrrolidin-3-yl)-3-(2-phenyl-2,4,5,6-tetrahydrocyclopenta[c]pyrazol-3-yl)urea | MS (apci) m/z = 482.2 (M + H). |

TABLE 7-continued

| Ex. # | Structure | Name | Data |
|---|---|---|---|
| 88 | 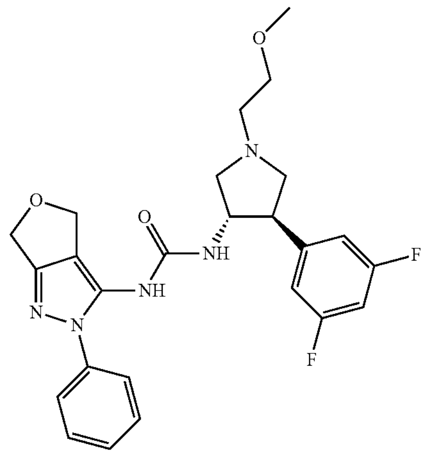 [SMILES: COCCN1C[C@@H](NC(=O)Nc2c3c(nn2-c2ccccc2)COC3)[C@H](c2cc(F)cc(F)c2)C1] | 1-((3S,4R)-4-(3,5-difluorophenyl)-1-(2-methoxyethyl)pyrrolidin-3-yl)-3-(2-phenyl-4,6-dihydro-2H-furo[3,4-c]pyrazol-3-yl)urea | MS (apci) m/z = 484.2 (M + H). |
| 89 | 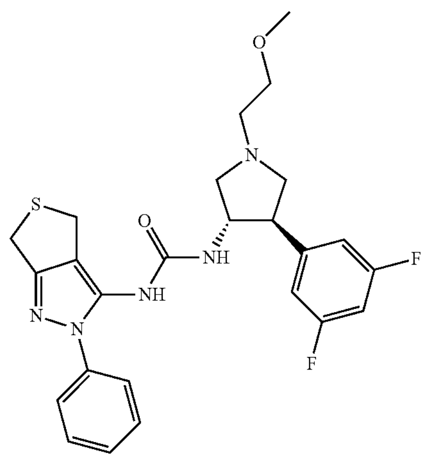 | 1-((3S,4R)-4-(3,5-difluorophenyl)-1-(2-methoxyethyl)pyrrolidin-3-yl)-3-(2-phenyl-4,6-dihydro-2H-thieno[3,4-c]pyrazol-3-yl)urea | MS (apci) m/z = 500.2 (M + H). |
| 90 | 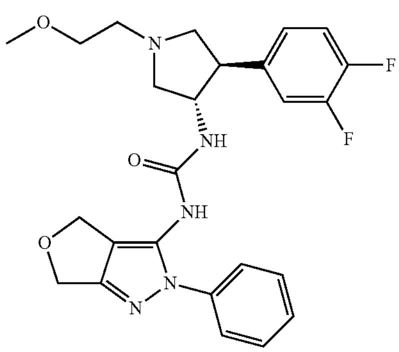 [SMILES: COCCN1C[C@@H](NC(=O)Nc2c3c(nn2-c2ccccc2)COC3)[C@H](c2ccc(F)c(F)c2)C1] | 1-((3S,4R)-4-(3,4-difluorophenyl)-1-(2-methoxyethyl)pyrrolidin-3-yl)-3-(2-phenyl-4,6-dihydro-2H-furo[3,4-c]pyrazol-3-yl)urea | MS (apci) m/z = 484.1 (M + H). |
| 91 | 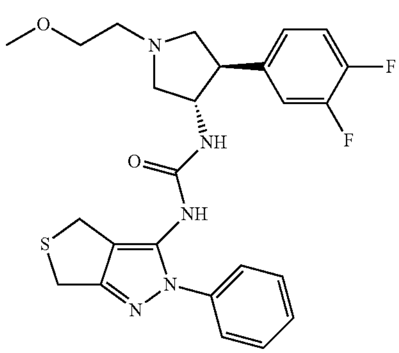 [SMILES: COCCN1C[C@@H](NC(=O)Nc2c3c(nn2-c2ccccc2)CSC3)[C@H](c2ccc(F)c(F)c2)C1] | 1-((3S,4R)-4-(3,4-difluorophenyl)-1-(2-methoxyethyl)pyrrolidin-3-yl)-3-(2-phenyl-4,6-dihydro-2H-thieno[3,4-c]pyrazol-3-yl)urea | MS (apci) m/z = 500.1 (M + H). |

TABLE 7-continued

| Ex. # | Structure | Name | Data |
|---|---|---|---|
| 92 | 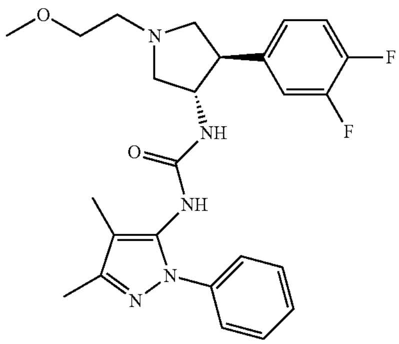 [SMILES: COCCN1C[C@@H](NC(=O)Nc2c(C)c(C)nn2-c2ccccc2)[C@H](c2ccc(F)c(F)c2)C1] | 1-((3S,4R)-4-(3,4-difluoro-phenyl)-1-(2-methoxyethyl)pyrrolidin-3-yl)-3-(3,4-dimethyl-1-phenyl-1H-pyrazol-5-yl)urea | MS (apci) m/z = 470.2 (M + H). |
| 93 | 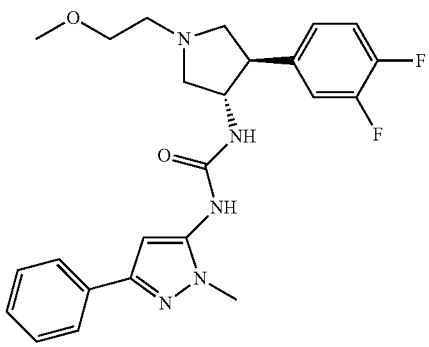 [SMILES: COCCN1C[C@@H](NC(=O)Nc2cc(-c3ccccc3)nn2C)[C@H](c2ccc(F)c(F)c2)C1] | 1-((3S,4R)-4-(3,4-difluoro-phenyl)-1-(2-methoxyethyl)pyrrolidin-3-yl)-3-(1-methyl-3-phenyl-1H-pyrazol-5-yl)urea | MS (apci) m/z = 456.1 (M + H). |
| 94 | 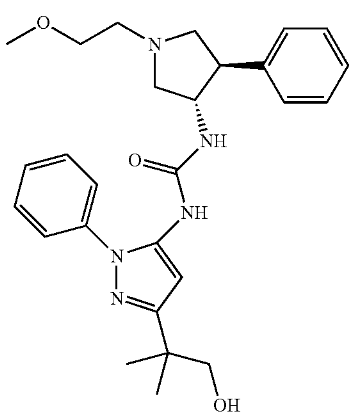 [SMILES: COCCN1C[C@@H](NC(=O)Nc2cc(C(C)(C)CO)nn2-c2ccccc2)[C@H](c2ccccc2)C1] | 1-(3-(1-hydroxy-2-methyl-propan-2-yl)-1-phenyl-1H-pyrazol-5-yl)-3-((3S,4R)-1-(2-methoxyethyl)-4-phenylpyrrolidin-3-yl)urea | MS (apci) m/z = 478.2 (M + H). |
| 95 | 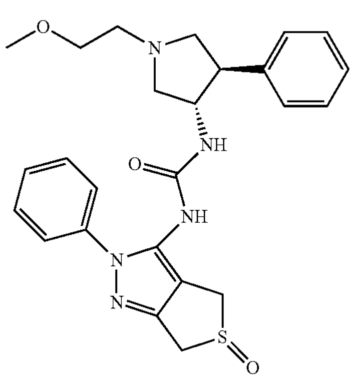 [SMILES: COCCN1C[C@@H](NC(=O)Nc2c3c(nn2-c2ccccc2)CS(=O)C3)[C@H](c2ccccc2)C1] | 1-((3S,4R)-1-(2-methoxy-ethyl)-4-phenylpyrrolidin-3-yl)-3-(5-oxido-2-phenyl-4,6-dihydro-2H-thieno[3,4-c]pyrazol-3-yl)urea | MS (apci) m/z = 480.1 (M + H). |

TABLE 7-continued

| Ex. # | Structure | Name | Data |
|---|---|---|---|
| 96 | 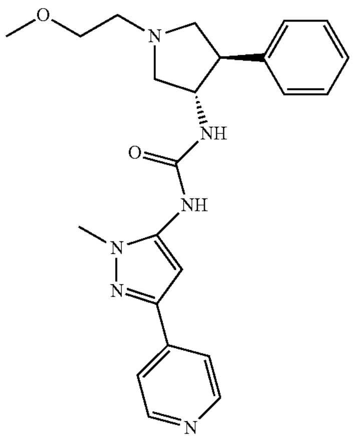 [SMILES: COCCN1C[C@@H](NC(=O)Nc2cc(-c3ccncc3)nn2C)[C@H](c2ccccc2)C1] | 1-((3S,4R)-1-(2-methoxyethyl)-4-phenylpyrrolidin-3-yl)-3-(1-methyl-3-(pyridin-4-yl)-1H-pyrazol-5-yl)urea | MS (apci) m/z = 421.1 (M + H). |
| 97 | 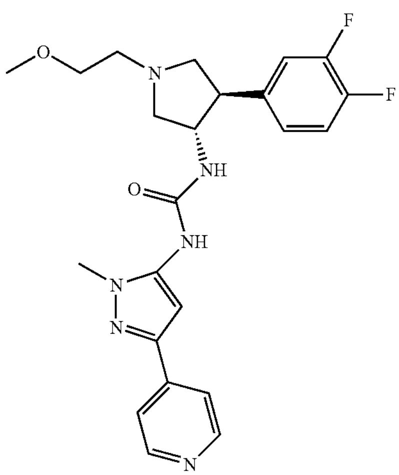 [SMILES: COCCN1C[C@@H](NC(=O)Nc2cc(-c3ccncc3)nn2C)[C@H](c2ccc(F)c(F)c2)C1] | 1-((3S,4R)-4-(3,4-difluorophenyl)-1-(2-methoxyethyl)pyrrolidin-3-yl)-3-(1-methyl-3-(pyridin-4-yl)-1H-pyrazol-5-yl)urea | MS (apci) m/z = 457.1 (M + H). |
| 98 | 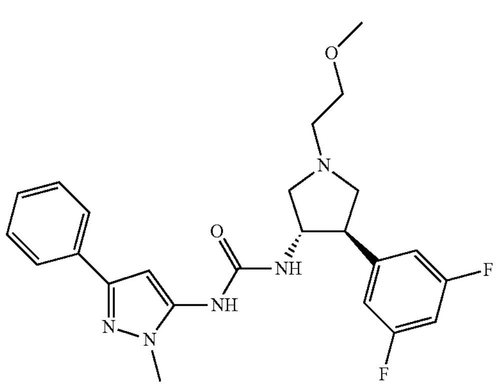 [SMILES: COCCN1C[C@@H](NC(=O)Nc2cc(-c3ccccc3)nn2C)[C@H](c2cc(F)cc(F)c2)C1] | 1-((3S,4R)-4-(3,5-difluorophenyl)-1-(2-methoxyethyl)pyrrolidin-3-yl)-3-(1-methyl-3-phenyl-1H-pyrazol-5-yl)urea | MS (apci) m/z = 456.1 (M + H). |

TABLE 7-continued

| Ex. # | Structure | Name | Data |
|---|---|---|---|
| 99 | 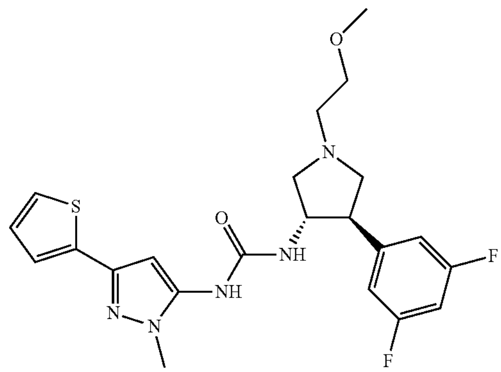 [SMILES: COCCN1C[C@@H](NC(=O)Nc2cc(-c3cccs3)nn2C)[C@H](c2cc(F)cc(F)c2)C1] | 1-((3S,4R)-4-(3,5-difluorophenyl)-1-(2-methoxyethyl)pyrrolidin-3-yl)-3-(1-methyl-3-(thiophen-2-yl)-1H-pyrazol-5-yl)urea | MS (apci) m/z = 462.0 (M + H). |
| 100 | 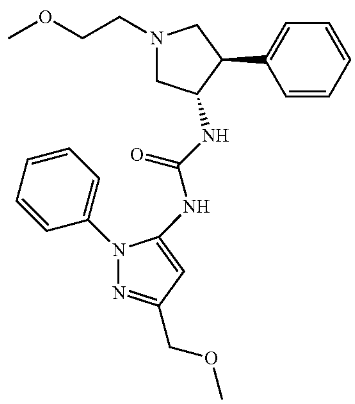 [SMILES: COCCN1C[C@@H](NC(=O)Nc2cc(COC)nn2-c2ccccc2)[C@H](c2ccccc2)C1] | 1-((3S,4R)-1-(2-methoxyethyl)-4-phenylpyrrolidin-3-yl)-3-(3-(methoxymethyl)-1-phenyl-1H-pyrazol-5-yl)urea | MS (apci) m/z = 450.2 (M + H). |
| 101 | 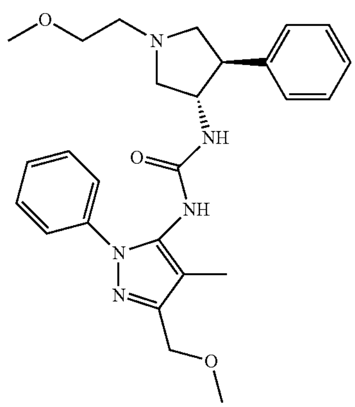 [SMILES: COCCN1C[C@@H](NC(=O)Nc2c(C)c(COC)nn2-c2ccccc2)[C@H](c2ccccc2)C1] | 1-((3S,4R)-1-(2-methoxyethyl)-4-phenylpyrrolidin-3-yl)-3-(3-(methoxymethyl)-4-methyl-1-phenyl-1H-pyrazol-5-yl)urea | MS (apci) m/z = 464.2 (M + H). |
| 102 | 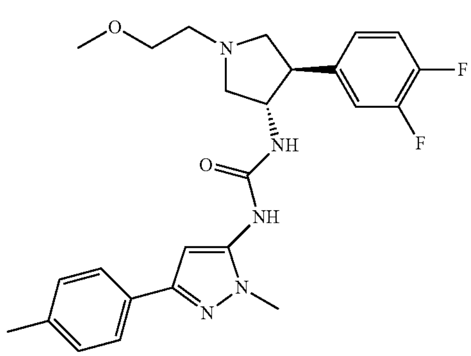 [SMILES: COCCN1C[C@@H](NC(=O)Nc2cc(-c3ccc(C)cc3)nn2C)[C@H](c2ccc(F)c(F)c2)C1] | 1-((3S,4R)-4-(3,4-difluorophenyl)-1-(2-methoxyethyl)pyrrolidin-3-yl)-3-(1-methyl-3-p-tolyl-1H-pyrazol-5-yl)urea | MS (apci) m/z = 470.1 (M + H). |

TABLE 7-continued

| Ex. # | Structure | Name | Data |
|---|---|---|---|
| 103 | 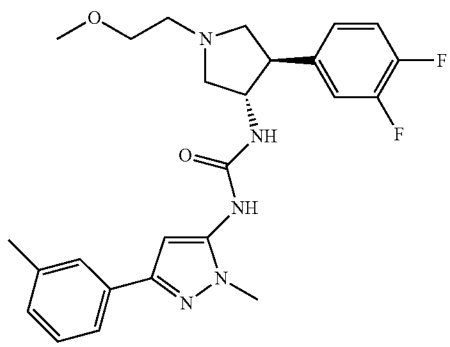 [SMILES: COCCN1C[C@@H](NC(=O)Nc2cc(-c3cccc(C)c3)nn2C)[C@H](c2ccc(F)c(F)c2)C1] | 1-((3S,4R)-4-(3,4-difluorophenyl)-1-(2-methoxyethyl)pyrrolidin-3-yl)-3-(1-methyl-3-m-tolyl-1H-pyrazol-5-yl)urea | MS (apci) m/z = 470.2 (M + H). |
| 104 | 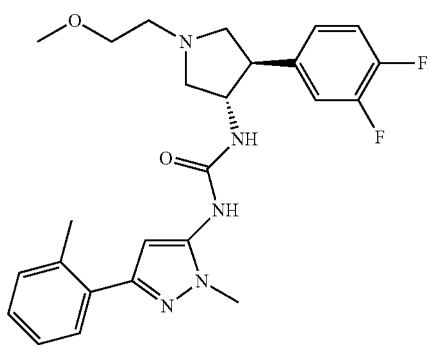 [SMILES: COCCN1C[C@@H](NC(=O)Nc2cc(-c3ccccc3C)nn2C)[C@H](c2ccc(F)c(F)c2)C1] | 1-((3S,4R)-4-(3,4-difluorophenyl)-1-(2-methoxyethyl)pyrrolidin-3-yl)-3-(1-methyl-3-o-tolyl-1H-pyrazol-5-yl)urea | MS (apci) m/z = 470.4 (M + H). |
| 105 | 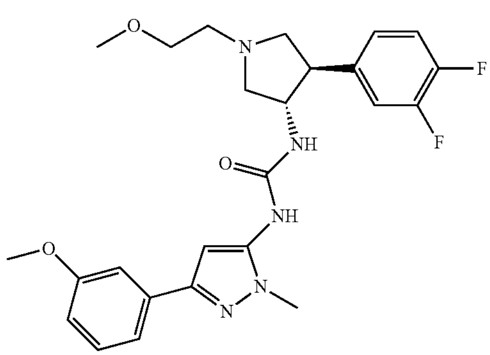 [SMILES: COCCN1C[C@@H](NC(=O)Nc2cc(-c3cccc(OC)c3)nn2C)[C@H](c2ccc(F)c(F)c2)C1] | 1-((3S,4R)-4-(3,4-difluorophenyl)-1-(2-methoxyethyl)pyrrolidin-3-yl)-3-(3-(3-methoxyphenyl)-1-methyl-1H-pyrazol-5-yl)urea | MS (apci) m/z = 486.1 (M + H). |
| 106 | 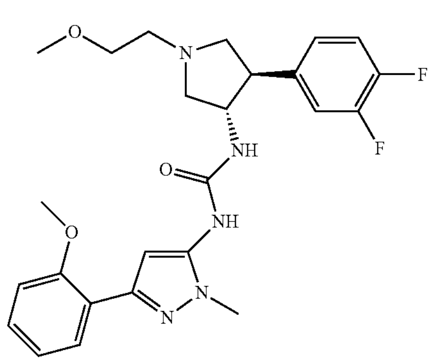 [SMILES: COCCN1C[C@@H](NC(=O)Nc2cc(-c3ccccc3OC)nn2C)[C@H](c2ccc(F)c(F)c2)C1] | 1-((3S,4R)-4-(3,4-difluorophenyl)-1-(2-methoxyethyl)pyrrolidin-3-yl)-3-(3-(2-methoxyphenyl)-1-methyl-1H-pyrazol-5-yl)urea | MS (apci) m/z = 486.2 (M + H). |

TABLE 7-continued

| Ex. # | Structure | Name | Data |
|---|---|---|---|
| 107 | 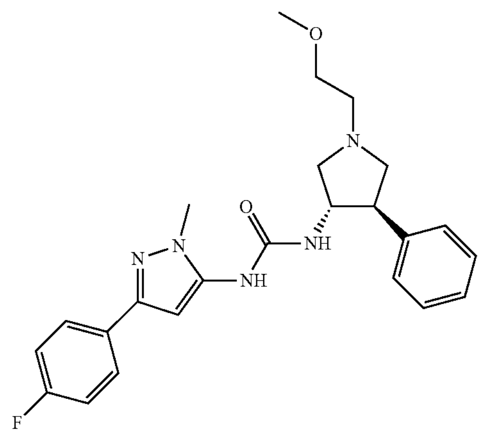 [SMILES: COCCN1C[C@@H](NC(=O)Nc2cc(-c3ccc(F)cc3)nn2C)[C@H](c2ccccc2)C1] | 1-(3-(4-fluorophenyl)-1-methyl-1H-pyrazol-5-yl)-3-((3S,4R)-1-(2-methoxyethyl)-4-phenylpyrrolidin-3-yl)urea | MS (apci) m/z = 438.2 (M + H). |
| 108 | 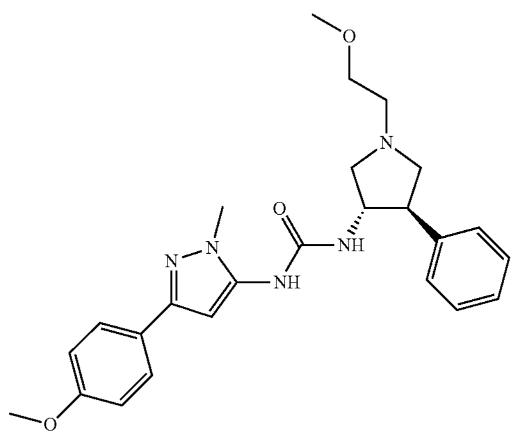 [SMILES: COCCN1C[C@@H](NC(=O)Nc2cc(-c3ccc(OC)cc3)nn2C)[C@H](c2ccccc2)C1] | 1-((3S,4R)-1-(2-methoxyethyl)-4-phenylpyrrolidin-3-yl)-3-(3-(4-methoxyphenyl)-1-methyl-1H-pyrazol-5-yl)urea | MS (apci) m/z = 450.2 (M + H). |
| 109 | 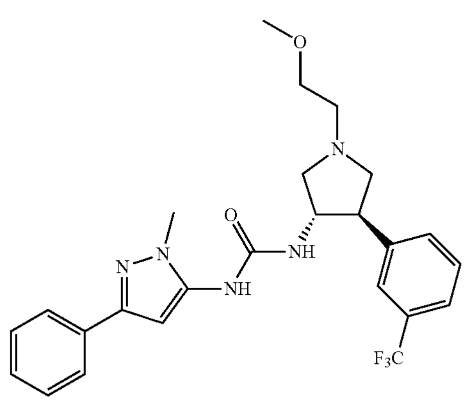 [SMILES: COCCN1C[C@@H](NC(=O)Nc2cc(-c3ccccc3)nn2C)[C@H](c2cccc(C(F)(F)F)c2)C1] | 1-((3S,4R)-1-(2-methoxyethyl)-4-(3-(trifluoromethyl)phenyl)pyrrolidin-3-yl)-3-(1-methyl-3-phenyl-1H-pyrazol-5-yl)urea | MS (apci) m/z = 488.0 (M + H). |

TABLE 7-continued

| Ex. # | Structure | Name | Data |
|---|---|---|---|
| 110 | 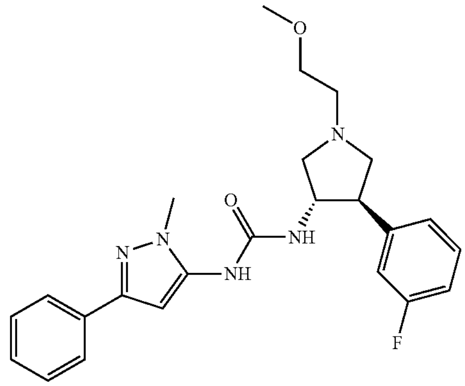 [SMILES: COCCN1C[C@@H](NC(=O)Nc2cc(-c3ccccc3)nn2C)[C@H](c2cccc(F)c2)C1] | 1-((3S,4R)-4-(3-fluoro-phenyl)-1-(2-methoxy-ethyl)pyrrolidin-3-yl)-3-(1-methyl-3-phenyl-1H-pyrazol-5-yl)urea | MS (apci) m/z = 438.2 (M + H). |
| 111 | 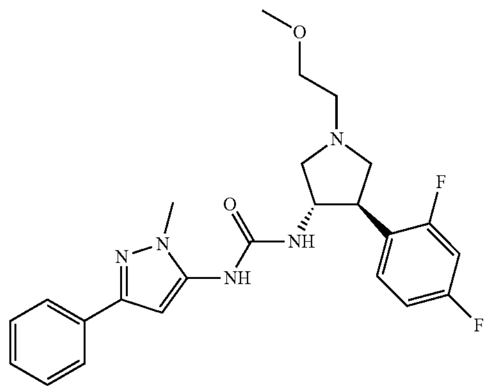 [SMILES: COCCN1C[C@@H](NC(=O)Nc2cc(-c3ccccc3)nn2C)[C@H](c2ccc(F)cc2F)C1] | 1-((3S,4R)-4-(2,4-difluorophenyl)-1-(2-methoxyethyl)pyrrolidin-3-yl)-3-(1-methyl-3-phenyl-1H-pyrazol-5-yl)urea | MS (apci) m/z = 455.9 (M + H). |
| 112 | 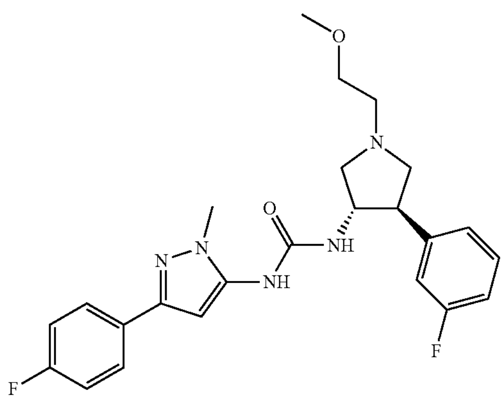 [SMILES: COCCN1C[C@@H](NC(=O)Nc2cc(-c3ccc(F)cc3)nn2C)[C@H](c2cccc(F)c2)C1] | 1-((3S,4R)-4-(3-fluoro-phenyl)-1-(2-methoxy-ethyl)pyrrolidin-3-yl)-3-(3-(4-fluorophenyl)-1-methyl-1H-pyrazol-5-yl)urea | MS (apci) m/z = 456.1 (M + H). |
| 113 | 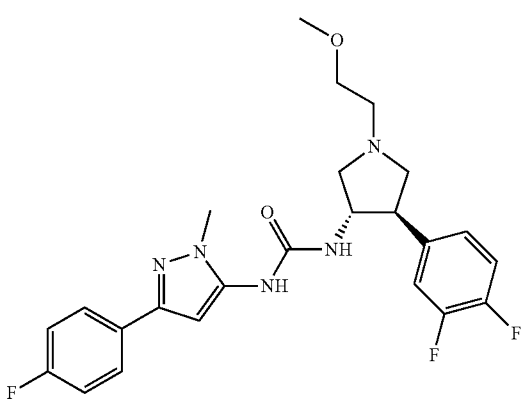 [SMILES: COCCN1C[C@@H](NC(=O)Nc2cc(-c3ccc(F)cc3)nn2C)[C@H](c2ccc(F)c(F)c2)C1] | 1-((3S,4R)-4-(3,4-difluorophenyl)-1-(2-methoxyethyl)pyrrolidin-3-yl)-3-(3-(4-fluoro-phenyl)-1-methyl-1H-pyrazol-5-yl)urea | MS (apci) m/z = 474.1 (M + H). |

TABLE 7-continued

| Ex. # | Structure | Name | Data |
|---|---|---|---|
| 114 | 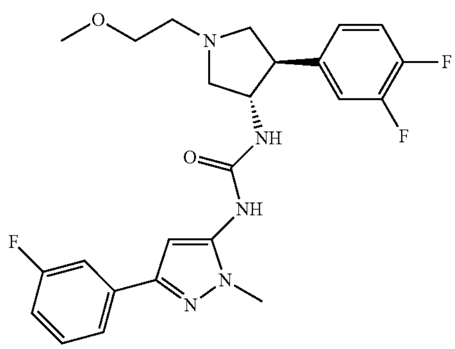 [SMILES: COCCN1C[C@@H](NC(=O)Nc2cc(-c3cccc(F)c3)nn2C)[C@H](c2ccc(F)c(F)c2)C1] | 1-((3S,4R)-4-(3,4-difluorophenyl)-1-(2-methoxyethyl)pyrrolidin-3-yl)-3-(3-(3-fluorophenyl)-1-methyl-1H-pyrazol-5-yl)urea | MS (apci) m/z = 474.1 (M + H). |
| 115 | 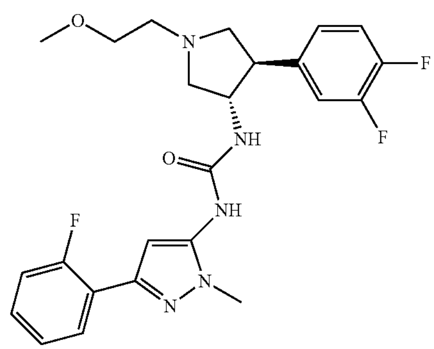 [SMILES: COCCN1C[C@@H](NC(=O)Nc2cc(-c3ccccc3F)nn2C)[C@H](c2ccc(F)c(F)c2)C1] | 1-((3S,4R)-4-(3,4-difluorophenyl)-1-(2-methoxyethyl)pyrrolidin-3-yl)-3-(3-(2-fluorophenyl)-1-methyl-1H-pyrazol-5-yl)urea | MS (apci) m/z = 474.1 (M + H). |
| 116 | 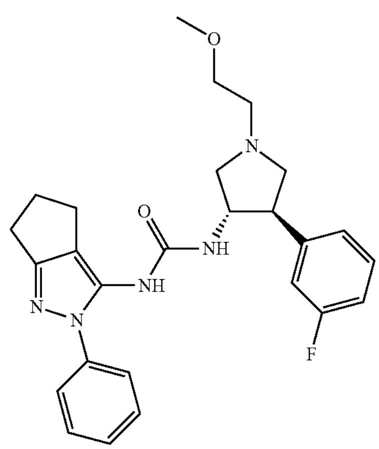 [SMILES: COCCN1C[C@@H](NC(=O)Nc2c3c(nn2-c2ccccc2)CCC3)[C@H](c2cccc(F)c2)C1] | 1-((3S,4R)-4-(3-fluorophenyl)-1-(2-methoxyethyl)pyrrolidin-3-yl)-3-(2-phenyl-2,4,5,6-tetrahydrocyclopenta[c]pyrazol-3-yl)urea | MS (apci) m/z = 464.2 (M + H). |
| 117 | 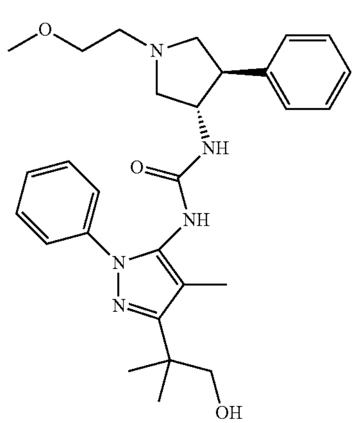 [SMILES: COCCN1C[C@@H](NC(=O)Nc2c(C)c(C(C)(C)CO)nn2-c2ccccc2)[C@H](c2ccccc2)C1] | 1-(3-(1-hydroxy-2-methylpropan-2-yl)-4-methyl-1-phenyl-1H-pyrazol-5-yl)-3-((3S,4R)-1-(2-methoxyethyl)-4-phenylpyrrolidin-3-yl)urea | MS (apci) m/z = 492.3 (M + H). |

TABLE 7-continued

| Ex. # | Structure | Name | Data |
|---|---|---|---|
| 118 | 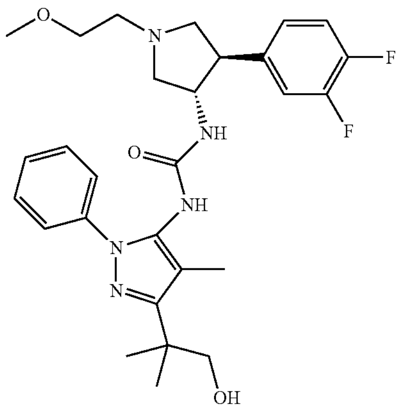 [SMILES: COCCN1C[C@@H](NC(=O)Nc2c(C)c(C(C)(C)CO)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(1-hydroxy-2-methylpropan-2-yl)-4-methyl-1-phenyl-1H-pyrazol-5-yl)urea | MS (apci) m/z = 528.2 (M + H). |
| 119 | 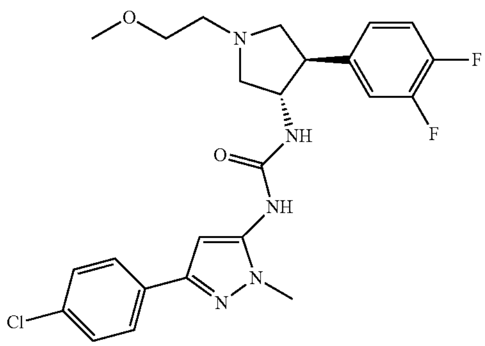 [SMILES: COCCN1C[C@@H](NC(=O)Nc2cc(-c3ccc(Cl)cc3)nn2C)[C@H](c2ccc(F)c(F)c2)C1] | 1-(3-(4-chlorophenyl)-1-methyl-1H-pyrazol-5-yl)-3-((3S,4R)-4-(3,4-difluorophenyl)-1-(2-methoxyethyl)pyrrolidin-3-yl)urea | MS (apci) m/z = 490.0 (M + H). |
| 120 | 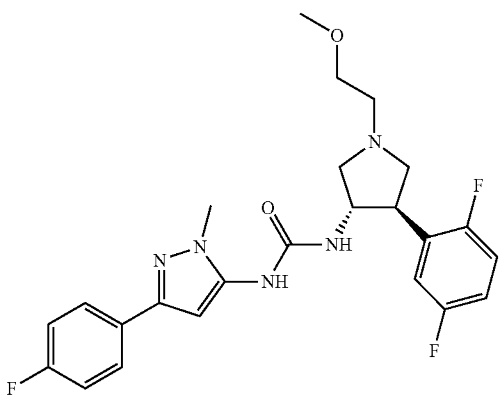 [SMILES: COCCN1C[C@@H](NC(=O)Nc2cc(-c3ccc(F)cc3)nn2C)[C@H](c2cc(F)ccc2F)C1] | 1-((3S,4R)-4-(2,5-difluorophenyl)-1-(2-methoxyethyl)pyrrolidin-3-yl)-3-(3-(4-fluorophenyl)-1-methyl-1H-pyrazol-5-yl)urea | MS (apci) m/z = 474.1 (M + H). |
| 121 | 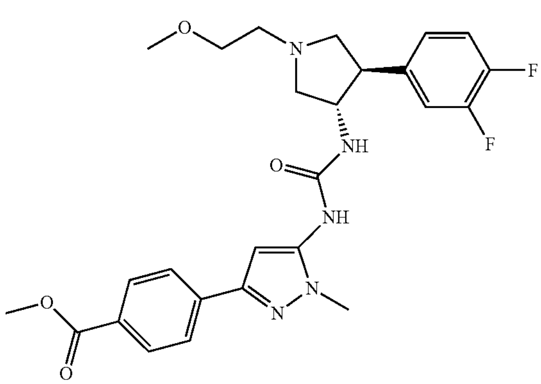 [SMILES: COCCN1C[C@@H](NC(=O)Nc2cc(-c3ccc(C(=O)OC)cc3)nn2C)[C@H](c2ccc(F)c(F)c2)C1] | methyl 4-(5-(3-((3S,4R)-4-(3,4-difluorophenyl)-1-(2-methoxyethyl)pyrrolidin-3-yl)ureido)-1-methyl-1H-pyrazol-3-yl)benzoate | MS (apci) m/z = 514.1 (M + H). |

| Ex. # | Structure | Name | Data |
|---|---|---|---|
| 122 | 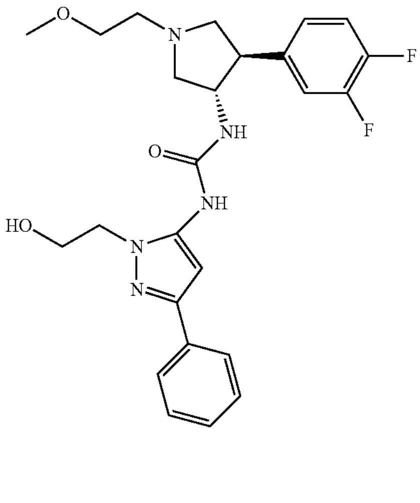 [SMILES: COCCN1C[C@@H](NC(=O)Nc2cc(-c3ccccc3)nn2CCO)[C@H](c2ccc(F)c(F)c2)C1] | 1-((3S,4R)-4-(3,4-difluorophenyl)-1-(2-methoxyethyl)pyrrolidin-3-yl)-3-(1-(2-hydroxyethyl)-3-phenyl-1H-pyrazol-5-yl)urea | MS (apci) m/z = 486.1 (M + H). |
| 123 | 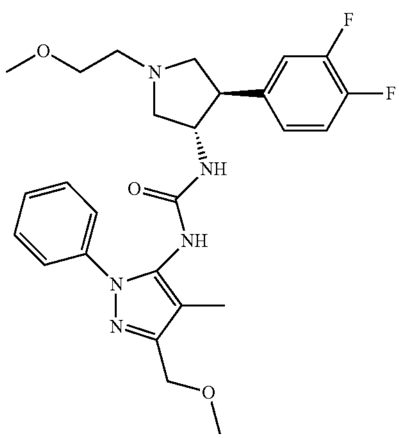 [SMILES: COCCN1C[C@@H](NC(=O)Nc2c(C)c(COC)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(methoxymethyl)-4-methyl-1-phenyl-1H-pyrazol-5-yl)urea | MS (apci) m/z = 500.1 (M + H). |
| 124 | 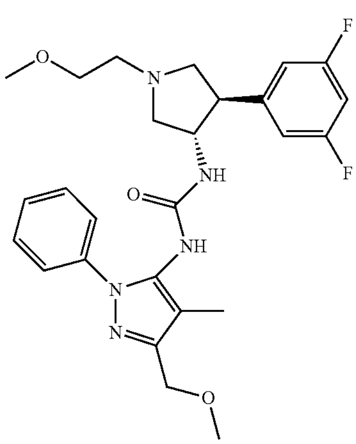 [SMILES: COCCN1C[C@@H](NC(=O)Nc2c(C)c(COC)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(3-(methoxymethyl)-4-methyl-1-phenyl-1H-pyrazol-5-yl)urea | MS (apci) m/z = 500.1 (M + H). |

TABLE 7-continued

| Ex. # | Structure | Name | Data |
|---|---|---|---|
| 125 | 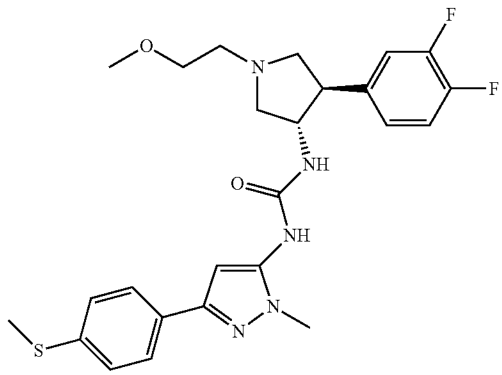 [SMILES: COCCN1C[C@@H](NC(=O)Nc2cc(-c3ccc(SC)cc3)nn2C)[C@H](c2ccc(F)c(F)c2)C1] | 1-((3S,4R)-4-(3,4-difluorophenyl)-1-(2-methoxyethyl)pyrrolidin-3-yl)-3-(1-methyl-3-(4-(methylthio)phenyl)-1H-pyrazol-5-yl)urea | MS (apci) m/z = 502.0 (M + H). |
| 126 | 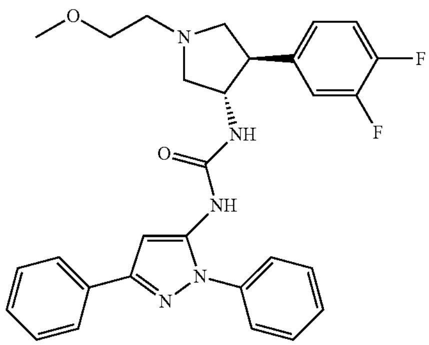 [SMILES: COCCN1C[C@@H](NC(=O)Nc2cc(-c3ccccc3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(1,3-diphenyl-1H-pyrazol-5-yl)urea | MS (apci) m/z = 518.1 (M + H). |
| 127 | 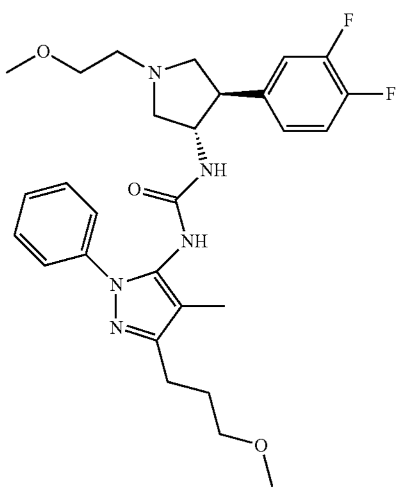 [SMILES: COCCCc1nn(-c2ccccc2)c(NC(=O)N[C@@H]2CN(CCOC)C[C@H]2c2ccc(F)c(F)c2)c1C] | 1-((3S,4R)-4-(3,4-difluorophenyl)-1-(2-methoxyethyl)pyrrolidin-3-yl)-3-(3-(3-methoxypropyl)-4-methyl-1-phenyl-1H-pyrazol-5-yl)urea | MS (apci) m/z = 528.1 (M + H). |
| 128 | 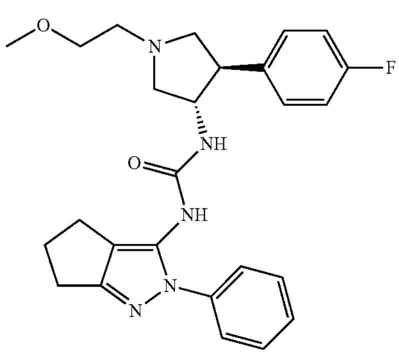 [SMILES: COCCN1C[C@@H](NC(=O)Nc2c3c(nn2-c2ccccc2)CCC3)[C@H](c2ccc(F)cc2)C1] | 1-((3S,4R)-4-(4-fluorophenyl)-1-(2-methoxyethyl)pyrrolidin-3-yl)-3-(2-phenyl-2,4,5,6-tetrahydrocyclopenta[c]pyrazol-3-yl)urea | MS (apci) m/z = 464.1 (M + H). |

TABLE 7-continued

| Ex. # | Structure | Name | Data |
|---|---|---|---|
| 129 | 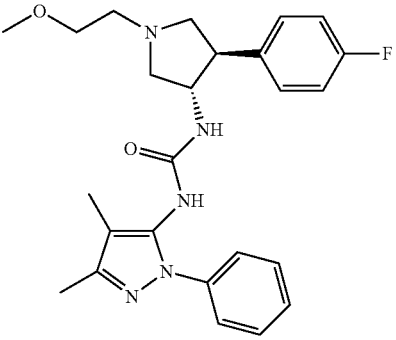 [SMILES: COCCN1C[C@@H](NC(=O)Nc2c(C)c(C)nn2-c2ccccc2)[C@H](c2ccc(F)cc2)C1] | 1-(3,4-dimethyl-1-phenyl-1H-pyrazol-5-yl)-3-((3S,4R)-4-(4-fluorophenyl)-1-(2-methoxyethyl)pyrrolidin-3-yl)urea | MS (apci) m/z = 452.1 (M + H). |
| 130 | 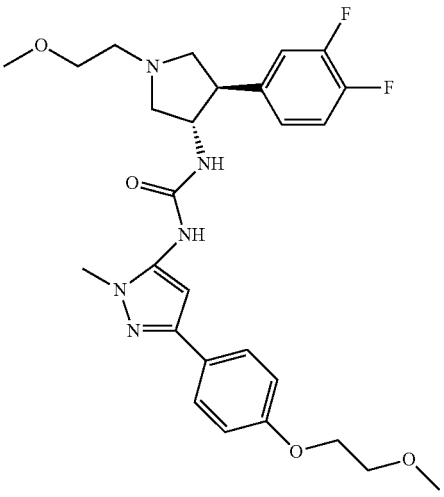 | 1-((3S,4R)-4-(3,4-difluorophenyl)-1-(2-methoxyethyl)pyrrolidin-3-yl)-3-(3-(4-(2-methoxyethoxy)phenyl)-1-methyl-1H-pyrazol-5-yl)urea | MS (apci) m/z = 530.1 (M + H). |
| 131 | 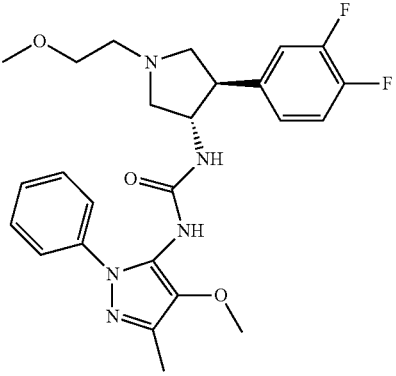 [SMILES: COCCN1C[C@@H](NC(=O)Nc2c(OC)c(C)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methoxy-3-methyl-1-phenyl-1H-pyrazol-5-yl)urea | MS (apci) m/z = 486.0 (M + H). |
| 132 | 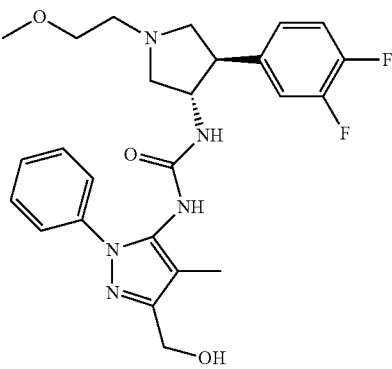 [SMILES: COCCN1C[C@@H](NC(=O)Nc2c(C)c(CO)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(hydroxymethyl)-4-methyl-1-phenyl-1H-pyrazol-5-yl)urea | MS (apci) m/z = 486.1 (M + H). |

TABLE 7-continued

| Ex. # | Structure | Name | Data |
|---|---|---|---|
| 133 | 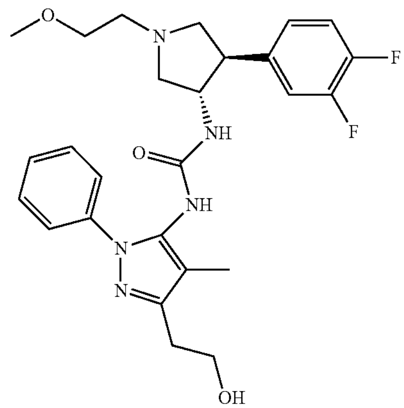 [SMILES: COCCN1C[C@@H](NC(=O)Nc2c(C)c(CCO)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(2-hydroxyethyl)-4-methyl-1-phenyl-1H-pyrazol-5-yl)urea | MS (apci) m/z = 500.1 (M + H). |
| 134 | 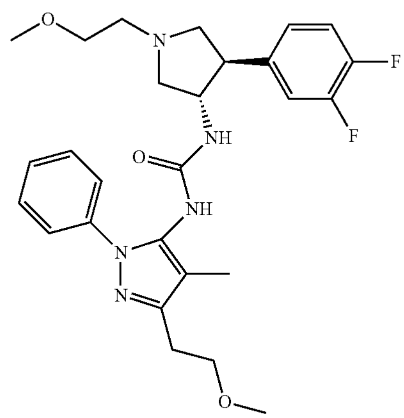 [SMILES: COCCc1nn(-c2ccccc2)c(NC(=O)N[C@@H]2CN(CCOC)C[C@H]2c2ccc(F)c(F)c2)c1C] | 1-((3S,4R)-4-(3,4-difluorophenyl)-1-(2-methoxyethyl)pyrrolidin-3-yl)-3-(3-(2-methoxyethyl)-4-methyl-1-phenyl-1H-pyrazol-5-yl)urea | MS (apci) m/z = 514.1 (M + H). |
| 135 | 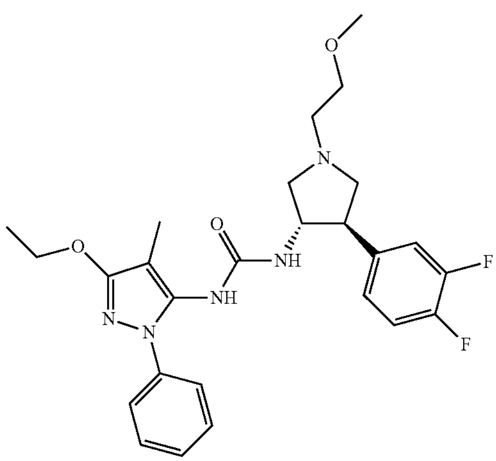 [SMILES: CCOc1nn(-c2ccccc2)c(NC(=O)N[C@@H]2CN(CCOC)C[C@H]2c2ccc(F)c(F)c2)c1C] | 1-((3S,4R)-4-(3,4-difluorophenyl)-1-(2-methoxyethyl)pyrrolidin-3-yl)-3-(3-ethoxy-4-methyl-1-phenyl-1H-pyrazol-5-yl)urea | MS (apci) m/z = 500.1 (M + H). |
| 136 | 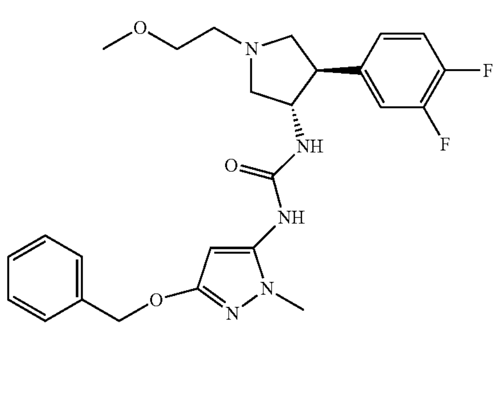 [SMILES: COCCN1C[C@@H](NC(=O)Nc2cc(OCc3ccccc3)nn2C)[C@H](c2ccc(F)c(F)c2)C1] | 1-(3-(benzyloxy)-1-methyl-1H-pyrazol-5-yl)-3-((3S,4R)-4-(3,4-difluorophenyl)-1-(2-methoxyethyl)pyrrolidin-3-yl)urea | MS (apci) m/z = 486.1 (M + H). |

TABLE 7-continued

| Ex. # | Structure | Name | Data |
|---|---|---|---|
| 137 | 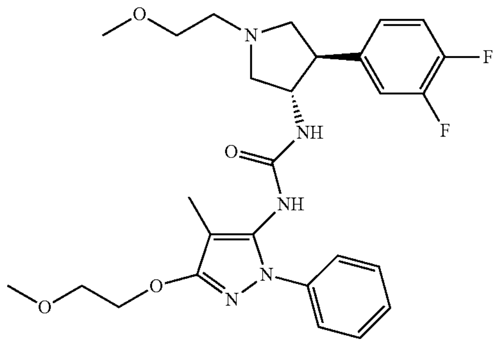 [SMILES: COCCOc1nn(-c2ccccc2)c(NC(=O)N[C@@H]2CN(CCOC)C[C@H]2c2ccc(F)c(F)c2)c1C] | 1-((3S,4R)-4-(3,4-difluorophenyl)-1-(2-methoxyethyl)pyrrolidin-3-yl)-3-(3-(2-methoxy-ethoxy)-4-methyl-1-phenyl-1H-pyrazol-5-yl)urea | MS (apci) m/z = 530.1 (M + H). |
| 138 | 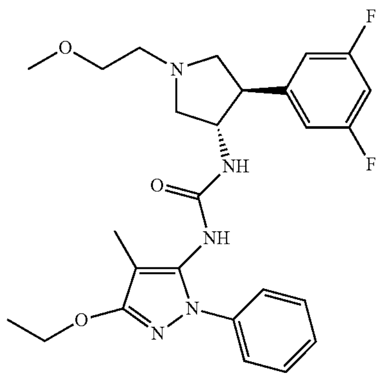 [SMILES: CCOc1nn(-c2ccccc2)c(NC(=O)N[C@@H]2CN(CCOC)C[C@H]2c2cc(F)cc(F)c2)c1C] | 1-((3S,4R)-4-(3,5-difluorophenyl)-1-(2-methoxyethyl)pyrrolidin-3-yl)-3-(3-ethoxy-4-methyl-1-phenyl-1H-pyrazol-5-yl)urea | MS (apci) m/z = 500.1 (M + H). |
| 139 | 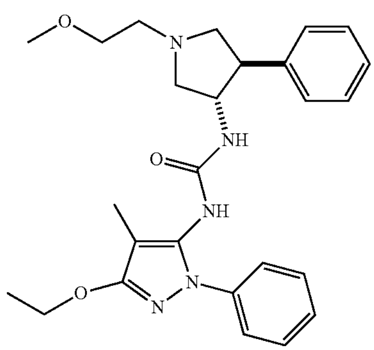 [SMILES: CCOc1nn(-c2ccccc2)c(NC(=O)N[C@@H]2CN(CCOC)C[C@H]2c2ccccc2)c1C] | trans-1-(3-ethoxy-4-methyl-1-phenyl-1H-pyrazol-5-yl)-3-1-(2-methoxyethyl)-4-phenylpyrrolidin-3-yl)urea | MS (apci) m/z = 464.1 (M + H). |
| 140 | 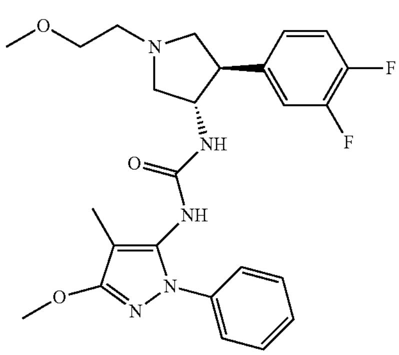 [SMILES: COCCN1C[C@@H](NC(=O)Nc2c(C)c(OC)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-methoxy-4-methyl-1-phenyl-1H-pyrazol-5-yl)urea | MS (apci) m/z = 486.1 (M + H). |

TABLE 7-continued

| Ex. # | Structure | Name | Data |
|---|---|---|---|
| 141 | 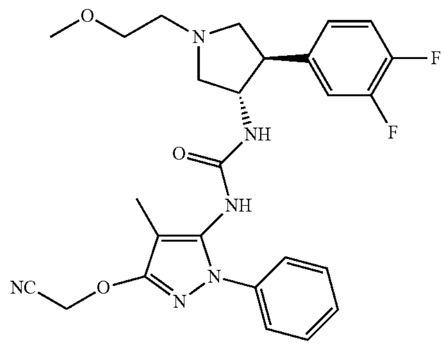 [SMILES: COCCN1C[C@@H](NC(=O)Nc2c(C)c(OCC#N)nn2-c2ccccc2)[C@H](c2ccc(F)c(F)c2)C1] | 1-(3-(cyanomethoxy)-4-methyl-1-phenyl-1H-pyrazol-5-yl)-3-((3S,4R)-4-(3,4-difluorophenyl)-1-(2-methoxyethyl)pyrrolidin-3-yl)urea | MS (apci) m/z = 511.1 (M + H). |

The compounds of Table 8 were prepared according to the method of Example 1 replacing the compound of Preparation B with the compound of Preparation F or K and using the appropriate pyrazole intermediate.

TABLE 8

| Ex. # | Structure | Name | Data |
|---|---|---|---|
| 142 | 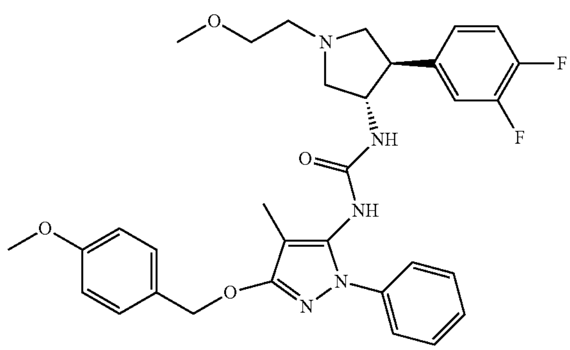 [SMILES: COCCN1C[C@@H](NC(=O)Nc2c(C)c(OCc3ccc(OC)cc3)nn2-c2ccccc2)[C@H](c2ccc(F)c(F)c2)C1] | 1-((3S,4R)-4-(3,4-difluoro-phenyl)-1-(2-methoxyethyl)pyrrolidin-3-yl)-3-(3-(4-methoxybenzyloxy)-4-methyl-1-phenyl-1H-pyrazol-5-yl)urea | MS (apci) m/z = 592.1 (M + H). |
| 143 | 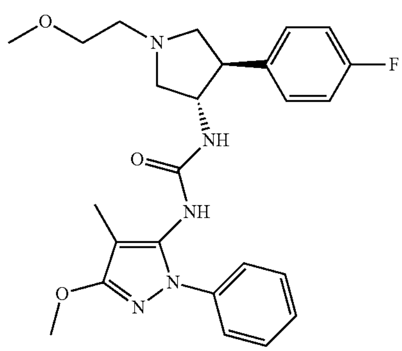 [SMILES: COCCN1C[C@@H](NC(=O)Nc2c(C)c(OC)nn2-c2ccccc2)[C@H](c2ccc(F)cc2)C1] | 1-((3S,4R)-4-(4-fluorophenyl)-1-(2-methoxyethyl)pyrrolidin-3-yl)-3-(3-methoxy-4-methyl-1-phenyl-1H-pyrazol-5-yl)urea | MS (apci) m/z = 468.1 (M + H). |
| 144 | 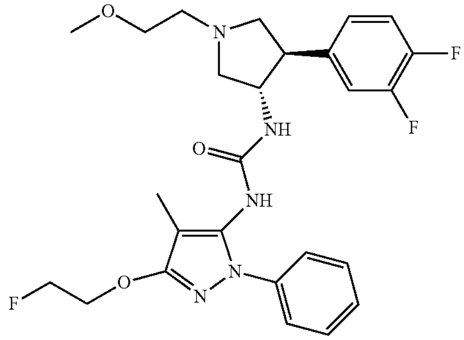 [SMILES: COCCN1C[C@@H](NC(=O)Nc2c(C)c(OCCF)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(2-fluoro-ethoxy)-4-methyl-1-phenyl-1H-pyrazol-5-yl)urea | MS (apci) m/z = 518.1 (M + H). |

TABLE 8-continued

| Ex. # | Structure | Name | Data |
|---|---|---|---|
| 145 | 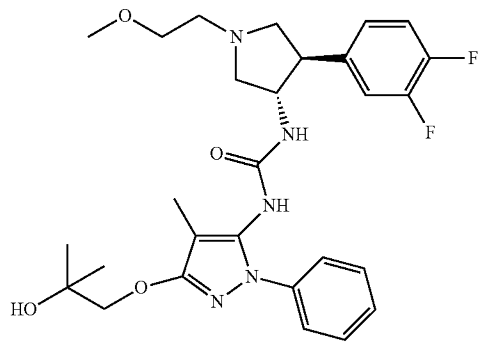 [SMILES: COCCN1C[C@@H](NC(=O)Nc2c(C)c(OCC(C)(C)O)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(2-hydroxy-2-methylpropoxy)-4-methyl-1-phenyl-1H-pyrazol-5-yl)urea | MS (apci) m/z = 544.3 (M + H). |

The compounds of Table 9 were prepared according to the method of Example 1 replacing the compound of Preparation B with the compound of Preparation E, F, H or K and using the appropriate pyrazole intermediate

TABLE 9

| Ex. # | Structure | Name | Data |
|---|---|---|---|
| 146 | 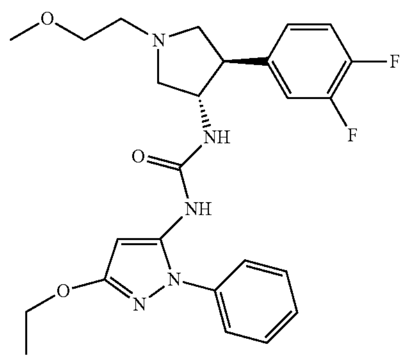 [SMILES: CCOc1cc(NC(=O)N[C@@H]2CN(CCOC)C[C@H]2c2ccc(F)c(F)c2)n(-c2ccccc2)n1] | 1-((3S,4R)-4-(3,4-difluorophenyl)-1-(2-methoxyethyl)pyrrolidin-3-yl)-3-(3-ethoxy-1-phenyl-1H-pyrazol-5-yl)urea | MS (apci) m/z = 486.2 (M + H). |
| 147 | 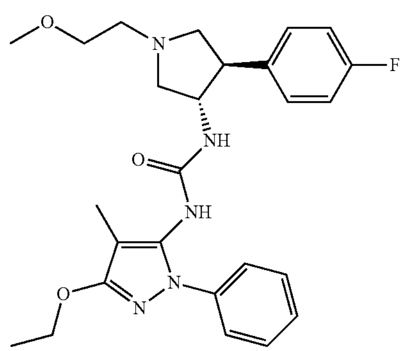 [SMILES: CCOc1nn(-c2ccccc2)c(NC(=O)N[C@@H]2CN(CCOC)C[C@H]2c2ccc(F)cc2)c1C] | 1-(3-ethoxy-4-methyl-1-phenyl-1H-pyrazol-5-yl)-3-((3S,4R)-4-(4-fluorophenyl)-1-(2-methoxyethyl)pyrrolidin-3-yl)urea | MS (apci) m/z = 482.3 (M + H) |
| 148 | 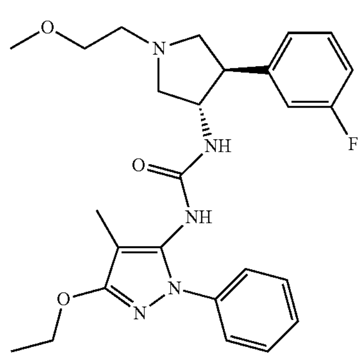 [SMILES: CCOc1nn(-c2ccccc2)c(NC(=O)N[C@@H]2CN(CCOC)C[C@H]2c2cccc(F)c2)c1C] | 1-(3-ethoxy-4-methyl-1-phenyl-1H-pyrazol-5-yl)-3-((3S,4R)-4-(3-fluorophenyl)-1-(2-methoxyethyl)pyrrolidin-3-yl)urea | MS (apci) m/z = 482.3 (M + H) |

TABLE 9-continued

| Ex. # | Structure | Name | Data |
|---|---|---|---|
| 149 | 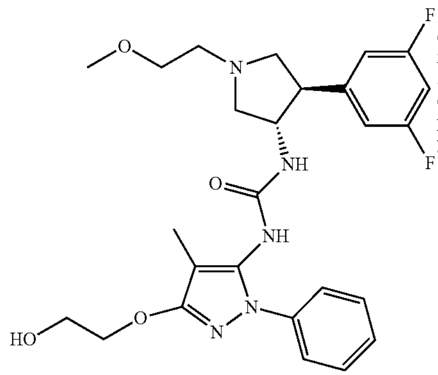 [SMILES: COCCN1C[C@@H](NC(=O)Nc2c(C)c(OCCO)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(3-(2-hydroxyethoxy)-4-methyl-1-phenyl-1H-pyrazol-5-yl)urea | MS (apci) m/z = 516.3 (M + H) |
| 150 | 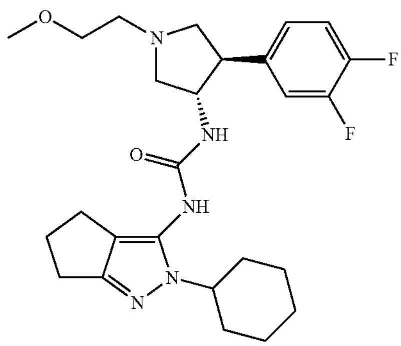 [SMILES: COCCN1C[C@@H](NC(=O)Nc2c3c(nn2C2CCCCC2)CCC3)[C@H](c2ccc(F)c(F)c2)C1] | 1-(2-cyclohexyl-2,4,5,6-tetrahydrocyclopenta[c]pyrazol-3-yl)-3-((3S,4R)-4-(3,4-difluorophenyl)-1-(2-methoxyethyl)pyrrolidin-3-yl)urea | MS (apci) m/z = 488.3 (M + H) |

Example 151

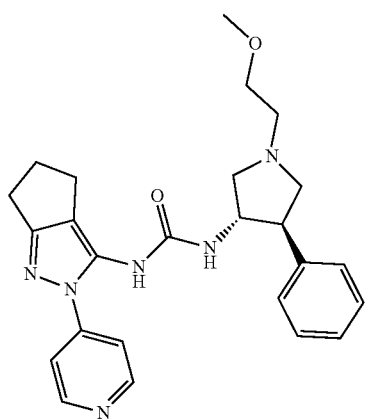 [SMILES: COCCN1C[C@@H](NC(=O)Nc2c3c(nn2-c2ccncc2)CCC3)[C@H](c2ccccc2)C1]

1-((3S,4R)-1-(2-methoxyethyl)-4-phenylpyrrolidin-3-yl)-3-(2-(pyridin-4-yl)-2,4,5,6-tetrahydrocyclopenta[c]pyrazol-3-yl)urea Step A: Preparation of 2-(pyridin-4-yl)-2,4,5,6-tetrahydrocyclopenta[c]pyrazol-3-amine: A solution of 2-oxocyclopentanecarbonitrile (0.4 g, 3.7 mmol, purchased from AAT Pharmaceutical) and 4-hydrazinylpyridine hydrochloride (0.53 g, 3.7 mmol) in methanol (35 mL) was sealed in a pressure vessel and heated at 80° C. overnight. After removal of solvent in vacuo, the residue was triturated with 1 N NaOH (20 mL) and extracted with DCM (3×25 mL). The combined organics was washed with brine, dried with MgSO₄, filtered and concentrated to yield the crude product as brownish solid, which was directly used in the next step. MS (apci) m/z=201.2 (M+H).

Step B: Preparation of 1-((3S,4R)-1-(2-methoxyethyl)-4-phenylpyrrolidin-3-yl)-3-(2-(pyridin-4-yl)-2,4,5,6-tetrahydrocyclopenta[c]pyrazol-3-yl)urea: To a mixture of 2-(pyridin-4-yl)-2,4,5,6-tetrahydrocyclopenta[c]pyrazol-3-amine (43 mg, 0.21 mmol) in DCM (2 mL) at 0° C. was added DIEA (0.075 mL, 0.43 mmol) followed by triphosgene (25 mg, 0.086 mmol) in one portion. The reaction was warmed up to ambient temperature and stirred for 2 hours. An aliquot (0.5 mL) of the reaction mixture (containing 3-isocyanato-2-(pyridin-4-yl)-2,4,5,6-tetrahydrocyclopenta[c]pyrazole (12.1 mg, 0.0535 mmol)) was removed and treated with (3S,4R)-1-(2-methoxyethyl)-4-phenylpyrrolidin-3-amine bis(2,2,2-trifluoroacetate) (Preparation D, 20 mg, 0.0446 mmol) and N-ethyl-N-isopropylpropan-2-amine (38.8 μL, 0.223 mmol) sequentially. After stirring for 30 minutes, the reaction mixture was directly purified by reverse-phase chromatography, eluting with 5-50% acetonitrile/water to yield the title final product as off-white solid (5 mg, 25% yield). MS (apci pos) m/z=447.2 (M+H).

The compounds of Table 10 were prepared according to the method of Example 151 replacing the pyrazole input with the appropriate analog and replacing the compound of Preparation D with the compound of Preparation F.

TABLE 10

| Ex. # | Structure | Name | Data |
|---|---|---|---|
| 152 | 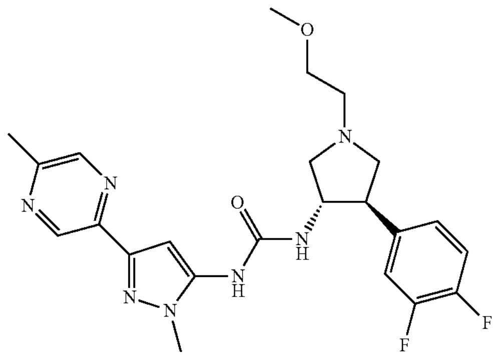 [SMILES: COCCN1C[C@@H](NC(=O)Nc2cc(-c3cnc(C)cn3)nn2C)[C@H](c2ccc(F)c(F)c2)C1] | 1-((3S,4R)-4-(3,4-difluorophenyl)-1-(2-methoxyethyl)pyrrolidin-3-yl)-3-(1-methyl-3-(5-methylpyrazin-2-yl)-1H-pyrazol-5-yl)urea | MS (apci) m/z = 472.0 (M + H). |
| 153 | 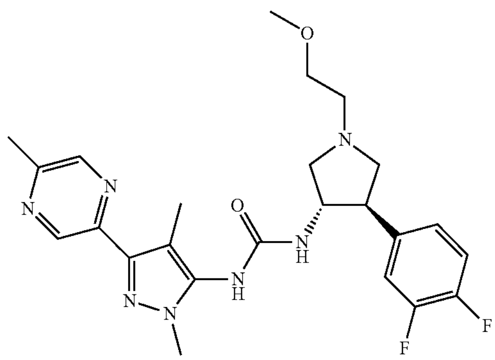 [SMILES: COCCN1C[C@@H](NC(=O)Nc2c(C)c(-c3cnc(C)cn3)nn2C)[C@H](c2ccc(F)c(F)c2)C1] | 1-((3S,4R)-4-(3,4-difluorophenyl)-1-(2-methoxyethyl)pyrrolidin-3-yl)-3-(1,4-dimethyl-3-(5-methylpyrazin-2-yl)-1H-pyrazol-5-yl)urea | MS (apci) m/z = 486.1 (M + H). |
| 154 | 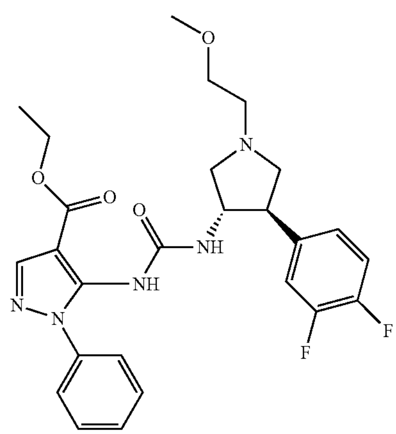 [SMILES: CCOC(=O)c1cnn(-c2ccccc2)c1NC(=O)N[C@@H]1CN(CCOC)C[C@H]1c1ccc(F)c(F)c1] | ethyl 5-(3-((3S,4R)-4-(3,4-difluorophenyl)-1-(2-methoxyethyl)pyrrolidin-3-yl)ureido)-1-phenyl-1H-pyrazole-4-carboxylate | MS (apci) m/z = 514.1 (M + H). |
| 155 | 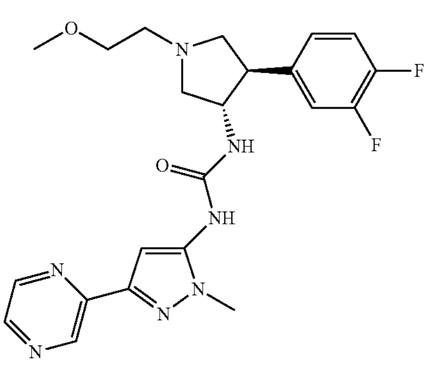 [SMILES: COCCN1C[C@@H](NC(=O)Nc2cc(-c3cnccn3)nn2C)[C@H](c2ccc(F)c(F)c2)C1] | 1-((3S,4R)-4-(3,4-difluorophenyl)-1-(2-methoxyethyl)pyrrolidin-3-yl)-3-(1-methyl-3-(pyrazin-2-yl)-1H-pyrazol-5-yl)urea | MS (apci) m/z = 458.1 (M + H). |

TABLE 10-continued

| Ex. # | Structure | Name | Data |
|---|---|---|---|
| 156 | 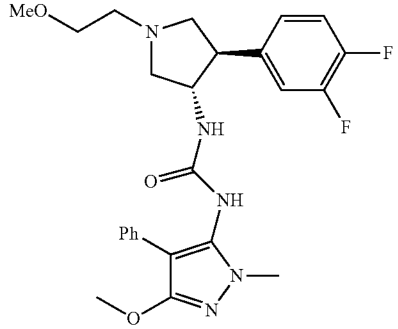 [SMILES: COCCN1C[C@@H](NC(=O)Nc2c(-c3ccccc3)c(OC)nn2C)[C@H](c2ccc(F)c(F)c2)C1] | 1-((3S,4R)-4-(3,4-difluorophenyl)-1-(2-methoxyethyl)pyrrolidin-3-yl)-3-(3-methoxy-1-methyl-4-phenyl-1H-pyrazol-5-yl)urea | MS (apci) m/z = 486.1 (M + H). |
| 157 | 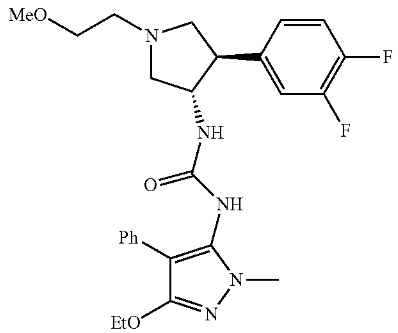 [SMILES: CCOc1nn(C)c(NC(=O)N[C@@H]2CN(CCOC)C[C@H]2c2ccc(F)c(F)c2)c1-c1ccccc1] | 1-((3S,4R)-4-(3,4-difluorophenyl)-1-(2-methoxyethyl)pyrrolidin-3-yl)-3-(3-ethoxy-1-methyl-4-phenyl-1H-pyrazol-5-yl)urea | MS (apci) m/z = 500.1 (M + H). |

Example 158

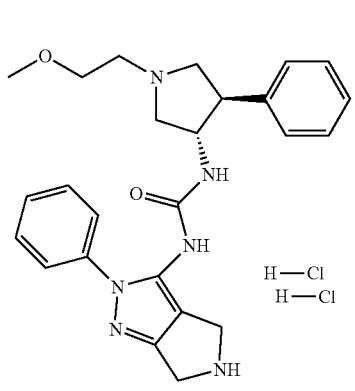

1-((3S,4R)-1-(2-methoxyethyl)-4-phenylpyrrolidin-3-yl)-3-(2-phenyl-2,4,5,6-tetrahydropyrrolo[3,4-c]pyrazol-3-yl)urea dihydrochloride tert-Butyl 3-(3-((3S,4R)-1-(2-methoxyethyl)-4-phenylpyrrolidin-3-yl)ureido)-2-phenyl-4,6-dihydropyrrolo[3,4-c]pyrazole-5(2H)-carboxylate (Example 79) was treated with 4N HCl in dioxane (2.0 mL, 0.017 mmol) and stirred at ambient temperature for 30 minutes. The resulting beige suspension was filtered and the solids rinsed with Et$_2$O to afford the product as a tan solid (6.4 mg, 74% yield). MS (apci) m/z=447.1 (M+H).

Example 159

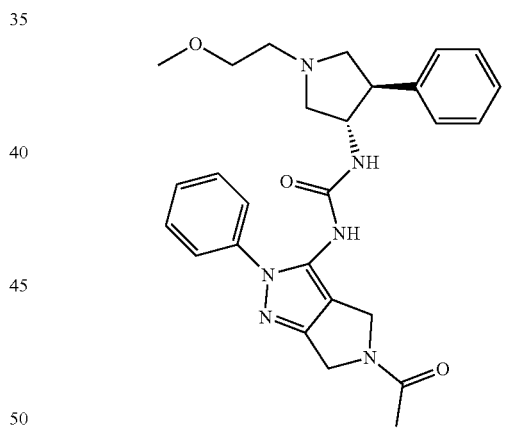

1-(5-acetyl-2-phenyl-2,4,5,6-tetrahydropyrrolo[3,4-c]pyrazol-3-yl)-3-((3S,4R)-1-(2-methoxyethyl)-4-phenylpyrrolidin-3-yl)urea To a solution of 1-((3S,4R)-1-(2-methoxyethyl)-4-phenylpyrrolidin-3-yl)-3-(2-phenyl-2,4,5,6-tetrahydropyrrolo[3,4-c]pyrazol-3-yl)urea dihydrochloride (Example 158, 2.0 mg, 0.0039 mmol) and DIEA (0.0067 mL, 0.039 mmol) in acetonitrile (1.0 mL, 19 mmol) was added acetic acid (0.0011 mL, 0.019 mmol) followed by HATU (2.9 mg, 0.0077 mmol). After stirring for 1 hour at ambient temperature, the reaction mixture was purified directly by silica column chromatography, eluting with 0-10% MeOH/DCM to afford the product (0.7 mg, 37% yield). MS (apci) m/z=489.2 (M+H).

Example 160

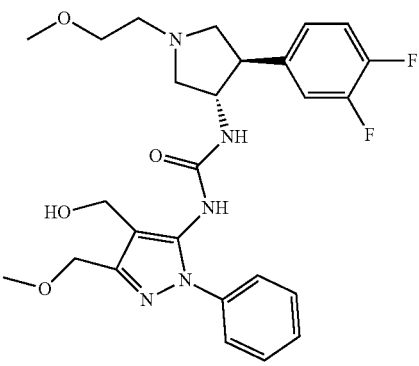 [SMILES: COCCN1C[C@@H](NC(=O)Nc2c(CO)c(COC)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-(hydroxymethyl)-3-(methoxymethyl)-1-phenyl-1H-pyrazol-5-yl)urea A solution of 1-((3S,4R)-4-(3,4-difluorophenyl)-1-(2-methoxyethyl)pyrrolidin-3-yl)-3-(2-phenyl-4,6-dihydro-2H-furo[3,4-c]pyrazol-3-yl)urea (Example 90, 250 mg, 0.517 mmol) in DCM (20 mL) was treated with 4N HCl/dioxane (5 mL). After concentrating to dryness, the residue was converted to the free base by partitioning with 1N NaOH and DCM, then purified by silica column chromatography, eluting with 2-4% MeOH/DCM to afford the product (29 mg, 11% yield). MS (apci) m/z=516.2 (M+H).

Example 161

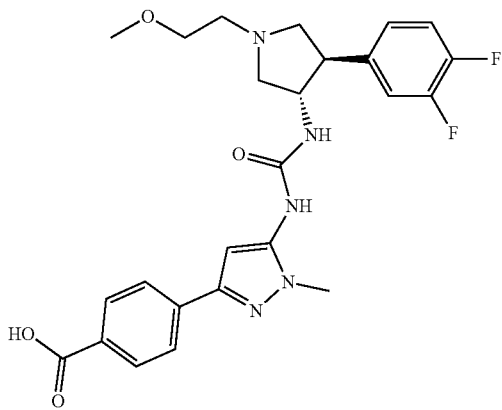 [SMILES: COCCN1C[C@@H](NC(=O)Nc2cc(-c3ccc(C(=O)O)cc3)nn2C)[C@H](c2ccc(F)c(F)c2)C1]

4-(5-(3-((3S,4R)-4-(3,4-difluorophenyl)-1-(2-methoxyethyl)pyrrolidin-3-yl)ureido)-1-methyl-1H-pyrazol-3-yl)benzoic acid To a solution of methyl 4-(5-(3-((3S,4R)-4-(3,4-difluorophenyl)-1-(2-methoxyethyl)pyrrolidin-3-yl)ureido)-1-methyl-1H-pyrazol-3-yl)benzoate (Example 121, 79 mg, 0.15 mmol) in THF (4.0 mL, 0.15 mmol) and MeOH (2.0 mL, 49 mmol) at 0° C. was added LiOH (2M aqueous) (0.15 mL, 0.31 mmol). This reaction was stirred at ambient temperature and additional LiOH was added until complete conversion was observed by HPLC analysis (approximately 2 days). After acidification with 2M HCl (1 mL), the mixture was diluted with water (10 mL), extracted with DCM (20 mL), then extracted with 10% MeOH/DCM (3×10 mL). The combined organic phases were washed with brine (25 mL), dried with MgSO₄, filtered and concentrated to give the product as a white solid (70 mg, 91% yield). MS (apci) m/z=500.1 (M+H).

Example 162

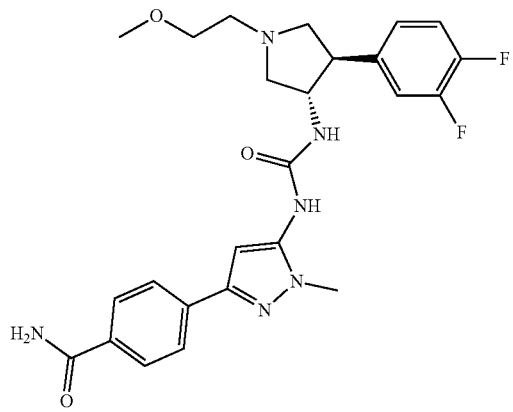 [SMILES: COCCN1C[C@@H](NC(=O)Nc2cc(-c3ccc(C(N)=O)cc3)nn2C)[C@H](c2ccc(F)c(F)c2)C1]

4-(5-(3-((3S,4R)-4-(3,4-difluorophenyl)-1-(2-methoxyethyl)pyrrolidin-3-yl)ureido)-1-methyl-1H-pyrazol-3-yl)benzamide To a solution of 4-(5-(3-((3S,4R)-4-(3,4-difluorophenyl)-1-(2-methoxyethyl)pyrrolidin-3-yl)ureido)-1-methyl-1H-pyrazol-3-yl)benzoic acid (Example 161, 12 mg, 0.024 mmol) in DMF (0.5 mL, 0.024 mmol) was added N-methylmorpholine (0.0079 mL, 0.072 mmol), NH₃ (0.5M in dioxane) (0.096 mL, 0.048 mmol) and HATU (10 mg, 0.026 mmol) sequentially. The reaction mixture was stirred overnight at ambient temperature and purified by reverse-phase column chromatography, eluting with 5-50% acetonitrile/water, to afford the title compound (5.1 mg, 43% yield). MS (apci) m/z=499.1 (M+H).

Example 163

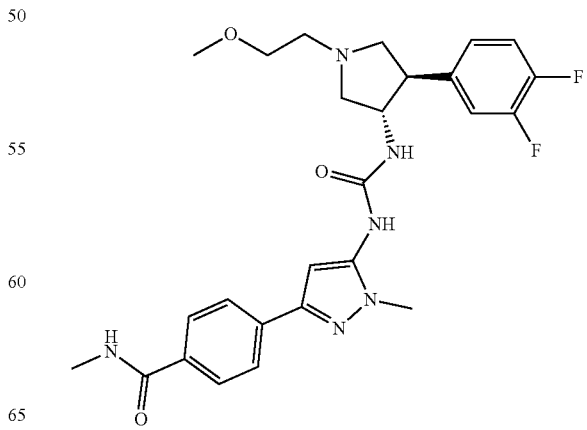

4-(5-(3-((3S,4R)-4-(3,4-difluorophenyl)-1-(2-methoxyethyl)pyrrolidin-3-yl)ureido)-1-methyl-1H-pyrazol-3-yl)-N-methylbenzamide Prepared according to the method described in Example 162, substituting NH₃ with methylamine (2 M in THF). MS (apci) m/z=513.1 (M+H).

Example 164

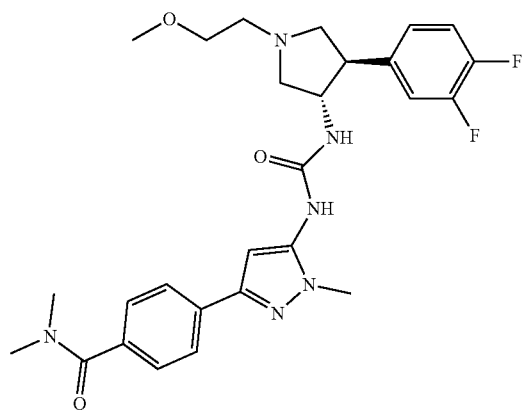 [SMILES: COCCN1C[C@@H](NC(=O)Nc2cc(-c3ccc(C(=O)N(C)C)cc3)nn2C)[C@H](c2ccc(F)c(F)c2)C1]

4-(5-(3-((3S,4R)-4-(3,4-difluorophenyl)-1-(2-methoxyethyl)pyrrolidin-3-yl)ureido)-1-methyl-1H-pyrazol-3-yl)-N,N-dimethylbenzamide Prepared according to the method described in Example 162, substituting NH₃ with dimethylamine (2 M in THF). MS (apci) m/z=5527.1 (M+H).

Example 165

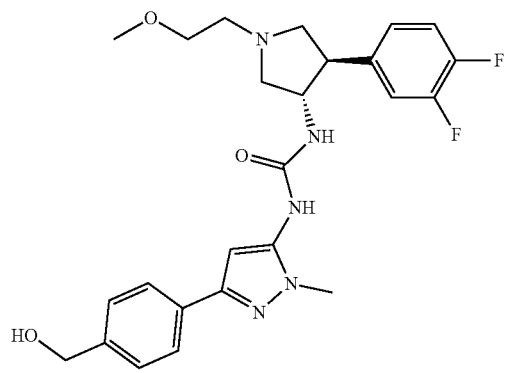 [SMILES: COCCN1C[C@@H](NC(=O)Nc2cc(-c3ccc(CO)cc3)nn2C)[C@H](c2ccc(F)c(F)c2)C1]

1-((3S,4R)-4-(3,4-difluorophenyl)-1-(2-methoxyethyl)pyrrolidin-3-yl)-3-(3-(4-(hydroxymethyl)phenyl)-1-methyl-1H-pyrazol-5-yl)urea To a suspension of methyl 4-(5-(3-((3S,4R)-4-(3,4-difluorophenyl)-1-(2-methoxyethyl)pyrrolidin-3-yl)ureido)-1-methyl-1H-pyrazol-3-yl)benzoate (Example 121; 20 mg, 0.039 mmol) in THF (2 mL, 0.081 mmol) at 0° C. under N₂ was added lithium aluminum hydride (1M bis-THF solution in toluene) (0.078 mL, 0.078 mmol). The reaction mixture was stirred at 0° C. for 1 hour, then quenched by the addition of 3 μL H₂O and 3 μL 1M aqueous NaOH, followed by 9 μL H₂O. The mixture was stirred at ambient temperature for 4 hours, then filtered through a syringe filter, rinsed with THF (2 mL), and concentrated to a white solid. The solid was purified by reverse phase chromatography eluting with 5-50% acetonitrile/water, to afford the title compound (10 mg, 53% yield). MS (apci) m/z=486.1 (M+H).

Example 166

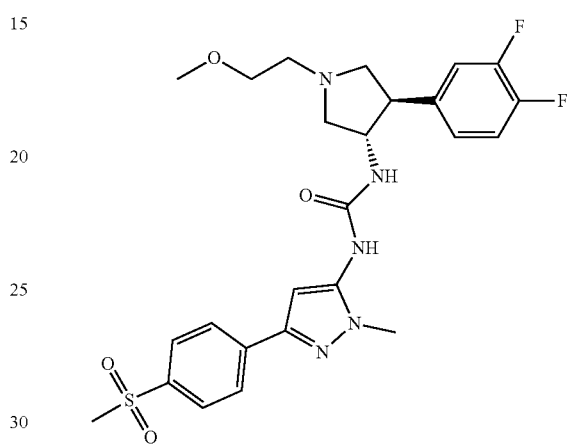

1-((3S,4R)-4-(3,4-difluorophenyl)-1-(2-methoxyethyl)pyrrolidin-3-yl)-3-(1-methyl-3-(4-(methylsulfonyl)phenyl)-1H-pyrazol-5-yl)urea Step A: Preparation of phenyl 1-methyl-3-(4-(methylthio)phenyl)-1H-pyrazol-5-ylcarbamate: Prepared according to Step A of Example 1, replacing the 3-tert-butyl-1-phenyl-1H-pyrazol-5-amine with 1-methyl-3-(4-(methylthio)phenyl)-1H-pyrazol-5-amine (Intermediate P121) to afford the product. MS (apci) m/z=340.0 (M+H).

Step B: Preparation of phenyl 1-methyl-3-(4-(methylsulfonyl)phenyl)-1H-pyrazol-5-ylcarbamate: To a solution of phenyl 1-methyl-3-(4-(methylthio)phenyl)-1H-pyrazol-5-ylcarbamate (110 mg, 0.324 mmol) in DCM (5 mL, 0.295 mmol) at 0° C. was added MCPBA (70-75% in H₂O) (72.6 mg, 0.295 mmol) in one portion. The reaction mixture was allowed to warm to ambient temperature and stirred for 2 hours, and then another portion of MCPBA (72.6 mg, 0.295 mmol) was added. After stirring for 5 hours at ambient temperature, the mixture was diluted with DCM (25 mL) and washed with saturated aqueous NaHCO₃ (2×10 mL) and saturated aqueous Na₂S₂O₃ (3×10 mL). The organic layer was dried with MgSO₄, filtered and concentrated in vacuo to give the crude product (101 mg, 92.3% yield). MS (apci) m/z=372.0 (M+H).

Step C: Preparation of 1-((3S,4R)-4-(3,4-difluorophenyl)-1-(2-methoxyethyl) pyrrolidin-3-yl)-3-(1-methyl-3-(4-(methylsulfonyl)phenyl)-1H-pyrazol-5-yl)urea: Prepared according to Step B of Example 1, substituting phenyl 1-methyl-3-(4-(methylsulfonyl)phenyl)-1H-pyrazol-5-ylcarbamate for phenyl 3-tert-butyl-1-phenyl-1H-pyrazol-5-ylcarbamate and substituting the compound of Preparation F for the compound of Preparation B. MS (apci) m/z=534.1 (M+H).

Example 167

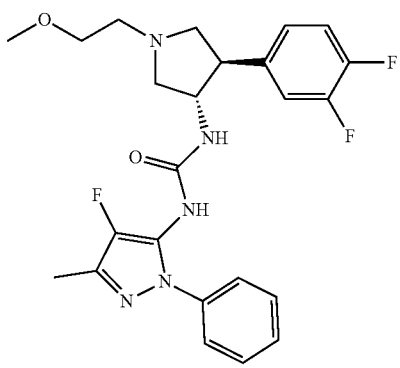 [SMILES: COCCN1C[C@@H](NC(=O)Nc2c(F)c(C)nn2-c2ccccc2)[C@H](c2ccc(F)c(F)c2)C1]

1-((3S,4R)-4-(3,4-difluorophenyl)-1-(2-methoxy-ethyl)pyrrolidin-3-yl)-3-(4-fluoro-3-methyl-1-phenyl-1H-pyrazol-5-yl)urea Step A: Preparation of phenyl 3-methyl-1-phenyl-1H-pyrazol-5-ylcarbamate: Prepared according to the method of Example 1, Step A, replacing 3-tert-butyl-1-phenyl-1H-pyrazol-5-amine with 3-methyl-1-phenyl-1H-pyrazol-5-amine to afford the product. MS (apci) m/z=294.1 (M+H).

Step B: Preparation of phenyl 4-fluoro-3-methyl-1-phenyl-H-pyrazol-5-ylcarbamate: To a solution of phenyl 3-methyl-1-phenyl-1H-pyrazol-5-ylcarbamate (20 mg, 0.0682 mmol) in acetonitrile (0.5 mL) was added Selectfluor (26.6 mg, 0.0750 mmol) in small portions at ambient temperature and the reaction mixture was stirred overnight. The reaction mixture was purified directly by reverse-phase column chromatography, eluting with 5-65% acetonitrile/water, to afford the product as a white foamy solid (12.4 mg, 58.4% yield). MS (apci) m/z=312.0 (M+H).

Step C: Preparation of 1-((3S,4R)-4-(3,4-difluorophenyl)-1-(2-methoxyethyl) pyrrolidin-3-yl)-3-(4-fluoro-3-methyl-1-phenyl-H-pyrazol-5-yl)urea: Prepared according to the method of Example 1, Step B, substituting phenyl 4-fluoro-3-methyl-1-phenyl-1H-pyrazol-5-ylcarbamate for phenyl 3-tert-butyl-1-phenyl-H-pyrazol-5-ylcarbamate and substituting the compound of Preparation F for the compound of Preparation B. MS (apci) m/z=474.1 (M+H).

Example 168

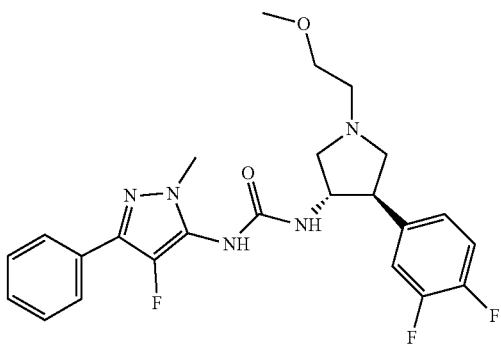 [SMILES: COCCN1C[C@@H](NC(=O)Nc2c(F)c(-c3ccccc3)nn2C)[C@H](c2ccc(F)c(F)c2)C1]

1-((3S,4R)-4-(3,4-difluorophenyl)-1-(2-methoxy-ethyl)pyrrolidin-3-yl)-3-(4-fluoro-1-methyl-3-phenyl-1H-pyrazol-5-yl)urea Prepared using the same procedure as Example 167, substituting 1-methyl-3-phenyl-1H-pyrazol-5-amine for 3-methyl-1-phenyl-1H-pyrazol-5-amine. MS (apci) m/z=474.1 (M+H).

Example 169

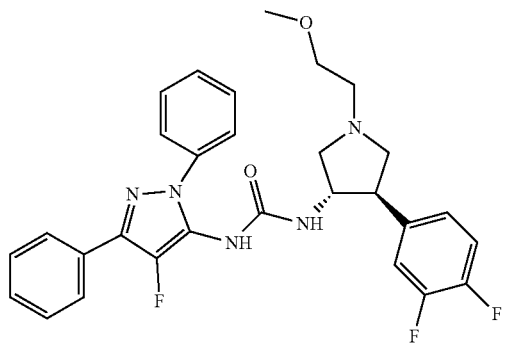 [SMILES: COCCN1C[C@@H](NC(=O)Nc2c(F)c(-c3ccccc3)nn2-c2ccccc2)[C@H](c2ccc(F)c(F)c2)C1]

1-((3S,4R)-4-(3,4-difluorophenyl)-1-(2-methoxy-ethyl)pyrrolidin-3-yl)-3-(4-fluoro-1,3-diphenyl-1H-pyrazol-5-yl)urea Prepared using the same procedure as Example 167, substituting 1,3-di-phenyl-1H-pyrazol-5-amine for 3-methyl-1-phenyl-1H-pyrazol-5-amine. MS (apci) m/z=536.1 (M+H).

Example 170

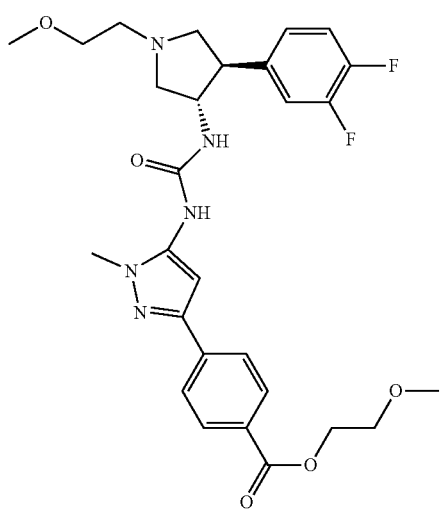

2-methoxyethyl 4-(5-(3-((3S,4R)-4-(3,4-difluorophenyl)-1-(2-methoxyethyl)pyrrolidin-3-yl)ureido)-1-methyl-1H-pyrazol-3-yl)benzoate Step A: Preparation of Lithium 4-(5-(3-((3S,4R)-4-(3,4-difluorophenyl)-1-(2-methoxyethyl)pyrrolidin-3-yl)ureido)-

1-methyl-1H-pyrazol-3-yl)benzoate: To a solution of methyl 4-(5-(3-((3S,4R)-4-(3,4-difluorophenyl)-1-(2-methoxyethyl)pyrrolidin-3-yl)ureido)-1-methyl-1H-pyrazol-3-yl)benzoate (Example 121; 158 mg, 0.308 mmol) in THF (4 mL, 0.308 mmol) and MeOH (2.00 mL, 49.4 mmol) at 0° C. was added LiOH (2M aqueous) (0.308 mL, 0.615 mmol). The reaction mixture was warmed to ambient temperature and stirred for 48 hours. Another portion of LiOH was added (70 µL, 0.4 equiv.) and the reaction mixture was stirred for an additional 4 days. The reaction mixture was concentrated to dryness and used directly in the next step, assuming quantitative yield. MS (apci) m/z=500.1 (M+H).

Step B: Preparation of 2-methoxyethyl 4-(5-(3-((3S,4R)-4-(3,4-difluorophenyl)-1-(2-methoxyethyl)pyrrolidin-3-yl)ureido)-1-methyl-1H-pyrazol-3-yl)benzoate: To a solution of lithium 4-(5-(3-((3S,4R)-4-(3,4-difluorophenyl)-1-(2-methoxyethyl)pyrrolidin-3-yl)ureido)-1-methyl-1H-pyrazol-3-yl)benzoate (15 mg, 0.030 mmol) in DMF (0.5 mL, 0.030 mmol) was added DIEA (0.016 mL, 0.089 mmol) and 2-methoxyethanol (9.0 mg, 0.12 mmol), followed by HATU (17 mg, 0.045 mmol). The reaction mixture was stirred overnight at ambient temperature, then purified directly by reverse-phase column chromatography, eluting with 5-65% acetonitrile/water, to afford the product as a white foamy solid (1.8 mg, 11% yield). MS (apci) m/z=558.0 (M+H).

Example 171

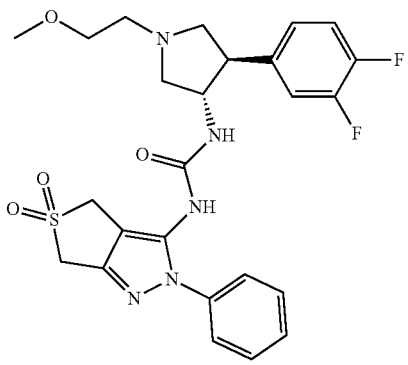 [SMILES: COCCN1C[C@@H](NC(=O)Nc2c3c(nn2-c2ccccc2)CS(=O)(=O)C3)[C@H](c2ccc(F)c(F)c2)C1]

1-((3S,4R)-4-(3,4-difluorophenyl)-1-(2-methoxyethyl)pyrrolidin-3-yl)-3-(5,5-dioxido-2-phenyl-4,6-dihydro-2H-thieno[3,4-c]pyrazol-3-yl)urea Step A: Preparation of 2-phenyl-4,6-dihydro-2H-thieno[3,4-c]pyrazol-3-amine: A suspension of 4-oxotetrahydrothiophene-3-carbonitrile (1.00 g, 7.86 mmol) and phenylhydrazine hydrochloride (1.25 g, 8.65 mmol) in absolute EtOH (40 mL, 7.86 mmol) was refluxed for 2 hours. The mixture was concentrated and the residue was triturated with 1N aqueous NaOH (40 mL). The solid was collected by filtration, washed sequentially with 0.1 N aqueous NaOH, water, and hexanes, then dried in vacuo to yield the product (1.62 g, 95% yield) as a white solid. MS (apci) m/z=218.1.

Step B: Preparation of phenyl 2-phenyl-4,6-dihydro-2H-thieno[3,4-c]pyrazol-3-ylcarbamate: To a suspension of 2-phenyl-4,6-dihydro-2H-thieno[3,4-c]pyrazol-3-amine (500 mg, 2.30 mmol) in EtOAc (10.0 mL, 2.30 mmol) was added NaOH (2.30 mL, 2M aqueous, 4.60 mmol) followed by phenylchloroformate (0.40 mL, 3.22 mmol) dropwise at ambient temperature. After stirring for 2 hours, additional phenylchloroformate (0.14 mL) was added. Stirring was continued for 5 minutes, and then another portion of phenyl chloroformate (0.081 mL) was added and the mixture was stirred for a further 16 hours. The reaction mixture was diluted with EtOAc and the phases were separated. The organic phase was washed with water and brine (25 mL each), dried over Na₂SO₄, filtered and concentrated. The residue was purified by reverse-phase column chromatography, eluting with 5-70% acetonitrile/water to afford the product (0.50 g, 64% yield) as a white solid (83% purity). MS (apci) m/z=338.1.

Step C: Preparation of phenyl (5,5-dioxido-2-phenyl-4,6-dihydro-2H-thieno[3,4-c]pyrazol-3-yl)carbamate: To a milky solution of phenyl 2-phenyl-4,6-dihydro-2H-thieno[3,4-c]pyrazol-3-ylcarbamate (100 mg, 0.29 mmol) in DCM (5 mL) at 0° C. was added MCPBA (170 mg, 70-75% water complex, 0.74 mmol). The mixture was removed from the bath and stirred at ambient temperature for 10 minutes, then diluted with DCM (20 mL) and washed successively with saturated NaHCO₃ (3×10 mL), saturated Na₂S₂O₃ (2×10 mL) and brine (10 mL). The organic layer was dried over Na₂SO₄ and concentrated to afford the product (107 mg, 98% yield) as a pale orange foam which was used without purification. MS (apci) m/z=371.4.

Step D: Preparation of 1-((3S,4R)-4-(3,4-difluorophenyl)-1-(2-methoxyethyl)pyrrolidin-3-yl)-3-(5,5-dioxido-2-phenyl-dihydro-2H-thieno[3,4-c]pyrazol-3-yl)urea: To a solution of (3S,4R)-4-(3,5-difluorophenyl)-1-(2-methoxyethyl)pyrrolidin-3-amine trifluoroacetate (Preparation E; 60 mg, 0.12 mmol) and phenyl (5,5-dioxido-2-phenyl-4,6-dihydro-2H-thieno[3,4-c]pyrazol-3-yl)carbamate (50.3 mg, 0.14 mmol) in anhydrous DMA (2 mL) was added DIEA (97 µL, 0.56 mmol). The mixture was stirred at ambient temperature for 15 hours. The reaction mixture was then partitioned between saturated NH₄Cl (20 mL) and EtOAc (10 mL). The aqueous layer was extracted with EtOAc (2×10 mL) and the combined organic phases were washed with water (5×10 mL) and brine (10 mL) then dried over Na₂SO₄ and concentrated. Purification of the crude product by silica column chromatography eluting with 2% MeOH/DCM afforded the product as a pale yellow foam (33 mg, 50% yield). MS (apci) m/z=532.1.

Example 172

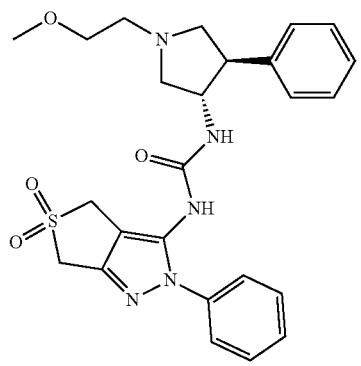 [SMILES: COCCN1C[C@@H](NC(=O)Nc2c3c(nn2-c2ccccc2)CS(=O)(=O)C3)[C@H](c2ccccc2)C1]

1-(5,5-dioxido-2-phenyl-4,6-dihydro-2H-thieno[3,4-c]pyrazol-3-yl)-3-((3S,4R)-1-(2-methoxyethyl)-4-phenylpyrrolidin-3-yl)urea Prepared according to the procedure used for Example 171, replacing (3S,4R)-4-(3,5-difluorophenyl)-1-(2- methoxyethyl)pyrrolidin-3-amine trifluoroacetate (Preparation E) with (3S,4R)-1-(2-methoxyethyl)-4-phenylpyrrolidin-3-amine dihydrochloride (Preparation D) in Step D. MS (apci) m/z=496.0 (M+H).

Example 173

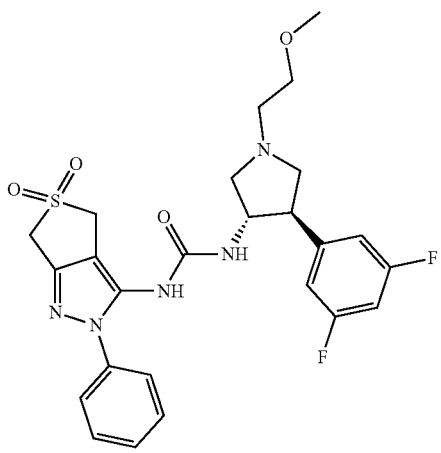 [SMILES: COCCN1C[C@@H](NC(=O)Nc2c3c(nn2-c2ccccc2)CS(=O)(=O)C3)[C@H](c2cc(F)cc(F)c2)C1]

1-((3S,4R)-4-(3,5-difluorophenyl)-1-(2-methoxyethyl)pyrrolidin-3-yl)-3-(5,5-dioxido-2-phenyl-4,6-dihydro-2H-thieno[3,4-c]pyrazol-3-yl)urea Prepared using the same procedure as Example 171, substituting (3S,4R)-4-(3,5-difluorophenyl)-1-(2-methoxyethyl)pyrrolidin-3-amine trifluoroacetate (Preparation E) for (3S,4R)-4-(3,4-difluorophenyl)-1-(2-methoxyethyl)pyrrolidin-3-amine (Preparation F). MS (apci) m/z=532.0 (M+H).

Example 174

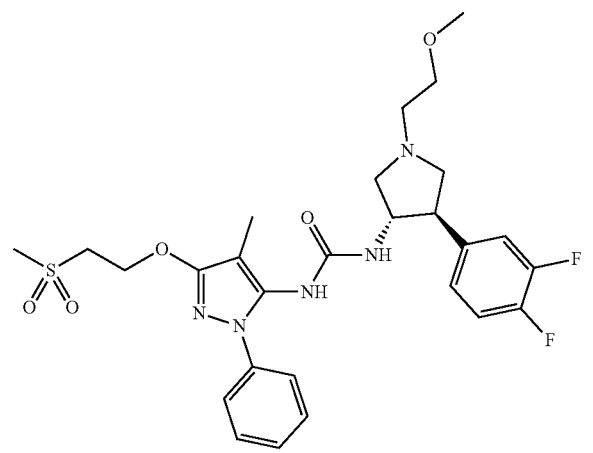 [SMILES: COCCN1C[C@@H](NC(=O)Nc2c(C)c(OCCS(C)(=O)=O)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-3-(2-(methylsulfonyl)ethoxy)-1-phenyl-1H-pyrazol-5-yl)urea Step A: Preparation of phenyl 4-methyl-3-(2-(methylthio)ethoxy)-1-phenyl-1H-pyrazol-5-ylcarbamate: Prepared according to the method described for Example 171, Step B, replacing 2-phenyl-4,6-dihydro-2H-thieno[3,4-c]pyrazol-3-amine with 4-methyl-3-(2-(methylthio)ethoxy)-1-phenyl-1H-pyrazol-5-amine (Intermediate P206). MS (apci) m/z=384.0 (M+H).

Step B: Preparation of phenyl 4-methyl-3-(2-(methylsulfonyl)ethoxy)-1-phenyl-1H-pyrazol-5-ylcarbamate: Phenyl 4-methyl-3-(2-(methylthio)ethoxy)-1-phenyl-1H-pyrazol-5-ylcarbamate (0.217 g, 0.566 mmol) was treated with THF (10 mL) and cooled to 0° C. A solution of 3-chlorobenzoperoxoic acid (MCPBA) with THF (4 mL) was added to the reaction mixture. After stirring for 1 hour, the mixture was warmed to ambient temperature and stirred for 2 hours. The reaction mixture was treated with EtOAc, quenched with $Na_2S_2O_3$ and water, extracted with EtOAc, washed with $NaHCO_3$ and brine, dried over $MgSO_4$, filtered and concentrated in vacuo. The resultant crude product was purified by silica column chromatography to afford the product (0.207 g, 88.0% yield). MS (apci) m/z=416.0 (M+H).

Step C: Preparation of 1-((3S,4R)-4-(3,4-difluorophenyl)-1-(2-methoxyethyl)pyrrolidin-3-yl)-3-(4-methyl-3-(2-(methylsulfonyl)ethoxy)-1-phenyl-1H-pyrazol-5-yl)urea:
To (3S,4R)-4-(3,4-difluorophenyl)-1-(2-methoxyethyl)pyrrolidin-3-amine (Preparation F; 50 mg, 0.15 mmol) in DCM (5 mL) at 0° C. was added phenyl 4-methyl-3-(2-(methylsulfonyl)ethoxy)-1-phenyl-1H-pyrazol-5-ylcarbamate (63 mg, 0.15 mmol) followed by addition of TEA (0.064 mL, 0.46 mmol). The resulting mixture was allowed to warm to ambient temperature and stirred for 17 hours. The reaction mixture was then treated with EtOAc, washed with saturated $NH_4Cl$, saturated $NaHCO_3$, and brine, dried with $MgSO_4$, filtered, concentrated, and purified by silica column chromatography, eluting with 3% MeOH/DCM to yield the title product as a white solid (47 mg, 53% yield). MS (apci) m/z=578.0 (M+H).

Example 175

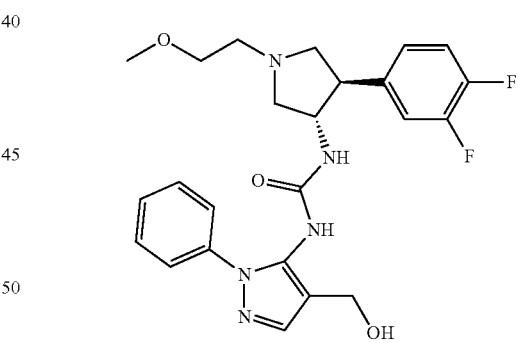

1-((3S,4R)-4-(3,4-difluorophenyl)-1-(2-methoxyethyl)pyrrolidin-3-yl)-3-(4-(hydroxymethyl)-1-phenyl-1H-pyrazol-5-yl)urea To a solution of ethyl 5-(3-((3S,4R)-4-(3,4-difluorophenyl)-1-(2-methoxyethyl)pyrrolidin-3-yl)ureido)-1-phenyl-1H-pyrazole-4-carboxylate (Example 154; 55 mg, 0.11 mmol) in THF (2 mL) at 0° C. under $N_2$ was added dropwise lithium aluminum hydride (1M bis-THF solution in toluene, 0.21 mL, 0.21 mmol). The reaction was stirred at 0° C. for 1.5 hours, then at ambient temperature for 3 hours. The reaction was quenched by sequential addition of $H_2O$ (0.008 mL), 1M aqueous NaOH (0.008 mL), and $H_2O$ (0.024 mL).

After stirring at ambient temperature for 2 hours, the reaction mixture was filtered, rinsed with THF (2 mL), and concentrated in vacuo. The crude product was purified by preparative TLC (0.5 mm plate) eluting with 10% MeOH/DCM to yield the product as a white solid (6 mg, 11% yield). MS (apci) m/z=472.0 (M+H).

Example 176

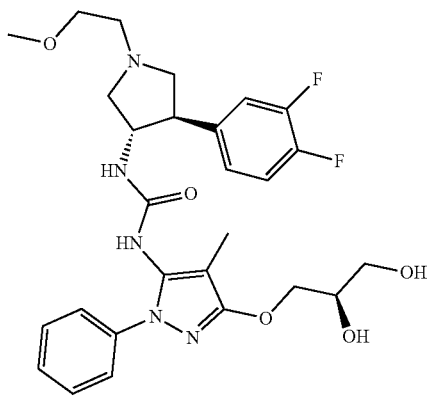 [SMILES: COCCN1C[C@@H](NC(=O)Nc2c(C)c(OC[C@H](O)CO)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(3-((R)-2,3-dihydroxypropoxy)-4-methyl-1-phenyl-1H-pyrazol-5-yl)urea To a solution of 1-((3S,4R)-4-(3,4-difluorophenyl)-1-(2-methoxyethyl)pyrrolidin-3-yl)-3-(3-(((S)-2,2-dimethyl-1,3-dioxolan-4-yl)methoxy)-4-methyl-1-phenyl-1H-pyrazol-5-yl)urea (Example 76; 65.0 mg, 0.111 mmol) in THF (2 mL) was added aqueous 1M HCl (2 mL). The reaction mixture was stirred at ambient temperature for 75 minutes and then concentrated to remove THF. The remaining aqueous solution was diluted with H₂O (2 mL) and treated with 2M NaOH to pH=10. The resulting milky mixture was treated with NaCl to saturation and extracted with EtOAc (2×). The combined organic extracts were dried over MgSO₄ and filtered through packed Celite®. The eluent was concentrated to a colorless gel that was washed with Et₂O and dried in vacuum to provide the title compound as a white solid (53 mg, 88% yield). MS (apci) m/z=546.1 (M+H).

Example 177

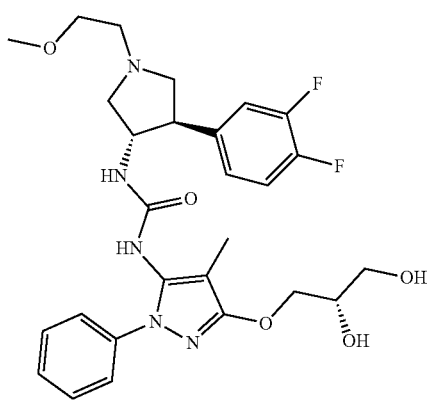 [SMILES: COCCN1C[C@@H](NC(=O)Nc2c(C)c(OC[C@@H](O)CO)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(3-((S)-2,3-dihydroxypropoxy)-4-methyl-1-phenyl-1H-pyrazol-5-yl)urea Prepared from 1-((3S,4R)-4-(3,4-difluorophenyl)-1-(2-methoxyethyl) pyrrolidin-3-yl)-3-(3-(((R)-2,2-dimethyl-1,3-dioxolan-4-yl)methoxy)-4-methyl-1-phenyl-1H-pyrazol-5-yl)urea (Example 77; 50.0 mg, 0.0854 mmol) according to the procedure described for Example 176, to provide title compound as a white solid (38 mg, 82% yield). MS (apci) m/z=546.2 (M+H).

Example 178

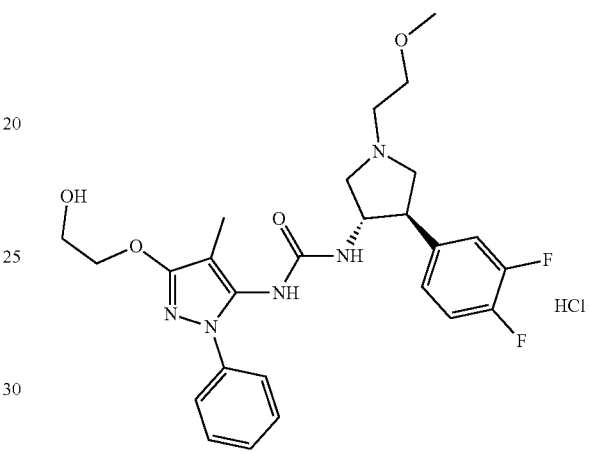

1-((3S,4R)-4-(3,4-difluorophenyl)-1-(2-methoxyethyl)pyrrolidin-3-yl)-3-(3-(2-hydroxyethoxy)-4-methyl-1-phenyl-1H-pyrazol-5-yl)urea hydrochloride To 1-(3-(2-(tert-butyldimethylsilyloxy)ethoxy)-4-methyl-1-phenyl-1H-pyrazol-5-yl)-3-((3S,4R)-4-(3,4-difluorophenyl)-1-(2-methoxyethyl)pyrrolidin-3-yl)urea (Preparation U-1; 46 mg, 0.073 mmol) in DCM (2 mL) at ambient temperature was added 2N HCl (22 mL, 0.44 mmol). After stirring for 1 hour, the reaction mixture was concentrated in vacuo and rinsed with Et₂O to give the product as the HCl salt (45 mg, 100% yield). MS (apci) m/z=516.1 (M+H).

Example 179

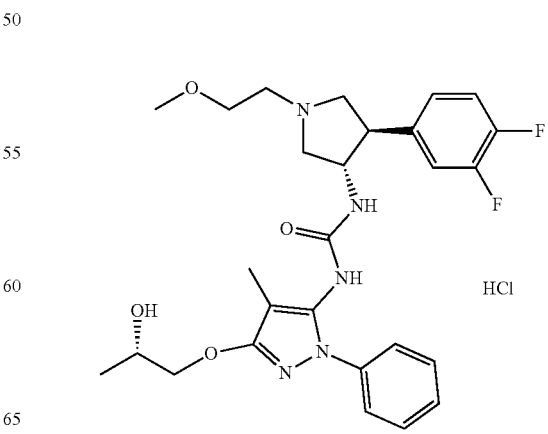

1-((3S,4R)-4-(3,4-difluorophenyl)-1-(2-methoxyethyl)pyrrolidin-3-yl)-3-(3-((S)-2-hydroxypropoxy)-4-methyl-1-phenyl-1H-pyrazol-5-yl)urea hydrochloride To 1-(3-((S)-2-(tert-butyldimethylsilyloxy)propoxy)-4-methyl-1-phenyl-1H-pyrazol-5-yl)-3-((3S,4R)-4-(3,4-difluorophenyl)-1-(2-methoxyethyl)pyrrolidin-3-yl)urea (Preparation U-2; 33 mg, 0.051 mmol) in DCM (2 mL) at ambient temperature was added 2N HCl (0.15 mL, 0.31 mmol). After stirring for 1 hour, the reaction mixture was concentrated in vacuo and rinsed with Et$_2$O to give the product HCl salt (29 mg, 100% yield). MS (apci) m/z=530.3 (M+H).

Example 180

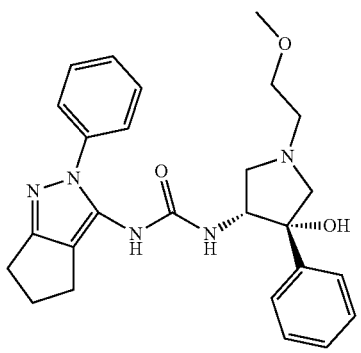 [SMILES: COCCN1C[C@@H](NC(=O)Nc2c3c(nn2-c2ccccc2)CCC3)[C@](O)(c2ccccc2)C1]

1-((3R,4S)-4-hydroxy-1-(2-methoxyethyl)-4-phenylpyrrolidin-3-yl)-3-(2-phenyl-2,4,5,6-tetrahydrocyclopenta[c]pyrazol-3-yl)urea Step A: Preparation of (3R,4R)-tert-butyl 3-azido-4-hydroxypyrrolidine-1-carboxylate: tert-Butyl 6-oxa-3-azabicyclo[3.1.0]hexane-3-carboxylate (15.42 g, 83.25 mmol), (1S,2S)-(−)-[1,2-cyclohexanediamino-N,N'-bis(3,5-di-t-butylsalicylidene)] chromium (III) chloride (1.181 g, 1.665 mmol) and azidotrimethylsilane (12.79 mL, 91.58 mmol) were stirred at ambient temperature under a nitrogen atmosphere for 18 hours. The resultant dark red-brown mixture was treated with MeOH (100 mL) and K$_2$CO$_3$ (13.81 g, 99.90 mmol) and the reaction was stirred at ambient temperature for 5 hours. The solution was filtered through a pad of Celite®, concentrated and taken up in EtOAc (100 mL) and water (50 mL). The layers were separated and the aqueous layer was extracted with EtOAc. The combined organic extracts were washed with saturated aqueous NaHCO$_3$, water, and brine, dried with MgSO$_4$ and concentrated to provide a brown oil. The oil was purified by silica column chromatography eluting with 20% EtOAc/hexanes to provide the title compound (ee=93%, 3.99 g, 102% yield). MS (apci) m/z=129.0 (M+H-Boc).

Step B: Preparation of (3R,4R)-4-azidopyrrolidin-3-ol hydrochloride: (3R,4R)-tert-butyl 3-azido-4-hydroxypyrrolidine-1-carboxylate (9.0 g, 39 mmol) and 4N HCl in dioxane (15 mL, 59 mmol) were combined in DCM (30 mL) and stirred at ambient temperature for 18 hours. The reaction was concentrated in vacuo to provide the title compound (6.5 g, 100% yield) as a yellow oil. MS (apci) m/z=129.0 (M+H).

Step C: Preparation of (3R,4R)-4-azido-1-(2-methoxyethyl)pyrrolidin-3-ol: (3R,4R)-4-azidopyrrolidin-3-ol hydrochloride (6.5 g, 39.5 mmol), 1-bromo-2-methoxyethane (6.59 g, 47.4 mmol) and DIEA (13.8 mL, 79.0 mmol) were combined in 10 mL of DMF and stirred at ambient temperature for 18 hours. MP-TsOH (39.5 g, 158 mmol) was added and the reaction was shaken for 1 hour, filtered, and the resin was washed with DCM. The amine was released from the resin by shaking with 7N NH$_3$ in MeOH (113 mL, 790 mmol) and DCM (113 mL) for 1 hour. The reaction was filtered and the resin was washed with DCM. The combined filtrates were concentrated to provide the crude title compound (7.09 g, 96.4% yield). MS (apci) m/z=187.0 (M+H).

Step D: Preparation of (3R,4R)-4-amino-1-(2-methoxyethyl)pyrrolidin-3-ol: (3R,4R)-4-azido-1-(2-methoxyethyl)pyrrolidin-3-ol (3.0 g, 16.1 mmol) and 10% Pd/C (1.71 g, 1.61 mmol) were combined in 40 mL of MeOH and the reaction was shaken at 40 psi H$_2$ in a Parr shaker for three days. The reaction was filtered through Celite® and concentrated to afford the title compound (2.53 g, 98.0% yield) as a brown oil. MS (apci) m/z=161.1 (M+H).

Step E: Preparation of tert-butyl (3R,4R)-4-hydroxy-1-(2-methoxyethyl) pyrrolidin-3-ylcarbamate: (3R,4R)-4-Amino-1-(2-methoxyethyl)pyrrolidin-3-ol (2.50 g, 15.6 mmol), Boc$_2$O (4.09 g, 18.7 mmol) and PS-DMAP (0.191 g, 1.56 mmol) were combined in 50 mL of DCM and shaken at ambient temperature for 18 hours. The reaction was filtered, concentrated and purified by silica column chromatography, eluting with 5-20% EtOAc/hexanes, to afford the title compound (3.17 g, 78.0% yield). MS (apci) m/z=261.0 (M+H).

Step F: Preparation of (R)-tert-butyl 1-(2-methoxyethyl)-4-oxopyrrolidin-3-ylcarbamate: A solution of oxalyl chloride (33.51 μL, 0.3841 mmol) in 5 mL of DCM was cooled to −78° C. and DMSO (54.52 μL, 0.7683 mmol) was added dropwise. The reaction was stirred for 15 minutes and a solution of tert-butyl (3R,4R)-4-hydroxy-1-(2-methoxyethyl)pyrrolidin-3-ylcarbamate (50 mg, 0.1921 mmol) in 2 mL of DCM was added dropwise. The reaction was allowed to warm to −40° C. over 1 hour and then cooled to −78° C. Triethylamine (267.7 μL, 1.921 mmol) was added dropwise, and the reaction was allowed to warm to 0° C. over 1 hour, then quenched with water and extracted with ether (40 mL). The organic layer was dried over MgSO$_4$, filtered and concentrated to afford the crude title compound (32 mg, 65% yield). MS (apci) m/z=259.0 (M+H).

Step G: Preparation of tert-butyl (3R,4S)-4-hydroxy-1-(2-methoxyethyl)-4-phenylpyrrolidin-3-ylcarbamate: (R)-tert-butyl 1-(2-methoxyethyl)-4-oxopyrrolidin-3-ylcarbamate (17.0 mg, 0.0658 mmol) was dissolved in THF (2 mL) and the solution was cooled to −78° C. A solution of phenyllithium in dibutyl ether (395 μL, 0.197 mmol) was added dropwise and the reaction was stirred at −78° C. for 1 hour and then allowed to warm to ambient temperature over 1 hour. The reaction was poured into brine (10 mL) and extracted with several portions of ether. The combined organic extracts were dried, concentrated and purified by reverse-phase column chromatography, eluting with 0-50% acetonitrile/water to provide the title compound as about a 4:1 mixture with tert-butyl (3R,4R)-4-hydroxy-1-(2-methoxyethyl)-4-phenylpyrrolidin-3-ylcarbamate (8.5 mg, 38% yield). MS (apci) m/z=337.1 (M+H).

Step H: Preparation of (3S,4R)-4-amino-1-(2-methoxyethyl)-3-phenylpyrrolidin-3-ol dihydrochloride: To a solution of the product from Step G (7.0 mg, 0.0208 mmol) in 0.1 mL of isopropanol was added a solution of HCl in isopropanol (29.7 μL, 0.208 mmol). The reaction mixture was stirred at ambient temperature for 1 hour, then concentrated to afford the title compound as about a 4:1 mixture with (3R,4R)-4-amino-1-(2-methoxyethyl)-3-phenylpyrrolidin-3-ol dihydrochloride (6.5 mg, 101% yield). MS (apci) m/z=237.1 (M+H).

Step I: Preparation of 1-((3R,4S)-4-hydroxy-1-(2-methoxyethyl)-4-phenylpyrrolidin-3-yl)-3-(2-phenyl-2,4,5,6-tetrahydrocyclopenta[c]pyrazol-3-yl)urea: The product from Step H (6.5 mg, 0.021 mmol) and DIEA (11 µL, 0.063 mmol) were combined in 0.5 mL of DCM and cooled to 0° C. Phenyl 2-phenyl-2,4,5,6-tetrahydrocyclopenta[c]pyrazol-3-ylcarbamate (7.4 mg, 0.023 mmol) was added and the reaction was allowed to warm to ambient temperature over 1 hour. The reaction was concentrated and purified by reverse-phase column chromatography, eluting with 0-60% acetonitrile/water to afford the title compound (3.8 mg, 39% yield). MS (apci) m/z=462.2 (M+H).

Example 181

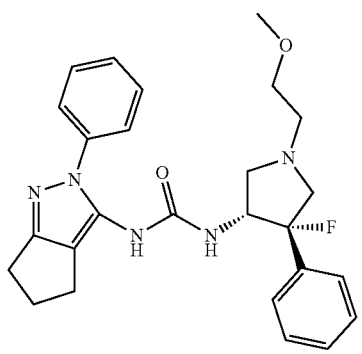 [SMILES: COCCN1C[C@@H](NC(=O)Nc2c3c(nn2-c2ccccc2)CCC3)[C@](F)(c2ccccc2)C1]

1-((3R,4S)-4-fluoro-1-(2-methoxyethyl)-4-phenylpyrrolidin-3-yl)-3-(2-phenyl-2,4,5,6-tetrahydrocyclopenta[c]pyrazol-3-yl)urea An approximately 2:1 mixture of 1-((3R,4S)-4-hydroxy-1-(2-methoxyethyl)-4-phenyl-pyrrolidin-3-yl)-3-(2-phenyl-2,4,5,6-tetrahydrocyclopenta[c]pyrazol-3-yl)urea and 1-((3R,4R)-4-hydroxy-1-(2-methoxyethyl)-4-phenylpyrrolidin-3-yl)-3-(2-phenyl-2,4,5,6-tetrahydrocyclopenta[c]pyrazol-3-yl)urea (5.0 mg, 0.011 mmol) (obtained as described in Example 177, Step I) was dissolved in DCM (2 mL) and cooled to −78° C. DAST (1.7 mg, 0.011 mmol) was added and the reaction was slowly allowed to warm to ambient temperature overnight. The reaction was quenched with MeOH, concentrated and purified by reverse phase MPLC to afford the title compound as about a 1:3 mixture with 1-((3R,4R)-4-fluoro-1-(2-methoxyethyl)-4-phenylpyrrolidin-3-yl)-3-(2-phenyl-2,4,5,6-tetrahydrocyclopenta[c]pyrazol-3-yl)urea (2.6 mg, 40% yield). The isomers were not separated. MS (apci) m/z=464.1 (M+H).

Example 182

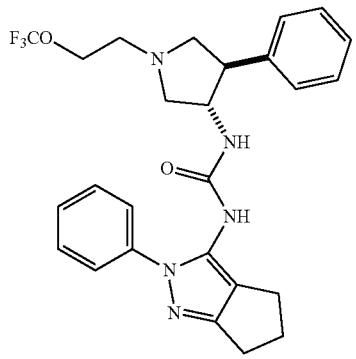

1-(trans-4-phenyl-1-(2-(trifluoromethoxy)ethyl)pyrrolidin-3-yl)-3-(2-phenyl-2,4,5,6-tetrahydrocyclopenta[c]pyrazol-3-yl)urea Step A: Preparation of trans-tert-butyl 3-phenyl-4-(3-(2-phenyl-2,4,5,6-tetrahydrocyclopenta[c]pyrazol-3-yl)ureido)pyrrolidine-1-carboxylate: To a solution of trans-tert-butyl 3-amino-4-phenylpyrrolidine-1-carboxylate (Preparation A2; 40 mg, 0.15 mmol) in DMA (0.5 mL, 0.15 mmol) was added phenyl 2-phenyl-2,4,5,6-tetrahydrocyclopenta[c]pyrazol-3-ylcarbamate (Example 38, Step C; 58 mg, 0.18 mmol) followed by cooling in an ice bath. DIEA (0.080 mL, 0.46 mmol) was added to the reaction mixture, which was then allowed to warm to ambient temperature overnight. The reaction mixture was directly purified by reverse-phase column chromatography, eluting with 5-75% acetonitrile/water, to afford the product as a white solid (30 mg, 41% yield). MS (apci) m/z=488.0 (M+H).

Step B: Preparation of 1-(2-phenyl-2,4,5,6-tetrahydrocyclopenta[c]pyrazol-3-yl)-3-(trans-4-phenylpyrrolidin-3-yl)urea hydrochloride salt: trans-tert-Butyl 3-phenyl-4-(3-(2-phenyl-2,4,5,6-tetrahydrocyclopenta[c]pyrazol-3-yl)ureido)pyrrolidine-1-carboxylate (30 mg, 0.062 mmol) was treated with 4N HCl in dioxane and stirred at ambient temperature for 15 hours, then concentrated in vacuo and triturated in Et$_2$O to afford the product (20 mg, 83% yield). MS (apci) m/z=388.1 (M+H).

Step C: Preparation of 1-(trans-4-phenyl-1-(2-(trifluoromethoxy)ethyl)pyrrolidin-3-yl)-3-(2-phenyl-2,4,5,6-tetrahydrocyclopenta[c]pyrazol-3-yl)urea: To a DMF (0.5 mL) solution of 1-(2-phenyl-2,4,5,6-tetrahydrocyclopenta[c]pyrazol-3-yl)-3-(trans-4-phenylpyrrolidin-3-yl)urea hydrochloride salt (16 mg, 0.038 mmol) was added N-ethyl-N-isopropylpropan-2-amine (21 µL, 0.11 mmol) and 1-bromo-2-(trifluoromethoxy)ethane (8.7 mg, 0.045 mmol) and stirred at ambient temperature for 3 hours, then heated to 40° C. for 15 hours. The reaction mixture was directly purified by purified by reverse-phase column chromatography, eluting with 5-75% acetonitrile/water, to afford the title compound (10 mg, 50% yield). MS (apci) m/z=499.9 (M+H).

Example 183

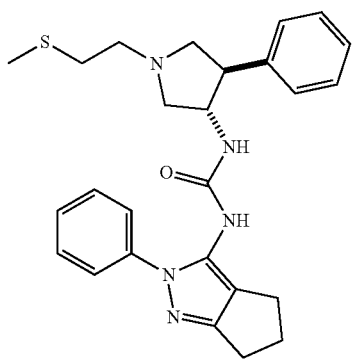

1-(trans-1-(2-(methylthio)ethyl)-4-phenylpyrrolidin-3-yl)-3-(2-phenyl-2,4,5,6-tetrahydrocyclopenta[c]pyrazol-3-yl)urea Prepared as in Example 182, substituting 1-bromo-2-(trifluoromethoxy)ethane with (2-chloroethyl)(methyl)sulfane to afford the product (2.6 mg, 24% yield) as a beige solid. MS (apci) m/z=462.1 (M+H).

Example 184

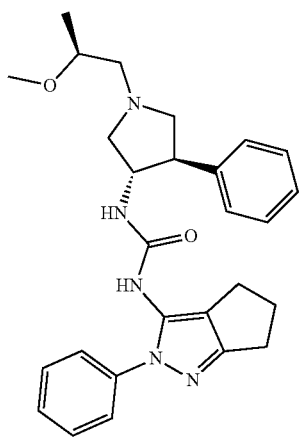 [SMILES: CO[C@@H](C)CN1C[C@@H](NC(=O)Nc2c3c(nn2-c2ccccc2)CCC3)[C@H](c2ccccc2)C1]

1-((3S,4R)-1-((S)-2-methoxypropyl)-4-phenylpyrrolidin-3-yl)-3-(2-phenyl-2,4,5,6-tetrahydrocyclopenta[c]pyrazol-3-yl)urea Step A: (S)-2-methoxypropyl methanesulfonate: A solution of (S)-2-methoxypropan-1-ol (451 mg, 5.00 mmol) and DIEA (1.74 mL, 10.0 mmol) in dry CH$_2$Cl$_2$ (4 mL) was cooled to 0° C. and MsCl (0.406 mL, 5.25 mmol) was added over 2 minutes. The mixture was stirred for 3 hours during which time the mixture reached ambient temperature. The mixture was washed with chilled H$_2$O, saturated NaHCO$_3$ and dried over Na$_2$SO$_4$. The dried solution was filtered through packed Celite® and concentrated to give the title product as a light gold oil (821 mg, 98% yield). $^1$H NMR (CDCl$_3$) δ 4.22 (m, 1H), 4.13 (m, 1H), 3.63 (m, 1H), 3.40 (s, 3H), 3.06 (s, 3H), 1.20 (d, J=6.4 Hz, 3H).

Step B: Tert-butyl (3S,4R)-1-((S)-2-methoxypropyl)-4-phenylpyrrolidin-3-ylcarbamate: To a solution of tert-butyl (3S,4R)-4-phenylpyrrolidin-3-ylcarbamate (Commercially available, 262 mg, 1.00 mmol) and DIEA (348 µL, 2.00 mmol) in DMF (2.0 mL) was added (S)-2-methoxypropyl methanesulfonate (252 mg, 1.50 mmol). The reaction was heated at 60° C. for 21 hours and additional (S)-2-methoxypropyl methanesulfonate (84.0 mg) was added. The reaction mixture was heated 60° C. for 2 hours, cooled to ambient temperature and added to H$_2$O (8 mL). The mixture was extracted with EtOAc (3×) and the combined extracts were washed with saturated NaCl (2×) and dried with MgSO$_4$. The dried solution was filtered through a SiO$_2$ plug eluting with EtOAc. The solution was concentrated to give the crude title compound as a light gold syrup (462 mg, 138% yield) that was used directly in the next step. MS (apci) m/z=335.1 (M+H).

Step C: (3S,4R)-1-((S)-2-methoxypropyl)-4-phenylpyrrolidin-3-amine dihydrochloride: To a solution of the crude tert-butyl (3S,4R)-1-((S)-2-methoxypropyl)-4-phenylpyrrolidin-3-ylcarbamate in EtOAc (10 mL) was added 4 M HCl in dioxane (10.0 mL, 40.0 mmol). The reaction mixture was stirred at ambient temperature for 3 hours and then diluted with MTBE (50 mL). The resulting precipitate was collected, washed with MTBE and dried in vacuum to afford the title compound as a tacky white solid (276 mg, 90% yield). MS (apci) m/z=235.1 (M+H).

Step D: 1-((3S,4R)-1-((S)-2-methoxypropyl)-4-phenylpyrrolidin-3-yl)-3-(2-phenyl-2,4,5,6-tetrahydrocyclopenta[c]pyrazol-3-yl)urea: To a solution of (3S,4R)-1-((S)-2-methoxypropyl)-4-phenylpyrrolidin-3-amine dihydrochloride (56.2 mg, 0.240 mmol) in dry DMF (0.8 mL) was added DIEA (139 µL, 0.796 mmol) and the mixture stirred at ambient temperature for 5 minutes. Phenyl 2-phenyl-2,4,5,6-tetrahydrocyclopenta[c]pyrazol-3-ylcarbamate (Example 38, Step E; 75.1 mg, 0.200 mmol) was added and the mixture stirred at ambient temperature for 4 hours. The mixture was added to H$_2$O (5 mL) and was extracted with EtOAc (3×). The combined extracts were washed with 1M NaOH (2×), H$_2$O and saturated NaCl. The solution was dried with MgSO$_4$, filtered and concentrated in vacuo. The residue was purified by silica chromatography eluting with EtOAc to provide the title compound as a waxy, white solid (31 mg, 34% yield). MS (apci) m/z=460.1 (M+H).

Example 185

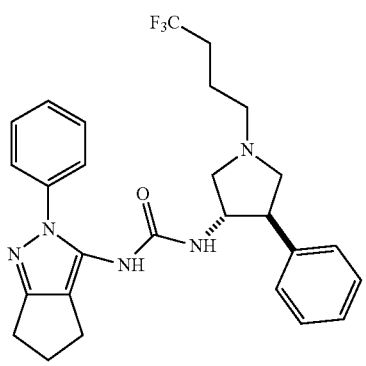

1-((3,4-trans)-4-phenyl-1-(4,4,4-trifluorobutyl)pyrrolidin-3-yl)-3-(2-phenyl-2,4,5,6-tetrahydrocyclopenta[c]pyrazol-3-yl)urea Prepared as in Example 182, substituting 1-bromo-2-(trifluoromethoxy)ethane with 4-bromo-1,1,1-trifluorobutane to afford the product (10 mg, 57% yield) as a white solid. MS (apci) m/z=498.2 (M+H).

Example 186

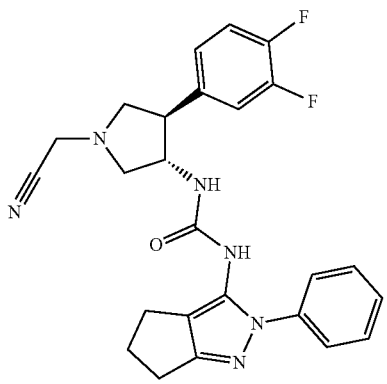 [SMILES: N#CCN1C[C@@H](NC(=O)Nc2c3c(nn2-c2ccccc2)CCC3)[C@H](c2ccc(F)c(F)c2)C1]

1-((3S,4R)-1-(cyanomethyl)-4-(3,4-difluorophenyl)pyrrolidin-3-yl)-3-(2-phenyl-2,4,5,6-tetrahydrocyclopenta[c]pyrazol-3-yl)urea Step A: Preparation of tert-butyl (3S,4R)-1-(cyanomethyl)-4-(3,4-difluorophenyl) pyrrolidin-3-ylcarbamate: To a solution of tert-butyl (3S,4R)-4-(3,4-difluorophenyl)pyrrolidin-3-ylcarbamate (100.0 mg, 0.3352 mmol, purchased from ACS Scientific) and TEA (51.39 µL, 0.3687 mmol) in THF (1.5 mL) was added 2-bromoacetonitrile (25.68 µL, 0.3687 mmol) dropwise. After stirring for two hours at ambient temperature, the reaction mixture was filtered and concentrated. The crude material was purified by silica column chromatography, eluting with 33% EtOAc/Hexanes to yield the product as white solid (98 mg, 87% yield). MS (apci pos) m/z=338.0 (M+H).

Step B: Preparation of 2-((3S,4R)-3-amino-4-(3,4-difluorophenyl)pyrrolidin-1-yl) acetonitrile hydrochloride: A mixture of tert-butyl (3S,4R)-1-(cyanomethyl)-4-(3,4-difluorophenyl)pyrrolidin-3-ylcarbamate (20 mg, 0.059 mmol) in HCl (150 µL, 0.59 mmol, 4 N dioxane) was stirred at ambient temperature for 15 minutes, then concentrated in vacuo, triturated with ether and dried on high vacuum to yield the product as white solid (16 mg, 99% yield). MS (apci pos) m/z=238.0 (M+H).

Step C: Preparation of 1-((3S,4R)-1-(cyanomethyl)-4-(3,4-difluorophenyl) pyrrolidin-3-yl)-3-(2-phenyl-2,4,5,6-tetrahydrocyclopenta[c]pyrazol-3-yl)urea: To a clear solution of 2-((3S,4R)-3-amino-4-(3,4-difluorophenyl)pyrrolidin-1-yl)acetonitrile hydrochloride (16 mg, 0.058 mmol) and phenyl 2-phenyl-2,4,5,6-tetrahydrocyclopenta[c]pyrazol-3-ylcarbamate (19 mg, 0.058 mmol) in DMA (0.5 mL) was added DIEA (0.041 mL, 0.23 mmol) dropwise at ambient temperature. After stirring for 1 hour, the reaction mixture was directly purified by reverse-phase column chromatography, eluting with 5-55% acetonitrile/water to yield the product as white solid (18 mg, 65% yield). MS (apci pos) m/z=463.0 (M+H).

Example 187

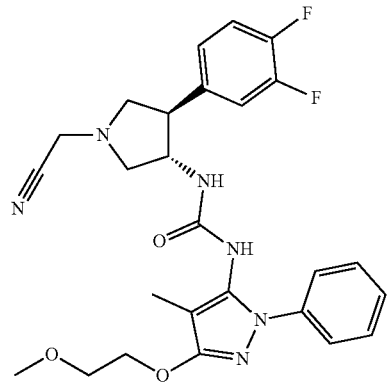 [SMILES: COCCOc1nn(-c2ccccc2)c(NC(=O)N[C@@H]2CN(CC#N)C[C@H]2c2ccc(F)c(F)c2)c1C]

1-((3S,4R)-1-(cyanomethyl)-4-(3,4-difluorophenyl)pyrrolidin-3-yl)-3-(3-(2-methoxyethoxy)-4-methyl-1-phenyl-1H-pyrazol-5-yl)urea To a clear solution of 2-((3S,4R)-3-amino-4-(3,4-difluorophenyl)pyrrolidin-1-yl)acetonitrile hydrochloride (Example 186, Step B, 10 mg, 0.037 mmol) and phenyl 3-(2-methoxyethoxy)-4-methyl-1-phenyl-1H-pyrazol-5-ylcarbamate (13 mg, 0.037 mmol) in DMA (180 µL, 0.037 mmol) was added DIEA (32 µL, 0.18 mmol) dropwise at ambient temperature. The reaction was heated to about 60° C. briefly (about 1 minute) then cooled to ambient temperature and stirred for 20 minutes. The reaction mixture was directly purified by reverse-phase column chromatography, eluting with 5-65% acetonitrile/water to yield the product as white solid (12 mg, 64% yield). MS (apci pos) m/z=511.1 (M+H).

Example 188

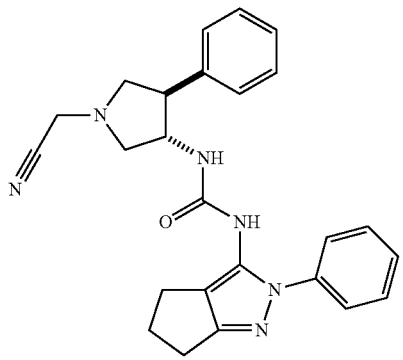 [SMILES: N#CCN1C[C@@H](NC(=O)Nc2c3c(nn2-c2ccccc2)CCC3)[C@H](c2ccccc2)C1]

1-((3,4-trans)-1-(cyanomethyl)-4-phenylpyrrolidin-3-yl)-3-(2-phenyl-2,4,5,6-tetrahydrocyclopenta[c]pyrazol-3-yl)urea Step A: Preparation of tert-butyl (3,4-trans)-1-(cyanomethyl)-4-phenylpyrrolidin-3-ylcarbamate: To a solution of tert-butyl (3,4-trans)-4-phenylpyrrolidin-3-ylcarbamate (206.0 mg, 0.7852 mmol, Preparation A) and TEA (120.4

µL, 0.8637 mmol) in THF (3 mL) was added 2-bromoacetonitrile (60.16 µL, 0.8637 mmol) dropwise. After stirring at ambient temperature overnight, the reaction mixture was filtered and concentrated to yield the product as white solid (230 mg, 97% yield). MS (apci pos) m/z=302.1 (M+H).

Step B: Preparation of 2-((3,4-trans)-3-amino-4-phenylpyrrolidin-1-yl)acetonitrile hydrochloride: A mixture of tert-butyl (3,4-trans)-1-(cyanomethyl)-4-phenylpyrrolidin-3-ylcarbamate (230 mg, 0.763 mmol) and HCl (4770 µL, 19.1 mmol, 4 N dioxane) was stirred at ambient temperature for 2 hours, then concentrated in vacuo, treated with ether and dried on high vacuum to yield the product as a pale-yellowish solid (180 mg, 99% yield). MS (apci pos) m/z=202.1 (M+H).

Step C: Preparation of 1-((3,4-trans)-1-(cyanomethyl)-4-phenylpyrrolidin-3-yl)-3-(2-phenyl-2,4,5,6-tetrahydrocyclopenta[c]pyrazol-3-yl)urea: To a clear solution of 2-(3,4-trans)-3-amino-4-phenylpyrrolidin-1-yl)acetonitrile hydrochloride (33 mg, 0.14 mmol) and phenyl 2-phenyl-2,4,5,6-tetrahydrocyclopenta[c]pyrazol-3-ylcarbamate (40 mg, 0.13 mmol) in DMA (630 µL) was added DIEA (110 µL, 0.63 mmol) dropwise at ambient temperature. After stirring at ambient temperature overnight, the reaction mixture was directly purified by reverse-phase column chromatography, eluting with 5-55% acetonitrile/water to yield the product as a white solid (45 mg, 84% yield). MS (apci pos) m/z=427.1 (M+H).

Example 189

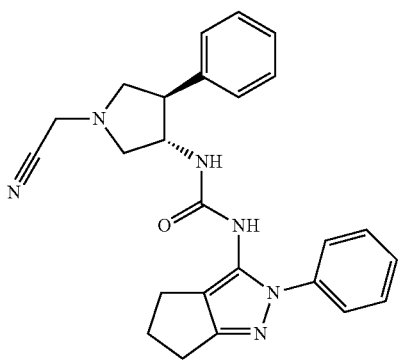 [SMILES: N#CCN1C[C@@H](NC(=O)Nc2c3c(nn2-c2ccccc2)CCC3)[C@H](c2ccccc2)C1]

1-((3S,4R)-1-(cyanomethyl)-4-phenylpyrrolidin-3-yl)-3-(2-phenyl-2,4,5,6-tetrahydrocyclopenta[c]pyrazol-3-yl)urea Step A: Preparation of tert-butyl (3S,4R)-1-(cyanomethyl)-4-phenylpyrrolidin-3-ylcarbamate: To a solution of tert-butyl (3S,4R)-4-phenylpyrrolidin-3-ylcarbamate (535 mg, 2.04 mmol, purchased from ACS Scientific) and TEA (313 µL, 2.24 mmol) in THF (8 mL) was added 2-bromoacetonitrile (156 µL, 2.24 mmol) dropwise. After stirring at ambient temperature overnight, the reaction mixture was filtered and concentrated in vacuo. The crude material was purified by silica column chromatography, eluting with 50% hexanes/EtOAc to yield the product as a white solid (510 mg, 83% yield). MS (apci pos) m/z=302.0 (M+H).

Step B: Preparation of 2-((3S,4R)-3-amino-4-phenylpyrrolidin-1-yl)acetonitrile hydrochloride: A mixture of tert-butyl (3S,4R)-1-(cyanomethyl)-4-phenylpyrrolidin-3-ylcarbamate (490 mg, 1.63 mmol) and HCl (20 mL, 80 mmol, 4 N dioxane) was stirred at ambient temperature for 2 hours. The reaction was concentrated in vacuo, triturated with ether and dried on high vacuum to yield a pale-yellowish solid. LCMS showed this to be a mixture of two products: 2-((3S,4R)-3-amino-4-phenylpyrrolidin-1-yl)acetonitrile hydrochloride and 2-((3S,4R)-3-amino-4-phenylpyrrolidin-1-yl)acetamide hydrochloride in approximately a 1:2 ratio.; MS (apci pos) m/z=202.1 and 220.1 (M+H), respectively. This mixture of the two products was used directly in the next step without further purification.

Step C: Preparation of 1-((3S,4R)-1-(cyanomethyl)-4-phenylpyrrolidin-3-yl)-3-(2-phenyl-2,4,5,6-tetrahydrocyclopenta[c]pyrazol-3-yl)urea: To a clear solution of the crude product from Step B (39 mg, 0.16 mmol) in DMA (420 µL, 0.13 mmol) was added phenyl 2-phenyl-2,4,5,6-tetrahydrocyclopenta[c]pyrazol-3-ylcarbamate (40 mg, 0.13 mmol), followed by DIEA (110 µL, 0.63 mmol) at ambient temperature and the reaction mixture was stirred for 18 hours. The reaction mixture was directly purified by reverse-phase column chromatography, eluting with 5-54% acetonitrile/water to yield the title product as a white solid (11 mg, 21% yield). MS (apci pos) m/z=427.1 (M+H).

Example 190

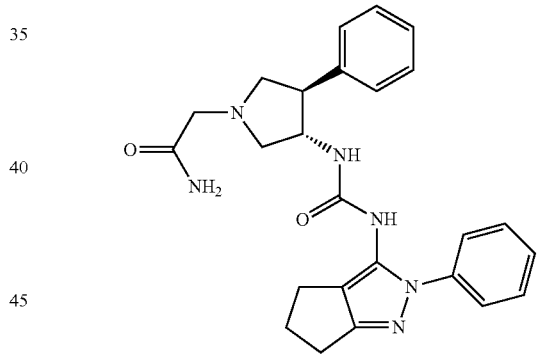

2-((3R,4S)-3-phenyl-4-(3-(2-phenyl-2,4,5,6-tetrahydrocyclopenta[c]pyrazol-3-yl)ureido)pyrrolidin-1-yl)acetamide To a clear solution of the crude product from Example 189, Step B containing 2-((3S,4R)-3-amino-4-phenylpyrrolidin-1-yl)acetamide hydrochloride (39 mg, 0.16 mmol) in DMA (420 µL, 0.13 mmol) was added phenyl 2-phenyl-2,4,5,6-tetrahydrocyclopenta[c]pyrazol-3-ylcarbamate (40 mg, 0.13 mmol), followed by DIEA (110 µL, 0.63 mmol) at ambient temperature, and the reaction mixture was stirred for 18 hours. The reaction mixture was directly purified by reverse-phase column chromatography, eluting with 5-54% acetonitrile/water to yield the title product as a white solid (20 mg, 36% yield). MS (apci pos) m/z=445.1 (M+H).

Example 191

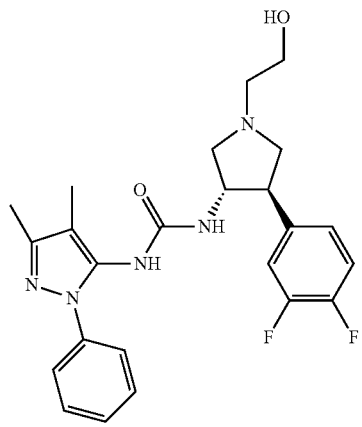 [SMILES: Cc1nn(-c2ccccc2)c(NC(=O)N[C@@H]2CN(CCO)C[C@H]2c2ccc(F)c(F)c2)c1C]

1-((3S,4R)-4-(3,4-difluorophenyvl)-1-(2-hydroxyethyl)pyrrolidin-3-yl)-3-(3,4-dimethyl-1-phenyl-1H-pyrazol-5-yl)urea Step A: Preparation of tert-butyl (3S,4R)-4-(3,4-difluorophenyl)-1-(2-hydroxyethyl)pyrrolidin-3-ylcarbamate: Tert-butyl (3S,4R)-4-(3,4-difluorophenyl)pyrrolidin-3-ylcarbamate (ACS Scientific, 410 mg, 1.37 mmol), 2-bromoethanol (180 mg, 1.44 mmol) and DIEA (533 mg, 4.12 mmol) were combined in 1 mL of DMF and stirred at ambient temperature for 72 hours. The reaction mixture was directly purified by reverse-phase column chromatography, eluting with 0-50% acetonitrile/water to afford the title compound (290 mg, 61.6% yield). MS (apci) m/z=343.0 (M+H).

Step B: Preparation of 2-((3S,4R)-3-amino-4-(3,4-difluorophenyl)pyrrolidin-1-yl)ethanol hydrochloride: Tert-butyl (3S,4R)-4-(3,4-difluorophenyl)-1-(2-hydroxyethyl) pyrrolidin-3-ylcarbamate (230 mg, 0.672 mmol) and hydrogen chloride in isopropanol (480 μL, 3.36 mmol) were combined and stirred at ambient temperature for 5 hours. The reaction was concentrated to afford the title compound (166 mg, 102% yield). MS (apci) m/z=243.0 (M+H).

Step C: Preparation of 1-((3S,4R)-4-(3,4-difluorophenyl)-1-(2-hydroxyethyl) pyrrolidin-3-yl)-3-(3,4-dimethyl-1-phenyl-1H-pyrazol-5-yl)urea: 2-((3S,4R)-3-Amino-4-(3,4-difluorophenyl)pyrrolidin-1-yl)ethanol hydrochloride (160 mg, 0.574 mmol), phenyl 3,4-dimethyl-1-phenyl-1H-pyrazol-5-ylcarbamate (168 mg, 0.547 mmol) and DIEA (286 μL, 1.64 mmol) were combined in 0.5 mL of DMF and stirred at ambient temperature for 1 hour. The reaction was directly purified by reverse-phase column chromatography, eluting with 0-50% acetonitrile/water, to afford the title compound (127 mg, 51.0% yield). MS (apci) m/z=456.0 (M+H).

Example 192

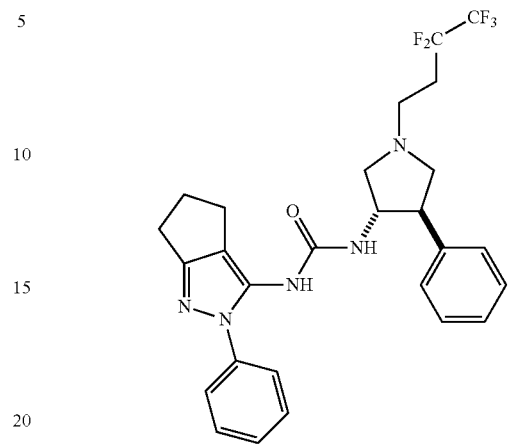

1-((trans)-1-(3,3,4,4,4-pentafluorobutyl)-4-phenlpyrrolidin-3-yl)-3-(2-phenyl-2,4,5,6-tetrahydrocyclopenta[c]pyrazol-3-yl)urea 1-(2-phenyl-2,4,5,6-tetrahydrocyclopenta[c]pyrazol-3-yl)-3-((trans)-4-phenylpyrrolidin-3-yl)urea (Example 182, Step B, 8.0 mg, 0.021 mmol), 1,1,1,2,2-pentafluoro-4-iodobutane (5.7 mg, 0.021 mmol) and DIEA (3.6 μL, 0.021 mmol) were combined in 0.1 mL of DMF and stirred at 60° C. for 2 hours. The reaction was directly purified by reverse-phase column chromatography, eluting with 0-65% acetonitrile/water to afford the title compound (3.2 mg, 29% yield). MS (apci) m/z=534.1 (M+H).

Example 193

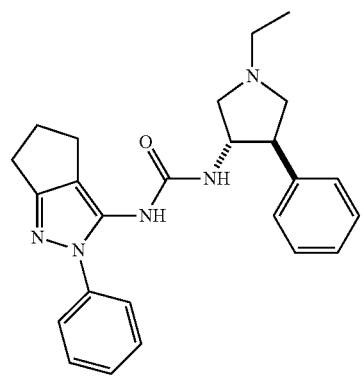 [SMILES: CCN1C[C@@H](NC(=O)Nc2c3c(nn2-c2ccccc2)CCC3)[C@H](c2ccccc2)C1]

1-((trans)-1-ethyl-4-phenylpyrrolidin-3-yl)-3-(2-phenyl-2,4,5,6-tetrahydrocyclopenta[c]pyrazol-3-yl)urea 1-(2-phenyl-2,4,5,6-tetrahydrocyclopenta[c]pyrazol-3-yl)-3-((trans)-4-phenylpyrrolidin-3-yl)urea (Example 182, Step B, 5.0 mg, 0.012 mmol), bromoethane (1.3 mg, 0.012 mmol) and DIEA (4.1 μL, 0.024 mmol) were combined in 0.1 mL of DMF and stirred at ambient temperature for 4 hours. The reaction was directly purified by reverse-phase column chromatography, eluting with 0-65% acetonitrile/water to afford the title compound (4.3 mg, 88% yield). MS (apci) m/z=416.1 (M+H).

Example 194

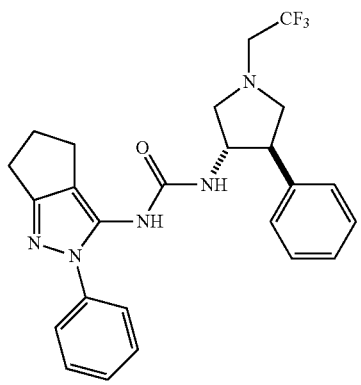 [SMILES: O=C(Nc1c2c(nn1-c1ccccc1)CCC2)N[C@@H]1CN(CC(F)(F)F)C[C@H]1c1ccccc1]

1-((trans)-4-phenyl-1-(2,2,2-trifluoroethyl)pyrrolidin-3-yl)-3-(2-phenyl-2,4,5,6-tetrahydrocyclopenta[c]pyrazol-3-yl)urea Step A: Preparation of tert-butyl (trans)-4-phenyl-1-(2,2,2-trifluoroethyl) pyrrolidin-3-ylcarbamate: Trans-tert-butyl-4-phenylpyrrolidin-3-ylcarbamate (1.00 g, 3.81 mmol), 2,2,2-trifluoroethyl trifluoromethanesulfonate (1.06 g, 4.57 mmol) and DIEA (1.48 g, 11.4 mmol) were combined in 2 mL of DMF and stirred at ambient temperature for 1 hour. The reaction was directly purified by reverse-phase column chromatography, eluting with 0-75% acetonitrile/water to afford the title compound (1.19 g, 90.7% yield). MS (apci) m/z=345.0 (M+H).

Step B: Preparation of (trans)-4-phenyl-1-(2,2,2-trifluoroethyl)pyrrolidin-3-amine hydrochloride: Tert-butyl (trans)-4-phenyl-1-(2,2,2-trifluoroethyl)pyrrolidin-3-yl carbamate (1.19 g, 3.46 mmol) and HCl (5 N in isopropanol, 1.48 mL, 10.4 mmol) were combined and stirred at ambient temperature for 5 hours. The reaction was concentrated to provide the title compound (0.85 g, 101% yield). MS (apci) m/z=245.0 (M+H).

Step C: Preparation of 1-((trans)-4-phenyl-1-(2,2,2-trifluoroethyl)pyrrolidin-3-yl)-3-(2-phenyl-2,4,5,6-tetrahydrocyclopenta[c]pyrazol-3-yl)urea: (trans)-4-Phenyl-1-(2,2,2-trifluoro-ethyl)pyrrolidin-3-amine hydrochloride (10.0 mg, 0.0356 mmol), phenyl 2-phenyl-2,4,5,6-tetrahydrocyclopenta[c]pyrazol-3-ylcarbamate (9.48 mg, 0.0297 mmol) and DIEA (15.5 µL, 0.0891 mmol) were combined in 0.2 mL of DMF and stirred at ambient temperature for 1 hour. The reaction was directly purified by reverse-phase column chromatography, eluting with 0-75% acetonitrile/water, to afford the title compound (11.5 mg, 82.5% yield). MS (apci) m/z=470.0 (M+H).

Example 195

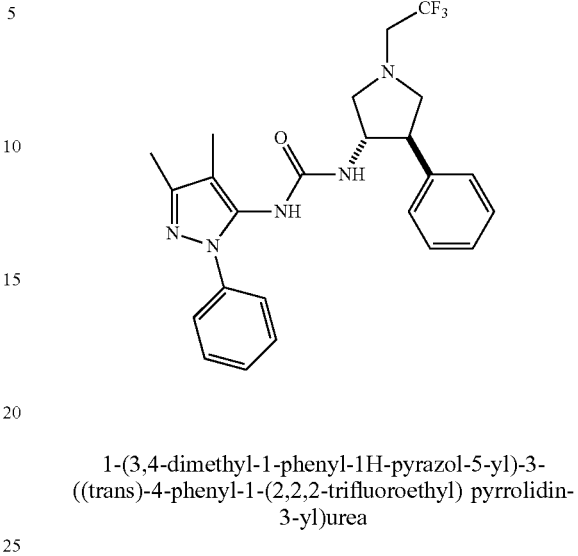

1-(3,4-dimethyl-1-phenyl-1H-pyrazol-5-yl)-3-((trans)-4-phenyl-1-(2,2,2-trifluoroethyl) pyrrolidin-3-yl)urea Prepared by the method as described in Example 194, substituting phenyl 3,4-dimethyl-1-phenyl-1H-pyrazol-5-ylcarbamate for phenyl 2-phenyl-2,4,5,6-tetrahydrocyclopenta [c]pyrazol-3-ylcarbamate in Step C. The material was purified by reverse-phase column chromatography eluting with 0-70% acetonitrile/H$_2$O to provide the title compound (6.5 mg, 48% yield). MS (apci) m/z=458.1 (M+H).

Example 196

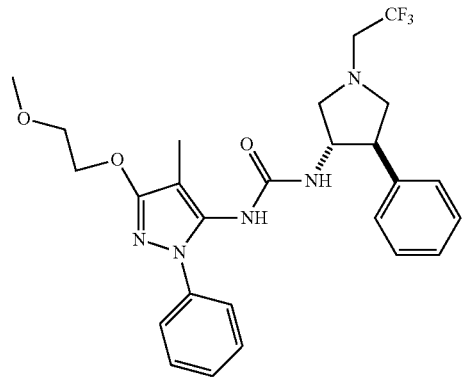 [SMILES: COCCOc1nn(-c2ccccc2)c(NC(=O)N[C@@H]2CN(CC(F)(F)F)C[C@H]2c2ccccc2)c1C]

1-(3-(2-methoxyethoxy)-4-methyl-1-phenyl-1H-pyrazol-5-yl)-3-((trans)-4-phenyl-1-(2,2,2-trifluoroethyl)pyrrolidin-3-yl)urea Prepared by the method as described in Example 194, substituting phenyl 3-(2-methoxyethoxy)-4-methyl-1-phenyl-1H-pyrazol-5-ylcarbamate for phenyl 2-phenyl-2,4,5,6-tetrahydrocyclopenta[c]pyrazol-3-ylcarbamate in Step C. The material was purified by reverse-phase column chromatography eluting with 0-70% acetonitrile/H$_2$O to provide the title compound (9.3 mg, 61% yield). MS (apci) m/z=518.1 (M+H).

Example 197

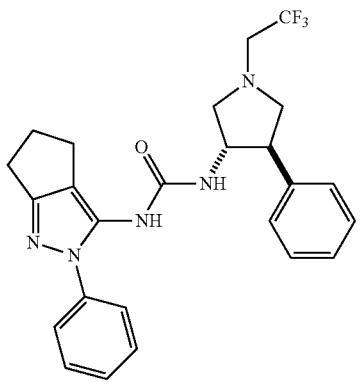 [SMILES: O=C(Nc1c2c(nn1-c1ccccc1)CCC2)N[C@@H]1CN(CC(F)(F)F)C[C@H]1c1ccccc1]

1-((trans)-4-phenyl-1-(2,2,2-trifluoroethyl)pyrrolidin-3-yl)-3-(2-phenyl-2,4,5,6-tetrahydrocyclopenta[c]pyrazol-3-yl)urea Prepared by the method as described in Example 194, Steps A-C, using tert-butyl (3S,4R)-4-phenylpyrrolidin-3-ylcarbamate, (purchased from ACS Scientific, catalog #3-1005) instead of trans-tert-butyl-4-phenylpyrrolidin-3-ylcarbamate in Step A. The final product was purified by reverse-phase column chromatography eluting with 0-60% acetonitrile/H$_2$O to provide the title compound (7.2 mg, 52% yield). MS (apci) m/z=470.0 (M+H).

Example 198

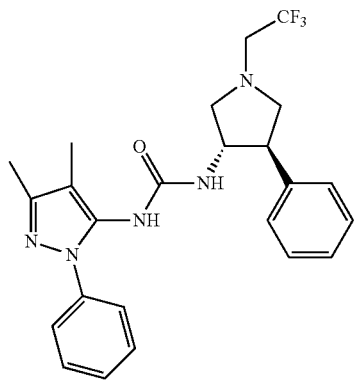 [SMILES: Cc1nn(-c2ccccc2)c(NC(=O)N[C@@H]2CN(CC(F)(F)F)C[C@H]2c2ccccc2)c1C]

1-(3,4-dimethyl-1-phenyl-1H-pyrazol-5-yl)-3-((3S,4R)-4-phenyl-1-(2,2,2-trifluoroethyl)pyrrolidin-3-yl)urea Prepared by the method as described in Example 197, substituting phenyl 3,4-dimethyl-1-phenyl-1H-pyrazol-5-ylcarbamate for phenyl 2-phenyl-2,4,5,6-tetrahydro-cyclopenta[c]pyrazol-3-ylcarbamate in Step C. The material was purified by reverse-phase column chromatography eluting with 0-60% acetonitrile/H$_2$O to provide the title compound (10.0 mg, 67.5% yield for the urea formation). MS (apci) m/z=458.0 (M+H).

Example 199

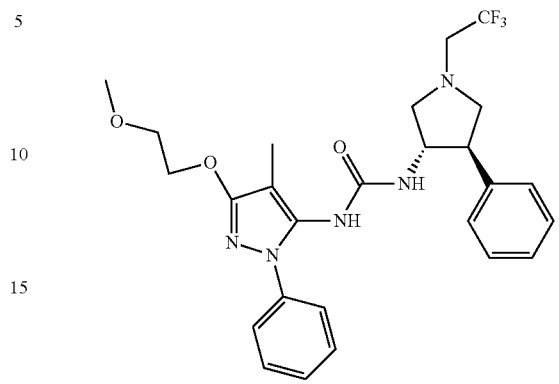

1-(3-(2-methoxyethoxy)-4-methyl-1-phenyl-1H-pyrazol-5-yl)-3-((3S,4R)-4-phenyl-1-(2,2,2-trifluoroethyl)pyrrolidin-3-yl)urea Prepared by the method as described in Example 197, substituting phenyl 3-(2-methoxyethoxy)-4-methyl-1-phenyl-1H-pyrazol-5-ylcarbamate for phenyl 2-phenyl-2,4,5,6-tetrahydrocyclopenta[c]pyrazol-3-ylcarbamate. The material was purified by reverse-phase column chromatography eluting with 0-70% acetonitrile/H$_2$O to provide the title compound (8.9 mg, 53% yield). MS (apci) m/z=518.1 (M+H).

Example 200

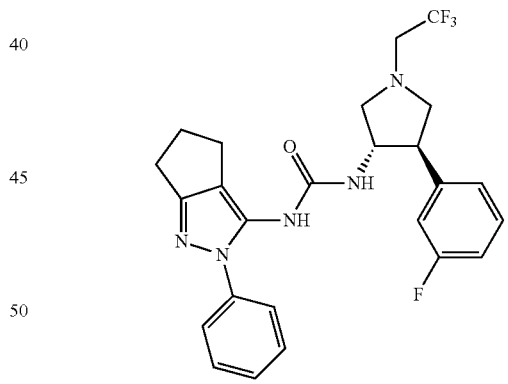

1-((3S,4R)-4-(3-fluorophenyl)-1-(2,2,2-trifluoroethyl)pyrrolidin-3-yl)-3-(2-phenyl-2,4,5,6-tetrahydrocyclopenta[c]pyrazol-3-yl)urea Prepared by the method as described in Example 194, Step A-C using tert-butyl (3S,4R)-4-(3-fluorophenyl)pyrrolidin-3-ylcarbamate (purchased from ACS Scientific, catalog #3-1029) instead of trans-tert-butyl-4-phenylpyrrolidin-3-ylcarbamate in Step A. The final product was purified by reverse-phase column chromatography eluting with 0-75% acetonitrile/H$_2$O to provide the title compound (12 mg, 92% yield). MS (apci) m/z=488.1 (M+H).

Example 201

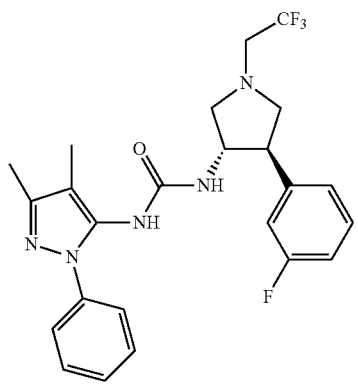 [SMILES: Cc1nn(-c2ccccc2)c(NC(=O)N[C@@H]2CN(CC(F)(F)F)C[C@H]2c2cccc(F)c2)c1C]

1-(3,4-dimethyl-1-phenyl-1H-pyrazol-5-yl)-3-((3S,4R)-4-(3-fluorophenyl)-1-(2,2,2-trifluoroethyl)pyrrolidin-3-yl)urea Prepared by the method as described in Example 200, substituting phenyl 3,4-dimethyl-1-phenyl-1H-pyrazol-5-ylcarbamate for phenyl 2-phenyl-2,4,5,6-tetrahydro-cyclopenta [c]pyrazol-3-ylcarbamate in Step C. The material was purified by reverse-phase column chromatography eluting with 5-80% acetonitrile/H₂O to provide the title compound (5.3 mg, 48% yield). MS (apci) m/z=476.0 (M+H).

Example 202

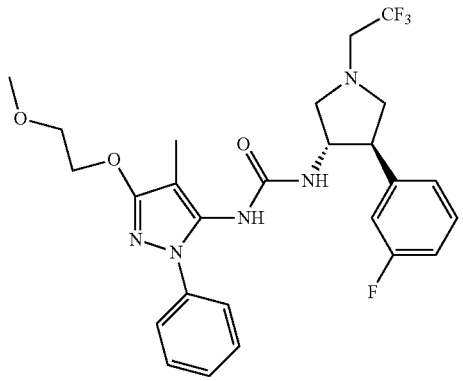 [SMILES: COCCOc1nn(-c2ccccc2)c(NC(=O)N[C@@H]2CN(CC(F)(F)F)C[C@H]2c2cccc(F)c2)c1C]

1-((3S,4R)-4-(3-fluorophenyl)-1-(2,2,2-trifluoroethyl)pyrrolidin-3-yl)-3-(3-(2-methoxyethoxy)-4-methyl-1-phenyl-1H-pyrazol-5-yl)urea Prepared by the method as described in Example 200, substituting phenyl 3-(2-methoxyethoxy)-4-methyl-1-phenyl-1H-pyrazol-5-ylcarbamate for phenyl 2-phenyl-2,4,5,6-tetrahydrocyclopenta[c]pyrazol-3-ylcarbamate. The material was purified by reverse-phase column chromatography eluting with 5-80% acetonitrile/H₂O to provide the title compound (6.6 mg, 58% yield). MS (apci) m/z=536.1 (M+H).

Example 203

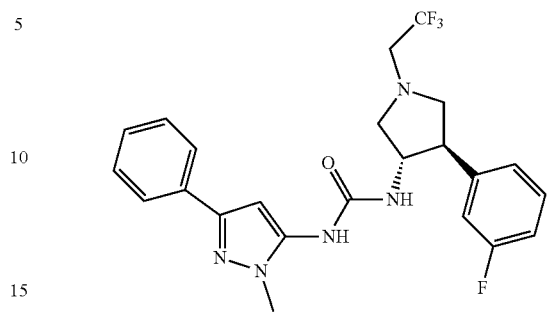

1-((3S,4R)-4-(3-fluorophenyl)-1-(2,2,2-trifluoroethyl)pyrrolidin-3-yl)-3-(1-methyl-3-phenyl-H-pyrazol-5-yl)urea Prepared by the method as described in Example 200, substituting phenyl 1-methyl-3-phenyl-1H-pyrazol-5-ylcarbamate for phenyl 2-phenyl-2,4,5,6-tetrahydro-cyclopenta [c]pyrazol-3-ylcarbamate. The material was purified by reverse-phase column chromatography eluting with 0-75% acetonitrile/H₂O to provide the title compound (6.3 mg, 64% yield). MS (apci) m/z=462.0 (M+H).

Example 204

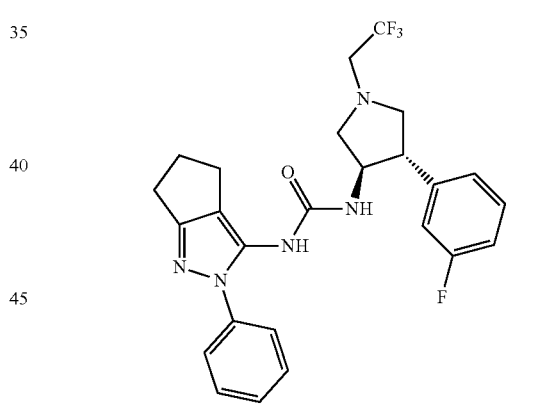

1-((3R,4S)-4-(3-fluorophenyl)-1-(2,2,2-trifluoroethyl)pyrrolidin-3-yl)-3-(2-phenyl-2,4,5,6-tetrahydrocyclopenta[c]pyrazol-3-yl)urea Step A: Preparation of (E)-3-(4-chloro-3-fluorophenyl) acryloyl chloride: (E)-3-(4-chloro-3-fluorophenyl)acrylic acid (28.1 g, 140 mmol) was suspended in chloroform (250 mL) and DMF (0.1 mL) was added followed by oxalyl chloride (20.0 mL, 229 mmol). The reaction was stirred for 18 hours and then evaporated to dryness. Heptane was added and the mixture was concentrated to afford the product (30.6 g, 99.7% yield) as pale yellow solid.

Step B: Preparation of (R)-4-benzyl-3-((3R,4S)-1-benzyl-4-(4-chloro-3-fluorophenyl)pyrrolidine-3-carbonyl)oxazolidin-2-one: (R)-4-benzyloxazolidin-2-one (21.8 g, 123 mmol) was dissolved in THF (600 mL) and cooled to −78°

C. Lithium bis(trimethylsilyl)amide in THF (127 mL, 127 mmol) was added dropwise over 15 minutes and the mixture was stirred for another 15 minutes at −78° C. A solution of (E)-3-(4-chloro-3-fluorophenyl)acryloyl chloride (28.3 g, 129 mmol) in THF (100 mL) was added and the mixture stirred for 1 hour at −78° C., then allowed to warm to ambient temperature and stirred for another hour. Saturated aqueous sodium bicarbonate solution (50 mL) was added and the reaction was stirred for 1 hour. Then THF was removed in vacuo, ethyl acetate (1 µL) was added and the reaction mixture was washed with water (2×) and brine, dried with MgSO$_4$, filtered and evaporated to give (R,E)-4-benzyl-3-(3-(4-chloro-3-fluorophenyl)acryloyl)oxazolidin-2-one (44.3 g, 100% yield) as tan solid. The solid was dissolved in toluene (500 mL) and 2,2,2-trifluoroacetic acid (0.9486 mL, 12.31 mmol) was added. The temperature was warmed to 35° C. and N-benzyl-1-methoxy-N-((trimethylsilyl) methyl)methanamine (52.50 mL, 184.7 mmol) was added over 20 minutes, keeping the temperature at 25-30° C. with an external water bath. The mixture was washed with saturated aqueous sodium bicarbonate solution and water and concentrated in vacuo to obtain an oily residue that was triturated with hexanes, filtered and washed with hexanes to obtain a white solid (55.7 g). This solid (55.7 g) was suspended in hexanes (200 mL) and heated to reflux. Benzene (220 mL) was added until the solid dissolved at reflux. The solution was allowed to slowly cool to ambient temperature and then placed into freezer for 4 hours. The resulting solid was collected by filtration and washed with 100 mL of cold 1:1 hexane/benzene. The resultant solid (7.6 g) was purified by silica column chromatography eluting with 20-40% EtOAc/Hexanes. (R)-4-benzyl-3-((3S,4R)-1-benzyl-4-(4-chloro-3-fluorophenyl)pyrrolidine-3-carbonyl)oxazolidin-2-one (3.2 g, 42% yield) eluted first followed by (R)-4-benzyl-3-((3R,4S)-1-benzyl-4-(4-chloro-3-fluorophenyl)pyrrolidine-3-carbonyl)oxazolidin-2-one (3.0 g, 39% yield). MS (apci) m/z=493.0 (M+H).

Step C: Preparation of (3R,4S)-1-benzyl-4-(4-chloro-3-fluorophenyl)pyrrolidine-3-carboxylic acid: Hydrogen peroxide (30% aqueous, 2.38 mL, 23.1 mmol) was added dropwise to a mixture of lithium hydroxide monohydrate (0.638 g, 15.2 mmol) and ice-water (50 g). The mixture was stirred for 30 minutes and the resultant solution was added to solution of (R)-4-benzyl-3-((3R,4S)-1-benzyl-4-(4-chloro-3-fluorophenyl)pyrrolidine-3-carbonyl)oxazolidin-2-one (3.00 g, 6.09 mmol) in THF (50 mL). The reaction was stirred at ambient temperature for 5 hours, quenched by addition of 2M aqueous Na$_2$SO$_3$ (20 mL) and agitated overnight. The pH was adjusted to 6 with solid KHSO$_4$ and the mixture was extracted with EtOAc (2×100 mL). The combined organic extracts were washed with brine, dried with MgSO$_4$, filtered and concentrated in vacuo. The residue was purified by silica column chromatography eluting with 10% MeOH/DCM to provide the product (1.80 g, 88.6% yield) as white solid. MS (apci) m/z=334.0 (M+H).

Step D: Preparation of tert-butyl (3R,4S)-1-benzyl-4-(4-chloro-3-fluorophenyl) pyrrolidin-3-ylcarbamate: (3R,4S)-1-benzyl-4-(4-chloro-3-fluorophenyl) pyrrolidine-3-carboxylic acid (120 mg, 0.360 mmol), NEt$_3$ (150 µL, 1.08 mmol), and diphenylphosphoryl azide (116 µL, 0.539 mmol) were combined in 2 mL of Toluene in a sealed vessel and stirred at 100° C. for 30 minutes. The reaction was allowed to cool to ambient temperature and lithium 2-methylpropan-2-olate in THF (1.44 mL, 0.719 mmol) was added. The reaction was stirred at 100° C. for 5 hours, cooled, concentrated and purified by reverse-phase column chromatography eluting with 20-90% acetonitrile/H$_2$O to afford the product (61.0 mg, 41.9% yield). MS (apci) m/z=405.0 (M+H).

Step E: Preparation of tert-butyl (3R,4S)-4-(3-fluorophenyl)pyrrolidin-3-ylcarbamate: Tert-butyl (3R,4S)-1-benzyl-4-(4-chloro-3-fluorophenyl)pyrrolidin-3-ylcarbamate (60 mg, 0.15 mmol) was dissolved in 5 mL of MeOH and 10% Pd/C (32 mg, 0.030 mmol) was added. The reaction was stirred under a hydrogen-filled balloon for 18 hours, filtered through Celite®, and then concentrated to afford the title compound (36 mg, 87% yield). MS (apci) m/z=281.1 (M+H).

Step F: Preparation of tert-butyl (3R,4S)-4-(3-fluorophenyl)-1-(2,2,2-trifluoroethyl) pyrrolidin-3-ylcarbamate: Tert-butyl (3R,4S)-4-(3-fluorophenyl)pyrrolidin-3-ylcarbamate (35 mg, 0.12 mmol), 2,2,2-trifluoroethyl trifluoromethanesulfonate (38 mg, 0.16 mmol) and DIEA (65 µL, 0.37 mmol) were combined in 0.5 mL of DMF and stirred at ambient temperature for 18 hours. The reaction was directly purified by reverse-phase column chromatography eluting with 0-80% acetonitrile/H$_2$O to afford the product (30 mg, 66% yield). MS (apci) m/z=363.0 (M+H).

Step G: Preparation of (3R,4S)-4-(3-fluorophenyl)-1-(2,2,2-trifluoroethyl)pyrrolidin-3-amine hydrochloride: Tert-butyl (3R,4S)-4-(3-fluorophenyl)-1-(2,2,2-trifluoroethyl) pyrrolidin-3-ylcarbamate (30 mg, 0.083 mmol) and hydrogen chloride in isopropanol (50 µL, 0.25 mmol) were combined in 1 mL of isopropanol and stirred at ambient temperature for 4 hours. The reaction was concentrated in vacuo to afford the product (21 mg, 97% yield). MS (apci) m/z=263.0 (M+H).

Step H: Preparation of 1-((3R,4S)-4-(3-fluorophenyl)-1-(2,2,2-trifluoroethyl) pyrrolidin-3-yl)-3-(2-phenyl-2,4,5,6-tetrahydrocyclopenta[c]pyrazol-3-yl)urea: (3R,4S)-4-(3-fluorophenyl)-1-(2,2,2-trifluoroethyl)pyrrolidin-3-amine (10.0 mg, 0.0381 mmol), phenyl 2-phenyl-2,4,5,6-tetrahydrocyclopenta[c]pyrazol-3-ylcarbamate (10.1 mg, 0.0318 mmol) and DIEA (16.6 µL, 0.0953 mmol) were combined in 0.2 mL of DMF and stirred at ambient temperature for 18 hours. The reaction was purified by reverse-phase column chromatography eluting with 0-70% acetonitrile/H$_2$O to provide the title compound (12.5 mg, 80.7% yield). MS (apci) m/z=488.1 (M+H).

Example 205

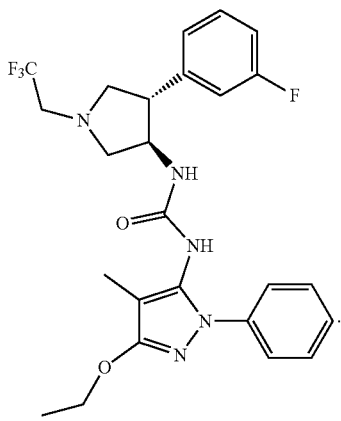 [SMILES: CCOc1nn(-c2ccccc2)c(NC(=O)N[C@H]2CN(CC(F)(F)F)C[C@@H]2c2cccc(F)c2)c1C]

1-(3-ethoxy-4-methyl-1-phenyl-1H-pyrazol-5-yl)-3-((3R,4S)-4-(3-fluorophenyl)-1-(2,2,2-trifluoroethyl)pyrrolidin-3-yl)urea Prepared by the method as described in Example 204, Step H, substituting phenyl 3-ethoxy-4-methyl-1-phenyl-1H-pyrazol-5-ylcarbamate for phenyl 2-phenyl-2,4,5,6-tetrahydrocyclopenta[c]pyrazol-3-ylcarbamate. The material was purified by reverse-phase column chromatography eluting with 0-80% acetonitrile/H$_2$O to provide the title compound (9.3 mg, 58% yield). MS (apci) m/z=476.0 (M+H).

Example 206

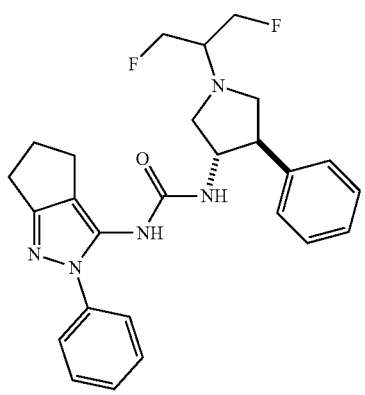

1-((trans)-1-(1,3-difluoropropan-2-yl)-4-phenylpyrrolidin-3-yl)-3-(2-phenyl-2,4,5,6-tetrahydrocyclopenta[c]pyrazol-3-yl)urea Step A: Preparation of tert-butyl (trans)-1-(1,3-difluoropropan-2-yl)-4-phenyl-pyrrolidin-3-ylcarbamate: 1,3-Difluoropropan-2-ol (150.0 mg, 1.561 mmol) was dissolved in DCM (5 mL) and the solution was cooled to 0° C. DIEA (339.9 µL, 1.952 mmol) was added followed by trifluoromethanesulfonic anhydride (197.0 µL, 1.171 mmol). The reaction was stirred at 0° C. for 1 hour and tert-butyl-4-phenylpyrrolidin-3-ylcarbamate (102.4 mg, 0.3903 mmol) was added. The reaction was allowed to warm to ambient temperature over 2 hours, concentrated, loaded onto a samplet using MeOH, and purified by reverse-phase column chromatography eluting with 0-70% acetonitrile/H$_2$O to afford the product (119.0 mg, 89.56% yield). MS (apci) m/z=341.1 (M+H).

Step B: Preparation of (trans)-1-(1,3-difluoropropan-2-yl)-4-phenylpyrrolidin-3-amine hydrochloride: Tert-butyl (trans)-1-(1,3-difluoropropan-2-yl)-4-phenylpyrrolidin-3-ylcarbamate (119 mg, 0.350 mmol) and hydrogen chloride (5 N in isopropanol, 210 µL, 1.05 mmol) were combined in 1 mL of isopropanol and stirred at ambient temperature for 4 hours. The reaction mixture was concentrated in vacuo to afford the product (85.0 mg, 101% yield). MS (apci) m/z=241.1 (M+H).

Step C: Preparation of 1-((trans)-1-(1,3-difluoropropan-2-yl)-4-phenylpyrrolidin-3-yl)-3-(2-phenyl-2,4,5,6-tetrahydrocyclopenta[c]pyrazol-3-yl)urea: (trans)-1-(1,3-Difluoropropan-2-yl)-4-phenylpyrrolidin-3-amine hydrochloride (10.0 mg, 0.0361 mmol), phenyl 2-phenyl-2,4,5,6-tetrahydrocyclopenta[c]pyrazol-3-ylcarbamate (9.62 mg, 0.0301 mmol) and DIEA (15.7 µL, 0.0903 mmol) were combined in 0.2 mL of DMF and stirred at ambient temperature for 18 hours. The reaction mixture was purified by reverse-phase column chromatography eluting with 0-70% acetonitrile/H$_2$O to provide the product (11.3 mg, 80.6% yield). MS (apci) m/z=466.1 (M+H).

Example 207

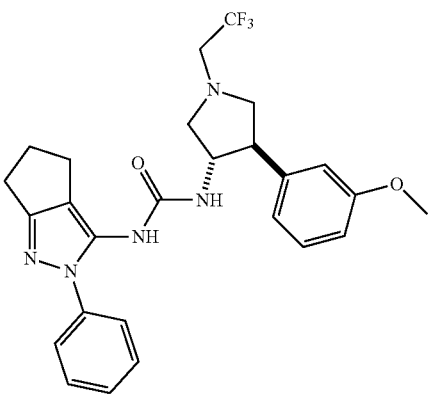

(trans)-tert-butyl 3-(3-methoxyphenyl)-4-(3-(2-phenyl-2,4,5,6-tetrahydrocyclopenta[c]pyrazol-3-yl)ureido)pyrrolidine-1-carboxylate Step A: Preparation of tert-butyl (trans)-1-(1,3-difluoropropan-2-yl)-4-phenylpyrrolidin-3-ylcarbamate: Trans-tert-butyl 3-amino-4-(3-methoxyphenyl) pyrrolidine-1-carboxylate (100.0 mg, 0.3420 mmol), phenyl 2-phenyl-2,4,5,6-tetrahydrocyclopenta[c]pyrazol-3-ylcarbamate (99.30 mg, 0.3109 mmol) and DIEA (162.5 µL, 0.9328 mmol) were combined in 0.2 mL of DMF and stirred at ambient temperature for 1 hour. The reaction mixture was purified by reverse-phase column chromatography eluting with 0-80% acetonitrile/H$_2$O to afford the product (102.0 mg, 63.38% yield). MS (apci) m/z=518.1 (M+H).

Step B: Preparation of 1-((trans)-4-(3-methoxyphenyl)pyrrolidin-3-yl)-3-(2-phenyl-2,4,5,6-tetrahydrocyclopenta[c]pyrazol-3-yl)urea hydrochloride: (Trans)-tert-butyl 3-(3-methoxy-phenyl)-4-(3-(2-phenyl-2,4,5,6-tetrahydrocyclopenta[c]pyrazol-3-yl)ureido) pyrrolidine-1-carboxy-late (102 mg, 0.197 mmol) and hydrogen chloride in isopropanol (118 µL, 0.591 mmol) were combined in 1 mL of isopropanol and stirred at ambient temperature for 4 hours. The reaction was concentrated in vacuo to afford the product (80.0 mg, 97.2% yield). MS (apci) m/z=418.1 (M+H).

Step C: Preparation of 1-((trans)-4-(3-methoxyphenyl)-1-(2,2,2-trifluoroethyl) pyrrolidin-3-yl)-3-(2-phenyl-2,4,5,6-tetrahydrocyclopenta[c]pyrazol-3-yl)urea: 1-((trans)-4-(3-methoxyphenyl)pyrrolidin-3-yl)-3-(2-phenyl-2,4,5,6-tetrahydrocyclopenta[c]pyrazol-3-yl)urea hydrochloride (8.0 mg, 0.018 mmol), 2,2,2-trifluoroethyl trifluoromethanesulfonate (6.1 mg, 0.026 mmol) and DIEA (9.2 µL, 0.053 mmol) were combined in 0.2 mL of DMF and stirred at ambient temperature for 1 hour. The reaction mixture was directly purified by reverse-phase column chromatography eluting with 0-80% acetonitrile/H$_2$O to provide the title compound (6.7 mg, 76% yield). MS (apci) m/z=500.1 (M+H).

Example 208

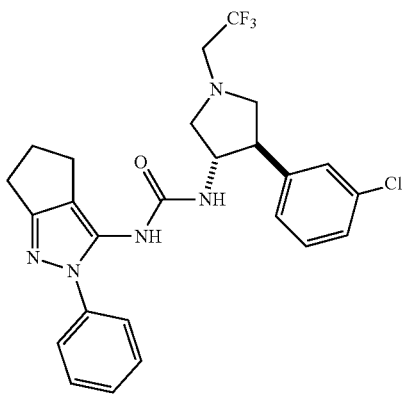

1-((trans)-4-(3-chlorophenyl)-1-(2,2,2-trifluoroethyl)pyrrolidin-3-yl)-3-(2-phenyl-2,4,5,6-tetrahydrocyclopenta[c]pyrazol-3-yl)urea Step A: Preparation of (trans)-tert-butyl 3-(3-chlorophenyl)-4-(3-(2-phenyl-2,4,5,6-tetrahydrocyclopenta[c]pyrazol-3-yl)ureido)pyrrolidine-1-carboxylate: (trans)-1-(tert-Butoxy-carbonyl)-4-(3-chlorophenyl)pyrrolidine-3-carboxylic acid (150 mg, 0.460 mmol), NEt$_3$ (193 μL, 1.38 mmol), and diphenylphosphoryl azide (149 μL, 0.691 mmol) were combined in 2 mL of toluene in a sealed vessel and stirred at 100° C. for 30 minutes. The reaction was cooled and 2-phenyl-2,4,5,6-tetrahydrocyclopenta[c]pyrazol-3-amine (Table 1; 183 mg, 0.921 mmol) was added. The reaction mixture was stirred at 100° C. for 16 hours, cooled, concentrated and purified by reverse-phase column chromatography eluting with 0-60% acetonitrile/H$_2$O to provide the product (42 mg, 18% yield). MS (apci) m/z=522.1 (M+H).

Step B: Preparation of 1-((trans)-4-(3-chlorophenyl)pyrrolidin-3-yl)-3-(2-phenyl-2,4,5,6-tetrahydrocyclopenta[c]pyrazol-3-yl)urea hydrochloride: (trans)-tert-butyl 3-(3-chloro-phenyl)-4-(3-(2-phenyl-2,4,5,6-tetrahydrocyclopenta[c]pyrazol-3-yl)ureido)pyrrolidine-1-carboxy-late (40 mg, 0.077 mmol) and hydrogen chloride in isopropanol (46 μL, 0.23 mmol) were combined in 10.1 mL of IPA and stirred at ambient temperature for 12 hours. The reaction mixture was concentrated in vacuo to afford the product (32 mg, 99% yield). MS (apci) m/z=422.0 (M+H).

Step C: Preparation of 1-((trans)-4-(3-chlorophenyl)-1-(2,2,2-trifluoroethyl) pyrrolidin-3-yl)-3-(2-phenyl-2,4,5,6-tetrahydrocyclopenta[c]pyrazol-3-yl)urea: 1-((trans)-4-(3-Chlorophenyl)pyrrolidin-3-yl)-3-(2-phenyl-2,4,5,6-tetrahydrocyclopenta[c]pyrazol-3-yl)urea hydrochloride (15 mg, 0.033 mmol), 2,2,2-trifluoroethyl trifluoromethanesulfonate (11 mg, 0.049 mmol) and DIEA (17 μL, 0.098 mmol) were combined in 0.2 mL of DMF and stirred at ambient temperature for 1 hour. The reaction mixture was directly purified by reverse-phase column chromatography eluting with 0-80% acetonitrile/H$_2$O to provide the title compound (8.2 mg, 50% yield). MS (apci) m/z=504.0 (M+H).

Example 209

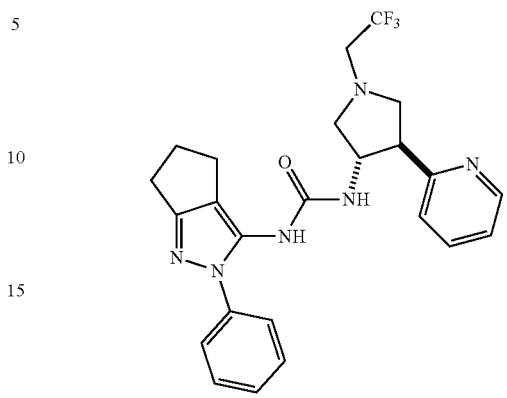

1-(2-phenyl-2,4,5,6-tetrahydrocyclopenta[c]pyrazol-3-yl)-3-((trans)-4-(pyridin-2-yl)-1-(2,2,2-trifluoroethyl)pyrrolidin-3-yl)urea Prepared by the method as described in Example 208, substituted (trans)-1-(tert-butoxycarbonyl)-4-(2-pyridyl)pyrrolidine-3-carboxylic acid for (trans)-1-(tert-butoxycarbonyl)-4-(3-chlorophenyl)pyrrolidine-3-carboxylic acid in Step A. The crude final product was purified by reverse-phase column chromatography eluting with 0-60% acetonitrile/H$_2$O to provide the title compound (4.2 mg, 23% yield for 3 steps). MS (apci) m/z=471.1 (M+H).

Example 210

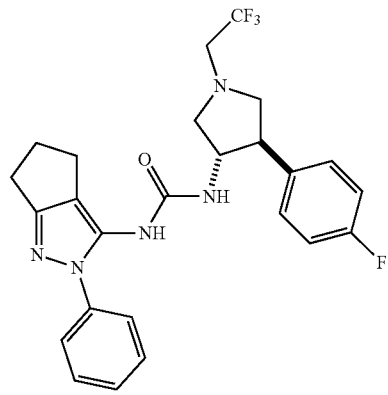

1-((trans)-4-(4-fluorophenyl)-1-(2,2,2-trifluoroethyl)pyrrolidin-3-yl)-3-(2-phenyl-2,4,5,6-tetrahydrocyclopenta[c]pyrazol-3-yl)urea Prepared by the method as described in Example 208, substituting (trans)-1-(tert-butoxycarbonyl)-4-(4-fluorophenyl)pyrrolidine-3-carboxylic acid for (trans)-1-(tert-butoxycarbonyl)-4-(3-chlorophenyl)pyrrolidine-3-carboxylic acid in Step A. The final product was purified by reverse-phase column chromatography eluting with 0-70% acetonitrile/H$_2$O to provide the title compound (10.0 mg, 65% yield for 3 steps). MS (apci) m/z=488.2 (M+H).

Example 211

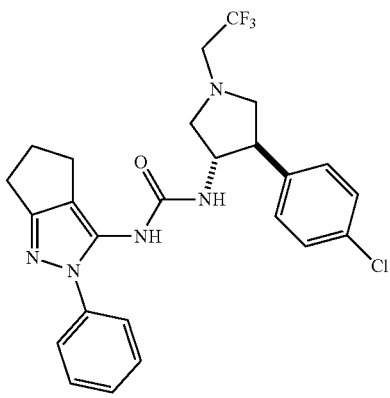

1-((trans)-4-(4-chlorophenyl)-1-(2,2,2-trifluoroethyl)pyrrolidin-3-yl)-3-(2-phenyl-2,4,5,6-tetrahydrocyclopenta[c]pyrazol-3-yl)urea Prepared by the method as described in Example 208, using (trans)-1-(tert-butoxycarbonyl)-4-(4-chlorophenyl)pyrrolidine-3-carboxylic acid instead of (trans)-1-(tert-butoxycarbonyl)-4-(3-chlorophenyl)pyrrolidine-3-carboxylic acid in Step A. The final product was purified by reverse-phase column chromatography eluting with 0-70% acetonitrile/H$_2$O to provide the title compound (7.3 mg, 14% yield for 3 steps). MS (apci) m/z=504.2 (M+H).

Example 212

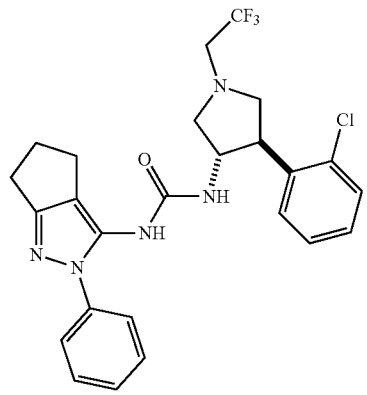

1-((trans)-4-(2-chlorophenyl)-1-(2,2,2-trifluoroethyl)pyrrolidin-3-yl)-3-(2-phenyl-2,4,5,6-tetrahydrocyclopenta[c]pyrazol-3-yl)urea Prepared by the method as described in Example 208, substituting (trans)-1-(tert-butoxycarbonyl)-4-(2-chlorophenyl)pyrrolidine-3-carboxylic acid for (trans)-1-(tert-butoxycarbonyl)-4-(3-chlorophenyl)pyrrolidine-3-carboxylic acid in Step A. The final product was purified by reverse-phase column chromatography eluting with 0-70% acetonitrile/H$_2$O to provide the title compound (5.2 mg, 34% yield for 3 steps). MS (apci) m/z=504.2 (M+H).

Example 213

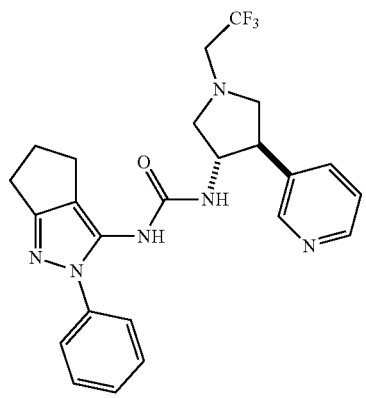

1-(2-phenyl-2,4,56-tetrahydrocyclopenta[c]pyrazol-3-yl)-3-((trans)-4-(pyridin-3-v)-1-(2,2,2-trifluoroethyl)pyrrolidin-3-yl)urea Prepared by the method as described in Example 208, substituting (trans)-1-(tert-butoxycarbonyl)-4-(3-pyridyl)pyrrolidine-3-carboxylic acid for (trans)-1-(tert-butoxycarbonyl)-4-(3-chlorophenyl)pyrrolidine-3-carboxylic acid in Step A. The final product was purified by reverse-phase column chromatography eluting with 0-60% acetonitrile/H$_2$O to provide the title compound (1.2 mg, 8% yield for 3 steps). MS (apci) m/z=471.2 (M+H).

Example 214

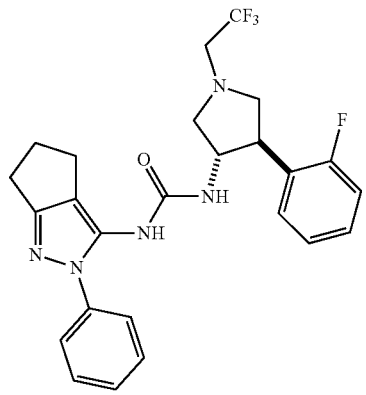

1-((trans)-4-(2-fluorophenyl)-1-(2,2,2-trifluoroethyl)pyrrolidin-3-yl)-3-(2-phenyl-2,4,5,6-tetrahydrocyclopenta[c]pyrazol-3-yl)urea Prepared by the method as described in Example 208, substituting (trans)-1-(tert-butoxycarbonyl)-4-(2-fluorophenyl)pyrrolidine-3-carboxylic acid for (trans)-1-(tert-butoxycarbonyl)-4-(3-chlorophenyl)pyrrolidine-3-carboxylic acid in Step A. The final product was purified by reverse-phase column chromatography eluting with 0-70% acetonitrile/H$_2$O to provide the title compound (7.7 mg, 57% yield for 3 steps). MS (apci) m/z=488.2 (M+H).

Example 215

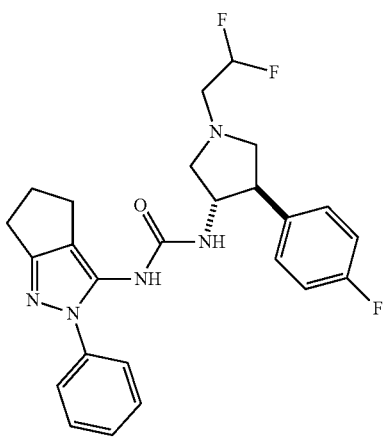

1-((trans)-4-(4-fluorophenyl)-1-(2,2-difluoroethyl)
pyrrolidin-3-yl)-3-(2-phenyl-2,4,5,6-tetrahydrocy-
clopenta[c]pyrazol-3-yl)urea Prepared by the method as described in Example 210, substituting 2,2-difluoroethyl trifluoromethanesulfonate for 2,2,2-trifluoroethyl trifluoromethanesulfonate. The final product was purified by reverse-phase column chromatography eluting with 0-60% acetonitrile/H$_2$O to provide the title compound (4.9 mg, 46% yield for the alkylation). MS (apci) m/z=471.2 (M+H).

Example 216

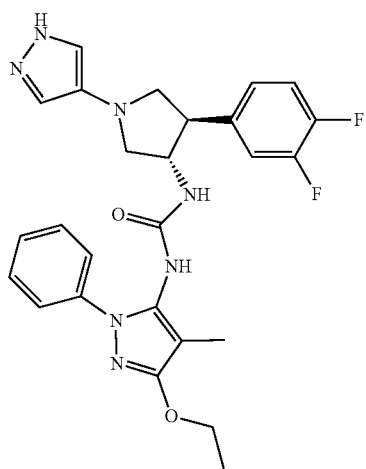 [SMILES: CCOc1nn(-c2ccccc2)c(NC(=O)N[C@@H]2CN(c3cn[nH]c3)C[C@H]2c2ccc(F)c(F)c2)c1C]

1-((3S,4R)-4-(3,4-difluorophenyl)-1-(1H-pyrazol-4-
yl)pyrrolidin-3-yl)-3-(3-ethoxy-4-methyl-1-phenyl-
1H-pyrazol-5-yl)urea Step A: Preparation of 4-iodo-1-(4-methoxybenzyl)-1H-pyrazole: To a solution of 4-iodo-1H-pyrazole (5.54 g, 28.6 mmol) and K$_2$CO$_3$ (4.74 g, 34.3 mmol) in DMF (20 mL) was added 1-(chloromethyl)-4-methoxybenzene (4.67 mL, 34.3 mmol) and stirred at ambient temperature for 2 hours. Ether (80 mL) and water (30 mL) were added. The organic phase was separated, washed with brine and dried over sodium sulfate. After removal of solvent, the residue was purified by silica column chromatography eluting with 25% EtOAc/hexanes to afford the title compound as white solid (8.0 g, 89% yield). $^1$H NMR (d6-DMSO) δ 7.97 (s, 1H), 7.52 (s, 1H), 7.21 (d, 2H), 6.89 (d, 2H), 5.24 (s, 2H), 3.73 (s, 3H).

Step B: Preparation of tert-butyl (3S,4R)-4-(3,4-difluorophenyl)-1-(1-(4-methoxybenzyl)-1H-pyrazol-4-yl)pyrrolidin-3-ylcarbamate: A mixture of tert-butyl (3S,4R)-4-(3,4-difluorophenyl)pyrrolidin-3-ylcarbamate (ACS Scientific, 522 mg, 1.75 mmol), 4-iodo-1-(4-methoxybenzyl)-1H-pyrazole (500 mg, 1.59 mmol), K$_2$CO$_3$ (660 mg, 4.78 mmol), (S)-pyrrolidine-2-carboxylic acid (73.3 mg, 0.637 mmol), and Cu(I)I (60.6 mg, 0.318 mmol) were combined in DMSO (4 mL) in a sealed vessel and heated to 100° C. for 18 hours. The reaction mixture was diluted with DCM (40 mL), washed with H$_2$O (2×20 mL), dried (MgSO$_4$), filtered and concentrated. Purified by silica column chromatography eluting with 1% MeOH/DCM to afford the title compound as a brown oil (376 mg, 49% yield). MS (apci) m/z=485.2 (M+H).

Step C: Preparation of (3S,4R)-4-(3,4-difluorophenyl)-1-(1-(4-methoxybenzyl)-1H-pyrazol-4-yl)pyrrolidin-3-amine dihydrochloride: A solution of tert-butyl (3S,4R)-4-(3,4-difluorophenyl)-1-(1-(4-methoxybenzyl)-1H-pyrazol-4-yl)pyrrolidin-3-ylcarbamate (376 mg, 0.776 mmol) in EtOH (2 mL) and HCl (5-6M in iPrOH) (3.10 mL, 15.5 mmol) was stirred at ambient temperature for 19 hours. Concentrated under vacuum, diluted with Et$_2$O (3×20 mL) and concentrated to afford the product as a greenish-brown solid (401 mg, 113%). MS (apci) m/z=385.2 (M+H).

Step D: Preparation of 1-((3S,4R)-4-(3,4-difluorophenyl)-1-(1-(4-methoxybenzyl)-1H-pyrazol-4-yl)pyrrolidin-3-yl)-3-(3-ethoxy-4-methyl-1-phenyl-1H-pyrazol-5-yl)urea: To a solution of (3S,4R)-4-(3,4-difluorophenyl)-1-(1-(4-methoxybenzyl)-1H-pyrazol-4-yl)pyrrolidin-3-amine dihydrochloride (40 mg, 0.088 mmol) in DIEA (0.061 mL, 0.35 mmol) and DMA (1 mL) was added phenyl 3-ethoxy-4-methyl-1-phenyl-1H-pyrazol-5-ylcarbamate (prepared as in Example 1, Step A starting with Intermediate P135; 29.5 mg, 0.088 mmol) and the reaction mixture as stirred at ambient temperature for 1 hour. The reaction mixture was directly purified by reverse-phase column chromatography, eluting with 5-70% acetonitrile/water to afford the product as a white solid (24 mg, 44% yield). MS (apci) m/z=628.3 (M+H).

Step E: Preparation of 1-((3S,4R)-4-(3,4-difluorophenyl)-1-(1H-pyrazol-4-yl)pyrrolidin-3-yl)-3-(3-ethoxy-4-methyl-1-phenyl-1H-pyrazol-5-yl)urea: A solution of 1-((3S,4R)-4-(3,4-difluorophenyl)-1-(1-(4-methoxybenzyl)-1H-pyrazol-4-yl)pyrrolidin-3-yl)-3-(3-ethoxy-4-methyl-1-phenyl-1H-pyrazol-5-yl)urea (22 mg, 0.035 mmol) in TFA (2 mL) was heated in a pressure tube to 60° C. for 18 hours. The reaction mixture was transferred to a round-bottomed flask, concentrated and azeotroped with toluene (2×10 mL). The crude product was dissolved in MeOH (5 mL), and residual TFA was removed by passing through a polymer-supported resin (StratoSpheres PL-HCO$_3$ MP). The crude product was purified by preparatory TLC (0.5 mm plate, eluted 10% MeOH/DCM) to afford the title compound as an off-white solid (13 mg, 73% yield). MS (apci) m/z=508.2 (M+H).

Example 217

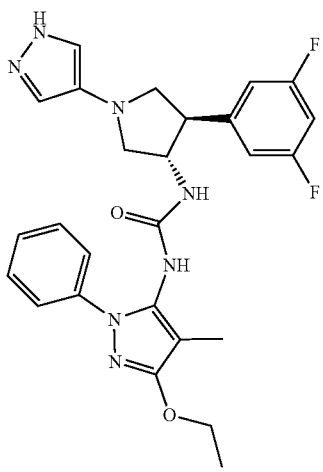 [SMILES: CCOc1nn(-c2ccccc2)c(NC(=O)N[C@@H]2CN(c3cn[nH]c3)C[C@H]2c2cc(F)cc(F)c2)c1C]

1-((3S,4R)-4-(3,5-difluorophenyl)-1-(1H-pyrazol-4-yl)pyrrolidin-3-yl)-3-(3-ethoxy-4-methyl-1-phenyl-1H-pyrazol-5-yl)urea Prepared according to the method described in Example 216, replacing tert-butyl (3S,4R)-4-(3,4-difluorophenyl)pyrrolidin-3-ylcarbamate with tert-butyl (3S,4R)-4-(3,5-difluorophenyl)pyrrolidin-3-ylcarbamate in Step B. MS (apci) m/z=508.2 (M+H).

Example 218

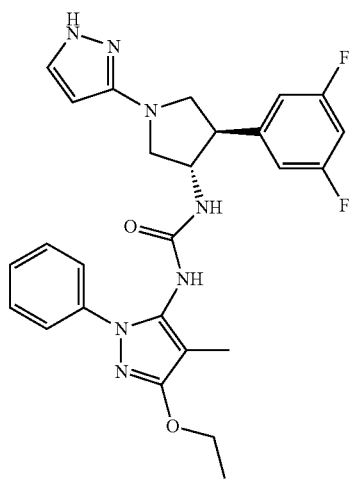 [SMILES: CCOc1nn(-c2ccccc2)c(NC(=O)N[C@@H]2CN(c3cc[nH]n3)C[C@H]2c2cc(F)cc(F)c2)c1C]

1-((3S,4R)-4-(3,5-difluorophenyvl)-1-(1H-pyrazol-3-yl)pyrrolidin-3-yl)-3-(3-ethoxy-4-methyl-1-phenyl-1H-pyrazol-5-yl)urea Prepared according to the method described in Example 216, replacing 4-iodo-1H-pyrazole with 3-iodo-1H-pyrazole in Step A and replacing tert-butyl (3S,4R)-4-(3,4-difluorophenyl)pyrrolidin-3-ylcarbamate with tert-butyl (3S,4R)-4-(3,5-difluorophenyl) pyrrolidin-3-ylcarbamate in Step B. MS (apci) m/z=508.2 (M+H).

Example 219

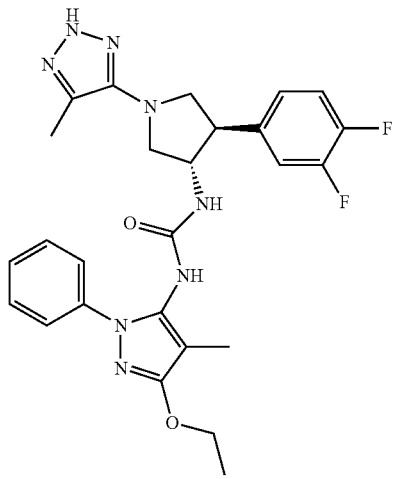 [SMILES: CCOc1nn(-c2ccccc2)c(NC(=O)N[C@@H]2CN(c3n[nH]nc3C)C[C@H]2c2ccc(F)c(F)c2)c1C]

1-((3S,4R)-4-(3,4-difluorophenyl)-1-(3-methyl-1H-pyrazol-4-yl)pyrrolidin-3-yl)-3-(3-ethoxy-4-methyl-1-phenyl-1H-pyrazol-5-yl)urea Prepared according to the method described in Example 216, replacing 4-iodo-1H-pyrazole with 4-iodo-3-methyl-1H-pyrazole in Step A. MS (apci) m/z=522.2 (M+H).

Example 220

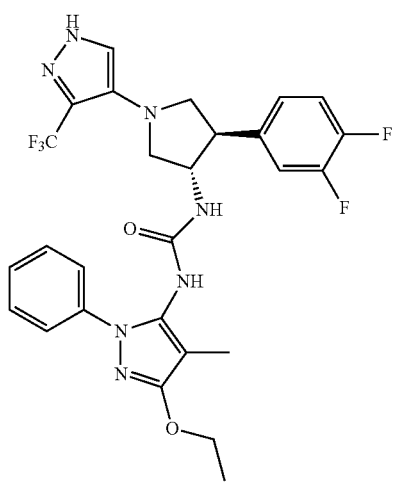 [SMILES: CCOc1nn(-c2ccccc2)c(NC(=O)N[C@@H]2CN(c3c[nH]nc3C(F)(F)F)C[C@H]2c2ccc(F)c(F)c2)c1C]

1-((3S,4R)-4-(3,4-difluorophenyl)-1-(3-(trifluoromethyl)-1H-pyrazol-4-yl)pyrrolidin-3-yl)-3-(3-ethoxy-4-methyl-1-phenyl-1H-pyrazol-5-yl)urea Prepared according to the method described in Example 216, replacing 4-iodo-1H-pyrazole with 4-iodo-3-methyl-1H-pyrazole in Step A. MS (apci) m/z=576.2 (M+H).

Example 221

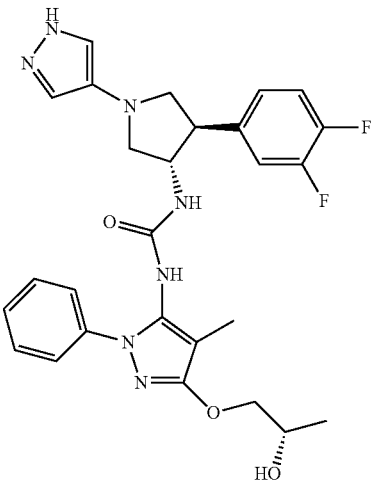 [SMILES: Cc1c(OC[C@H](C)O)nn(-c2ccccc2)c1NC(=O)N[C@@H]1CN(c2cn[nH]c2)C[C@H]1c1ccc(F)c(F)c1]

1-((3S,4R)-4-(3,4-difluorophenyl)-1-(1H-pyrazol-4-yl)pyrrolidin-3-yl)-3-(3-((S)-2-hydroxypropoxy)-4-methyl-1-phenyl-1H-pyrazol-5-yl)urea Step A: Preparation of 1-(3-((S)-2-(tert-butyldimethylsilyloxy)propoxy)-4-methyl-1-phenyl-1H-pyrazol-5-yl)-3-((3S,4R)-4-(3,4-difluorophenyl)-1-(1-(4-methoxybenzyl)-1H-pyrazol-4-yl)pyrrolidin-3-yl)urea: To a solution of (3S,4R)-4-(3,4-difluorophenyl)-1-(1-(4-methoxybenzyl)-1H-pyrazol-4-yl)pyrrolidin-3-amine dihydro-chloride (Example 216, Step C, 35 mg, 0.077 mmol) in DIEA (0.053 mL, 0.31 mmol) and DMA (1 mL) was added (S)-phenyl 3-(2-(tert-butyldimethylsilyloxy)propoxy)-4-methyl-1-phenyl-1H-pyrazol-5-ylcarbamate (prepared as in Example 1, Step A starting with Intermediate P211; 37 mg, 0.077 mmol) and the reaction mixture as stirred at ambient temperature for 1 hour. The reaction mixture was directly purified by reverse-phase column chromatography, eluting with 5-95% acetonitrile/water to afford the product as a white solid (40 mg, 68% yield). MS (apci) m/z=772.4 (M+H).

Step B: Preparation of (S)-1-(5-(3-((3S,4R)-4-(3,4-difluorophenyl)-1-(1H-pyrazol-4-yl)pyrrolidin-3-yl)ureido)-4-methyl-1-phenyl-1H-pyrazol-3-yloxy)propan-2-yl 2,2,2-trifluoro acetate: A solution of 1-(3-((S)-2-(tert-butyldimethylsilyloxy)propoxy)-4-methyl-1-phenyl-1H-pyrazol-5-yl)-3-((3S,4R)-4-(3,4-difluorophenyl)-1-(1-(4-methoxybenzyl)-1H-pyrazol-4-yl)pyrroli-din-3-yl)urea (39 mg, 0.051 mmol) in TFA (2 mL) was heated in a pressure tube to 60° C. for 16 hours. The reaction mixture was transferred to a round-bottomed flask, concentrated and azeotroped with toluene (2×10 mL) to afford the product as a tan solid (32 mg, 99%). MS (apci) m/z=634.2 (M+H).

Step C: Preparation of 1-((3S,4R)-4-(3,4-difluorophenyl)-1-(1H-pyrazol-4-yl)pyrrolidin-3-yl)-3-(3-((S)-2-hydroxypropoxy)-4-methyl-1-phenyl-1H-pyrazol-5-yl)urea: To a solution of (S)-1-(5-(3-((3S,4R)-4-(3,4-difluorophenyl)-1-(1H-pyrazol-4-yl)pyrrolidin-3-yl)ureido)-4-methyl-1-phenyl-1H-pyrazol-3-yloxy)propan-2-yl 2,2,2-trifluoroacetate (32 mg, 0.051 mmol) in MeOH (1 mL) and THF (2 mL) was added 2M aqueous LiOH (0.5 mL, 1.0 mmol). The reaction was stirred at ambient temperature for 3 hours, diluted with H₂O (20 mL), extracted 10:90 MeOH/DCM (2×20 mL) and the combined organic phases were dried (MgSO₄), filtered and concentrated under reduced pressure. Purified by silica column chromatography eluting with 10% MeOH/DCM to afford the title compound as a white solid (19 mg, 72% yield). MS (apci) m/z=538.2 (M+H).

Example 222

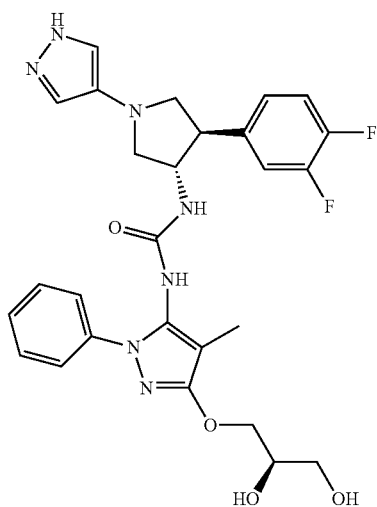 [SMILES: Cc1c(OC[C@H](O)CO)nn(-c2ccccc2)c1NC(=O)N[C@@H]1CN(c2cn[nH]c2)C[C@H]1c1ccc(F)c(F)c1]

1-((3S,4R)-4-(3,4-difluorophenyl)-1-(1H-pyrazol-4-yl)pyrrolidin-3-yl)-3-(3-((R)-2,3-dihydroxypropoxy)-4-methyl-1-phenyl-1H-pyrazol-5-yl)urea Prepared according to the method described in Example 221 replacing (S)-phenyl 3-(2-(tert-butyldimethylsilyloxy) propoxy)-4-methyl-1-phenyl-1H-pyrazol-5-ylcarbamate with (S)-phenyl 3-((2,2-dimethyl-1,3-dioxolan-4-yl) methoxy)-4-methyl-1-phenyl-1H-pyrazol-5-ylcarbamate (prepared as in Example 1, Step A starting with Intermediate P209) in Step A. MS (apci) m/z=554.2 (M+H).

The compounds in the following table were prepared according to the method of Example 216, substituting the appropriate starting material in Steps A and B and substituting the appropriate pyrazole intermediate in Step D.

| Ex. # | Structure | Name | MS (apci) m/z |
|---|---|---|---|
| 223 | 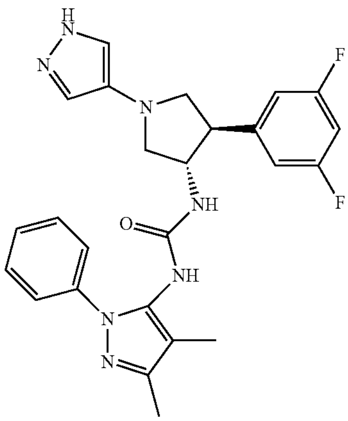 [SMILES: Cc1nn(-c2ccccc2)c(NC(=O)N[C@@H]2CN(c3cn[nH]c3)C[C@H]2c2cc(F)cc(F)c2)c1C] | 1-((3S,4R)-4-(3,5-difluoro-phenyl)-1-(1H-pyrazol-4-yl)pyrrolidin-3-yl)-3-(3,4-dimethyl-1-phenyl-1H-pyrazol-5-yl)urea | 478.2 (M + H) |
| 224 | 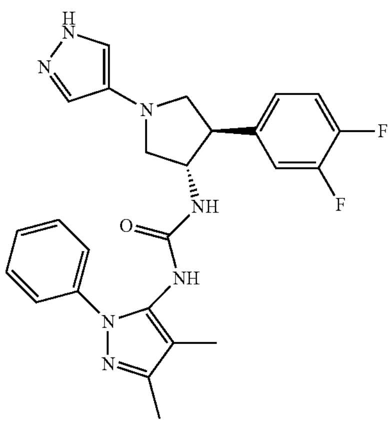 [SMILES: Cc1nn(-c2ccccc2)c(NC(=O)N[C@@H]2CN(c3cn[nH]c3)C[C@H]2c2ccc(F)c(F)c2)c1C] | 1-((3S,4R)-4-(3,4-difluorophenyl)-1-(1H-pyrazol-4-yl)pyrrolidin-3-yl)-3-(3,4-dimethyl-1-phenyl-1H-pyrazol-5-yl)urea | 478.2 (M + H) |
| 225 | 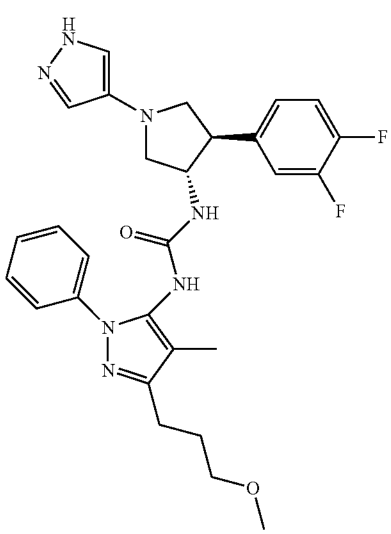 [SMILES: COCCCc1nn(-c2ccccc2)c(NC(=O)N[C@@H]2CN(c3cn[nH]c3)C[C@H]2c2ccc(F)c(F)c2)c1C] | 1-((3S,4R)-4-(3,4-difluorophenyl)-1-(1H-pyrazol-4-yl)pyrrolidin-3-yl)-3-(3-(3-methoxypropyl)-4-methyl-1-phenyl-1H-pyrazol-5-yl)urea | 536.3 (M + H) |

| Ex. # | Structure | Name | MS (apci) m/z |
|---|---|---|---|
| 226 | 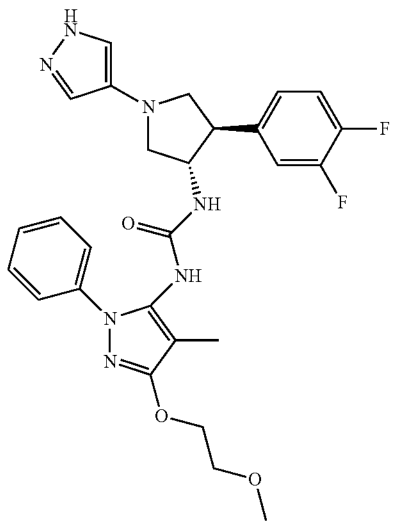 [SMILES: COCCOc1nn(-c2ccccc2)c(NC(=O)N[C@@H]2CN(c3cn[nH]c3)C[C@H]2c2ccc(F)c(F)c2)c1C] | 1-((3S,4R)-4-(3,4-difluorophenyl)-1-(1H-pyrazol-4-yl)pyrrolidin-3-yl)-3-(3-(2-methoxyethoxy)-4-methyl-1-phenyl-1H-pyrazol-5-yl)urea | 538.2 (M + H) |
| 227 | 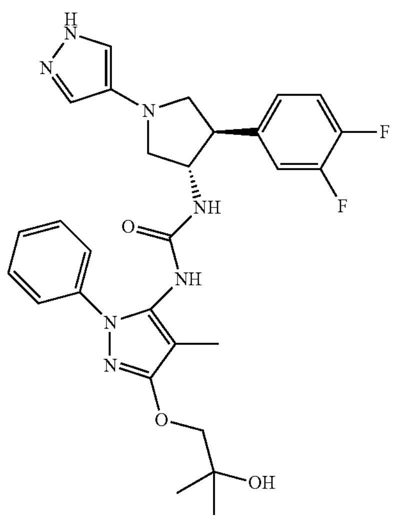 [SMILES: Cc1c(OCC(C)(C)O)nn(-c2ccccc2)c1NC(=O)N[C@@H]1CN(c2cn[nH]c2)C[C@H]1c1ccc(F)c(F)c1] | 1-((3S,4R)-4-(3,4-difluorophenyl)-1-(1H-pyrazol-4-yl)pyrrolidin-3-yl)-3-(3-(2-hydroxy-2-methylpropoxy)-4-methyl-1-phenyl-1H-pyrazol-5-yl)urea | 552.2 (M + H) |
| 228 | 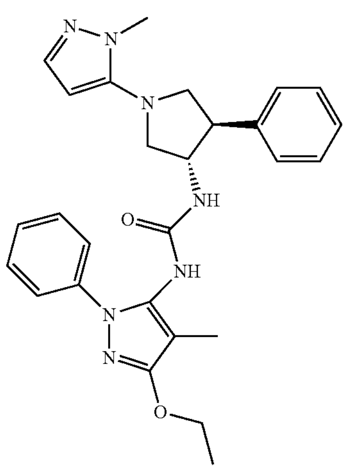 [SMILES: CCOc1nn(-c2ccccc2)c(NC(=O)N[C@@H]2CN(c3ccnn3C)C[C@H]2c2ccccc2)c1C] | 1-(3-ethoxy-4-methyl-1-phenyl-1H-pyrazol-5-yl)-3-((3S,4R)-1-(1-methyl-1H-pyrazol-5-yl)-4-phenylpyrrolidin-3-yl)urea | 486.3 (M + H) |

| Ex. # | Structure | Name | MS (apci) m/z |
|---|---|---|---|
| 229 | 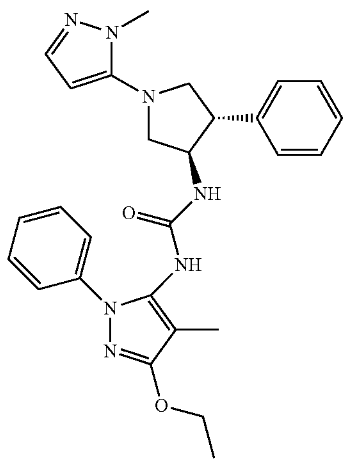 [SMILES: CCOc1nn(-c2ccccc2)c(NC(=O)N[C@H]2CN(c3ccnn3C)C[C@@H]2c2ccccc2)c1C] | 1-(3-ethoxy-4-methyl-1-phenyl-1H-pyrazol-5-yl)-3-((3R,4S)-1-(1-methyl-1H-pyrazol-5-yl)-4-phenylpyrrolidin-3-yl)urea | 486.3 (M + H) |
| 230 | 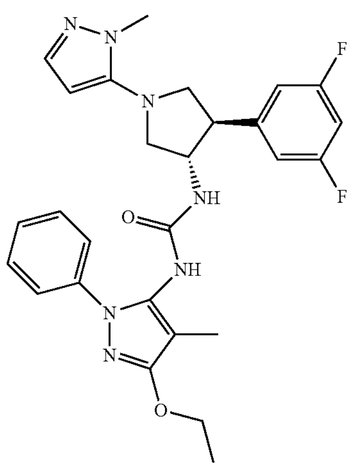 [SMILES: CCOc1nn(-c2ccccc2)c(NC(=O)N[C@@H]2CN(c3ccnn3C)C[C@H]2c2cc(F)cc(F)c2)c1C] | 1-((3S,4R)-4-(3,5-difluorophenyl)-1-(1-methyl-1H-pyrazol-5-yl)pyrrolidin-3-yl)-3-(3-ethoxy-4-methyl-1-phenyl-1H-pyrazol-5-yl)urea | 522.2 (M + H) |
| 231 | 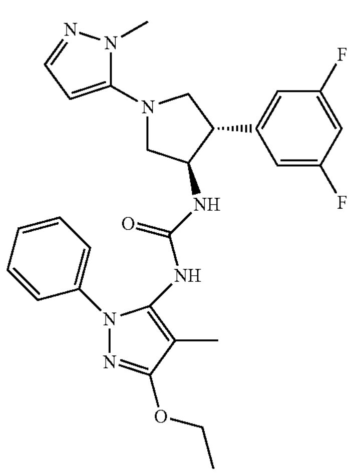 [SMILES: CCOc1nn(-c2ccccc2)c(NC(=O)N[C@H]2CN(c3ccnn3C)C[C@@H]2c2cc(F)cc(F)c2)c1C] | 1-((3R,4S)-4-(3,5-difluorophenyl)-1-(1-methyl-1H-pyrazol-5-yl)pyrrolidin-3-yl)-3-(3-ethoxy-4-methyl-1-phenyl-1H-pyrazol-5-yl)urea | 522.2 (M + H) |

-continued

| Ex. # | Structure | Name | MS (apci) m/z |
|---|---|---|---|
| 232 | 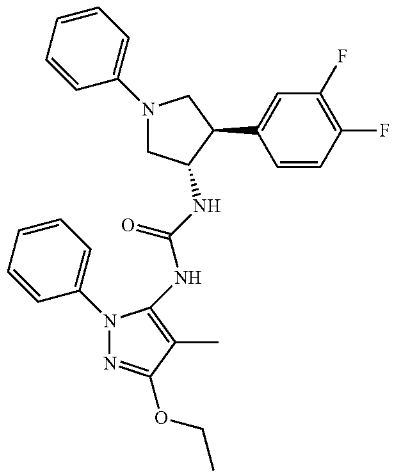 [SMILES: CCOc1nn(-c2ccccc2)c(NC(=O)N[C@@H]2CN(c3ccccc3)C[C@H]2c2ccc(F)c(F)c2)c1C] | 1-((3S,4R)-4-(3,4-difluorophenyl)-1-phenylpyrrolidin-3-yl)-3-(3-ethoxy-4-methyl-1-phenyl-1H-pyrazol-5-yl)urea | 518.2 (M + H) |
| 233 | 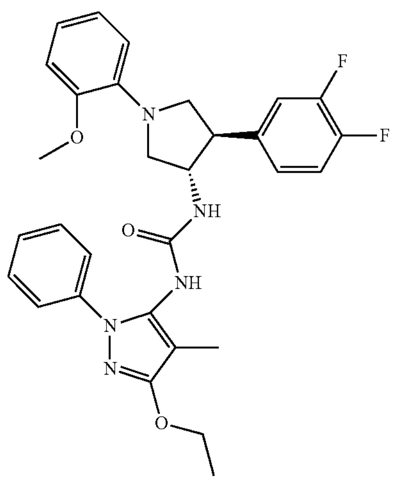 [SMILES: CCOc1nn(-c2ccccc2)c(NC(=O)N[C@@H]2CN(c3ccccc3OC)C[C@H]2c2ccc(F)c(F)c2)c1C] | 1-((3S,4R)-4-(3,4-difluorophenyl)-1-(2-methoxyphenyl)pyrrolidin-3-yl)-3-(3-ethoxy-4-methyl-1-phenyl-1H-pyrazol-5-yl)urea | 548.3 (M + H) |
| 234 | 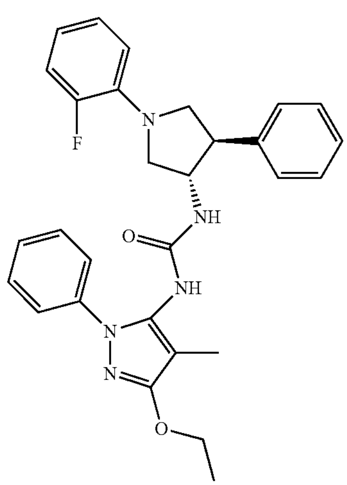 [SMILES: CCOc1nn(-c2ccccc2)c(NC(=O)N[C@@H]2CN(c3ccccc3F)C[C@H]2c2ccccc2)c1C] | 1-(3-ethoxy-4-methyl-1-phenyl-1H-pyrazol-5-yl)-3-((3S,4R)-1-(2-fluorophenyl)-4-phenylpyrrolidin-3-yl)urea | 500.2 (M + H) |

-continued

| Ex. # | Structure | Name | MS (apci) m/z |
|---|---|---|---|
| 235 | 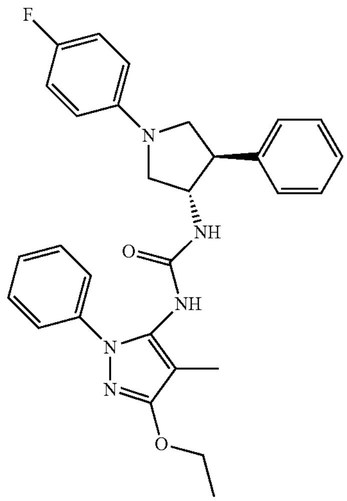 [SMILES: CCOc1nn(-c2ccccc2)c(NC(=O)N[C@@H]2CN(c3ccc(F)cc3)C[C@H]2c2ccccc2)c1C] | 1-(3-ethoxy-4-methyl-1-phenyl-1H-pyrazol-5-yl)-3-((3S,4R)-1-(4-fluorophenyl)-4-phenylpyrrolidin-3-yl)urea | 500.2 (M + H) |
| 236 | 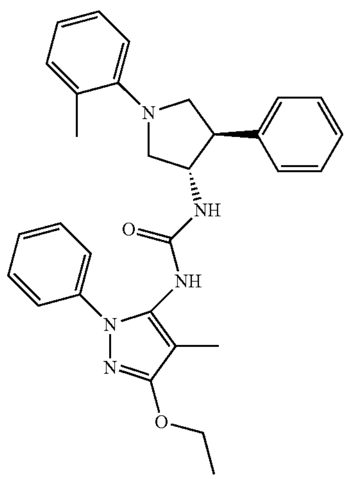 [SMILES: CCOc1nn(-c2ccccc2)c(NC(=O)N[C@@H]2CN(c3ccccc3C)C[C@H]2c2ccccc2)c1C] | 1-(3-ethoxy-4-methyl-1-phenyl-1H-pyrazol-5-yl)-3-((3S,4R)-1-(2-methylphenyl)-4-phenylpyrrolidin-3-yl)urea | 496.3 (M + H) |
| 237 | 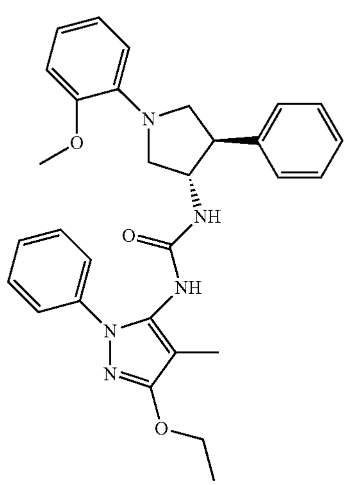 [SMILES: CCOc1nn(-c2ccccc2)c(NC(=O)N[C@@H]2CN(c3ccccc3OC)C[C@H]2c2ccccc2)c1C] | 1-(3-ethoxy-4-methyl-1-phenyl-1H-pyrazol-5-yl)-3-((3S,4R)-1-(2-methoxyphenyl)-4-phenylpyrrolidin-3-yl)urea | 512.3 (M + H) |

| Ex. # | Structure | Name | MS (apci) m/z |
|---|---|---|---|
| 238 | 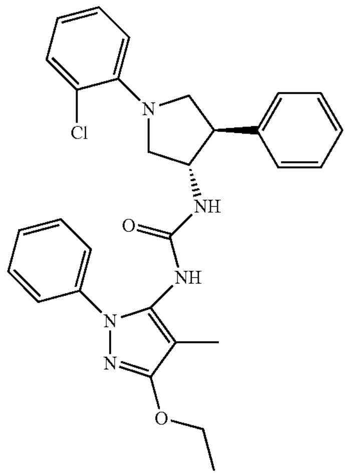 [SMILES: CCOc1nn(-c2ccccc2)c(NC(=O)N[C@@H]2CN(c3ccccc3Cl)C[C@H]2c2ccccc2)c1C] | 1-(3-ethoxy-4-methyl-1-phenyl-1H-pyrazol-5-yl)-3-((3S,4R)-1-(2-chlorophenyl)-4-phenylpyrrolidin-3-yl)urea | 516.3 (M + H) |
| 239 | 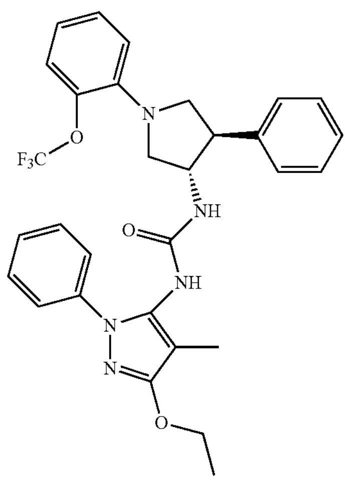 [SMILES: CCOc1nn(-c2ccccc2)c(NC(=O)N[C@@H]2CN(c3ccccc3OC(F)(F)F)C[C@H]2c2ccccc2)c1C] | 1-(3-ethoxy-4-methyl-1-phenyl-1H-pyrazol-5-yl)-3-((3S,4R)-4-phenyl-1-(2-(trifluoromethoxy)phenyl)pyrrolidin-3-yl)urea | 566.2 (M + H) |
| 240 | 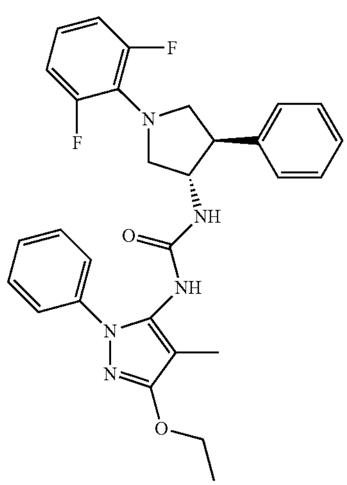 | 1-((3S,4R)-1-(2,6-difluorophenyl)-4-phenylpyrrolidin-3-yl)-3-(3-ethoxy-4-methyl-1-phenyl-1H-pyrazol-5-yl)urea | 566.2 (M + H) |

| Ex. # | Structure | Name | MS (apci) m/z |
|---|---|---|---|
| 241 | 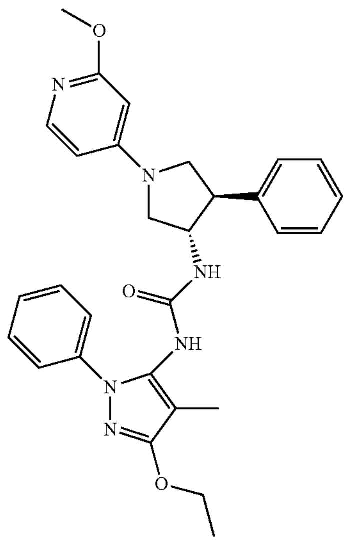 | 1-(3-ethoxy-4-methyl-1-phenyl-1H-pyrazol-5-yl)-3-((3S,4R)-1-(2-methoxypyridin-4-yl)-4-phenylpyrrolidin-3-yl)urea | 487.2 (M + H) |
| 242 | 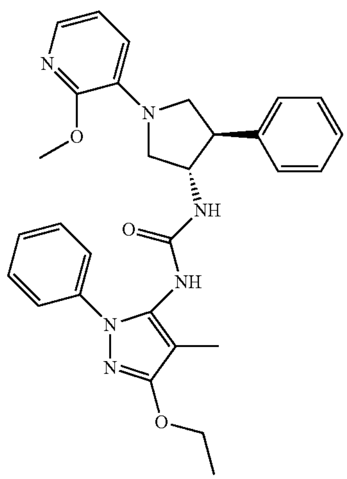 [SMILES: CCOc1nn(-c2ccccc2)c(NC(=O)N[C@@H]2CN(c3cccnc3OC)C[C@H]2c2ccccc2)c1C] | 1-(3-ethoxy-4-methyl-1-phenyl-1H-pyrazol-5-yl)-3-((3S,4R)-1-(2-methoxypyridin-3-yl)-4-phenylpyrrolidin-3-yl)urea | 513.3 (M + H) |
| 243 | 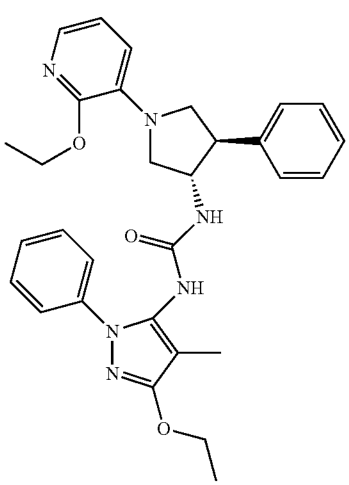 [SMILES: CCOc1ncccc1N1C[C@@H](NC(=O)Nc2c(C)c(OCC)nn2-c2ccccc2)[C@H](c2ccccc2)C1] | 1-(3-ethoxy-4-methyl-1-phenyl-1H-pyrazol-5-yl)-3-((3S,4R)-1-(2-ethoxypyridin-3-yl)-4-phenylpyrrolidin-3-yl)urea | 527.2 (M + H) |

| Ex. # | Structure | Name | MS (apci) m/z |
|---|---|---|---|
| 244 | 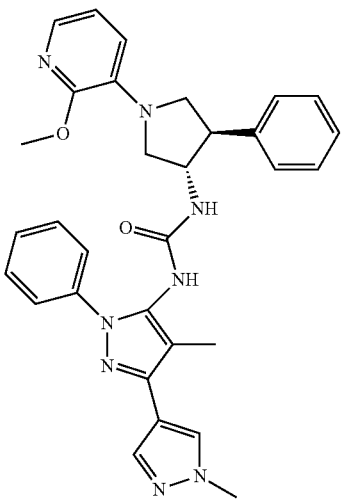 | 1-(1',4-dimethyl-1-phenyl-1H,1'H-[3,4'-bipyrazol]-5-yl)-3-((3S,4R)-1-(2-methoxypyridin-3-yl)-4-phenylpyrrolidin-3-yl)urea | 513.2 (M + H) |
| 245 | 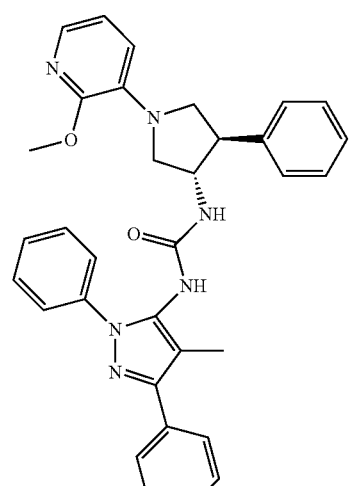 | 1-((3S,4R)-1-(2-methoxypyridin-3-yl)-4-phenylpyrrolidin-3-yl)-3-(4-methyl-1,3-diphenyl-1H-pyrazol-5-yl)urea | 545.3 (M + H) |
| 246 | 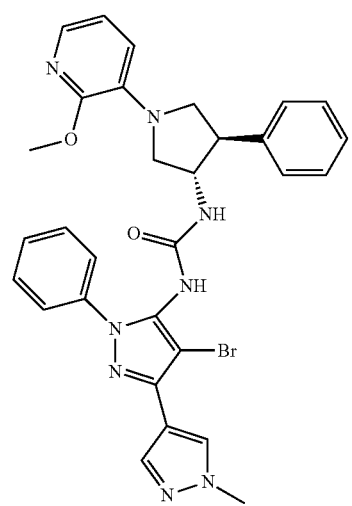 [SMILES: COc1ncccc1N1C[C@@H](NC(=O)Nc2c(Br)c(-c3cnn(C)c3)nn2-c2ccccc2)[C@H](c2ccccc2)C1] | 1-(4-bromo-1'-methyl-1-phenyl-1H,1'H-[3,4'-bipyrazol]-5-yl)-3-((3S,4R)-1-(2-methoxypyridin-3-yl)-4-phenylpyrrolidin-3-yl)urea | 613.2 (M + H) |

| Ex. # | Structure | Name | MS (apci) m/z |
|---|---|---|---|
| 247 | 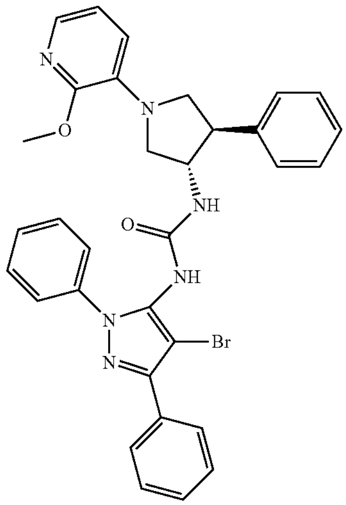 [SMILES: COc1ncccc1N1C[C@@H](NC(=O)Nc2c(Br)c(-c3ccccc3)nn2-c2ccccc2)[C@H](c2ccccc2)C1] | 1-(4-bromo-1,3-diphenyl-1H-pyrazol-5-yl)-3-((3S,4R)-1-(2-methoxypyridin-3-yl)-4-phenylpyrrolidin-3-yl)urea | 611.2 (M + H) |

Example 248

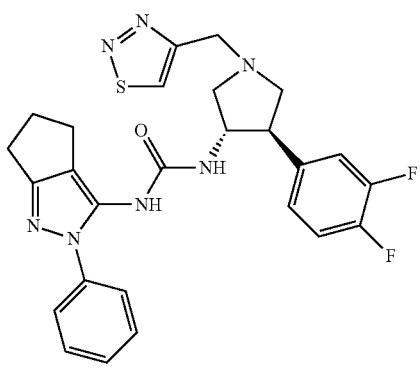 [SMILES: O=C(Nc1c2c(nn1-c1ccccc1)CCC2)N[C@@H]1CN(Cc2csnn2)C[C@H]1c1ccc(F)c(F)c1]

1-((3S,4R)-1-((1,2,3-thiadiazol-4-yl)methyl)-4-(3,4-difluorophenyl)pyrrolidin-3-yl)-3-(2-phenyl-2,4,5,6-tetrahydrocyclopenta[c]pyrazol-3-yl)urea Step A: Preparation of tert-butyl ((3S,4R)-1-((1,2,3-thiadiazol-4-yl)methyl)-4-(3,4-difluorophenyl)pyrrolidin-3-yl)carbamate: Tert-butyl (3S,4R)-4-(3,4-difluorophenyl)pyrrolidin-3-ylcarbamate (150 mg, 0.503 mmol), 1,2,3-thiadiazole-4-carbaldehyde (68.9 mg, 0.603 mmol) and DIEA (186 µL, 1.01 mmol) were combined in 1 mL of DCM and stirred at ambient temperature for 30 minutes. Sodium triacetoxyborohydride (213 mg, 1.01 mmol) was added and the reaction was stirred at ambient temperature overnight and concentrated. The crude material was purified by reverse-phase column chromatography, eluting with 0-50% acetonitrile/water to afford the product (168 mg, 0.424 mmol, 84.3% yield). MS (apci) m/z=397.1 (M+H).

Step B: Preparation of (3S,4R)-1-((1,2,3-thiadiazol-4-yl)methyl)-4-(3,4-difluorophenyl)pyrrolidin-3-amine dihydrochloride: tert-butyl (3S,4R)-1-((1,2,3-thiadiazol-4-yl)methyl)-4-(3,4-difluorophenyl)pyrrolidin-3-ylcarbamate (150 mg, 0.378 mmol) and 5N HCl in IPA (378 µl, 1.89 mmol) were combined in 1 mL of IPA and left to stand at ambient temperature overnight. The reaction was concentrated to afford the product (140 mg, 0.379 mmol, 100% yield). MS (apci) m/z=297.0 (M+H).

Step C: Preparation of 1-((3S,4R)-1-((1,2,3-thiadiazol-4-yl)methyl)-4-(3,4-difluorophenyl)pyrrolidin-3-yl)-3-(2-phenyl-2,4,5,6-tetrahydrocyclopenta[c]pyrazol-3-yl)urea. (3S,4R)-1-((1,2,3-thiadiazol-4-yl)methyl)-4-(3,4-difluorophenyl)pyrrolidin-3-amine dihydrochloride (20 mg, 0.054 mmol), phenyl 2-phenyl-2,4,5,6-tetrahydro-cyclopenta[c]pyrazol-3-ylcarbamate (16 mg, 0.049 mmol, prepared as described for Example 38, step E) and DIEA (26 µl, 0.15 mmol) were combined in 0.2 mL of DMF and stirred at ambient temperature for 1 hour. The reaction was loaded onto a samplet and purified by reverse-phase column chromatography, eluting with 0-80% acetonitrile/water, to afford the title compound (24 mg, 0.046 mmol, 93% yield). MS (apci) m/z=522.2 (M+H).

Example 249

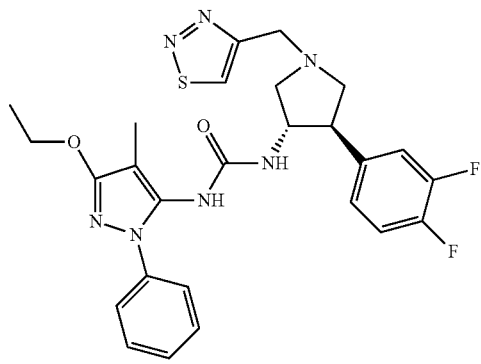 [SMILES: CCOc1nn(-c2ccccc2)c(NC(=O)N[C@@H]2CN(Cc3csnn3)C[C@H]2c2ccc(F)c(F)c2)c1C]

1-((3S,4R)-1-((1,2,3-thiadiazol-4-yl)methyl)-4-(3,4-difluorophenyl)pyrrolidin-3-yl)-3-(3-ethoxy-4-methyl-1-phenyl-1H-pyrazol-5-yl)urea Prepared by the method as described in Example 216, Step C using phenyl 3-ethoxy-4-methyl-1-phenyl-1H-pyrazol-5-ylcarbamate (which was prepared according to the method of Example 1, Step A, starting with Intermediate P135) instead of phenyl 2-phenyl-2,4,5,6-tetrahydrocyclopenta[c]pyrazol-3-ylcarbamate. The material was purified by reverse-phase column chromatography using 0-80% acetonitrile/H$_2$O as the eluent to provide the title compound (23 mg, 0.043 mmol, 87% yield). MS (apci) m/z=540.2 (M+H).

Example 250

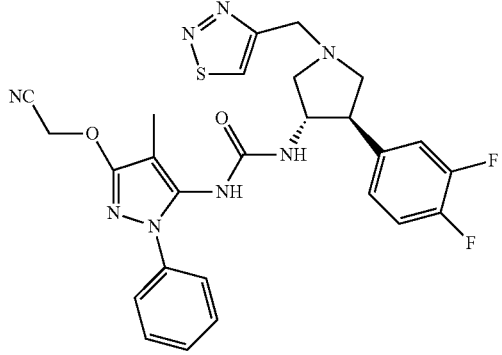 [SMILES: Cc1c(OCC#N)nn(-c2ccccc2)c1NC(=O)N[C@@H]1CN(Cc2csnn2)C[C@H]1c1ccc(F)c(F)c1]

1-((3S,4R)-1-((1,2,3-thiadiazol-4-yl)methyl)-4-(3,4-difluorophenyl)pyrrolidin-3-yl)-3-(3-(cyanomethoxy)-4-methyl-1-phenyl-1H-pyrazol-5-yl)urea Prepared by the method as described in Example 216, Step C, using phenyl 3-(cyanomethoxy)-4-methyl-1-phenyl-1H-pyrazol-5-ylcarbamate instead of phenyl 2-phenyl-2,4,5,6-tetrahydrocyclopenta[c]pyrazol-3-ylcarbamate. The material was purified by reverse-phase column chromatography using 0-80% acetonitrile/H$_2$O as the eluent to provide the title compound (3.4 mg, 0.0062 mmol, 50% yield). MS (apci) m/z=551.2 (M+H).

Example 251

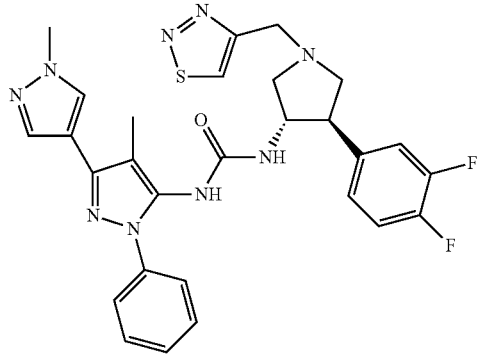 [SMILES: Cc1c(-c2cnn(C)c2)nn(-c2ccccc2)c1NC(=O)N[C@@H]1CN(Cc2csnn2)C[C@H]1c1ccc(F)c(F)c1]

1-((3S,4R)-1-((1,2,3-thiadiazol-4-yl)methyl)-4-(3,4-difluorophenyl)pyrrolidin-3-yl)-3-(1',4-dimethyl-1-phenyl-1H, 1'H-3,4'-bipyrazol-5-yl)urea Prepared by the method as described in Example 216, Step C, using phenyl 1',4-dimethyl-1-phenyl-1H, 1'H-3,4'-bipyrazol-5-ylcarbamate (9.2 mg, 0.025 mmol) instead of phenyl 2-phenyl-2,4,5,6-tetrahydrocyclopenta[c]pyrazol-3-ylcarbamate. The material was purified by reverse-phase column chromatography using 0-70% acetonitrile/H$_2$O as the eluent to provide the title compound (4.2 mg, 0.0073 mmol, 30% yield). MS (apci) m/z=576.2 (M+H).

Example 252

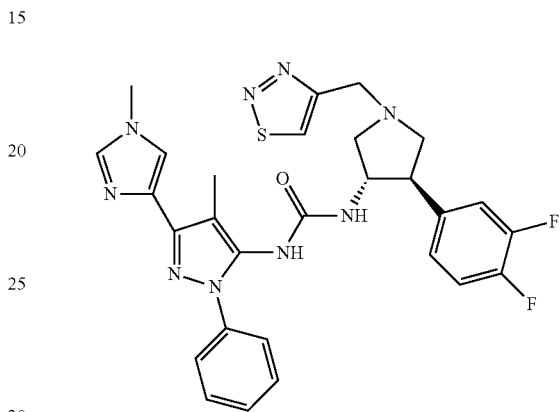

1-((3S,4R)-1-((1,2,3-thiadiazol-4-yl)methyl)-4-(3,4-difluorophenyl)pyrrolidin-3-yl)-3-(4-methyl-3-(1-methyl-1H-imidazol-4-yl)-1-phenyl-1H-pyrazol-5-yl)urea Prepared by the method as described in Example 216, Step C, using 1-methyl-4-(4-methyl-5-(phenoxycarbonylamino)-1-phenyl-1H-pyrazol-3-yl)-3-(phenoxycarbonyl)-1H-imidazol-3-ium chloride instead of phenyl 2-phenyl-2,4,5,6-tetrahydrocyclopenta[c]pyrazol-3-ylcarbamate and adding an extra equivalent of (3S,4R)-1-((1,2,3-thiadiazol-4-yl)methyl)-4-(3,4-difluorophenyl)pyrrolidin-3-amine dihydrochloride. The material was purified by reverse-phase column chromatography using 0-80% acetonitrile/H$_2$O as the eluent to provide the title compound (6.2 mg, 0.011 mmol, 42% yield). MS (apci) m/z=576.2 (M+H).

Example 253

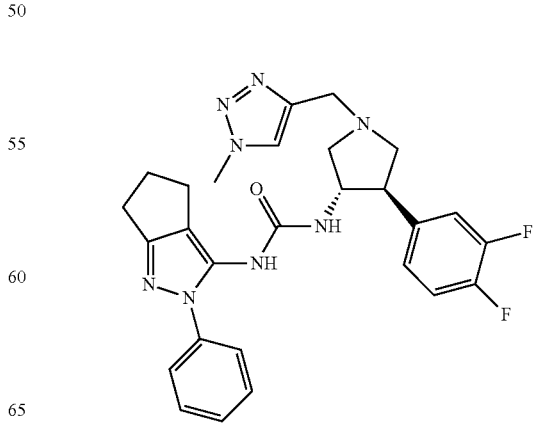

1-((3S,4R)-4-(3,4-difluorophenyl)-1-((1-methyl-1H-1,2,3-triazol-4-yl)methyl)pyrrolidin-3-yl)-3-(2-phenyl-2,4,5,6-tetrahydrocyclopenta[c]pyrazol-3-yl)urea Prepared by the method as described in Example 216, using 1-methyl-1H-1,2,3-triazole-4-carbaldehyde instead of 1,2,3-thiadiazole-4-carbaldehyde in Step A. The final product was purified by reverse-phase column chromatography using 0-80% acetonitrile/H$_2$O as the eluent to provide the title compound (17 mg, 0.033 mmol, 76% yield for 3 steps). MS (apci) m/z=519.2 (M+H).

Example 254

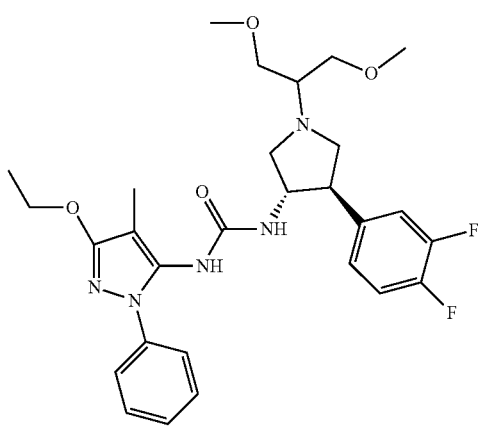 [SMILES: CCOc1nn(-c2ccccc2)c(NC(=O)N[C@@H]2CN(C(COC)COC)C[C@H]2c2ccc(F)c(F)c2)c1C]

1-((3S,4R)-4-(3,4-difluorophenyl)-1-(1,3-dimethoxypropan-2-yl)pyrrolidin-3-yl)-3-(3-ethoxy-4-methyl-1-phenyl-1H-pyrazol-5-yl)urea Prepared by the method as described in Example 249, using 1,3-dimethoxypropan-2-one instead of 1,2,3-thiadiazole-4-carbaldehyde in Step A. The final product was purified by reverse-phase column chromatography using 5-80% acetonitrile/H$_2$O as the eluent to provide the title compound (17.3 mg, 0.0318 mmol, 57.4% yield for 3 steps). MS (apci) m/z=544.3 (M+H).

Example 255

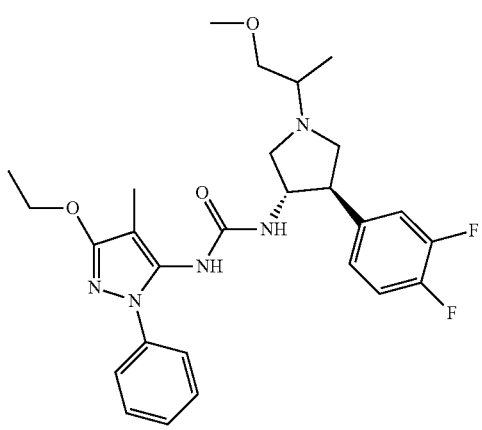 [SMILES: CCOc1nn(-c2ccccc2)c(NC(=O)N[C@@H]2CN(C(C)COC)C[C@H]2c2ccc(F)c(F)c2)c1C]

1-((3S,4R)-4-(3,4-difluorophenyl)-1-(1-methoxypropan-2-yl)pyrrolidin-3-yl)-3-(3-ethoxy-4-methyl-1-phenyl-1H-pyrazol-5-yl)urea Prepared by the method as described in Example 249, using 1-methoxypropan-2-one instead of 1,2,3-thiadiazole-4-carbaldehyde in Step A. The final product was purified by reverse-phase column chromatography using 0-80% acetonitrile/H$_2$O as the eluent to provide the title compound (8.2 mg, 0.016 mmol, 70.1% yield for 3 steps). MS (apci) m/z=514.3 (M+H).

Example 256

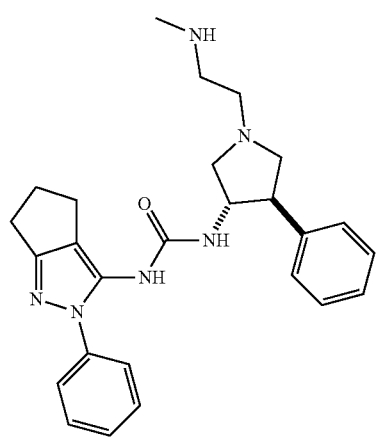

1-((trans)-4-(4-fluorophenyl)-1-(2-(methylamino)ethyl)pyrrolidin-3-yl)-3-(2-phenyl-2,4,5,6-tetrahydrocyclopenta[c]pyrazol-3-yl)urea 1-((3S,4R)-4-(4-fluorophenyl)pyrrolidin-3-yl)-3-(2-phenyl-2,4,5,6-tetrahydro-cyclopenta[c]pyrazol-3-yl)urea hydrochloride (11 mg, 0.0249 mmol, prepared as for Example 210), 2-iodo-N-methyl-N-tritylethanamine (19.1 mg, 0.0448 mmol) and DIEA (9.65 mg, 0.0747 mmol) were combined in 0.2 mL od DMF and stirred at ambient temperature overnight. HCl (7N in IPA, 35.6 µL, 0.249 mmol) was added and the reaction was stirred at ambient temperature for 4 hours. 1N NaOH (2 mL) was added and the reaction was extracted with several portions of DCM in a phase separator frit. The combined organic extracts were concentrated and purified by reverse-phase column chromatography using 0-60% acetonitrile/H$_2$O as the eluent to provide the title compound (2.2 mg, 0.00476 mmol, 19.1% yield). MS (apci) m/z=463.3 (M+H).

Example 257

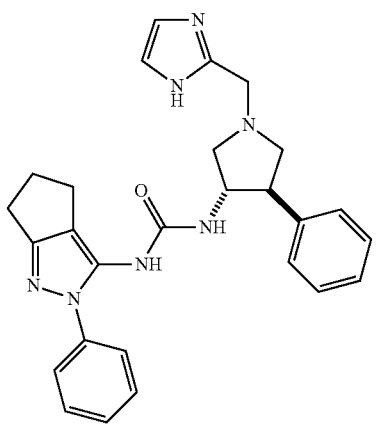

1-((trans)-1-((1H-imidazol-2-yl)methyl)-4-phenylpyrrolidin-3-yl)-3-(2-phenyl-2,4,5,6-tetrahydrocyclopenta[c]pyrazol-3-yl)urea 1-(2-phenyl-2,4,5,6-tetrahydrocyclopenta[c]pyrazol-3-yl)-3-((trans)-4-phenyl-pyrrolidin-3-yl)urea (15 mg, 0.039 mmol, prepared as described in Example 182, Step B), 2-(chloromethyl)-1H-imidazole hydrochloride (5.9 mg, 0.039 mmol) and DIEA (14 µL, 0.077 mmol) were combined in 0.2 mL of DMF and stirred at ambient temperature for 30 minutes. The reaction was loaded onto a samplet and purified by reverse-phase column chromatography using 0-70% acetonitrile/H$_2$O as the eluent to provide the title compound (7.9 mg, 0.017 mmol, 44% yield). MS (apci) m/z=468.2 (M+H).

Example 258

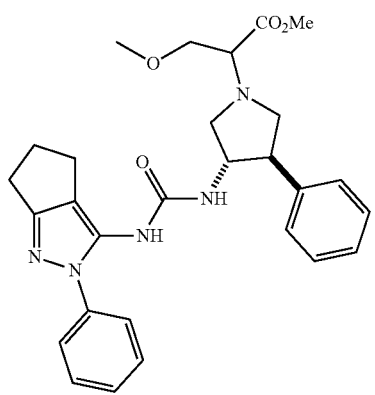

methyl 3-methoxy-2-((trans)-3-phenyl-4-(3-(2-phenyl-2,4,5,6-tetrahydrocyclopenta[c]pyrazol-3-yl)ureido)pyrrolidin-1-yl)propanoate 1-(2-phenyl-2,4,5,6-tetrahydrocyclopenta[c]pyrazol-3-yl)-3-((trans)-4-phenyl-pyrrolidin-3-yl)urea (30 mg, 0.077 mmol, prepared as described in Example 182, Step B), methyl 2-bromo-3-methoxypropanoate (15 mg, 0.077 mmol) and DIEA (29 µL, 0.15 mmol) were combined in 0.2 mL of DCM and stirred at ambient temperature for 3 days. The reaction was loaded onto a samplet and purified by reverse-phase column chromatography using 5-80% acetonitrile/H$_2$O as the eluent to provide the title compound (24 mg, 0.048 mmol, 62% yield) as a mixture of diastereomers. MS (apci) m/z=504.3 (M+H).

Example 259

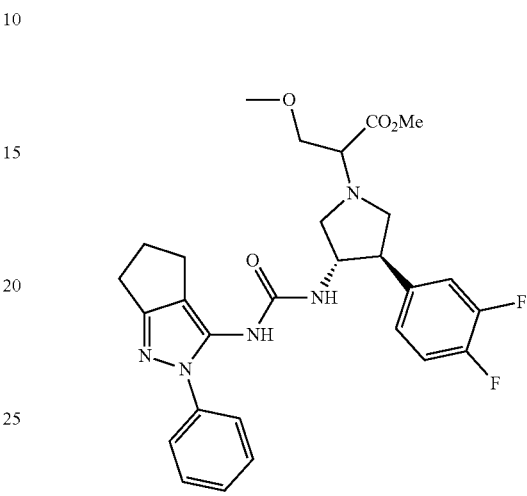

methyl 2-((3R,4S)-3-(3,4-difluorophenyl)-4-(3-(2-phenyl-2,4,5,6-tetrahydrocyclopenta[c]pyrazol-3-yl)ureido)pyrrolidin-1-yl)-3-methoxypropanoate Prepared by the method as described in Example 194, substituting methyl 2-bromo-3-methoxypropanoate for 2,2,2-trifluoroethyl trifluoromethanesulfonate and stirring for 3 days instead of 1 hour in Step A. The final product was purified by reverse-phase column chromatography using 5-80% acetonitrile/H$_2$O as the eluent to provide the title compound (260 mg, 0.482 mmol, 83.5% yield for 3 steps) as a mixture of diastereomers. MS (apci) m/z=540.3 (M+H).

Example 260

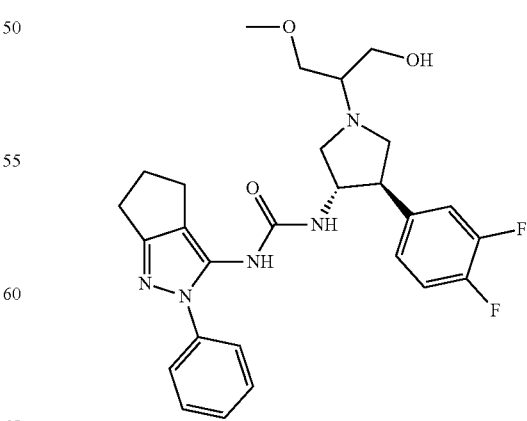

1-((3S,4R)-4-(3,4-difluorophenyl)-1-(1-hydroxy-3-methoxypropan-2-yl)pyrrolidin-3-yl)-3-(2-phenyl-2,4,5,6-tetrahydrocyclopenta[c]pyrazol-3-yl)urea Methyl 2-((3R,4S)-3-(3,4-difluorophenyl)-4-(3-(2-phenyl-2,4,5,6-tetrahydro-cyclo-penta[c]pyrazol-3-yl)ureido)pyrrolidin-1-yl)-3-methoxypropanoate (200 mg, 0.371 mmol, prepared as described in Example 259) was dissolved in 5 mL of THF and the solution was cooled to 0° C. LiAlH$_4$ (28.1 mg, 0.741 mmol) was added and the reaction was allowed to warm to ambient temperature over 2 hours. Sodium sulfate decahydrate (1194 mg, 3.71 mmol) was added and the reaction was stirred at ambient temperature for 2 hours, filtered and concentrated. The crude product was purified by reverse-phase column chromatography using 0-70% acetonitrile/H$_2$O as the eluent to provide the title compound (20 mg, 0.0391 mmol, 10.5% yield) as a mixture of diastereomers. MS (apci) m/z=512.3 (M+H).

Example 261

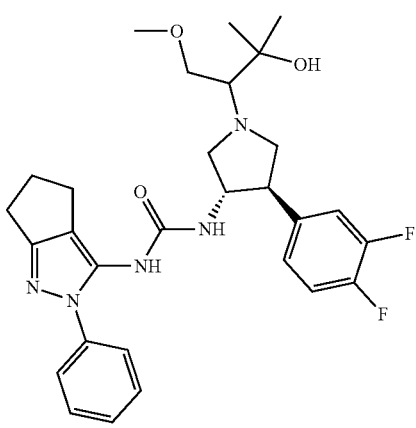 [SMILES: COCC(N1C[C@@H](NC(=O)Nc2c3c(nn2-c2ccccc2)CCC3)[C@H](c2ccc(F)c(F)c2)C1)C(C)(C)O]

1-((3S,4R)-4-(3,4-difluorophenyl)-1-(3-hydroxy-1-methoxy-3-methylbutan-2-yl)pyrrolidin-3-yl)-3-(2-phenyl-2,4,5,6-tetrahydrocyclopenta[c]pyrazol-3-yl)urea Methyl 2-((3R,4S)-3-(3,4-difluorophenyl)-4-(3-(2-phenyl-2,4,5,6-tetrahydrocyclopenta[c]pyrazol-3-yl)ureido)pyrrolidin-1-yl)-3-methoxypropanoate (20 mg, 0.037 mmol, prepared as described in Example 12) was dissolved in 1 mL of THF and cooled to 0° C. Methylmagnesium bromide (2M in THF, 93 µL, 0.19 mmol) was added and the reaction was allowed to warm to ambient temperature overnight. H$_2$O (2 mL) was added and the reaction was extracted with DCM (2×5 mL) in a phase separator frit. The combined organic extracts were concentrated and purified by reverse-phase column chromatography using 0-70% acetonitrile/H$_2$O as the eluent to provide the title compound (7.9 mg, 0.015 mmol, 39% yield) as a mixture of diastereomers. MS (apci) m/z=539.6 (M+H).

Example 262

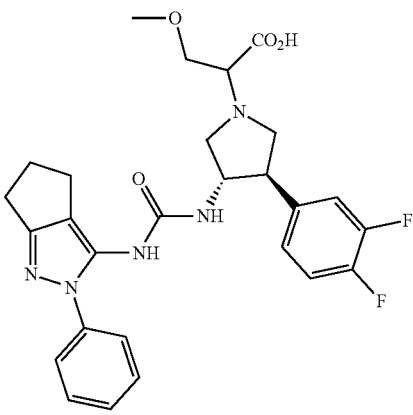 [SMILES: COCC(C(=O)O)N1C[C@@H](NC(=O)Nc2c3c(nn2-c2ccccc2)CCC3)[C@H](c2ccc(F)c(F)c2)C1]

2-((3R,4S)-3-(3,4-difluorophenyl)-4-(3-(2-phenyl-2,4,5,6-tetrahydrocyclopenta[c]pyrazol-3-yl)ureido)pyrrolidin-1-yl)-3-methoxypropanoic acid hydrochloride Methyl 2-((3R,4S)-3-(3,4-difluorophenyl)-4-(3-(2-phenyl-2,4,5,6-tetrahydro-cyclopenta[c]pyrazol-3-yl)ureido)pyrrolidin-1-yl)-3-methoxypropanoate (300 mg, 0.556 mmol, prepared as described in Example 259) and NaOH (1N aqueous, 834 µL, 0.834 mmol) were combined in 1 mL of MeOH and stirred at ambient temperature overnight. The reaction was loaded onto a samplet and purified by reverse-phase column chromatography using 0-50% acetonitrile/0.01M aqueous HCl as the eluent to provide the title compound (298 mg, 0.530 mmol, 95.4% yield) as a mixture of diastereomers. MS (apci) m/z=526.2 (M+H).

Example 263

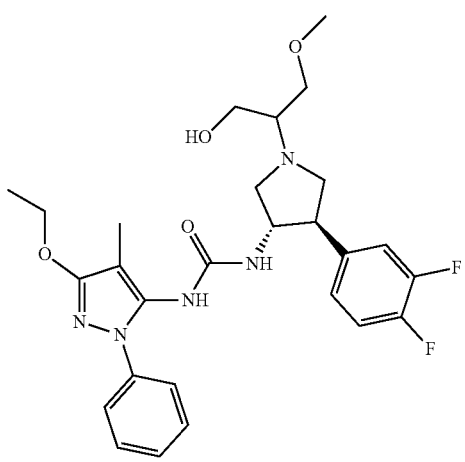 [SMILES: CCOc1nn(-c2ccccc2)c(NC(=O)N[C@@H]2CN(C(CO)COC)C[C@H]2c2ccc(F)c(F)c2)c1C]

1-((3S,4R)-4-(3,4-difluorophenyl)-1-(1-hydroxy-3-methoxypropan-2-yl)pyrrolidin-3-yl)-3-(3-ethoxy-4-methyl-1-phenyl-1H-pyrazol-5-yl)urea Step A: Preparation of tert-butyl (3S,4R)-4-(3,4-difluorophenyl)-1-(1-hydroxy-3-methoxypropan-2-yl)pyrrolidin-3- ylcarbamate. Methyl 2-((3S,4R)-3-(tert-butoxycarbonylamino)-4-(3,4-difluorophenyl)pyrrolidin-1-yl)-3-methoxypropanoate (220 mg, 0.531 mmol, prepared as described in Example 259, Step A), was dissolved in 5 mL of THF and NaBH$_4$ (100 mg, 2.65 mmol) was added in small portions. The reaction was stirred at ambient temperature for 1 hour, at 40° C. for 3 h and then at 50° C. overnight. The reaction was filtered, concentrated, and purified by reverse-phase column chromatography, eluting with 0-70% acetonitrile/water to afford the title compound (154 mg, 0.399 mmol, 75.1% yield). MS (apci) m/z=387.2 (M+H).

Step B: Preparation of 2-((3S,4R)-3-amino-4-(3,4-difluorophenyl)pyrrolidin-1-yl)-3-methoxypropan-1-ol dihydrochloride. Tert-butyl (3S,4R)-4-(3,4-difluorophenyl)-1-(1-hydroxy-3-methoxypropan-2-yl)pyrrolidin-3-ylcarbamate (120 mg, 0.311 mmol) and HCl (5N in IPA, 186 µl, 0.932 mmol) were combined in 5 mL of DCM and stirred at ambient temperature for 6 h. The reaction was concentrated to afford the title compound (87 mg, 0.304 mmol, 97.9% yield).

Step C: Preparation of 1-((3S,4R)-4-(3,4-difluorophenyl)-1-(1-hydroxy-3-methoxypropan-2-yl)pyrrolidin-3-yl)-3-(3-ethoxy-4-methyl-1-phenyl-1H-pyrazol-5-yl)urea. 2-((3S,4R)-3-amino-4-(3,4-difluorophenyl)pyrrolidin-1-yl)-3-methoxypropan-1-ol dihydro-chloride (13.0 mg, 0.0362 mmol), phenyl 3-ethoxy-4-methyl-1-phenyl-1H-pyrazol-5-ylcarbamate (prepared according to the method of Example 1, Step A starting with Intermediate P135; 10.2 mg, 0.0302 mmol) and DIEA (11.7 mg, 0.0905 mmol) were combined in 0.2 mL of DMF and stirred at ambient temperature for 1 hour. The reaction was loaded onto a samplet and purified by reverse-phase column chromatography, eluting with 0-60% acetonitrile/water, to afford the title compound (10.9 mg, 0.0206 mmol, 68.3% yield) MS (apci) m/z=530.2 (M+H).

Example 264

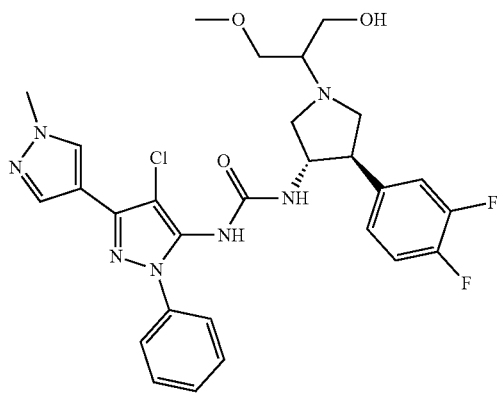 [SMILES: COCC(CO)N1C[C@@H](NC(=O)Nc2c(Cl)c(-c3cnn(C)c3)nn2-c2ccccc2)[C@H](c2ccc(F)c(F)c2)C1]

1-(3,4-dimethyl-1-phenyl-1H-pyrazol-5-yl)-3-((3R,4S)-4-phenyl-1-(2,2,2-trifluoroethyl)pyrrolidin-3-yl)urea Prepared by the method as described in Example 263, using phenyl 4-chloro-1'-methyl-1-phenyl-1H,1'H-3,4'-bipyrazol-5-ylcarbamate instead of phenyl 3-ethoxy-4-methyl-1-phenyl-1H-pyrazol-5-ylcarbamate. The material was purified by reverse-phase column chromatography using 0-80% acetonitrile/H$_2$O as the eluent to provide the title compound (17.2 mg, 0.0293 mmol, 63.3% yield). MS (apci) m/z=586.2 (M+H).

Example 265

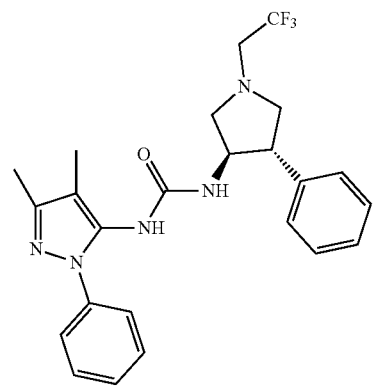 [SMILES: Cc1nn(-c2ccccc2)c(NC(=O)N[C@H]2CN(CC(F)(F)F)C[C@@H]2c2ccccc2)c1C]

1-((3S,4R)-4-(3,4-difluorophenyl)-1-(2-methoxyethyl)pyrrolidin-3-yl)-3-(3-methoxy-1-phenyl-4-(trifluoromethyl)-1H-pyrazol-5-yl)urea Step A: Separation of racemic (trans)-4-phenyl-1-(2,2,2-trifluoroethyl)pyrrolidin-3-amine hydrochloride. (trans)-4-phenyl-1-(2,2,2-trifluoroethyl)pyrrolidin-3-amine hydrochloride (3.80 g, 11.0 mmol, prepared according to the procedure described for Example 194, Step B) was separated by supercritical fluid chromatography (SFC) using a 20 mm×250 mm Chiral Tech Chiralcell OD-H column, Part #14345. The eluent was 9:1 supercritical CO$_2$:MeOH with 0.1% NH$_4$OH as a modifier. Peak 1 was isolated to provide (3R,4S)-4-phenyl-1-(2,2,2-trifluoroethyl)pyrrolidin-3-amine (1.07 g, 3.81 mmol, 34.6% yield, 98% ee). MS (apci) m/z=245.1 (M+H).

Step B: Preparation of 1-(3,4-dimethyl-1-phenyl-1H-pyrazol-5-yl)-3-((3R,4S)-4-phenyl-1-(2,2,2-trifluoroethyl)pyrrolidin-3-yl)urea. (3R,4S)-4-phenyl-1-(2,2,2-trifluoroethyl)pyro-lidin-3-amine (15.0 mg, 0.0614 mmol), phenyl 3,4-dimethyl-1-phenyl-1H-pyrazol-5-ylcarbamate (17.2 mg, 0.0558 mmol) and DIEA (21.6 mg, 0.167 mmol) were combined in 0.2 mL of DMF and stirred at ambient temperature for 1 hour. The reaction was loaded onto a samplet and purified by reverse-phase column chromatography, eluting with 0-80% acetonitrile/water, to afford the title compound (7.2 mg, 0.0157 mmol, 28.2% yield)). (MS (apci) m/z=458.2 (M+H).

Example 266

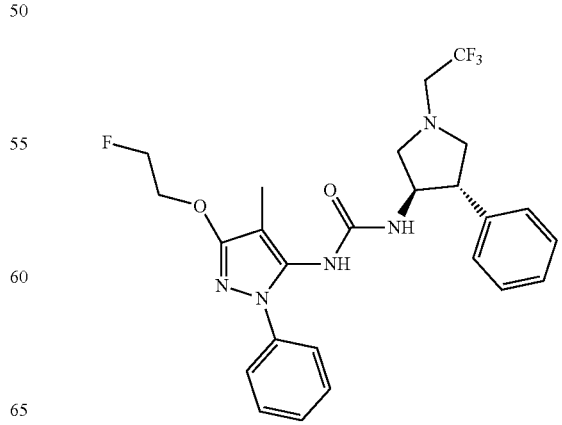

1-(3-(2-fluoroethoxy)-4-methyl-1-phenyl-1H-pyrazol-5-yl)-3-((3R,4S)-4-phenyl-1-(2,2,2-trifluoroethyl)pyrrolidin-3-yl)urea Prepared by the method as described in Example 1, Step B, using phenyl 3-(2-fluoroethoxy)-4-methyl-1-phenyl-1H-pyrazol-5-ylcarbamate instead of phenyl 3,4-dimethyl-1-phenyl-1H-pyrazol-5-ylcarbamate. The material was purified by reverse-phase column chromatography using 0-80% acetonitrile/H₂O as the eluent to provide the title compound (2.2 mg, 0.0044 mmol, 26% yield). MS (apci) m/z=506.2 (M+H).

Example 267

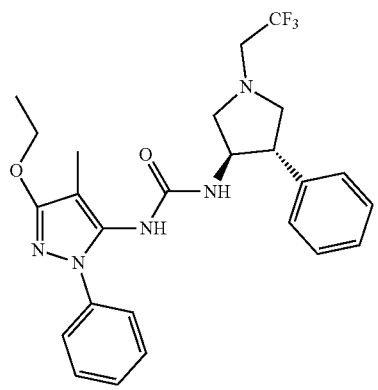 [SMILES: CCOc1nn(-c2ccccc2)c(NC(=O)N[C@H]2CN(CC(F)(F)F)C[C@@H]2c2ccccc2)c1C]

1-(3-ethoxy-4-methyl-1-phenyl-1H-pyrazol-5-yl)-3-((3R,4S)-4-phenyl-1-(2,2,2-trifluoroethyl)pyrrolidin-3-yl)urea Prepared by the method as described in Example 1, Step B, using phenyl 3-ethoxy-4-methyl-1-phenyl-1H-pyrazol-5-ylcarbamate (which was prepared according to the method of Example 1, Step A, starting with Intermediate P135) instead of phenyl 3,4-dimethyl-1-phenyl-1H-pyrazol-5-ylcarbamate. The material was purified by reverse-phase column chromatography using 0-80% acetonitrile/H₂O as the eluent to provide the title compound (7.1 mg, 0.0146 mmol, 42.7% yield). MS (apci) m/z=488.2 (M+H).

Example 268

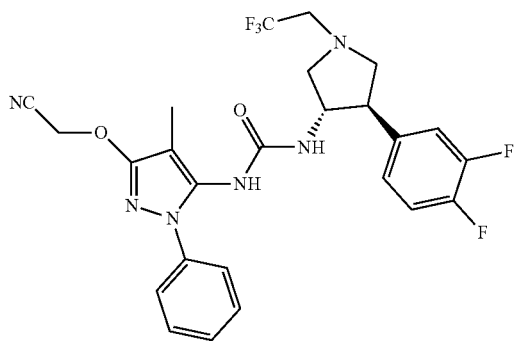 [SMILES: Cc1c(OCC#N)nn(-c2ccccc2)c1NC(=O)N[C@@H]1CN(CC(F)(F)F)C[C@H]1c1ccc(F)c(F)c1]

1-(3-(cyanomethoxy)-4-methyl-1-phenyl-1H-pyrazol-5-yl)-3-((3R,4S)-4-phenyl-1-(2,2,2-trifluoroethyl)pyrrolidin-3-yl)urea Prepared by the method as described in Example 1, Step B, using phenyl 3-(cyanomethoxy)-4-methyl-1-phenyl-1H-pyrazol-5-ylcarbamate instead of phenyl 3,4-dimethyl-1-phenyl-1H-pyrazol-5-ylcarbamate. The material was purified by reverse-phase column chromatography using 0-80% acetonitrile/H₂O as the eluent to provide the title compound (11.4 mg, 0.0229 mmol, 67.0% yield). MS (apci) m/z=499.2 (M+H).

Example 269

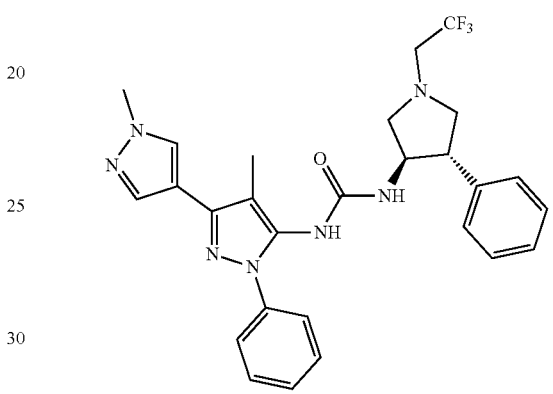

1-(1',4-dimethyl-1-phenyl-1H,1'H-3,4'-bipyrazol-5-yl)-3-((3R,4S)-4-phenyl-1-(2,2,2-trifluoroethyl)pyrrolidin-3-yl)urea Prepared by the method as described in Example 1, Step B, using phenyl 1',4-dimethyl-1-phenyl-1H,1'H-3,4'-bipyrazol-5-ylcarbamate instead of phenyl 3,4-dimethyl-1-phenyl-1H-pyrazol-5-ylcarbamate. The material was purified by reverse-phase column chromatography using 0-70% acetonitrile/H₂O as the eluent to provide the title compound (6.1 mg, 0.012 mmol, 68% yield). MS (apci) m/z=524.2 (M+H).

Example 270

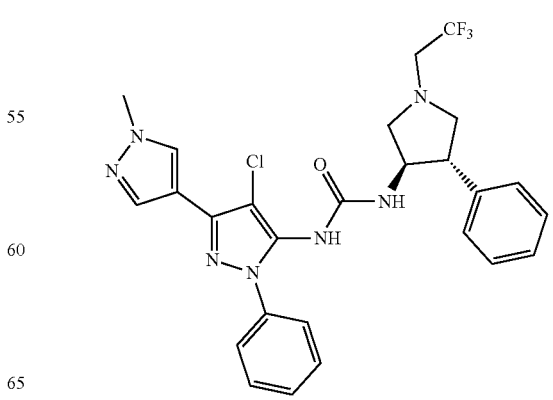

1-(4-chloro-1'-methyl-1-phenyl-1H,1'H-3,4'-bipyrazol-5-yl)-3-((3R,4S)-4-phenyl-1-(2,2,2-trifluoroethyl)pyrrolidin-3-yl)urea Prepared by the method as described in Example 1, Step B, using phenyl 4-chloro-1'-methyl-1-phenyl-1H,1'H-3,4'-bipyrazol-5-ylcarbamate instead of phenyl 3,4-dimethyl-1-phenyl-1H-pyrazol-5-ylcarbamate. The material was purified by reverse-phase column chromatography using 0-70% acetonitrile/H₂O as the eluent to provide the title compound (11.3 mg, 0.0208 mmol, 60.9% yield). MS (apci) m/z=488.2 (M+H).

Example 271

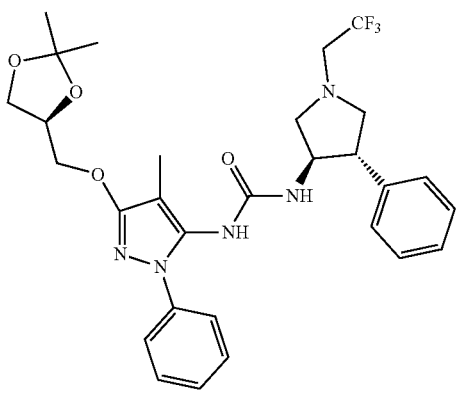 [SMILES: Cc1c(OC[C@H]2COC(C)(C)O2)nn(-c2ccccc2)c1NC(=O)N[C@H]1CN(CC(F)(F)F)C[C@@H]1c1ccccc1]

1-(3-(((S)-2,2-dimethyl-1,3-dioxolan-4-yl)methoxy)-4-methyl-1-phenyl-1H-pyrazol-5-yl)-3-((3R,4S)-4-phenyl-1-(2,2,2-trifluoroethyl)pyrrolidin-3-yl)urea Prepared by the method as described in Example 1, Step B, using (S)-phenyl 3-((2,2-dimethyl-1,3-dioxolan-4-yl)methoxy)-4-methyl-1-phenyl-1H-pyrazol-5-ylcarbamate instead of phenyl 3,4-dimethyl-1-phenyl-1H-pyrazol-5-ylcarbamate. The material was purified by reverse-phase column chromatography using 0-80% acetonitrile/H₂O as the eluent to provide the title compound (5.6 mg, 0.00976 mmol, 28.6% yield). MS (apci) m/z=574.3 (M+H).

Example 272

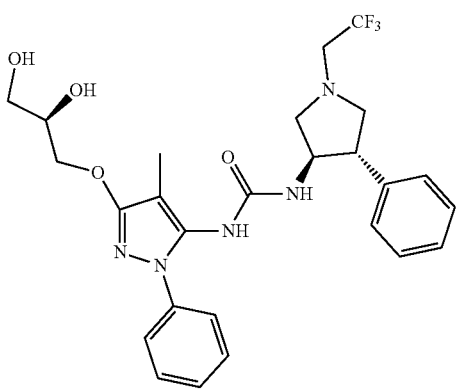 [SMILES: Cc1c(OC[C@H](O)CO)nn(-c2ccccc2)c1NC(=O)N[C@H]1CN(CC(F)(F)F)C[C@@H]1c1ccccc1]

1-(3-((R)-2,3-dihydroxypropoxy)-4-methyl-1-phenyl-1H-pyrazol-5-yl)-3-((3R,4S)-4-phenyl-1-(2,2,2-trifluoroethyl)pyrrolidin-3-yl)urea 1-(3-(((S)-2,2-dimethyl-1,3-dioxolan-4-yl)methoxy)-4-methyl-1-phenyl-1H-pyrazol-5-yl)-3-((3R,4S)-4-phenyl-1-(2,2,2-trifluoroethyl)pyrrolidin-3-yl)urea (4.4 mg, 0.0077 mmol, prepared as described in Example 7) and HCl (7N in IPA, 3.3 µL, 0.023 mmol) were combined in 0.2 mL of IPA and stirred at ambient temperature for 1 hour. The reaction was concentrated and DIEA (1.3 µL, 0.0077 mmol) was added. The crude material was purified by reverse-phase column chromatography using 0-60% acetonitrile/H₂O as the eluent to provide the title compound (3.7 mg, 0.0069 mmol, 90% yield). MS (apci) m/z=534.2 (M+H).

Example 273

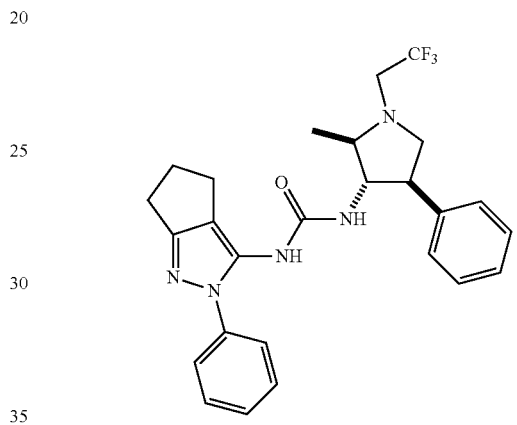

(R,S)1-((2α,3β,4α)-2-methyl-4-phenyl-1-(2,2,2-trifluoroethyl)pyrrolidin-3-yl)-3-(2-phenyl-2,4,5,6-tetrahydrocyclopenta[c]pyrazol-3-yl)urea Step A: Preparation of N-benzyl-1-(trimethylsilyl)ethanamine. (1-chloroethyl)trimethylsilane (6.3 g, 46.1 mmol) and benzylamine (14.8 g, 138 mmol) were combined in a pressure vessel and heated at 180° C. overnight. The reaction was taken up in EtOAc (200 mL), washed with 1N NaOH (100 mL), dried (MgSO₄) and concentrated. The crude product was purified by silica gel column chromatography, eluting with 10% MeOH/CH₂Cl₂ to afford the title compound (8.10 g, 39.1 mmol, 84.7% yield). (MS (apci) m/z=208.1 (M+H).

Step B: Preparation of N-benzyl-N-(methoxymethyl)-1-(trimethylsilyl) ethanamine. A mixture of formaldehyde (37% aqueous solution, 3.45 mL, 46.3 mmol) and methanol (1.88 mL, 46.3 mmol) at 0° C. was treated with N-benzyl-1-(trimethylsilyl)ethanamine (8.00 g, 38.6 mmol) in small portions over 10 minutes. Additional MeOH (2 mL) was used to rinse in residual amine. The mixture was stirred at 0° C. for 3 hours, K₂CO₃ (8.00 g, 57.9 mmol) was added and the mixture was allowed to warm to ambient temperature overnight. The mixture was decanted into a new flask with the aid of a small amount of Et₂O and additional K₂CO₃ (50 g) was added. The mixture was stirred for 30 minutes and filtered, washed with a small amount of Et₂O and carefully concentrated to afford the title compound (9.60 g, 38.2 mmol, 99.0% yield) as a pale yellow liquid. (MS (apci) m/z=208.1 (M+2H—CH₂OCH₃).

Step C: Preparation of (R,S)(2α,3β,4α)-1-benzyl-2-methyl-3-nitro-4-phenylpyrroli-dine and (R,S)(3β,4α,5α)-1-benzyl-2-methyl-4-nitro-3-phenylpyrrolidine. A solution of (E)-(2-nitrovinyl)benzene (0.500 g, 3.35 mmol) and TFA (0.0258 mL, 0.335 mmol) in 10 mL of CH₂Cl₂ was cooled to 0° C. and N-benzyl-N-(methoxymethyl)-1-(trimethylsilyl)ethanamine (1.01 g, 4.02 mmol) added dropwise. The reaction was stirred at 0° C. for 2 hours and then allowed to warm to ambient temperature overnight. The reaction was concentrated, loaded onto a samplet using MeOH (2 mL) and DIEA (0.584 mL, 3.35 mmol), and purified by reverse-phase column chromatography, eluting with 0.1% ammonium acetate buffered 5-95% acetonitrile/water, to afford the title compounds (287 mg, 0.925 mmol, 56.5% yield) as a 5:3 mixture. (MS (apci) m/z=297.1 (M+H).

Step D: Preparation of (R,S)-1-((2α,3β,4α)-1-benzyl-2-methyl-4-phenyl-pyrrolidin-3-yl)-3-(2-phenyl-2,4,5,6-tetrahydrocyclopenta[c]pyrazol-3-yl)urea and (R,S)-1-((3β,4α,5α)-1-benzyl-5-methyl-4-phenylpyrrolidin-3-yl)-3-(2-phenyl-2,4,5,6-tetrahydro cyclopenta[c]pyrazol-3-yl)urea. ((2α,3β,4α)-1-benzyl-2-methyl-3-nitro-4-phenylpyrrolidine and (3β,4α,5α)-1-benzyl-2-methyl-4-nitro-3-phenylpyrrolidine (110 mg of a 5:3 mixture, 0.371 mmol) were dissolved in 10 mL of THF and Raney Nickel (3.18 mg, 0.0371 mmol) added. The reaction was stirred under a H₂ balloon for 3 days, filtered through Celite®, concentrated, and taken up in 0.2 mL of DMF. Phenyl 2-phenyl-2,4,5,6-tetrahydrocyclopenta[c]pyrazol-3-ylcarbamate (149 mg, 0.467 mmol) and DIEA (222 μL, 1.27 mmol) were added and the reaction was stirred at ambient temperature for 1 hour. The reaction was loaded onto a samplet and purified by reverse-phase column chromatography, eluting with 0-80% acetonitrile/water, to afford the title compounds (172 mg, 0.350 mmol, 82% yield) as a ~7:3 mixture. (MS (apci) m/z=492.3 (M+H).

Step E: Preparation of (R,S)-1-((2α,3β,4α)-2-methyl-4-phenylpyrrolidin-3-yl)-3-(2-phenyl-2,4,5,6-tetrahydrocyclopenta[c]pyrazol-3-yl)urea and 1-((3β,4α,5α)-5-methyl-4-phenyl-pyrroidin-3-yl)-3-(2-phenyl-2,4,5,6-tetrahydrocyclopenta[c]pyrazol-3-yl)urea. 1-((2α,3β,4α)-1-benzyl-2-methyl-4-phenylpyrrolidin-3-yl)-3-(2-phenyl-2,4,5,6-tetrahydrocyclopenta[c]pyrazol-3-yl)urea and 1-((3β,4α,5α)-1-benzyl-5-methyl-4-phenylpyrrolidin-3-yl)-3-(2-phenyl-2,4,5,6-tetrahydrocyclopenta[c]pyrazol-3-yl)urea (170 mg of a 7:3 mixture, 0.346 mmol) were dissolved in 10 mL of THF and 10% Pd/C (36.8 mg, 0.0346 mmol) added. The reaction was stirred under a H₂ balloon for 16 hours, filtered through Celite, and concentrated to afford the title compounds (133 mg, 0.335 mmol, 96% yield) as a ~7:3 mixture. (MS (apci) m/z=402.2 (M+H).

Step F: Preparation of (R,S)-1-((2α,3β,4α)-2-methyl-4-phenyl-1-(2,2,2-trifluoro-ethyl)pyrrolidin-3-yl)-3-(2-phenyl-2,4,5,6-tetrahydrocyclopenta[c]pyrazol-3-yl)urea. 1-((2α, 3β,4α)-2-methyl-4-phenylpyrrolidin-3-yl)-3-(2-phenyl-2,4,5,6-tetrahydrocyclopenta[c]pyrazol-3-yl)urea and 1-((3β,4α,5α)-5-methyl-4-phenylpyrrolidin-3-yl)-3-(2-phenyl-2,4,5,6-tetrahydrocyclopenta[c]pyrazol-3-yl)urea (20 mg of a 7:3 mixture, 0.050 mmol) and DIEA (8.7 μL, 0.050 mmol) were combined in 0.2 mL of DMF and 2,2,2-trifluoroethyl trifluoromethanesulfonate (35 mg, 0.15 mmol) was added. The reaction was stirred at ambient temperature for 1 hour, loaded onto a samplet and separated by reverse-phase column chromatography, eluting with 0-80% acetonitrile/water. Peak 1 was isolated to afford the title compound (3.0 mg, 0.0062 mmol, 12% yield). (MS (apci) m/z=484.2 (M+H).

Example 274

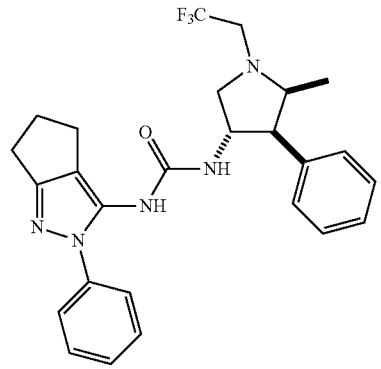

(R,S)-1-((3β,4α,5α)-5-methyl-4-phenyl-1-(2,2,2-trifluoroethyl)pyrrolidin-3-yl)-3-(2-phenyl-2,4,5,6-tetrahydrocyclopenta[c]pyrazol-3-yl)urea Prepared by the method described in Example 9, isolating peak 2 instead of peak 1 in Step F, to provide the title compound (1.9 mg, 0.0039 mmol, 7.9% yield). MS (apci) m/z=484.2 (M+H).

Example 275

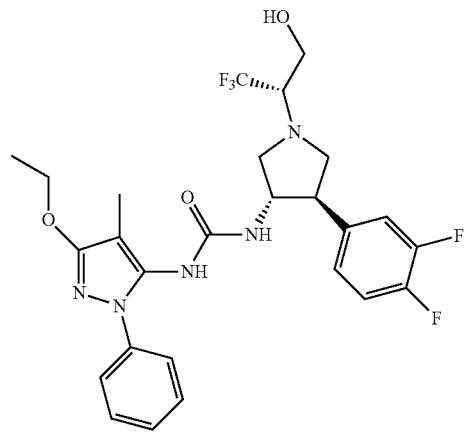 [SMILES: CCOc1nn(-c2ccccc2)c(NC(=O)N[C@@H]2CN([C@@H](CO)C(F)(F)F)C[C@H]2c2ccc(F)c(F)c2)c1C]

1-((3S,4R)-4-(3,4-difluorophenyl)-1-((S)-1,1,1-trifluoro-3-hydroxypropan-2-yl)pyrrolidin-3-yl)-3-(3-ethoxy-4-methyl-1-phenyl-1H-pyrazol-5-yl)urea Step A: Preparation of tert-butyl (3S,4R)-4-(3,4-difluorophenyl)-1-((R)-3,3,3-trifluoro-2-hydroxypropyl)pyrrolidin-3-ylcarbamate. tert-butyl (3S,4R)-4-(3,4-difluorophenyl)pyrrolidin-3-ylcarbamate (900 mg, 3.017 mmol), (R)-2-(trifluoromethyl)oxirane (338.0 mg, 3.017 mmol) and DIEA (779.8 mg, 6.034 mmol) were combined in 2 mL of DMF and stirred at ambient temperature overnight. The reaction was loaded onto a samplet and purified by reverse-phase column chromatography, eluting with 0-80% acetonitrile/water, to afford the title compound (1144 mg, 2.788 mmol, 92.40% yield). (MS (apci) m/z=411.2 (M+H).

Step B: Preparation of (R)-3-((3S,4R)-3-(tert-butoxycarbonylamino)-4-(3,4-difluorophenyl)pyrrolidin-1-yl)-1,1,1-trifluoropropan-2-yl methanesulfonate. Tert-butyl (3S,4R)-4-(3,4-difluorophenyl)-1-((R)-3,3,3-trifluoro-2-hydroxypropyl)pyrrolidin-3-ylcarbamate (900 mg, 2.19 mmol) was dissolved in 5 mL of CH$_2$Cl$_2$ and cooled to 0° C. DIEA (1146 μL, 6.58 mmol) was added followed by MsCl (204 μL, 2.63 mmol). The reaction was allowed to warm to ambient temperature over 1 hour, concentrated and purified by reverse-phase column chromatography, eluting with 5-90% acetonitrile/water, to afford the title compound (805 mg, 1.65 mmol, 75.1% yield). (MS (apci) m/z=489.1 (M+H).

Step C: Preparation of (S)-2-((3S,4R)-3-amino-4-(3,4-difluorophenyl) pyrrolidin-1-yl)-3,3,3-trifluoropropan-1-ol. N,N,N-trimethylhexadecan-1-aminium chloride (25% solution in H$_2$O, 3144 mg, 2.46 mmol) and (R)-3-((3S,4R)-3-(tert-butoxycarbonylamino)-4-(3,4-difluorophenyl)pyrrolidin-1-yl)-1,1,1-trifluoropropan-2-yl methanesulfonate (800 mg, 1.64 mmol) were combined in 0.5 mL of THF and heated at 150° C. for 3 days. The reaction was loaded onto a samplet and purified by reverse-phase column chromatography, eluting with 0-50% acetonitrile/water, to afford the title compound (287 mg, 0.925 mmol, 56.5% yield). (MS (apci) m/z=311.1 (M+H).

Step D: Preparation of 1-((3S,4R)-4-(3,4-difluorophenyl)-1-((S)-1,1,1-trifluoro-3-hydroxypropan-2-yl)pyrrolidin-3-yl)-3-(3-ethoxy-4-methyl-1-phenyl-1H-pyrazol-5-yl)urea. (S)-2-((3S,4R)-3-amino-4-(3,4-difluorophenyl)pyrrolidin-1-yl)-3,3,3-trifluoro-propan-1-ol (10 mg, 0.032 mmol), phenyl 3-ethoxy-4-methyl-1-phenyl-1H-pyrazol-5-ylcarbamate (prepared according to the method of Example 1, Step A. starting with Intermediate P135; 9.1 mg, 0.027 mmol) and DIEA (10 mg, 0.081 mmol) were combined in 0.2 mL of DMF and stirred at ambient temperature for 1 hour. The reaction was loaded onto a samplet and purified by reverse-phase column chromatography, eluting with 0-60% acetonitrile/water, to afford the title compound (8.1 mg, 0.015 mmol, 54% yield). (MS (apci) m/z=554.2 (M+H).

Example 276

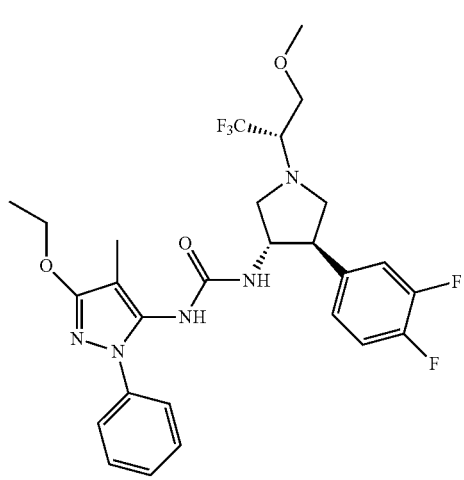 [SMILES: CCOc1nn(-c2ccccc2)c(NC(=O)N[C@@H]2CN([C@@H](COC)C(F)(F)F)C[C@H]2c2ccc(F)c(F)c2)c1C]

1-((3S,4R)-4-(3,4-difluorophenyl)-1-((S)-1,1,1-trifluoro-3-methoxypropan-2-yl) pyrrolidin-3-yl)-3-(3-ethoxy-4-methyl-1-phenyl-1H-pyrazol-5-yl)urea Step A: Preparation of tert-butyl (3S,4R)-4-(3,4-difluorophenyl)-1-((S)-1,1,1-trifluoro-3-hydroxypropan-2-yl)pyrrolidin-3-ylcarbamate. (S)-2-((3S,4R)-3-amino-4-(3,4-difluoro-phenyl)pyrrolidin-1-yl)-3,3,3-trifluoropropan-1-ol (120 mg, 0.387 mmol, prepared as described in Example 11, Step C), Boc$_2$O (92.9 mg, 0.425 mmol) and PS-DMAP (27.2 mg, 0.0387 mmol) were combined in 5 mL of CH$_2$Cl$_2$ and left to stand at ambient temperature overnight. Additional Boc$_2$O (30 mg, 0.14 mmol) was added followed by additional PS-DMAP (27.2 mg, 0.0387 mmol). The reaction was left to stand for 2 hours, filtered, concentrated and purified by reverse-phase column chromatography, eluting with 5-95% acetonitrile/water, to afford the title compound (63 mg, 0.154 mmol, 39.7% yield). (MS (apci) m/z=411.2 (M+H).

Step B: Preparation of tert-butyl (3S,4R)-4-(3,4-difluorophenyl)-1-((S)-1,1,1-trifluoro-3-methoxypropan-2-yl)pyrrolidin-3-ylcarbamate. Tert-butyl (3S,4R)-4-(3,4-difluorophenyl)-1-((S)-1,1,1-trifluoro-3-hydroxypropan-2-yl) pyrrolidin-3-ylcarbamate (25 mg, 0.061 mmol) and Ag$_2$O (28 mg, 0.12 mmol) ware combined in 1 mL of toluene and stirred at 0° C. Iodomethane (10 mg, 0.073 mmol) was added and the reaction was allowed to warm to ambient temperature and stirred for 5 hours. Acetonitrile (0.5 mL) and additional iodomethane (10 mg, 0.073 mmol) were added and the reaction was stirred at ambient temperature overnight, filtered through Celite®, concentrated and purified by purified by reverse-phase column chromatography, eluting with 5-95% acetonitrile/water, to afford the title compound (22 mg, 0.052 mmol, 85% yield). (MS (apci) m/z=425.2 (M+H).

Step C: Preparation of (3S,4R)-4-(3,4-difluorophenyl)-1-((S)-1,1,1-trifluoro-3-methoxypropan-2-yl)pyrrolidin-3-amine dihydrochloride. Tert-butyl (3S,4R)-4-(3,4-difluorophenyl)-1-((S)-1,1,1-trifluoro-3-methoxypropan-2-yl) pyrrolidin-3-ylcarbamate (20 mg, 0.0471 mmol) and HCl (5N in IPA, 37.7 μL, 0.188 mmol) were combined in 5 mL of CH$_2$Cl$_2$ and stirred at ambient temperature for 6 hours. The reaction was concentrated to afford the title compound (15 mg, 0.0463 mmol, 98.2% yield). (MS (apci) m/z=325.1 (M+H).

Step D: Preparation of 1-((3S,4R)-4-(3,4-difluorophenyl)-1-((S)-1,1,1-trifluoro-3-methoxypropan-2-yl)pyrrolidin-3-yl)-3-(3-ethoxy-4-methyl-1-phenyl-1H-pyrazol-5-yl) urea. (3S,4R)-4-(3,4-difluorophenyl)-1-((S)-1,1,1-trifluoro-3-methoxypropan-2-yl)pyrrolidin-3-amine dihydrochloride (7.5 mg. 0.019 mmol), phenyl 3-ethoxy-4-methyl-1-phenyl-1H-pyrazol-5-ylcarbamate (prepared according to the method of Example 1, Step A, starting with Intermediate P135; 5.8 mg, 0.017 mmol) and DIEA (6.7 mg, 0.051 mmol) were combined in 0.2 mL of DMF and stirred at ambient temperature for 1 hour. The reaction was loaded onto a samplet and purified by reverse-phase column chromatography, eluting with 0-90% acetonitrile/water, to afford the title compound (6.8 mg, 0.012 mmol, 70% yield). (MS (apci) m/z=568.2 (M+H).

Example 277

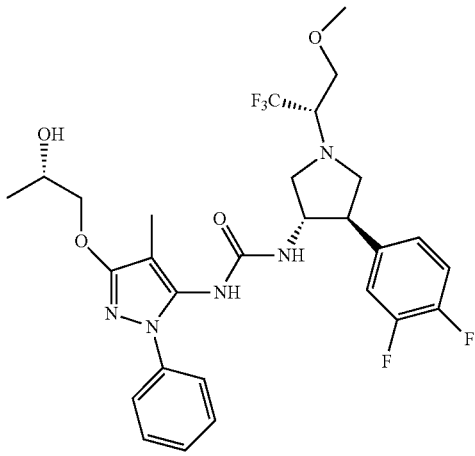 [SMILES: COC[C@H](N1C[C@@H](NC(=O)Nc2c(C)c(OC[C@H](C)O)nn2-c2ccccc2)[C@H](c2ccc(F)c(F)c2)C1)C(F)(F)F]

1-((3S,4R)-4-(3,4-difluorophenyl)-1-((S)-1,1,1-trifluoro-3-methoxypropan-2-yl)pyrrolidin-3-yl)-3-(3-((S)-2-hydroxypropoxy)-4-methyl-1-phenyl-1H-pyrazol-5-yl)urea Prepared by the method as described in Example 12, Step D using (S)-phenyl 3-(2-hydroxypropoxy)-4-methyl-1-phenyl-1H-pyrazol-5-ylcarbamate instead of phenyl 3-ethoxy-4-methyl-1-phenyl-1H-pyrazol-5-ylcarbamate. The material was purified by reverse-phase column chromatography using 0-70% acetonitrile/H$_2$O as the eluent to provide the title compound (7.7 mg, 0.013 mmol, 75% yield). MS (apci) m/z=598.3 (M+H).

Example 278

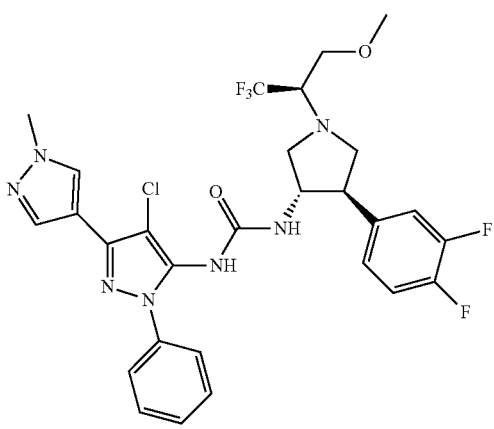 [SMILES: COC[C@@H](N1C[C@@H](NC(=O)Nc2c(Cl)c(-c3cnn(C)c3)nn2-c2ccccc2)[C@H](c2ccc(F)c(F)c2)C1)C(F)(F)F]

1-(4-chloro-1'-methyl-1-phenyl-1H, 1'H-3,4'-bipyrazol-5-yl)-3-((3S,4R)-4-(3,4-difluorophenyl)-1-((R)-1,1,1-trifluoro-3-methoxypropan-2-yl)pyrrolidin-3-yl)urea Step A: Preparation of (S)-3-((3S,4R)-3-(tert-butoxycarbonylamino)-4-(3,4-difluorophenyl)pyrrolidin-1-yl)-1,1,1-trifluoropropan-2-yl methanesulfonate. (tert-butyl (3S,4R)-4-(3,4-difluorophenyl)pyrrolidin-3-ylcarbamate (1000 mg, 3.352 mmol), (S)-2-(trifluoromethyl)oxirane (413.2 mg, 3.687 mmol) and DIEA (866.4 mg, 6.704 mmol) were combined in 2 mL of DMF and stirred at ambient temperature overnight. Methanesulfonyl chloride (285.4 μL, 3.687 mmol) was added and the reaction was stirred for 1 hour. Additional methanesulfonyl chloride (285.4 μL, 3.687 mmol) was added two more times with stirring for 20 minutes each. The reaction was loaded onto a samplet and purified by reverse-phase column chromatography, eluting with 0-80% acetonitrile/water, to afford the title compound (1194 mg, 2.444 mmol, 72.92% yield). (MS (apci) m/z=411.1 (M+H).

Step B: Preparation of (3S,4R)-4-(3,4-difluorophenyl)-1-((R)-1,1,1-trifluoro-3-methoxypropan-2-yl)pyrrolidin-3-amine. N,N,N-trimethylhexadecan-1-aminium hydrogensulfate (281 mg, 0.737 mmol) and (S)-3-((3S,4R)-3-(tert-butoxycarbonylamino)-4-(3,4-difluorophenyl)pyrrolidin-1-yl)-1,1,1-trifluoropropan-2-yl methanesulfonate (180 mg, 0.368 mmol) were combined in 10 mL of MeOH in a pressure vessel and heated 170° C. for 20 hours. The reaction was loaded onto a samplet and purified by reverse-phase column chromatography, eluting with 0-95% acetonitrile/water, to afford the title compound (67 mg, 0.207 mmol, 56.1% yield). (MS (apci) m/z=425.1 (M+H).

Step C: 1-(4-chloro-1'-methyl-1-phenyl-1H, 1'H-3,4'-bipyrazol-5-yl)-3-((3S,4R)-4-(3,4-difluorophenyl)-1-((R)-1,1,1-trifluoro-3-methoxypropan-2-yl)pyrrolidin-3-yl)urea.
Phenyl 4-chloro-1'-methyl-1-phenyl-1H, 1'H-3,4'-bipyrazol-5-ylcarbamate (25 mg, 0.0635 mmol), (3S,4R)-4-(3,4-difluorophenyl)-1-((R)-1,1,1-trifluoro-3-methoxypropan-2-yl)pyrrolidin-3-amine dihydrochloride (27.7 mg, 0.069 mmol) and DIEA (24.6 mg, 0.190 mmol) were combined in 0.2 mL of DMF and stirred at ambient temperature for 1 hour. The reaction was loaded onto a samplet and purified by reverse-phase column chromatography, eluting with 0-80% acetonitrile/water, to afford the title compound (17.2 mg, 0.0276 mmol, 43.4% yield). (MS (apci) m/z=624.2 (M+H).

Example 279

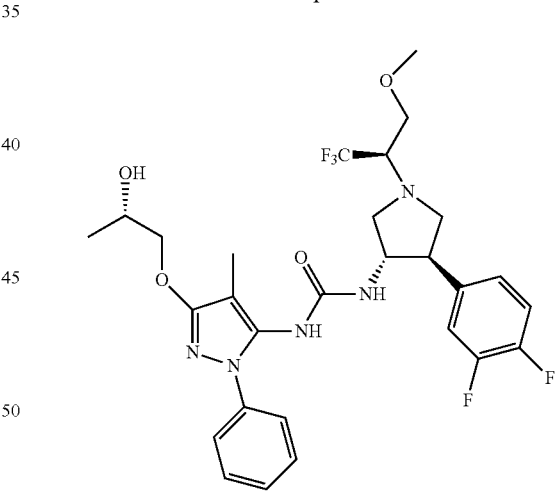

1-((3S,4R)-4-(3,4-difluorophenyl)-1-((R)-1,1,1-trifluoro-3-methoxypropan-2-yl)pyrrolidin-3-yl)-3-(3-((S)-2-hydroxypropoxy)-4-methyl-1-phenyl-1H-pyrazol-5-yl)urea Prepared by the method as described in Example 14, Step C using (S)-phenyl 3-(2-hydroxypropoxy)-4-methyl-1-phenyl-1H-pyrazol-5-ylcarbamate instead of phenyl 4-chloro-1'-methyl-1-phenyl-1H,1'H-3,4'-bipyrazol-5-ylcarbamate. The material was purified by reverse-phase column chromatography using 0-75% acetonitrile/H$_2$O as the eluent to provide the title compound (13.0 mg, 0.0218 mmol, 95.1% yield). MS (apci) m/z=598.3 (M+H).

The following compound was prepared according to the method of Example 52 using the appropriate starting materials.

| Ex. # | Structure | Name | |
|---|---|---|---|
| 280 | 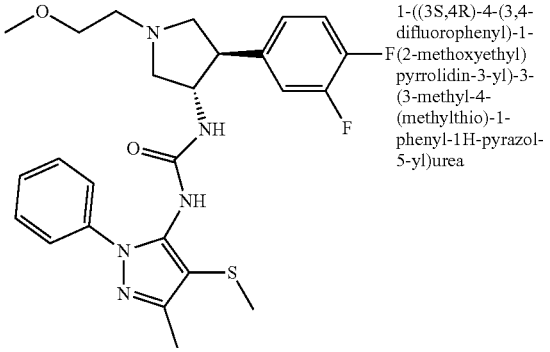 | 1-((3S,4R)-4-(3,4-difluorophenyl)-1-(2-methoxyethyl)pyrrolidin-3-yl)-3-(3-methyl-4-(methylthio)-1-phenyl-1H-pyrazol-5-yl)urea | MS (apci) m/z = 518.2 (M+H). |

The following compounds were prepared according to the method of Example 1, Step B, using the appropriate starting materials.

| Ex. # | Structure | Name | MS (apci) m/z |
|---|---|---|---|
| 281 | 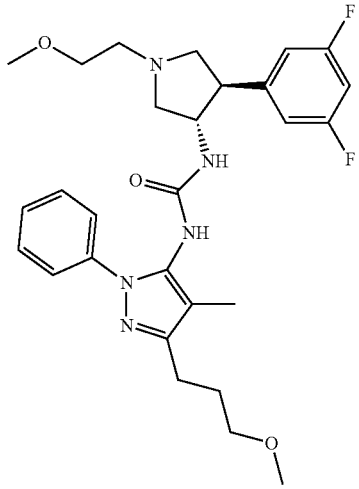 [SMILES: COCCCc1nn(-c2ccccc2)c(NC(=O)N[C@@H]2CN(CCOC)C[C@H]2c2cc(F)cc(F)c2)c1C] | 1-((3S,4R)-4-(3,5-difluorophenyl)-1-(2-methoxyethyl)pyrrolidin-3-yl)-3-(3-(3-methoxypropyl)-4-methyl-1-phenyl-1H-pyrazol-5-yl)urea | 528.3 (M + H) |
| 282 | 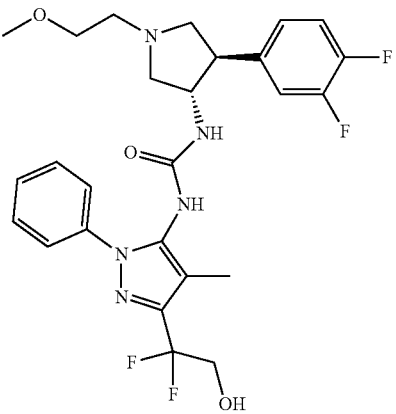 [SMILES: COCCN1C[C@@H](NC(=O)Nc2c(C)c(C(F)(F)CO)nn2-c2ccccc2)[C@H](c2ccc(F)c(F)c2)C1] | 1-(3-(1,1-difluoro-2-hydroxyethyl)-4-methyl-1-phenyl-1H-pyrazol-5-yl)-3-((3S,4R)-4-(3,4-difluorophenyl)-1-(2-methoxyethyl)pyrrolidin-3-yl)urea | 536.3 (M + H) |

| Ex. # | Structure | Name | MS (apci) m/z |
|---|---|---|---|
| 283 | 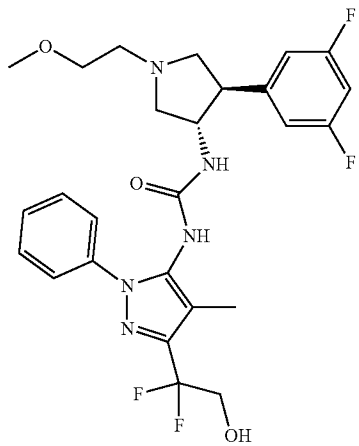 [SMILES: COCCN1C[C@@H](NC(=O)Nc2c(C)c(C(F)(F)CO)nn2-c2ccccc2)[C@H](c2cc(F)cc(F)c2)C1] | 1-(3-(1,1-difluoro-2-hydroxyethyl)-4-methyl-1-phenyl-1H-pyrazol-5-yl)-3-((3S,4R)-4-(3,5-difluorophenyl)-1-(2-methoxyethyl)pyrrolidin-3-yl)urea | 536.2 (M + H) |
| 284 | 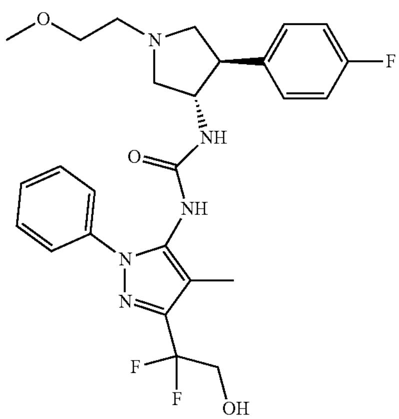 [SMILES: COCCN1C[C@@H](NC(=O)Nc2c(C)c(C(F)(F)CO)nn2-c2ccccc2)[C@H](c2ccc(F)cc2)C1] | 1-(3-(1,1-difluoro-2-hydroxyethyl)-4-methyl-1-phenyl-1H-pyrazol-5-yl)-3-((3S,4R)-4-(4-fluorophenyl)-1-(2-methoxyethyl)pyrrolidin-3-yl)urea | 518.2 (M + H) |
| 285 | 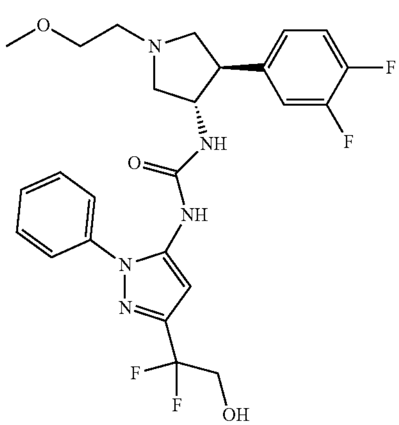 [SMILES: COCCN1C[C@@H](NC(=O)Nc2cc(C(F)(F)CO)nn2-c2ccccc2)[C@H](c2ccc(F)c(F)c2)C1] | 1-(3-(1,1-difluoro-2-hydroxyethyl)-1-phenyl-1H-pyrazol-5-yl)-3-((3S,4R)-4-(3,4-difluorophenyl)-1-(2-methoxyethyl)pyrrolidin-3-yl)urea | 522.2 (M + H) |

-continued

| Ex. # | Structure | Name | MS (apci) m/z |
|---|---|---|---|
| 286 | 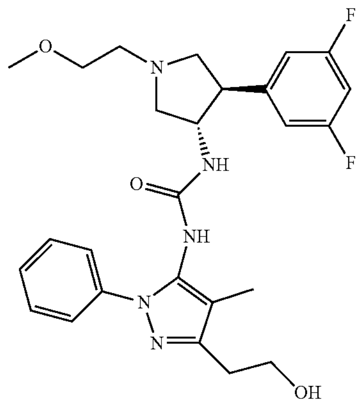 [SMILES: COCCN1C[C@@H](NC(=O)Nc2c(C)c(CCO)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(3-(2-hydroxyethyl)-4-methyl-1-phenyl-1H-pyrazol-5-yl)urea | 500.3 (M + H) |
| 287 | 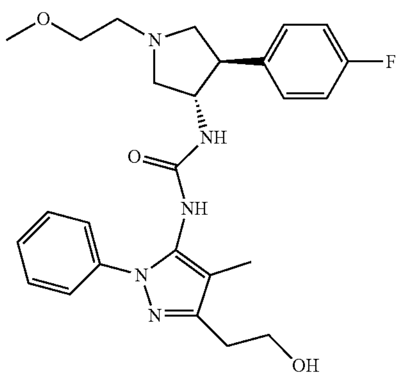 [SMILES: COCCN1C[C@@H](NC(=O)Nc2c(C)c(CCO)nn2-c2ccccc2)[C@H](c2ccc(F)cc2)C1] | 1-((3S,4R)-4-(4-fluorophenyl)-1-(2-methoxyethyl)pyrrolidin-3-yl)-3-(3-(2-hydroxyethyl)-4-methyl-1-phenyl-1H-pyrazol-5-yl)urea | 482.3 (M + H) |
| 288 | 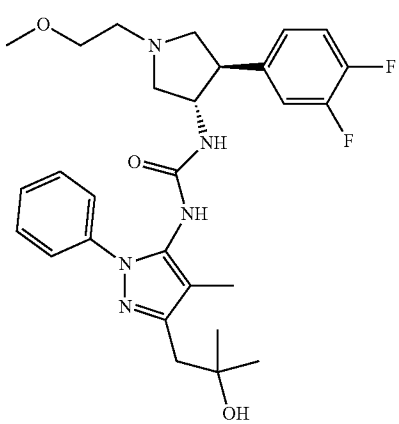 [SMILES: COCCN1C[C@@H](NC(=O)Nc2c(C)c(CC(C)(C)O)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(2-hydroxy-2-methylpropyl)-4-methyl-1-phenyl-1H-pyrazol-5-yl)urea | 528.3 (M + H) |

-continued

| Ex. # | Structure | Name | MS (apci) m/z |
|---|---|---|---|
| 289 | 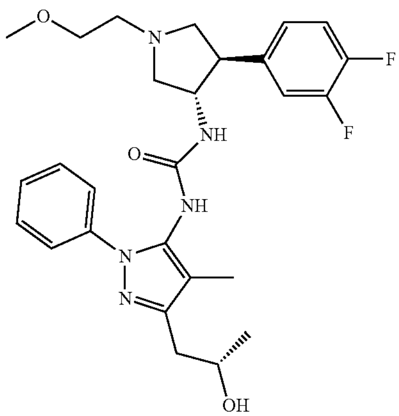 [SMILES: COCCN1C[C@@H](NC(=O)Nc2c(C)c(C[C@H](C)O)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-((S)-2-hydroxypropyl)-4-methyl-1-phenyl-1H-pyrazol-5-yl)urea | 514.3 (M + H) |
| 290 | 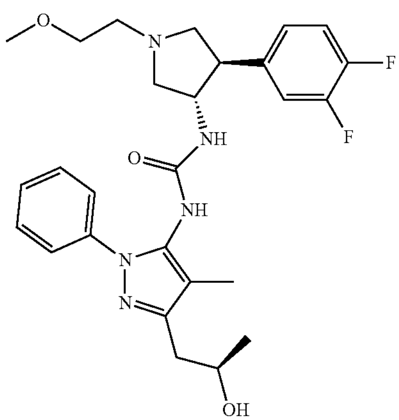 [SMILES: COCCN1C[C@@H](NC(=O)Nc2c(C)c(C[C@@H](C)O)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-((R)-2-hydroxypropyl)-4-methyl-1-phenyl-1H-pyrazol-5-yl)urea | 514.3 (M + H) |
| 291 | 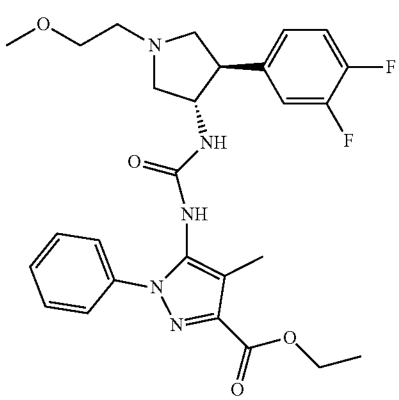 [SMILES: CCOC(=O)c1nn(-c2ccccc2)c(NC(=O)N[C@@H]2CN(CCOC)C[C@H]2c2ccc(F)c(F)c2)c1C] | ethyl 5-(3-((3S,4R)-4-(3,4-difluorophenyl)-1-(2-methoxyethyl)pyrrolidin-3-yl)ureido)-4-methyl-1-phenyl-1H-pyrazole-3-carboxylate | 528.3 (M + H) |

-continued

| Ex. # | Structure | Name | MS (apci) m/z |
|---|---|---|---|
| 292 | 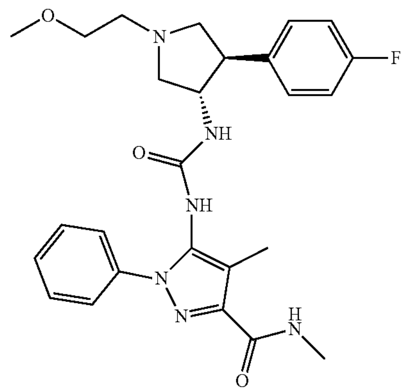 [SMILES: CNC(=O)c1nn(-c2ccccc2)c(NC(=O)N[C@@H]2CN(CCOC)C[C@H]2c2ccc(F)cc2)c1C] | 5-(3-((3S,4R)-4-(4-fluorophenyl)-1-(2-methoxyethyl)pyrrolidin-3-yl)ureido)-N,4-dimethyl-1-phenyl-1H-pyrazole-3-carboxamide | 495.2 (M + H) |
| 293 | 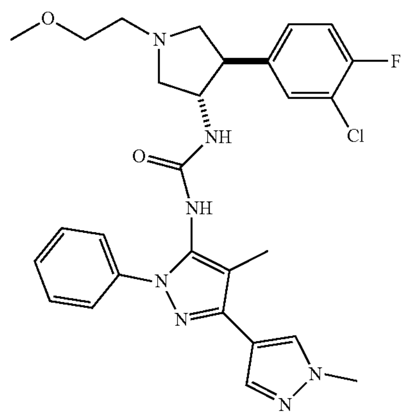 | 1-(trans-4-(3-chloro-4-fluorophenyl)-1-(2-methoxyethyl)pyrrolidin-3-yl)-3-(1',4-dimethyl-1-phenyl-1H,1'H-[3,4'-bipyrazol]-5-yl)urea | 552.2 (M + H) |
| 294 | 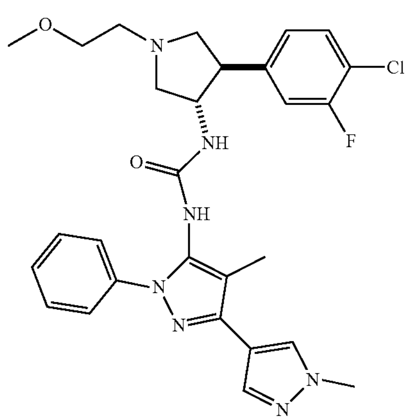 | 1-(trans-4-(4-chloro-3-fluorophenyl)-1-(2-methoxyethyl)pyrrolidin-3-yl)-3-(1',4-dimethyl-1-phenyl-1H,1'H-[3,4'-bipyrazol]-5-yl)urea | 552.2 (M + H) |

-continued

| Ex. # | Structure | Name | MS (apci) m/z |
|---|---|---|---|
| 295 | 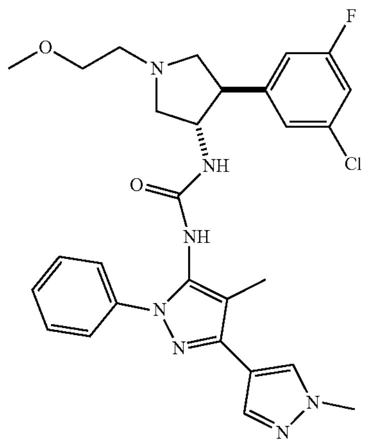 | 1-(trans-4-(3-chloro-5-fluorophenyl)-1-(2-methoxyethyl)pyrrolidin-3-yl)-3-(1',4-dimethyl-1-phenyl-1H,1'H-[3,4'-bipyrazol]-5-yl)urea | 552.2 (M + H) |
| 296 | 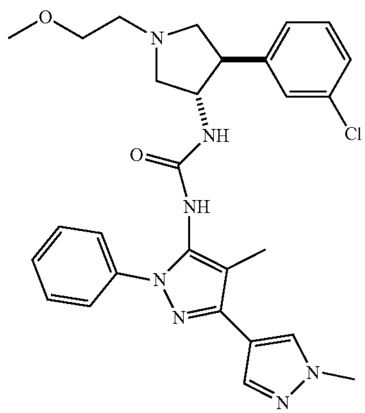 | 1-(trans-4-(3-chlorophenyl)-1-(2-methoxyethyl)pyrrolidin-3-yl)-3-(1',4-dimethyl-1-phenyl-1H,1'H-[3,4'-bipyrazol]-5-yl)urea | 534.2 (M + H) |
| 297 | 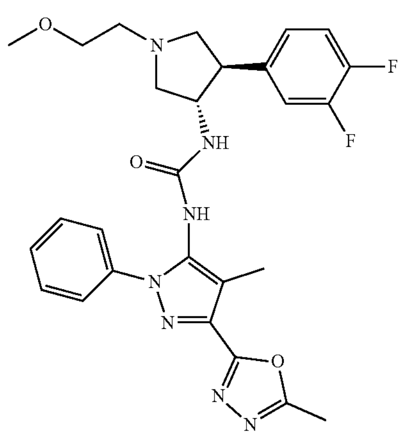 [SMILES: COCCN1C[C@@H](NC(=O)Nc2c(C)c(-c3nnc(C)o3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-3-(5-methyl-1,3,4-oxadiazol-2-yl)-1-phenyl-1H-pyrazol-5-yl)urea | 538.2 (M + H) |

| Ex. # | Structure | Name | MS (apci) m/z |
|---|---|---|---|
| 298 | 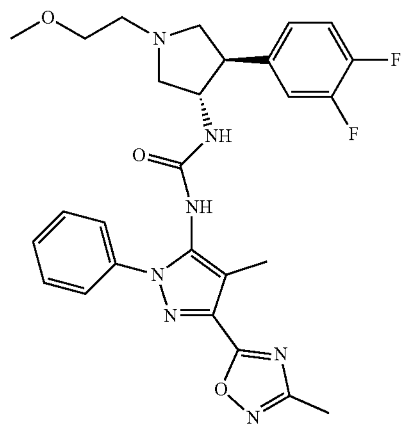 [SMILES: COCCN1C[C@@H](NC(=O)Nc2c(C)c(-c3nc(C)no3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-3-(3-methyl-1,2,4-oxadiazol-5-yl)-1-phenyl-1H-pyrazol-5-yl)urea | 538.2 (M + H) |
| 299 | 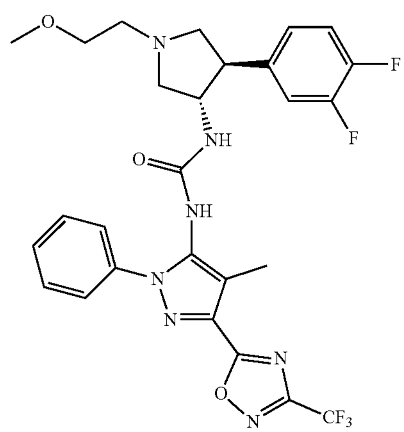 [SMILES: COCCN1C[C@@H](NC(=O)Nc2c(C)c(-c3nc(C(F)(F)F)no3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-1-phenyl-3-(3-(trifluoromethyl)-1,2,4-oxadiazol-5-yl)-1H-pyrazol-5-yl)urea | 592.2 (M + H) |
| 300 | 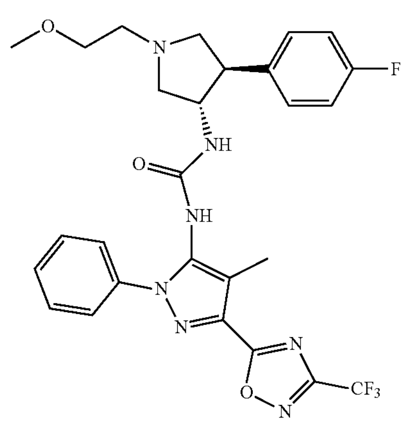 [SMILES: COCCN1C[C@@H](NC(=O)Nc2c(C)c(-c3nc(C(F)(F)F)no3)nn2-c2ccccc2)[C@H](c2ccc(F)cc2)C1] | 1-((3S,4R)-4-(4-fluorophenyl)-1-(2-methoxyethyl)pyrrolidin-3-yl)-3-(4-methyl-1-phenyl-3-(3-(trifluoromethyl)-1,2,4-oxadiazol-5-yl)-1H-pyrazol-5-yl)urea | 574.2 (M + H) |

-continued

| Ex. # | Structure | Name | MS (apci) m/z |
|---|---|---|---|
| 301 | 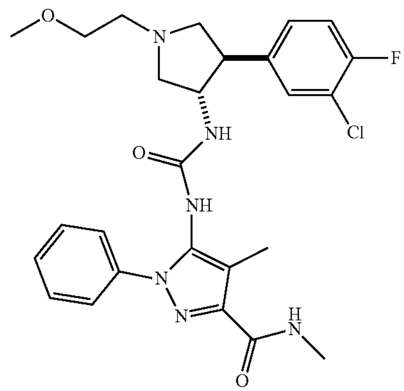 | 5-(3-(trans-4-(3-chloro-4-fluorophenyl)-1-(2-methoxyethyl)pyrrolidin-3-yl)ureido)-N,4-dimethyl-1-phenyl-1H-pyrazole-3-carboxamide | 529.2 (M + H) |
| 302 | 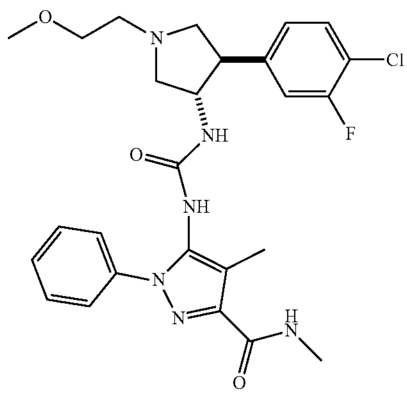 | 5-(3-(trans-4-(4-chloro-3-fluorophenyl)-1-(2-methoxyethyl)pyrrolidin-3-yl)ureido)-N,4-dimethyl-1-phenyl-1H-pyrazole-3-carboxamide | 529.2 (M + H) |
| 303 | 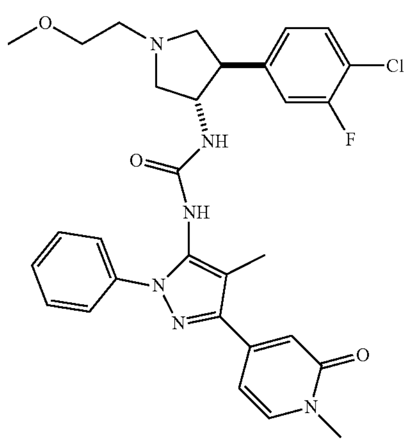 | 1-(trans-4-(4-chloro-3-fluorophenyl)-1-(2-methoxyethyl)pyrrolidin-3-yl)-3-(4-methyl-3-(1-methyl-2-oxo-1,2-dihydropyridin-4-yl)-1-phenyl-1H-pyrazol-5-yl)urea | 579.2 (M + H) |

-continued

| Ex. # | Structure | Name | MS (apci) m/z |
|---|---|---|---|
| 304 | 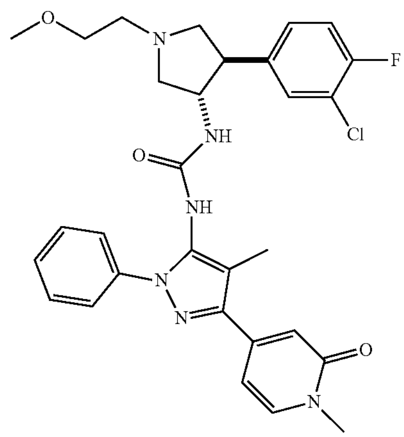 | 1-(trans-4-(3-chloro-4-fluorophenyl)-1-(2-methoxyethyl)pyrrolidin-3-yl)-3-(4-methyl-3-(1-methyl-2-oxo-1,2-dihydropyridin-4-yl)-1-phenyl-1H-pyrazol-5-yl)urea | 579.2 (M + H) |
| 305 | 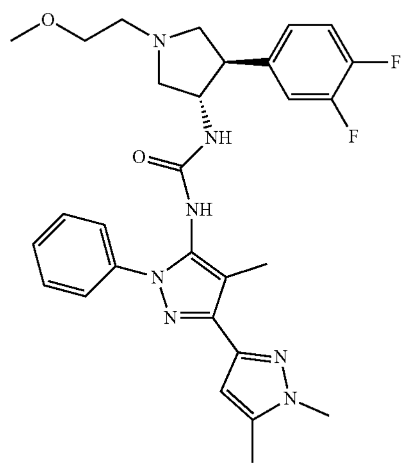 [SMILES: COCCN1C[C@@H](NC(=O)Nc2c(C)c(-c3cc(C)n(C)n3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(1',4,5'-trimethyl-1-phenyl-1H,1'H-[3,3'-bipyrazol]-5-yl)urea | 550.2 (M + H) |
| 306 | 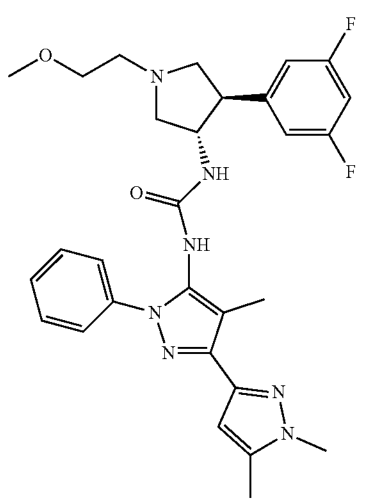 [SMILES: COCCN1C[C@@H](NC(=O)Nc2c(C)c(-c3cc(C)n(C)n3)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(1',4,5'-trimethyl-1-phenyl-1H,1'H-[3,3'-bipyrazol]-5-yl)urea | 550.2 (M + H) |

| Ex. # | Structure | Name | MS (apci) m/z |
|---|---|---|---|
| 307 | 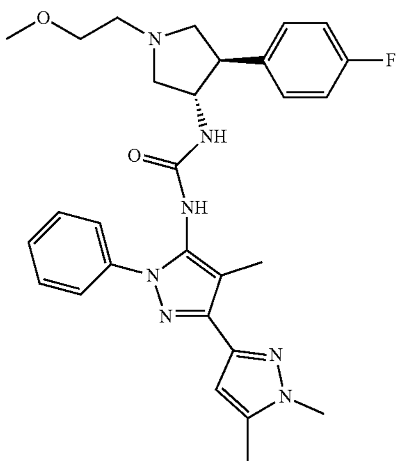 [SMILES: COCCN1C[C@@H](NC(=O)Nc2c(C)c(-c3cc(C)n(C)n3)nn2-c2ccccc2)[C@H](c2ccc(F)cc2)C1] | 1-((3S,4R)-4-(4-fluorophenyl)-1-(2-methoxyethyl)pyrrolidin-3-yl)-3-(1',4,5'-trimethyl-1-phenyl-1H,1'H-[3,3'-bipyrazol]-5-yl)urea | 532.3 (M + H) |
| 308 | 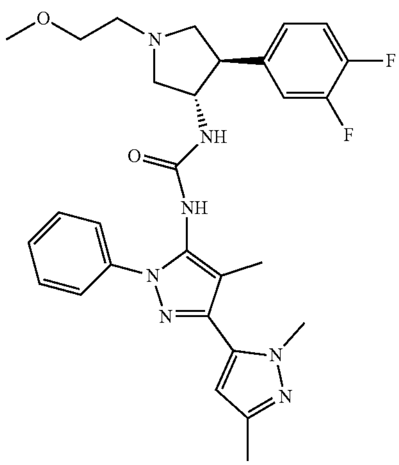 [SMILES: COCCN1C[C@@H](NC(=O)Nc2c(C)c(-c3cc(C)nn3C)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(2',4,5'-trimethyl-1-phenyl-1H,2'H-[3,3'-bipyrazol]-5-yl)urea | 550.2 (M + H) |
| 309 | 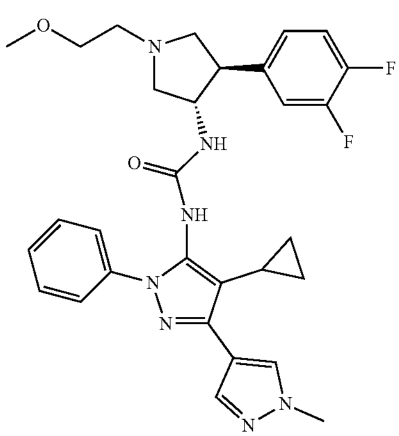 [SMILES: COCCN1C[C@@H](NC(=O)Nc2c(C3CC3)c(-c3cnn(C)c3)nn2-c2ccccc2)[C@H](c2ccc(F)c(F)c2)C1] | 1-(4-cyclopropyl-1'-methyl-1-phenyl-1H,1'H-[3,4'-bipyrazol]-5-yl)-3-((3S,4R)-4-(3,4-difluorophenyl)-1-(2-methoxyethyl)pyrrolidin-3-yl)urea | 562.2 (M + H) |

| Ex. # | Structure | Name | MS (apci) m/z |
|---|---|---|---|
| 310 | 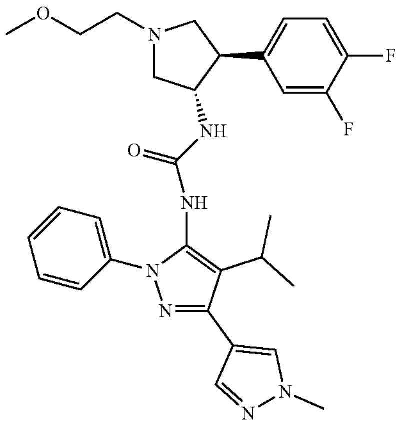 [SMILES: COCCN1C[C@@H](NC(=O)Nc2c(C(C)C)c(-c3cnn(C)c3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-isopropyl-1'-methyl-1-phenyl-1H,1'H-[3,4'-bipyrazol]-5-yl)urea | 564.3 (M + H) |
| 311 | 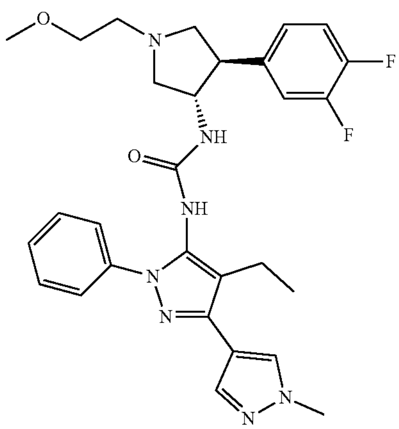 [SMILES: CCc1c(-c2cnn(C)c2)nn(-c2ccccc2)c1NC(=O)N[C@@H]1CN(CCOC)C[C@H]1c1ccc(F)c(F)c1] | 1-((3S,4R)-4-(3,4-difluorophenyl)-1-(2-methoxyethyl)pyrrolidin-3-yl)-3-(4-ethyl-1'-methyl-1-phenyl-1H,1'H-[3,4'-bipyrazol]-5-yl)urea | 550.2 (M + H) |
| 312 | 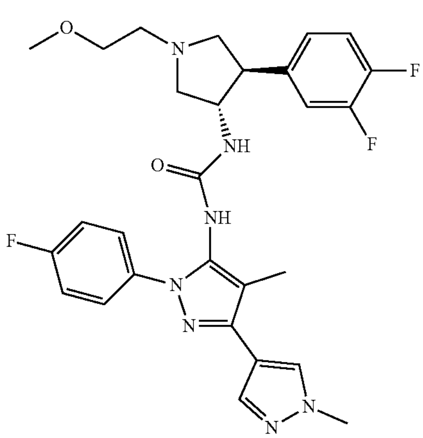 [SMILES: COCCN1C[C@@H](NC(=O)Nc2c(C)c(-c3cnn(C)c3)nn2-c2ccc(F)cc2)[C@H](c2ccc(F)c(F)c2)C1] | 1-((3S,4R)-4-(3,4-difluorophenyl)-1-(2-methoxyethyl)pyrrolidin-3-yl)-3-(1-(4-fluorophenyl)-1',4-dimethyl-1H,1'H-[3,4'-bipyrazol]-5-yl)urea | 554.2 (M + H) |

-continued

| Ex. # | Structure | Name | MS (apci) m/z |
|---|---|---|---|
| 313 | 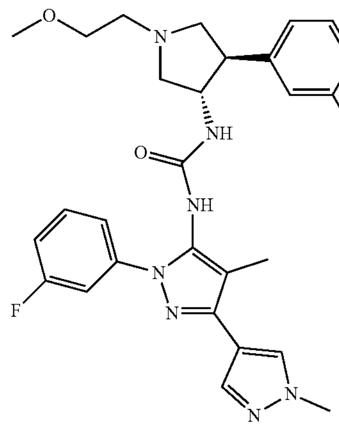 | 1-((3S,4R)-4-(3,4-difluorophenyl)-1-(2-methoxyethyl)pyrrolidin-3-yl)-3-(1-(3-fluorophenyl)-1',4-dimethyl-1H,1'H-[3,4'-bipyrazol]-5-yl)urea | 554.2 (M + H) |
| 314 | 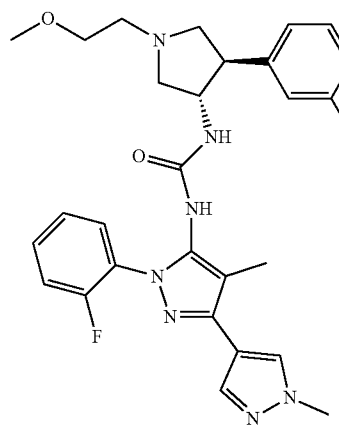 | 1-((3S,4R)-4-(3,4-difluorophenyl)-1-(2-methoxyethyl)pyrrolidin-3-yl)-3-(1-(2-fluorophenyl)-1',4-dimethyl-1H,1'H-[3,4'-bipyrazol]-5-yl)urea | 554.2 (M + H) |
| 315 | 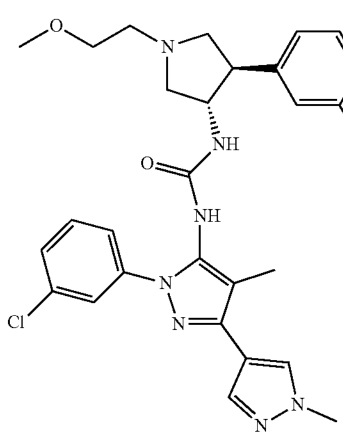 | 1-((3S,4R)-4-(3,4-difluorophenyl)-1-(2-methoxyethyl)pyrrolidin-3-yl)-3-(1-(3-chlorophenyl)-1',4-dimethyl-1H,1'H-[3,4'-bipyrazol]-5-yl)urea | 571.2 (M + H) |

| Ex. # | Structure | Name | MS (apci) m/z |
|---|---|---|---|
| 316 | 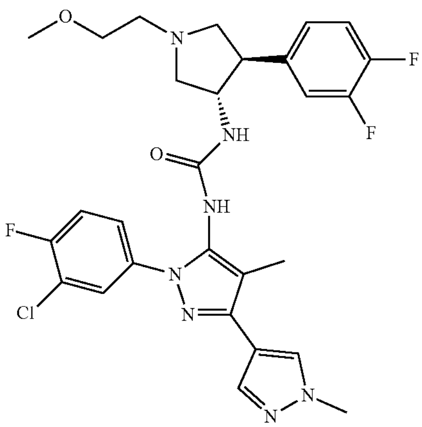 [SMILES: COCCN1C[C@@H](NC(=O)Nc2c(C)c(-c3cnn(C)c3)nn2-c2ccc(F)c(Cl)c2)[C@H](c2ccc(F)c(F)c2)C1] | 1-(1-(3-chloro-4-fluorophenyl)-1',4-dimethyl-1H,1'H-[3,4'-bipyrazol]-5-yl)-3-((3S,4R)-4-(3,4-difluorophenyl)-1-(2-methoxyethyl)pyrrolidin-3-yl)urea | 589.2 (M + H) |
| 317 | 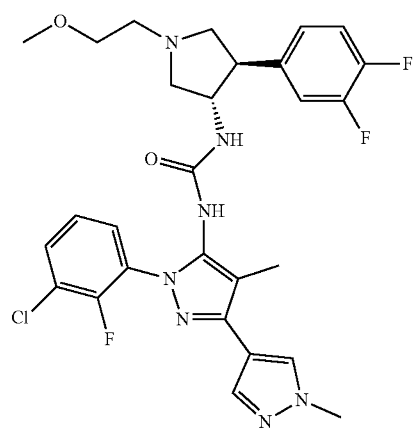 [SMILES: COCCN1C[C@@H](NC(=O)Nc2c(C)c(-c3cnn(C)c3)nn2-c2cccc(Cl)c2F)[C@H](c2ccc(F)c(F)c2)C1] | 1-(1-(3-chloro-2-fluorophenyl)-1',4-dimethyl-1H,1'H-[3,4'-bipyrazol]-5-yl)-3-((3S,4R)-4-(3,4-difluorophenyl)-1-(2-methoxyethyl)pyrrolidin-3-yl)urea | 589.2 (M + H) |
| 318 | 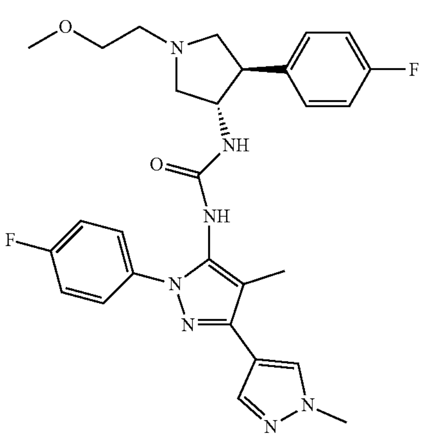 | 1-((3S,4R)-4-(4-fluorophenyl)-1-(2-methoxyethyl)pyrrolidin-3-yl)-3-(1-(4-fluorophenyl)-1',4-dimethyl-1H,1'H-[3,4'-bipyrazol]-5-yl)urea | 568.2 (M + H) |

-continued

| Ex. # | Structure | Name | MS (apci) m/z |
|---|---|---|---|
| 319 | 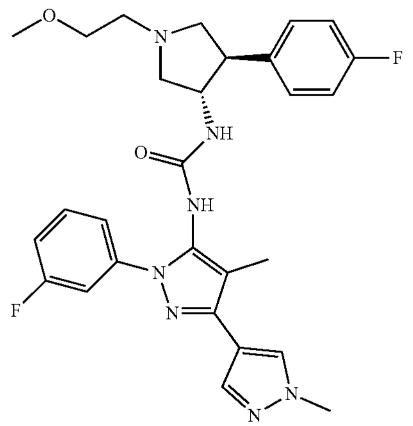 | 1-((3S,4R)-4-(4-fluorophenyl)-1-(2-methoxyethyl)pyrrolidin-3-yl)-3-(1-(3-fluorophenyl)-1',4-dimethyl-1H,1'H-[3,4'-bipyrazol]-5-yl)urea | 568.2 (M + H) |
| 320 | 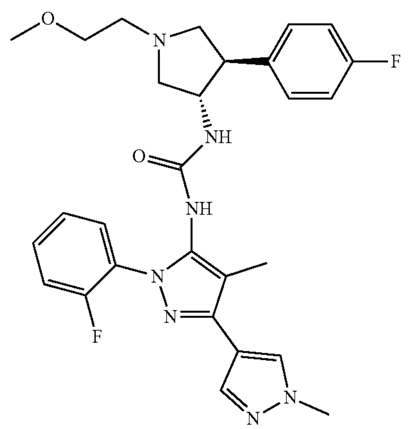 | 1-((3S,4R)-4-(4-fluorophenyl)-1-(2-methoxyethyl)pyrrolidin-3-yl)-3-(1-(2-fluorophenyl)-1',4-dimethyl-1H,1'H-[3,4'-bipyrazol]-5-yl)urea | 568.2 (M + H) |
| 321 | 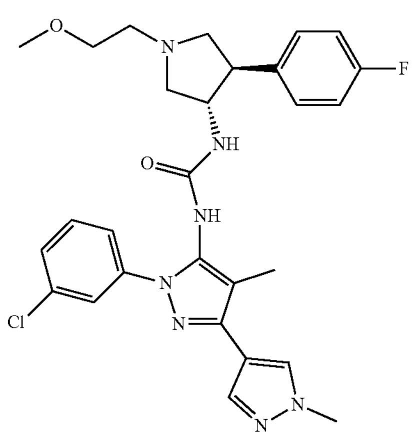 [SMILES: COCCN1C[C@@H](NC(=O)Nc2c(C)c(-c3cnn(C)c3)nn2-c2cccc(Cl)c2)[C@H](c2ccc(F)cc2)C1] | 1-((3S,4R)-4-(3,4-fluorophenyl)-1-(2-methoxyethyl)pyrrolidin-3-yl)-3-(1-(3-chlorophenyl)-1',4-dimethyl-1H,1'H-[3,4'-bipyrazol]-5-yl)urea | 550.2 (M + H) |

| Ex. # | Structure | Name | MS (apci) m/z |
|---|---|---|---|
| 322 | 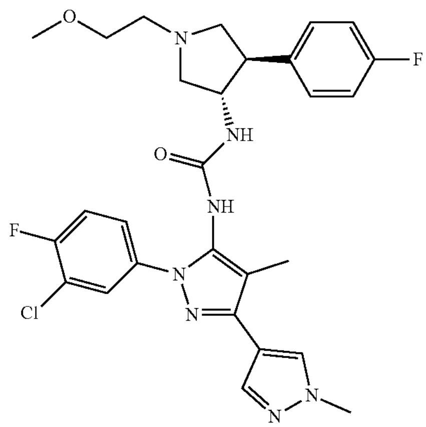 [SMILES: COCCN1C[C@@H](NC(=O)Nc2c(C)c(-c3cnn(C)c3)nn2-c2ccc(F)c(Cl)c2)[C@H](c2ccc(F)cc2)C1] | 1-(1-(3-chloro-4-fluorophenyl)-1',4-dimethyl-1H,1'H-[3,4'-bipyrazol]-5-yl)-3-((3S,4R)-4-(4-difluorophenyl)-1-(2-methoxyethyl)pyrrolidin-3-yl)urea | 568.2 (M − H). |
| 323 | 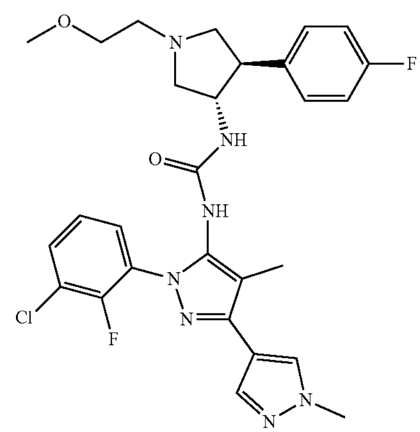 [SMILES: COCCN1C[C@@H](NC(=O)Nc2c(C)c(-c3cnn(C)c3)nn2-c2cccc(Cl)c2F)[C@H](c2ccc(F)cc2)C1] | 1-(1-(3-chloro-2-fluorophenyl)-1',4-dimethyl-1H,1'H-[3,4'-bipyrazol]-5-yl)-3-((3S,4R)-4-(4-difluorophenyl)-1-(2-methoxyethyl)pyrrolidin-3-yl)urea | 568.2 (M − H). |
| 324 | 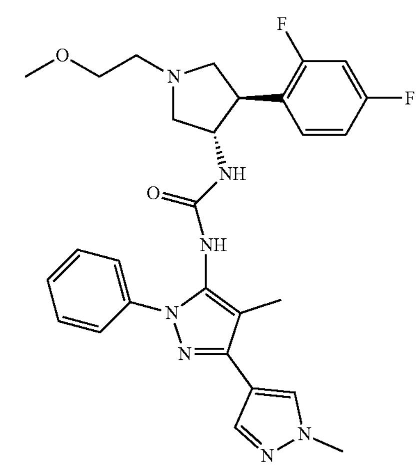 [SMILES: COCCN1C[C@@H](NC(=O)Nc2c(C)c(-c3cnn(C)c3)nn2-c2ccccc2)[C@H](c2ccc(F)cc2F)C1] | 1-((3S,4R)-4-(2,4-difluorophenyl)-1-(2-methoxyethyl)pyrrolidin-3-yl)-3-(1',4-dimethyl-1-phenyl-1H,1'H-[3,4'-bipyrazol]-5-yl)urea | 536.2 (M + H) |

-continued

| Ex. # | Structure | Name | MS (apci) m/z |
|---|---|---|---|
| 325 | 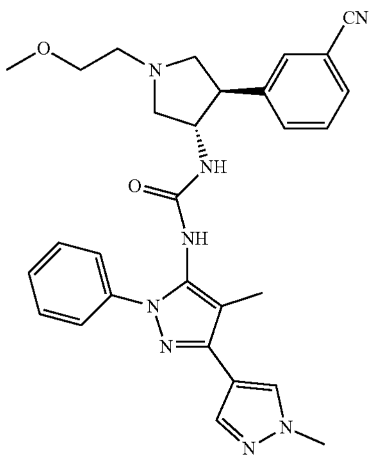 [SMILES: COCCN1C[C@@H](NC(=O)Nc2c(C)c(-c3cnn(C)c3)nn2-c2ccccc2)[C@H](c2cccc(C#N)c2)C1] | 1-((3S,4R)-4-(3-cyanophenyl)-1-(2-methoxyethyl)pyrrolidin-3-yl)-3-(1',4-dimethyl-1-phenyl-1H,1'H-[3,4'-bipyrazol]-5-yl)urea | 523.2 (M + H) |
| 326 | 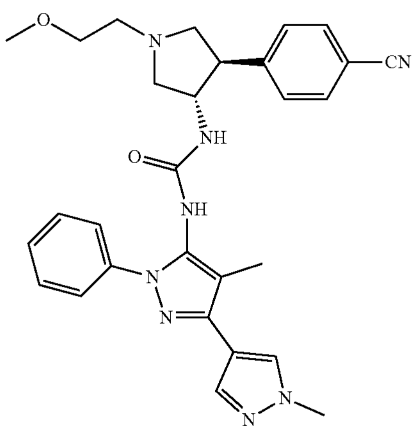 [SMILES: COCCN1C[C@@H](NC(=O)Nc2c(C)c(-c3cnn(C)c3)nn2-c2ccccc2)[C@H](c2ccc(C#N)cc2)C1] | 1-((3S,4R)-4-(4-cyanophenyl)-1-(2-methoxyethyl)pyrrolidin-3-yl)-3-(1',4-dimethyl-1-phenyl-1H,1'H-[3,4'-bipyrazol]-5-yl)urea | 523.2 (M + H) |
| 327 | 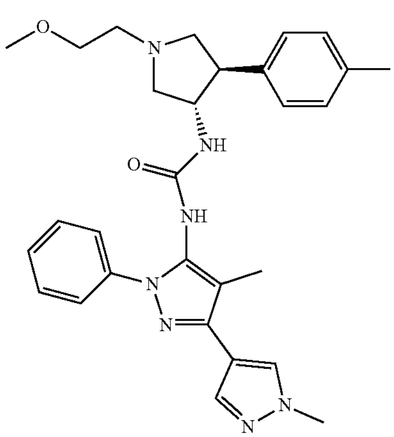 | 1-(1',4-dimethyl-1-phenyl-1H,1'H-[3,4'-bipyrazol]-5-yl)-3-((3S,4R)-1-(2-methoxyethyl)-4-(p-tolyl)pyrrolidin-3-yl)urea | 514.3 (M + H) |

| Ex. # | Structure | Name | MS (apci) m/z |
|---|---|---|---|
| 328 | 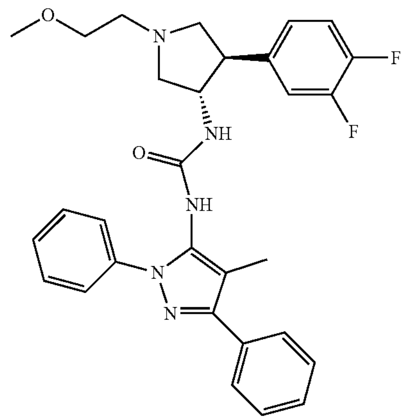 [SMILES: COCCN1C[C@@H](NC(=O)Nc2c(C)c(-c3ccccc3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-1,3-diphenyl-1H-pyrazol-5-yl)urea | 532.2 (M + H) |
| 329 | 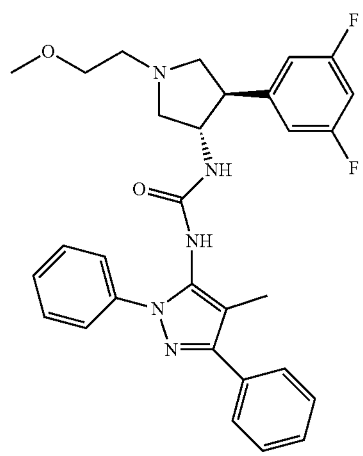 [SMILES: COCCN1C[C@@H](NC(=O)Nc2c(C)c(-c3ccccc3)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(4-methyl-1,3-diphenyl-1H-pyrazol-5-yl)urea | 532.2 (M + H) |
| 330 | 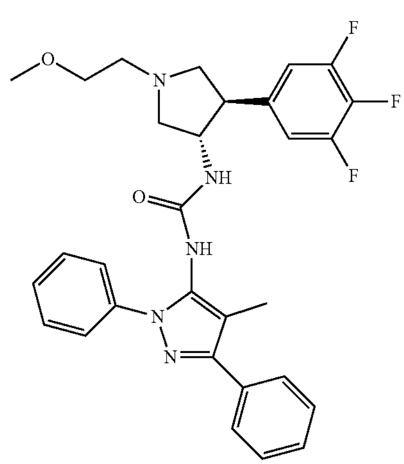 [SMILES: COCCN1C[C@@H](NC(=O)Nc2c(C)c(-c3ccccc3)nn2-c2ccccc2)[C@H](c2cc(F)c(F)c(F)c2)C1] | 1-((3S,4R)-4-(3,4,5-trifluorophenyl)-1-(2-methoxyethyl)pyrrolidin-3-yl)-3-(4-methyl-1,3-diphenyl-1H-pyrazol-5-yl)urea | 550.2 (M + H) |

| Ex. # | Structure | Name | MS (apci) m/z |
|---|---|---|---|
| 331 | 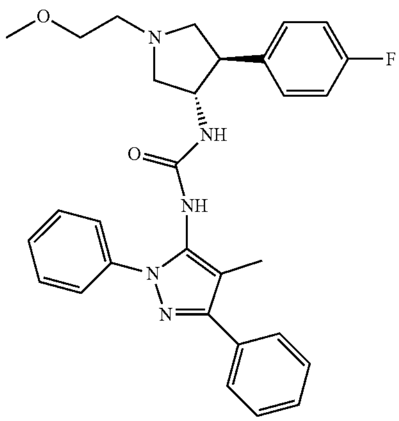 [SMILES: COCCN1C[C@@H](NC(=O)Nc2c(C)c(-c3ccccc3)nn2-c2ccccc2)[C@H](c2ccc(F)cc2)C1] | 1-((3S,4R)-4-(4-fluorophenyl)-1-(2-methoxyethyl)pyrrolidin-3-yl)-3-(4-methyl-1,3-diphenyl-1H-pyrazol-5-yl)urea | 514.3 (M + H) |
| 332 | 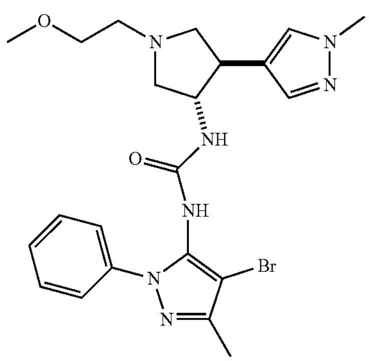 | 1-(4-bromo-3-methyl-1-phenyl-1H-pyrazol-5-yl)-3-trans-1-(2-methoxyethyl)-4-(1-methyl-1H-pyrazol-4-yl)pyrrolidin-3-yl)urea | 502.1 (M + H) |
| 333 | 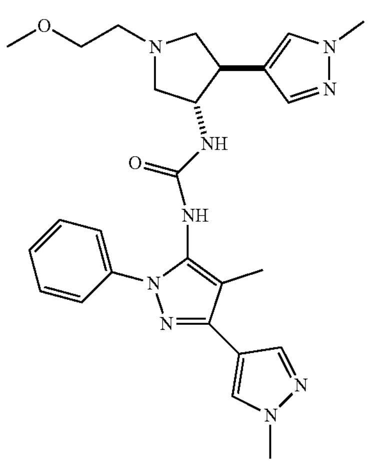 | 1-(1',4-dimethyl-1-phenyl-1H,1'H-[3,4'-bipyrazol]-5-yl)-3-(trans-1-(2-methoxyethyl)-4-(1-methyl-1H-pyrazol-4-yl)pyrrolidin-3-yl)urea | 519.2 (M + H) |

| Ex. # | Structure | Name | MS (apci) m/z |
|---|---|---|---|
| 334 | 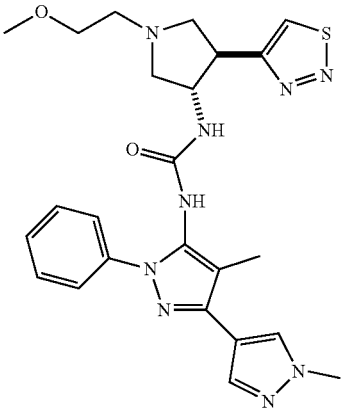 | 1-(1',4-dimethyl-1-phenyl-1H,1'H-[3,4'-bipyrazol]-5-yl)-3-(trans-1-(2-methoxyethyl)-4-(1,2,3-thiadiazol-4-yl)pyrrolidin-3-yl)urea | 507.6 (M + H) |
| 335 | 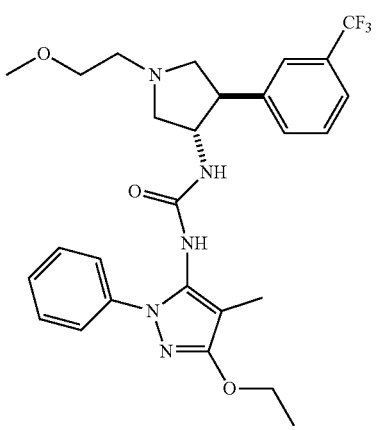 | 1-(3-ethoxy-4-methyl-1-phenyl-1H-pyrazol-5-yl)-3-(trans-1-(2-methoxyethyl)-4-(3-(trifluoromethyl)phenyl)pyrrolidin-3-yl)urea | 532.3 (M + H) |
| 336 | 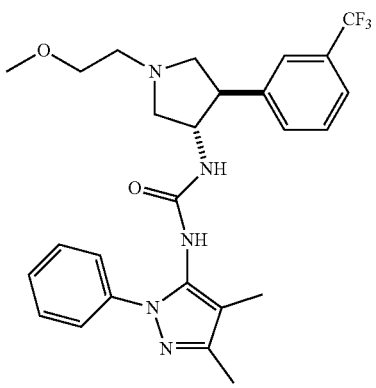 | 1-(3,4-dimethyl-1-phenyl-1H-pyrazol-5-yl)-3-((3S,4R)-1-(2-methoxyethyl)-4-(3-(trifluoromethyl)phenyl)pyrrolidin-3-yl)urea | 502.2 (M + H) |

-continued

| Ex. # | Structure | Name | MS (apci) m/z |
|---|---|---|---|
| 337 | 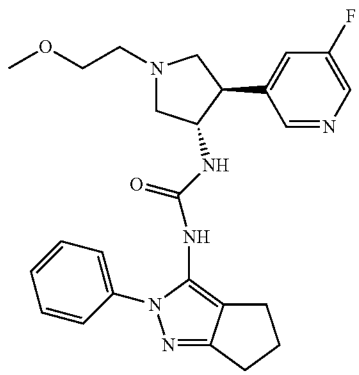 [SMILES: COCCN1C[C@@H](NC(=O)Nc2c3c(nn2-c2ccccc2)CCC3)[C@H](c2cncc(F)c2)C1] | 1-((3S,4R)-4-(5-fluoropyridin-3-yl)-1-(2-methoxyethyl)pyrrolidin-3-yl)-3-(2-phenyl-2,4,5,6-tetrahydrocyclopenta[c]pyrazol-3-yl)urea | 465.2 (M + H) |
| 338 | 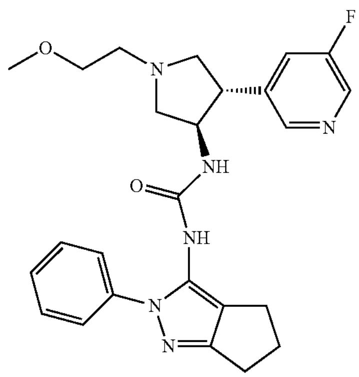 [SMILES: COCCN1C[C@H](NC(=O)Nc2c3c(nn2-c2ccccc2)CCC3)[C@@H](c2cncc(F)c2)C1] | 1-((3R,4S)-4-(5-fluoropyridin-3-yl)-1-(2-methoxyethyl)pyrrolidin-3-yl)-3-(2-phenyl-2,4,5,6-tetrahydrocyclopenta[c]pyrazol-3-yl)urea | 465.2 (M + H) |
| 339 | 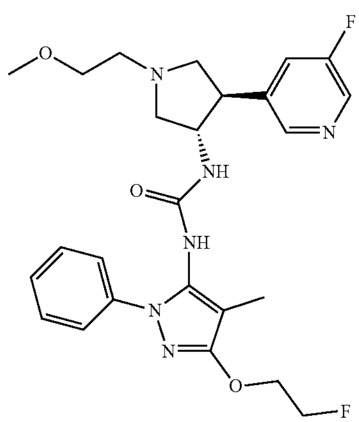 [SMILES: COCCN1C[C@@H](NC(=O)Nc2c(C)c(OCCF)nn2-c2ccccc2)[C@H](c2cncc(F)c2)C1] | 1-(3-(2-fluoroethoxy)-4-methyl-1-phenyl-1H-pyrazol-5-yl)-3-((3S,4R)-4-(5-fluoropyridin-3-yl)-1-(2-methoxyethyl)pyrrolidin-3-yl)urea | 501.2 (M + H) |
| 340 | 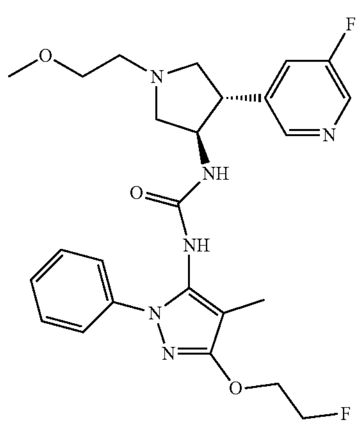 [SMILES: COCCN1C[C@H](NC(=O)Nc2c(C)c(OCCF)nn2-c2ccccc2)[C@@H](c2cncc(F)c2)C1] | 1-(3-(2-fluoroethoxy)-4-methyl-1-phenyl-1H-pyrazol-5-yl)-3-((3R,4S)-4-(5-fluoropyridin-3-yl)-1-(2-methoxyethyl)pyrrolidin-3-yl)urea | 501.2 (M + H) |

| Ex. # | Structure | Name | MS (apci) m/z |
|---|---|---|---|
| 341 | 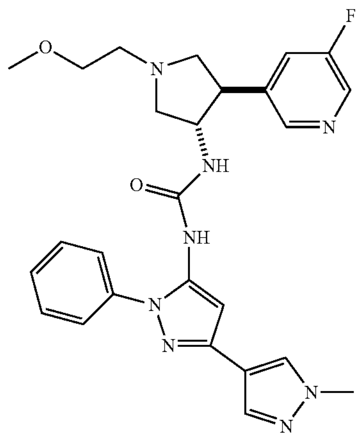 | 1-(trans-4-(5-fluoropyridin-3-yl)-1-(2-methoxyethyl)pyrrolidin-3-yl)-3-(2-phenyl-2,4,5,6-tetrahydrocyclopenta[c]pyrazol-3-yl)urea | 465.2 (M + H) |
| 342 | 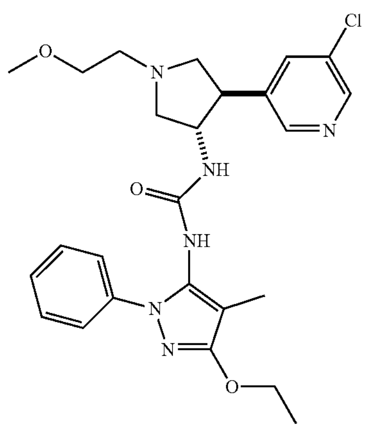 | 1-(trans-4-(5-chloropyridin-3-yl)-1-(2-methoxyethyl)pyrrolidin-3-yl)-3-(3-ethoxy-4-methyl-1-phenyl-1H-pyrazol-5-yl)urea | 500.2 (M + H) |
| 343 | 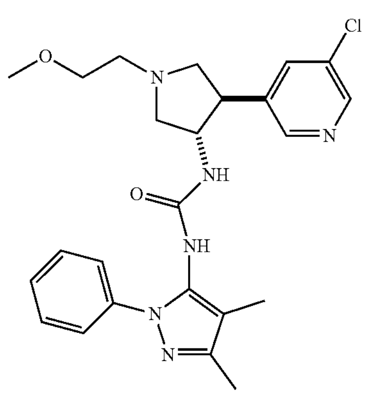 | 1-(trans-4-(5-chloropyridin-3-yl)-1-(2-methoxyethyl)pyrrolidin-3-yl)-3-(3,4-dimethyl-1-phenyl-1H-pyrazol-5-yl)urea | 469.2 (M + H) |

| Ex. # | Structure | Name | MS (apci) m/z |
|---|---|---|---|
| 344 | 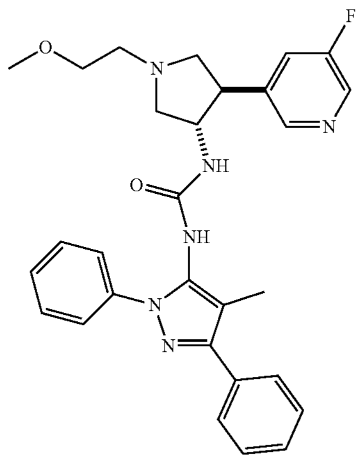 | 1-(trans-4-(5-fluoropyridin-3-yl)-1-(2-methoxyethyl)pyrrolidin-3-yl)-3-(4-methyl-1,3-diphenyl-1H-pyrazol-5-yl)urea | 515.3 (M + H) |
| 345 | 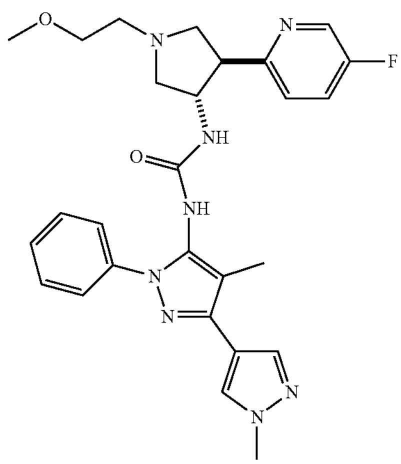 | 1-(1',4-dimethyl-1-phenyl-1H,1'H-[3,4'-bipyrazol]-5-yl)-3-(trans-4-(5-fluoropyridin-2-yl)-1-(2-methoxyethyl)pyrrolidin-3-yl)urea | 515.3 (M + H) |
| 346 | 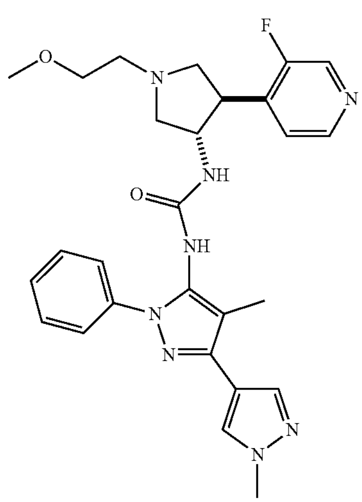 | 1-(1',4-dimethyl-1-phenyl-1H,1'H-[3,4'-bipyrazol]-5-yl)-3-((3S,4R)-4-(3-fluoropyridin-4-yl)-1-(2-methoxyethyl)pyrrolidin-3-yl)urea | 519.2 (M + H) |

| Ex. # | Structure | Name | MS (apci) m/z |
|---|---|---|---|
| 347 | 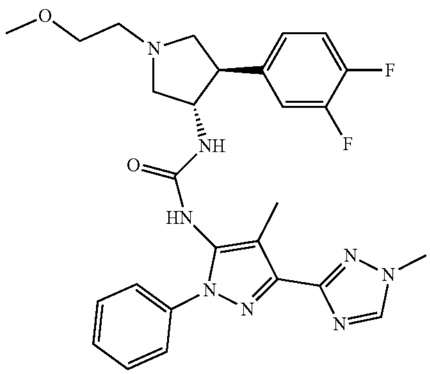 | 1-((3S,4R)-4-(3,4-difluorophenyl)-1-(2-methoxyethyl)pyrrolidin-3-yl)-3-(4-methyl-3-(1-methyl-1H-1,2,4-triazol-3-yl)-1-phenyl-1H-pyrazol-5-yl)urea | 537.2 (M + H) |
| 348 | 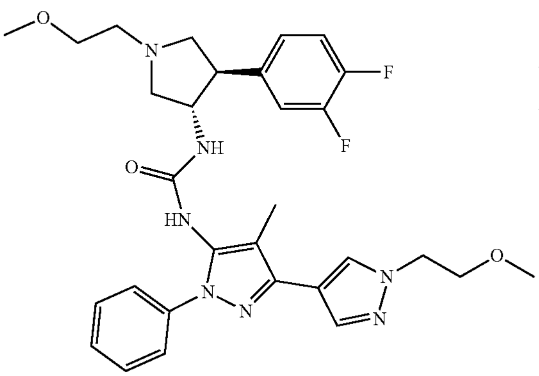 | 1-((3S,4R)-4-(3,4-difluorophenyl)-1-(2-methoxyethyl)pyrrolidin-3-yl)-3-(1'-(2-methoxyethyl)-4-methyl-1-phenyl-1H,1'H-[3,4'-bipyrazol]-5-yl)urea | 580.3 (M + H) |
| 349 | 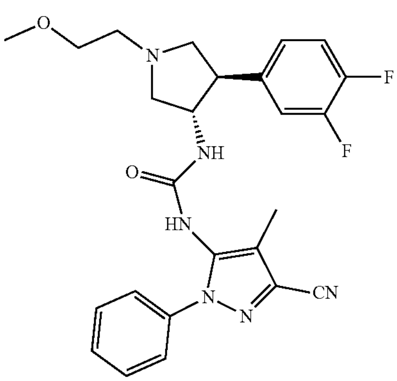 [SMILES: COCCN1C[C@@H](NC(=O)Nc2c(C)c(C#N)nn2-c2ccccc2)[C@H](c2ccc(F)c(F)c2)C1] | 1-(3-cyano-4-methyl-1-phenyl-1H-pyrazol-5-yl)-3-((3S,4R)-4-(3,4-difluorophenyl)-1-(2-methoxyethyl)pyrrolidin-3-yl)urea | 480.8 (M + H) |
| 350 | 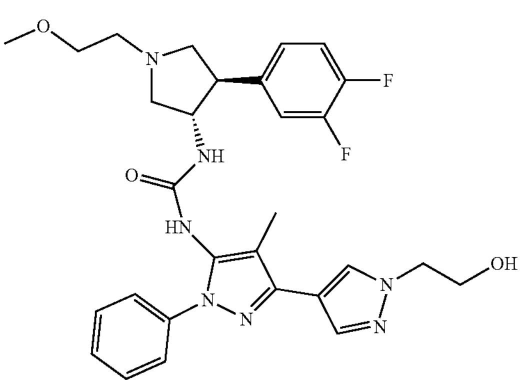 [SMILES: COCCN1C[C@@H](NC(=O)Nc2c(C)c(-c3cnn(CCO)c3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(1'-(2-hydroxyethyl)-4-methyl-1-phenyl-1H,1'H-[3,4'-bipyrazol]-5-yl)urea | 565.8 (M + H) |

| Ex. # | Structure | Name | MS (apci) m/z |
|---|---|---|---|
| 351 | 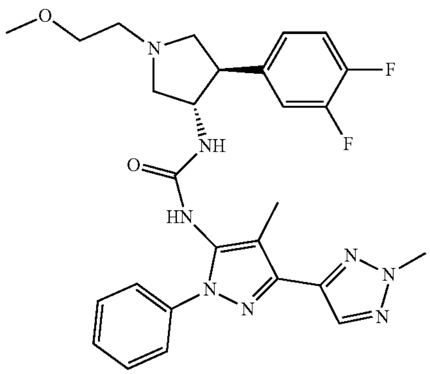 | 1-((3S,4R)-4-(3,4-difluorophenyl)-1-(2-methoxyethyl)pyrrolidin-3-yl)-3-(4-methyl-3-(2-methyl-2H-1,2,3-triazol-4-yl)-1-phenyl-1H-pyrazol-5-yl)urea | 536.8 (M + H) |
| 352 | 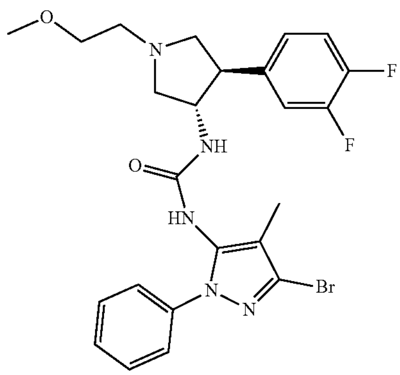 [SMILES: COCCN1C[C@@H](NC(=O)Nc2c(C)c(Br)nn2-c2ccccc2)[C@H](c2ccc(F)c(F)c2)C1] | 1-(3-bromo-4-methyl-1-phenyl-1H-pyrazol-5-yl)-3-((3S,4R)-4-(3,4-difluorophenyl)-1-(2-methoxyethyl)pyrrolidin-3-yl)urea | 533.7 (M + H) |
| 353 | 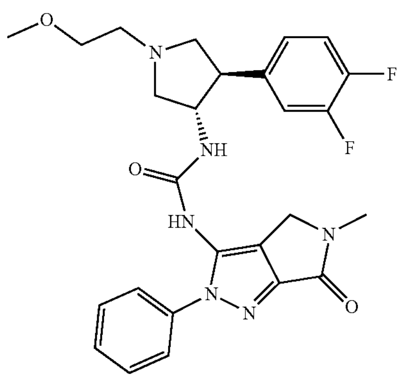 [SMILES: COCCN1C[C@@H](NC(=O)Nc2c3c(nn2-c2ccccc2)C(=O)N(C)C3)[C@H](c2ccc(F)c(F)c2)C1] | 1-((3S,4R)-4-(3,4-difluorophenyl)-1-(2-methoxyethyl)pyrrolidin-3-yl)-3-(5-methyl-6-oxo-2-phenyl-2,4,5,6-tetrahydropyrrolo[3,4-c]pyrazol-3-yl)urea | 510.8 (M + H) |
| 354 | 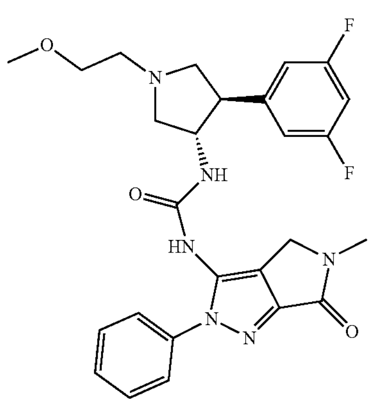 | 1-((3S,4R)-4-(3,4-difluorophenyl)-1-(2-methoxyethyl)pyrrolidin-3-yl)-3-(5-methyl-6-oxo-2-phenyl-2,4,5,6-tetrahydropyrrolo[3,4-c]pyrazol-3-yl)urea | 510.8 (M + H) |

| Ex. # | Structure | Name | MS (apci) m/z |
|---|---|---|---|
| 555 | 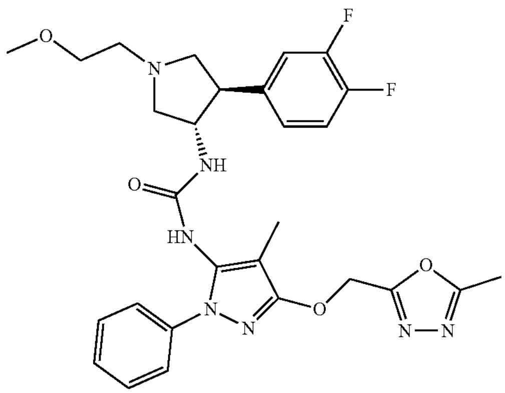 | 1-((3S,4R)-4-(3,4-difluorophenyl)-1-(2-methoxyethyl)pyrrolidin-3-yl)-3-(4-methyl-3-((5-methyl-1,3,4-oxadiazol-2-yl)methoxy)-1-phenyl-1H-pyrazol-5-yl)urea | 568.3 (M + H) |
| 356 | 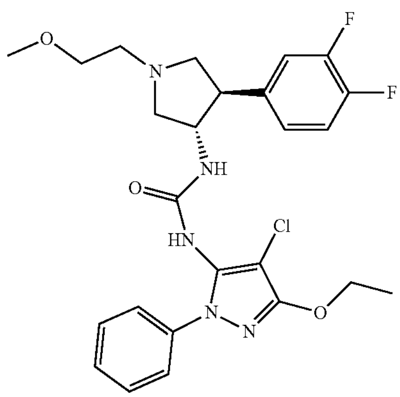 [SMILES: CCOc1nn(-c2ccccc2)c(NC(=O)N[C@@H]2CN(CCOC)C[C@H]2c2ccc(F)c(F)c2)c1Cl] | 1-(4-chloro-3-ethoxy-1-phenyl-1H-pyrazol-5-yl)-3-((3S,4R)-4-(3,4-difluorophenyl)-1-(2-methoxyethyl)pyrrolidin-3-yl)urea | 520.2 (M + H) |
| 357 | 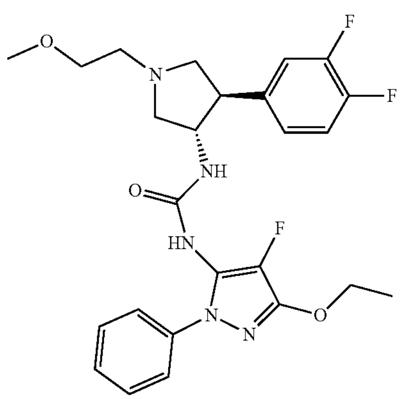 [SMILES: CCOc1nn(-c2ccccc2)c(NC(=O)N[C@@H]2CN(CCOC)C[C@H]2c2ccc(F)c(F)c2)c1F] | 1-((3S,4R)-4-(3,4-difluorophenyl)-1-(2-methoxyethyl)pyrrolidin-3-yl)-3-(3-ethoxy-4-fluoro-1-phenyl-1H-pyrazol-5-yl)urea | 504.2 (M + H) |
| 358 | 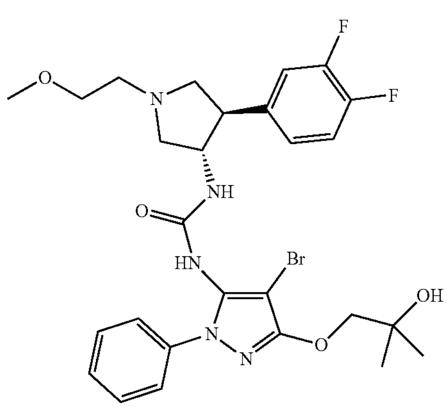 [SMILES: COCCN1C[C@@H](NC(=O)Nc2c(Br)c(OCC(C)(C)O)nn2-c2ccccc2)[C@H](c2ccc(F)c(F)c2)C1] | 1-(4-bromo-3-(2-hydroxy-2-methylpropoxy)-1-phenyl-1H-pyrazol-5-yl)-3-((3S,4R)-4-(3,4-difluorophenyl)-1-(2-methoxyethyl)pyrrolidin-3-yl)urea | 608.2 (M + H) |

-continued

| Ex. # | Structure | Name | MS (apci) m/z |
|---|---|---|---|
| 359 | 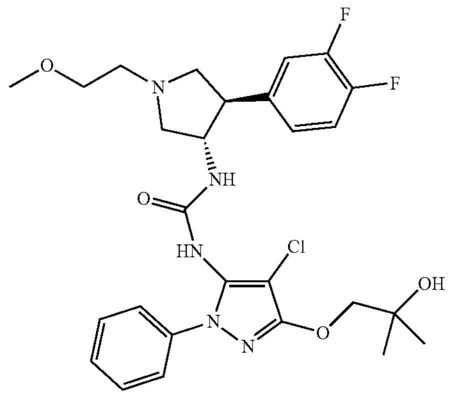 [SMILES: COCCN1C[C@@H](NC(=O)Nc2c(Cl)c(OCC(C)(C)O)nn2-c2ccccc2)[C@H](c2ccc(F)c(F)c2)C1] | 1-(4-chloro-3-(2-hydroxy-2-methylpropoxy)-1-phenyl-1H-pyrazol-5-yl)-3-((3S,4R)-4-(3,4-difluorophenyl)-1-(2-methoxyethyl)pyrrolidin-3-yl)urea | 564.2 (M + H) |
| 360 | 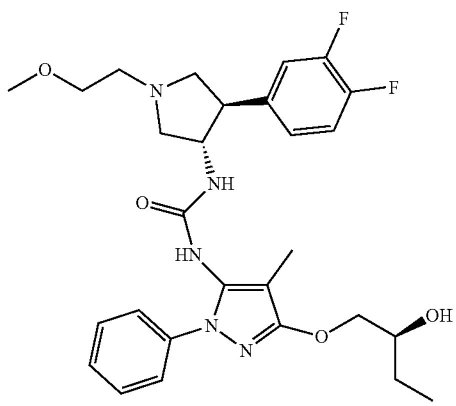 [SMILES: CC[C@H](O)COc1nn(-c2ccccc2)c(NC(=O)N[C@@H]2CN(CCOC)C[C@H]2c2ccc(F)c(F)c2)c1C] | 1-((3S,4R)-4-(3,4-difluorophenyl)-1-(2-methoxyethyl)pyrrolidin-3-yl)-3-(3-((S)-2-hydroxybutoxy)-4-methyl-1-phenyl-1H-pyrazol-5-yl)urea | 544.3 (M + H) |
| 361 | 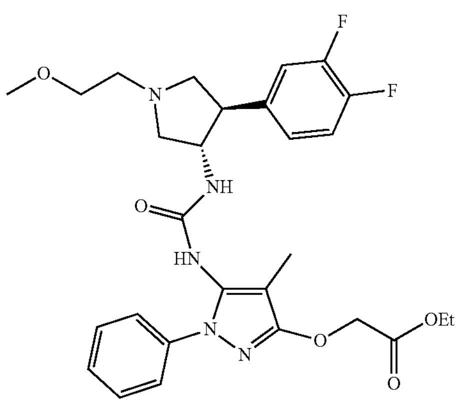 [SMILES: CCOC(=O)COc1nn(-c2ccccc2)c(NC(=O)N[C@@H]2CN(CCOC)C[C@H]2c2ccc(F)c(F)c2)c1C] | ethyl 2-((5-(3-((3S,4R)-4-(3,4-difluorophenyl)-1-(2-methoxyethyl)pyrrolidin-3-yl)ureido)-4-methyl-1-phenyl-1H-pyrazol-3-yl)oxy)acetate | 558.3 (M + H) |
| 362 | 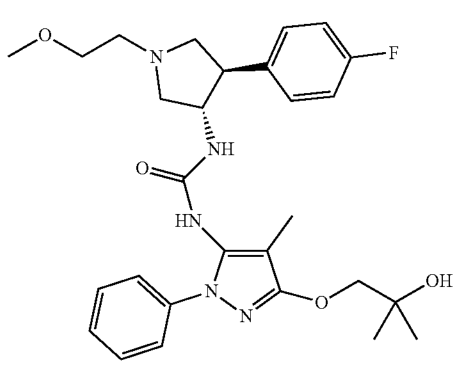 [SMILES: COCCN1C[C@@H](NC(=O)Nc2c(C)c(OCC(C)(C)O)nn2-c2ccccc2)[C@H](c2ccc(F)cc2)C1] | 1-((3S,4R)-4-(4-fluorophenyl)-1-(2-methoxyethyl)pyrrolidin-3-yl)-3-(3-(2-hydroxy-2-methylpropoxy)-4-methyl-1-phenyl-1H-pyrazol-5-yl)urea | 526.3 (M + H) |

| Ex. # | Structure | Name | MS (apci) m/z |
|---|---|---|---|
| 363 | 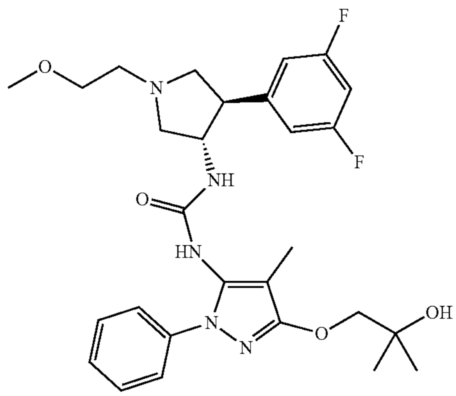 [SMILES: COCCN1C[C@@H](NC(=O)Nc2c(C)c(OCC(C)(C)O)nn2-c2ccccc2)[C@H](c2cc(F)cc(F)c2)C1] | 1-((3S,4R)-4-(3,4-difluorophenyl)-1-(2-methoxyethyl)pyrrolidin-3-yl)-3-(3-(2-hydroxy-2-methylpropoxy)-4-methyl-1-phenyl-1H-pyrazol-5-yl)urea | 544.3 (M + H) |
| 364 | 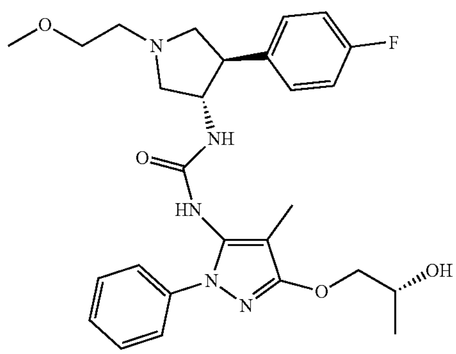 [SMILES: COCCN1C[C@@H](NC(=O)Nc2c(C)c(OC[C@@H](C)O)nn2-c2ccccc2)[C@H](c2ccc(F)cc2)C1] | 1-((3S,4R)-4-(4-fluorophenyl)-1-(2-methoxyethyl)pyrrolidin-3-yl)-3-(3-((R)-2-hydroxypropoxy)-4-methyl-1-phenyl-1H-pyrazol-5-yl)urea | 512.3 (M + H) |
| 365 | 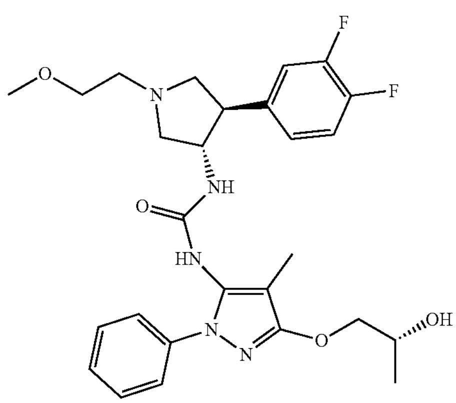 [SMILES: COCCN1C[C@@H](NC(=O)Nc2c(C)c(OC[C@@H](C)O)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-((R)-2-hydroxypropoxy)-4-methyl-1-phenyl-1H-pyrazol-5-yl)urea | 530.3 (M + H) |
| 366 | 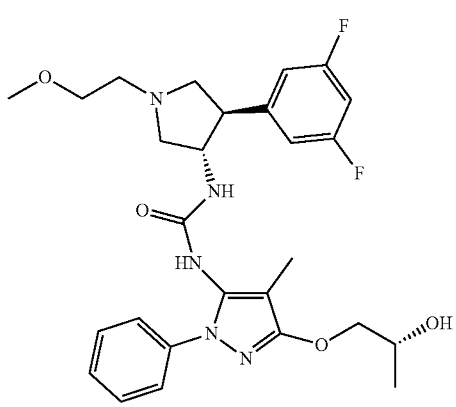 [SMILES: COCCN1C[C@@H](NC(=O)Nc2c(C)c(OC[C@@H](C)O)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(3-((R)-2-hydroxypropoxy)-4-methyl-1-phenyl-1H-pyrazol-5-yl)urea | 530.3 (M + H) |

-continued

| Ex. # | Structure | Name | MS (apci) m/z |
|---|---|---|---|
| 367 | 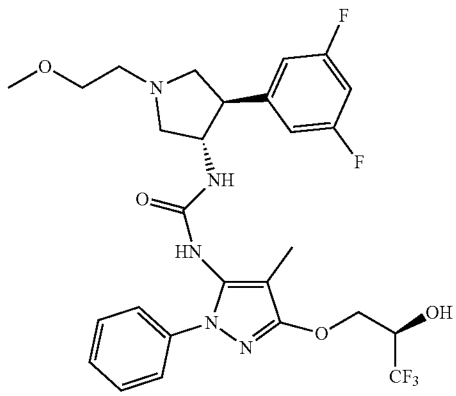 [SMILES: COCCN1C[C@@H](NC(=O)Nc2c(C)c(OC[C@@H](O)C(F)(F)F)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(4-methyl-1-phenyl-3-((R)-3,3,3-trifluoro-2-hydroxypropoxy)-1H-pyrazol-5-yl)urea | 584.2 (M + H) |
| 368 | 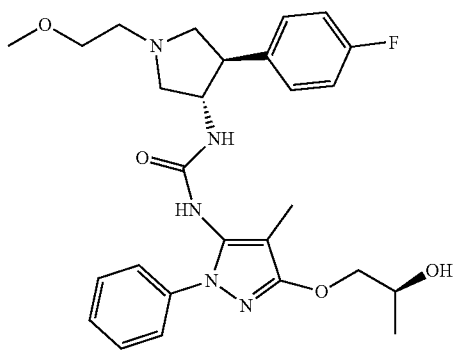 [SMILES: COCCN1C[C@@H](NC(=O)Nc2c(C)c(OC[C@H](C)O)nn2-c2ccccc2)[C@H](c2ccc(F)cc2)C1] | 1-((3S,4R)-4-(4-fluorophenyl)-1-(2-methoxyethyl)pyrrolidin-3-yl)-3-(3-((S)-2-hydroxypropoxy)-4-methyl-1-phenyl-1H-pyrazol-5-yl)urea | 512.3 (M + H) |
| 369 | 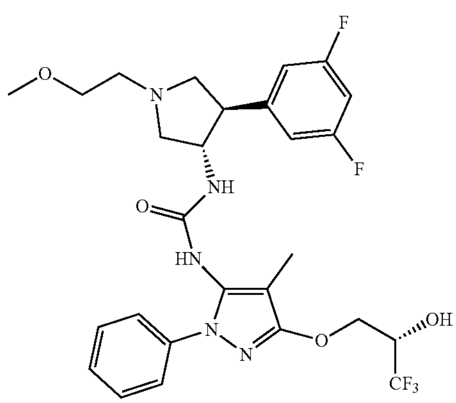 [SMILES: COCCN1C[C@@H](NC(=O)Nc2c(C)c(OC[C@H](O)C(F)(F)F)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(4-methyl-1-phenyl-3-((S)-3,3,3-trifluoro-2-hydroxypropoxy)-1H-pyrazol-5-yl)urea | 584.3 (M + H) |
| 370 | 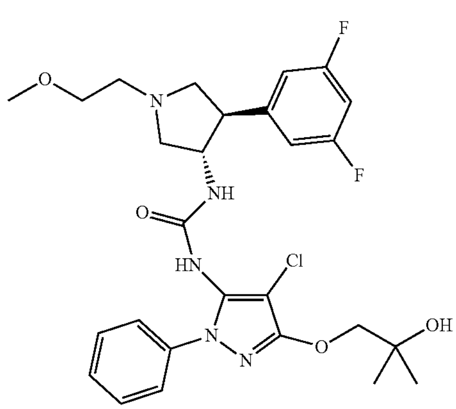 [SMILES: COCCN1C[C@@H](NC(=O)Nc2c(Cl)c(OCC(C)(C)O)nn2-c2ccccc2)[C@H](c2cc(F)cc(F)c2)C1] | 1-(4-chloro-3-(2-hydroxy-2-methylpropoxy)-1-phenyl-1H-pyrazol-5-yl)-3-((3S,4R)-4-(3,5-difluorophenyl)-1-(2-methoxyethyl)pyrrolidin-3-yl)urea | 564.2 (M + H) |

| Ex. # | Structure | Name | MS (apci) m/z |
|---|---|---|---|
| 371 | 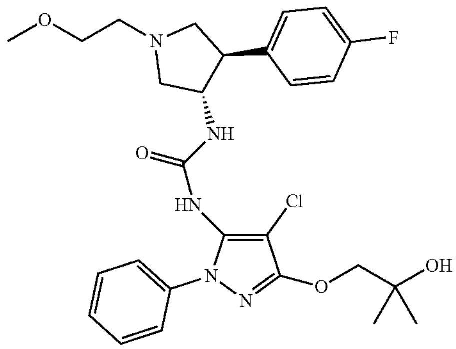 [SMILES: COCCN1C[C@@H](NC(=O)Nc2c(Cl)c(OCC(C)(C)O)nn2-c2ccccc2)[C@H](c2ccc(F)cc2)C1] | 1-(4-chloro-3-(2-hydroxy-2-methylpropoxy)-1-phenyl-1H-pyrazol-5-yl)-3-((3S,4R)-4-(4-fluorophenyl)-1-(2-methoxyethyl)pyrrolidin-3-yl)urea | 546.2 (M + H) |
| 372 | 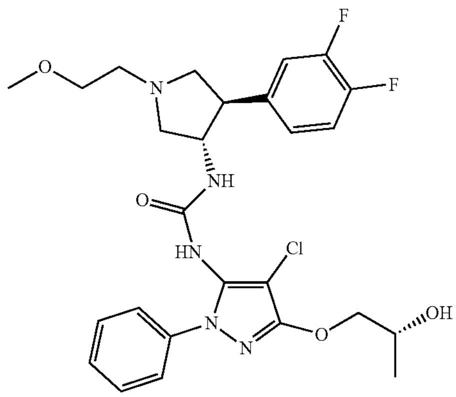 [SMILES: COCCN1C[C@@H](NC(=O)Nc2c(Cl)c(OC[C@@H](C)O)nn2-c2ccccc2)[C@H](c2ccc(F)c(F)c2)C1] | 1-(4-chloro-3-((R)-2-hydroxypropoxy)-1-phenyl-1H-pyrazol-5-yl)-3-((3S,4R)-4-(3,4-difluorophenyl)-1-(2-methoxyethyl)pyrrolidin-3-yl)urea | 550.2 (M + H) |
| 373 | 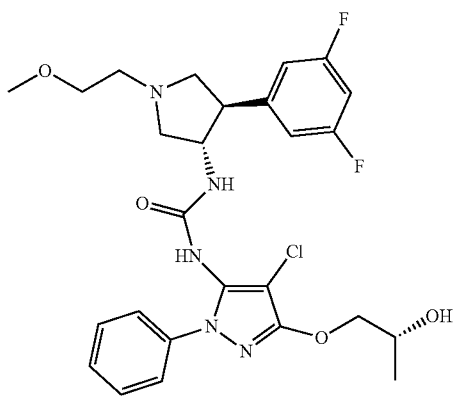 [SMILES: COCCN1C[C@@H](NC(=O)Nc2c(Cl)c(OC[C@@H](C)O)nn2-c2ccccc2)[C@H](c2cc(F)cc(F)c2)C1] | 1-(4-chloro-3-((R)-2-hydroxypropoxy)-1-phenyl-1H-pyrazol-5-yl)-3-((3S,4R)-4-(3,5-difluorophenyl)-1-(2-methoxyethyl)pyrrolidin-3-yl)urea | 550.2 (M + H) |
| 374 | 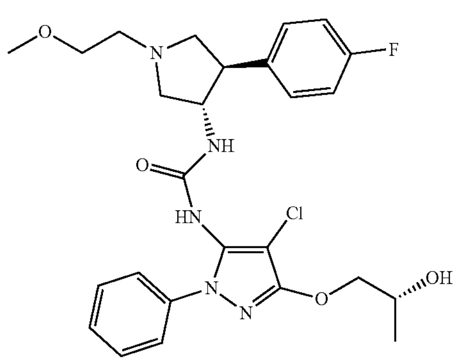 [SMILES: COCCN1C[C@@H](NC(=O)Nc2c(Cl)c(OC[C@@H](C)O)nn2-c2ccccc2)[C@H](c2ccc(F)cc2)C1] | 1-(4-chloro-3-((R)-2-hydroxypropoxy)-1-phenyl-1H-pyrazol-5-yl)-3-((3S,4R)-4-(4-fluorophenyl)-1-(2-methoxyethyl)pyrrolidin-3-yl)urea | 532.2 (M + H) |

| Ex. # | Structure | Name | MS (apci) m/z |
|---|---|---|---|
| 375 | 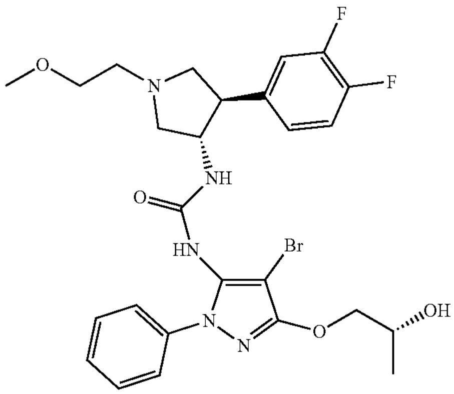 [SMILES: COCCN1C[C@@H](NC(=O)Nc2c(Br)c(OC[C@@H](C)O)nn2-c2ccccc2)[C@H](c2ccc(F)c(F)c2)C1] | 1-(4-bromo-3-((R)-2-hydroxypropoxy)-1-phenyl-1H-pyrazol-5-yl)-3-((3S,4R)-4-(3,4-difluorophenyl)-1-(2-methoxyethyl)pyrrolidin-3-yl)urea | 594.2 (M + H) |
| 376 | 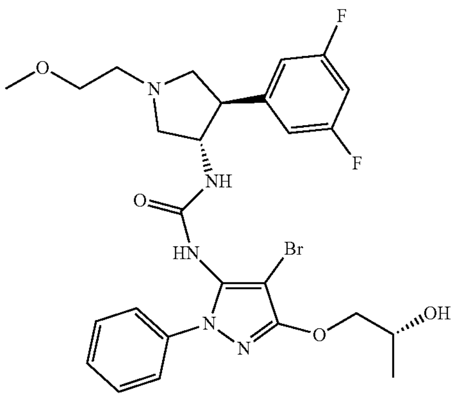 [SMILES: COCCN1C[C@@H](NC(=O)Nc2c(Br)c(OC[C@@H](C)O)nn2-c2ccccc2)[C@H](c2cc(F)cc(F)c2)C1] | 1-(4-bromo-3-((R)-2-hydroxypropoxy)-1-phenyl-1H-pyrazol-5-yl)-3-((3S,4R)-4-(3,5-difluorophenyl)-1-(2-methoxyethyl)pyrrolidin-3-yl)urea | 594.2 (M + H) |
| 377 | 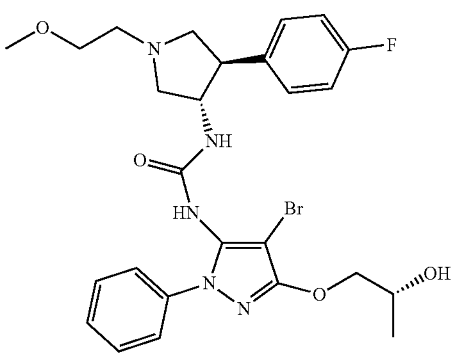 [SMILES: COCCN1C[C@@H](NC(=O)Nc2c(Br)c(OC[C@@H](C)O)nn2-c2ccccc2)[C@H](c2ccc(F)cc2)C1] | 1-(4-bromo-3-((R)-2-hydroxypropoxy)-1-phenyl-1H-pyrazol-5-yl)-3-((3S,4R)-4-(4-fluorophenyl)-1-(2-methoxyethyl)pyrrolidin-3-yl)urea | 576.2 (M + H) |
| 378 | 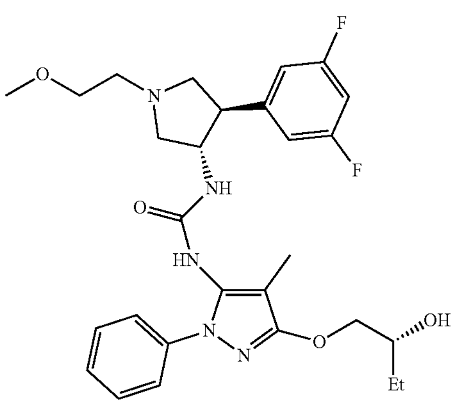 [SMILES: CC[C@@H](O)COc1nn(-c2ccccc2)c(NC(=O)N[C@@H]2CN(CCOC)C[C@H]2c2cc(F)cc(F)c2)c1C] | 1-((3S,4R)-4-(3,5-difluorophenyl)-1-(2-methoxyethyl)pyrrolidin-3-yl)-3-(3-((R)-2-hydroxybutoxy)-4-methyl-1-phenyl-1H-pyrazol-5-yl)urea | 544.3 (M + H) |

-continued

| Ex. # | Structure | Name | MS (apci) m/z |
|---|---|---|---|
| 379 | 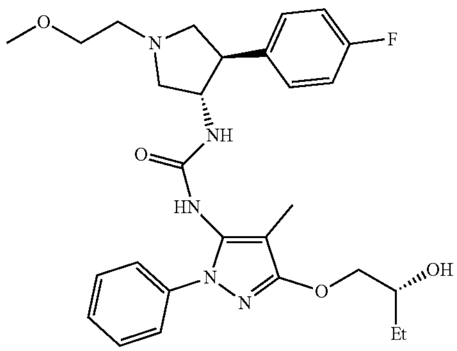 [SMILES: CC[C@@H](O)COc1nn(-c2ccccc2)c(NC(=O)N[C@@H]2CN(CCOC)C[C@H]2c2ccc(F)cc2)c1C] | 1-((3S,4R)-4-(4-fluorophenyl)-1-(2-methoxyethyl)pyrrolidin-3-yl)-3-(3-((R)-2-hydroxybutoxy)-4-methyl-1-phenyl-1H-pyrazol-5-yl)urea | 526.3 (M + H) |
| 380 | 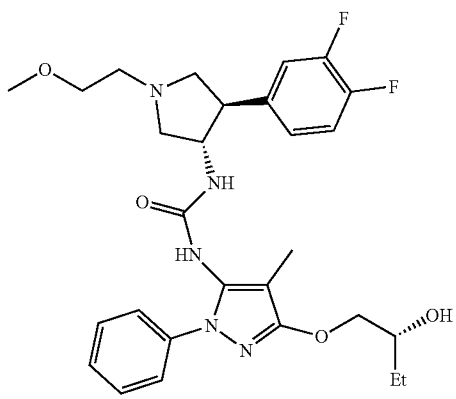 [SMILES: CC[C@@H](O)COc1nn(-c2ccccc2)c(NC(=O)N[C@@H]2CN(CCOC)C[C@H]2c2ccc(F)c(F)c2)c1C] | 1-((3S,4R)-4-(3,4-difluorophenyl)-1-(2-methoxyethyl)pyrrolidin-3-yl)-3-(3-((R)-2-hydroxybutoxy)-4-methyl-1-phenyl-1H-pyrazol-5-yl)urea | 544.3 (M + H) |
| 381 | 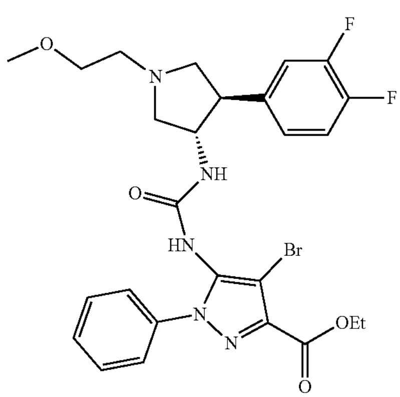 [SMILES: CCOC(=O)c1nn(-c2ccccc2)c(NC(=O)N[C@@H]2CN(CCOC)C[C@H]2c2ccc(F)c(F)c2)c1Br] | ethyl 4-bromo-5-(3-((3S,4R)-4-(3,4-difluorophenyl)-1-(2-methoxyethyl)pyrrolidin-3-yl)ureido)-1-phenyl-1H-pyrazole-3-carboxylate | 592.2 (M + H) |
| 382 | 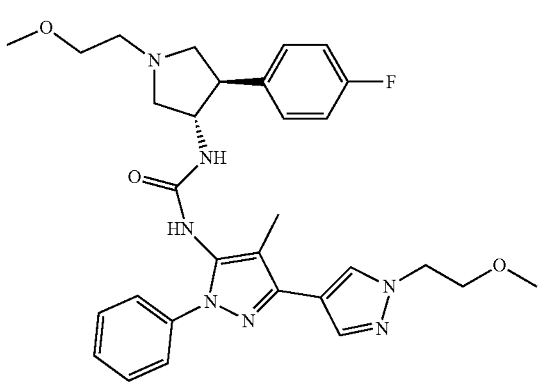 | 1-((3S,4R)-4-(4-fluorophenyl)-1-(2-methoxyethyl)pyrrolidin-3-yl)-3-(1'-(2-methoxyethyl)-4-methyl-1-phenyl-1H,1'H-[3,4'-bipyrazol]-5-yl)urea | 562.3 (M + H) |

| Ex. # | Structure | Name | MS (apci) m/z |
|---|---|---|---|
| 383 | 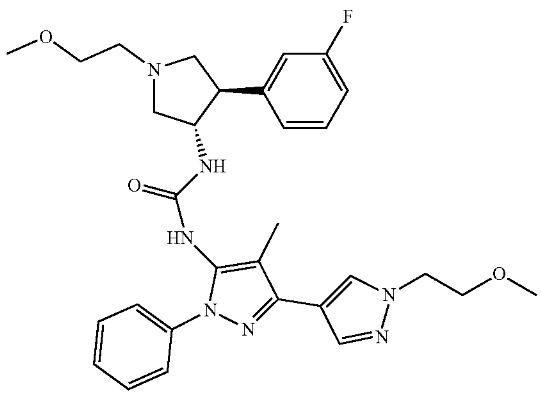 | 1-((3S,4R)-4-(3-fluorophenyl)-1-(2-methoxyethyl)pyrrolidin-3-yl)-3-(1'-(2-methoxyethyl)-4-methyl-1-phenyl-1H,1'H-[3,4'-bipyrazol]-5-yl)urea | 562.3 (M + H) |
| 384 | 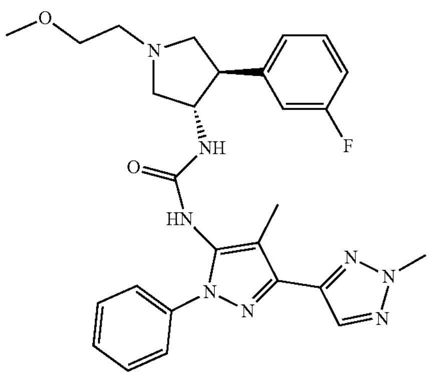 | 1-((3S,4R)-4-(3-fluorophenyl)-1-(2-methoxyethyl)pyrrolidin-3-yl)-3-(4-methyl-3-(2-methyl-2H-1,2,3-triazol-4-yl)-1-phenyl-1H-pyrazol-5-yl)urea | 519.3 (M + H) |
| 385 | 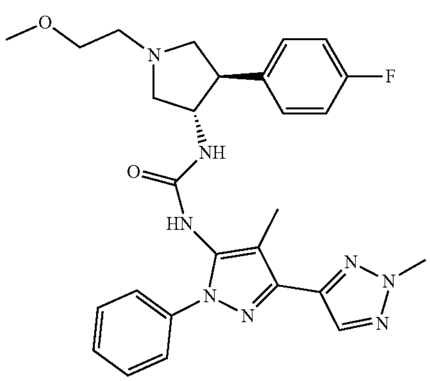 | 1-((3S,4R)-4-(4-fluorophenyl)-1-(2-methoxyethyl)pyrrolidin-3-yl)-3-(4-methyl-3-(2-methyl-2H-1,2,3-triazol-4-yl)-1-phenyl-1H-pyrazol-5-yl)urea | 519.3 (M + H) |
| 386 | 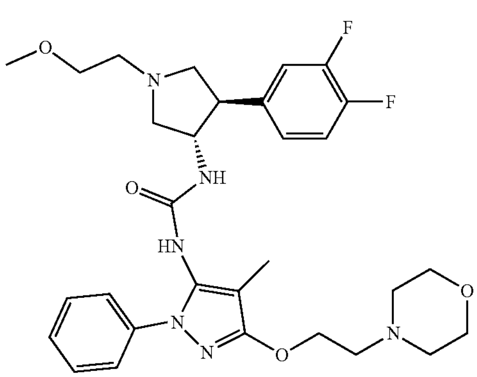 [SMILES: COCCN1C[C@@H](NC(=O)Nc2c(C)c(OCCN3CCOCC3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-3-(2-morpholinoethoxy)-1-phenyl-1H-pyrazol-5-yl)urea | 585.3 (M + H) |

-continued

| Ex. # | Structure | Name | MS (apci) m/z |
|---|---|---|---|
| 387 | 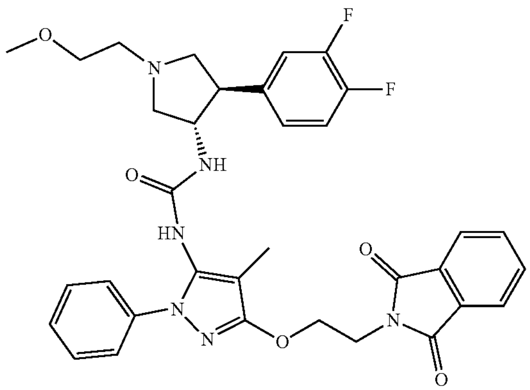 [SMILES: COCCN1C[C@@H](NC(=O)Nc2c(C)c(OCCN3C(=O)c4ccccc4C3=O)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(2-(1,3-dioxoisoindolin-2-yl)ethoxy)-4-methyl-1-phenyl-1H-pyrazol-5-yl)urea | 645.3 (M + H) |
| 388 | 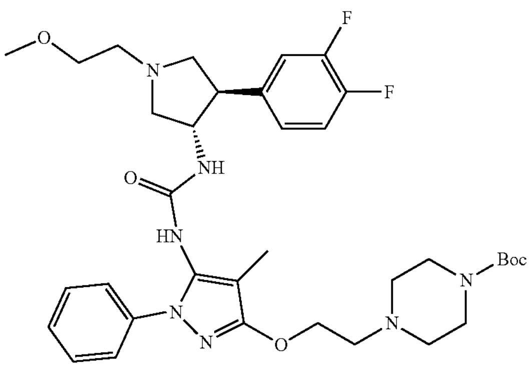 [SMILES: COCCN1C[C@@H](NC(=O)Nc2c(C)c(OCCN3CCN(C(=O)OC(C)(C)C)CC3)nn2-c2ccccc2)[C@H](c2ccc(F)c(F)c2)C1] | tert-butyl 4-(2-((5-(3-((3S,4R)-4-(3,4-difluorophenyl)-1-(2-methoxyethyl)pyrrolidin-3-yl)ureido)-4-methyl-1-phenyl-1H-pyrazol-3-yl)oxy)ethyl)piperazine-1-carboxylate | 684.4 (M + H) |
| 389 | 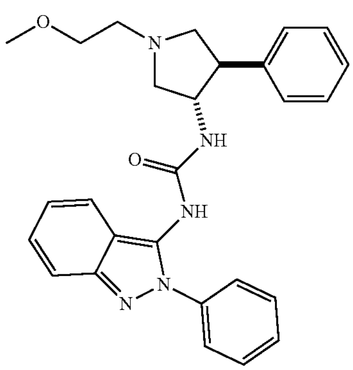 [SMILES: COCCN1C[C@@H](NC(=O)Nc2c3ccccc3nn2-c2ccccc2)[C@H](c2ccccc2)C1] | Trans-1-(2-methoxyethyl)-4-phenylpyrrolidin-3-yl)-3-(2-phenyl-2H-indazol-3-yl)urea | 456.2 (M + H) |
| 390 | 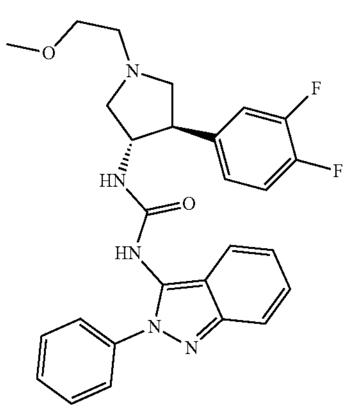 [SMILES: COCCN1C[C@@H](NC(=O)Nc2c3ccccc3nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(2-phenyl-2H-indazol-3-yl)urea | 492.0 (M + H) |

| Ex. # | Structure | Name | MS (apci) m/z |
|---|---|---|---|
| 391 | 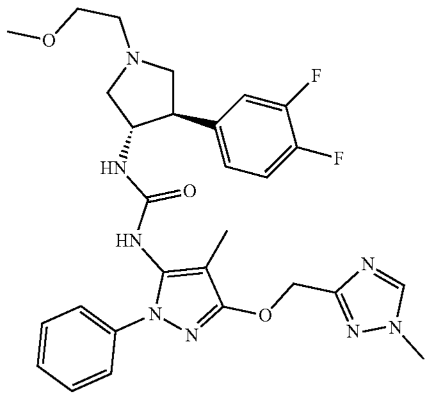 | 1-((3S,4R)-4-(3,4-difluorophenyl)-1-(2-methoxyethyl)pyrrolidin-3-yl)-3-(4-methyl-3-((1-methyl-1H-1,2,4-triazol-3-yl)methoxy)-1-phenyl-1H-pyrazol-5-yl)urea | 567.3 (M + H) |
| 392 | 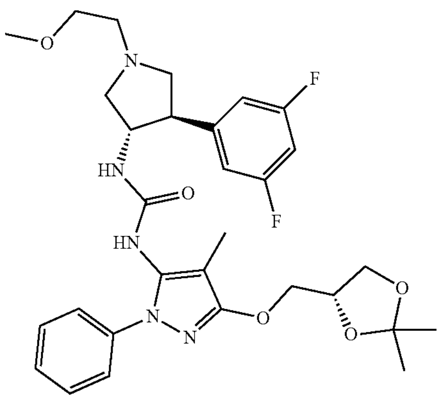 | 1-((3S,4R)-4-(3,5-difluorophenyl)-1-(2-methoxyethyl)pyrrolidin-3-yl)-3-(3-(((R)-2,2-dimethyl-1,3-dioxolan-4-yl)methoxy)-4-methyl-1-phenyl-1H-pyrazol-5-yl)urea | 586.2 (M + H) |
| 393 | 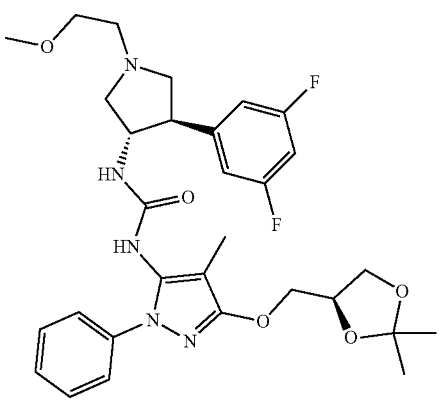 | 1-((3S,4R)-4-(3,5-difluorophenyl)-1-(2-methoxyethyl)pyrrolidin-3-yl)-3-(3-(((S)-2,2-dimethyl-1,3-dioxolan-4-yl)methoxy)-4-methyl-1-phenyl-1H-pyrazol-5-yl)urea | 586.2 (M + H) |
| 394 | 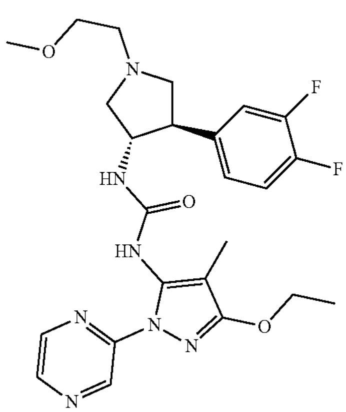 [SMILES: CCOc1nn(-c2cnccn2)c(NC(=O)N[C@@H]2CN(CCOC)C[C@H]2c2ccc(F)c(F)c2)c1C] | 1-((3S,4R)-4-(3,4-difluorophenyl)-1-(2-methoxyethyl)pyrrolidin-3-yl)-3-(3-ethoxy-4-methyl-1-(pyrazin-2-yl)-1H-pyrazol-5-yl)urea | 502.2 (M + H) |

| Ex. # | Structure | Name | MS (apci) m/z |
|---|---|---|---|
| 395 | 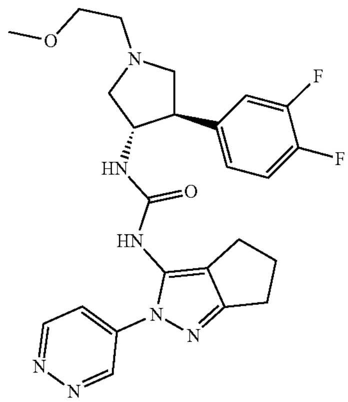 [SMILES: COCCN1C[C@@H](NC(=O)Nc2c3c(nn2-c2ccnnc2)CCC3)[C@H](c2ccc(F)c(F)c2)C1] | 1-((3S,4R)-4-(3,4-difluorophenyl)-1-(2-methoxyethyl)pyrrolidin-3-yl)-3-(2-(pyridazin-4-yl)-2,4,5,6-tetrahydrocyclopenta[c]pyrazol-3-yl)urea | 484.2 (M + H) |
| 396 | 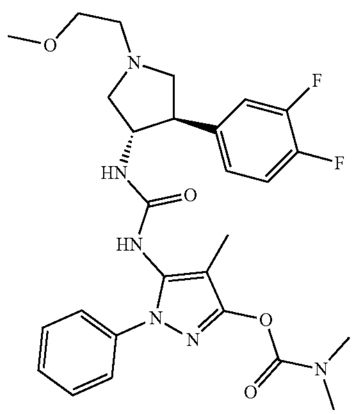 | 5-(3-((3S,4R)-4-(3,4-difluorophenyl)-1-(2-methoxyethyl)pyrrolidin-3-yl)ureido)-4-methyl-1-phenyl-1H-pyrazol-3-yl dimethylcarbamate | 543.2 (M + H) |
| 397 | 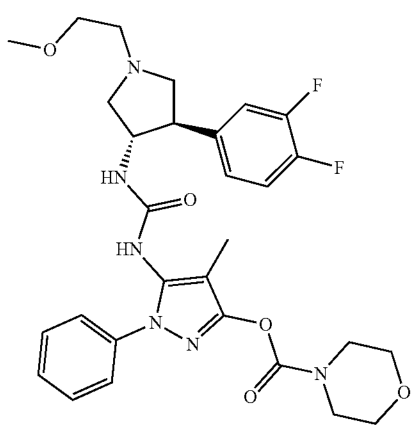 [SMILES: COCCN1C[C@@H](NC(=O)Nc2c(C)c(OC(=O)N3CCOCC3)nn2-c2ccccc2)[C@H](c2ccc(F)c(F)c2)C1] | 5-(3-((3S,4R)-4-(3,4-difluorophenyl)-1-(2-methoxyethyl)pyrrolidin-3-yl)ureido)-4-methyl-1-phenyl-1H-pyrazol-3-yl morpholine-4-carboxylate | 585.3 (M + H) |

| Ex. # | Structure | Name | MS (apci) m/z |
|---|---|---|---|
| 398 | 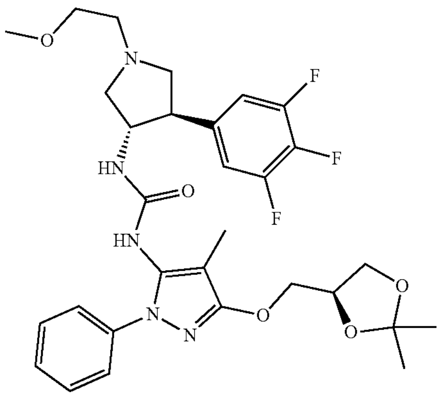 | 1-(3-(((S)-2,2-dimethyl-1,3-dioxolan-4-yl)methoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea | 604.3 (M + H) |
| 399 | 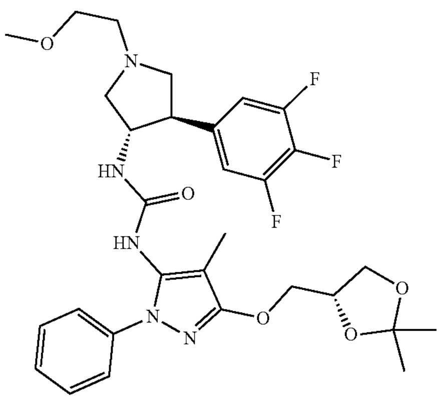 | 1-(3-(((R)-2,2-dimethyl-1,3-dioxolan-4-yl)methoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea | 604.3 (M + H) |
| 400 | 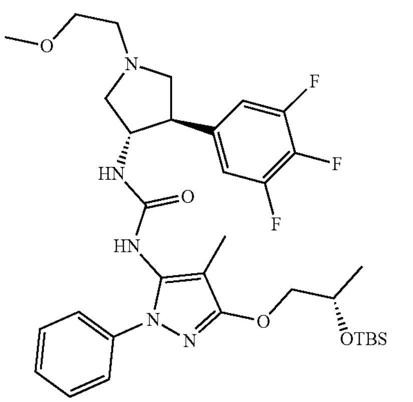 [SMILES: COCCN1C[C@@H](NC(=O)Nc2c(C)c(OC[C@H](C)O[Si](C)(C)C(C)(C)C)nn2-c2ccccc2)[C@H](c2cc(F)c(F)c(F)c2)C1] | 1-(3-((S)-2-(tert-butyldimethylsilyloxy)propoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea | 662.3 (M + H) |
| 401 | 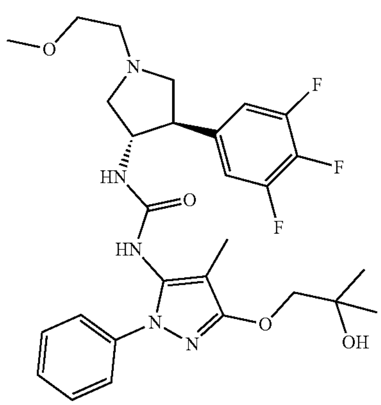 [SMILES: COCCN1C[C@@H](NC(=O)Nc2c(C)c(OCC(C)(C)O)nn2-c2ccccc2)[C@H](c2cc(F)c(F)c(F)c2)C1] | 1-(3-(2-hydroxy-2-methylpropoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea | 562.3 (M + H) |

| Ex. # | Structure | Name | MS (apci) m/z |
|---|---|---|---|
| 402 | 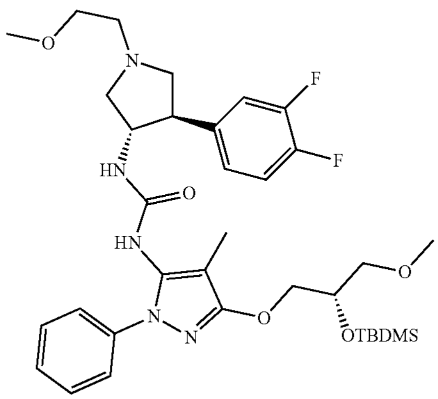 | 1-(3-((S)-2-(tert-butyldimethylsilyloxy)-3-methoxypropoxy)-4-methyl-1-phenyl-1H-pyrazol-5-yl)-3-((3S,4R)-4-(3,4-difluorophenyl)-1-(2-methoxyethyl)pyrrolidin-3-yl)urea_ | 674.3 (M + H) |

The following compounds were prepared according to the method of Example 1, Step B, using the appropriate halogenated pyrazole carbamate starting materials.

| Ex. # | Structure | Name | MS (apci) m/z |
|---|---|---|---|
| 403 | 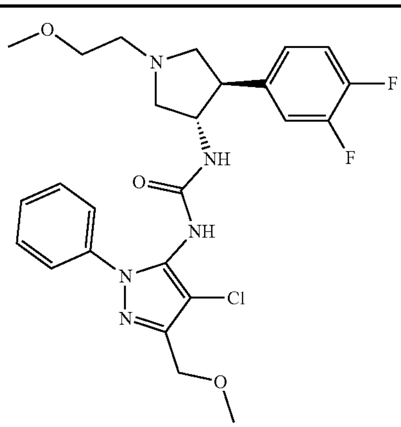 | 1-(4-chloro-3-(methoxymethyl)-1-phenyl-1H-pyrazol-5-yl)-3-((3S,4R)-4-(3,4-difluorophenyl)-1-(2-methoxyethyl)pyrrolidin-3-yl)urea | 520.2 (M + H) |
| 404 | 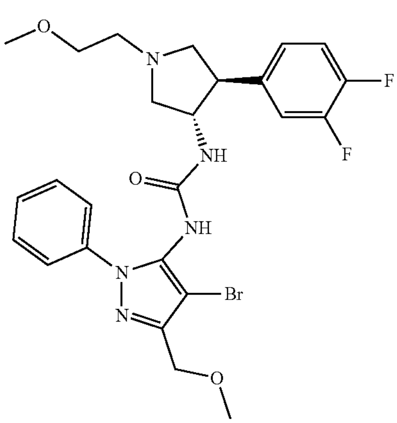 [SMILES: COCCN1C[C@@H](NC(=O)Nc2c(Br)c(COC)nn2-c2ccccc2)[C@H](c2ccc(F)c(F)c2)C1] | 1-(4-bromo-3-(methoxymethyl)-1-phenyl-1H-pyrazol-5-yl)-3-((3S,4R)-4-(3,4-difluorophenyl)-1-(2-methoxyethyl)pyrrolidin-3-yl)urea | 564.1 (M + H) |

| Ex. # | Structure | Name | MS (apci) m/z |
|---|---|---|---|
| 405 | 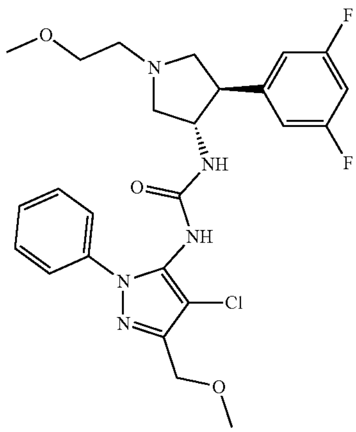 [SMILES: COCCN1C[C@@H](NC(=O)Nc2c(Cl)c(COC)nn2-c2ccccc2)[C@H](c2cc(F)cc(F)c2)C1] | 1-(4-chloro-3-(methoxymethyl)-1-phenyl-1H-pyrazol-5-yl)-3-((3S,4R)-4-(3,5-difluorophenyl)-1-(2-methoxyethyl)pyrrolidin-3-yl)urea | 520.2 (M + H) |
| 406 | 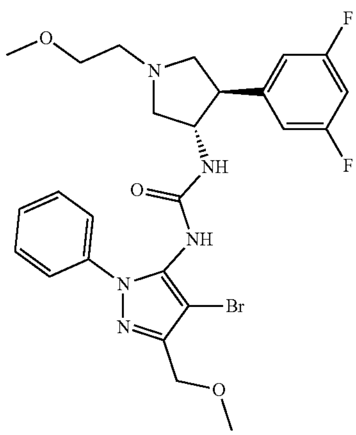 [SMILES: COCCN1C[C@@H](NC(=O)Nc2c(Br)c(COC)nn2-c2ccccc2)[C@H](c2cc(F)cc(F)c2)C1] | 1-(4-bromo-3-(methoxymethyl)-1-phenyl-1H-pyrazol-5-yl)-3-((3S,4R)-4-(3,5-difluorophenyl)-1-(2-methoxyethyl)pyrrolidin-3-yl)urea | 564.1 (M + H) |
| 407 | 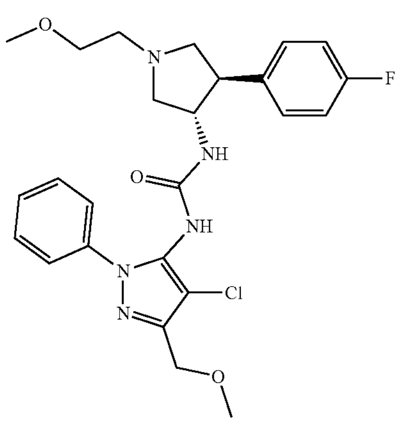 [SMILES: COCCN1C[C@@H](NC(=O)Nc2c(Cl)c(COC)nn2-c2ccccc2)[C@H](c2ccc(F)cc2)C1] | 1-(4-chloro-3-(methoxymethyl)-1-phenyl-1H-pyrazol-5-yl)-3-((3S,4R)-4-(4-fluorophenyl)-1-(2-methoxyethyl)pyrrolidin-3-yl)urea | 502.2 (M + H) |

-continued

| Ex. # | Structure | Name | MS (apci) m/z |
|---|---|---|---|
| 408 | 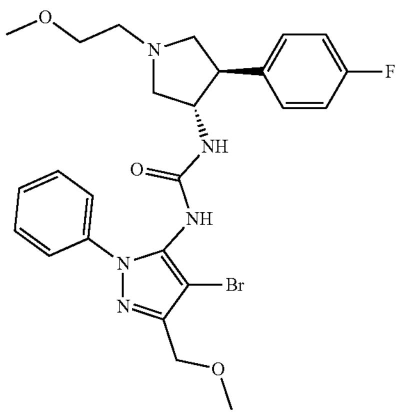 [SMILES: COCCN1C[C@@H](NC(=O)Nc2c(Br)c(COC)nn2-c2ccccc2)[C@H](c2ccc(F)cc2)C1] | 1-(4-bromo-3-(methoxymethyl)-1-phenyl-1H-pyrazol-5-yl)-3-((3S,4R)-4-(4-fluorophenyl)-1-(2-methoxyethyl)pyrrolidin-3-yl)urea | 546.2 (M + H) |
| 409 | 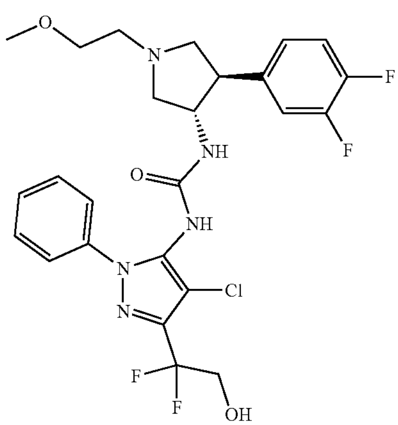 [SMILES: COCCN1C[C@@H](NC(=O)Nc2c(Cl)c(C(F)(F)CO)nn2-c2ccccc2)[C@H](c2ccc(F)c(F)c2)C1] | 1-(4-chloro-3-(1,1-difluoro-2-hydroxyethyl)-1-phenyl-1H-pyrazol-5-yl)-3-((3S,4R)-4-(3,4-difluorophenyl)-1-(2-methoxyethyl)pyrrolidin-3-yl)urea | 556.2 (M + H) |
| 410 | 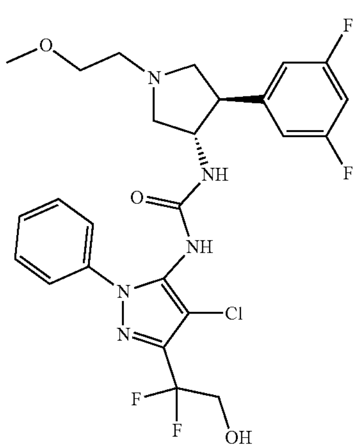 [SMILES: COCCN1C[C@@H](NC(=O)Nc2c(Cl)c(C(F)(F)CO)nn2-c2ccccc2)[C@H](c2cc(F)cc(F)c2)C1] | 1-(4-chloro-3-(1,1-difluoro-2-hydroxyethyl)-1-phenyl-1H-pyrazol-5-yl)-3-((3S,4R)-4-(3,5-difluorophenyl)-1-(2-methoxyethyl)pyrrolidin-3-yl)urea | 556.2 (M + H) |

-continued

| Ex. # | Structure | Name | MS (apci) m/z |
|---|---|---|---|
| 411 | 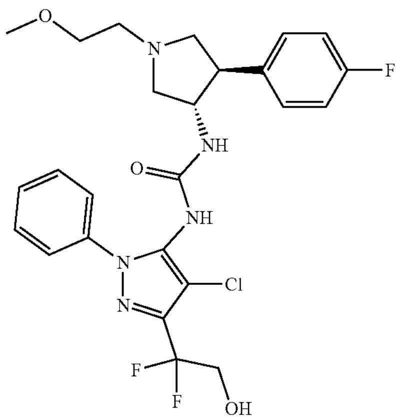 [SMILES: COCCN1C[C@@H](NC(=O)Nc2c(Cl)c(C(F)(F)CO)nn2-c2ccccc2)[C@H](c2ccc(F)cc2)C1] | 1-(4-chloro-3-(1,1-difluoro-2-hydroxyethyl)-1-phenyl-1H-pyrazol-5-yl)-3-((3S,4R)-4-(4-fluorophenyl)-1-(2-methoxyethyl)pyrrolidin-3-yl)urea | 538.2 (M + H) |
| 412 | 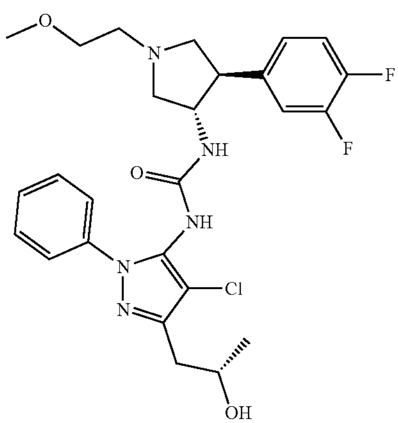 [SMILES: COCCN1C[C@@H](NC(=O)Nc2c(Cl)c(C[C@H](C)O)nn2-c2ccccc2)[C@H](c2ccc(F)c(F)c2)C1] | 1-(4-chloro-3-((S)-2-hydroxypropyl)-1-phenyl-1H-pyrazol-5-yl)-3-((3S,4R)-4-(3,4-difluorophenyl)-1-(2-methoxyethyl)pyrrolidin-3-yl)urea | 534.2 (M + H) |
| 413 | 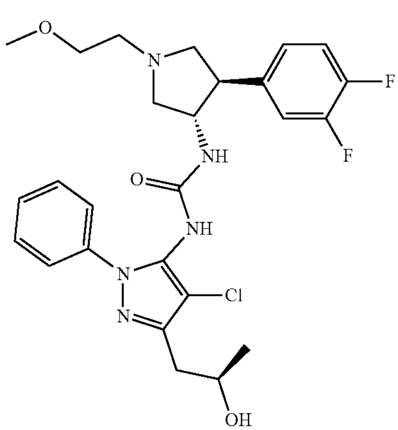 [SMILES: COCCN1C[C@@H](NC(=O)Nc2c(Cl)c(C[C@@H](C)O)nn2-c2ccccc2)[C@H](c2ccc(F)c(F)c2)C1] | 1-(4-chloro-3-((R)-2-hydroxypropyl)-1-phenyl-1H-pyrazol-5-yl)-3-((3S,4R)-4-(3,4-difluorophenyl)-1-(2-methoxyethyl)pyrrolidin-3-yl)urea | 534.2 (M + H) |

| Ex. # | Structure | Name | MS (apci) m/z |
|---|---|---|---|
| 414 | 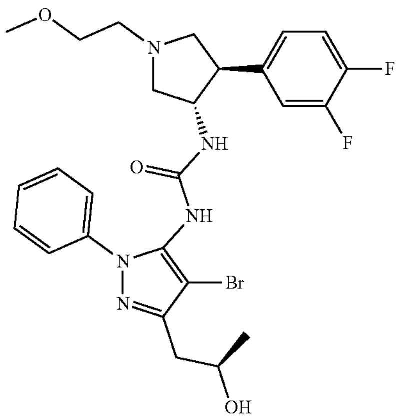 [SMILES: COCCN1C[C@@H](NC(=O)Nc2c(Br)c(C[C@@H](C)O)nn2-c2ccccc2)[C@H](c2ccc(F)c(F)c2)C1] | 1-(4-bromo-3-((R)-2-hydroxypropyl)-1-phenyl-1H-pyrazol-5-yl)-3-((3S,4R)-4-(3,4-difluorophenyl)-1-(2-methoxyethyl)pyrrolidin-3-yl)urea | 578.2 (M + H) |
| 415 | 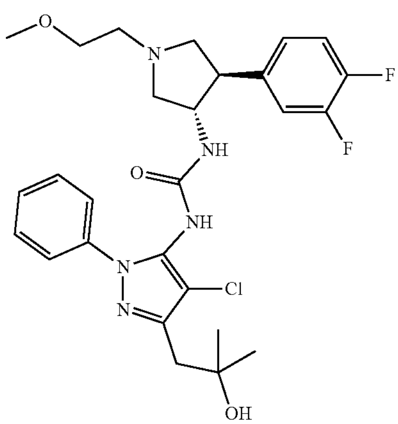 [SMILES: COCCN1C[C@@H](NC(=O)Nc2c(Cl)c(CC(C)(C)O)nn2-c2ccccc2)[C@H](c2ccc(F)c(F)c2)C1] | 1-(4-chloro-3-(2-hydroxy-2-methylpropyl)-1-phenyl-1H-pyrazol-5-yl)-3-((3S,4R)-4-(3,4-difluorophenyl)-1-(2-methoxyethyl)pyrrolidin-3-yl)urea | 548.2 (M + H) |
| 416 | 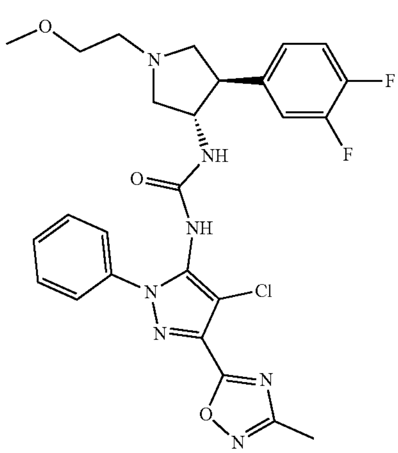 [SMILES: COCCN1C[C@@H](NC(=O)Nc2c(Cl)c(-c3nc(C)no3)nn2-c2ccccc2)[C@H](c2ccc(F)c(F)c2)C1] | 1-(4-chloro-3-(3-methyl-1,2,4-oxadiazol-5-yl)-1-phenyl-1H-pyrazol-5-yl)-3-((3S,4R)-4-(3,4-difluorophenyl)-1-(2-methoxyethyl)pyrrolidin-3-yl)urea | 558.1 (M + H) |

| Ex. # | Structure | Name | MS (apci) m/z |
|---|---|---|---|
| 417 | 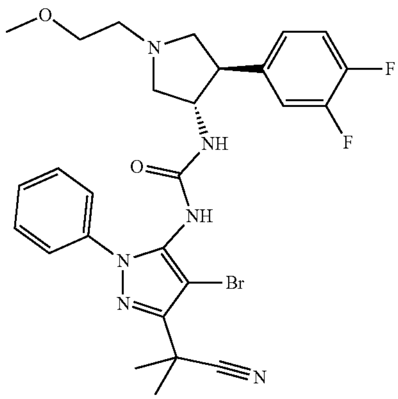 [SMILES: COCCN1C[C@@H](NC(=O)Nc2c(Br)c(C(C)(C)C#N)nn2-c2ccccc2)[C@H](c2ccc(F)c(F)c2)C1] | 1-(4-bromo-3-(2-cyanopropan-2-yl)-1-phenyl-1H-pyrazol-5-yl)-3-((3S,4R)-4-(3,4-difluorophenyl)-1-(2-methoxyethyl)pyrrolidin-3-yl)urea | 587.2 (M + H) |
| 418 | 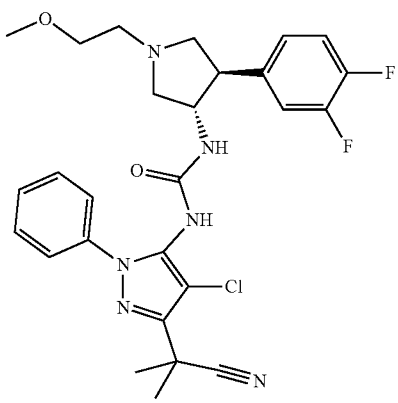 [SMILES: COCCN1C[C@@H](NC(=O)Nc2c(Cl)c(C(C)(C)C#N)nn2-c2ccccc2)[C@H](c2ccc(F)c(F)c2)C1] | 1-(4-chloro-3-(2-cyanopropan-2-yl)-1-phenyl-1H-pyrazol-5-yl)-3-((3S,4R)-4-(3,4-difluorophenyl)-1-(2-methoxyethyl)pyrrolidin-3-yl)urea | 543.2 (M + H) |
| 419 | 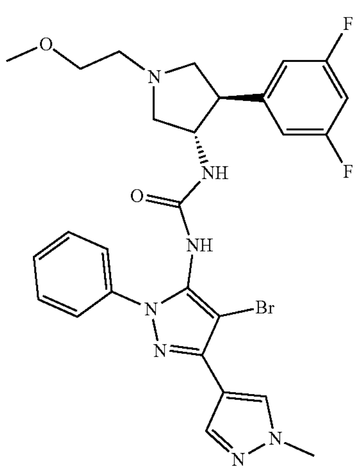 | 1-(4-bromo-1'-methyl-1-phenyl-1H,1'H-[3,4'-bipyrazol]-5-yl)-3-((3S,4R)-4-(3,5-difluorophenyl)-1-(2-methoxyethyl)pyrrolidin-3-yl)urea | 602.2 (M + H) |

-continued

| Ex. # | Structure | Name | MS (apci) m/z |
|---|---|---|---|
| 420 | 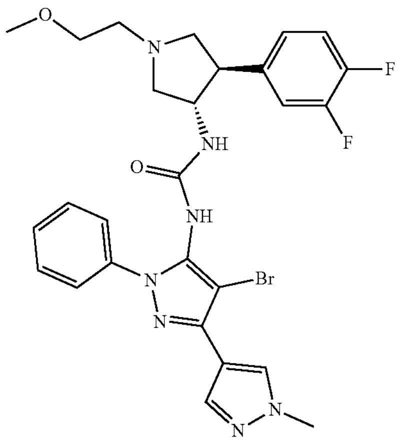 [SMILES: COCCN1C[C@@H](NC(=O)Nc2c(Br)c(-c3cnn(C)c3)nn2-c2ccccc2)[C@H](c2ccc(F)c(F)c2)C1] | 1-(4-bromo-1'-methyl-1-phenyl-1H,1'H-[3,4'-bipyrazol]-5-yl)-3-((3S,4R)-4-(3,4-difluorophenyl)-1-(2-methoxyethyl)pyrrolidin-3-yl)urea | 602.2 (M + H) |
| 421 | 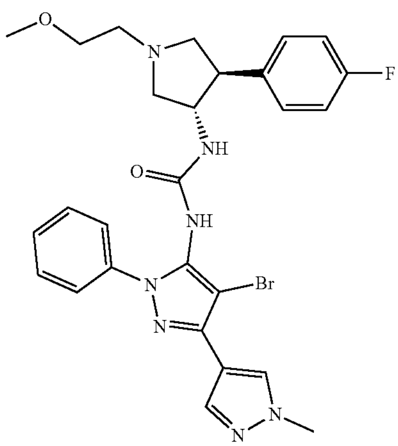 [SMILES: COCCN1C[C@@H](NC(=O)Nc2c(Br)c(-c3cnn(C)c3)nn2-c2ccccc2)[C@H](c2ccc(F)cc2)C1] | 1-(4-bromo-1'-methyl-1-phenyl-1H,1'H-[3,4'-bipyrazol]-5-yl)-3-((3S,4R)-4-(4-difluorophenyl)-1-(2-methoxyethyl)pyrrolidin-3-yl)urea | 582.2 (M + H) |
| 422 | 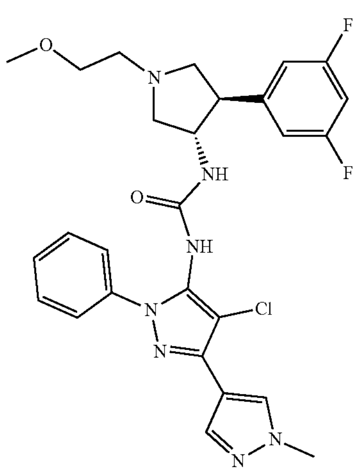 [SMILES: COCCN1C[C@@H](NC(=O)Nc2c(Cl)c(-c3cnn(C)c3)nn2-c2ccccc2)[C@H](c2cc(F)cc(F)c2)C1] | 1-(4-chloro-1'-methyl-1-phenyl-1H,1'H-[3,4'-bipyrazol]-5-yl)-3-((3S,4R)-4-(3,5-difluorophenyl)-1-(2-methoxyethyl)pyrrolidin-3-yl)urea | 556.2 (M + H) |

-continued

| Ex. # | Structure | Name | MS (apci) m/z |
|---|---|---|---|
| 423 | 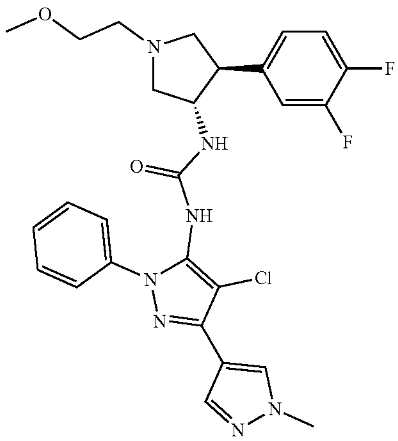 | 1-(4-chloro-1'-methyl-1-phenyl-1H,1'H-[3,4'-bipyrazol]-5-yl)-3-((3S,4R)-4-(3,4-difluorophenyl)-1-(2-methoxyethyl)pyrrolidin-3-yl)urea | 556.2 (M + H) |
| 424 | 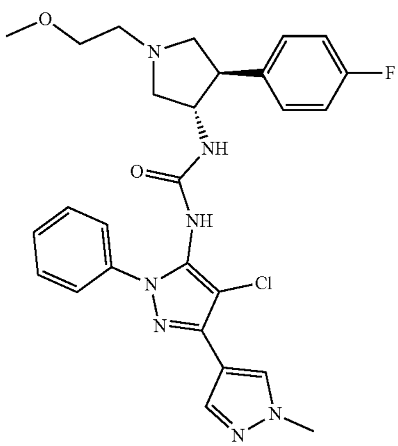 [SMILES: COCCN1C[C@@H](NC(=O)Nc2c(Cl)c(-c3cnn(C)c3)nn2-c2ccccc2)[C@H](c2ccc(F)cc2)C1] | 1-(4-chloro-1'-methyl-1-phenyl-1H,1'H-[3,4'-bipyrazol]-5-yl)-3-((3S,4R)-4-(4-fluorophenyl)-1-(2-methoxyethyl)pyrrolidin-3-yl)urea | 538.2 (M + H) |
| 425 | 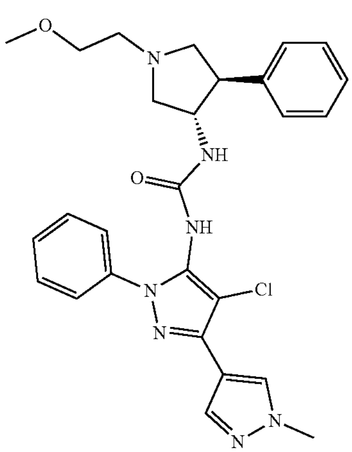 [SMILES: COCCN1C[C@@H](NC(=O)Nc2c(Cl)c(-c3cnn(C)c3)nn2-c2ccccc2)[C@H](c2ccccc2)C1] | 1-(4-chloro-1'-methyl-1-phenyl-1H,1'H-[3,4'-bipyrazol]-5-yl)-3-((3S,4R)-4-phenyl-1-(2-methoxyethyl)pyrrolidin-3-yl)urea | 520.0 (M + H) |

-continued

| Ex. # | Structure | Name | MS (apci) m/z |
|---|---|---|---|
| 426 | 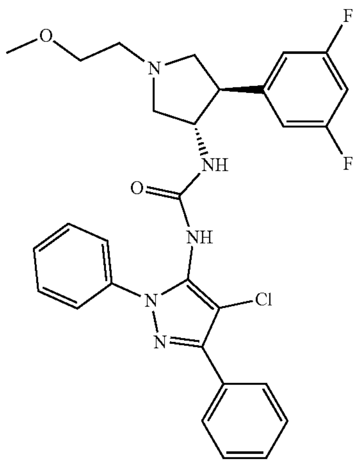 | 1-(4-chloro-1,3-diphenyl-1H-pyrazol-5-yl)-3-((3S,4R)-4-(3,5-difluorophenyl)-1-(2-methoxyethyl)pyrrolidin-3-yl)urea | 552.2 (M + H) |
| 427 | 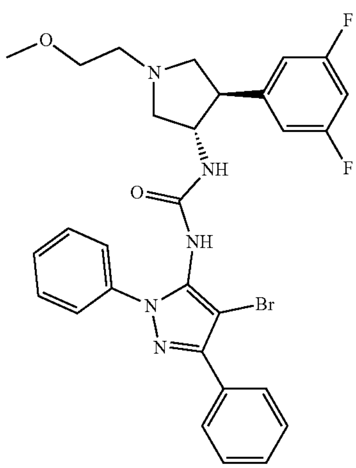 [SMILES: COCCN1C[C@@H](NC(=O)Nc2c(Br)c(-c3ccccc3)nn2-c2ccccc2)[C@H](c2cc(F)cc(F)c2)C1] | 1-(4-bromo-1,3-diphenyl-1H-pyrazol-5-yl)-3-((3S,4R)-4-(3,5-difluorophenyl)-1-(2-methoxyethyl)pyrrolidin-3-yl)urea | 598.2 (M + H) |
| 428 | 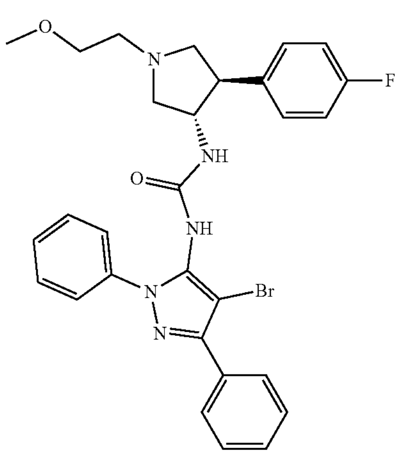 [SMILES: COCCN1C[C@@H](NC(=O)Nc2c(Br)c(-c3ccccc3)nn2-c2ccccc2)[C@H](c2ccc(F)cc2)C1] | 1-(4-bromo-1,3-diphenyl-1H-pyrazol-5-yl)-3-((3S,4R)-4-(4-fluorophenyl)-1-(2-methoxyethyl)pyrrolidin-3-yl)urea | 578.4 (M + H) |

-continued

| Ex. # | Structure | Name | MS (apci) m/z |
|---|---|---|---|
| 429 | 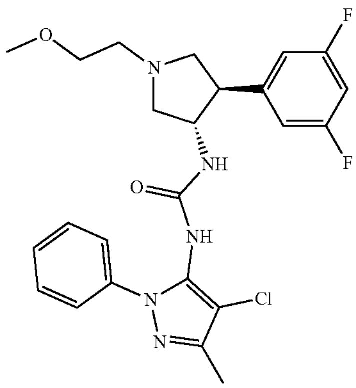 | 1-(4-chloro-3-methyl-1-phenyl-1H-pyrazol-5-yl)-3-((3S,4R)-4-(3,5-difluorophenyl)-1-(2-methoxyethyl)pyrrolidin-3-yl)urea | 554.2 (M + H) |
| 430 | 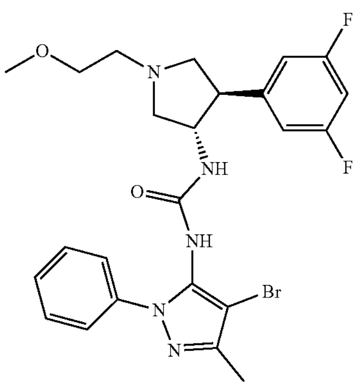 | 1-(4-bromo-3-methyl-1-phenyl-1H-pyrazol-5-yl)-3-((3S,4R)-4-(3,5-difluorophenyl)-1-(2-methoxyethyl)pyrrolidin-3-yl)urea | 501.1 (M + H) |
| 431 | 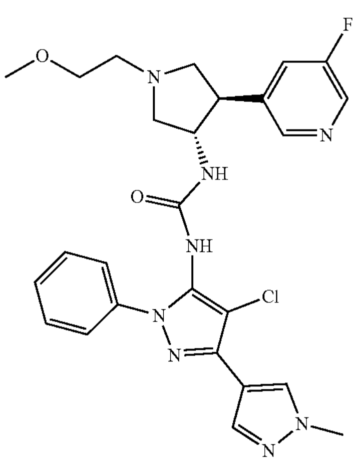 [SMILES: COCCN1C[C@@H](NC(=O)Nc2c(Cl)c(-c3cnn(C)c3)nn2-c2ccccc2)[C@H](c2cncc(F)c2)C1] | 1-(4-chloro-1'-methyl-1-phenyl-1H,1'H-[3,4'-bipyrazol]-5-yl)-3-((3S,4R)-4-(5-fluoropyridin-3-yl)-1-(2-methoxyethyl)pyrrolidin-3-yl)urea | 540.2 (M + H) |

-continued

| Ex. # | Structure | Name | MS (apci) m/z |
|---|---|---|---|
| 432 | 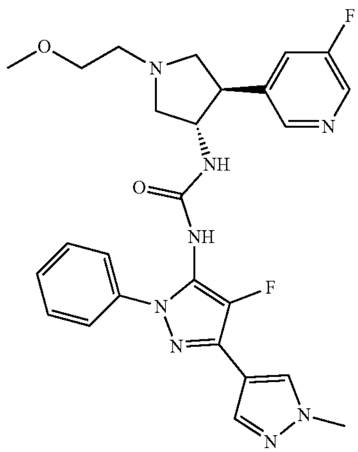 [SMILES: COCCN1C[C@@H](NC(=O)Nc2c(F)c(-c3cnn(C)c3)nn2-c2ccccc2)[C@H](c2cncc(F)c2)C1] | 1-(4-fluoro-1'-methyl-1-phenyl-1H,1'H-[3,4'-bipyrazol]-5-yl)-3-((3S,4R)-4-(5-fluoropyridin-3-yl)-1-(2-methoxyethyl)pyrrolidin-3-yl)urea | 523.2 (M + H) |
| 433 | 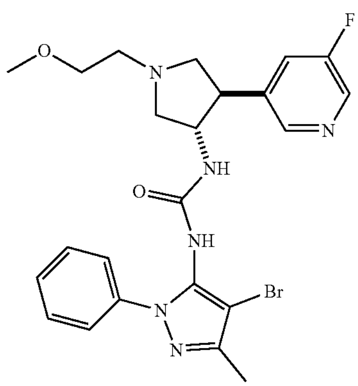 | 1-(4-bromo-3-methyl-1-phenyl-1H-pyrazol-5-yl)-3-trans-4-(5-fluoropyridin-3-yl)-1-(2-methoxyethyl)pyrrolidin-3-yl)urea | 519.1 (M + H) |
| 434 | 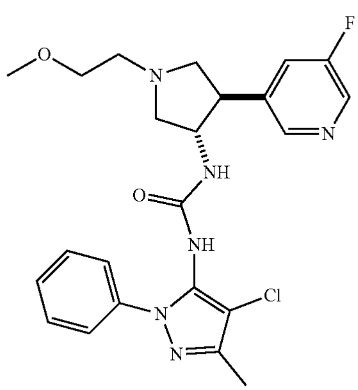 [SMILES: COCCN1C[C@@H](NC(=O)Nc2c(Cl)c(C)nn2-c2ccccc2)[C@H](c2cncc(F)c2)C1] | 1-(4-bromo-3-methyl-1-phenyl-1H-pyrazol-5-yl)-3-trans-4-(5-fluoropyridin-3-yl)-1-(2-methoxyethyl)pyrrolidin-3-yl)urea | 473.2 (M + H) |

| Ex. # | Structure | Name | MS (apci) m/z |
|---|---|---|---|
| 435 | 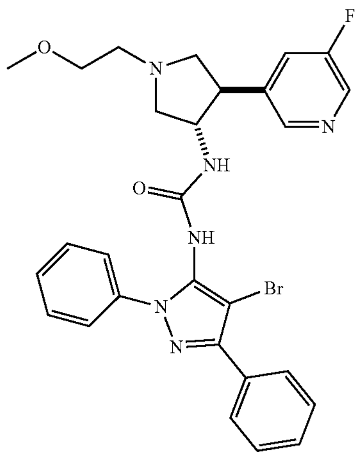 [SMILES: COCCN1C[C@@H](NC(=O)Nc2c(Br)c(-c3ccccc3)nn2-c2ccccc2)[C@H](c2cncc(F)c2)C1] | 1-(4-bromo-1,3-diphenyl-1H-pyrazol-5-yl)-3-(trans-4-(5-fluoropyridin-3-yl)-1-(2-methoxyethyl)pyrrolidin-3-yl)urea | 579.2 (M + H) |
| 436 | 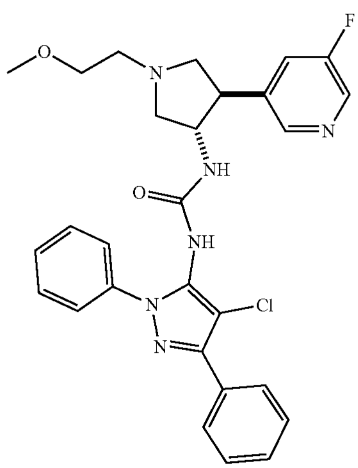 [SMILES: COCCN1C[C@@H](NC(=O)Nc2c(Cl)c(-c3ccccc3)nn2-c2ccccc2)[C@H](c2cncc(F)c2)C1] | 1-(4-chloro-1,3-diphenyl-1H-pyrazol-5-yl)-3-(trans-4-(5-fluoropyridin-3-yl)-1-(2-methoxyethyl)pyrrolidin-3-yl)urea | 535.2 (M + H) |
| 437 | 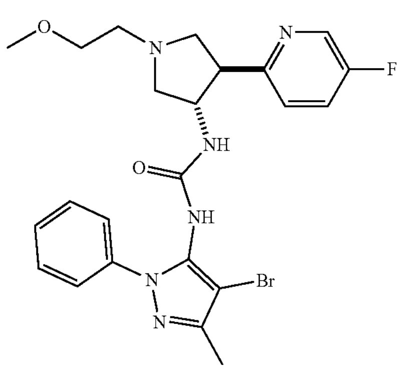 | 1-(4-bromo-3-methyl-1-phenyl-1H-pyrazol-5-yl)-3-(trans-4-(5-fluoropyridin-2-yl)-1-(2-methoxyethyl)pyrrolidin-3-yl)urea | 525.2 (M + H) |

| Ex. # | Structure | Name | MS (apci) m/z |
|---|---|---|---|
| 438 | 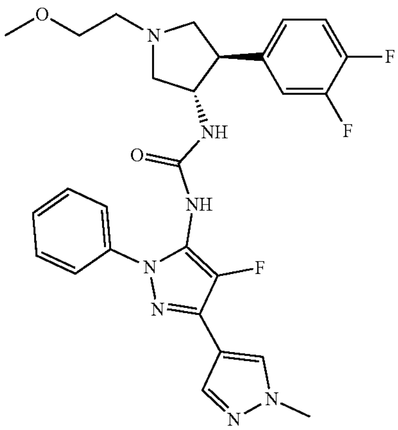 [SMILES: COCCN1C[C@@H](NC(=O)Nc2c(F)c(-c3cnn(C)c3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-fluoro-1'-methyl-1-phenyl-1H,1'H-[3,4'-bipyrazol]-5-yl)urea | 540.2 (M + H) |
| 439 | 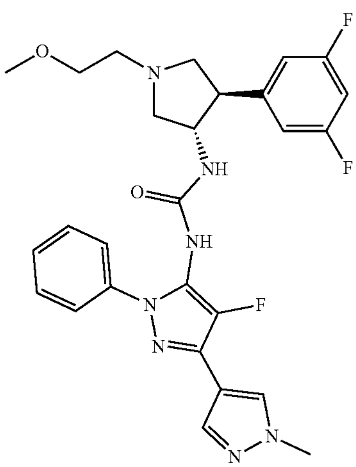 [SMILES: COCCN1C[C@@H](NC(=O)Nc2c(F)c(-c3cnn(C)c3)nn2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(4-fluoro-1'-methyl-1-phenyl-1H,1'H-[3,4'-bipyrazol]-5-yl)urea | 540.2 (M + H) |
| 440 | 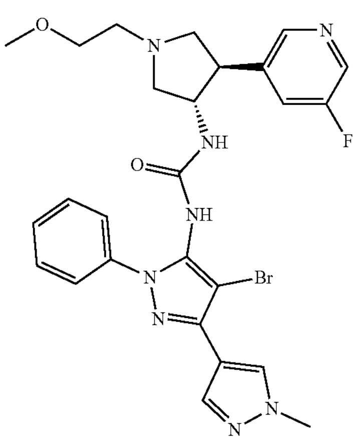 [SMILES: COCCN1C[C@@H](NC(=O)Nc2c(Br)c(-c3cnn(C)c3)nn2-c2ccccc2)[C@H](c2cncc(F)c2)C1] | 1-(4-bromo-1'-methyl-1-phenyl-1H,1'H-[3,4'-bipyrazol]-5-yl)-3-((3S,4R)-4-(5-fluoropyridin-3-yl)-1-(2-methoxyethyl)pyrrolidin-3-yl)urea | 585.2 (M + H) |

Example 441

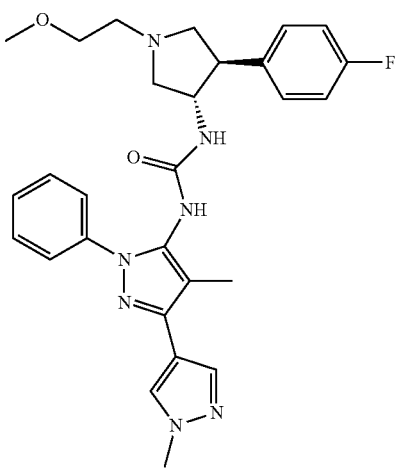 [SMILES: COCCN1C[C@@H](NC(=O)Nc2c(C)c(-c3cnn(C)c3)nn2-c2ccccc2)[C@H](c2ccc(F)cc2)C1]

1-(1',4-dimethyl-1-phenyl-1H, 1'H-[3,4'-bipyrazol]-5-yl)-3-((3S,4R)-4-(4-fluorophenyl)-1-(2-methoxyethyl)pyrrolidin-3-yl)urea To a suspension of (3S,4R)-4-(4-fluorophenyl)-1-(2-methoxyethyl)pyrrolidin-3-amine dihydrochloride (Preparation L1; 40 mg, 0.13 mmol) in DMA (428 μL) was added DIEA (112 μL, 0.64 mmol) to obtain a clear solution. To this solution was added phenyl 1',4-dimethyl-1-phenyl-1H,1'H-3,4'-bipyrazol-5-ylcarbamate (Intermediate 199; 53 mg, 0.14 mmol). After overnight stirring, the reaction was directly purified by reverse-phase chromatography (C18, 5 to 42% acetonitrile/water) to yield the 1-(1',4-dimethyl-1-phenyl-1H, 1'H-[3,4'-bipyrazol]-5-yl)-3-((3S,4R)-4-(4-fluorophenyl)-1-(2-methoxyethyl)pyrrolidin-3-yl)urea as white solid (42 mg, 63%). MS (apci) m/z=518.3 (M+H). $^1$H NMR (400 MHz, CDCl$_3$) δ 7.85 (s, 1H), 7.74 (s, 1H), 7.48-7.5 (m, 2H), 7.34-7.38 (m, 2H), 7.27-7.31 (m, 1H), 7.05-7.1 (m, 2H), 6.81-6.85 (m, 2H), 5.37 (br s, 1H), 4.27 (br s, 1H), 3.96 (s, 3H), 3.33-3.43 (m, 2H), 3.25 (br s, 3H), 3.16-3.19 (m, 1H), 2.98 (br s, 1H), 2.70-2.83 (m, 2H), 2.49-2.65 (m, 2H), 2.27 (t, 1H), 2.09 (s, 3H).

Example 442

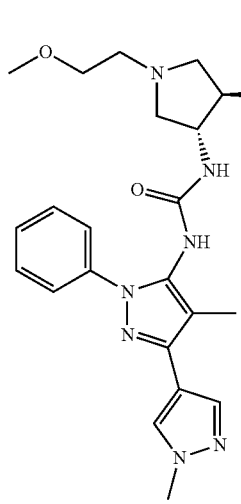

1-(1',4-dimethyl-1-phenyl-1H, 1'H-[3,4'-bipyrazol]-5-yl)-3-((3S,4R)-4-(3,5-difluorophenyl)-1-(2-methoxyethyl)pyrrolidin-3-yl)urea Prepared according to the method described in for Example 441, replacing (3S,4R)-4-(4-fluorophenyl)-1-(2-methoxyethyl)pyrrolidin-3-amine dihydrochloride with (3S,4R)-4-(3,5-difluorophenyl)-1-(2-methoxyethyl)pyrrolidin-3-amine dihydrochloride in Step F. MS (apci) m/z=536.3 (M+H). $^1$H NMR (400 MHz, CDCl$_3$) δ 7.86 (s, 1H), 7.74 (s, 1H), 7.49-7.52 (m, 2H), 7.36-7.41 (m, 2H), 7.28-7.33 (m, 1H), 6.62-6.70 (m, 3H), 5.33 (br s, 1H), 4.27 (br s, 1H), 3.96 (s, 3H), 3.36-3.45 (m, 2H), 3.27 (br s, 3H), 3.15-3.20 (m, 1H), 2.96 (br s, 1H), 2.72-2.81 (m, 2H), 2.54-2.67 (m, 2H), 2.31 (t, 1H), 2.11 (s, 3H).

Example 443

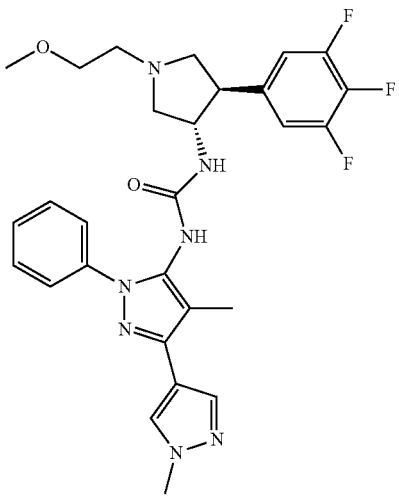 [SMILES: COCCN1C[C@@H](NC(=O)Nc2c(C)c(-c3cnn(C)c3)nn2-c2ccccc2)[C@H](c2cc(F)c(F)c(F)c2)C1]

1-(1',4-dimethyl-1-phenyl-1H, 1'H-[3,4'-bipyrazol]-5-yl)-3-((3S,4R)-4-(3,4,5-trifluorophenyl)-1-(2-methoxyethyl)pyrrolidin-3-yl)urea Prepared according to the method described in for Example 441, replacing (3S,4R)-4-(4-fluorophenyl)-1-(2-methoxyethyl)pyrrolidin-3-amine dihydrochloride with (3S,4R)-4-(3,4,5-trifluorophenyl)-1-(2-methoxyethyl)pyrrolidin-3-amine dihydrochloride in Step F. MS (apci) m/z=554.3 (M+H).

Example 444

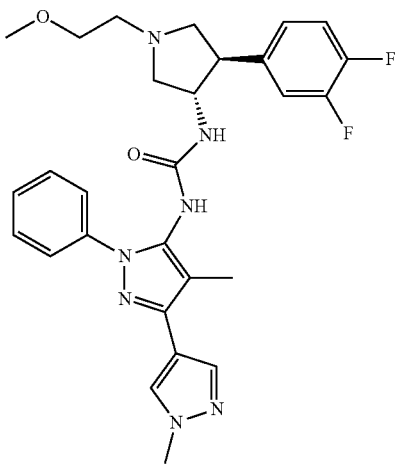 [SMILES: COCCN1C[C@@H](NC(=O)Nc2c(C)c(-c3cnn(C)c3)nn2-c2ccccc2)[C@H](c2ccc(F)c(F)c2)C1]

1-(1',4-dimethyl-1-phenyl-1H, 1'H-[3,4'-bipyrazol]-5-yl)-3-((3S,4R)-4-(3,4-difluorophenyl)-1-(2-methoxyethyl)pyrrolidin-3-yl)urea Prepared according to the method described in Example 441, replacing (3S,4R)-4-(2,4-fluorophenyl)-1-(2-methoxyethyl)pyrrolidin-3-amine dihydrochloride with (3S,4R)-4-(3,4-difluorophenyl)-1-(2-methoxyethyl)pyrrolidin-3-amine dihydrochloride and in Step F. MS (apci) m/z=554.3 (M+H). $^1$H NMR (400 MHz, CDCl$_3$) δ 7.86 (s, 1H), 7.74 (s, 1H), 7.48-7.52 (m, 2H), 7.34-7.39 (m, 2H), 7.28-7.32 (m, 1H), 6.92-7.04 (m, 2H), 6.81-6.85 (m, 1H), 5.32 (br s, 1H), 4.24 (br s, 1H), 3.96 (s, 3H), 3.38-3.40 (m, 2H), 3.26 (br s, 3H), 3.12-3.17 (m, 1H), 2.91 (br s, 1H), 2.72-2.77 (m, 2H), 2.52-2.66 (m, 2H), 2.27 (t, 1H), 2.1 (s, 3H).

Example 445

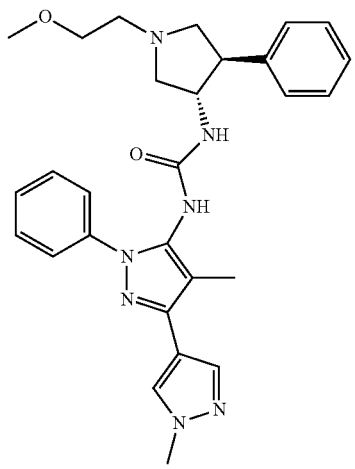 [SMILES: COCCN1C[C@@H](NC(=O)Nc2c(C)c(-c3cnn(C)c3)nn2-c2ccccc2)[C@H](c2ccccc2)C1]

1-(1',4-dimethyl-1-phenyl-1H, 1'H-[3,4'-bipyrazol]-5-yl)-3-((3S,4R)-4-(fluorophenyl)-1-(2-methoxyethyl)pyrrolidin-3-yl)urea Prepared according to the method described in Example 441, replacing (3S,4R)-4-(4-fluorophenyl)-1-(2-methoxyethyl)pyrrolidin-3-amine dihydrochloride with (3S,4R)-4-(phenyl)-1-(2-methoxyethyl)pyrrolidin-3-amine dihydrochloride in Step F. MS (apci) m/z=500.3 (M+H).

Example 446

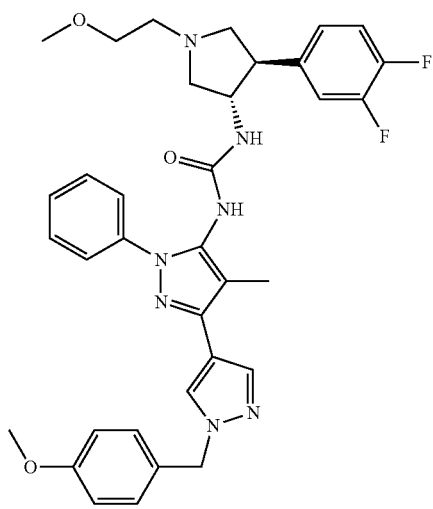 [SMILES: COCCN1C[C@@H](NC(=O)Nc2c(C)c(-c3cnn(Cc4ccc(OC)cc4)c3)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(1'-(4-methoxybenzyl)-4-methyl-1-phenyl-1H, 1'H-[3,4'-bipyrazol]-5-yl)urea Prepared according to the method described in Example 441, replacing (3S,4R)-4-(4-fluorophenyl)-1-(2-methoxyethyl)pyrrolidin-3-amine dihydrochloride with (3S,4R)-4-(3,4-fluorophenyl)-1-(2-methoxyethyl)pyrrolidin-3-amine dihydrochloride and phenyl 1',4-dimethyl-1-phenyl-1H,1'H-3,4'-bipyrazol-5-ylcarbamate with phenyl (1'-(4-methoxybenzyl)-4-methyl-1-phenyl-1H,1'H-[3,4'-bipyrazol]-5-yl)carbamate in Step F. MS (apci) m/z=642.3 (M+H).

Example 447

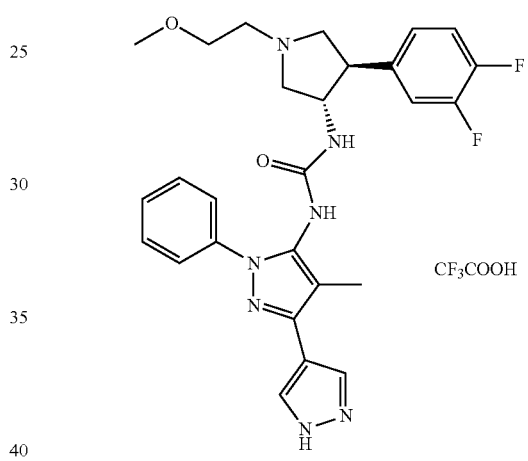

1-((3S,4R)-4-(3,4-difluorophenyl)-1-(2-methoxyethyl)pyrrolidin-3-yl)-3-(4-methyl)-1-phenyl-1H, 1'H-[3,4'-bipyrazol]-5-yl)urea 2,2,2-trifluoroacetate A mixture of 1-((3S,4R)-4-(3,4-difluorophenyl)-1-(2-methoxyethyl)pyrrolidin-3-yl)-3-(1'-(4-methoxybenzyl)-4-methyl-1-phenyl-1H, 1'H-3,4'-bipyrazol-5-yl)urea (300 mg, 0.468 mmol) and TFA (720 µL, 9.35 mmol) in a pressure vessel was sealed and heated at 60° C. The reaction was heated for 18 hours, then cooled and ether (30 mL) was added and the resulting mixture was sonicated to provide the crude product as a beige solid. The solid was dissolved in minimal amount of MeOH and purified by reverse-phase chromatography (C18, 5 to 35% to 50% acetonitrile/water) to provide 1-((3S,4R)-4-(3,4-difluorophenyl)-1-(2-methoxyethyl)pyrrolidin-3-yl)-3-(4-methyl)-1-phenyl-1H, 1'H-[3,4'-bipyrazol]-5-yl)urea 2,2,2-trifluoroacetate as the triflate salt (135 mg. 38%).

Example 448

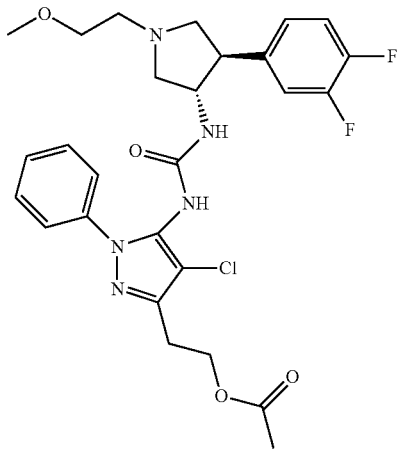 [SMILES: COCCN1C[C@@H](NC(=O)Nc2c(Cl)c(CCOC(C)=O)nn2-c2ccccc2)[C@H](c2ccc(F)c(F)c2)C1]

2-(4-chloro-5-(3-((3S,4R)-4-(3,4-difluorophenyl)-1-(2-methoxyethyl)pyrrolidin-3-yl)ureido)-1-phenyl-1H-pyrazol-3-yl)ethyl acetate Step A: Preparation of 2-(4-chloro-5-((phenoxycarbonyl)amino)-1-phenyl-1H-pyrazol-3-yl)ethyl acetate and phenyl (3-(2-((phenoxycarbonyl)oxy)ethyl)-1-phenyl-1H-pyrazol-5-yl)carbamate: To a solution of 2-(5-amino-1-phenyl-1H-pyrazol-3-yl)ethanol (Intermediate 161, 242 mg, 1.191 mmol) in EtOAc (10 mL) was added aqueous sodium hydroxide (2M, 1.19 mL, 2.38 mmol) then phenyl carbonochloridate (0.179 mL, 1.43 mmol). The reaction was stirred at ambient temperature for 4 hours and then the phases were separated. The organic phase was washed with $H_2O$ (5 mL), brine (5 mL), dried with $MgSO_4$, filtered and concentrated to afford the product as a tan solid (250 mg), a mixture of two components: 2-(4-chloro-5-((phenoxycarbonyl)amino)-1-phenyl-1H-pyrazol-3-yl)ethyl acetate and phenyl (3-(2-((phenoxycarbonyl)oxy)ethyl)-1-phenyl-1H-pyrazol-5-yl)carbamate which were used without purification in the next step.

Step B: Preparation of 2-(4-chloro-5-((phenoxycarbonyl)amino)-1-phenyl-1H-pyrazol-3-yl)ethyl acetate and phenyl (4-chloro-3-(2-((phenoxycarbonyl)oxy)ethyl)-1-phenyl-1H-pyrazol-5-yl)carbamate: To a solution of 2-(4-chloro-5-((phenoxycarbonyl)amino)-1-phenyl-1H-pyrazol-3-yl)ethyl acetate and phenyl (3-(2-((phenoxycarbonyl)oxy)ethyl)-1-phenyl-1H-pyrazol-5-yl)carbamate (250 mg, 0.773 mmol) in DCM (10 mL) were added pyridinium 4-methylbenzenesulfonate (PPTS) (19.4 mg, 0.077 mmol) and n-chlorosuccinimide (155 mg, 1.16 mmol). The reaction was stirred at ambient temperature for 4 days, then diluted with $H_2O$ (10 mL), phases separated and aqueous phase extracted DCM (2×20 mL). The combined organic phases were dried ($MgSO_4$), filtered and concentrated. The crude oil was purified by silica column chromatography eluting with 40% acetone/hexanes to afford a the product as an orange oil (63 mg), a mixture of two components: 2-(4-chloro-5-((phenoxycarbonyl)amino)-1-phenyl-1H-pyrazol-3-yl)ethyl acetate, MS (apci) m/z=400.1 (M+H), and phenyl (4-chloro-3-(2-((phenoxycarbonyl) oxy)ethyl)-1-phenyl-1H-pyrazol-5-yl)carbamate, MS(apci) m/z=478.1 (M+H).

Step C: Preparation of 2-(4-chloro-5-(3-((3S,4R)-4-(3,4-difluorophenyl)-1-(2-methoxyethyl)pyrrolidin-3-yl)ureido)-1-phenyl-1H-pyrazol-3-yl)ethyl acetate: To a solution of (3S,4R)-4-(3,4-difluorophenyl)-1-(2-methoxyethyl)pyrrolidin-3-amine dihydrochloride (Preparation F, 52 mg, 0.158 mmol) in DMA (0.6 mL) was added DIEA (0.110 mL, 0.630 mmol) was added a mixture of 2-(4-chloro-5-((phenoxycarbonyl)amino)-1-phenyl-1H-pyrazol-3-yl)ethyl acetate and phenyl (4-chloro-3-(2-((phenoxycarbonyl)oxy)ethyl)-1-phenyl-1H-pyrazol-5-yl)carbamate (63 mg). The reaction mixture was stirred at ambient temperature for 2 hours then purified directly by reverse-phase column chromatography, eluting with 5-80% acetonitrile/water and collecting Peak 1 to afford the title compound as an orange solid (21.8 mg). MS (apci) m/z=562.2 (M+H).

Example 449

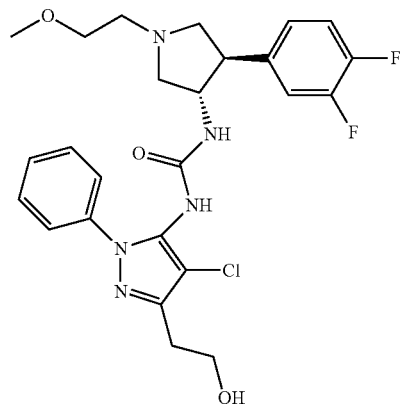 [SMILES: COCCN1C[C@@H](NC(=O)Nc2c(Cl)c(CCO)nn2-c2ccccc2)[C@H](c2ccc(F)c(F)c2)C1]

1-(4-chloro-3-(2-hydroxyethyl)-1-phenyl-1H-pyrazol-5-yl)-3-((3S,4R)-4-(3,4-difluorophenyl)-1-(2-methoxyethyl)pyrrolidin-3-yl)urea Step A: Preparation of 2-(4-chloro-5-(3-((3S,4R)-4-(3,4-difluorophenyl)-1-(2-methoxyethyl)pyrrolidin-3-yl)ureido)-1-phenyl-1H-pyrazol-3-yl)ethyl phenyl carbonate: The reaction mixture from Example 448, Step C, was purified directly by reverse-phase column chromatography, eluting with 5-80% acetonitrile/water and collecting Peak 2 to afford the title compound as a pale yellow gum (28 mg). MS (apci) m/z=640.2 (M+H).

Step B: Preparation of 1-(4-chloro-3-(2-hydroxyethyl)-1-phenyl-1H-pyrazol-5-yl)-3-((3S,4R)-4-(3,4-difluorophenyl)-1-(2-methoxyethyl)pyrrolidin-3-yl)urea: To a solution of 2-(4-chloro-5-(3-((3S,4R)-4-(3,4-difluorophenyl)-1-(2-methoxyethyl)pyrrolidin-3-yl)ureido)-1-phenyl-1H-pyrazol-3-yl)ethyl phenyl carbonate (28 mg, 0.044 mmol) in THF (2 mL) and MeOH (1 mL) was added aqueous LiOH (2M, 0.066 mL, 0.132 mmol). The reaction mixture was stirred at ambient temperature for 2 hours then diluted with aqueous HCl (2M, 0.06 mL) and $H_2O$ (5 mL), and extracted with DCM (10 mL) then 10:90 MeOH/DCM (2×10 mL). The combined organic extracts were dried ($MgSO_4$), filtered and concentrated. The crude product was purified by silica column chromatography eluting with 0-10% MeOH/DCM to afford the product as an off-white solid (14 mg, 61% yield). MS (apci) m/z=520.2 (M+H).

Example 450

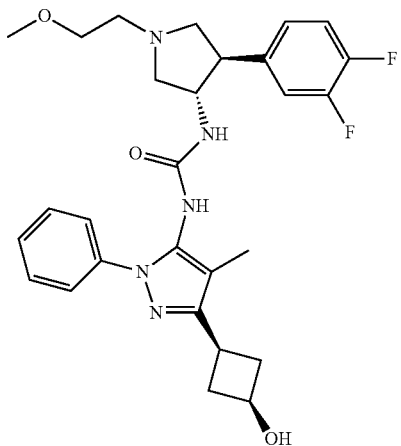

1-((3S,4R)-4-(3,4-difluorophenyl)-1-(2-methoxy-ethyl)pyrrolidin-3-yl)-3-(3-(cis-3-hydroxycyclobutyl)-4-methyl-1-phenyl-1H-pyrazol-5-yl)urea Step A: Preparation of cis- and trans-1-((3S,4R)-4-(3,4-difluorophenyl)-1-(2-methoxyethyl)pyrrolidin-3-yl)-3-(3-(3-hydroxycyclobutyl)-4-methyl-1-phenyl-1H-pyrazol-5-yl)urea: To a solution of (3S,4R)-4-(3,4-difluorophenyl)-1-(2-methoxyethyl)pyrrolidin-3-amine dihydrochloride (Preparation F, 67 mg, 0.204 mmol) in DMA (1 mL) and DIEA (0.142 mL, 0.815 mmol) was added phenyl 3-(3-hydroxycyclobutyl)-4-methyl-1-phenyl-1H-pyrazol-5-yl-carbamate (Intermediate 209; 74 mg, 0.204 mmol) and the reaction mixture as stirred at ambient temperature for 1 hour. The reaction mixture was directly purified by reverse-phase column chromatography, eluting with 5-70% acetonitrile/water to yield the product as a white solid (59 mg, 55% yield). MS (apci) m/z=526.3 (M+H).

Step B: Preparation of 1-((3S,4R)-4-(3,4-difluorophenyl)-1-(2-methoxyethyl) pyrrolidin-3-yl)-3-(3-(cis-3-hydroxycyclobutyl)-4-methyl-1-phenyl-1H-pyrazol-5-yl)urea: The mixture of cis- and trans-1-((3S,4R)-4-(3,4-difluorophenyl)-1-(2-methoxyethyl)pyrrolidin-3-yl)-3-(3-(3-hydroxycyclobutyl)-4-methyl-1-phenyl-1H-pyrazol-5-yl)urea (55 mg, 0.105 mmol) was separated by preparatory HPLC on a benzamide column (Princeton Analytical, 4.6 mm×250 mm, 5 μm), eluted with 10% EtOH/hexanes. Peak 1 was collected to afford the title compound as a white solid (21.1 mg, 38% yield). MS (apci) m/z=526.3 (M+H). $^1$H NMR (d$_6$-DMSO) δ 7.79 (br s, 1H), 7.42 (m, 4H), 7.30 (m, 3H), 7.06 (m, 1H), 6.70 (d, 1H), 5.06 (d, 1H), 4.04 (m, 2H), 3.43 (t, 2H), 3.24 (s, 3H), 3.05 (m, 2H), 2.85 (m, 2H), 2.47-2.66 (m, 6H), 2.08 (m, 2H), 1.77 (s, 3H).

Example 451

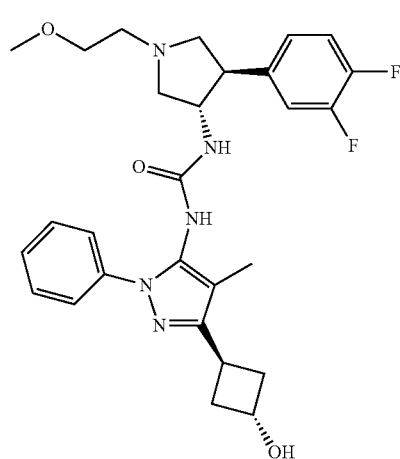

1-((3S,4R)-4-(3,4-difluorophenyl)-1-(2-methoxy-ethyl)pyrrolidin-3-yl)-3-(3-(trans-3-hydroxycyclobutyl)-4-methyl-1-phenyl-1H-pyrazol-5-yl)urea A mixture of cis and trans hydroxycyclobutyl diastereomers 1-((3S,4R)-4-(3,4-difluorophenyl)-1-(2-methoxyethyl)pyrrolidin-3-yl)-3-(3-(3-hydroxycyclobutyl)-4-methyl-1-phenyl-1H-pyrazol-5-yl)urea (Example 450, Step A, 55 mg, 0.105 mmol) was separated by preparatory HPLC on a benzamide column (Princeton Analytical, 4.6 mm×250 mm, 5 μm), eluted with 10% EtOH/hexanes. Peak 2 was collected to afford the title compound as a white solid (27.5 mg, 50% yield). MS (apci) m/z=526.3 (M+H). $^1$H NMR (d$_6$-DMSO) δ 7.80 (br s, 1H), 7.42 (m, 4H), 7.31 (m, 3H), 7.06 (m, 1H), 6.70 (d, 1H), 5.02 (d, 1H), 4.33 (m, 1H), 4.04 (m, 1H), 3.43 (t, 2H), 3.34 (m, 1H), 3.24 (s, 3H), 3.05 (m, 2H), 2.88 (t, 1H), 2.43-2.67 (m, 6H), 2.19 (m, 2H), 1.74 (s, 3H).

Example 452

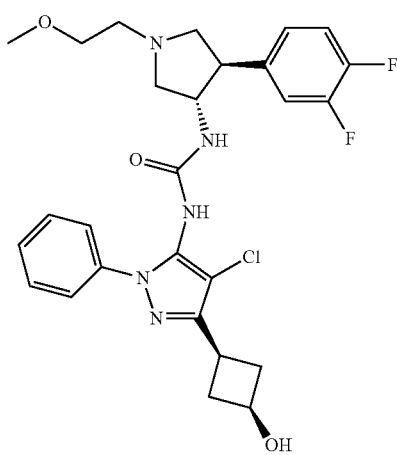 [SMILES: COCCN1C[C@@H](NC(=O)Nc2c(Cl)c([C@H]3C[C@@H](O)C3)nn2-c2ccccc2)[C@H](c2ccc(F)c(F)c2)C1]

1-(4-chloro-3-(cis-3-hydroxycyclobutyl)-1-phenyl-1H-pyrazol-5-yl)-3-((3S,4R)-4-(3,4-difluorophenyl)-1-(2-methoxyethyl)pyrrolidin-3-yl)urea Step A: cis- and trans-1-(4-chloro-3-(3-hydroxycyclobutyl)-1-phenyl-1H-pyrazol-5-yl)-3-((3S,4R)-4-(3,4-difluorophenyl)-1-(2-methoxyethyl)pyrrolidin-3-yl)urea: Prepared according to the method described in Example 450, Step A, replacing phenyl 3-(3-hydroxycyclobutyl)-4-methyl-1-phenyl-1H-pyrazol-5-ylcarbamate with phenyl (4-chloro-3-(3-hydroxycyclobutyl)-1-phenyl-1H-pyrazol-5-yl)carbamate (Intermediate 238) in Step A to afford the product as a mixture of cis and trans hydroxycyclobutyl diastereomers. MS (apci) m/z=546.2 (M+H).

Step B: Preparation of 1-(4-chloro-3-(cis-3-hydroxycyclobutyl)-1-phenyl-1H-pyrazol-5-yl)-3-((3S,4R)-4-(3,4-difluorophenyl)-1-(2-methoxyethyl)pyrrolidin-3-yl)urea: To a mixture of cis and trans hydroxycyclobutyl diastereomers 1-(4-chloro-3-(3-hydroxycyclobutyl)-1-phenyl-1H-pyrazol-5-yl)-3-((3S,4R)-4-(3,4-difluorophenyl)-1-(2-methoxyethyl)pyrrolidin-3-yl)urea (41 mg, 0.075 mmol) was separated by preparatory HPLC on a DEAP column (Princeton Analytical, 4.6 mm×250 mm, 5 µm), eluted with 10% EtOH/hexanes. Peak 1 was collected to afford the title compound as a white solid (10.2 mg, 25% yield). MS (apci) m/z=546.2 (M+H). $^1$H NMR (CDCl$_3$) 7.50 (d, 2H), 7.41 (t, 2H), 7.30 (m, 1H), 7.05 (m, 1H), 6.97 (m, 1H), 6.86 (m, 1H), 5.48 (m, 1H), 4.30 (m, 1H), 3.43 (br m, 2H), 3.33 (m, 1H), 3.25 (br m, 2H), 3.10 (m, 2H), 2.96 (br m, 1H), 2.60-2.83 (m, 5H), 2.33 (m, 3H).

Example 453

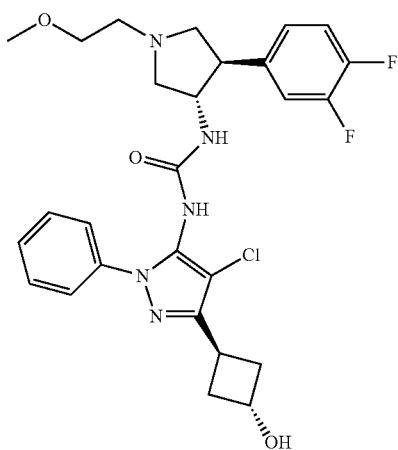 [SMILES: COCCN1C[C@@H](NC(=O)Nc2c(Cl)c([C@H]3C[C@H](O)C3)nn2-c2ccccc2)[C@H](c2ccc(F)c(F)c2)C1]

1-(4-chloro-3-((1r,3S)-3-hydroxycyclobutyl)-1-phenyl-1H-pyrazol-5-yl)-3-(trans-4-(3,4-difluorophenyl)-1-(2-methoxyethyl)pyrrolidin-3-yl)urea A mixture of cis- and trans-1-(4-chloro-3-(3-hydroxycyclobutyl)-1-phenyl-1H-pyrazol-5-yl)-3-((3S,4R)-4-(3,4-difluorophenyl)-1-(2-methoxyethyl)pyrrolidin-3-yl)urea (Example 452, Step A, 41 mg, 0.075 mmol) was separated by preparatory HPLC on a DEAP column (Princeton Analytical, 4.6 mm×250 mm, 5 µm), eluted with 10% EtOH/hexanes. Peak 1 was collected to afford the title compound as a white solid (16.4 mg, 40% yield). MS (apci) m/z=546.2 (M+H). $^1$H NMR (CDCl$_3$) 7.51 (d, 2H), 7.41 (t, 2H), 7.33 (m, 1H), 7.04 (m, 1H), 6.96 (m, 1H), 6.85 (m, 1H), 5.53 (br d, 1H), 4.65 (m, 1H), 3.60 (m, 1H), 3.41 (br m, 2H), 3.25 (br m, 5H), 3.08 (br m, 1H), 2.89 (br m, 1H), 2.57-2.77 (m, 7H), 2.37 (m, 3H).

Example 454

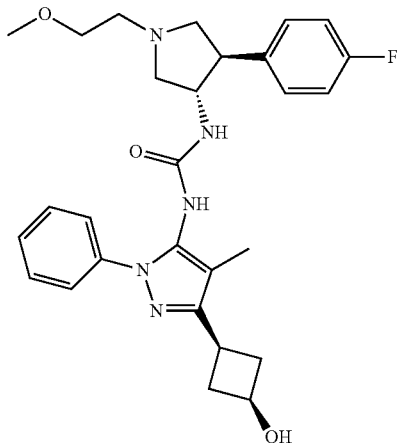 [SMILES: COCCN1C[C@@H](NC(=O)Nc2c(C)c([C@H]3C[C@@H](O)C3)nn2-c2ccccc2)[C@H](c2ccc(F)cc2)C1]

1-((3S,4R)-4-(4-fluorophenyl)-1-(2-methoxyethyl)pyrrolidin-3-yl)-3-(3-(cis-3-hydroxycyclobutyl)-4-methyl-1-phenyl-1H-pyrazol-5-yl)urea Step A: Preparation of cis- and trans-1-((3S,4R)-4-(4-fluorophenyl)-1-(2-methoxyethyl)pyrrolidin-3-yl)-3-(3-(3-hydroxycyclobutyl)-4-methyl-1-phenyl-1H-pyrazol-5-yl)urea: Prepared according to the method described in Example 450, Step A, replacing (3S,4R)-4-(3,4-difluorophenyl)-1-(2-methoxyethyl)pyrrolidin-3-amine dihydrochloride with (3S,4R)-4-(4-fluorophenyl)-1-(2-methoxyethyl)pyrrolidin-3-amine dihydrochloride (Preparation K) in Step A to afford the product as a mixture of cis and trans hydroxycyclobutyl diastereomers. MS (apci) m/z=508.3 (M+H).

Step B: Preparation of 1-((3S,4R)-4-(4-fluorophenyl)-1-(2-methoxyethyl) pyrrolidin-3-yl)-3-(3-(cis-3-hydroxycyclobutyl)-4-methyl-1-phenyl-H-pyrazol-5-yl)urea: The mixture of cis- and trans-1-((3S,4R)-4-(4-fluorophenyl)-1-(2-methoxyethyl)pyrrolidin-3-yl)-3-(3-(3-hydroxycyclobutyl)-4-methyl-1-phenyl-1H-pyrazol-5-yl)urea (49 mg, 0.096 mmol) was separated by supercritical fluid chromatography (SFC) on a cyano column (YMC-Pack CN, 250×20 mm, 10 µm), mobile phase 95% CO$_2$ and 5% 80/20/0.1 MeOH/IPA/diethylamine. Peak 1 was collected to afford the title compound as a white solid (16.4 mg, 34% yield). MS (apci) m/z=508.2 (M+H). $^1$H NMR (d$_6$-DMSO) δ 7.85 (br s, 1H), 7.42 (m, 4H), 7.28 (m, 3H), 7.10 (t, 2H), 6.75 (br d, 1H), 5.06 (br s, 1H), 4.04 (m, 2H), 3.42 (t, 2H), 3.24 (s, 3H), 3.06 (m, 2H), 2.84 (m, 2H), 2.46-2.64 (m, 6H), 2.08 (m, 2H), 1.76 (s, 3H).

Example 455

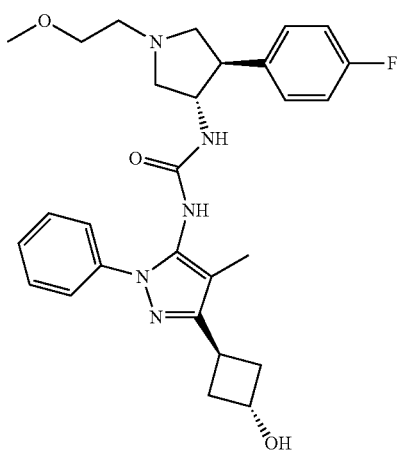 [SMILES: COCCN1C[C@@H](NC(=O)Nc2c(C)c([C@H]3C[C@H](O)C3)nn2-c2ccccc2)[C@H](c2ccc(F)cc2)C1]

1-((3S,4R)-4-(4-fluorophenyl)-1-(2-methoxyethyl)
pyrrolidin-3-yl)-3-(3-(trans-3-hydroxycyclobutyl)-4-
methyl-1-phenyl-1H-pyrazol-5-yl)urea A mixture of cis- and trans-1-((3S,4R)-4-(4-fluorophenyl)-1-(2-methoxyethyl)pyrrolidin-3-yl)-3-(3-(3-hydroxycyclobutyl)-4-methyl-1-phenyl-1H-pyrazol-5-yl)urea (Example 454, Step A, 49 mg, 0.096 mmol) was separated by supercritical fluid chromatography (SFC) on a cyano column (YMC-Pack CN, 250×20 mm, 10 μm), mobile phase 95% $CO_2$ and 5% 80/20/0.1 MeOH/IPA/diethylamine. Peak 2 was collected to afford the title compound as a white solid (19.0 mg, 39% yield). MS (apci) m/z=508.2 (M+H). $^1$H NMR ($d_6$-DMSO) δ 7.86 (br s, 1H), 7.42 (m, 4H), 7.28 (m, 3H), 7.10 (t, 2H), 6.75 (br d, 1H), 5.03 (br s, 1H), 4.33 (m, 1H), 4.03 (m, 1H), 3.42 (t, 2H), 3.34 (m, 1H), 3.24 (s, 3H), 3.07 (m, 2H), 2.84 (t, 1H), 2.43-2.64 (m, 6H), 2.19 (m, 2H), 1.73 (s, 3H).

Example 456

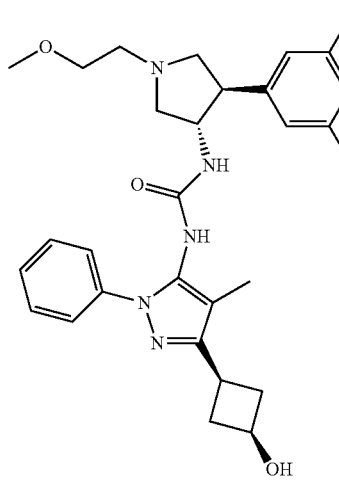

1-((3S,4R)-4-(3,5-difluorophenyl)-1-(2-methoxy-
ethyl)pyrrolidin-3-yl)-3-(3-(cis-3-hydroxycyclobu-
tyl)-4-methyl-1-phenyl-1H-pyrazol-5-yl)urea Step A: Preparation of cis- and trans-1-((3S,4R)-4-(3,5-difluorophenyl)-1-(2-meth-oxyethyl)pyrrolidin-3-yl)-3-(3-(3-hydroxycyclobutyl)-4-methyl-1-phenyl-1H-pyrazol-5-yl)urea: Prepared according to the method described in Example 450, Step A, replacing (3S,4R)-4-(3,4-difluorophenyl)-1-(2-methoxyethyl)pyrrolidin-3-amine dihydrochloride with (3S,4R)-4-(3,5-difluorophenyl)-1-(2-methoxyethyl)pyrrolidin-3-amine dihydrochloride (Preparation E) in Step A to afford the product as a mixture of cis and trans hydroxycyclobutyl diastereomers. MS (apci) m/z=526.3 (M+H).

Step B: Preparation of 1-((3S,4R)-4-(3,5-difluorophenyl)-1-(2-methoxyethyl) pyrrolidin-3-yl)-3-(3-(cis-3-hydroxvcyclobutyl)-4-methyl-1-phenyl-H-pyrazol-5-yl)urea: The mixture of cis and trans hydroxycyclobutyl diastereomers 1-((3S,4R)-4-(3,5-difluorophenyl)-1-(2-methoxyethyl)pyrrolidin-3-yl)-3-(3-(3-hydroxycyclobutyl)-4-methyl-1-phenyl-1H-pyrazol-5-yl)urea (53 mg, 0.10 mmol) was separated by supercritical fluid chromatography (SFC) on a cyano column (YMC-Pack CN, 250×20 mm, 10 μm), mobile phase 95% $CO_2$ and 5% 80/20/0.1 MeOH/IPA/diethylamine. Peak 1 was collected to afford the title compound as a white solid (17.6 mg, 33% yield). MS (apci) m/z=526.2 (M+H). $^1$H NMR ($d_6$-DMSO) δ 7.95 (br s, 1H), 7.45 (d, 2H), 7.39 (t, 2H), 7.28 (t, 1H), 7.05 (tt, 1H), 6.97 (m, 2H), 6.85 (m, 1H), 5.08 (br s, 1H), 4.05 (m, 2H), 3.43 (t, 2H), 3.24 (s, 3H), 3.08 (m, 1H), 3.02 (m, 1H), 2.89 (m, 1H), 2.84 (m, 1H), 2.45-2.65 (m, 6H), 2.08 (m, 2H), 1.77 (s, 3H).

Example 457

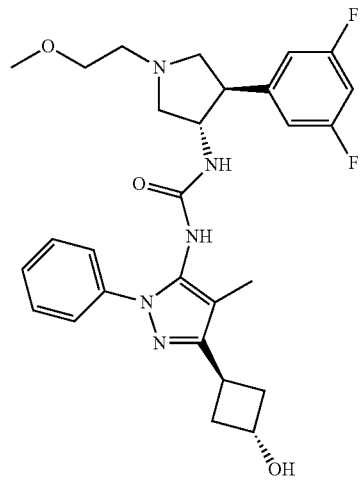 [SMILES: COCCN1C[C@@H](NC(=O)Nc2c(C)c([C@H]3C[C@H](O)C3)nn2-c2ccccc2)[C@H](c2cc(F)cc(F)c2)C1]

1-((3S,4R)-4-(3,5-difluorophenyl)-1-(2-methoxy-
ethyl)pyrrolidin-3-yl)-3-(3-(trans-3-hydroxycyclobu-
tyl)-4-methyl-1-phenyl-1H-pyrazol-5-yl)urea A mixture of cis and trans hydroxycyclobutyl diastereomers 1-((3S,4R)-4-(3,5-difluorophenyl)-1-(2-methoxyethyl) pyrrolidin-3-yl)-3-(3-(3-hydroxycyclobutyl)-4-methyl-1-phenyl-1H-pyrazol-5-yl)urea (Example 456, Step A, 53 mg, 0.10 mmol) was separated by supercritical fluid chromatography (SFC) on a cyano column (YMC-Pack CN, 250×20 mm, 10 μm), mobile phase 95% $CO_2$ and 5% 80/20/0.1 MeOH/IPA/diethylamine. Peak 2 was collected to afford the title compound as a white solid (20.7 mg, 39% yield). MS (apci) m/z=526.2 (M+H). $^1$H NMR ($d_6$-DMSO) δ 7.96 (br s, 1H), 7.46 (d, 2H), 7.40 (t, 2H), 7.28 (t, 1H), 7.05 (tt, 1H), 6.97 (m, 2H), 6.85 (m, 1H), 5.04 (br s, 1H), 4.34 (m, 1H), 4.06 (m, 1H), 3.43 (t, 2H), 3.35 (m, 1H), 3.24 (s, 3H), 3.09 (q, 1H), 3.02 (t, 1H), 2.90 (t, 1H), 2.44-2.66 (m, 6H), 2.19 (m, 2H), 1.74 (s, 3H).

Example 458

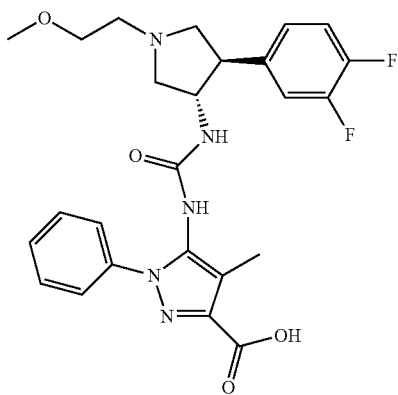 [SMILES: COCCN1C[C@@H](NC(=O)Nc2c(C)c(C(=O)O)nn2-c2ccccc2)[C@H](c2ccc(F)c(F)c2)C1]

5-(3-((3S,4R)-4-(3,4-difluorophenyl)-1-(2-methoxy-ethyl)pyrroidin-3-yl)ureido)-4-methyl-1-phenyl-1H-pyrazole-3-carboxylic acid To a solution of ethyl 5-(3-((3S,4R)-4-(3,4-difluorophenyl)-1-(2-methoxy-ethyl)pyrrolidin-3-yl)ureido)-4-methyl-1-phenyl-1H-pyrazole-3-carboxylate (Example 291; 333 mg, 6.21 mmol) in THF (4 mL) and MeOH (2 mL) was added aqueous LiOH (2M, 0.95 mL, 1.89 mmol). The reaction mixture was stirred at ambient temperature for 4 hours, then partially concentrated under reduced pressure, then neutralized with aqueous HCl (1M, 1 mL). The suspension was filtered and the white precipitate was collected to afford the title compound as a white solid (247 mg, 78% yield). MS (apci) m/z=500.2 (M+H).

Example 459

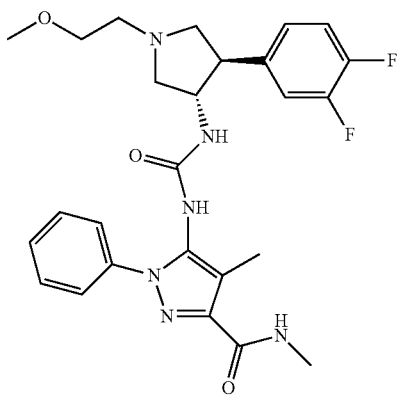 [SMILES: CNC(=O)c1nn(-c2ccccc2)c(NC(=O)N[C@@H]2CN(CCOC)C[C@H]2c2ccc(F)c(F)c2)c1C]

5-(3-((3S,4R)-4-(3,4-difluorophenyl)-1-(2-methoxy-ethyl)pyrrolidin-3-yl)ureido)-N,4-dimethyl-1-phenyl-1H-pyrazole-3-carboxamide To a solution of 5-(3-((3S,4R)-4-(3,4-difluorophenyl)-1-(2-methoxyethyl)pyrrolidin-3-yl)ureido)-4-methyl-1-phenyl-1H-pyrazole-3-carboxylic acid (Example 458, 25 mg, 0.050 mmol) in DMF (0.5 mL) were added DIEA (0.026 mL, 0.150 mmol), methanamine hydrochloride (6.8 mg, 0.100 mmol), then HATU (20.9 mg, 0.055 mmol). The reaction mixture was stirred at ambient temperature for 19 hours. The reaction mixture was directly purified by reverse-phase column chromatography, eluting with 5-60% acetonitrile/water to afford the product as a white solid (13.5 mg, 53% yield). MS (apci) m/z=513.3 (M+H).

Example 460

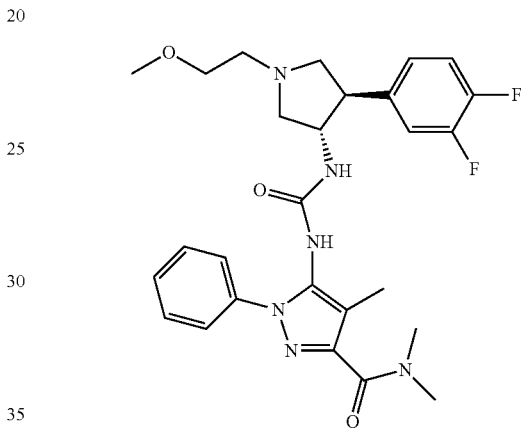

5-(3-((3S,4R)-4-(3,4-difluorophenyl)-1-(2-methoxy-ethyl)pyrrolidin-3-yl)ureido)-N,N,4-trimethyl-1-phenyl-1H-pyrazole-3-carboxamide Prepared according to the method described in Example 459 replacing methanamine hydrochloride with dimethylamine (2M in THF) to afford the product as a white solid (13.0 mg, 49% yield). MS (apci) m/z=527.2 (M+H).

Example 461

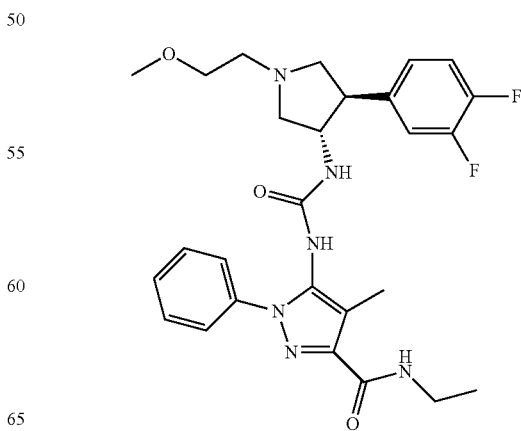

5-(3-((3S,4R)-4-(3,4-difluorophenyl)-1-(2-methoxyethyl)pyrrolidin-3-yl)ureido)-N-ethyl-4-methyl-1-phenyl-1H-pyrazole-3-carboxamide Prepared according to the method described in Example 459 replacing methanamine hydrochloride with ethanamine (2M in THF) to afford the product as a white solid (11.2 mg, 48% yield). MS (apci) m/z=527.2 (M+H).

Example 462

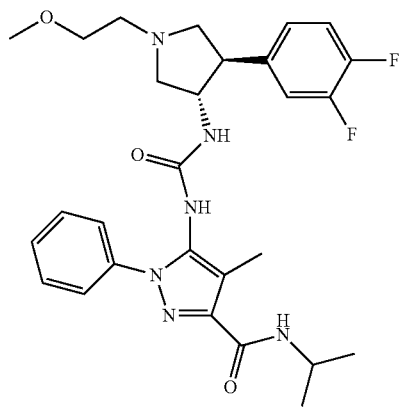 [SMILES: COCCN1C[C@@H](NC(=O)Nc2c(C)c(C(=O)NC(C)C)nn2-c2ccccc2)[C@H](c2ccc(F)c(F)c2)C1]

5-(3-((3S,4R)-4-(3,4-difluorophenyl)-1-(2-methoxyethyl)pyrrolidin-3-yl)ureido)-N-isopropyl-4-methyl-1-phenyl-1H-pyrazole-3-carboxamide Prepared according to the method described in Example 459 replacing methanamine hydrochloride with propan-2-amine to afford the product as a white solid (5.6 mg, 24% yield). MS (apci) m/z=541.3 (M+H).

Example 463

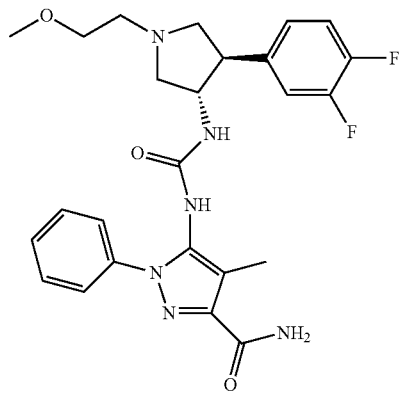 [SMILES: COCCN1C[C@@H](NC(=O)Nc2c(C)c(C(N)=O)nn2-c2ccccc2)[C@H](c2ccc(F)c(F)c2)C1]

5-(3-((3S,4R)-4-(3,4-difluorophenyl)-1-(2-methoxyethyl)pyrrolidin-3-yl)ureido)-4-methyl-1-phenyl-1H-pyrazole-3-carboxamide A solution of 1-(3-cyano-4-methyl-1-phenyl-1H-pyrazol-5-yl)-3-((3S,4R)-4-(3,4-difluorophenyl)-1-(2-methoxyethyl)pyrrolidin-3-yl)urea (Example 349, 25 mg, 0.52 mmol) in concentrated $H_2SO_4$ (0.2 mL) was stirred at ambient temperature for 20 hours. The reaction mixture was cooled to 0° C. and neutralized by the addition of aqueous NaOH (15 wt %, 4 mL), then extracted 10% MeOH/DCM (3×10 mL), and the combined organic extracts were washed with brine, dried ($MgSO_4$), filtered and concentrated under reduced pressure. The crude product was purified by reverse-phase column chromatography, eluting with 5-60% acetonitrile/water to yield the product as a white solid (1.4 mg, 5% yield). MS (apci) m/z=499.2 (M+H).

Example 464

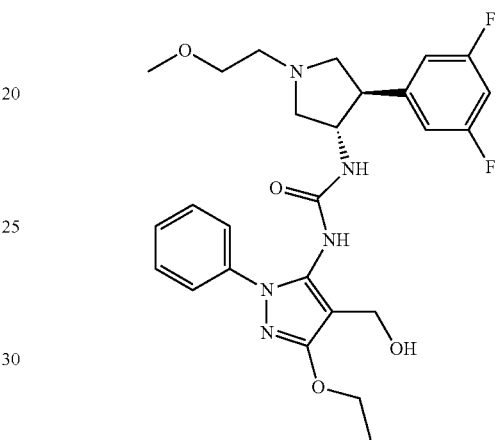

1-((3S,4R)-4-(3,5-difluorophenyl)-1-(2-methoxyethyl)pyrrolidin-3-yl)-3-(3-ethoxy-4-(hydroxymethyl)-1-phenyl-1H-pyrazol-5-yl)urea Step A: Preparation of ethyl 5-(3-((3S,4R)-4-(3,5-difluorophenyl)-1-(2-methoxyethyl)pyrrolidin-3-yl)ureido)-3-ethoxy-1-phenyl-1H-pyrazole-4-carboxylate: To a solution of ethyl 5-amino-3-ethoxy-1-phenyl-1H-pyrazole-4-carboxylate (Intermediate 174, 68 mg, 0.25 mmol) in DCM (1 mL) was added DIEA (0.086 mL, 0.49 mmol) then triphosgene (26 mg, 0.086 mmol). The reaction mixture was stirred at ambient temperature for 2 hours, then additional triphosgene (26 mg, 0.086 mmol) was added. The reaction mixture was stirred at ambient temperature for 22 hours, and then additional triphosgene (26 mg, 0.086 mmol) was added. The reaction mixture was stirred at ambient temperature for another 5 hours, then a solution of (3S,4R)-4-(3,5-difluorophenyl)-1-(2-methoxyethyl)pyrrolidin-3-amine dihydrochloride (Preparation E, 81 mg, 0.25 mmol) and DIEA (0.13 mL, 0.74 mmol) in DCM (0.5 mL) was added. The reaction mixture was stirred at ambient temperature for 1 hour, then concentrated under reduced pressure and purified by reverse-phase column chromatography, eluting with 5-70% acetonitrile/water to yield the product as a white solid (12 mg, 9% yield). MS (apci) m/z=558.3 (M+H).

Step B: Preparation of 1-((3S,4R)-4-(3,5-difluorophenyl)-1-(2-methoxyethyl) pyrrolidin-3-yl)-3-(3-ethoxy-4-(hydroxymethyl)-1-phenyl-1H-pyrazol-5-yl)urea: To a solution of ethyl 5-(3-((3S,4R)-4-(3,5-difluorophenyl)-1-(2-methoxyethyl)pyrrolidin-3-yl)ureido)-3-ethoxy-1-phenyl-1H-pyrazole-4-carboxylate (18 mg, 0.032 mmol) in THF (2 mL) under $N_2$ cooled to 0° C. was added $LiAlH_4$ (1M bis-THF in toluene, 0.032 mL, 0.032 mmol). The reaction mixture was stirred at 0° C. for 2 hours, then at ambient temperature for 90 minutes, then cooled to 0° C. and quenched by addition of H₂O (0.005 mL), 5 μL aqueous NaOH (1M, 0.005 mL), then H₂O (0.015 mL), stirred for 10 minutes, then filtered, rinsed with THF (2×5 mL), and concentrated. The crude product was purified by preparatory TLC (0.5 mm plate, eluted with 5% MeOH/DCM) to afford the product as a colorless residue (1.6 mg, 10% yield). MS (apci) m/z=516.3 (M+H).

Example 465

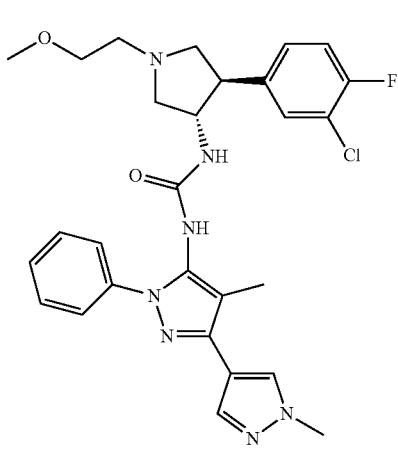 [SMILES: COCCN1C[C@@H](NC(=O)Nc2c(C)c(-c3cnn(C)c3)nn2-c2ccccc2)[C@H](c2ccc(F)c(Cl)c2)C1]

1-((3S,4R)-4-(3-chloro-4-fluorophenyl)-1-(2-methoxyethyl)pyrrolidin-3-yl)-3-(1',4-dimethyl-1-phenyl-1H, 1'H-3,4'-bipyrazol-5-yl)urea The racemic mixture 1-(trans-4-(3-chloro-4-fluorophenyl)-1-(2-methoxyethyl)pyrrolidin-3-yl)-3-(1',4-dimethyl-1-phenyl-1H, 1'H-3,4'-bipyrazol-5-yl)urea (Example 293, 30 mg, 0.054 mmol) was separated by chiral HPLC (Chiralcel OD column) eluted with 10% EtOH/hexanes. Peak 1 was collected to afford the title compound as a white solid (9.8 mg, 33% yield). MS (apci) m/z=552.2 (M+H).

Example 466

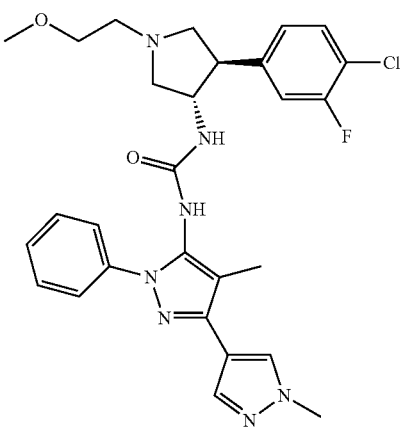 [SMILES: COCCN1C[C@@H](NC(=O)Nc2c(C)c(-c3cnn(C)c3)nn2-c2ccccc2)[C@H](c2ccc(Cl)c(F)c2)C1]

1-((3S,4R)-4-(4-chloro-3-fluorophenyl)-1-(2-methoxyethyl)pyrrolidin-3-yl)-3-(1',4-dimethyl-1-phenyl-1H, 1'H-3,4'-bipyrazol-5-yl)urea The racemic mixture 1-(trans-4-(4-chloro-3-fluorophenyl)-1-(2-methoxyethyl) pyrrolidin-3-yl)-3-(1',4-dimethyl-1-phenyl-1H,1'H-3,4'-bipyrazol-5-yl)urea (Example 294, 42 mg, 0.076 mmol) was separated by chiral HPLC (Chiralcel OD column) eluted with 10% EtOH/hexanes. Peak 1 was collected to afford the title compound as a white solid (17.1 mg, 41% yield). MS (apci) m/z=552.2 (M+H).

Example 467

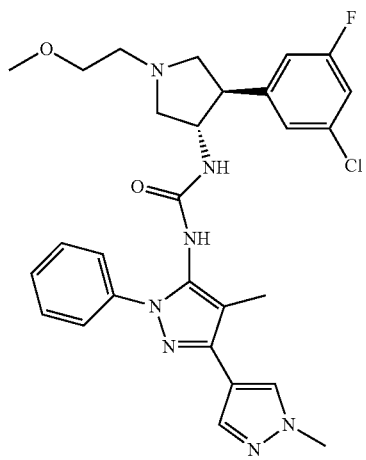 [SMILES: COCCN1C[C@@H](NC(=O)Nc2c(C)c(-c3cnn(C)c3)nn2-c2ccccc2)[C@H](c2cc(F)cc(Cl)c2)C1]

1-((3S,4R)-4-(3-chloro-5-fluorophenyl)-1-(2-methoxyethyl)pyrrolidin-3-yl)-3-(1',4-dimethyl-1-phenyl-1H, 1'H-3,4'-bipyrazol-5-yl)urea The racemic mixture 1-(trans-4-(3-chloro-5-fluorophenyl)-1-(2-methoxyethyl) pyrrolidin-3-yl)-3-(1',4-dimethyl-1-phenyl-1H,1'H-3,4'-bipyrazol-5-yl)urea (Example 295, 32 mg, 0.058 mmol) was separated by chiral HPLC (Chiralpak IA column) eluted with 15% EtOH/hexanes. Peak 2 was collected to afford the title compound as a white solid (12.5 mg, 39% yield). MS (apci) m/z=552.2 (M+H).

Example 468

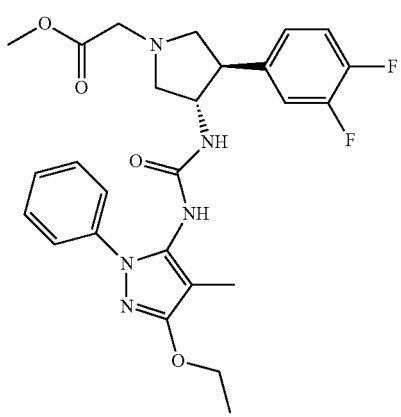 [SMILES: CCOc1nn(-c2ccccc2)c(NC(=O)N[C@@H]2CN(CC(=O)OC)C[C@H]2c2ccc(F)c(F)c2)c1C]

451 methyl 2-((3R,4S)-3-(3,4-difluorophenyl)-4-(3-(3-ethoxy-4-methyl-1-phenyl-1H-pyrazol-5-yl)ureido)pyrrolidin-1-yl)acetate Prepared according to the method described in Example 191, replacing 2-bromoethanol with methyl 2-bromoacetate in Step A and replacing phenyl 3,4-dimethyl-1-phenyl-1H-pyrazol-5-ylcarbamate with phenyl 3-ethoxy-4-methyl-1-phenyl-1H-pyrazol-5-ylcarbamate (prepared according to Example 1, Step A, starting with Intermediate P135) in Step C to afford the product as a white solid (23 mg, 50% yield). MS (apci) m/z=514.2 (M+H).

Example 469

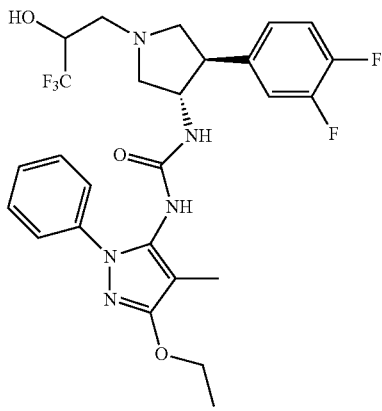 [SMILES: CCOc1nn(-c2ccccc2)c(NC(=O)N[C@@H]2CN(CC(O)C(F)(F)F)C[C@H]2c2ccc(F)c(F)c2)c1C]

1-((3S,4R)-4-(3,4-difluorophenyl)-1-(3,3,3-trifluoro-2-hydroxypropyl)pyrrolidin-3-yl)-3-(3-ethoxy-4-methyl-1-phenyl-1H-pyrazol-5-yl)urea Prepared according to the method described in Example 191, replacing 2-bromoethanol with 3-bromo-1,1,1-trifluoropropan-2-ol in Step A and replacing phenyl 3,4-dimethyl-1-phenyl-1H-pyrazol-5-ylcarbamate with phenyl 3-ethoxy-4-methyl-1-phenyl-1H-pyrazol-5-ylcarbamate (prepared according to Example 1, Step A, starting with Intermediate P135) in Step C to afford the product as a white solid (38 mg, 78% yield). MS (apci) m/z=554.2 (M+H).

Example 470

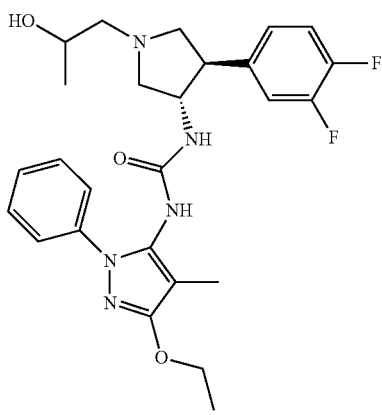 [SMILES: CCOc1nn(-c2ccccc2)c(NC(=O)N[C@@H]2CN(CC(C)O)C[C@H]2c2ccc(F)c(F)c2)c1C]

452

1-((3S,4R)-4-(3,4-difluorophenyvl)-1-(2-hydroxypropyl)pyrrolidin-3-yl)-3-(3-ethoxy-4-methyl-1-phenyl-1H-pyrazol-5-yl)urea Prepared according to the method described in Example 191, replacing 2-bromoethanol with 1-chloropropan-2-ol (Aldrich, 70% purity with <25% of 2-chloropropan-1-ol) in Step A and replacing phenyl 3,4-dimethyl-1-phenyl-1H-pyrazol-5-ylcarbamate with phenyl 3-ethoxy-4-methyl-1-phenyl-1H-pyrazol-5-ylcarbamate (prepared according to Example 1, Step A starting with Intermediate P135) in Step C to afford the product as a white solid (10 mg, 53% yield). MS (apci) m/z=500.2 (M+H).

Example 471

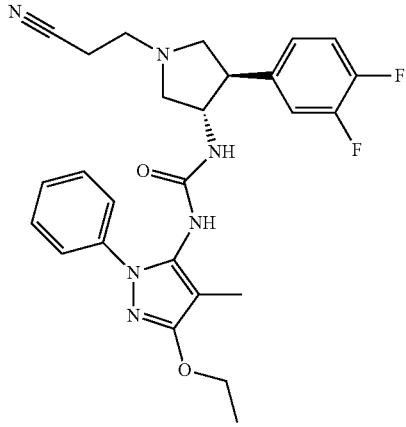 [SMILES: CCOc1nn(-c2ccccc2)c(NC(=O)N[C@@H]2CN(CCC#N)C[C@H]2c2ccc(F)c(F)c2)c1C]

1-((3S,4R)-1-(2-cyanoethyl)-4-(3,4-difluorophenyl)pyrrolidin-3-yl)-3-(3-ethoxy-4-methyl-1-phenyl-1H-pyrazol-5-yl)urea Prepared according to the method described in Example 191, replacing acrylonitrile with 1-chloropropan-2-ol in Step A and replacing phenyl 3,4-dimethyl-1-phenyl-1H-pyrazol-5-ylcarbamate with phenyl 3-ethoxy-4-methyl-1-phenyl-1H-pyrazol-5-ylcarbamate (prepared according to Example 1, Step A, starting with Intermediate P135) in Step C to afford the product as a white solid (16 mg, 59% yield). MS (apci) m/z=459.3 (M+H).

Example 472

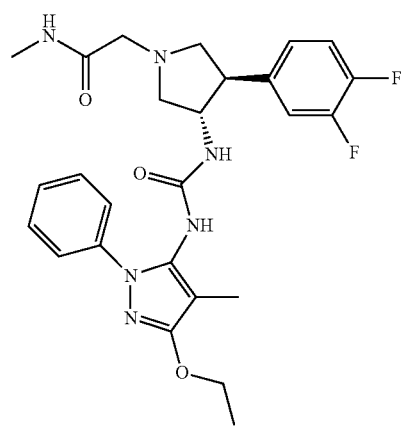 [SMILES: CCOc1nn(-c2ccccc2)c(NC(=O)N[C@@H]2CN(CC(=O)NC)C[C@H]2c2ccc(F)c(F)c2)c1C]

2-((3R,4S)-3-(3,4-difluorophenyl)-4-(3-(3-ethoxy-4-methyl-1-phenyl-1H-pyrazol-5-yl)ureido)pyrrolidin-1-yl)-N-methylacetamide Step A: Preparation of 2-((3R,4S)-3-(3,4-difluorophenyl)-4-(3-(3-ethoxy-4-methyl-1-phenyl-1H-pyrazol-5-yl)ureido)pyrrolidin-1-yl)acetic acid: To a solution of methyl 2-((3R,4S)-3-(3,4-difluorophenyl)-4-(3-(3-ethoxy-4-methyl-1-phenyl-1H-pyrazol-5-yl)ureido)pyrrolidin-1-yl)acetate (Example 468; 15 mg, 0.029 mmol) in THF (0.8 mL) and MeOH (0.4 mL) was added aqueous LiOH (2M, 0.044 mL, 0.088 mmol). The reaction mixture was stirred at ambient temperature for 3 hours, then diluted with aqueous HCl (1M, 1 mL) and brine (2 mL) and extracted with DCM (2×5 mL). The combined organic extracts were dried (MgSO₄), filtered and concentrated afford the product as an off-white solid (13.0 mg, 89% yield). MS (apci) m/z=500.2 (M+H).

Step B: Preparation of 2-((3R,4S)-3-(3,4-difluorophenyl)-4-(3-(3-ethoxy-4-methyl-1-phenyl-1H-pyrazol-5-yl)ureido)pyrrolidin-1-yl)-N-methylacetamide: To a suspension of 2-((3R,4S)-3-(3,4-difluorophenyl)-4-(3-(3-ethoxy-4-methyl-1-phenyl-1H-pyrazol-5-yl)ureido) pyrrolidin-1-yl) acetic acid (7.4 mg, 0.015 mmol) in DMF (0.5 mL) were added N-methylmorpholine (0.005 mL, 0.044 mmol), methylamine (2M in THF, 0.009 mL, 0.018 mmol) then HATU (6.8 mg, 0.018 mmol). The reaction mixture was stirred at ambient temperature for 19 hours then purified directly by reverse-phase column chromatography, eluting with 5-70% acetonitrile/water to afford the title compound as a pale white solid (4.2 mg, 55% yield). MS (apci) m/z=513.3 (M+H).

Example 473

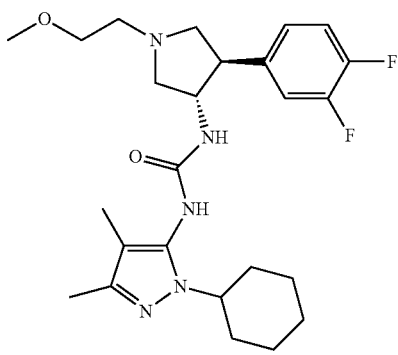 [SMILES: COCCN1C[C@@H](NC(=O)Nc2c(C)c(C)nn2C2CCCCC2)[C@H](c2ccc(F)c(F)c2)C1]

1-(1-cyclohexyl-3,4-dimethyl-1H-pyrazol-5-yl)-3-((3S,4R)-4-(3,4-difluorophenyl)-1-(2-methoxyethyl)pyrrolidin-3-yl)urea Step A: Preparation of 1-cyclohexyl-3,4-dimethyl-1H-pyrazol-5-amine: To a suspension of cyclohexylhydrazine hydrochloride (0.465 g, 3.09 mmol) in ethanol (30 mL) was added 2-oxocyclopentanecarbonitrile (0.30 g, 3.09 mmol). The mixture was heated to reflux for 18 hours, then cooled to ambient temperature and concentrated in vacuo. The residue was partitioned between saturated NaHCO₃ (30 mL) and EtOAc (30 mL). The aqueous layer was extracted with EtOAc (2×20 mL) and the combined organic phases were washed with brine (20 mL), dried over Na₂SO₄, filtered and concentrated to afford 1-cyclohexyl-3,4-dimethyl-1H-pyrazol-5-amine (0.523 g, 88% yield) as a cream solid. ¹H NMR (CDCl₃) δ 3.78-3.93 (m, 1H), 3.13 (br s, 2H), 2.12 (s, 3H), 1.85-1.95 (m, 6H), 1.83 (s, 3H), 1.63-1.73 (m, 1H), 1.18-1.44 (m, 3H) ppm.

Step B: Preparation of phenyl (1-cyclohexyl-3,4-dimethyl-1H-pyrazol-5-yl)carbamate: To a solution of 1-cyclohexyl-3,4-dimethyl-1H-pyrazol-5-amine (200 mg, 1.04 mmol) in EtOAc (5 mL) was added 2N NaOH (1.04 mL, 2.1 mmol) followed by phenyl chloroformate (182 µL, 1.45 mmol). The mixture was stirred at ambient temperature for 5 hours then diluted with water (30 mL) and extracted with EtOAc (3×20 mL). The combined organic phases were washed with saturated NaHCO₃ (20 mL) and brine (20 mL) then dried over Na₂SO₄ and concentrated in vacuo to afford phenyl (1-cyclohexyl-3,4-dimethyl-1H-pyrazol-5-yl)carbamate as a pale purple foam which was used without purification assuming quantitative yield.

Step C: Preparation of 1-(1-cyclohexyl-3,4-dimethyl-1H-pyrazol-5-yl)-3-((3S,4R)-4-(3,4-difluorophenyl)-1-(2-methoxyethyl)pyrrolidin-3-yl)urea: To a solution of (3S,4R)-4-(3,4-difluorophenyl)-1-(2-methoxyethyl)pyrrolidin-3-amine (Preparation F) (50 mg, 0.15 mmol) and phenyl (1-cyclohexyl-3,4-dimethyl-1H-pyrazol-5-yl)carbamate (52 mg, 0.17 mmol) in DMA (2 mL) was added DIEA (93 µL, 0.53 mmol). The mixture was stirred at ambient temperature for 18 hours then partitioned between saturated NH₄Cl (20 mL) and EtOAc (20 mL) and the aqueous layer extracted with EtOAc (2×10 mL). The combined organic phases were washed with water (5×10 mL) and brine (10 mL) then dried over Na₂SO₄, filtered and concentrated in vacuo. The residue was purified by silica column chromatography, eluting with 2% MeOH/DCM to yield the title compound (42 mg, 58% yield) as a colorless glass. MS (apci) m/z=476.3 (M+H).

Example 474

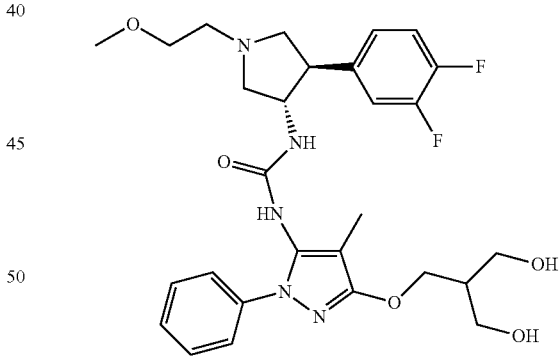

1-((3S,4R)-4-(3,4-difluorophenyl)-1-(2-methoxyethyl)pyrrolidin-3-yl)-3-(3-(3-hydroxy-2-(hydroxymethyl)propoxy)-4-methyl-1-phenyl-1H-pyrazol-5-yl)urea Step A: Preparation of (2,2-dimethyl-1,3-dioxan-5-yl)methanol: To a suspension of 2-(hydroxymethyl)propane-1,3-diol (5.0 g, 47.1 mmol) in THF (100 mL) was added p-toluenesulfonic acid monohydrate (269 mg, 1.41 mmol) followed by 2,2-dimethoxypropane (6.72 mL, 54.7 mmol). The mixture was stirred at ambient temperature for 3 hours then a further 200 mg of p-toluenesulfonic acid monohydrate added and stirring continued for a further 60 hours. The solution was treated with triethylamine (3 mL) then concentrated in vacuo. The residue was purified by silica column chromatography eluting with 5% MeOH/DCM to afford (2,2-dimethyl-1,3-dioxan-5-yl)methanol (5.04 g, 73% yield) as a colorless liquid. $^1$H NMR (CDCl$_3$) δ 4.02 (dd, J=12.0, 4.1 Hz, 2H), 3.74-3.80 (m, 4H), 1.90 (t, J=5.1 Hz, 1H), 1.80-1.88 (m, 1H), 1.45 (s, 3H), 1.40 (s, 3H) ppm.

Step B: Preparation of (2,2-dimethyl-1,3-dioxan-5-yl) methyl methanesulfonate: To a solution of (2,2-dimethyl-1,3-dioxan-5-yl)methanol (1.0 g, 6.84 mmol) in DCM (30 mL) at 0° C. was added triethylamine (1.43 mL, 10.3 mmol) followed by mesyl chloride (0.58 mL, 7.52 mmol). The mixture was allowed to warm slowly to ambient temperature with stirring over 18 hours. The mixture was partitioned between 0.5 M HCl (40 mL) and DCM (20 mL) and the aqueous layer was extracted with DCM (2×20 mL). The combined organic phases were washed with brine (20 mL), dried over Na$_2$SO$_4$, filtered and concentrated to afford (2,2-dimethyl-1,3-dioxan-5-yl)methyl methanesulfonate (1.29 g, 84% yield) as a colorless oil. $^1$H NMR (CDCl$_3$) δ 4.42 (d, J=7.3 Hz, 2H), 4.08 (dd, J=12.5, 3.5 Hz, 2H), 3.77 (dd, J=12.5, 3.9 Hz, 2H), 3.04 (s, 3H), 1.98-2.03 (m, 1H), 1.46 (s, 3H), 1.39 (s, 3H) ppm.

Step C: Preparation of 3-((2,2-dimethyl-1,3-dioxan-5-yl) methoxy)-4-methyl-1-phenyl-1H-pyrazol-5-amine: To a solution of 5-amino-4-methyl-1-phenyl-1H-pyrazol-3(2H)-one (Intermediate P135, Step A; 500 mg, 2.64 mmol) in DMF (5 mL) was added K$_2$CO$_3$ (1.10 g, 7.93 mmol) followed by a solution of (2,2-dimethyl-1,3-dioxan-5-yl) methyl methanesulfonate (711 mg, 3.17 mmol) in DMF (2 mL). The mixture was stirred at 50° C. for 18 hours then cooled, treated with water (30 mL) and extracted with EtOAc (3×20 mL). The combined organic phases were washed with water (5×10 mL) and brine (10 mL) then dried over Na$_2$SO$_4$, filtered and concentrated in vacuo. The residue was purified by silica column chromatography eluting with 4:1 to 2:1 hexanes/EtOAc, to afford 3-((2,2-dimethyl-1,3-dioxan-5-yl)methoxy)-4-methyl-1-phenyl-1H-pyrazol-5-amine (198 mg, 24%) as a yellow gum. MS (apci) m/z=318.1 (M+H).

Step D: Preparation of phenyl (3-(3-hydroxy-2-(hydroxymethyl)propoxy)-4-methyl-1-phenyl-1H-pyrazol-5-yl)carbamate: To a solution of 3-((2,2-dimethyl-1,3-dioxan-5-yl)methoxy)-4-methyl-1-phenyl-1H-pyrazol-5-amine (198 mg, 0.62 mmol) in EtOAc (5 mL) was added 2M NaOH (780 μL, 1.56 mmol) followed by phenyl chloroformate (117 μL, 0.94 mmol). The mixture was stirred at ambient temperature for 18 hours then partitioned between water (20 mL) and EtOAc (20 mL) and the aqueous layer extracted with EtOAc (2×20 mL). The combined organic phases were washed with saturated NaHCO$_3$ (20 mL) and brine (20 mL) then dried over Na$_2$SO$_4$, filtered and concentrated in vacuo. The residue was purified by silica column chromatography eluting with 2-4% MeOH/DCM to afford (3-(3-hydroxy-2-(hydroxymethyl)propoxy)-4-methyl-1-phenyl-1H-pyrazol-5-yl)carbamate (75 mg, 30% yield) as a cream foam. MS (apci) m/z=398.2 (M+H).

Step E: Preparation of 1-((3S,4R)-4-(3,4-difluorophenyl)-1-(2-methoxyethyl)pyrrolidin-3-yl)-3-(3-(3-hydroxy-2-(hydroxymethyl)propoxy)-4-methyl-1-phenyl-1H-pyrazol-5-yl)urea: Prepared according to the method of Example 473, Step C, replacing phenyl (1-cyclohexyl-3,4-dimethyl-1H-pyrazol-5-yl)carbamate with (3-(3-hydroxy-2-(hydroxymethyl) propoxy)-4-methyl-1-phenyl-1H-pyrazol-5-yl)carbamate. The material was purified by silica column chromatography eluting with 2-5% MeOH/DCM to afford the title compound (26 mg, 55% yield) as a colorless glass. MS (apci) m/z=560.3 (M+H).

Example 475

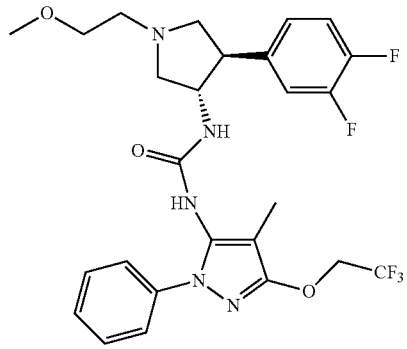 [SMILES: COCCN1C[C@@H](NC(=O)Nc2c(C)c(OCC(F)(F)F)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-1-phenyl-3-(2,2,2-trifluoroethoxy)-1H-pyrazol-5-yl)urea Step A: Preparation of 4-methyl-1-phenyl-3-(2,2,2-trifluoroethoxy)-1H-pyrazol-5-amine: Prepared according to the method of Example 474, Step C, replacing (2,2-dimethyl-1,3-dioxan-5-yl)methyl methanesulfonate with 1,1,1-trifluoro-2-iodoethane. MS (apci) m/z=272.1 (M+H).

Step B: Preparation of phenyl (4-methyl-1-phenyl-3-(2,2,2-trifluoroethoxy)-1H-pyrazol-5-yl)carbamate: Prepared according to the method of Example 474, Step D, replacing 3-((2,2-dimethyl-1,3-dioxan-5-yl)methoxy)-4-methyl-1-phenyl-1H-pyrazol-5-amine with 4-methyl-1-phenyl-3-(2,2,2-trifluoroethoxy)-1H-pyrazol-5-amine. MS (apci) m/z=392.1 (M+H).

Step C: Preparation of 1-((3S,4R)-4-(3,4-difluorophenyl)-1-(2-methoxyethyl) pyrrolidin-3-yl)-3-(4-methyl-1-phenyl-3-(2,2,2-trifluoroethoxy)-1H-pyrazol-5-yl)urea: Prepared according to the method of Example 473, Step C, replacing phenyl (1-cyclohexyl-3,4-dimethyl-1H-pyrazol-5-yl)carbamate with phenyl (4-methyl-1-phenyl-3-(2,2,2-trifluoroethoxy)-1H-pyrazol-5-yl)carbamate. The material was purified by silica column chromatography eluting with 5% MeOH/DCM followed by prep HPLC (5-95% ACN/H$_2$O/ 0.1% TFA, over 20 minutes) to afford the title compound (16 mg, 38% yield) after extractive work-up (DCM/1N NaOH) as a white solid. MS (apci) m/z=554.2 (M+H).

Example 476

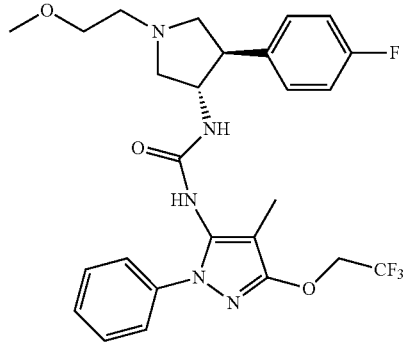 [SMILES: COCCN1C[C@@H](NC(=O)Nc2c(C)c(OCC(F)(F)F)nn2-c2ccccc2)[C@H](c2ccc(F)cc2)C1]

457

1-((3S,4R)-4-(4-fluorophenyl)-1-(2-methoxyethyl)pyrrolidin-3-yl)-3-(4-methyl-1-phenyl-3-(2,2,2-trifluoroethoxy)-1H-pyrazol-5-yl)urea Prepared according to the method of Example 475, replacing (3S,4R)-4-(3,4-difluorophenyl)-1-(2-methoxyethyl)pyrrolidin-3-amine (Preparation F) with (3S,4R)-4-(4-fluorophenyl)-1-(2-methoxyethyl)pyrrolidin-3-amine dihydrochloride (Preparation K). The material was purified by silica column chromatography eluting with 2% MeOH/DCM to afford the title compound (56 mg, 65% yield) as a white solid. MS (apci) m/z=536.2 (M+H).

Example 477

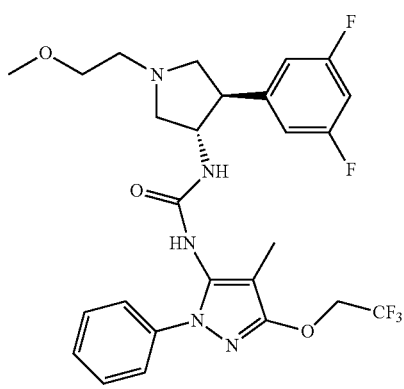 [SMILES: COCCN1C[C@@H](NC(=O)Nc2c(C)c(OCC(F)(F)F)nn2-c2ccccc2)[C@H](c2cc(F)cc(F)c2)C1]

1-((3S,4R)-4-(3,5-difluorophenyvl)-1-(2-methoxyethyl)pyrrolidin-3-yl)-3-(4-methyl-1-phenyl-3-(2,2,2-trifluoroethoxy)-1H-pyrazol-5-yl)urea Prepared according to the method of Example 475, replacing (3S,4R)-4-(3,4-difluorophenyl)-1-(2-methoxyethyl)pyrrolidin-3-amine (Preparation F) with (3S,4R)-4-(3,5-difluorophenyl)-1-(2-methoxyethyl)pyrrolidin-3-amine trifluoroacetate (Preparation E). The material was purified by silica column chromatography eluting with 2% MeOH/DCM to afford the title compound (53 mg, 63% yield) as a colorless glass. MS (apci) m/z=554.2 (M+H).

Example 478

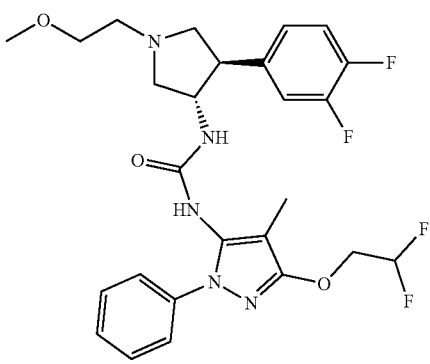 [SMILES: COCCN1C[C@@H](NC(=O)Nc2c(C)c(OCC(F)F)nn2-c2ccccc2)[C@H](c2ccc(F)c(F)c2)C1]

458

1-(3-(2,2-difluoroethoxy)-4-methyl-1-phenyl-1H-pyrazol-5-yl)-3-((3S,4R)-4-(3,4-difluorophenyl)-1-(2-methoxyethyl)pyrrolidin-3-yl)urea Prepared according to the method of Example 475, replacing 1,1,1-trifluoro-2-iodoethane with 1,1-difluoro-2-iodoethane in Step A. The material was purified by silica column chromatography eluting with 2% MeOH/DCM to afford the title compound (55 mg, 68% yield) as a white solid. (MS (apci) m/z=536.2 (M+H).

Example 479

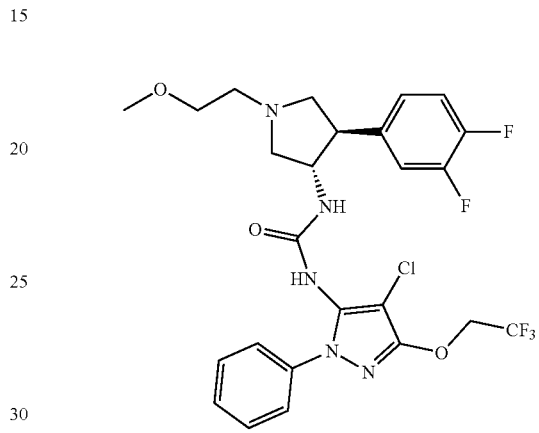

1-(4-chloro-1-phenyl-3-(2,2,2-trifluoroethoxy)-1H-pyrazol-5-yl)-3-((3S,4R)-4-(3,4-difluorophenyl)-1-(2-methoxyethyl)pyrrolidin-3-yl)urea Step A: Preparation of 1-((3S,4R)-4-(3,4-difluorophenyl)-1-(2-methoxyethyl) pyrrolidin-3-yl)-3-(1-phenyl-3-(2,2,2-trifluoroethoxy)-1H-pyrazol-5-yl)urea: Prepared according to the method of Example 475, replacing 5-amino-4-methyl-1-phenyl-1H-pyrazol-3(2H)-one (Intermediate P135, Step A) with 5-amino-1-phenyl-1H-pyrazol-3(2H)-one (Intermediate P136, Step A).

Step B: Preparation of 1-(4-chloro-1-phenyl-3-(2,2,2-trifluoroethoxy)-1H-pyrazol-5-yl)-3-((3S,4R)-4-(3,4-difluorophenyl)-1-(2-methoxyethyl)pyrrolidin-3-yl)urea: To a solution of 1-((3S,4R)-4-(3,4-difluorophenyl)-1-(2-methoxyethyl)pyrrolidin-3-yl)-3-(1-phenyl-3-(2,2,2-trifluoroethoxy)-1H-pyrazol-5-yl)urea (50 mg, 0.09 mmol) in DCM (1 mL) was added N-chlorosuccinimide (15 mg, 0.11 mmol) followed by pyridin-1-ium 4-methylbenzenesulfonate (2 mg, 0.009 mmol). The mixture was stirred at ambient temperature for 18 hours then treated with a further 5 mg of N-chlorosuccinimide and stirred for 2.5 hours. The mixture was partitioned between saturated NaHCO₃ (20 mL) and DCM (20 mL) and the aqueous layer was extracted with DCM (2×10 mL). The combined organic phases were washed with brine (10 mL), dried over Na₂SO₄ and concentrated in vacuo. The residue was purified by silica column chromatography eluting with 2.5% MeOH/DCM to afford the title compound (28 mg, 53% yield) as a pale yellow foam. MS (apci) m/z=574.2 (M+H).

Example 480

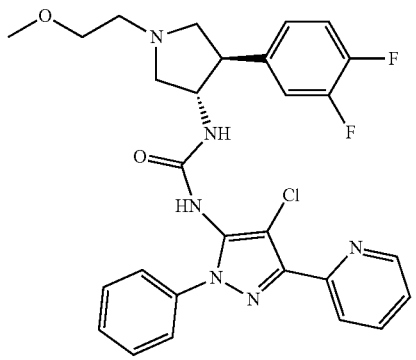 [SMILES: COCCN1C[C@@H](NC(=O)Nc2c(Cl)c(-c3ccccn3)nn2-c2ccccc2)[C@H](c2ccc(F)c(F)c2)C1]

1-(4-chloro-1-phenyl-3-(pyridin-2-yl)-1H-pyrazol-5-yl)-3-((3S,4R)-4-(3,4-difluorophenyl)-1-(2-methoxyethyl)pyrrolidin-3-yl)urea Step A: Preparation of 1-phenyl-3-(pyridin-2-yl)-1H-pyrazol-5-amine: Prepared according to the method of Example 473, Step A, replacing cyclohexylhydrazine hydrochloride with phenylhydrazine hydrochloride and 2-oxocyclopentanecarbonitrile with 3-oxo-3-(pyridin-2-yl)propanenitrile. MS (apci) m/z=237.1 (M+H).

Step B: Preparation of 4-chloro-1-phenyl-3-(pyridin-2-yl)-1H-pyrazol-5-amine: A solution of 1-phenyl-3-(pyridin-2-yl)-1H-pyrazol-5-amine (300 mg, 1.27 mmol) was dissolved in DCM (20 mL) and treated with N-chlorosuccinimide (187 mg, 1.40 mmol) followed by pyridin-1-ium 4-methylbenzenesulfonate (32 mg, 0.13 mmol). The solution was stirred at ambient temperature for 3 hours then partitioned between DCM (20 mL) and saturated NaHCO₃ (20 mL) and the aqueous layer extracted with DCM (2×20 mL). The combined organic phases were washed with brine (20 mL), dried over Na₂SO₄, filtered and concentrated in vacuo. The residue was purified by silica column chromatography eluting with 2:1 hexanes/EtOAc to afford 4-chloro-1-phenyl-3-(pyridin-2-yl)-1H-pyrazol-5-amine (211 mg, 61%) as a pink foam. MS (apci) m/z=271.0 (M+H).

Step C: Preparation of 1-(4-chloro-1-phenyl-3-(pyridin-2-yl)-1H-pyrazol-5-yl)-3-((3S,4R)-4-(3,4-difluorophenyl)-1-(2-methoxyethyl)pyrrolidin-3-yl)urea: To a solution of 4-chloro-1-phenyl-3-(pyridin-2-yl)-1H-pyrazol-5-amine (37 mg, 0.14 mmol) in DCM (2 mL) was added triphosgene (21 mg, 0.07 mmol) followed by DIEA (72 μL, 0.41 mmol). The mixture was stirred at ambient temperature for 1 hour then treated with (3S,4R)-4-(3,4-difluorophenyl)-1-(2-methoxyethyl)pyrrolidin-3-amine (Preparation F) (50 mg, 0.15 mmol) followed by DIEA (72 μL, 0.41 mmol). After stirring for a further 18 hours the mixture was partitioned between saturated NH₄Cl (20 mL) and DCM (20 mL) and the aqueous layer extracted with DCM (2×10 mL). The combined organic phases were washed with brine (20 mL), dried over Na₂SO₄, filtered and concentrated in vacuo. The residue was purified by silica column chromatography eluting with 2.5% MeOH/DCM followed by reverse phase HPLC purification (5-95% ACN/water/0.5% TFA over 20 minutes). The title compound (10 mg, 13% yield) was obtained after aqueous work-up (1N NaOH/DCM) as a white solid. MS (apci) m/z=553.2 (M+).

Example 481

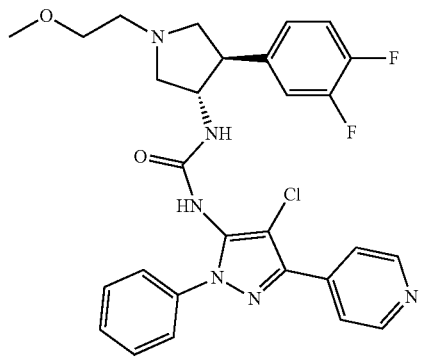 [SMILES: COCCN1C[C@@H](NC(=O)Nc2c(Cl)c(-c3ccncc3)nn2-c2ccccc2)[C@H](c2ccc(F)c(F)c2)C1]

1-(4-chloro-1-phenyl-3-(pyridin-4-yl)-1H-pyrazol-5-yl)-3-((3S,4R)-4-(3,4-difluorophenyl)-1-(2-methoxyethyl)pyrrolidin-3-yl)urea Prepared according to the method of Example 480 replacing 3-oxo-3-(pyridin-2-yl)propanenitrile with 3-oxo-3-(pyridin-4-yl)propanenitrile in Step A. The material was purified by silica column chromatography eluting with 2% MeOH/DCM followed by reverse phase HPLC purification (5-95% ACN/water/0.5% TFA over 20 minutes). The title compound (3 mg, 4% yield) was obtained after aqueous work-up (1N NaOH/DCM) as a white solid. MS (apci) m/z=553.2 (M+).

Example 482

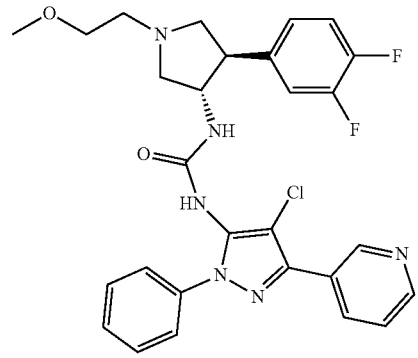

1-(4-chloro-1-phenyl-3-(pyridin-3-yl)-1H-pyrazol-5-yl)-3-((3S,4R)-4-(3,4-difluorophenyl)-1-(2-methoxyethyl)pyrrolidin-3-yl)urea Step A: Preparation of 1-phenyl-3-(pyridin-3-yl)-1H-pyrazol-5-amine: Prepared according to the method of Example 480, Step A, replacing 3-oxo-3-(pyridin-2-yl)propanenitrile with 3-oxo-3-(pyridin-3-yl)propanenitrile. MS (apci) m/z=237.1 (M+H).

Step B: Preparation of 1-((3S,4R)-4-(3,4-difluorophenyl)-1-(2-methoxyethyl) pyrrolidin-3-yl)-3-(1-phenyl-3-(pyridin-3-yl)-1H-pyrazol-5-yl)urea: To a solution of 1-phenyl-3-(pyridin-3-yl)-1H-pyrazol-5-amine (50 mg, 0.21 mmol)

and CDI (72 mg, 0.44 mmol) in DMF (2 mL) was added DIEA (147 μL, 0.85 mmol) and the mixture stirred at 50° C. for 4 hours. To the cooled mixture was added (3S,4R)-4-(3,4-difluorophenyl)-1-(2-methoxyethyl)pyrrolidin-3-amine (Preparation F) (146 mg, 0.44 mmol) and DIEA (147 μL, 0.85 mmol) and stirring was continued at ambient temperature for 18 hours. The mixture was partitioned between saturated NH₄Cl (20 mL) and EtOAc (20 mL) and the aqueous layer extracted with EtOAc (2×10 mL). The combined organic phases were washed with water (5×10 mL) and brine (10 mL) then dried over Na₂SO₄, filtered and concentrated in vacuo. The residue was purified by silica column chromatography eluting with 5% MeOH/DCM to afford 1-((3S,4R)-4-(3,4-difluorophenyl)-1-(2-methoxyethyl)pyrrolidin-3-yl)-3-(1-phenyl-3-(pyridin-3-yl)-1H-pyrazol-5-yl)urea (80 mg, 73%) as a white solid. MS (apci) m/z=519.3 (M+H).

Step C: Preparation of 1-(4-chloro-1-phenyl-3-(pyridin-3-yl)-1H-pyrazol-5-yl)-3-((3S,4R)-4-(3,4-difluorophenyl)-1-(2-methoxyethyl)pyrrolidin-3-yl)urea: To a solution of 1-((3S,4R)-4-(3,4-difluorophenyl)-1-(2-methoxyethyl)pyrrolidin-3-yl)-3-(1-phenyl-3-(pyridin-3-yl)-1H-pyrazol-5-yl)urea (40 mg, 0.08 mmol) in DCM (1 mL) was added N-chlorosuccinimide (12 mg, 0.09 mmol) followed by pyridin-1-ium 4-methylbenzenesulfonate (2 mg, 0.008 mmol). The mixture was stirred at ambient temperature for 18 hours then partitioned between saturated NaHCO₃ (20 mL) and DCM (20 mL) and the aqueous layer extracted with DCM (2×10 mL). The combined organic phases were washed with brine (10 mL), dried over Na₂SO₄, filtered and concentrated in vacuo. The residue was purified by silica column chromatography eluting with 2.5-5% MeOH/DCM to afford the title compound (16 mg, 38% yield) as a pale yellow solid. MS (apci) m/z=553.2 (M+).

Example 483

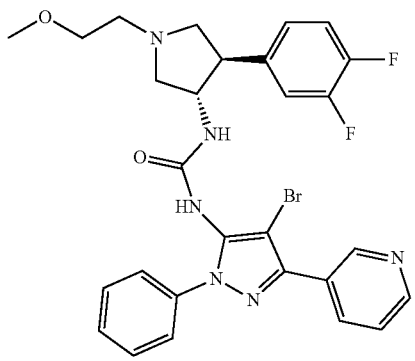 [SMILES: COCCN1C[C@@H](NC(=O)Nc2c(Br)c(-c3cccnc3)nn2-c2ccccc2)[C@H](c2ccc(F)c(F)c2)C1]

1-(4-bromo-1-phenyl-3-(pyridin-3-yl)-1H-pyrazol-5-yl)-3-((3 S,4R)-4-(3,4-difluorophenyl)-1-(2-methoxyethyl)pyrrolidin-3-yl)urea Prepared according to the method of Example 482, replacing N-chlorosuccinimide with N-bromosuccinimide in Step C. The material was purified by silica column chromatography eluting with 3% MeOH/DCM to afford the title compound (31 mg, 67% yield) as a yellow solid. MS (apci) m/z=597.2 (M+H).

Example 484

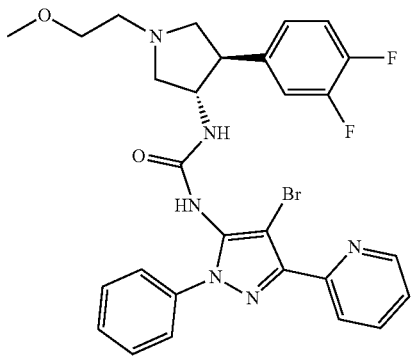 [SMILES: COCCN1C[C@@H](NC(=O)Nc2c(Br)c(-c3ccccn3)nn2-c2ccccc2)[C@H](c2ccc(F)c(F)c2)C1]

1-(4-bromo-1-phenyl-3-(pyridin-2-yl)-1H-pyrazol-5-yl)-3-((3S,4R)-4-(3,4-difluorophenyl)-1-(2-methoxyethyl)pyrrolidin-3-yl)urea Step A: Preparation of 1-((3S,4R)-4-(3,4-difluorophenyl)-1-(2-methoxyethyl) pyrrolidin-3-yl)-3-(1-phenyl-3-(pyridin-2-yl)-1H-pyrazol-5-yl)urea: Prepared according to the method of Example 480, replacing 4-chloro-1-phenyl-3-(pyridin-2-yl)-1H-pyrazol-5-amine with 1-phenyl-3-(pyridin-2-yl)-1H-pyrazol-5-amine in Step C. MS (apci) m/z=519.2 (M+H).

Step B: Preparation of 1-(4-bromo-1-phenyl-3-(pyridin-2-yl)-1H-pyrazol-5-yl)-3-((3S,4R)-4-(3,4-difluorophenyl)-1-(2-methoxyethyl)pyrrolidin-3-yl)urea: Prepared according to the method of Example 483, replacing 1-((3S,4R)-4-(3,4-difluorophenyl)-1-(2-methoxy ethyl)pyrrolidin-3-yl)-3-(1-phenyl-3-(pyridin-3-yl)-1H-pyrazol-5-yl)urea with 1-((3S,4R)-4-(3,4-difluorophenyl)-1-(2-methoxyethyl)pyrrolidin-3-yl)-3-(1-phenyl-3-(pyridin-2-yl)-1H-pyrazol-5-yl)urea in Step C. Material was purified by silica column chromatography eluting with 2.5-5% MeOH/DCM to afford the title compound (14 mg, 40% yield) as a colorless glass. MS (apci) m/z=597.2 (M+).

Example 485

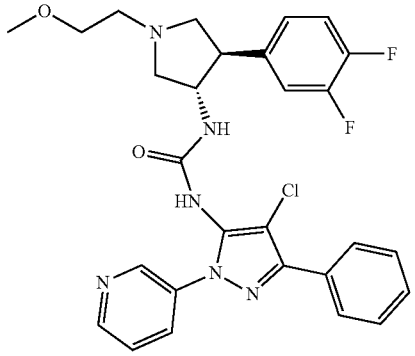 [SMILES: COCCN1C[C@@H](NC(=O)Nc2c(Cl)c(-c3ccccc3)nn2-c2cccnc2)[C@H](c2ccc(F)c(F)c2)C1]

1-(4-chloro-3-phenyl-1-(pyridin-3-yl)-1H-pyrazol-5-yl)-3-((3S,4R)-4-(3,4-difluorophenyl)-1-(2-methoxyethyl)pyrrolidin-3-yl)urea Prepared according to the procedure of Example 482, replacing 3-oxo-3-(pyridin-3-yl)propanenitrile with 3-oxo- 3-phenylpropanenitrile and phenylhydrazine hydrochloride with 3-hydrazinylpyridine hydrochloride in Step A. Material was purified by silica column chromatography eluting with 2.5% MeOH/DCM to afford the title compound (22 mg, 49% yield) as a beige solid. MS (apci) m/z=553.2 (M+).

Example 486

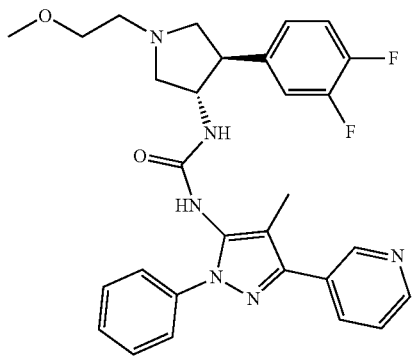 [SMILES: COCCN1C[C@@H](NC(=O)Nc2c(C)c(-c3cccnc3)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-1-phenyl-3-(pyridin-3-yl)-1H-pyrazol-5-yl)urea Step A: Preparation of 2-methyl-3-oxo-3-(pyridin-3-yl)propanenitrile: A solution of LiHMDS (13.6 mL, 1.0M/THF, 13.6 mmol) was cooled to −78° C. under N₂ atmosphere and treated dropwise with propionitrile (991 μL, 13.9 mmol). The resulting yellow slurry was stirred at this temperature for 2 hours then treated dropwise with a solution of ethyl nicotinate (1.0 g, 6.62 mmol) in THF (5 mL) over 10 minutes. The mixture was allowed to warm slowly to ambient temperature over 18 hours then poured into ice-cold water (100 mL) and extracted with Et₂O (2×30 mL). The aqueous phase was cooled in ice, acidified to pH 5 with 1N HCl and extracted with DCM (3×30 mL). The combined DCM extracts were washed with brine (30 mL), dried over Na₂SO₄, filtered and concentrated to afford 2-methyl-3-oxo-3-(pyridin-3-yl)propanenitrile (1.06 g, 100% yield) as a yellow oil. MS (apci) m/z=161.1 (M+H).

Step B: Preparation of 4-methyl-1-phenyl-3-(pyridin-3-yl)-1H-pyrazol-5-amine: A suspension of 2-methyl-3-oxo-3-(pyridin-3-yl)propanenitrile (1.06 g, 6.62 mmol) and phenylhydrazine hydrochloride (1.05 g, 7.28 mmol) in EtOH (30 mL) was stirred at reflux for 18 hours then cooled to ambient temperature. The mixture was concentrated then treated with saturated NaHCO₃ (50 mL) and extracted with DCM (3×30 mL). The combined organic phases were washed with brine (30 mL), dried over Na₂SO₄, filtered and concentrated in vacuo. The residue was purified by silica column chromatography eluting with 1:1 to 1:2 hexanes/EtOAc, to afford 4-methyl-1-phenyl-3-(pyridin-3-yl)-1H-pyrazol-5-amine (984 mg, 59% yield) as a pale yellow foam. MS (apci) m/z=251.1 (M+H).

Step C: Preparation of 1-((3S,4R)-4-(3,4-difluorophenyl)-1-(2-methoxyethyl) pyrrolidin-3-yl)-3-(4-methyl-1-phenyl-3-(pyridin-3-yl)-1H-pyrazol-5-yl)urea: To a solution of 4-methyl-1-phenyl-3-(pyridin-3-yl)-1H-pyrazol-5-amine (100 mg, 0.40 mmol) in DCM (2 mL) was added triphosgene (59 mg, 0.20 mmol) followed by DIEA (209 uLμL 1.20 mmol). The mixture was stirred for 1 hour at ambient temperature then treated with (3S,4R)-4-(3,4-difluorophenyl)-1-(2-methoxyethyl)pyrrolidin-3-amine (Preparation F; 145 mg, 0.44 mmol) and DIEA (209 μL, 1.20 mmol). After stirring at ambient temperature for 18 hours, the mixture was partitioned between saturated NH₄Cl (20 mL) and DCM (20 mL) and the aqueous layer extracted with DCM (2×10 mL). The combined organic phases were washed with brine (10 mL), dried over Na₂SO₄, filtered and concentrated in vacuo. The residue was purified by silica column chromatography eluting with 3-4% MeOH/DCM to afford the title compound (99 mg, 47% yield) as a white solid. MS (apci) m/z=533.2 (M+H).

The following compounds were made according to Example 486, replacing ethyl nicotinate with the appropriate reagent in Step A, and for Example 490 also replacing phenylhydrazine hydrochloride with 3-hydrazinylpyridine hydrochloride in Step B.

| Ex. # | Structure | Name | MS (apci) m/z |
|---|---|---|---|
| 487 | 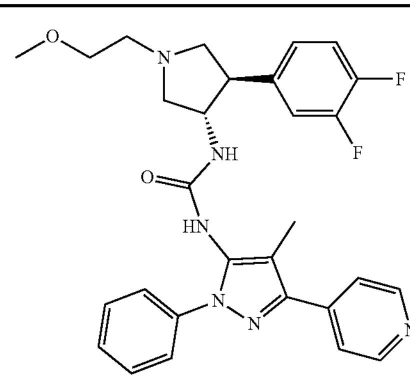 | 1-((3S,4R)-4-(3,4-difluorophenyl)-1-(2-methoxyethyl)pyrrolidin-3-yl)-3-(4-methyl-1-phenyl-3-(pyridin-4-yl)-1H-pyrazol-5-yl)urea | 533.2 (M + H) |

-continued

| Ex. # | Structure | Name | MS (apci) m/z |
|---|---|---|---|
| 488 | 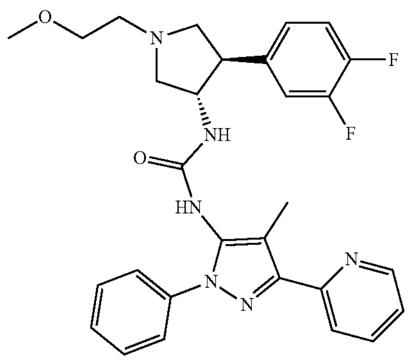 [SMILES: COCCN1C[C@@H](NC(=O)Nc2c(C)c(-c3ccccn3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-1-phenyl-3-(pyridin-2-yl)-1H-pyrazol-5-yl)urea | 533.2 (M + H) |
| 489 | 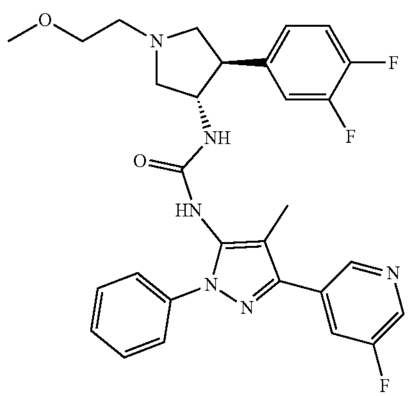 [SMILES: COCCN1C[C@@H](NC(=O)Nc2c(C)c(-c3cncc(F)c3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(5-fluoropyridin-3-yl)-4-methyl-1-phenyl-1H-pyrazol-5-yl)urea | 551.2 (M + H) |
| 490 | 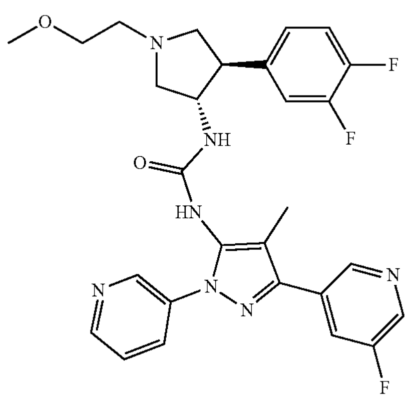 [SMILES: COCCN1C[C@@H](NC(=O)Nc2c(C)c(-c3cncc(F)c3)nn2-c2cccnc2)[C@H](c2ccc(F)c(F)c2)C1] | 1-((3S,4R)-4-(3,4-difluorophenyl)-1-(2-methoxyethyl)pyrrolidin-3-yl)-3-(3-(5-fluoropyridin-3-yl)-4-methyl-1-(pyridin-3-yl)-1H-pyrazol-5-yl)urea | 552.2 (M + H) |
| 491 | 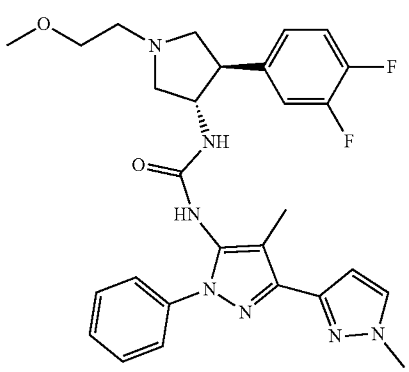 | 1-((3S,4R)-4-(3,4-difluorophenyl)-1-(2-methoxyethyl)pyrrolidin-3-yl)-3-(1',4-dimethyl-1-phenyl-1H,1'H-[3,3'-bipyrazol]-5-yl)urea | 536.2 (M + H) |

Example 492

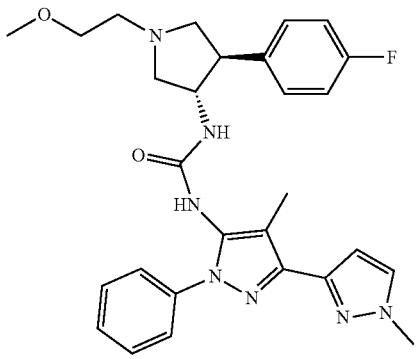

1-(1',4-dimethyl-1-phenyl-1H, 1'H-[3,3'-bipyrazol]-5-yl)-3-((3S,4R)-4-(4-fluorophenyl)-1-(2-methoxyethyl)pyrrolidin-3-yl)urea Prepared according to the procedure of Example 491, replacing (3S,4R)-4-(3,4-difluorophenyl)-1-(2-methoxyethyl)pyrrolidin-3-amine (Preparation F) with (3S,4R)-4-(4-fluorophenyl)-1-(2-methoxyethyl)pyrrolidin-3-amine dihydrochloride (Preparation K) in Step C. Material was purified by silica column chromatography eluting with 3% MeOH/DCM to afford the title compound (52 mg, 51% yield) as a pale yellow foam. MS (apci) m/z=518.2 (M+H).

Example 493

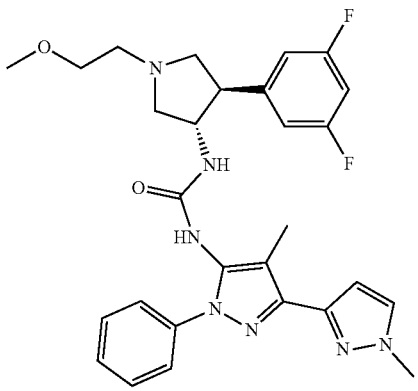

1-((3S,4R)-4-(3,5-difluorophenyvl)-1-(2-methoxyethyl)pyrrolidin-3-yl)-3-(1',4-dimethyl-1-phenyl-1H, 1'H-[3,3'-bipyrazol]-5-yl)urea Prepared according to the procedure of Example 491, replacing (3S,4R)-4-(3,4-difluorophenyl)-1-(2-methoxyethyl)pyrrolidin-3-amine (Preparation F) with (3S,4R)-4-(3,5-difluorophenyl)-1-(2-methoxyethyl)pyrrolidin-3-amine trifluoroacetate (Preparation E) in Step C. Material was purified by silica column chromatography eluting with 3% MeOH/DCM to afford the title compound (33 mg, 31% yield) as a white solid. MS (apci) m/z=536.2 (M+H).

Example 494

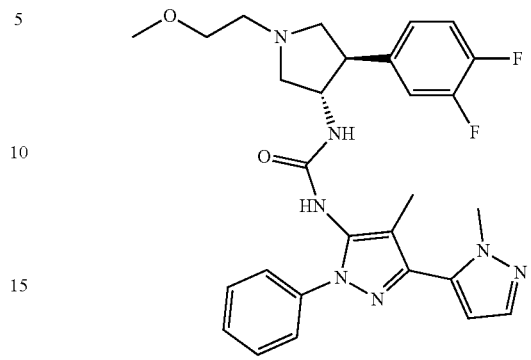

1-((3S,4R)-4-(3,4-difluorophenyl)-1-(2-methoxyethyl)pyrrolidin-3-yl)-3-(2',4-dimethyl-1-phenyl-1H, 2'H-[3,3'-bipyrazol]-5-yl)urea Step A: Preparation of 2',4-dimethyl-1-phenyl-1H,2'H-[3,3'-bipyrazol]-5-amine: Prepared according to the method of Example 486, Step A, replacing ethyl nicotinate with ethyl 1-methyl-1H-pyrazole-5-carboxylate. $^1$H NMR (CDCl$_3$) δ 7.55 (d, J=2.2 Hz, 1H), 7.01 (d, J=2.2 Hz, 1H), 4.19 (s, 3H), 4.12 (q, J=7.2 Hz, 1H), 1.65 (d, J=7.2 Hz, 3H) ppm.

Step B: Preparation of phenyl (2',4-dimethyl-1-phenyl-1H,2'H-[3,3'-bipyrazol]-5-yl)carbamate: To a solution of 2',4-dimethyl-1-phenyl-1H,2'H-[3,3'-bipyrazol]-5-amine (100 mg, 0.39 mmol) in EtOAc (2 mL) was added 2N NaOH (395 µL, 0.79 mmol) followed by phenyl chloroformate (75 µL, 0.59 mmol). The mixture was stirred at ambient temperature for 4 hours then treated with a further aliquot of phenyl chloroformate (50 µL) and stirred for 18 hours. The mixture was partitioned between water (20 mL) and EtOAc (10 mL) and the aqueous layer extracted with EtOAc (2×10 mL). The combined organic phases were washed with saturated NaHCO$_3$ (10 mL) and brine (10 mL) then dried over Na$_2$SO$_4$, filtered and concentrated in vacuo to afford phenyl (2',4-dimethyl-1-phenyl-1H,2'H-[3,3'-bipyrazol]-5-yl)carbamate (140 mg, 95% yield) as a pale yellow gum. MS (apci) m/z=374.2 (M+H).

Step C: Preparation of 1-((3S,4R)-4-(3,4-difluorophenyl)-1-(2-methoxyethyl)pyrrolidin-3-yl)-3-(2',4-dimethyl-1-phenyl-1H,2'H-[3,3'-bipyrazol]-5-yl)urea: To a solution of (3S,4R)-4-(3,4-difluorophenyl)-1-(2-methoxyethyl)pyrrolidin-3-amine (Preparation F; 68 mg, 0.21 mmol) and phenyl (2',4-dimethyl-1-phenyl-1H,2'H-[3,3'-bipyrazol]-5-yl)carbamate (70 mg, 0.19 mmol) in DCM (2 mL) was added DIEA (114 µL, 0.66 mmol). After stirring at ambient temperature for 3 hours the mixture was partitioned between saturated NH$_4$Cl (20 mL) and DCM (20 mL) and the aqueous layer extracted with DCM (2×10 mL). The combined organic phases were washed with brine (10 mL) then dried over Na$_2$SO$_4$, filtered and concentrated in vacuo. The residue was purified by silica column chromatography eluting with 1-3% MeOH/DCM to afford the title compound (68 mg, 68% yield) as a white solid. MS (apci) m/z=536.2 (M+H).

Example 495

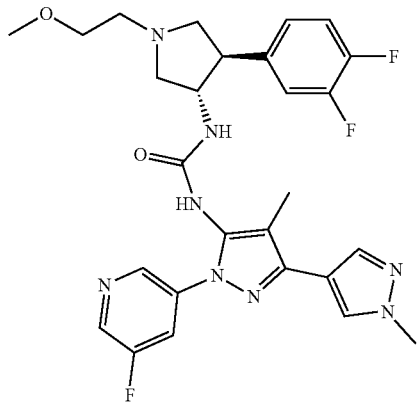

1-((3S,4R)-4-(3,4-difluorophenyl)-1-(2-methoxy-ethyl)pyrrolidin-3-yl)-3-(1-(5-fluoropyridin-3-yl)-1',4-dimethyl-1H, 1'H-[3,4'-bipyrazol]-5-yl)urea Step A: Preparation of 3-(2-(diphenylmethylene)hydrazinyl)-5-fluoropyridine: A solution of 3-bromo-5-fluoropyridine (5.0 g, 28.4 mmol), benzophenonehydrazone (6.13 g, 31.3 mmol) and Xantphos (164 mg, 0.28 mmol) was degassed with $N_2$ for 10 minutes then treated with sodium t-butoxide (3.82 g, 39.8 mmol) and palladium (II) acetate (64 mg, 0.28 mmol). The heterogeneous mixture was stirred at 85° C. in a sealed vessel for 18 hours. The cooled mixture was partitioned between water (100 mL) and EtOAc (100 mL) and the aqueous layer extracted with EtOAc (2×50 mL). The combined organic phases were washed with brine (50 mL), dried over $Na_2SO_4$, filtered and concentrated in vacuo. The residue was triturated with $Et_2O$, filtered and dried in vacuo to afford 3-(2-(diphenylmethylene)hydrazinyl)-5-fluoropyridine (6.3 g, 72% yield) as a beige powder. MS (apci) m/z=292.1 (M+H).

Step B: Preparation of 1-(5-fluoropyridin-3-yl)-1',4-dimethyl-1H, 1'H-[3,4'-bipyrazol]-5-amine: A solution of 2-methyl-3-(1-methyl-1H-pyrazol-4-yl)-3-oxopropanenitrile (Example 491, Step A; 100 mg, 0.61 mmol), 3-(2-(diphenylmethylene)hydrazinyl)-5-fluoropyridine (162 mg, 0.56 mmol) and p-toluenesulfonic acid monohydrate (530 mg, 2.79 mmol) in EtOH (3 mL) was stirred at 80° C. in a sealed vial for 18 hours. The cooled mixture was treated with saturated $NaHCO_3$ (30 mL) and extracted with DCM (3×10 mL). The combined organic phases were washed with brine (10 mL), dried over $Na_2SO_4$, filtered and concentrated in vacuo. The residue was purified by silica column chromatography eluting with 1-3% MeOH/DCM to afford 1-(5-fluoropyridin-3-yl)-1',4-dimethyl-1H,1'H-[3,4'-bipyrazol]-5-amine (71 mg, 47%) as a pale yellow solid. MS (apci) m/z=273.1 (M+H).

Step C: Preparation of 1-((3S,4R)-4-(3,4-difluorophenyl)-1-(2-methoxyethyl)pyrrolidin-3-yl)-3-(1-(5-fluoropyridin-3-yl)-1',4-dimethyl-1H, 1'H-[3,4'-bipyrazol]-5-yl)urea: To a solution of 1-(5-fluoropyridin-3-yl)-1',4-dimethyl-1H,1'H-[3,4'-bipyrazol]-5-amine (35 mg, 0.13 mmol) in DCM (2 mL) was added triphosgene (19 mg, 0.06 mmol) followed by DIEA (67 µL, 0.39 mmol). The mixture was stirred for 1 hour at ambient temperature then treated with (3S,4R)-4-(3,4-difluorophenyl)-1-(2-methoxyethyl)pyrrolidin-3-amine (Preparation F; 42 mg, 0.13 mmol) and DIEA (67 µL, 0.39 mmol) and stirring continued for 18 hours. The mixture was partitioned between saturated $NH_4Cl$ (20 mL) and DCM (20 mL) and the aqueous layer extracted with DCM (2×10 mL). The combined organic phases were washed with brine (10 mL), dried over $Na_2SO_4$, filtered and concentrated in vacuo. The residue was purified by silica column chromatography eluting with 2.5-4% MeOH/DCM to afford the title compound (33 mg, 46%) as a white solid. MS (apci) m/z=555.2 (M+H).

Example 496

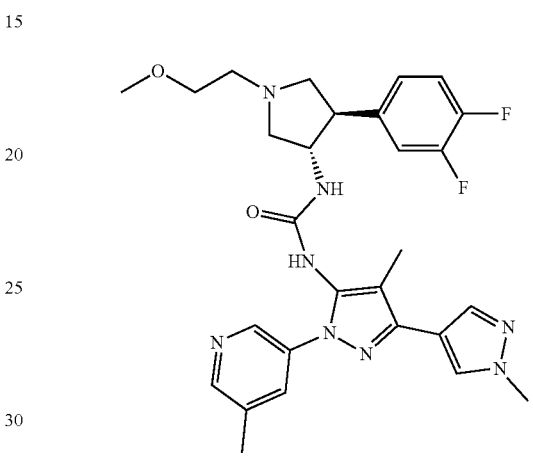

1-((3S,4R)-4-(3,4-difluorophenyvl)-1-(2-methoxy-ethyl)pyrrolidin-3-yl)-3-(1',4-dimethyl-1-(5-methyl-pyridin-3-yl)-1H, 1'H-[3,4'-bipyrazol]-5-yl)urea Prepared according to the procedure of Example 495, replacing 3-bromo-5-fluoropyridine with 3-bromo-5-methylpyridine in Step A. Material was purified by silica column chromatography eluting with 5-10% MeOH/DCM to afford the title compound (41 mg, 56% yield) as a cream solid. MS (apci) m/z=551.2 (M+H).

Example 497

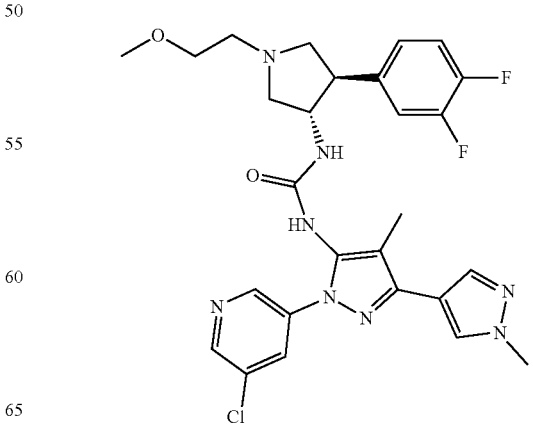

1-(1-(5-chloropyridin-3-yl)-1',4-dimethyl-1H, 1'H-[3,4'-bipyrazol]-5-yl)-3-((3 S,4R)-4-(3,4-difluorophenyl)-1-(2-methoxyethyl)pyrrolidin-3-yl)urea Prepared according to the procedure of Example 495, replacing 3-bromo-5-fluoropyridine with 3-bromo-5-chloropyridine in Step A. Material was purified by silica column chromatography eluting with 2-5% MeOH/DCM to afford the title compound (85 mg, 86% yield) as a pale pink solid. MS (apci) m/z=571.2 (M+).

Example 498

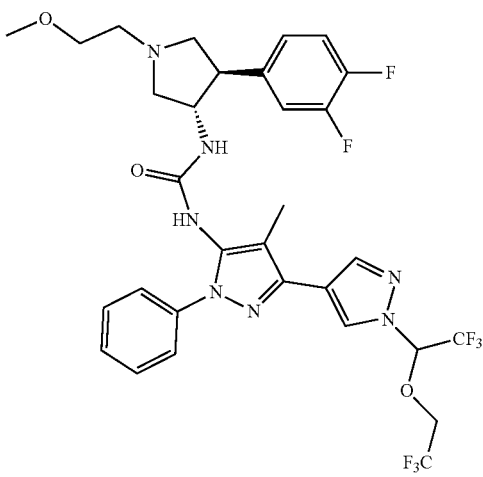 [SMILES: COCCN1C[C@@H](NC(=O)Nc2c(C)c(-c3cnn(C(OCC(F)(F)F)C(F)(F)F)c3)nn2-c2ccccc2)[C@H](c2ccc(F)c(F)c2)C1]

1-((3S,4R)-4-(3,4-difluorophenyvl)-1-(2-methoxyethyl)pyrrolidin-3-yl)-3-(4-methyl-1-phenyl-1'-(2,2,2-trifluoro-1-(2,2,2-trifluoroethoxy)ethyl)-1H,1'H-[3,4'-bipyrazol]-5-yl)urea Step A: Preparation of ethyl 1-(4-methoxybenzyl)-1H-pyrazole-4-carboxylate: To a mixture of ethyl 1H-pyrazole-4-carboxylate (3 g, 21.4 mmol) and K$_2$CO$_3$ (3.55 g, 25.7 mmol) in DMF (10 mL) was added 1-(chloromethyl)-4-methoxybenzene (3.50 mL, 25.7 mmol). The reaction was stirred at ambient temperature for 18 hours then ether (30 mL) and water (10 mL) were added. The organic layer was separated, washed with brine, dried over Na$_2$SO$_4$ and concentrated in vacuo. The residue was purified by silica column chromatography eluting with 3:1 hexanes/EtOAc to afford ethyl 1-(4-methoxybenzyl)-1H-pyrazole-4-carboxylate (5.7 g, 102%) as a colorless oil. $^1$H NMR (CDCl$_3$) δ 7.92 (m, 1H), 7.80 (m, 1H), 7.21 (m, 2H), 6.89 (m, 2H), 5.23 (s, 2H), 4.27 (m, 2H), 3.80 (s, 3H), 1.32 (m, 3H) ppm.

Step B: Preparation of 1-((3S,4R)-4-(3,4-difluorophenyl)-1-(2-methoxyethyl) pyrrolidin-3-yl)-3-(1'-(4-methoxybenzyl)-4-methyl-1-phenyl-1H,1'H-[3,4'-bipyrazol]-5-yl)urea: Prepared according to the procedure of Example 494, replacing ethyl 1-methyl-1H-pyrazole-5-carboxylate with ethyl 1-(4-methoxybenzyl)-1H-pyrazole-4-carboxylate in Step A. Material was purified by silica column chromatography eluting with 1:1 to 1:1.2 hexanes/acetone plus 0.5% NH$_4$OH to afford 1-((3S,4R)-4-(3,4-difluorophenyl)-1-(2-methoxyethyl)pyrrolidin-3-yl)-3-(1'-(4-methoxybenzyl)-4-methyl-1-phenyl-1H, 1'H-[3,4'-bipyrazol]-5-yl)urea (800 mg, 60% yield) as a white solid. MS (apci) m/z=642.3 (M+H).

Step C: Preparation of 1-((3S,4R)-4-(3,4-difluorophenyl)-1-(2-methoxyethyl) pyrrolidin-3-yl)-3-(4-methyl-1-phenyl-1H, 1'H-[3,4'-bipyrazol]-5-yl)urea: 1-((3S,4R)-4-(3,4-difluoro phenyl)-1-(2-methoxyethyl)pyrrolidin-3-yl)-3-(1'-(4-methoxybenzyl)-4-methyl-1-phenyl-1H,1'H-[3,4'-bipyrazol]-5-yl)urea (241 mg, 0.38 mmol) was combined with TFA (2 mL) in a sealed tube and stirred at 70° C. for 18 hours. The cooled mixture was concentrated in vacuo and the residue partitioned between 1N NaOH (20 mL) and DCM (10 mL). The aqueous layer was extracted with DCM (2×10 mL) and the combined organic phases were washed with saturated NaHCO$_3$ (10 mL) and brine (10 mL) then dried over Na$_2$SO$_4$, filtered and concentrated in vacuo. The residue was purified by silica column chromatography eluting with 2-5% MeOH/DCM to afford 1-((3S,4R)-4-(3,4-difluorophenyl)-1-(2-methoxyethyl) pyrrolidin-3-yl)-3-(4-methyl-1-phenyl-1H, 1'H-[3,4'-bipyrazol]-5-yl)urea (144 mg, 74% yield) as a white solid. MS (apci) m/z=522.2 (M+).

Step D: Preparation of 1-((3S,4R)-4-(3,4-difluorophenyl)-1-(2-methoxyethyl) pyrrolidin-3-yl)-3-(4-methyl-1-phenyl-1'-(2,2,2-trifluoro-1-(2,2,2-trifluoro-ethoxv)ethyl)-1H, 1'H-[3,4'-bipyrazol]-5-yl)urea: To a solution of 1-((3S, 4R)-4-(3,4-difluorophenyl)-1-(2-methoxyethyl)pyrrolidin-3-yl)-3-(4-methyl-1-phenyl-1H,1'H-[3,4'-bipyrazol]-5-yl) urea (50 mg, 0.10 mmol) in DMF (2.5 mL) at −78° C. was added potassium t-butoxide (264 μL, 1M/THF, 0.264 mmol). The mixture was stirred for 10 minutes then treated with 2,2,2-trifluoroethyl trifluoromethanesulfonate (13.1 μL, 0.09 mmol). After stirring at ambient temperature for 2 hours the mixture was partitioned between saturated NH$_4$Cl (20 mL) and EtOAc (10 mL) and the aqueous layer extracted with EtOAc (2×10 mL). The combined organic phases were washed with water (2×10 mL) and brine (10 mL) then dried over Na$_2$SO$_4$, filtered and concentrated in vacuo. The residue was purified by silica column chromatography eluting with 2.5% MeOH/DCM to afford the title compound (29 mg, 43% yield) as a colorless glass. MS (apci) m/z=702.2 (M+H).

Example 499

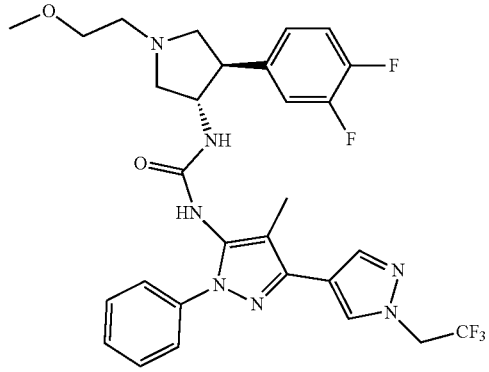 [SMILES: COCCN1C[C@@H](NC(=O)Nc2c(C)c(-c3cnn(CC(F)(F)F)c3)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-1-phenyl-1'-(2,2,2-trifluoroethyl)-1H, 1'H-[3,4'-bipyrazol]-5-yl)urea To a solution of 1-((3S,4R)-4-(3,4-difluorophenyl)-1-(2-methoxyethyl)pyrrolidin-3-yl)-3-(4-methyl-1-phenyl-1H, 1'H-[3,4'-bipyrazol]-5-yl)urea (Example 498, Step C; 20 mg, 0.04 mmol) in DMF (0.5 mL) was added K$_2$CO$_3$ (16 mg, 0.12 mmol) followed by trifluoroethyl triflate (6 μL, 0.04 mmol). The mixture was sealed and stirred at ambient temperature for 5 hours. A further aliquot of trifluoroethyl triflate (30 μL) was added and stirring was continued for 18 hours. The mixture was partitioned between water (10 mL) and EtOAc (10 mL) and the aqueous layer extracted with EtOAc (2×10 mL). The combined organic phases were washed with water (4×10 mL) and brine (10 mL) then dried over Na₂SO₄, filtered and concentrated in vacuo. The residue was purified by silica column chromatography eluting with 2-5% MeOH/DCM to afford the title compound (8 mg, 35% yield) as a colorless glass. MS (apci) m/z=604.2 (M+H).

Example 500

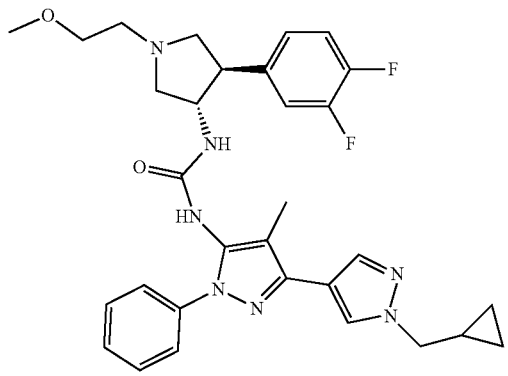 [SMILES: COCCN1C[C@@H](NC(=O)Nc2c(C)c(-c3cnn(CC4CC4)c3)nn2-c2ccccc2)[C@H](c2ccc(F)c(F)c2)C1]

1-(1'-(cyclopropylmethyl)-4-methyl-1-phenyl-1H, 1'H-[3,4'-bipyrazol]-5-yl)-3-((3S,4R)-4-(3,4-difluorophenyl)-1-(2-methoxyethyl)pyrrolidin-3-yl)urea Prepared according to the procedure of Example 499, replacing trifluoroethyl triflate with (bromomethyl)cyclopropane. Material was purified by silica column chromatography eluting with 2.5-5% MeOH/DCM to afford the title compound (16 mg, 31% yield) as a white solid. MS (apci) m/z=576.3 (M+H).

Example 501

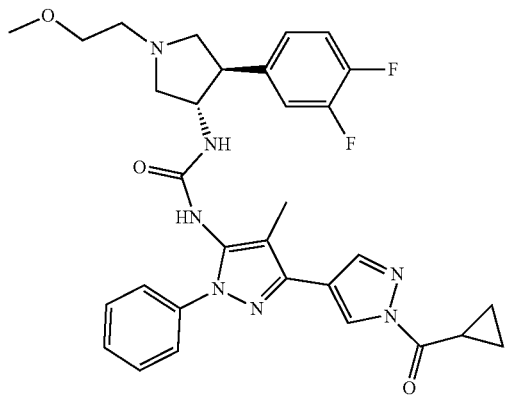 [SMILES: COCCN1C[C@@H](NC(=O)Nc2c(C)c(-c3cnn(C(=O)C4CC4)c3)nn2-c2ccccc2)[C@H](c2ccc(F)c(F)c2)C1]

1-(1'-(cyclopropanecarbonyl)-4-methyl-1-phenyl-1H,1'H-[3,4'-bipyrazol]-5-yl)-3-((3S,4R)-4-(3,4-difluorophenyl)-1-(2-methoxyethyl)pyrrolidin-3-yl)urea To a solution of 1-((3S,4R)-4-(3,4-difluorophenyl)-1-(2-methoxyethyl)pyrrolidin-3-yl)-3-(4-methyl-1-phenyl-1H, 1'H-[3,4'-bipyrazol]-5-yl)urea (Example 498, Step C; 50 mg, 0.09 mmol) in DCM (2 mL) at 0° C. was added cyclopropylcarbonyl chloride (13 µL, 0.14 mmol) followed by DIEA (67 µL, 0.38 mmol). The mixture was allowed to warm slowly to ambient temperature over 18 hours then partitioned between saturated NaHCO₃ (20 mL) and DCM (10 mL) and the aqueous layer extracted with DCM (2×10 mL). The combined organic phases were washed with brine (10 mL), dried over Na₂SO₄, filtered and concentrated in vacuo. The residue was purified by silica column chromatography eluting with 2.5% MeOH/DCM to afford the title compound (26 mg, 46% yield) as a white solid. MS (apci) m/z=590.2 (M+H).

Example 502

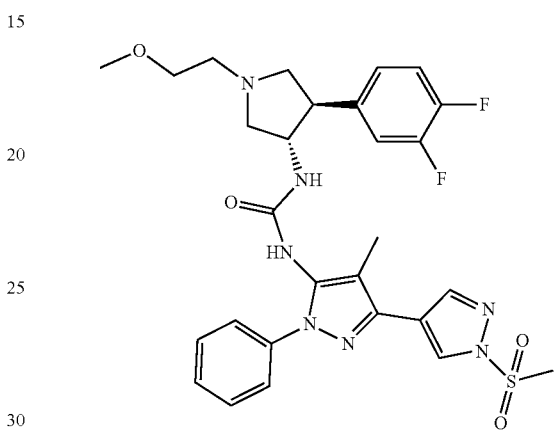

1-((3S,4R)-4-(3,4-difluorophenyl)-1-(2-methoxyethyl)pyrrolidin-3-yl)-3-(4-methyl-1'-(methylsulfonyl)-1-phenyl-1H, 1'H-[3,4'-bipyrazol]-5-yl)urea Prepared according to the procedure of Example 501, replacing cyclopropyl carbonyl chloride with mesyl chloride. Material was purified by silica column chromatography eluting with 2-5% MeOH/DCM to afford the title compound (39 mg, 68% yield) as a colorless glass. MS (apci) m/z=600.2 (M+H).

Example 503

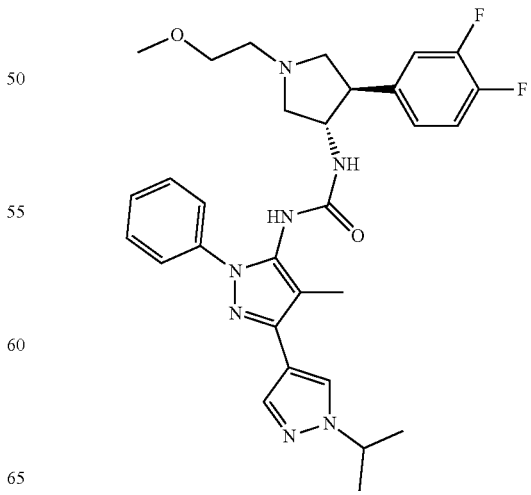

1-((3S,4R)-4-(3,4-difluorophenyvl)-1-(2-methoxy-ethyl)pyrrolidin-3-yl)-3-(1'-isopropyl-4-methyl-1-phenyl-1H, 1'H-[3,4'-bipyrazol]-5-yl)urea Step A: Preparation of 3-bromo-4-methyl-1H-pyrazol-5-amine: To a suspension of 5-amino-4-methyl-1-phenyl-1H-pyrazol-3(2H)-one (Intermediate P135, Step A; 1.60 g, 8.46 mmol) in acetonitrile (30 mL) was added phosphorus oxybromide (3.64 g, 12.7 mmol) in one portion. The mixture was stirred at reflux for 3 hours then cooled and concentrated in vacuo. The residue was treated with DCM (50 mL) then saturated NaHCO$_3$ (50 mL) was slowly added. The mixture was stirred for 30 minutes then the layers separated and the aqueous layer extracted with DCM (2×50 mL). The combined organic phases were washed with brine (20 mL), dried over Na$_2$SO$_4$, filtered and concentrated in vacuo. The residue was purified by silica column chromatography eluting with 2:1 hexanes/EtOAc, to afford 3-bromo-4-methyl-1-phenyl-1H-pyrazol-5-amine (273 mg, 13% yield) as a white solid. MS (apci) m/z=254.0 (M+H).

Step B: Preparation of phenyl (3-bromo-4-methyl-1-phenyl-1H-pyrazol-5-yl)carbamate: To a solution of 3-bromo-4-methyl-1-phenyl-1H-pyrazol-5-amine (339 mg, 1.34 mmol) in EtOAc (10 mL) was added 2N NaOH (2 mL, 4.0 mmol) followed by phenyl chloroformate (337 µL, 2.69 mmol). The mixture was stirred at ambient temperature for 5 hours then partitioned between water (30 mL) and EtOAc (30 mL) and the aqueous layer extracted with EtOAc (2×20 mL). The combined organic phases were washed with saturated NaHCO$_3$ (30 mL) and brine (30 mL) then dried over Na$_2$SO$_4$, filtered and concentrated in vacuo to afford phenyl (3-bromo-4-methyl-1-phenyl-1H-pyrazol-5-yl)carbamate which was used directly assuming quantitative yield. MS (apci) m/z=374.0 (M+H).

Step C: Preparation of 1-(3-bromo-4-methyl-1-phenyl-1H-pyrazol-5-yl)-3-((3S,4R)-4-(3,4-difluorophenyl)-1-(2-methoxyethyl)pyrrolidin-3-yl)urea: To a solution of (3S,4R)-4-(3,4-difluorophenyl)-1-(2-methoxyethyl)pyrrolidin-3-amine (Preparation F; 464 mg, 1.41 mmol) and phenyl (3-bromo-4-methyl-1-phenyl-1H-pyrazol-5-yl)carbamate (500 mg, 1.34 mmol) in DCM (10 mL) was added DIEA (819 µL, 4.7 mmol). The solution was stirred at ambient temperature for 18 hours then partitioned between saturated NH$_4$Cl (30 mL) and DCM (30 mL) and the aqueous layer extracted with DCM (2×20 mL). The combined organic phases were washed with brine (20 mL), dried over Na$_2$SO$_4$, filtered and concentrated in vacuo. The residue was purified by silica column chromatography eluting with 2% MeOH/DCM to afford 1-(3-bromo-4-methyl-1-phenyl-1H-pyrazol-5-yl)-3-((3S,4R)-4-(3,4-difluorophenyl)-1-(2-methoxyethyl)pyrrolidin-3-yl)urea (483 mg, 67% yield) as a white solid. MS (apci) m/z=534.1 (M+).

Step D: Preparation of 1-((3S,4R)-4-(3,4-difluorophenyl)-1-(2-methoxyethyl)pyrrolidin-3-yl)-3-(1'-isopropyl-4-methyl-1-phenyl-1H, 1'H-[3,4'-bipyrazol]-5-yl)urea: 1-(3-Bromo-4-methyl-1-phenyl-1H-pyrazol-5-yl)-3-((3S,4R)-4-(3,4-difluorophenyl)-1-(2-methoxyethyl) pyrrolidin-3-yl) urea (30 mg, 0.06 mmol), 1-isopropyl-4-(4,4,5,5-tetramethyl-1,3,2-dioxaborolan-2-yl)-1H-pyrazole (20 mg, 0.08 mmol), tricyclohexyl phospine (3 mg, 0.01 mmol) and Pd$_2$(dba)$_3$ (5 mg, 0.006 mmol) were combined in a sealed tube and 1,4-dioxanes (561 µL) were added. The solution was purged with N$_2$ for 30 seconds then treated with K$_3$PO$_4$ (130 µL, 1.3 M, 0.17 mmol), sealed and stirred at 100° C. for 1 hour. The cooled mixture was concentrated in vacuo and the residue purified by silica column chromatography eluting with 2.5-10% MeOH/DCM to afford the title compound (12 mg, 38% yield) as a colorless glass. MS (apci) m/z=564.2 (M+H).

The following compounds were made according to the method of Example 503, replacing 1-isopropyl-4-(4,4,5,5-tetramethyl-1,3,2-dioxaborolan-2-yl)-1H-pyrazole with the appropriate reagent in Step D.

| Ex. # | Structure | Name | MS (apci) m/z |
|---|---|---|---|
| 504 | 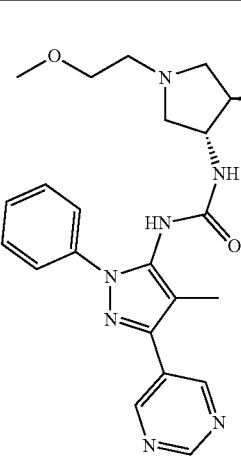 | 1-((3S,4R)-4-(3,4-difluorophenyl)-1-(2-methoxyethyl)pyrrolidin-3-yl)-3-(4-methyl-1-phenyl-3-(pyrimidin-5-yl)-1H-pyrazol-5-yl)urea | 534.2 (M + H) |

-continued

| Ex. # | Structure | Name | MS (apci) m/z |
|---|---|---|---|
| 505 | 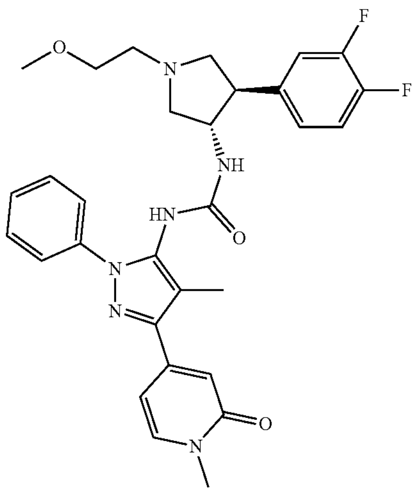 [SMILES: COCCN1C[C@@H](NC(=O)Nc2c(C)c(-c3ccn(C)c(=O)c3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-3-(1-methyl-2-oxo-1,2-dihydropyridin-4-yl)-1-phenyl-1H-pyrazol-5-yl)urea | 563.3 (M + H) |
| 506 | 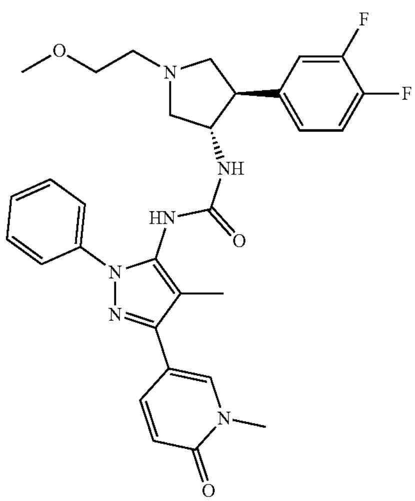 [SMILES: COCCN1C[C@@H](NC(=O)Nc2c(C)c(-c3ccc(=O)n(C)c3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-3-(1-methyl-6-oxo-1,6-dihydropyridin-3-yl)-1-phenyl-1H-pyrazol-5-yl)urea | 563.3 (M + H) |
| 507 | 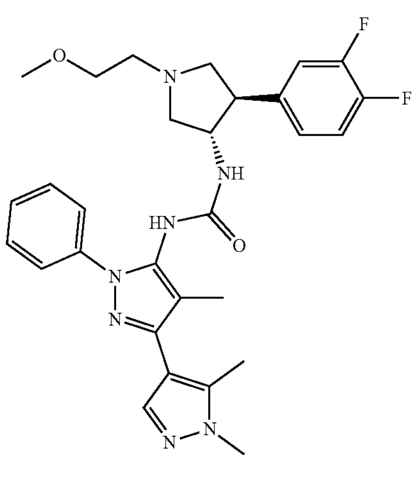 [SMILES: COCCN1C[C@@H](NC(=O)Nc2c(C)c(-c3cnn(C)c3C)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(1',4,5'-trimethyl-1-phenyl-1H,1'H-[3,4'-bipyrazol]-5-yl)urea | 550.2 (M + H) |

| Ex. # | Structure | Name | MS (apci) m/z |
|---|---|---|---|
| 508 | 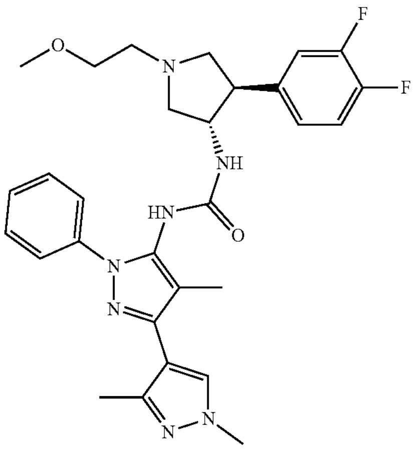 [SMILES: COCCN1C[C@@H](NC(=O)Nc2c(C)c(-c3cn(C)nc3C)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(1',3',4-trimethyl-1-phenyl-1H,1'H-[3,4'-bipyrazol]-5-yl)urea | 550.2 (M + H) |
| 509 | 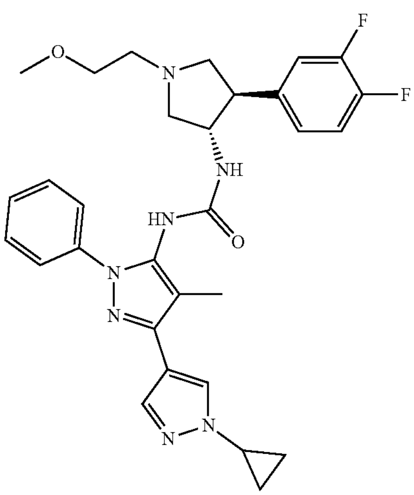 [SMILES: COCCN1C[C@@H](NC(=O)Nc2c(C)c(-c3cnn(C4CC4)c3)nn2-c2ccccc2)[C@H](c2ccc(F)c(F)c2)C1] | 1-(1'-cyclopropyl-4-methyl-1-phenyl-1H,1'H-[3,4'-bipyrazol]-5-yl)-3-((3S,4R)-4-(3,4-difluorophenyl)-1-(2-methoxyethyl)pyrrolidin-3-yl)urea | 562.2 (M + H) |
| 510 | 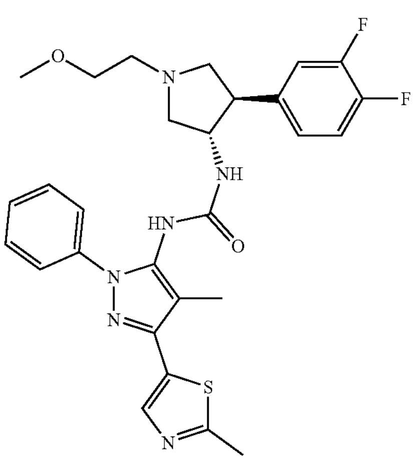 [SMILES: COCCN1C[C@@H](NC(=O)Nc2c(C)c(-c3cnc(C)s3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-3-(2-methylthiazol-5-yl)-1-phenyl-1H-pyrazol-5-yl)urea | 553.2 (M + H) |

-continued

| Ex. # | Structure | Name | MS (apci) m/z |
|---|---|---|---|
| 511 | 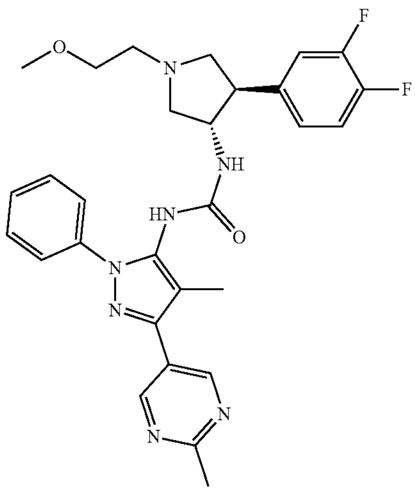 [SMILES: COCCN1C[C@@H](NC(=O)Nc2c(C)c(-c3cnc(C)nc3)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(4-methyl-3-(2-methylpyrimidin-5-yl)-1-phenyl-1H-pyrazol-5-yl)urea | 548.2 (M + H) |
| 512 | 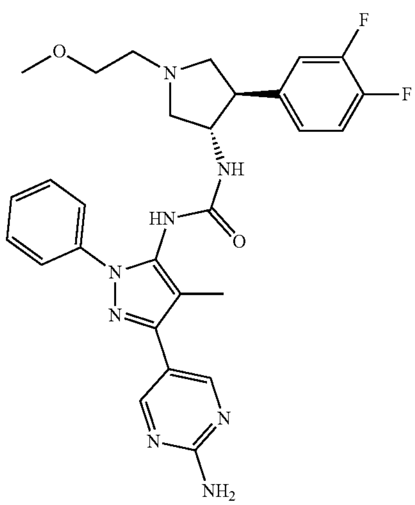 [SMILES: COCCN1C[C@@H](NC(=O)Nc2c(C)c(-c3cnc(N)nc3)nn2-c2ccccc2)[C@H](c2ccc(F)c(F)c2)C1] | 1-(3-(2-aminopyrimidin-5-yl)-4-methyl-1-phenyl-1H-pyrazol-5-yl)-3-((3S,4R)-4-(3,4-difluorophenyl)-1-(2-methoxyethyl)pyrrolidin-3-yl)urea | 549.2 (M + H) |
| 513 | 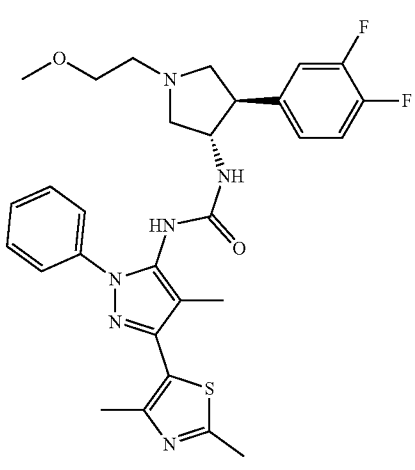 [SMILES: COCCN1C[C@@H](NC(=O)Nc2c(C)c(-c3sc(C)nc3C)nn2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(3-(2,4-dimethylthiazol-5-yl)-4-methyl-1-phenyl-1H-pyrazol-5-yl)urea | 567.2 (M + H) |

| Ex. # | Structure | Name | MS (apci) m/z |
|---|---|---|---|
| 514 | 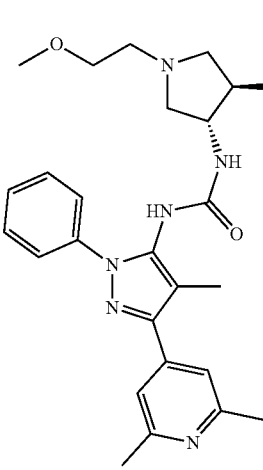 | 1-((3S,4R)-4-(3,4-difluorophenyl)-1-(2-methoxyethyl)pyrrolidin-3-yl)-3-(3-(2,6-dimethylpyridin-4-yl)-4-methyl-1-phenyl-1H-pyrazol-5-yl)urea | 561.3 (M + H) |
| 515 | 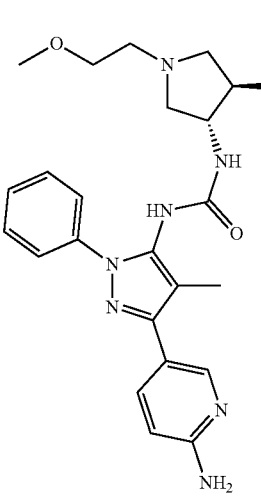 | 1-(3-(6-aminopyridin-3-yl)-4-methyl-1-phenyl-1H-pyrazol-5-yl)-3-((3S,4R)-4-(3,4-difluorophenyl)-1-(2-methoxyethyl)pyrrolidin-3-yl)urea | 548.2 (M + H) |

Example 516

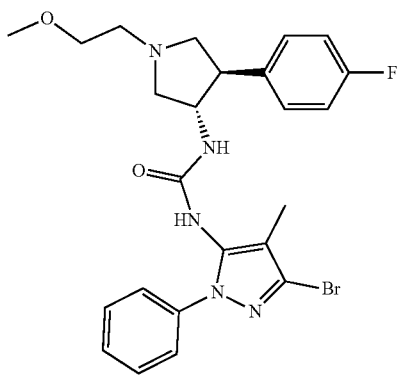 [SMILES: COCCN1C[C@@H](NC(=O)Nc2c(C)c(Br)nn2-c2ccccc2)[C@H](c2ccc(F)cc2)C1]

1-(3-bromo-4-methyl-1-phenyl-1H-pyrazol-5-yl)-3-((3S,4R)-4-(4-fluorophenyl)-1-(2-methoxyethyl)pyrrolidin-3-yl)urea Prepared according to the procedure of Example 503, Step C, replacing (3S,4R)-4-(3,4-difluorophenyl)-1-(2-methoxyethyl)pyrrolidin-3-amine (Preparation F) with (3S,4R)-4-(4-fluorophenyl)-1-(2-methoxyethyl)pyrrolidin-3-amine dihydrochloride (Preparation K). Material was purified by silica column chromatography eluting with 2-3% MeOH/DCM to afford the title compound (526 mg, 63%) as a cream solid. MS (apci) m/z=518.1 (M+H).

Example 517

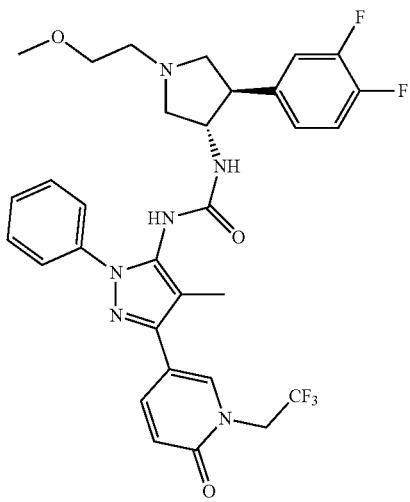 [SMILES: COCCN1C[C@@H](NC(=O)Nc2c(C)c(-c3ccc(=O)n(CC(F)(F)F)c3)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-3-(6-oxo-1-(2,2,2-trifluoroethyl)-1,6-dihydropyridin-3-yl)-1-phenyl-1H-pyrazol-5-yl)urea Prepared according to the procedure of Example 503, replacing 1-isopropyl-4-(4,4,5,5-tetramethyl-1,3,2-dioxaborolan-2-yl)-1H-pyrazole with 5-(4,4,5,5-tetramethyl-1,3,2-dioxaborolan-2-yl)-1-(2,2,2-trifluoroethyl)pyridin-2(1H)-one in Step D. Material was purified by silica column chromatography eluting with 2% MeOH/DCM followed by reverse phase HPLC purification (5-95% ACN/water/0.5% TFA over 20 minutes). The title compound (5.5 mg, 9% yield) was obtained after aqueous work-up (1N NaOH/DCM) as a white solid. MS (apci) m/z=631.2 (M+H).

Example 518

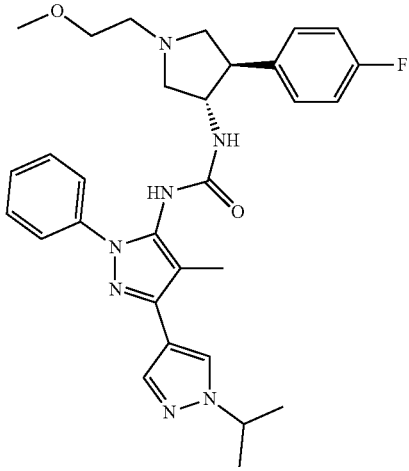 [SMILES: COCCN1C[C@@H](NC(=O)Nc2c(C)c(-c3cnn(C(C)C)c3)nn2-c2ccccc2)[C@H](c2ccc(F)cc2)C1]

1-((3S,4R)-4-(4-fluorophenyl)-1-(2-methoxyethyl)pyrrolidin-3-yl)-3-(1'-isopropyl-4-methyl-1-phenyl-1H,1'H-[3,4'-bipyrazol]-5-yl)urea Prepared according to the procedure of Example 503, replacing (3S,4R)-4-(3,4-difluorophenyl)-1-(2-methoxyethyl)pyrrolidin-3-amine (Preparation F) with (3S,4R)-4-(4-fluorophenyl)-1-(2-methoxyethyl)pyrrolidin-3-amine dihydrochloride (Preparation K) in Step C. Material was purified by silica column chromatography eluting with 2-3% MeOH/DCM followed by reverse phase HPLC purification (5-95% ACN/water/0.5% TFA over 20 minutes). The title compound (37 mg, 18% yield) was obtained after aqueous work-up (1N NaOH/DCM) as a colorless gum. MS (apci) m/z=546.3 (M+H).

Example 519

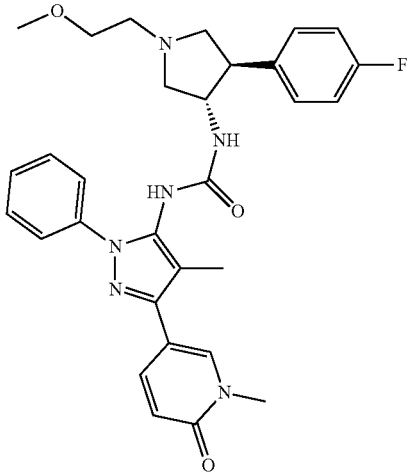 [SMILES: COCCN1C[C@@H](NC(=O)Nc2c(C)c(-c3ccc(=O)n(C)c3)nn2-c2ccccc2)[C@H](c2ccc(F)cc2)C1]

487

1-((3S,4R)-4-(4-fluorophenyl)-1-(2-methoxyethyl)
pyrrolidin-3-yl)-3-(4-methyl-3-(1-methyl-6-oxo-1,6-
dihydropyridin-3-yl)-1-phenyl-1H-pyrazol-5-yl)urea Prepared according to the procedure of Example 518, replacing 1-isopropyl-4-(4,4,5,5-tetramethyl-1,3,2-dioxaborolan-2-yl)-1H-pyrazole with 1-methyl-5-(4,4,5,5-tetramethyl-1,3,2-dioxaborolan-2-yl)pyridin-2(1H)-one in Step D. Material was purified by silica column chromatography eluting with 2-5% MeOH/DCM to afford the title product (29 mg, 27% yield) as a white solid. MS (apci) m/z=545.2 (M+H).

Example 520

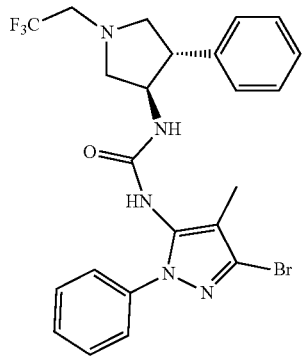 [SMILES: Cc1c(Br)nn(-c2ccccc2)c1NC(=O)N[C@H]1CN(CC(F)(F)F)C[C@@H]1c1ccccc1]

1-(3-bromo-4-methyl-1-phenyl-1H-pyrazol-5-yl)-3-
((3R,4S)-4-phenyl-1-(2,2,2-trifluoroethyl)pyrrolidin-
3-yl)urea Prepared according to the procedure of Example 516, replacing (3S,4R)-4-(4-fluorophenyl)-1-(2-methoxyethyl) pyrrolidin-3-amine dihydrochloride (Preparation K) with (3R,4S)-4-phenyl-1-(2,2,2-trifluoroethyl)pyrrolidin-3-amine hydrochloride (Example 265, Step A). Material was purified by silica column chromatography eluting with 2:1 hexanes/EtOAc to afford the title compound (173 mg, 62% yield) as a white solid. MS (apci) m/z=522.1 (M+).

Example 521

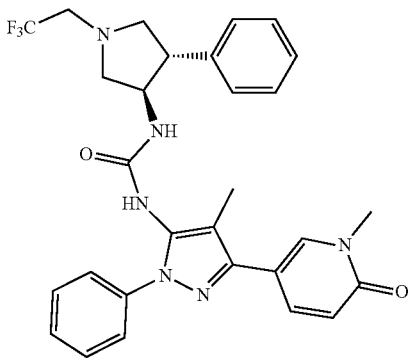 [SMILES: Cc1c(-c2ccc(=O)n(C)c2)nn(-c2ccccc2)c1NC(=O)N[C@H]1CN(CC(F)(F)F)C[C@@H]1c1ccccc1]

488

1-(4-methyl-3-(1-methyl-6-oxo-1,6-dihydropyridin-
3-yl)-1-phenyl-1H-pyrazol-5-yl)-3-((3R,4S)-4-phe-
nyl-1-(2,2,2-trifluoroethyl)pyrrolidin-3-yl)urea Prepared according to the procedure of Example 519, replacing (3S,4R)-4-(4-fluorophenyl)-1-(2-methoxyethyl) pyrrolidin-3-amine dihydrochloride (Preparation K) with (3R,4S)-4-phenyl-1-(2,2,2-trifluoroethyl)pyrrolidin-3-amine hydrochloride (Example 265, Step A) in Step C. Material was purified by silica column chromatography eluting with 2% MeOH/DCM to afford the title product (28 mg, 33% yield) as a pale yellow solid. MS (apci) m/z=550.2 (M+).

Example 522

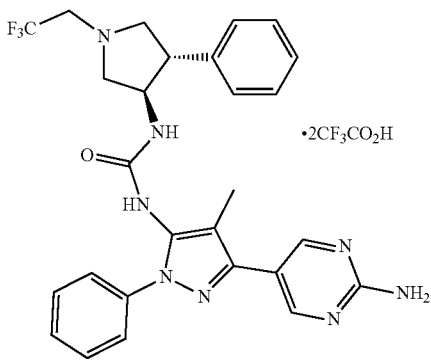 [SMILES: Cc1c(-c2cnc(N)nc2)nn(-c2ccccc2)c1NC(=O)N[C@H]1CN(CC(F)(F)F)C[C@@H]1c1ccccc1]

1-(3-(2-aminopyrimidin-5-yl)-4-methyl-1-phenyl-
1H-pyrazol-5-yl)-3-((3R,4S)-4-phenyl-1-(2,2,2-trif-
luoroethyl)pyrrolidin-3-yl)urea bis(2,2,2-trifluoroac-
etate)

Prepared according to the procedure of Example 512, replacing (3S,4R)-4-(4-fluorophenyl)-1-(2-methoxyethyl) pyrrolidin-3-amine dihydrochloride (Preparation K) with (3R,4S)-4-phenyl-1-(2,2,2-trifluoroethyl)pyrrolidin-3-amine hydrochloride (Example 265, Step A) in Step C. Material was purified by silica column chromatography eluting with 2-5% MeOH/DCM followed by reverse phase HPLC purification (5-95% ACN/water/0.5% TFA over 20 minutes). The title compound (3 mg, 3% yield) was obtained as a white solid as a di-TFA salt. MS (apci) m/z=537.2 (M+H).

Example 523

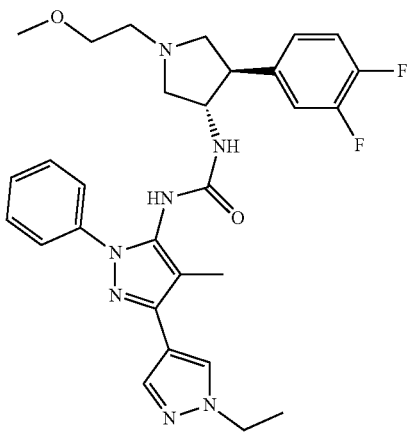 [SMILES: CCn1cc(-c2nn(-c3ccccc3)c(NC(=O)N[C@@H]3CN(CCOC)C[C@H]3c3ccc(F)c(F)c3)c2C)cn1]

1-((3S,4R)-4-(3,4-difluorophenyl)-1-(2-methoxy-ethyl)pyrrolidin-3-yl)-3-(1'-ethyl-4-methyl-1-phenyl-1H, 1'H-[3,4'-bipyrazol]-5-yl)urea Step A: Preparation of 1'-ethyl-4-methyl-1-phenyl-1H, 1'H-[3,4'-bipyrazol]-5-amine: 3-Bromo-4-methyl-1-phenyl-1H-pyrazol-5-amine (Example 503, Step A; 100 mg, 0.39 mmol), 1-ethyl-4-(4,4,5,5-tetramethyl-1,3,2-dioxaborolan-2-yl)-1H-pyrazole (176 mg, 0.79 mmol), $K_2CO_3$ (219 mg, 1.59 mmol) and Pd(PPh$_3$)$_4$(46 mg, 0.039 mmol) were combined in toluene (2 mL), water (1 mL) and EtOH (0.5 mL) and stirred at 95° C. in a sealed tube for 18 hours. The cooled mixture was filtered through GF paper and the filtrate partitioned between water (10 mL) and EtOAc (10 mL). The aqueous layer was extracted with EtOAc (2×10 mL) and the combined organic phases were washed with brine (10 mL), dried over Na$_2$SO$_4$, filtered and concentrated in vacuo. The residue was purified by silica column chromatography eluting with 1.5% MeOH/DCM to afford 1'-ethyl-4-methyl-1-phenyl-1H,1'H-[3,4'-bipyrazol]-5-amine (78 mg, 74% yield) as a colorless gum. MS (apci) m/z=268.1 (M+H).

Step B: Preparation of phenyl (1'-ethyl-4-methyl-1-phenyl-1H,1'H-[3,4'-bipyrazol]-5-yl)carbamate: To a solution of 1'-ethyl-4-methyl-1-phenyl-1H, 1'H-[3,4'-bipyrazol]-5-amine (78 mg, 0.29 mmol) in EtOAc (5 mL) was added 2N NaOH (0.44 mL, 0.87 mmol) followed by phenyl chloroformate (73 µL, 0.58 mmol). The mixture was stirred at ambient temperature for 18 hours then partitioned between water (20 mL) and EtOAc (20 mL) and the aqueous layer extracted with EtOAc (2×10 mL). The combined organic phases were washed with saturated NaHCO$_3$ (10 mL) and brine (10 mL) then dried over Na$_2$SO$_4$, filtered and concentrated in vacuo to afford phenyl (1'-ethyl-4-methyl-1-phenyl-1H,1'H-[3,4'-bipyrazol]-5-yl)carbamate as a pale yellow oil. Used directly assuming quantitative yield. MS (apci) m/z=388.2 (M+H).

Step C: Preparation of 1-((3S,4R)-4-(3,4-difluorophenyl)-1-(2-methoxyethyl) pyrrolidin-3-yl)-3-(1'-ethyl-4-methyl-1-phenyl-1H,1'H-[3,4'-bipyrazol]-5-yl)urea: To a solution of (3S,4R)-4-(3,4-difluorophenyl)-1-(2-methoxyethyl)pyrrolidin-3-amine (Preparation F; 56 mg, 0.17 mmol) and phenyl (1'-ethyl-4-methyl-1-phenyl-1H, 1'H-[3,4'-bipyrazol]-5-yl) carbamate (66 mg, 0.17 mmol) in DCM (2 mL) was added DIEA (150 µL, 0.85 mmol). After stirring at ambient temperature for 18 hours the mixture was partitioned between saturated NH$_4$Cl (10 mL) and DCM (10 mL) and the aqueous layer extracted with DCM (2×10 mL). The combined organic phases were washed with brine (10 mL) then dried over Na$_2$SO$_4$, filtered and concentrated in vacuo. The residue was purified by silica column chromatography eluting with 2.5-3.5% MeOH/DCM to afford the title compound (35 mg, 37% yield) as a colorless glass. MS (apci) m/z=550.2 (M+H).

Example 524

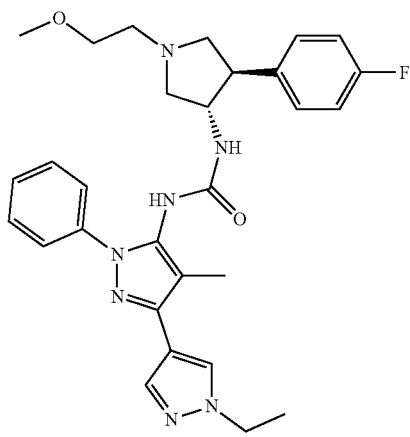 [SMILES: CCn1cc(-c2nn(-c3ccccc3)c(NC(=O)N[C@@H]3CN(CCOC)C[C@H]3c3ccc(F)cc3)c2C)cn1]

1-(1'-ethyl-4-methyl-1-phenyl-1H, 1'H-[3,4'-bipyrazol]-5-yl)-3-((3S,4R)-4-(4-fluorophenyl)-1-(2-methoxyethyl)pyrrolidin-3-yl)urea Prepared according to the procedure of Example 523, replacing (3S,4R)-4-(3,4-difluorophenyl)-1-(2-methoxyethyl)pyrrolidin-3-amine (Preparation F) with (3S,4R)-4-(4-fluorophenyl)-1-(2-methoxyethyl)pyrrolidin-3-amine dihydrochloride (Preparation K) in Step C. Material was purified by silica column chromatography eluting with 3% MeOH/DCM to afford the title product (29 mg, 30% yield) as a white solid. MS (apci) m/z=532.3 (M+H).

Example 525

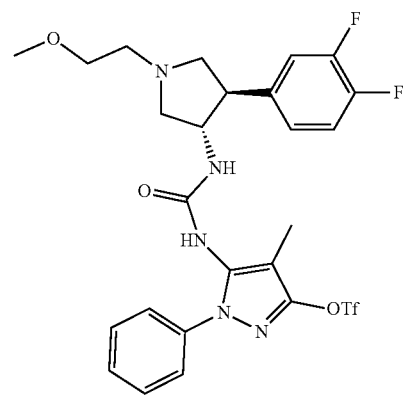 [SMILES: COCCN1C[C@@H](NC(=O)Nc2c(C)c(OS(=O)(=O)C(F)(F)F)nn2-c2ccccc2)[C@H](c2ccc(F)c(F)c2)C1]

5-(3-((3S,4R)-4-(3,4-difluorophenyl)-1-(2-methoxyethyl)pyrrolidin-3-yl)ureido)-4-methyl-1-phenyl-1H-pyrazol-3-yl trifluoromethanesulfonate Step A: Preparation of 5-amino-4-methyl-1-phenyl-1H-pyrazol-3-yl trifluoromethane sulfonate: A suspension of 5-amino-4-methyl-1-phenyl-1H-pyrazol-3(2H)-one (Intermediate P135, Step A; 0.50 g, 2.64 mmol) and N-phenylbis(trifluoromethylsulfonamide) (0.99 g, 2.77 mmol) in DMF (5 mL) was treated with DIEA (1.38 mL, 7.93 mmol) and the mixture stirred at ambient temperature for 64 hours. The mixture was partitioned between saturated NaHCO$_3$ (30 mL) and EtOAc (30 mL) and the aqueous layer was extracted with EtOAc (2×20 mL). The combined organic phases were washed with water (5×10 mL) and brine (10 mL) then dried over Na$_2$SO$_4$, filtered and concentrated in vacuo. The residue was purified by silica column chromatography eluting with 2:1 hexanes/EtOAc, to afford 5-amino-4-methyl-1-phenyl-1H-pyrazol-3-yl trifluoromethane sulfonate (817 mg, 92% yield) as a pale yellow oil. MS (apci) m/z=322.0 (M+H).

Step B: Preparation of 4-methyl-5-((phenoxycarbonyl) amino)-1-phenyl-1H-pyrazol-3-yl trifluoromethanesulfonate: Prepared according to the procedure of Example 503, Step B, replacing 3-bromo-4-methyl-1-phenyl-1H-pyrazol-5-amine with 5-amino-4-methyl-1-phenyl-1H-pyrazol-3-yl trifluoromethane sulfonate. MS (apci) m/z=442.0 (M+H).

Step C: Preparation of 5-(3-((3S,4R)-4-(3,4-difluorophenyl)-1-(2-methoxyethyl)pyrrolidin-3-yl)ureido)-4-methyl-1-phenyl-1H-pyrazol-3-yltrifluoromethanesulfonate: Prepared according to the procedure for Example 503, Step C, replacing phenyl (3-bromo-4-methyl-1-phenyl-1H-pyrazol-5-yl)carbamate with 4-methyl-5-((phenoxycarbonyl)amino)-1-phenyl-1H-pyrazol-3-yl trifluoromethanesulfonate. Material was purified by silica column chromatography eluting with 1.5-4% MeOH/DCM to afford the title compound (191 mg, 62% yield) as a white solid. MS (apci) m/z=604.2 (M+H).

Example 526

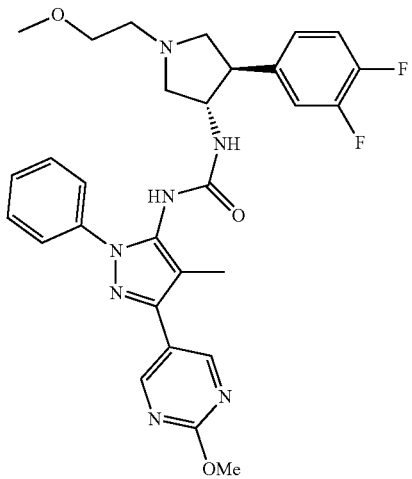 [SMILES: COCCN1C[C@@H](NC(=O)Nc2c(C)c(-c3cnc(OC)nc3)nn2-c2ccccc2)[C@H](c2ccc(F)c(F)c2)C1]

1-((3S,4R)-4-(3,4-difluorophenyvl)-1-(2-methoxyethyl)pyrrolidin-3-yl)-3-(3-(2-methoxypyrimidin-5-yl)-4-methyl-1-phenyl-1H-pyrazol-5-yl)urea Step A: Preparation of 3-(2-methoxypyrimidin-5-yl)-4-methyl-1-phenyl-1H-pyrazol-5-amine: 5-Amino-4-methyl-1-phenyl-1H-pyrazol-3-yl trifluoromethane sulfonate (Example 525, Step A; 200 mg, 0.62 mmol), 2-methoxypyrimidin-5-ylboronic acid (192 mg, 1.25 mmol), K$_2$CO$_3$ (344 mg, 2.49 mmol) and Pd(PPh$_3$)$_4$(72 mg, 0.06 mmol) were combined in toluene (2 mL), water (1 mL) and EtOH (0.5 mL) and stirred at 95° C. in a sealed tube for 18 hours. The cooled mixture was filtered through GF paper and the filtrate partitioned between water (20 mL) and EtOAc (20 mL). The aqueous layer was extracted with EtOAc (2×20 mL) and the combined organic phases were washed with brine (20 mL), dried over Na$_2$SO$_4$, filtered and concentrated in vacuo. The residue was purified by silica column chromatography eluting with 1% MeOH/DCM to afford 3-(2-methoxypyrimidin-5-yl)-4-methyl-1-phenyl-1H-pyrazol-5-amine (138 mg, 79% yield) as a cream foam. MS (apci) m/z=282.1 (M+H).

Step B: Preparation of phenyl (3-(2-methoxypyrimidin-5-yl)-4-methyl-1-phenyl-1H-pyrazol-5-yl)carbamate: Prepared according to the procedure of Example 503, Step B, replacing 3-bromo-4-methyl-1-phenyl-1H-pyrazol-5-amine with 3-(2-methoxypyrimidin-5-yl)-4-methyl-1-phenyl-1H-pyrazol-5-amine. Material was purified by silica column chromatography eluting with 1% MeOH/DCM to afford phenyl (3-(2-methoxypyrimidin-5-yl)-4-methyl-1-phenyl-1H-pyrazol-5-yl)carbamate (92 mg, 47% yield) as a cream foam. MS (apci) m/z=402.1 (M+H).

Step C: Preparation of 1-((3S,4R)-4-(3,4-difluorophenyl)-1-(2-methoxyethyl)pyrrolidin-3-yl)-3-(3-(2-methoxypyrimidin-5-yl)-4-methyl-1-phenyl-1H-pyrazol-5-yl)urea: Prepared according to the procedure of Example 503, Step C, replacing phenyl (3-bromo-4-methyl-1-phenyl-1H-pyrazol-5-yl)carbamate with phenyl (3-(2-methoxypyrimidin-5-yl)-4-methyl-1-phenyl-1H-pyrazol-5-yl)carbamate. Material was purified by silica column chromatography eluting with 2.5% MeOH/DCM to afford the title compound (31 mg, 48% yield) as a white solid. MS (apci) m/z=564.2 (M+H).

Example 527

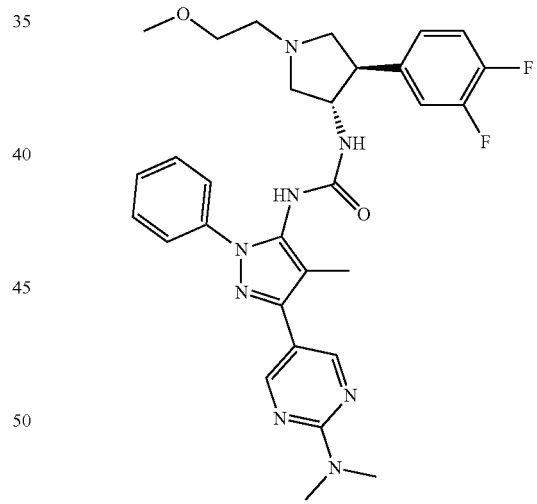

1-((3S,4R)-4-(3,4-difluorophenyl)-1-(2-methoxyethyl)pyrrolidin-3-yl)-3-(3-(2-(dimethylamino)pyrimidin-5-yl)-4-methyl-l-phenyl-1H-pyrazol-5-yl)urea Prepared according to the procedure of Example 526, replacing 2-methoxypyrimidin-5-ylboronic acid with N,N-dimethyl-5-(4,4,5,5-tetramethyl-1,3,2-dioxaboralan-2-yl) pyrimidin-2-amine in Step A. Material was purified by silica column chromatography eluting with 3% MeOH/DCM to afford the title compound (22 mg, 32% yield) as a white solid. MS (apci) m/z=577.3 (M+H).

Example 528

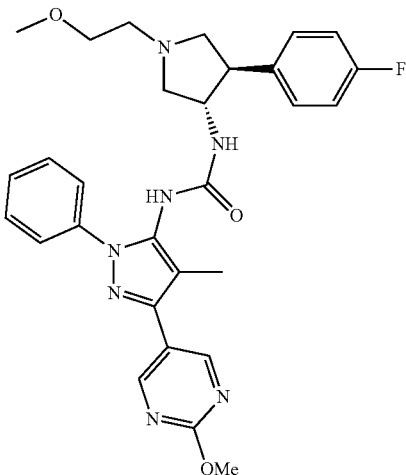 [SMILES: COCCN1C[C@@H](NC(=O)Nc2c(C)c(-c3cnc(OC)nc3)nn2-c2ccccc2)[C@H](c2ccc(F)cc2)C1]

1-((3S,4R)-4-(4-fluorophenyl)-1-(2-methoxyethyl)pyrrolidin-3-yl)-3-(3-(2-methoxypyrimidin-5-yl)-4-methyl-1-phenyl-1H-pyrazol-5-yl)urea Prepared according to the procedure of Example 526, replacing (3S,4R)-4-(3,4-difluorophenyl)-1-(2-methoxyethyl)pyrrolidin-3-amine (Preparation F) with (3S,4R)-4-(4-fluorophenyl)-1-(2-methoxyethyl)pyrrolidin-3-amine (2S,3S)-2,3-bis((4-methylbenzoyl) oxy) succinate (Preparation L1, Steps A-D) in Step C. Material was purified by silica column chromatography eluting with 3% MeOH/DCM to afford the title compound (32 mg, 51% yield) as a white solid. MS (apci) m/z=546.2 (M+H).

Example 529

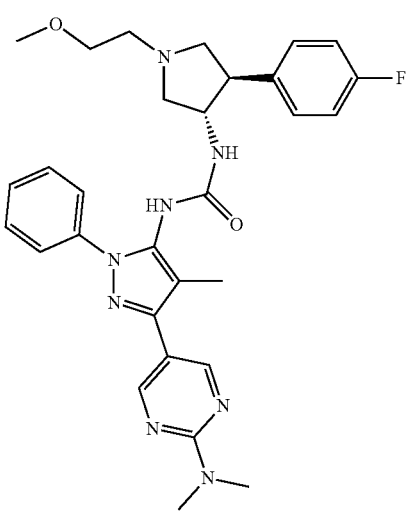 [SMILES: COCCN1C[C@@H](NC(=O)Nc2c(C)c(-c3cnc(N(C)C)nc3)nn2-c2ccccc2)[C@H](c2ccc(F)cc2)C1]

1-(3-(2-(dimethylamino)pyrimidin-5-yl)-4-methyl-1-phenyl-1H-pyrazol-5-yl)-3-((3S,4R)-4-(4-fluorophenyl)-1-(2-methoxyethyl)pyrrolidin-3-yl)urea Prepared according to the procedure of Example 527, replacing (3S,4R)-4-(3,4-difluorophenyl)-1-(2-methoxyethyl)pyrrolidin-3-amine (Preparation F) with (3S,4R)-4-(4-fluorophenyl)-1-(2-methoxyethyl)pyrrolidin-3-amine dihydrochloride (Preparation K) in Step C. Material was purified by silica column chromatography eluting with 3% MeOH/DCM to afford the title compound (27 mg, 40% yield) as a white solid. MS (apci) m/z=559.3 (M+H).

Example 530

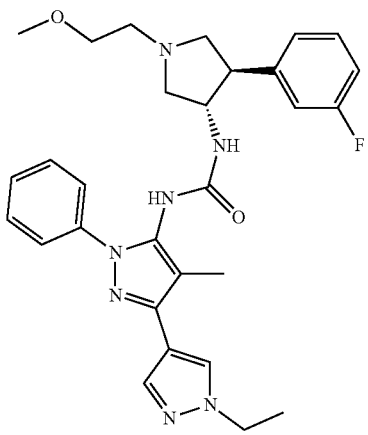 [SMILES: CCn1cc(-c2nn(-c3ccccc3)c(NC(=O)N[C@@H]3CN(CCOC)C[C@H]3c3cccc(F)c3)c2C)cn1]

1-(1'-ethyl-4-methyl-1-phenyl-1H,1'H-[3,4'-bipyrazol]-5-yl)-3-((3S,4R)-4-(3-fluorophenyl)-1-(2-methoxyethyl)pyrrolidin-3-yl)urea Prepared according to the procedure of Example 526, replacing 2-methoxypyrimidin-5-ylboronic acid with 1-ethyl-4-(4,4,5,5-tetramethyl-1,3,2-dioxaborolan-2-yl)-1H-pyrazole in Step A, and (3S,4R)-4-(3,4-difluorophenyl)-1-(2-methoxyethyl)pyrrolidin-3-amine (Preparation F) with (3S,4R)-4-(3-fluorophenyl)-1-(2-methoxyethyl)pyrrolidin-3-amine dihydrochloride (Preparation L11) in Step C. Material was purified by silica column chromatography eluting with 3% MeOH/DCM to afford the title compound (39 mg, 57% yield) as a white solid. MS (apci) m/z=532.3 (M+H).

Example 531

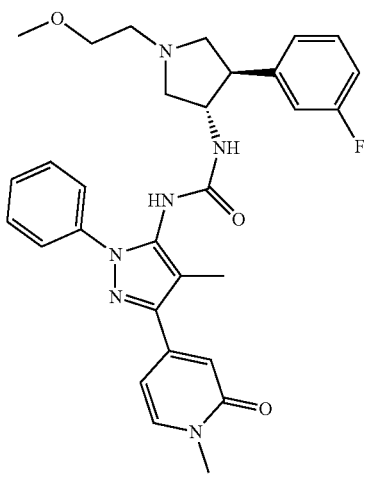 [SMILES: COCCN1C[C@@H](NC(=O)Nc2c(C)c(-c3ccn(C)c(=O)c3)nn2-c2ccccc2)[C@H](c2cccc(F)c2)C1]

1-((3S,4R)-4-(3-fluorophenyl)-1-(2-methoxyethyl)pyrrolidin-3-yl)-3-(4-methyl-3-(1-methyl-2-oxo-1,2-dihydropyridin-4-yl)-1-phenyl-1H-pyrazol-5-yl)urea Prepared according to the procedure of Example 526, replacing 2-methoxypyrimidin-5-ylboronic acid with 1-methyl-4-(4,4,5,5-tetramethyl-1,3,2-dioxaborolan-2-yl)pyridin-2(1H)-one in Step A, and (3S,4R)-4-(3,4-difluorophenyl)-1-(2-methoxyethyl)pyrrolidin-3-amine (Preparation F) with (3S,4R)-4-(3-fluorophenyl)-1-(2-methoxyethyl)pyrrolidin-3-amine dihydrochloride (Preparation L1) in Step C. Material was purified by silica column chromatography eluting with 3-8% MeOH/DCM to afford the title compound (38 mg, 54% yield) as a white solid. MS (apci) m/z=545.2 (M+H).

Example 532

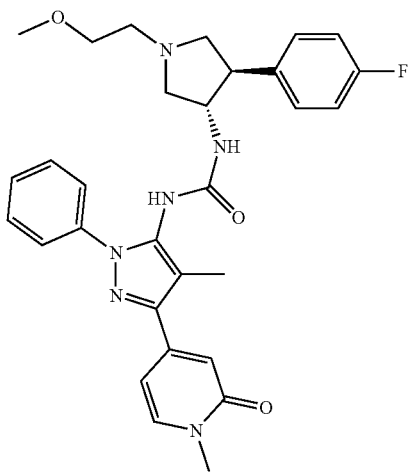 [SMILES: COCCN1C[C@@H](NC(=O)Nc2c(C)c(-c3ccn(C)c(=O)c3)nn2-c2ccccc2)[C@H](c2ccc(F)cc2)C1]

1-((3S,4R)-4-(4-fluorophenyl)-1-(2-methoxyethyl)pyrrolidin-3-yl)-3-(4-methyl-3-(1-methyl-2-oxo-1,2-dihydropyridin-4-yl)-1-phenyl-1H-pyrazol-5-yl)urea Prepared according to the procedure of Example 526, replacing 2-methoxypyrimidin-5-ylboronic acid with 1-methyl-4-(4,4,5,5-tetramethyl-1,3,2-dioxaborolan-2-yl)pyridin-2(1H)-one in Step A, and (3S,4R)-4-(3,4-difluorophenyl)-1-(2-methoxyethyl)pyrrolidin-3-amine (Preparation F) with (3S,4R)-4-(4-fluorophenyl)-1-(2-methoxyethyl)pyrrolidin-3-amine (2S,3S)-2,3-bis((4-methylbenzoyl)oxy)succinate (Preparation L1, Steps A-D) in Step C. Material was purified by silica column chromatography eluting with 3-8% MeOH/DCM to afford the title compound (34 mg, 49% yield) as a white solid. MS (apci) m/z=545.3 (M+H).

Example 533

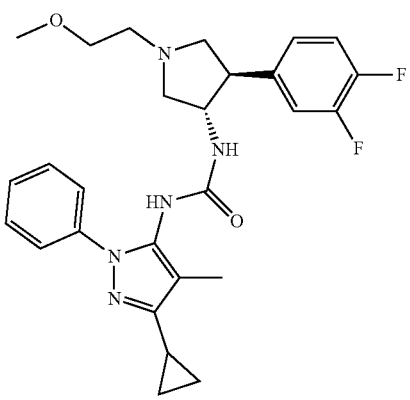 [SMILES: COCCN1C[C@@H](NC(=O)Nc2c(C)c(C3CC3)nn2-c2ccccc2)[C@H](c2ccc(F)c(F)c2)C1]

1-(3-cyclopropyl-4-methyl-1-phenyl-1H-pyrazol-5-yl)-3-((3S,4R)-4-(3,4-difluorophenyl)-1-(2-methoxyethyl)pyrrolidin-3-yl)urea Step A: Preparation of 3-cyclopropyl-4-methyl-1-phenyl-1H-pyrazol-5-amine: A suspension of 5-amino-4-methyl-1-phenyl-1H-pyrazol-3-yl trifluoromethane sulfonate (Example 525, Step A; 200 mg, 0.62 mmol) in toluene:water, 10:1 (5.5 mL) in a sealed tube was degassed with Argon for 5 minutes. Potassium cyclopropyltrifluoroborate (368 mg, 2.49 mmol), Pd(OAc)$_2$ (21 mg, 0.09 mmol) and K$_3$PO$_4$ (396 mg, 1.87 mmol) were then added, followed by dicyclohexyl(2',6'-diisopropylbiphenyl-2-yl)phosphine (87 mg, 0.19 mmol). The mixture was degassed with Argon for another 5 minutes then sealed and stirred at 110° C. for 18 hours. The cooled mixture was diluted with water (30 mL) and extracted with EtOAc (3×20 mL). The combined organic phases were washed with brine (20 mL), dried over Na$_2$SO$_4$, filtered and concentrated in vacuo. The residue was purified by silica column chromatography eluting with 1% MeOH/DCM to afford 3-cyclopropyl-4-methyl-1-phenyl-1H-pyrazol-5-amine (100 mg, 75% yield) as a yellow oil. MS (apci) m/z=214.1 (M+H).

Step B: Preparation of 1-(3-cyclopropyl-4-methyl-1-phenyl-1H-pyrazol-5-yl)-3-((3S,4R)-4-(3,4-difluorophenyl)-1-(2-methoxyethyl)pyrrolidin-3-yl)urea: Prepared according to the procedure of Example 526, Steps B and C, replacing 3-(2-methoxypyrimidin-5-yl)-4-methyl-1-phenyl-1H-pyrazol-5-amine with 3-cyclopropyl-4-methyl-1-phenyl-1H-pyrazol-5-amine in Step B. Material was purified by silica column chromatography eluting with 1-3% MeOH/DCM to afford the title product (29 mg, 39% yield) as a colorless glass. MS (apci) m/z=496.3 (M+H).

Example 534

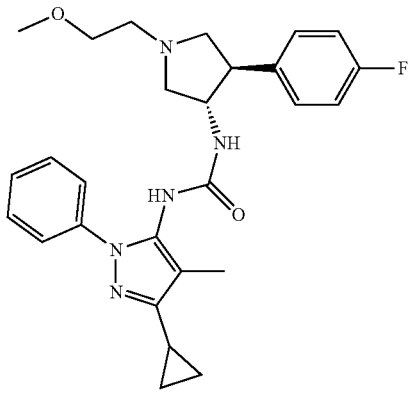 [SMILES: COCCN1C[C@@H](NC(=O)Nc2c(C)c(C3CC3)nn2-c2ccccc2)[C@H](c2ccc(F)cc2)C1]

1-(3-cyclopropyl-4-methyl-1-phenyl-1H-pyrazol-5-yl)-3-((3S,4R)-4-(4-fluorophenyl)-1-(2-methoxyethyl)pyrrolidin-3-yl)urea Prepared according to the procedure of Example 533, replacing (3S,4R)-4-(3,4-difluorophenyl)-1-(2-methoxyethyl)pyrrolidin-3-amine (Preparation F) with (3S,4R)-4-(4-fluorophenyl)-1-(2-methoxyethyl)pyrrolidin-3-amine (2S,3S)-2,3-bis((4-methylbenzoyl)oxy) succinate (Preparation L1, Steps A-D) in Step C. Material was purified by silica column chromatography eluting with 2-4% MeOH/DCM to afford the title compound (11 mg, 15% yield) as a colorless glass. MS (apci) m/z=478.3 (M+H).

Example 535

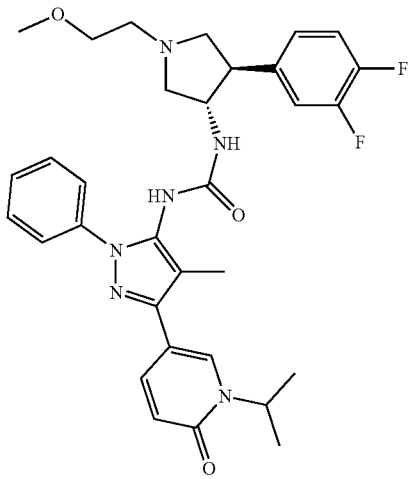 [SMILES: COCCN1C[C@@H](NC(=O)Nc2c(C)c(-c3ccc(=O)n(C(C)C)c3)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(3-(1-isopropyl-6-oxo-1,6-dihydropyridin-3-yl)-4-methyl-1-phenyl-1H-pyrazol-5-yl)urea Step A: Preparation of 1-isopropyl-5-(4,4,5,5-tetramethyl-1,3,2-dioxaborolan-2-yl)pyridin-2(1H)-one:

5-Bromo-1-isopropylpyridin-2(1H)-one (500 mg, 2.31 mmol), bis(pinnacolato) diboron (881 mg, 3.47 mmol) and potassium acetate (681 mg, 6.94 mmol) were combined in a sealed vessel in 1,4-dioxanes (5 mL) and purged with Argon for 5 minutes. PdCl$_2$(dppf)dcm (189 mg, 0.23 mmol) was then added, purging continued for 1 minute, then the vessel sealed and heated at 100° C. for 18 hours. The cooled mixture was filtered through GF paper and rinsed with EtOAc and DCM. The filtrate was concentrated in vacuo and the residue purified by silica column chromatography eluting with 1% MeOH/DCM, followed by a second column eluting with 1:1 hexanes/EtOAc. The resulting solid was triturated with Et$_2$O, filtered and the filtrate concentrated in vacuo to afford 1-isopropyl-5-(4,4,5,5-tetramethyl-1,3,2-dioxaborolan-2-yl)pyridin-2(1H)-one (308 mg, 51% yield) as a peach solid. MS (apci) m/z=264.2 (M+H).

Step B: Preparation of 1-((3S,4R)-4-(3,4-difluorophenyl)-1-(2-methoxyethyl) pyrrolidin-3-yl)-3-(3-(1-isopropyl-6-oxo-1,6-dihydropyridin-3-yl)-4-methyl-1-phenyl-1H-pyrazol-5-yl)urea: Prepared according to the procedure of Example 526, replacing 2-methoxypyrimidin-5-ylboronic acid with 1-isopropyl-5-(4,4,5,5-tetramethyl-1,3,2-dioxaborolan-2-yl)pyridin-2(1H)-one. Material was purified by silica column chromatography eluting with 2.5-4% MeOH/DCM to afford the title compound (37 mg, 53% yield) as a colorless glass. MS (apci) m/z=591.3 (M+H).

Example 536

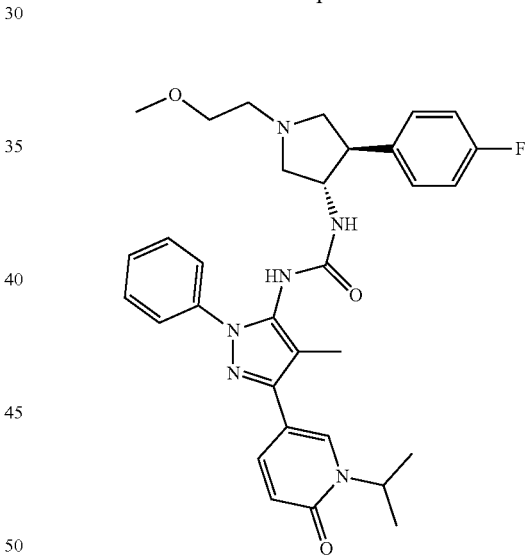

1-((3S,4R)-4-(4-fluorophenyl)-1-(2-methoxyethyl)pyrrolidin-3-yl)-3-(3-(1-isopropyl-6-oxo-1,6-dihydropyridin-3-yl)-4-methyl-1-phenyl-1H-pyrazol-5-yl)urea Prepared according to the procedure of Example 535, replacing (3S,4R)-4-(3,4-difluorophenyl)-1-(2-methoxyethyl)pyrrolidin-3-amine (Preparation F) with (3S,4R)-4-(4-fluoro-phenyl)-1-(2-methoxyethyl)pyrrolidin-3-amine (2S,3S)-2,3-bis((4-methylbenzoyl)oxy) succinate (Preparation L1, Steps A-D) in the final step. Material was purified by silica column chromatography eluting with 3-5% MeOH/DCM to afford the title compound (34 mg, 50% yield) as a colorless glass. MS (apci) m/z=573.3 (M+H).

Example 537

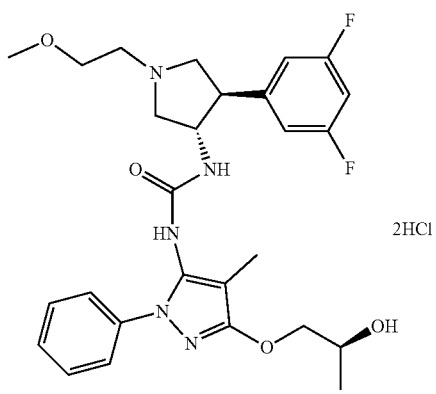 [SMILES: COCCN1C[C@@H](NC(=O)Nc2c(C)c(OC[C@H](C)O)nn2-c2ccccc2)[C@H](c2cc(F)cc(F)c2)C1]

1-((3S,4R)-4-(3,5-difluorophenyl)-1-(2-methoxy-ethyl)pyrrolidin-3-yl)-3-(3-((S)-2-hydroxypropoxy)-4-methyl-1-phenyl-1H-pyrazol-5-yl)urea dihydrochloride Step A: Preparation of 1-(3-((S)-2-((tert-butyldimethylsilyl)oxy)propoxy)-4-methyl-1-phenyl-1H-pyrazol-5-yl)-3-((3S,4R)-4-(3,5-difluorophenyl)-1-(2-methoxyethyl) pyrrolidin-3-yl)urea: Prepared according to the method described for Example 1 using Intermediate P211 as a replacement for 3-tert-butyl-1-phenyl-1H-pyrazol-5-amine in Step A, and substituting (3S,4R)-4-(3,5-difluorophenyl)-1-(2-methoxyethyl)pyrrolidin-3-amine dihydrochloride for trans-1-(2-methoxyethyl)-4-phenylpyrrolidin-3-amine dihydrochloride (Preparation B) in Step B. MS (apci) m/z=644.4 (M+H).

Step B: Preparation of 1-((3S,4R)-4-(3,5-difluorophenyl)-1-(2-methoxyethyl)pyrrolidin-3-yl)-3-(3-((S)-2-hydroxypropoxy)-4-methyl-1-phenyl-1H-pyrazol-5-yl) urea dihydrochloride: Prepared according to the procedure described for Example 179, using 1-(3-((S)-2-((tert-butyldimethylsilyl)oxy)propoxy)-4-methyl-1-phenyl-1H-pyrazol-5-yl)-3-((3S,4R)-4-(3,5-difluorophenyl)-1-(2-methoxyethyl)pyrrolidin-3-yl)urea as a replacement for 1-(3-((S)-2-((tert-butyldimethylsilyl)oxy)propoxy)-4-methyl-1-phenyl-1H-pyrazol-5-yl)-3-((3S,4R)-4-(3,4-difluoro-phenyl)-1-(2-methoxyethyl)pyrrolidin-3-yl)urea (Preparation U-2). MS (apci) m/z=530.3 (M+H).

Example 538

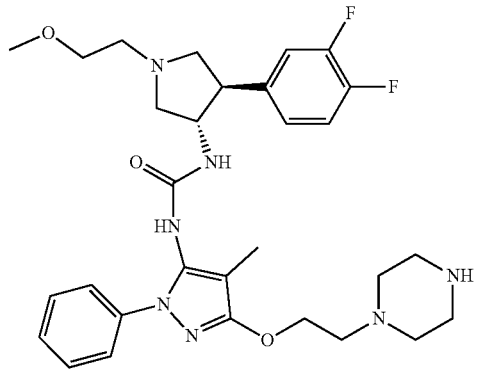

1-((3S,4R)-4-(3,5-difluorophenyl)-1-(2-methoxy-ethyl)pyrrolidin-3-yl)-3-(4-methyl-1-phenyl-3-(2-(piperazin-1-yl)ethoxy)-1H-pyrazol-5-yl)urea trihydrochloride To a stirred solution of tert-butyl 4-(2-((5-(3-((3S,4R)-4-(3,4-difluorophenyl)-1-(2-methoxyethyl)pyrrolidin-3-yl)ureido)-4-methyl-1-phenyl-1H-pyrazol-3-yl)oxy)ethyl) piperazine-1-carboxylate (Example 388, 52 mg, 0.076 mmol) in DCM (3 mL) was added 2 N HCl in ether (0.15 mL). After stirring at ambient temperature for 1 hour, the solvents were evaporated under reduced pressure to give the title compound (50 mg, 110% yield). MS (apci) m/z=584.3 (M+H).

Example 539

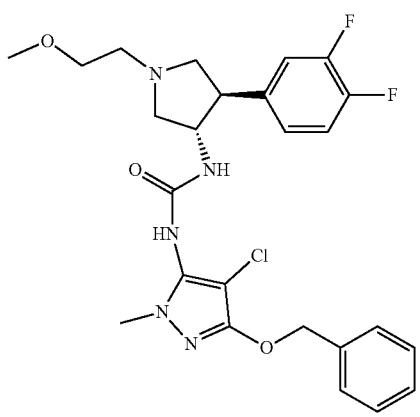 [SMILES: COCCN1C[C@@H](NC(=O)Nc2c(Cl)c(OCc3ccccc3)nn2C)[C@H](c2ccc(F)c(F)c2)C1]

1-(3-(benzyloxy)-4-chloro-1-methyl-1H-pyrazol-5-yl)-3-((3S,4R)-4-(3,4-difluorophenyl)-1-(2-methoxyethyl)pyrrolidin-3-yl)urea Prepared according to the method described for Intermediate 201, Step B, using 1-(3-(benzyloxy)-1-methyl-1H-pyrazol-5-yl)-3-((3S,4R)-4-(3,4-difluorophenyl)-1-(2-methoxyethyl)pyrrolidin-3-yl)urea (Example 136) as a replacement for phenyl 3-ethoxy-1-phenyl-1H-pyrazol-5-ylcarbamate. MS (apci) m/z=520.2 (M+H).

Example 540

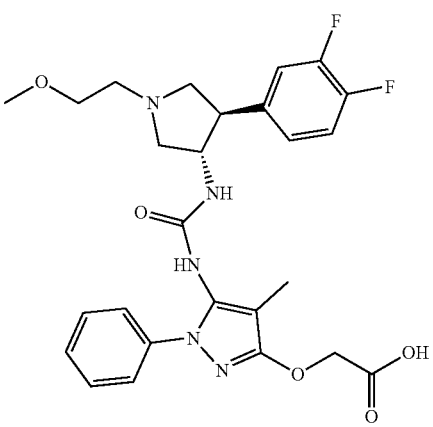 [SMILES: COCCN1C[C@@H](NC(=O)Nc2c(C)c(OCC(=O)O)nn2-c2ccccc2)[C@H](c2ccc(F)c(F)c2)C1]

2-((5-(3-((3S,4R)-4-(3,4-difluorophenyl)-1-(2-methoxyethyl)pyrrolidin-3-yl)ureido)-4-methyl-1-phenyl-1H-pyrazol-3-yl)oxy)acetic acid A mixture of ethyl 2-((5-(3-((3S,4R)-4-(3,4-difluorophenyl)-1-(2-methoxyethyl)pyrrolidin-3-yl)ureido)-4-methyl-1-phenyl-1H-pyrazol-3-yl)oxy)acetate (Example 361, 190 mg, 0.341 mmol) and 1.0 N aqueous LiOH solution (0.682 mL, 0.682 mmol) in THF (4 mL) and MeOH (2 mL) was stirred at ambient temperature for 1 hour. The reaction mixture was diluted with water. 1.0 N HCl aqueous solution (0.8 mL) was added dropwise to adjust the pH to 4. The mixture was extracted with EtOAc. The combined extracts were washed with brine, dried over MgSO₄, filtered, and concentrated to give the title compound as an off white solid (150 mg, 83% yield). MS (apci) m/z=530.2 (M+H).

Example 541

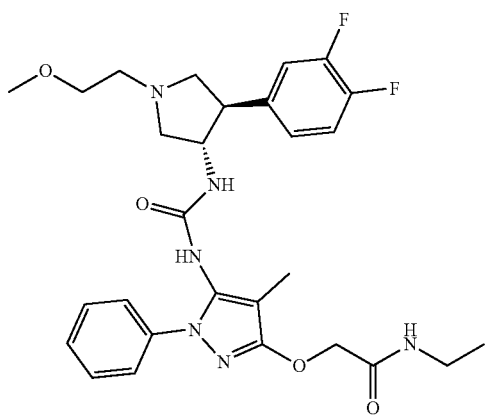 [SMILES: CCNC(=O)COc1nn(-c2ccccc2)c(NC(=O)N[C@@H]2CN(CCOC)C[C@H]2c2ccc(F)c(F)c2)c1C]

2-((5-(3-((3S,4R)-4-(3,4-difluorophenyl)-1-(2-methoxyethyl)pyrrolidin-3-yl)ureido)-4-methyl-1-phenyl-1H-pyrazol-3-yl)oxy)-N-ethylacetamide To a stirred solution of 2-(5-(3-((3S,4R)-4-(3,4-difluorophenyl)-1-(2-methoxyethyl)pyrrolidin-3-yl)ureido)-4-methyl-1-phenyl-1H-pyrazol-3-yloxy)acetic acid (Example 540, 22 mg, 0.042 mmol) in DMF (2 mL) was added EDCI (24 mg, 0.12 mmol) and HOBt (17 mg, 0.12 mmol). The resulting mixture was stirred at ambient temperature for 10 minutes. Ethylamine (2.0 M in THF, 0.062 mL, 0.12 mmol) was added followed by TEA (0.017 mL, 0.12 mmol). The reaction mixture was stirred at ambient temperature for 3 days. The mixture was diluted with EtOAc, washed sequentially with saturated aqueous NH₄Cl solution, saturated aqueous NaHCO₃ solution, and brine, dried over MgSO₄, and concentrated. The residue was purified by flash chromatography on silica gel (5% MeOH in DCM) to give the title compound (16 mg, 69% yield). MS (apci) m/z=557.3 (M+H).

Example 542

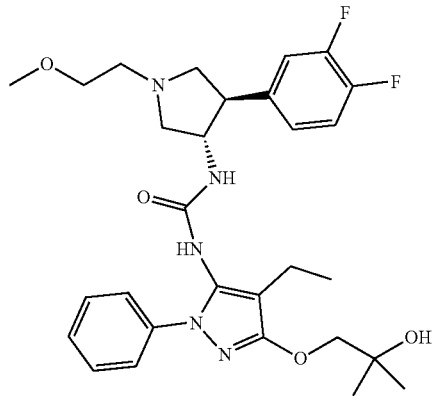 [SMILES: CCc1c(OCC(C)(C)O)nn(-c2ccccc2)c1NC(=O)N[C@@H]1CN(CCOC)C[C@H]1c1ccc(F)c(F)c1]

1-((3S,4R)-4-(3,4-difluorophenyvl)-1-(2-methoxyethyl)pyrrolidin-3-yl)-3-(4-ethyl-3-(2-hydroxy-2-methylpropoxy)-1-phenyl-1H-pyrazol-5-yl)urea Step A: Preparation of 5-amino-4-ethyl-1-phenyl-1H-pyrazol-3(2H)-one: A mixture of ethyl 2-cyanobutanoate (10.0 g, 70.8 mmol), phenylhydrazine (7.66 g, 70.8 mmol), dioxane (20 mL), EtOH (50 mL) and NaOEt (3.0 M in EtOH, 2.36 mL, 7.08 mmol) was heated at 90° C. for 7 days. After cooling, the reaction mixture was concentrated. The residue was treated with Et₂O. The solid was collected by filtration, washed with Et₂O, and dried in vacuum to give the title compound (7.50 g, 52% yield). MS (apci) m/z=204.1 (M+H).

Step B: Preparation of 1-((5-amino-4-ethyl-1-phenyl-1H-pyrazol-3-yl)oxy)-2-methylpropan-2-ol: Prepared according to the procedure described for Intermediate 203, using 5-amino-4-ethyl-1-phenyl-1H-pyrazol-3 (2H)-one as a replacement for 5-amino-1-phenyl-1H-pyrazol-3(2H)-one. MS (apci) m/z=276.2 (M+H).

Step C: Preparation of 1-((3S,4R)-4-(3,4-difluorophenyl)-1-(2-methoxyethyl) pyrrolidin-3-yl)-3-(4-ethyl-3-(2-hydroxy-2-methylpropoxy)-1-phenyl-1H-pyrazol-5-yl)urea: Prepared according to the procedure described for Example 1 using 1-((5-amino-4-ethyl-1-phenyl-1H-pyrazol-3-yl) oxy)-2-methylpropan-2-ol as a replacement for 3-tert-butyl-1-phenyl-1H-pyrazol-5-amine in Step A, and substituting (3S,4R)-4-(3,4-difluorophenyl)-1-(2-methoxyethyl)pyrrolidin-3-amine dihydrochloride for trans-1-(2-methoxyethyl)-4-phenylpyrrolidin-3-amine dihydrochloride (Preparation B) in Step B. MS (apci) m/z=558.3 (M+H).

Example 543

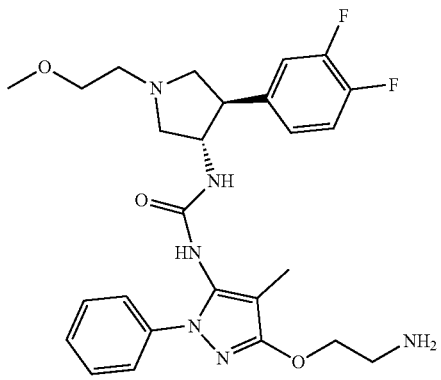 [SMILES: COCCN1C[C@@H](NC(=O)Nc2c(C)c(OCCN)nn2-c2ccccc2)[C@H](c2ccc(F)c(F)c2)C1]

1-(3-(2-aminoethoxy)-4-methyl-1-phenyl-1H-pyrazol-5-yl)-3-((3S,4R)-4-(3,4-difluorophenyl)-1-(2-methoxyethyl)pyrrolidin-3-yl)urea To a solution of 1-((3S,4R)-4-(3,4-difluorophenyl)-1-(2-methoxyethyl)pyrrolidin-3-yl)-3-(3-(2-(1,3-dioxoisoindolin-2-yl)ethoxy)-4-methyl-1-phenyl-1H-pyrazol-5-yl)urea (Example 387, 170 mg, 0.264 mmol) in 1:1 MeOH:THF (10 mL) at ambient temperature was added hydrazine monohydrate (132 mg, 2.64 mmol). The reaction was heated at 50° C. for 17 hours. After cooling, the mixture was concentrated. The residue was triturated with DCM and the solid was removed by filtration. The filtrate was concentrated to give the title compound (106 mg, 78% yield). MS (apci) m/z=515.3 (M+H).

Example 544

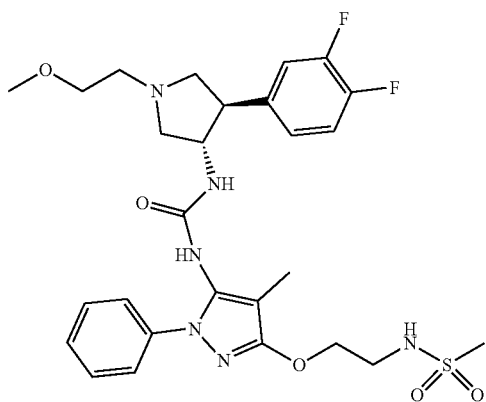

N-(2-((5-(3-((3S,4R)-4-(3,4-difluorophenyl)-1-(2-methoxyethyl)pyrrolidin-3-yl)ureido)-4-methyl-1-phenyl-1H-pyrazol-3-yl)oxy)ethyl)methanesulfonamide A mixture of 1-(3-(2-aminoethoxy)-4-methyl-1-phenyl-1H-pyrazol-5-yl)-3-((3S,4R)-4-(3,4-difluorophenyl)-1-(2-methoxyethyl)pyrrolidin-3-yl)urea (Example 543, 30 mg, 0.058 mmol), methanesulfonyl chloride (7.3 mg, 0.064 mmol) and TEA (0.016 mL, 0.12 mmol) in DCM (3 mL) was stirred at ambient temperature for 1 hour. The reaction mixture was diluted with EtOAc, washed with water and brine, dried over MgSO₄ and concentrated. The residue was purified by flash chromatography on silica gel (3% MeOH in DCM) to give the title compound (25 mg, 72% yield). MS (apci) m/z=593.2 (M+H).

Example 545

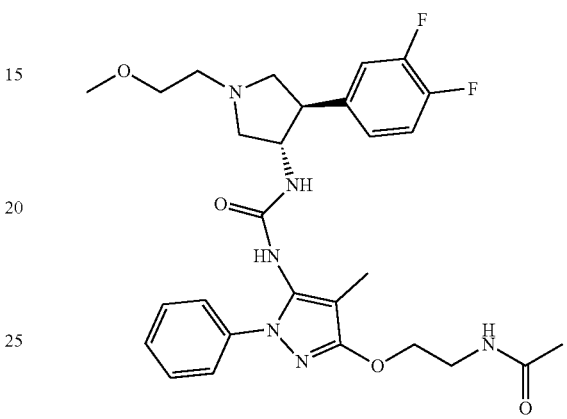

N-(2-((5-(3-((3S,4R)-4-(3,4-difluorophenyl)-1-(2-methoxyethyl)pyrrolidin-3-yl)ureido)-4-methyl-1-phenyl-1H-pyrazol-3-yl)oxy)ethyl)acetamide Prepared according to the procedure described for Example 544, using acetic anhydride as a replacement for methanesulfonyl chloride. MS (apci) m/z=557.3 (M+H).

Example 546

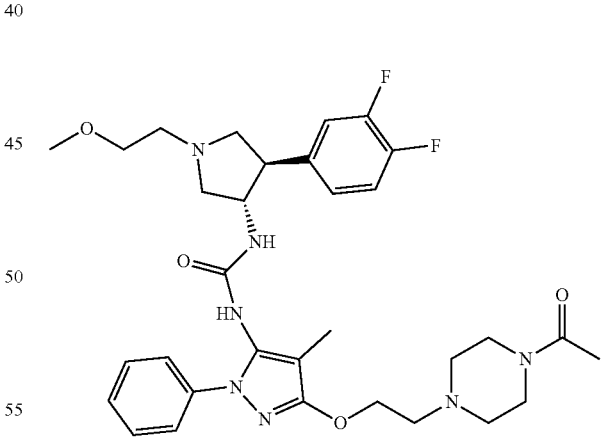

1-(3-(2-(4-acetylpiperazin-1-yl)ethoxy)-4-methyl-1-phenyl-1H-pyrazol-5-yl)-3-((3S,4R)-4-(3,4-difluorophenyl)-1-(2-methoxyethyl)pyrrolidin-3-yl)urea Prepared according to the procedure described for Example 544, using acetic anhydride as a replacement for methanesulfonyl chloride, and substituting 1-((3S,4R)-4-(3,5-difluorophenyl)-1-(2-methoxyethyl)pyrrolidin-3-yl)-3-(4-methyl-1-phenyl-3-(2-(piperazin-1-yl)ethoxy)-1H-pyrazol- 5-yl)urea trihydrochloride (Example 538) for 1-(3-(2-aminoethoxy)-4-methyl-1-phenyl-H-pyrazol-5-yl)-3-((3S,4R)-4-(3,4-difluorophenyl)-1-(2-methoxyethyl)pyrrolidin-3-yl)urea (Example 543). MS (apci) m/z=626.4 (M+H).

Example 547

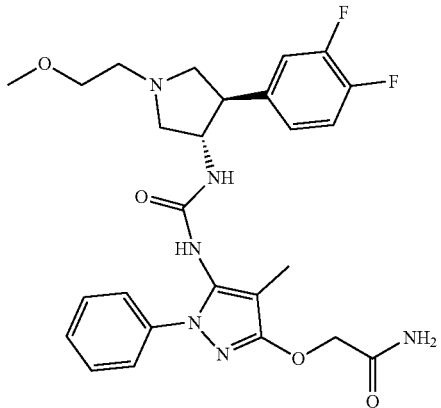 [SMILES: COCCN1C[C@@H](NC(=O)Nc2c(C)c(OCC(N)=O)nn2-c2ccccc2)[C@H](c2ccc(F)c(F)c2)C1]

2-((5-(3-((3S,4R)-4-(3,4-difluorophenyl)-1-(2-methoxyethyl)pyrrolidin-3-yl)ureido)-4-methyl-1-phenyl-1H-pyrazol-3-yl)oxy)acetamide Prepared according to the procedure described for Example 544, using ammonium chloride as a replacement for ethylamine. MS (apci) m/z=529.2 (M+H).

Example 548

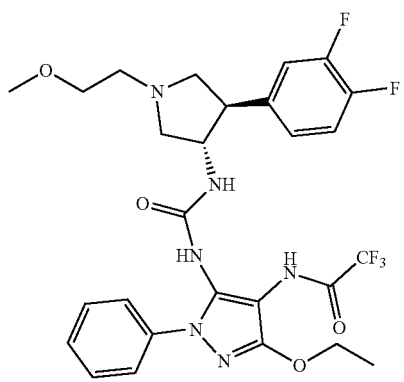 [SMILES: CCOc1nn(-c2ccccc2)c(NC(=O)N[C@@H]2CN(CCOC)C[C@H]2c2ccc(F)c(F)c2)c1NC(=O)C(F)(F)F]

N-(5-(3-((3S,4R)-4-(3,4-difluorophenyl)-1-(2-methoxyethyl)pyrrolidin-3-yl)ureido)-3-ethoxy-1-phenyl-1H-pyrazol-4-yl)-2,2,2-trifluoroacetamide Step A: Preparation of benzyl (5-amino-3-oxo-1-phenyl-2,3-dihydro-1H-pyrazol-4-yl)carbamate: Prepared according to the method described for Example 542, Step A, using ethyl 2-(benzyloxycarbonylamino)-2-cyanoacetate as a replacement for ethyl 2-cyanobutanoate. MS (apci) m/z=325.1 (M+H).

Step B: Preparation of benzyl (5-amino-3-ethoxy-1-phenyl-1H-pyrazol-4-yl)carbamate: Prepared according to the method described for Intermediate P135, Step B, using benzyl (5-amino-3-oxo-1-phenyl-2,3-dihydro-1H-pyrazol-4-yl)carbamate as a replacement for 5-amino-4-methyl-1-phenyl-1H-pyrazol-3(2H)-one. MS (apci) m/z=353.1 (M+H).

Step C: Preparation of benzyl (5-(3-((3S,4R)-4-(3,4-difluorophenyl)-1-(2-methoxyethyl)pyrrolidin-3-yl)ureido)-3-ethoxy-1-phenyl-1H-pyrazol-4-yl)carbamate: Prepared according to the procedure described for Example 151, Step B using benzyl (5-amino-3-ethoxy-1-phenyl-1H-pyrazol-4-yl)carbamate as a replacement for 2-(pyridin-4-yl)-2,4,5,6-tetrahydrocyclo-penta[c]pyrazol-3-amine, and substituting (3S,4R)-4-(3,4-difluorophenyl)-1-(2-methoxyethyl) pyrrolidin-3-amine dihydrochloride for (3S,4R)-1-(2-methoxyethyl)-4-phenylpyrrolidin-3-amine bis(2,2,2-trifluoroacetate) (Preparation D). MS (apci) m/z=635.3 (M+H).

Step D: Preparation of N-(5-(3-((3S,4R)-4-(3,4-difluorophenyl)-1-(2-methoxyethyl) pyrrolidin-3-yl)ureido)-3-ethoxy-1-phenyl-1H-pyrazol-4-yl)-2,2,2-trifluoro-acetamide: A solution of benzyl (5-(3-((3S,4R)-4-(3,4-difluorophenyl)-1-(2-methoxyethyl)pyrrolidin-3-yl)ureido)-3-ethoxy-1-phenyl-1H-pyrazol-4-yl)carbamate (75 mg, 0.12 mmol) in TFA (1 mL) was heated at 60° C. for 17 hours. The reaction mixture was concentrated under reduced pressure. 5% EtOH in toluene was added to the residue and the mixture was concentrated again to afford the crude product as a TFA salt. The crude material was taken up in EtOAc, washed with saturated aqueous NaHCO₃ solution and brine, dried over MgSO₄, and concentrated under reduced pressure. The residue was purified by column chromatography on silica gel (2% MeOH in DCM) to give the title compound (9 mg, 13% yield) as a minor product. MS (apci) m/z=597.2 (M+H).

Example 549

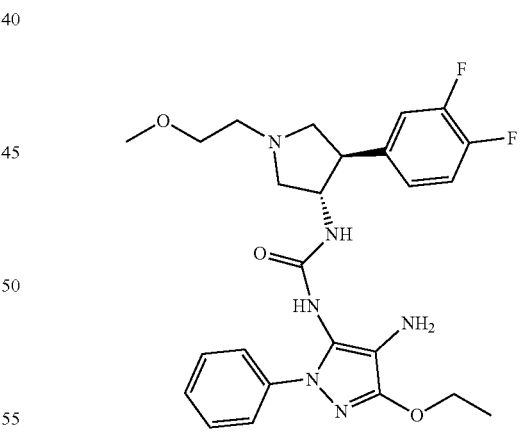

1-(4-amino-3-ethoxy-1-phenyl-1H-pyrazol-5-yl)-3-((3S,4R)-4-(3,4-difluorophenyl)-1-(2-methoxyethyl) pyrrolidin-3-yl)urea Prepared according to the procedure described for Example 548, Step C. The title compound was isolated as a major product by column chromatography on silica gel (5% MeOH in DCM). MS (apci) m/z=501.2 (M+H).

Example 550

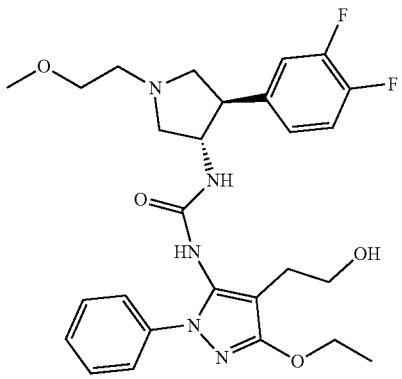 [SMILES: CCOc1nn(-c2ccccc2)c(NC(=O)N[C@@H]2CN(CCOC)C[C@H]2c2ccc(F)c(F)c2)c1CCO]

1-((3S,4R)-4-(3,4-difluorophenyvl)-1-(2-methoxy-ethyl)pyrrolidin-3-yl)-3-(3-ethoxy-4-(2-hydroxy-ethyl)-1-phenyl-1H-pyrazol-5-yl)urea Step A: Preparation of 5-amino-4-(2,2-diethoxyethyl)-1-phenyl-1H-pyrazol-3(2H)-one: Prepared according to the method described for Example 542, Step A using ethyl 2-cyano- 4,4-diethoxybutanoate as a replacement for ethyl 2-cyanobutanoate. MS (apci) m/z=292.1 (M+H).

Step B: Preparation of 4-(2,2-diethoxyethyl)-3-ethoxy-1-phenyl-1H-pyrazol-5-amine: Prepared according to the method described for Intermediate P135, Step B, using 5-amino-4-(2,2-diethoxyethyl)-1-phenyl-1H-pyrazol-3 (2H)-one as a replacement for 5-amino-4-methyl-1-phenyl-1H-pyrazol-3(2H)-one. MS (apci) m/z=320.2 (M+H).

Step C: Preparation of 1-(4-(2,2-diethoxyethyl)-3-ethoxy-1-phenyl-1H-pyrazol-5-yl)-3-((3S,4R)-4-(3,4-difluorophe-nyl)-1-(2-methoxyethyl)pyrrolidin-3-yl)urea: Prepared according to the procedure described for Example 1 using 4-(2,2-diethoxyethyl)-3-ethoxy-1-phenyl-1H-pyrazol-5-amine as a replacement for 3-tert-butyl-1-phenyl-1H-pyra-zol-5-amine in Step A, and substituting (3S,4R)-4-(3,4-difluorophenyl)-1-(2-methoxyethyl)pyrrolidin-3-amine dihydrochloride for trans-1-(2-methoxyethyl)-4-phenylpyr-rolidin-3-amine dihydrochloride (Preparation B) in step B. MS (apci) m/z=602.3 (M+H).

Step D: Preparation of 1-((3S,4R)-4-(3,4-difluorophe-nyl)-1-(2-methoxyethyl) pyrrolidin-3-yl)-3-(3-ethoxy-4-(2-oxoethyl)-1-phenyl-1H-pyrazol-5-yl)urea: A mixture of 1-(4-(2,2-diethoxyethyl)-3-ethoxy-1-phenyl-1H-pyrazol-5-yl)-3-((3S,4R)-4-(3,4-difluorophenyl)-1-(2-methoxyethyl) pyrrolidin-3-yl)urea (0.13 g, 0.22 mmol), acetic acid (1 mL) and water (0.2 mL) was stirred at ambient temperature for 17 hours. The reaction was not complete by HPLC. Two drops of 30 wt. % HBr in AcOH solution was added. The reaction mixture was stirred for additional 17 hours. The reaction was quenched by the addition of saturated aqueous NaHCO₃ solution, extracted with EtOAc, washed with saturated aque-ous NaHCO₃ (2×) and brine, dried over MgSO₄, and con-centrated to give the title compound which was used in next step without further purification. MS (apci) m/z=528.2 (M+H).

Step E: Preparation of 1-((3S,4R)-4-(3,4-difluorophenyl)-1-(2-methoxyethyl)pyrrolidin-3-yl)-3-(3-ethoxy-4-(2-hy-droxyethyl)-1-phenyl-1H-pyrazol-5-yl)urea: To a stirred solution of 1-((3S,4R)-4-(3,4-difluorophenyl)-1-(2-methoxyethyl)pyrrolidin-3-yl)-3-(3-ethoxy-4-(2-oxoethyl)-1-phenyl-1H-pyrazol-5-yl)urea (40 mg, 0.076 mmol) in THF (1 mL) was added dropwise a 2.0 M solution of LiBH₄ in THF (0.038 mL, 0.076 mmol) at 0° C. The reaction was allowed to warm to ambient temperature and stirred for 3 hours. The reaction was diluted with EtOAc, washed with 0.1 N HCl, saturated aqueous NaHCO₃ solution and brine, dried over MgSO₄, and concentrated. The residue was purified by flash chromatography on silica gel (4% MeOH in DCM) to give the title compound (4 mg, 10% yield). MS (apci) m/z=530.3 (M+H).

Example 551

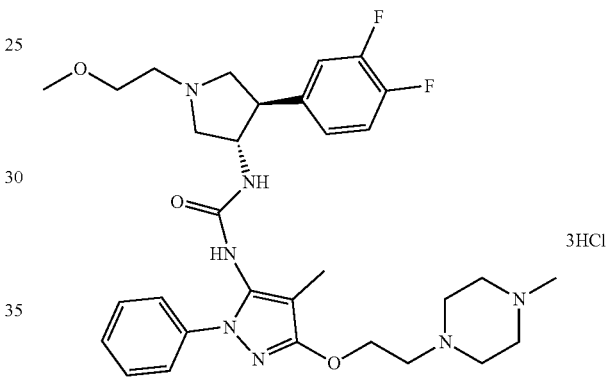

1-((3S,4R)-4-(3,4-difluorophenyl)-1-(2-methoxy-ethyl)pyrrolidin-3-yl)-3-(4-methyl-3-(2-(4-methyl-piperazin-1-yl)ethoxy)-1-phenyl-1H-pyrazol-5-yl) urea trihydrochloride To a mixture of 1-((3S,4R)-4-(3,5-difluorophenyl)-1-(2-methoxyethyl)pyrrolidin-3-yl)-3-(4-methyl-1-phenyl-3-(2-(piperazin-1-yl)ethoxy)-1H-pyrazol-5-yl)urea trihydrochlo-ride (Example 538, 50 mg, 0.086 mmol), NaBH(OAc)₃ (73 mg, 0.34 mmol) and THF (2 mL) was added formaldehyde (37% aqueous solution, 14 mg, 0.17 mmol) at 0° C. The reaction mixture was warmed to ambient temperature and stirred for 17 hours. The mixture was diluted with H₂O (20 mL) and extracted with DCM. The combined organic layers were dried over MgSO₄ and concentrated. The residue was purified by flash chromatography on silica gel (3% 7 N ammonia-MeOH in DCM) to give the free base, which was treated with 2 N HCl in ether (3 drops). The mixture was concentrated and triturated with Et₂O to give the title compound (22 mg, 43% yield). MS (apci) m/z=598.3 (M+H).

Example 552

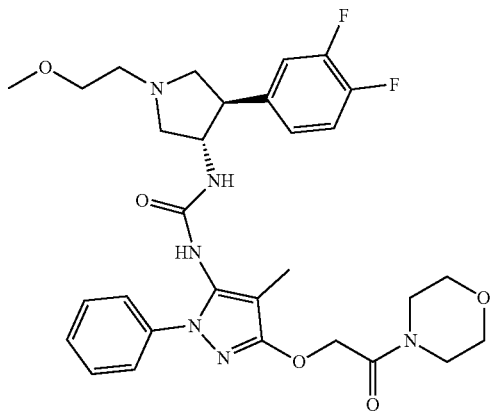 [SMILES: COCCN1C[C@@H](NC(=O)Nc2c(C)c(OCC(=O)N3CCOCC3)nn2-c2ccccc2)[C@H](c2ccc(F)c(F)c2)C1]

1-((3S,4R)-4-(3,4-difluorophenyvl)-1-(2-methoxy-ethyl)pyrrolidin-3-yl)-3-(4-methyl-3-(2-morpholino-2-oxoethoxy)-1-phenyl-1H-pyrazol-5-yl)urea Prepared according to the procedure described for Example 541, using morpholine as a replacement for ethylamine. MS (apci) m/z=599.3 (M+H).

Example 553

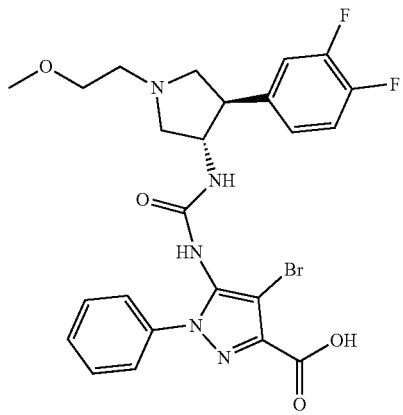 [SMILES: COCCN1C[C@@H](NC(=O)Nc2c(Br)c(C(=O)O)nn2-c2ccccc2)[C@H](c2ccc(F)c(F)c2)C1]

4-bromo-5-(3-((3S,4R)-4-(3,4-difluorophenyl)-1-(2-methoxyethyl)pyrrolidin-3-yl)ureido)-1-phenyl-1H-pyrazole-3-carboxylic acid Prepared according to the procedure described for Example 540, using ethyl 4-bromo-5-(3-((3S,4R)-4-(3,4-difluorophenyl)-1-(2-methoxyethyl)pyrrolidin-3-yl)ureido)-1-phenyl-1H-pyrazole-3-carboxylate (Example 381) as a replacement for ethyl 2-((5-(3-((3S,4R)-4-(3,4-difluorophenyl)-1-(2-methoxyethyl)pyrrolidin-3-yl)ureido)-4-methyl-1-phenyl-1H-pyrazol-3-yl)oxy)acetate (Example 361). MS (apci) m/z=564.2 (M+H).

Example 554

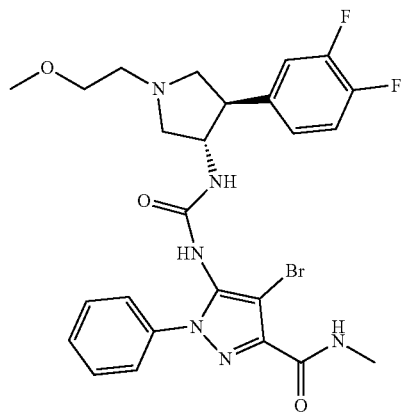 [SMILES: CNC(=O)c1nn(-c2ccccc2)c(NC(=O)N[C@@H]2CN(CCOC)C[C@H]2c2ccc(F)c(F)c2)c1Br]

4-bromo-5-(3-((3S,4R)-4-(3,4-difluorophenyl)-1-(2-methoxyethyl)pyrrolidin-3-yl)ureido)-N-methyl-1-phenyl-1H-pyrazole-3-carboxamide Prepared according to the procedure described for Example 541 using 4-bromo-5-(3-((3S,4R)-4-(3,4-difluorophenyl)-1-(2-methoxyethyl)pyrrolidin-3-yl)ureido)-1-phenyl-1H-pyrazole-3-carboxylic acid (Example 553) as a replacement for 2-(5-(3-((3S,4R)-4-(3,4-difluorophenyl)-1-(2-methoxyethyl)pyrrolidin-3-yl)ureido)-4-methyl-1-phenyl-1H-pyrazol-3-yloxy)acetic acid (Example 540), and substituting methylamine for ethylamine. MS (apci) m/z=577.1 (M+H).

Example 555

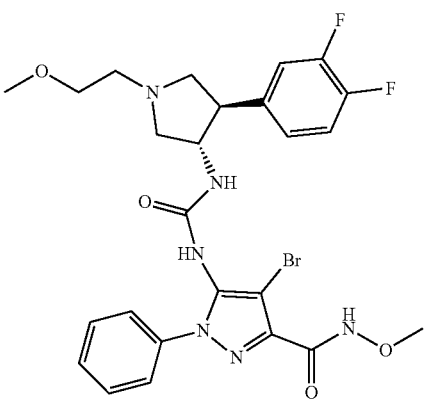

4-bromo-5-(3-((3S,4R)-4-(3,4-difluorophenyl)-1-(2-methoxyethyl)pyrrolidin-3-yl)ureido)-N-methoxy-1-phenyl-1H-pyrazole-3-carboxamide Prepared according to the procedure described for Example 541, using 4-bromo-5-(3-((3S,4R)-4-(3,4-difluorophenyl)-1-(2-methoxyethyl)pyrrolidin-3-yl)ureido)-1-phenyl-1H-pyrazole-3-carboxylic acid (Example 553) as a replacement for 2-(5-(3-((3S,4R)-4-(3,4-difluorophenyl)-1-(2-methoxyethyl)pyrrolidin-3-yl)ureido)-4-methyl-1-phenyl-1H-pyrazol-3-yloxy)acetic acid (Example 540), and substituting O-methylhydroxylamine hydrochloride for ethylamine. MS (apci) m/z=593.1 (M+H).

Example 556

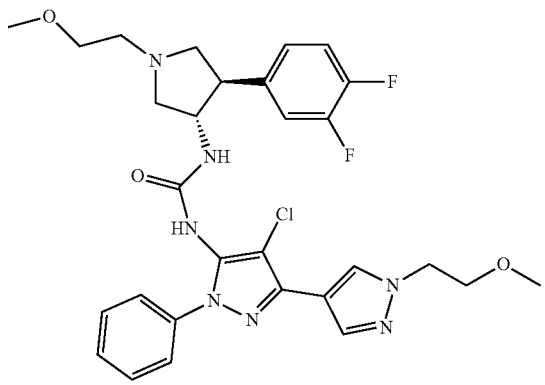

1-(4-chloro-1'-(2-methoxyethyl)-1-phenyl-1H, 1'H-[3,4'-bipyrazol]-5-yl)-3-((3S,4R)-4-(3,4-difluorophenyl)-1-(2-methoxyethyl)pyrrolidin-3-yl)urea Step A: Preparation of ethyl 1-(2-methoxyethyl)-1H-pyrazole-4-carboxylate: A mixture of ethyl 1H-pyrazole-4-carboxylate (5.00 g, 35.7 mmol), DMF (120 mL), K₂CO₃ (19.7 g, 143 mmol) and 1-bromo-2-methoxyethane (9.92 g, 71.4 mmol) was stirred at 80° C. for 4 hours. After cooling, the reaction mixture was poured into water and extracted with EtOAc. The combined extracts were washed with water and brine, dried and concentrated. The residue was purified by column chromatography (4:1 hexanes/EtOAc) to give the title compound (5.57 g, 79% yield) as a colorless oil. MS (apci) m/z=199.1 (M+H).

Step B: Preparation of 1'-(2-methoxyethyl)-1-phenyl-1H, 1'H-[3,4'-bipyrazol]-5-amine: Prepared according to the method described for Intermediate P109, replacing methyl 2-methoxyacetate with ethyl 1-(2-methoxyethyl)-1H-pyrazole-4-carboxylate in Step A. MS (apci) m/z=284.1 (M+H).

Step C: Preparation of 1-((3S,4R)-4-(3,4-difluorophenyl)-1-(2-methoxyethyl) pyrrolidin-3-yl)-3-(1'-(2-methoxyethyl)-1-phenyl-1H, 1'H-3,4'-bipyrazol-5-yl)urea: Prepared according to the procedure described for Example 1 using 1'-(2-methoxyethyl)-1-phenyl-1H,1'H-[3,4'-bipyrazol]-5-amine as a replacement for 3-tert-butyl-1-phenyl-1H-pyrazol-5-amine in Step A, and substituting (3S,4R)-4-(3,4-difluorophenyl)-1-(2-methoxyethyl)pyrrolidin-3-amine dihydrochloride for trans-1-(2-methoxyethyl)-4-phenylpyrrolidin-3-amine dihydrochloride (Preparation B) in Step B. MS (apci) m/z=566.2 (M+H).

Step D: Preparation of 1-(4-chloro-1'-(2-methoxyethyl)-1-phenyl-1H, 1'H-[3,4'-bipyrazol]-5-yl)-3-((3S,4R)-4-(3,4-difluorophenyl)-1-(2-methoxyethyl)pyrrolidin-3-yl)urea: To a solution of 1-((3S,4R)-4-(3,4-difluorophenyl)-1-(2-methoxyethyl)pyrrolidin-3-yl)-3-(1'-(2-methoxyethyl)-1-phenyl-1H,1'H-3,4'-bipyrazol-5-yl)urea (40 mg, 0.071 mmol) in DCM (1 mL) was added N-chlorosuccinimide (11 mg, 0.085 mmol) followed by catalytic amount of pyridinium 4-methylbenzenesulfonate (PPTS). The mixture was stirred at ambient temperature overnight. Additional N-chlorosuccinimide (4 mg) was added. The reaction was stirred at ambient temperature for 4 additional hours. The reaction mixture was partitioned between DCM and saturated aqueous NaHCO₃ solution. The aqueous layer was extracted with DCM. The combined organic layers were washed with brine, dried and concentrated. The residue was purified by reverse phase preparative HPLC (5-95% acetonitrile in water) to give the title compound (15 mg, 35% yield) as a white solid. MS (apci) m/z=600.2 (M+H).

Example 557

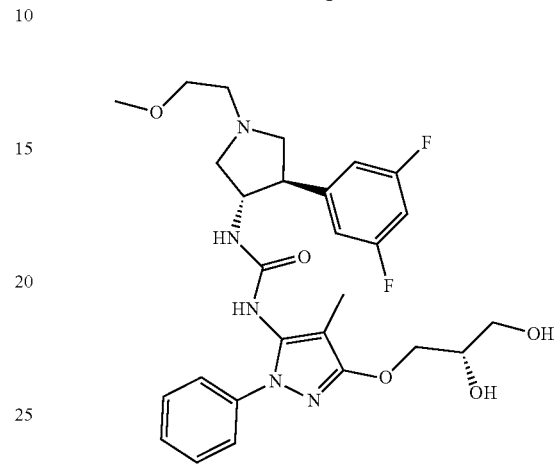

1-((3S,4R)-4-(3,5-difluorophenyl)-1-(2-methoxyethyl)pyrrolidin-3-yl)-3-(3-((S)-2,3-dihydroxypropoxy)-4-methyl-1-phenyl-1H-pyrazol-5-yl)urea Prepared from 1-((3S,4R)-4-(3,5-difluorophenyl)-1-(2-methoxyethyl) pyrrolidin-3-yl)-3-(3-(((R)-2,2-dimethyl-1,3-dioxolan-4-yl)methoxy)-4-methyl-1-phenyl-1H-pyrazol-5-yl)urea (Example 392; 38.0 mg, 0.065 mmol) according to the procedure described for Example 176, to provide title compound as a white solid (32 mg, 90% yield). MS (apci) m/z=546.2 (M+H).

Example 558

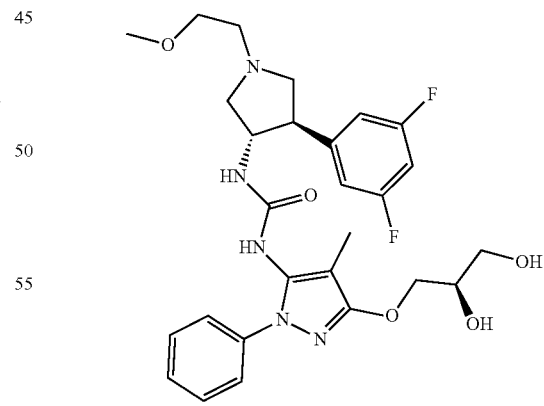

1-((3S,4R)-4-(3,5-difluorophenyl)-1-(2-methoxyethyl)pyrrolidin-3-yl)-3-(3-((R)-2,3-dihydroxypropoxy)-4-methyl-1-phenyl-1H-pyrazol-5-yl)urea Prepared from 1-((3S,4R)-4-(3,5-difluorophenyl)-1-(2-methoxyethyl) pyrrolidin-3-yl)-3-(3-(((S)-2,2-dimethyl-1,3- dioxolan-4-yl)methoxy)-4-methyl-1-phenyl-1H-pyrazol-5-yl)urea (Example 393; 82.0 mg, 0.130 mmol) according to the procedure described for Example 176, to provide title compound as a white solid (67 mg, 97% yield). MS (apci) m/z=546.2 (M+H).

Example 559

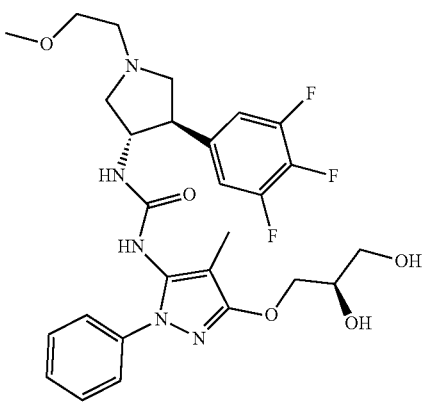 [SMILES: COCCN1C[C@@H](NC(=O)Nc2c(C)c(OC[C@H](O)CO)nn2-c2ccccc2)[C@H](c2cc(F)c(F)c(F)c2)C1]

1-(3-((R)-2,3-dihydroxypropoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea Prepared from 1-(3-(((S)-2,2-dimethyl-1,3-dioxolan-4-yl)methoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea (Example 398; 90.0 mg, 0.149 mmol) according to the procedure described for Example 176, to provide title compound as a white solid (83 mg, 99% yield). MS (apci) m/z=564.2 (M+H).

Example 560

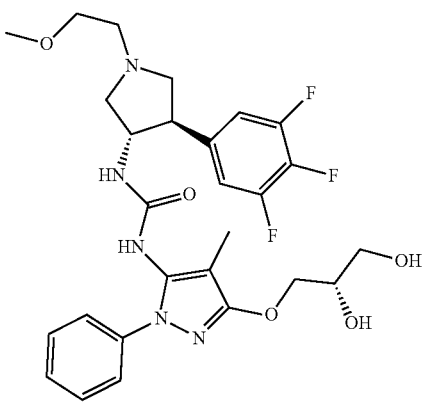 [SMILES: COCCN1C[C@@H](NC(=O)Nc2c(C)c(OC[C@@H](O)CO)nn2-c2ccccc2)[C@H](c2cc(F)c(F)c(F)c2)C1]

1-(3-((S)-2,3-dihydroxypropoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea Prepared from 1-(3-(((R)-2,2-dimethyl-1,3-dioxolan-4-yl)methoxy)-4-methyl-1-phenyl-1H-pyrazol-5-yl)-3-((3S,4R)-1-(2-methoxyethyl)-4-(3,4,5-trifluorophenyl) pyrrolidin-3-yl)urea (Example 399; 64.0 mg, 0.096 mmol) according to the procedure described for Example 176, to provide title compound as a white solid (44 mg, 81% yield). MS (apci) m/z=564.2 (M+H).

Example 561

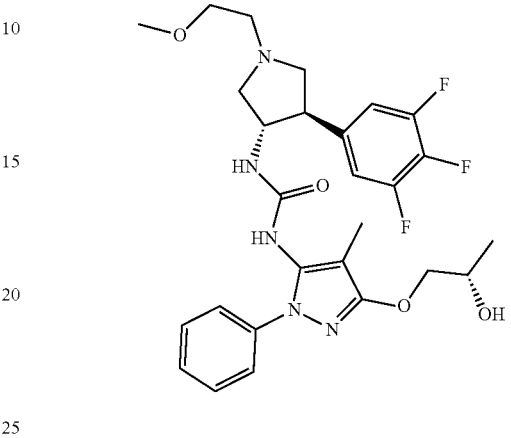

1-(3-((S)-2-hydroxypropoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea Prepared from 1-(3-((S)-2-(tert-butyldimethylsilyloxy)propoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea (Example 400, 64.0 mg, 0.097 mmol) according to the procedure described for Example 176, to provide title compound as a white solid (44 mg, 83% yield). MS (apci) m/z=548.3 (M+H).

Example 562

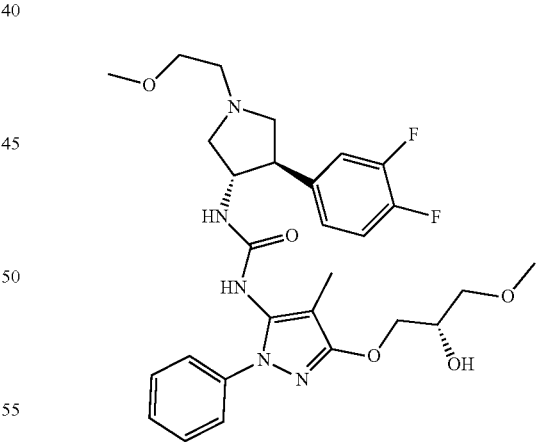

1-((3S,4R)-4-(3,4-difluorophenyl)-1-(2-methoxyethyl)pyrrolidin-3-yl)-3-(3-((S)-2-hydroxy-3-methoxypropoxy)-4-methyl-1-phenyl-1H-pyrazol-5-yl)urea To a solution of 1-(3-((S)-2-(tert-butyldimethylsilyloxy)-3-methoxypropoxy)-4-methyl-1-phenyl-1H-pyrazol-5-yl)-3-((3S,4R)-4-(3,4-difluorophenyl)-1-(2-methoxyethyl) pyrrolidin-3-yl)urea (Example 402, 110 mg, 0.163 mmol) in THF (5 mL) was added 1M HCl (5 mL) and the mixture stirred at ambient temperature for 90 minutes. The mixture was concentrated to 3 mL and diluted with 1M HCl (3 mL). The mixture washed with Et₂O (2×) and the aqueous solution was treated with 50% NaOH syrup to pH=7. NaCl added to saturation and the mixture was extracted with EtOAc (3×). The combined extracts were dried over MgSO₄, filtered through packed Celite® (EtOAc elution) and concentrated to give a white solid. The solid was pulverized and dried in vacuum to furnish the title compound as a white powder (64 mg, 70%). MS (apci) m/z=560.3 (M+H).

Example 563

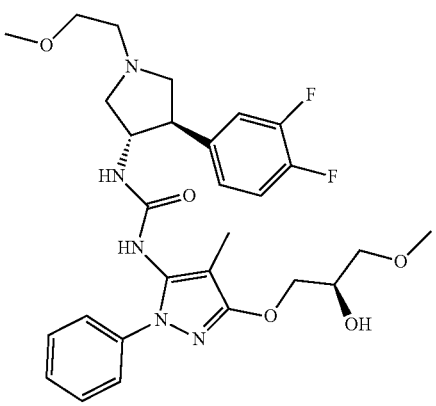

1-((3S,4R)-4-(3,4-difluorophenyl)-1-(2-methoxyethyl)pyrrolidin-3-yl)-3-(3-((R)-2-hydroxy-3-methoxypropoxy)-4-methyl-1-phenyl-1H-pyrazol-5-yl)urea Prepared from 1-(3-((R)-2-(tert-butyldimethylsilyloxy)-3-methoxypropoxy)-4-methyl-1-phenyl-1H-pyrazol-5-yl)-3-((3S,4R)-4-(3,4-difluorophenyl)-1-(2-methoxyethyl)pyrrolidin-3-yl)urea (prepared according to the method of Example 402, 104 mg, 0.154 mmol) according to the procedure described for Example 564. The title compound was obtained as a white solid (76 mg, 88% yield). MS (apci) m/z=560.3 (M+H).

Example 564

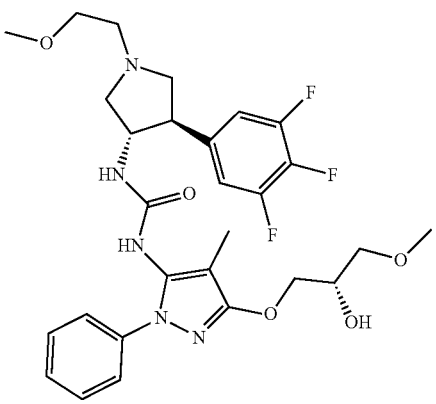

1-(3-((S)-2-hydroxy-3-methoxypropoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea Step A: 1-(3-((S)-2-(tert-butyldimethylsilyloxy)-3-methoxypropoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea: Prepared according to the procedure described for Example 1 using the appropriate starting materials. The title compound was obtained as a colorless wax (122 mg, 88% yield). MS (apci) m/z=692.3 (M+H).

Step B: 1-(3-((S)-2-hydroxy-3-methoxypropoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea: To a solution of 1-(3-((S)-2-(tert-butyldimethylsilyloxy)-3-methoxypropoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea (120 mg, 0.173 mmol) in THF (5 mL) was added 1M HCl (5 mL) and the mixture stirred at ambient temperature for 3.5 hours. The mixture was concentrated to 5 mL and washed with Et₂O (3×). The aqueous solution was treated with 50% NaOH syrup to pH=7. NaCl added to saturation and mixture extracted with EtOAc (3×). The combined extracts were dried over MgSO₄ and filtered through packed Celite®, eluting with EtOAc. The filtrate was concentrated and the residual white solid was washed with Et₂O (3×) and dried in vacuum to furnished the title compound (76 mg, 76%). MS (apci) m/z=578.3 (M+H).

Example 565

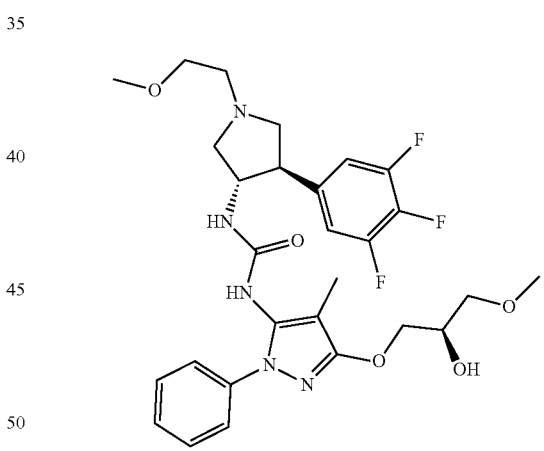

1-(3-((R)-2-hydroxy-3-methoxypropoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea Step A: 1-(3-((R)-2-(tert-butyldimethylsilyloxy)-3-methoxypropoxy)-4-methyl-1-phenyl-1H-pyrazol-5-yl)-3-((3S,4R)-1-(2-methoxyethyl)-4-(3,4,5-trifluorophenyl) pyrrolidin-3-yl)urea: Prepared according to the procedure described for Example 1 using the appropriate starting materials. The compound was obtained as a colorless wax (131 mg, 95% yield). MS (apci) m/z=692.3 (M+H).

Step B: 1-(3-((R)-2-hydroxy-3-methoxypropoxy)-4-methyl-1-phenyl-1H-pyrazol-5-yl)-3-((3S,4R)-1-(2- methoxyethyl)-4-(3,4,5-trifluorophenyl)pyrrolidin-3-yl) urea: Utilizing 1-(3-((R)-2-hydroxy-3-methoxypropoxy)-4-methyl-1-phenyl-1H-pyrazol-5-yl)-3-((3S,4R)-1-(2-methoxyethyl)-4-(3,4,5-trifluorophenyl)pyrrolidin-3-yl)urea in the procedure described for Example 563, Step B, the title compound was obtained as a white solid (77 mg, 73%). MS (apci) m/z=578.3 (M+H).

Example 566

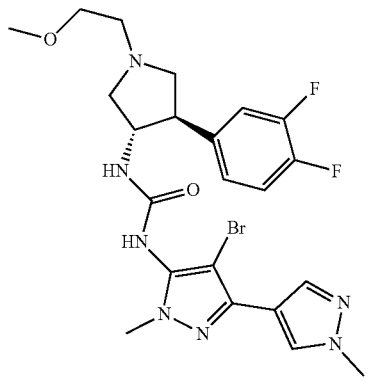

1-(4-bromo-1,1'-dimethyl-1H, 1'H-[3,4'-bipyrazol]-5-yl)-3-((3S,4R)-4-(3,4-difluorophenyl)-1-(2-methoxyethyl)pyrrolidin-3-yl)urea Step A: phenyl 1,1'-dimethyl-1H, 1'H-3,4'-bipyrazol-5-ylcarbamate: A fine suspension of 1,1'-dimethyl-1H, 1'H-3,4'-bipyrazol-5-amine (Intermediate P114, 159 mg, 0.897 mmol) in EtOAc (4 mL) was cooled to 0° C. NaOH (987 µL, 1.97 mmol) and phenylchloroformate (135 µL, 1.08 mmol) were added sequentially and the mixture was stirred for 5 minutes. The mixture was allowed to reach ambient temperature and stirred for 24 hours. Mixture washed with H$_2$O (2×) and saturated NaCl. The solution was dried over MgSO$_4$/activated carbon and was eluted through a SiO$_2$ plug eluting with EtOAc. The filtrate was concentrated, and the residue was washed with hexanes (3×) and dried in vacuum to furnish the title compound as a colorless wax (232 mg, 87%). MS (apci) m/z=298.1 (M+H).

Step B: 1-(4-bromo-1,1'-dimethyl-1H, 1'H-[3,4'-bipyrazol]-5-yl)-3-((3S,4R)-4-(3,4-difluorophenyl)-1-(2-methoxyethyl)pyrrolidin-3-yl)urea: A solution of phenyl 1,1'-dimethyl-1H, 1'H-3,4'-bipyrazol-5-ylcarbamate (44.6 mg, 0.150 mmol) in dry CH$_2$Cl$_2$ (1.0 mL) was cooled to 0° C. and N-bromosuccinimide (28.0 mg, 0.157 mmol) was added in one portion. The mixture was stirred at 0° C. for 5 minutes, allowed to reach ambient temperature and stirred until complete consumption of starting material was observed by TLC analysis (16 hours). To the mixture was added (3S,4R)-4-(3,4-difluorophenyl)-1-(2-methoxyethyl)pyrrolidin-3-amine dihydrochloride (Preparation F, 59.3 mg, 0.180 mmol) followed by DIEA (78.4 µL, 0.450 mmol) and the mixture stirred at ambient temperature for 3 hours. The mixture was diluted with CH$_2$Cl$_2$ (3 mL) and was washed with H$_2$O (3×). The CH$_2$Cl$_2$ solution was dried over Na$_2$SO$_4$ and the dried solution was eluted through a short SiO$_2$ column eluting with CH$_2$Cl$_2$, EtOAc and 10% (9:1 MeOH/NH$_4$OH)/EtOAc. The product pools were combined and concentrated to give a colorless glass. The glass was dissolved in EtOAc and the cloudy solution and filtered through packed Celite®. The filtrate was concentrated and the residual white solid was washed with Et$_2$O and dried in vacuum to afford the title compound (57 mg, 71%). MS (apci) m/z=538.2 (M+H).

Example 567

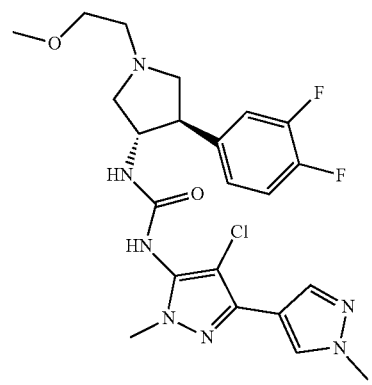

1-(4-chloro-1,1'-dimethyl-1H, 1'H-[3,4'-bipyrazol]-5-yl)-3-((3S,4R)-4-(3,4-difluorophenyl)-1-(2-methoxyethyl)pyrrolidin-3-yl)urea The title compound was prepared using the procedure outlined for Example 566 substituting N-bromosuccinimide with N-chlorosuccinimide in Step B. The compound was isolated as a white solid (51 mg, 69%). MS (apci) m/z=494.1 (M+H).

Example 568

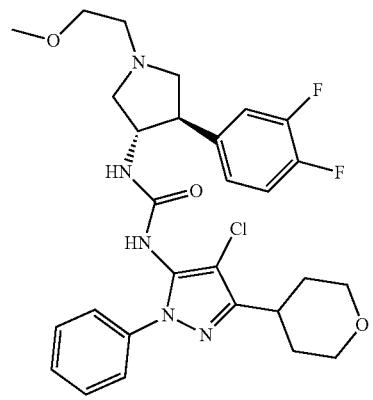

1-(4-chloro-1-phenyl-3-(tetrahydro-2H-pyran-4-yl)-1H-pyrazol-5-yl)-3-((3S,4R)-4-(3,4-difluorophenyl)-1-(2-methoxyethyl)pyrrolidin-3-yl)urea A solution of phenyl 1-phenyl-3-(tetrahydro-2H-pyran-4-yl)-1H-pyrazol-5-ylcarbamate (90.9 mg, 0.250 mmol) in dry CH$_2$Cl$_2$ (1.0 mL) was treated with N-chlorosuccinimide (37.5 mg, 0.275 mmol) in one portion and the mixture was stirred at ambient temperature until complete by TLC analysis (72 hours). To the mixture was added (3S,4R)-4-(3,4-difluorophenyl)-1-(2-methoxyethyl)pyrrolidin-3-amine dihydrochloride (Preparation F, 98.8 mg, 0.300 mmol) followed by DIEA (131 μL, 0.750 mmol) and the mixture was stirred at ambient temperature for 5 hours. The mixture was diluted with CH$_2$Cl$_2$ (3 mL) and was washed with H$_2$O (2×), 1M NaOH (2×) and H$_2$O. The CH$_2$Cl$_2$ solution was dried over Na$_2$SO$_4$/activated carbon and the dried solution was filtered through packed Celite® and concentrated. The residue was purified on a SiO$_2$ column using step gradient elution: 50% EtOAc-hexanes, EtOAc, and then 5% MeOH/EtOAc. The combined product pools were concentrated to give a colorless syrup. The syrup was treated with 50% Et$_2$O-hexanes and sonicated until granular white suspension formed. The solvent was decanted, the solid was washed with 50% Et2O-hexanes (2×) and dried in vacuum to afford the title compound as a white solid (106 mg, 76%). MS (apci) m/z=560.3 (M+H).

The compounds in the following table were prepared according to the method of Example 568 using the appropriate phenylcarbamate and aminopyrrolidine intermediates.

| Ex. # | Structure | Name | Data |
|---|---|---|---|
| 569 | 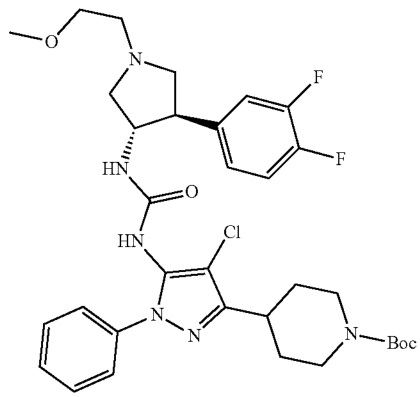 [SMILES: COCCN1C[C@@H](NC(=O)Nc2c(Cl)c(C3CCN(C(=O)OC(C)(C)C)CC3)nn2-c2ccccc2)[C@H](c2ccc(F)c(F)c2)C1] | Tert-butyl 4-(4-chloro-5-(3-((3S,4R)-4-(3,4-difluorophenyl)-1-(2-methoxyethyl)pyrrolidin-3-yl)ureido)-1-phenyl-1H-pyrazol-3-yl)piperidine-1-carboxylate | MS (apci) m/z = 659.3 (M + H). |
| 570 | 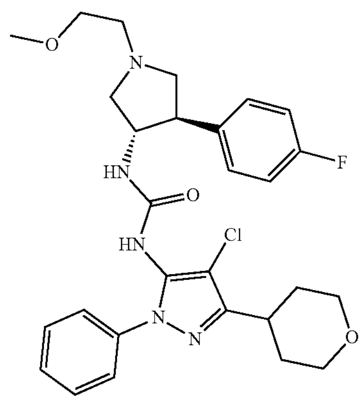 [SMILES: COCCN1C[C@@H](NC(=O)Nc2c(Cl)c(C3CCOCC3)nn2-c2ccccc2)[C@H](c2ccc(F)cc2)C1] | 1-(4-chloro-1-phenyl-3-(tetrahydro-2H-pyran-4-yl)-1H-pyrazol-5-yl)-3-((3S,4R)-4-(4-fluorophenyl)-1-(2-methoxyethyl)pyrrolidin-3-yl)urea | MS (apci) m/z = 542.3 (M + H). |
| 571 | 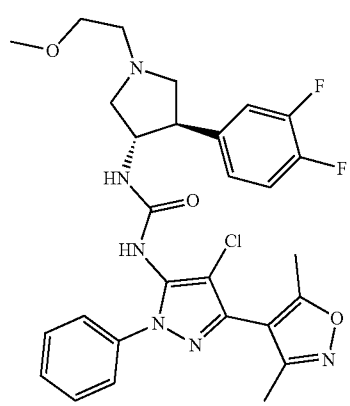 [SMILES: COCCN1C[C@@H](NC(=O)Nc2c(Cl)c(-c3c(C)noc3C)nn2-c2ccccc2)[C@H](c2ccc(F)c(F)c2)C1] | 1-(4-chloro-3-(3,5-dimethylisoxazol-4-yl)-1-phenyl-1H-pyrazol-5-yl)-3-((3S,4R)-4-(3,4-difluorophenyl)-1-(2-methoxyethyl)pyrrolidin-3-yl)urea | MS (apci) m/z = 571.3 (M + H). |

| Ex. # | Structure | Name | Data |
|---|---|---|---|
| 572 | 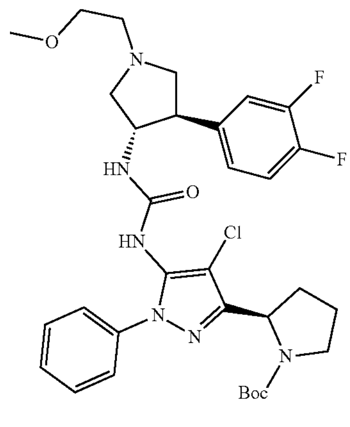 [SMILES: COCCN1C[C@@H](NC(=O)Nc2c(Cl)c([C@H]3CCCN3C(=O)OC(C)(C)C)nn2-c2ccccc2)[C@H](c2ccc(F)c(F)c2)C1] | (R)-tert-butyl 2-(4-chloro-5-(3-((3S,4R)-4-(3,4-difluorophenyl)-1-(2-methoxyethyl)pyrrolidin-3-yl)ureido)-1-phenyl-1H-pyrazol-3-yl)pyrrolidine-1-carboxylate | MS (apci) m/z = 645.3 (M + H). |
| 573 | 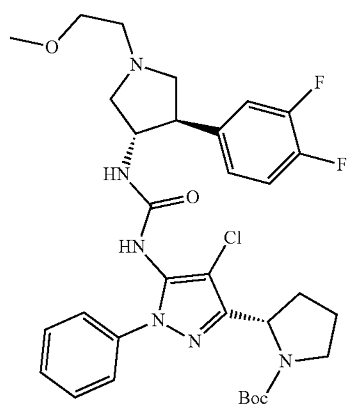 [SMILES: COCCN1C[C@@H](NC(=O)Nc2c(Cl)c([C@@H]3CCCN3C(=O)OC(C)(C)C)nn2-c2ccccc2)[C@H](c2ccc(F)c(F)c2)C1] | (S)-tert-butyl 2-(4-chloro-5-(3-((3S,4R)-4-(3,4-difluorophenyl)-1-(2-methoxyethyl)pyrrolidin-3-yl)ureido)-1-phenyl-1H-pyrazol-3-yl)pyrrolidine-1-carboxylate | MS (esi) m/z = 645.1 (M + H). |

Example 574

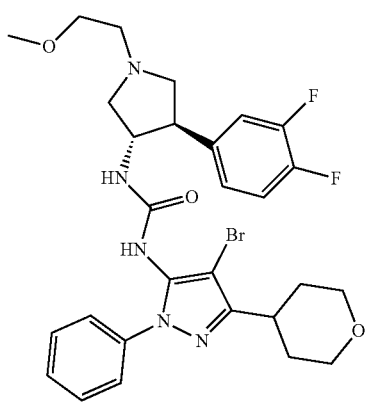 [SMILES: COCCN1C[C@@H](NC(=O)Nc2c(Br)c(C3CCOCC3)nn2-c2ccccc2)[C@H](c2ccc(F)c(F)c2)C1]

1-(4-bromo-1-phenyl-3-(tetrahydro-2H-pyran-4-yl)-1H-pyrazol-5-yl)-3-((3S,4R)-4-(3,4-difluorophenyl)-1-(2-methoxyethyl)pyrrolidin-3-yl)urea A solution of phenyl 1-phenyl-3-(tetrahydro-2H-pyran-4-yl)-1H-pyrazol-5-ylcarbamate (90.9 mg, 0.250 mmol) in dry CH₂Cl₂ (1.0 mL) was treated with N-bromosuccinimide (53.4 mg, 0.300 mmol) in one portion and mixture was stirred at ambient temperature until complete by TLC analysis (4 hours). To the mixture was added (3S,4R)-4-(3,4-difluorophenyl)-1-(2-methoxyethyl)pyrrolidin-3-amine dihydrochloride (Preparation F, 98.8 mg, 0.300 mmol) followed by DIEA (131 μL, 0.750 mmol) and the mixture stirred at ambient temperature for 3 hours. The mixture was diluted with CH₂Cl₂ (3 mL) and was washed with H₂O (2×), 1M NaOH (2×) and H₂O. The CH₂Cl₂ solution was dried over Na₂SO₄/activated carbon and the dried solution was filtered through packed Celite® and concentrated. The residue was purified on a SiO₂ column eluting with a step gradient: 50% EtOAc-hexanes, EtOAc then 5% MeOH/EtOAc. The combined product pools were concentrated to give a colorless glass. The glass was dissolved in Et₂O and treated with hexanes until a suspension formed. The suspension was concentrated to provide the title compound as a white solid that was dried in vacuum (142 mg, 94%). MS (apci) m/z=604.2 (M+H).

The compounds in the following table were prepared according to the method of Example 574 using the appropriate phenylcarbamate and aminopyrrolidine intermediates.

| Ex. # | Structure | Name | MS (apci) m/z |
|---|---|---|---|
| 575 | 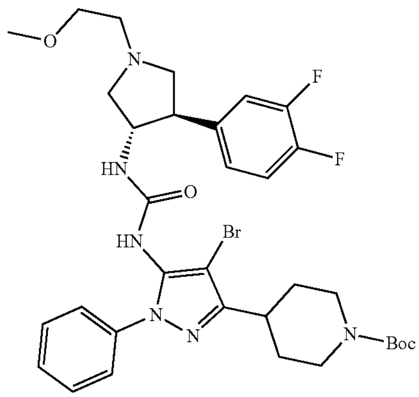 [SMILES: COCCN1C[C@@H](NC(=O)Nc2c(Br)c(C3CCN(C(=O)OC(C)(C)C)CC3)nn2-c2ccccc2)[C@H](c2ccc(F)c(F)c2)C1] | Tert-butyl 4-(4-bromo-5-(3-((3S,4R)-4-(3,4-difluorophenyl)-1-(2-methoxyethyl)pyrrolidin-3-yl)ureido)-1-phenyl-1H-pyrazol-3-yl)piperidine-1-carboxylate | 703.5 (M + H) |
| 576 | 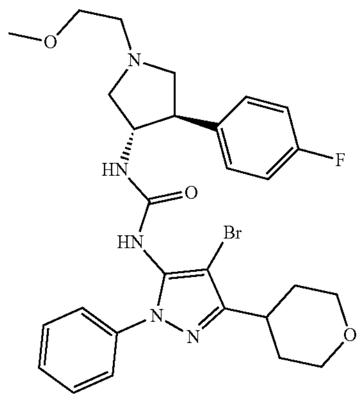 | 1-(4-bromo-1-phenyl-3-(tetrahydro-2H-pyran-4-yl)-1H-pyrazol-5-yl)-3-((3S,4R)-4-(4-fluorophenyl)-1-(2-methoxyethyl)pyrrolidin-3-yl)urea | 586.2 (M + H) |
| 577 | 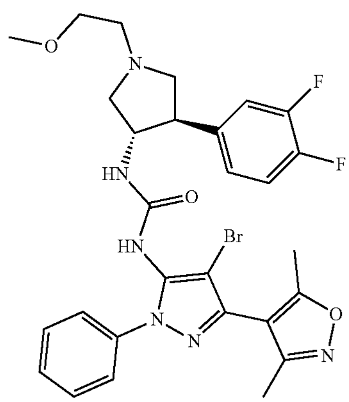 [SMILES: COCCN1C[C@@H](NC(=O)Nc2c(Br)c(-c3c(C)noc3C)nn2-c2ccccc2)[C@H](c2ccc(F)c(F)c2)C1] | 1-(4-bromo-3-(3,5-dimethylisoxazol-4-yl)-1-phenyl-1H-pyrazol-5-yl)-3-((3S,4R)-4-(3,4-difluorophenyl)-1-(2-methoxyethyl)pyrrolidin-3-yl)urea | 615.2 (M + H). |
| 578 | 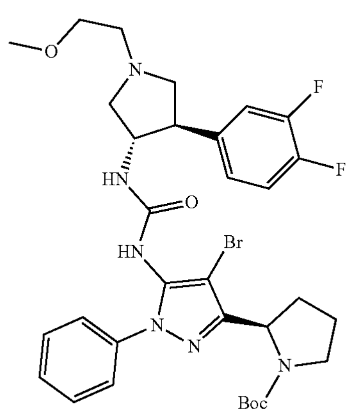 [SMILES: COCCN1C[C@@H](NC(=O)Nc2c(Br)c([C@H]3CCCN3C(=O)OC(C)(C)C)nn2-c2ccccc2)[C@H](c2ccc(F)c(F)c2)C1] | (R)-tert-butyl 2-(4-bromo-5-(3-((3S,4R)-4-(3,4-difluorophenyl)-1-(2-methoxyethyl)pyrrolidin-3-yl)ureido)-1-phenyl-1H-pyrazol-3-yl)pyrrolidine-1-carboxylate | 689.2 (M + H) |

-continued

| Ex. # | Structure | Name | MS (apci) m/z |
|---|---|---|---|
| 579 | 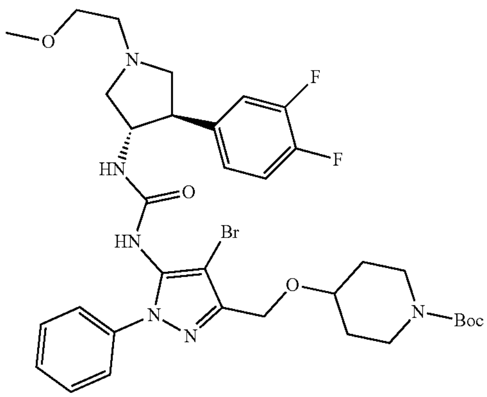 [SMILES: COCCN1C[C@@H](NC(=O)Nc2c(Br)c(COC3CCN(C(=O)OC(C)(C)C)CC3)nn2-c2ccccc2)[C@H](c2ccc(F)c(F)c2)C1] | tert-butyl 4-((4-bromo-5-(3-((3S,4R)-4-(3,4-difluorophenyl)-1-(2-methoxyethyl)pyrrolidin-3-yl)ureido)-1-phenyl-1H-pyrazol-3-yl)methoxy)piperidine-1-carboxylate | 733.2 (M + H) |

Example 580

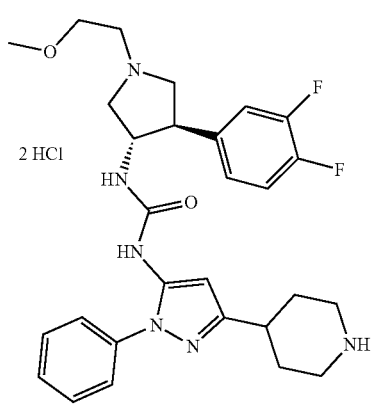 [SMILES: COCCN1C[C@@H](NC(=O)Nc2cc(C3CCNCC3)nn2-c2ccccc2)[C@H](c2ccc(F)c(F)c2)C1]

1-((3S,4R)-4-(3,4-difluorophenyvl)-1-(2-methoxyethyl)pyrrolidin-3-yl)-3-(1-phenyl-3-(piperidin-4-yl)-1H-pyrazol-5-yl)urea dihydrochloride To a solution of tert-butyl 4-(5-(3-((3S,4R)-4-(3,4-difluorophenyl)-1-(2-methoxyethyl)pyrrolidin-3-yl)ureido)-1-phenyl-1H-pyrazol-3-yl)piperidine-1-carboxylate (prepared according to the method of Example 569; 73 mg, 0.12 mmol) in 2:1 EtOAc/MeOH (4 mL) was added 4M HCl in dioxane (3 mL) and the reaction was stirred at ambient temperature until complete by HPLC analysis (2 hours). The mixture was concentrated and the residue was treated with 50% EtOAc-hexanes. The mixture was sonicated until fine granular suspension formed. The solid was collected, washed with 50% EtOAc-hexanes and dried in vacuum to afford the title compound as a white solid (70 mg, 100%). MS (apci) m/z=525.8 (M+H).

The compounds in the following table were prepared according to the method of Example 580 using the appropriate N-Boc intermediates.

| Ex. # | Structure | Name | MS (apci) m/z |
|---|---|---|---|
| 581 | 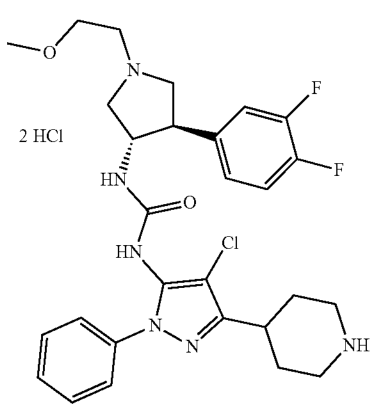 [SMILES: COCCN1C[C@@H](NC(=O)Nc2c(Cl)c(C3CCNCC3)nn2-c2ccccc2)[C@H](c2ccc(F)c(F)c2)C1] | 1-(4-chloro-1-phenyl-3-(piperidin-4-yl)-1H-pyrazol-5-yl)-3-((3S,4R)-4-(3,4-difluorophenyl)-1-(2-methoxyethyl)pyrrolidin-3-yl)urea dihydrochloride | 559.2 (M + H) |

-continued

| Ex. # | Structure | Name | MS (apci) m/z |
|---|---|---|---|
| 582 | 2 HCl | 1-(4-bromo-1-phenyl-3-(piperidin-4-yl)-1H-pyrazol-5-yl)-3-((3S,4R)-4-(3,4-difluorophenyl)-1-(2-methoxyethyl)pyrrolidin-3-yl)urea dihydrochloride | 603.2 (M + H) |
| 583 | 2 HCl | 1-((3S,4R)-4-(3,4-difluorophenyl)-1-(2-methoxyethyl)pyrrolidin-3-yl)-3-(4-methyl-1-phenyl-3-((R)-pyrrolidin-2-yl)-1H-pyrazol-5-yl)urea dihydrochloride | 525.3 (M + H) |
| 584 | 2 HCl | 1-((3S,4R)-4-(3,4-difluorophenyl)-1-(2-methoxyethyl)pyrrolidin-3-yl)-3-(4-methyl-1-phenyl-3-((S)-pyrrolidin-2-yl)-1H-pyrazol-5-yl)urea dihydrochloride | 525.3 (M + H) |
| 585 | 2 HCl | 1-((3S,4R)-4-(3,4-difluorophenyl)-1-(2-methoxyethyl)pyrrolidin-3-yl)-3-(4-chloro-1-phenyl-3-((R)-pyrrolidin-2-yl)-1H-pyrazol-5-yl)urea dihydrochloride | 545.2 (M + H) |

| Ex. # | Structure | Name | MS (apci) m/z |
|---|---|---|---|
| 586 | 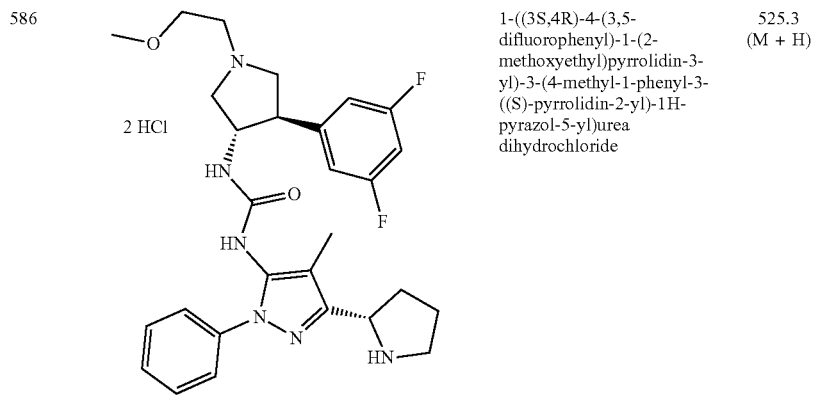 | 1-((3S,4R)-4-(3,5-difluorophenyl)-1-(2-methoxyethyl)pyrrolidin-3-yl)-3-(4-methyl-1-phenyl-3-((S)-pyrrolidin-2-yl)-1H-pyrazol-5-yl)urea dihydrochloride | 525.3 (M + H) |
| 587 | 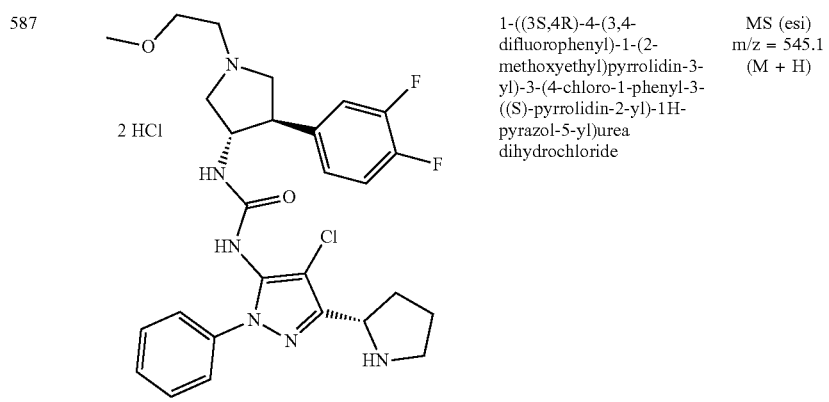 | 1-((3S,4R)-4-(3,4-difluorophenyl)-1-(2-methoxyethyl)pyrrolidin-3-yl)-3-(4-chloro-1-phenyl-3-((S)-pyrrolidin-2-yl)-1H-pyrazol-5-yl)urea dihydrochloride | MS (esi) m/z = 545.1 (M + H) |
| 588 | 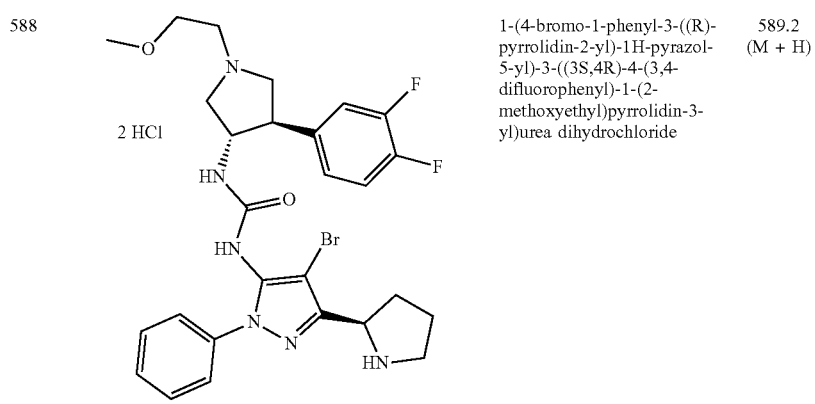 | 1-(4-bromo-1-phenyl-3-((R)-pyrrolidin-2-yl)-1H-pyrazol-5-yl)-3-((3S,4R)-4-(3,4-difluorophenyl)-1-(2-methoxyethyl)pyrrolidin-3-yl)urea dihydrochloride | 589.2 (M + H) |

-continued

| Ex. # | Structure | Name | MS (apci) m/z |
|---|---|---|---|
| 589 | 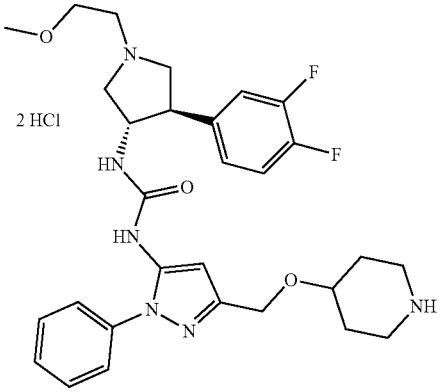 [SMILES: COCCN1C[C@@H](NC(=O)Nc2cc(COC3CCNCC3)nn2-c2ccccc2)[C@H](c2ccc(F)c(F)c2)C1] 2 HCl | 1-((3S,4R)-4-(3,4-difluorophenyl)-1-(2-methoxyethyl)pyrrolidin-3-yl)-3-(1-phenyl-3-((piperidin-4-yloxy)methyl)-1H-pyrazol-5-yl)urea dihydrochloride | 555.2 (M + H) |
| 590 | 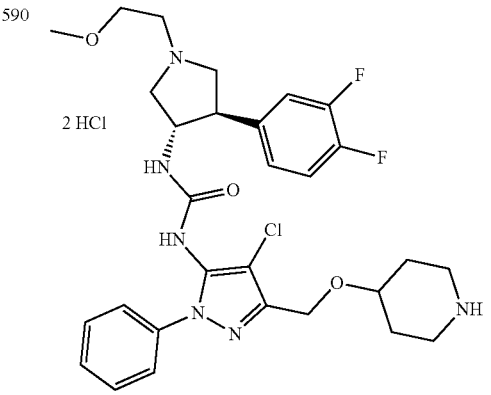 2 HCl | 1-(4-chloro-1-phenyl-3-((piperidin-4-yloxy)methyl)-1H-pyrazol-5-yl)-3-((3S,4R)-4-(3,4-difluorophenyl)-1-(2-methoxyethyl)pyrrolidin-3-yl)urea dihydrochloride | 589.3 (M + H) |
| 591 | 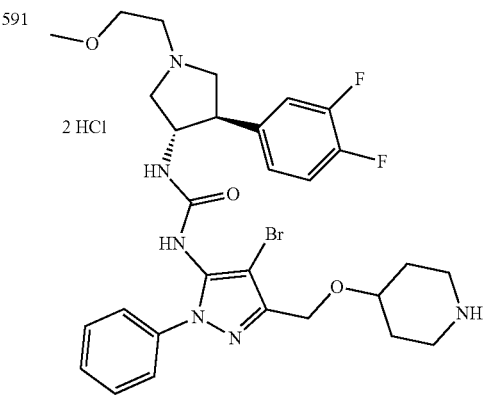 2 HCl | 1-(4-bromo-1-phenyl-3-((piperidin-4-yloxy)methyl)-1H-pyrazol-5-yl)-3-((3S,4R)-4-(3,4-difluorophenyl)-1-(2-methoxyethyl)pyrrolidin-3-yl)urea dihydrochloride | 633.2 (M + H) |

Example 592

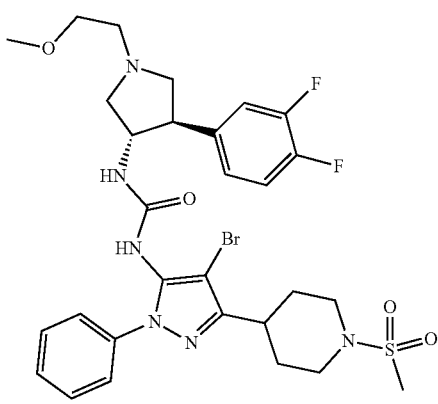 [SMILES: COCCN1C[C@@H](NC(=O)Nc2c(Br)c(C3CCN(S(C)(=O)=O)CC3)nn2-c2ccccc2)[C@H](c2ccc(F)c(F)c2)C1]

1-(4-bromo-3-(1-(methylsulfonyl)piperidin-4-yl)-1-phenyl-1H-pyrazol-5-yl)-3-((3S,4R)-4-(3,4-difluorophenyl)-1-(2-methoxyethyl)pyrrolidin-3-yl)urea A suspension of 1-(4-bromo-1-phenyl-3-(piperidin-4-yl)-1H-pyrazol-5-yl)-3-((3S,4R)-4-(3,4-difluorophenyl)-1-(2-methoxyethyl)pyrrolidin-3-yl)urea dihydrochloride (Example 582, 70 mg, 0.103 mmol) in dry CH$_2$Cl$_2$ (1 mL) was treated with DIEA (72.1 µL, 0.414 mmol) and the mixture was stirred at ambient temperature for 5 minutes. The resulting homogeneous solution was cooled to 0° C. and MsCl (8.41 µL, 0.109 mmol) was added. The mixture was stirred for 2 hours during which time temperature gradually increased to ambient temperature. The mixture was diluted with CH$_2$Cl$_2$ (3 mL) and was washed with H$_2$O (2×). The CH$_2$Cl$_2$ solution was dried over Na$_2$SO$_4$, filtered and concentrated. The residue was purified on SiO$_2$ eluting with 50% EtOAc-hexanes then 5% MeOH/EtOAc. The combined product pools were concentrated and the residual colorless glass was sonicated under 50% Et$_2$O-hexanes until a granular suspension formed. The solvent was decanted and the solid dried in vacuum to afford the title compound as a faint pink solid (54 mg, 77%). MS (apci) m/z=681.2 (M+H).

Example 593

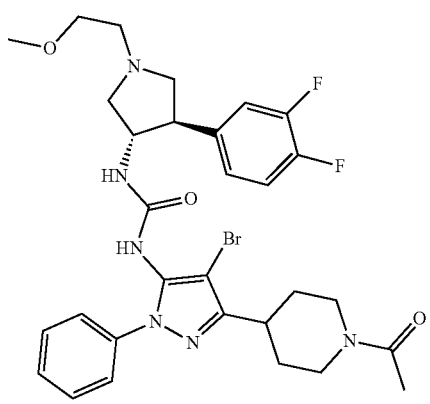 [SMILES: COCCN1C[C@@H](NC(=O)Nc2c(Br)c(C3CCN(C(C)=O)CC3)nn2-c2ccccc2)[C@H](c2ccc(F)c(F)c2)C1]

1-(3-(1-acetylpiperidin-4-yl)-4-bromo-1-phenyl-1H-pyrazol-5-yl)-3-((3S,4R)-4-(3,4-difluorophenyl)-1-(2-methoxyethyl)pyrrolidin-3-yl)urea A suspension of 1-(4-bromo-1-phenyl-3-(piperidin-4-yl)-1H-pyrazol-5-yl)-3-((3S,4R)-4-(3,4-difluorophenyl)-1-(2-methoxyethyl)pyrrolidin-3-yl)urea dihydrochloride (Example 582, 71 mg, 0.105 mmol) in dry CH$_2$Cl$_2$ (1 mL) was treated with DIEA (73.3 µL, 0.420 mmol) and the mixture stirred at ambient temperature for 5 minutes. The resulting homogeneous solution was cooled to 0° C. and Ac$_2$O (10.4 µL, 0.110 mmol) was added. The mixture stirred for 1 hour during which time the temperature gradually reached 10° C. The mixture was diluted with CH$_2$Cl$_2$ (3 mL) and was washed with H$_2$O (2×). The solution was dried over Na$_2$SO$_4$, filtered and concentrated. The residue was purified on SiO$_2$ eluting with a step gradient: EtOAc, 5% then 10% MeOH/EtOAc. The combined product pools were concentrated and the residual colorless glass was dissolved in 50% CH$_2$Cl$_2$/hexanes. The solution was concentrated to furnish the title compound as ivory white solid, dried in vacuum (50 mg, 74%). MS (apci) m/z=645.2 (M+H).

Example 594

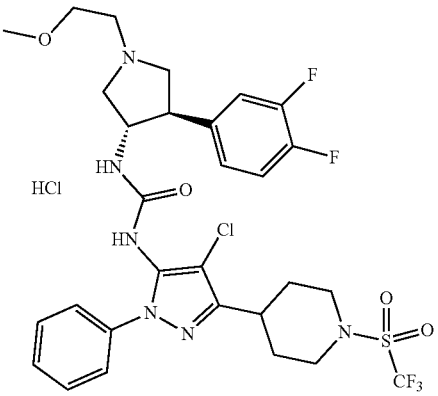 [SMILES: COCCN1C[C@@H](NC(=O)Nc2c(Cl)c(C3CCN(S(=O)(=O)C(F)(F)F)CC3)nn2-c2ccccc2)[C@H](c2ccc(F)c(F)c2)C1 ; Cl]

1-(4-chloro-1-phenyl-3-(1-(trifluoromethylsulfonyl)piperidin-4-yl)-1H-pyrazol-5-yl)-3-((3S,4R)-4-(3,4-difluorophenyl)-1-(2-methoxyethyl)pyrrolidin-3-yl)urea hydrochloride A suspension of 1-(4-chloro-1-phenyl-3-(piperidin-4-yl)-1H-pyrazol-5-yl)-3-((3S,4R)-4-(3,4-difluorophenyl)-1-(2-methoxyethyl)pyrrolidin-3-yl)urea dihydrochloride (Example 581, 60 mg, 0.0949 mmol) in dry CH$_2$Cl$_2$ (1.5 mL) was treated with DIEA (66.3 µL, 0.380 mmol) and the mixture stirred at ambient temperature for 5 minutes. The resulting homogeneous solution was cooled to −40° C. (dry ice, CH$_3$CN bath) and trifluoromethanesulfonic anhydride (17.3 µL, 0.103 mmol) was added. The mixture was stirred for 1 hour during which time temp reached −5° C. The reaction mixture was concentrated and the residue was washed with H$_2$O (3× with sonication) and treated with 50%

EtOAc-hexanes. The mixture was sonicated, treated with MgSO₄ and stirred for 30 minutes. The mixture was filtered through packed Celite® capped with a MgSO₄ layer using 50% EtOAc-hexanes for rinsing and elution. The filtrate was concentrated to give a colorless foam. The foam was dissolved in EtOAc (3 mL) and treated with 2M HCl in Et₂O (300 µL). The resulting cloudy white mixture was stirred for 5 minutes and filtered through packed Celite® (EtOAc rinse). The filtrate was concentrated to provide the title compound as an ivory white solid, dried in vacuum (32 mg, 46%). MS (apci) m/z=691.2 (M+H).

Example 595

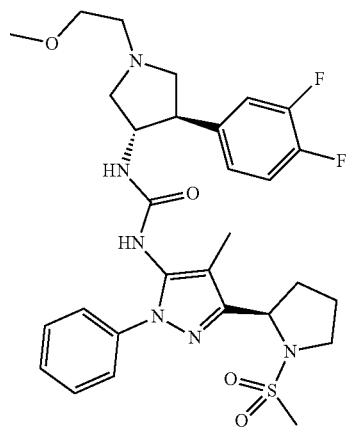 [SMILES: COCCN1C[C@@H](NC(=O)Nc2c(C)c([C@H]3CCCN3S(C)(=O)=O)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-3-((R)-1-(methylsulfonyl)pyrrolidin-2-yl)-1-phenyl-1H-pyrazol-5-yl)urea Prepared according to the procedure described for Example 592 using 1-((3S,4R)-4-(3,4-difluorophenyl)-1-(2-methoxyethyl)pyrrolidin-3-yl)-3-(4-methyl-1-phenyl-3-((R)-pyrrolidin-2-yl)-1H-pyrazol-5-yl)urea dihydrochloride (Example 583) to provide the title compound as a white solid (84 mg, 83%). MS (apci) m/z=603.3 (M+H).

Example 596

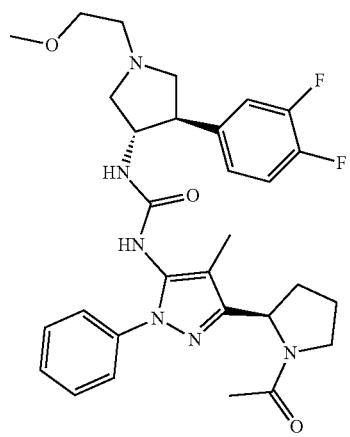 [SMILES: COCCN1C[C@@H](NC(=O)Nc2c(C)c([C@H]3CCCN3C(C)=O)nn2-c2ccccc2)[C@H](c2ccc(F)c(F)c2)C1]

1-(3-((R)-1-acetylpyrrolidin-2-yl)-4-methyl-1-phenyl-1H-pyrazol-5-yl)-3-((3S,4R)-4-(3,4-difluorophenyl)-1-(2-methoxyethyl)pyrrolidin-3-yl)urea Prepared according to the procedure described for Example 593 using 1-((3S,4R)-4-(3,4-difluorophenyl)-1-(2-methoxyethyl)pyrrolidin-3-yl)-3-(4-methyl-1-phenyl-3-((R)-pyrrolidin-2-yl)-1H-pyrazol-5-yl)urea dihydrochloride (Example 583) to provide the title compound as an ivory white solid (89 mg, 94%). MS (apci) m/z=567.3 (M+H).

Example 597

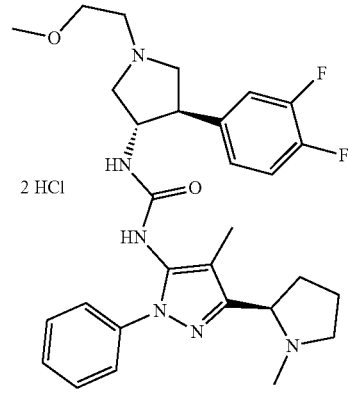 [SMILES: COCCN1C[C@@H](NC(=O)Nc2c(C)c([C@H]3CCCN3C)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-3-((R)-1-methylpyrrolidin-2-yl)-1-phenyl-1H-pyrazol-5-yl)urea dihydrochloride A solution of 1-((3S,4R)-4-(3,4-difluorophenyl)-1-(2-methoxyethyl)pyrrolidin-3-yl)-3-(4-methyl-1-phenyl-3-((R)-pyrrolidin-2-yl)-1H-pyrazol-5-yl)urea dihydro-chloride (Example 583, 80 mg, 0.134 mmol) and DIEA (93.5 µL, 0.536 mmol) in dry CH₂Cl₂ (2 mL) was cooled to 0° C. and iodomethane (9.26 µL, 0.147 mmol) was added. The mixture was stirred for 3 hours during which time temperature gradually reached ambient temperature. The mixture was diluted with CH₂Cl₂ (2 mL) and H₂O (3 mL) and 1M NaOH was added to pH=11. The aqueous layer was removed and the CH₂Cl₂ fraction was washed with H₂O (2×), dried over Na₂SO₄, filtered and concentrated. The residue was purified by SiO₂ chromatography using step gradient elution (EtOAc, 10% MeOH/EtOAc and 10% (9:1 MeOH/NH₄OH)/EtOAc). The combined product pools were concentrated to furnish the free base product as a colorless wax that was dried in vacuum. The free base of the product was dissolved in EtOAc (3 mL) and treated with 2M HCl in Et₂O (0.4 mL). The resulting suspension was stirred for 10 minutes and was concentrated to afford the title compound as a light tan solid that was dried in vacuum (25 mg, 31%). MS (apci) m/z=539.3 (M+H).

Example 598

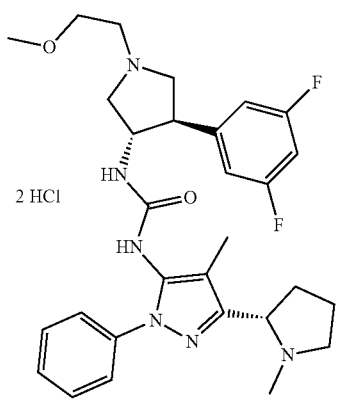 [SMILES: COCCN1C[C@@H](NC(=O)Nc2c(C)c([C@@H]3CCCN3C)nn2-c2ccccc2)[C@H](c2cc(F)cc(F)c2)C1]

1-((3S,4R)-4-(3,5-difluorophenyl)-1-(2-methoxy-ethyl)pyrrolidin-3-yl)-3-(4-methyl-3-((S)-1-methyl-pyrrolidin-2-yl)-1-phenyl-1H-pyrazol-5-yl)urea dihydrochloride Prepared according to the procedure described for Example 597 using 1-((3S,4R)-4-(3,5-difluorophenyl)-1-(2-methoxyethyl)pyrrolidin-3-yl)-3-(4-methyl-1-phenyl-3-((S)-pyrrolidin-2-yl)-1H-pyrazol-5-yl)urea dihydrochloride (Example 586) to provide the title compound as an ivory white solid (31 mg, 39%). MS (apci) m/z=539.3 (M+H).

Example 599

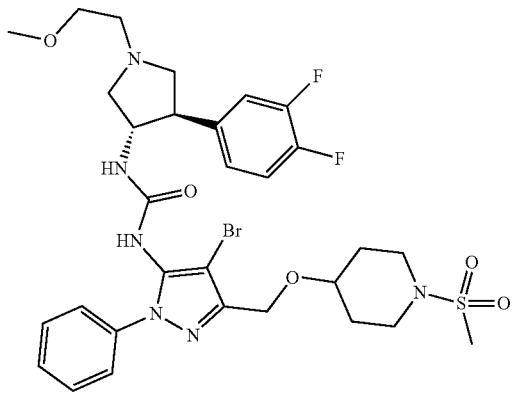 [SMILES: COCCN1C[C@@H](NC(=O)Nc2c(Br)c(COC3CCN(S(C)(=O)=O)CC3)nn2-c2ccccc2)[C@H](c2ccc(F)c(F)c2)C1]

1-(4-bromo-3-((1-(methyl sulfonyl)piperidin-4-yloxy)methyl)-1-phenyl-1H-pyrazol-5-yl)-3-((3S,4R)-4-(3,4-difluorophenyl)-1-(2-methoxyethyl)pyrrolidin-3-yl)urea Using 1-(4-bromo-1-phenyl-3-((piperidin-4-yloxy)methyl)-1H-pyrazol-5-yl)-3-((3S,4R)-4-(3,4-difluorophenyl)-1-(2-methoxyethyl)pyrrolidin-3-yl)urea dihydrochloride (Example 591) in the procedure described for the synthesis of Example 592, the title compound was obtained as a white solid (23 mg, 88%). MS (apci) m/z=711.2 (M+H).

Example 600

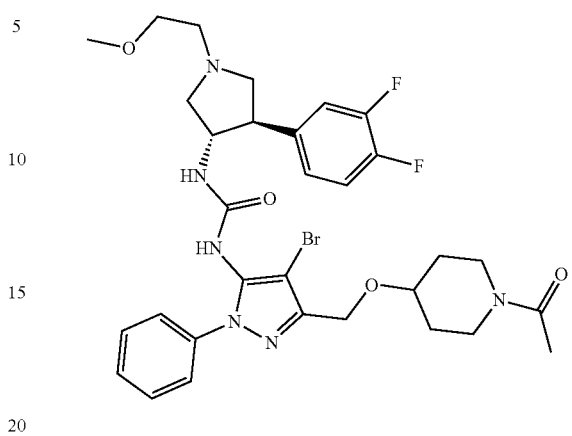

1-(3-((1-acetylpiperidin-4-yloxy)methyl)-4-bromo-1-phenyl-1H-pyrazol-5-yl)-3-((3S,4R)-4-(3,4-difluorophenyl)-1-(2-methoxyethyl)pyrrolidin-3-yl)urea Prepared according to the procedure described for Example 593 using 1-(4-bromo-1-phenyl-3-((piperidin-4-yloxy)methyl)-1H-pyrazol-5-yl)-3-((3S,4R)-4-(3,4-difluorophenyl)-1-(2-methoxyethyl)pyrrolidin-3-yl)urea dihydrochloride (Example 591) to provide the title compound a white solid (24 mg, 96%). MS (apci) m/z=675.2 (M+H).

Example 601

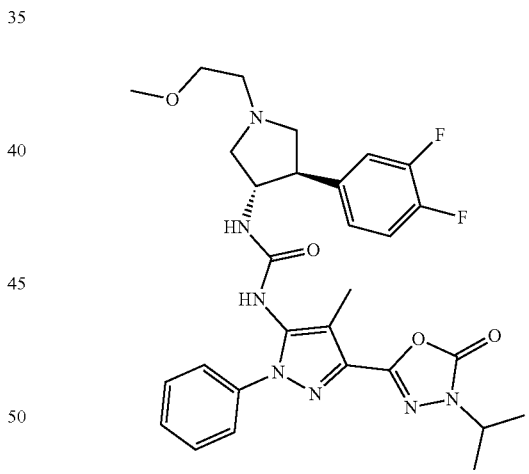

1-((3S,4R)-4-(3,4-difluorophenyvl)-1-(2-methoxy-ethyl)pyrrolidin-3-yl)-3-(3-(4-isopropyl-5-oxo-4,5-dihydro-1,3,4-oxadiazol-2-yl)-4-methyl-1-phenyl-1H-pyrazol-5-yl)urea Step A: 5-amino-N'-isopropyl-4-methyl-1-phenyl-1H-pyrazole-3-carbohydrazide: To a solution of 5-amino-4-methyl-1-phenyl-1H-pyrazole-3-carboxylic acid (Intermediate 171, 146 mg, 0.672 mmol) and DIEA (468 μL, 2.69 mmol) in dry $CH_2Cl_2$ (3.0 mL) was added isobutyl chloroformate (98.1 μL, 0.739 mmol). The mixture was stirred at ambient temperature for 1 hour and was cooled to 0° C. Isopropylhydrazine hydrochloride (149 mg, 1.34 mmol) was added in one portion and the mixture was stirred at ambient temperature for 48 hours. The mixture was washed with H$_2$O (2×) and dried over Na$_2$SO$_4$. The dried solution was eluted through a SiO$_2$ plug eluting with 50% EtOAc-hexanes. The eluent was concentrated to a syrup. The syrup was washed with hexanes and was dissolved Et$_2$O. The solution was concentrated to provide the crude title compound as an oily white solid (148 mg, 54%). MS (apci) m/z=274.1 (M+H). The crude product contained 30% of the undesired regioisomer (5-amino-N-isopropyl-4-methyl-1-phenyl-1H-pyrazole-3-carbohydrazide) and was taken directly to the next step.

Step B: 5-(5-amino-4-methyl-1-phenyl-1H-pyrazol-3-yl)-3-isopropyl-1,3,4-oxadiazol-2(3H)-one: To a solution of the crude 5-amino-N'-isopropyl-4-methyl-1-phenyl-1H-pyrazole-3-carbohydrazide (148 mg, 0.379 mmol) in dry CH$_2$Cl$_2$ (3 mL) was added triphosgene (57.4 mg, 0.190 mmol) in one portion and the resulting white suspension was stirred for 17 hours at ambient temperature. DIEA (264 µL, 1.52 mmol) was slowly added and the resulting homogeneous solution was stirred at ambient temperature for 4 hours. The mixture was washed with H$_2$O (3×), dried over Na$_2$SO$_4$, filtered and concentrated. The residue was purified on a SiO$_2$ column using 25% EtOAc-hexanes for elution. The product was obtained as a white foam that was dried in vacuum (35 mg, 31%). MS (apci) m/z=300.1 (M+H).

Step C: Phenyl 3-(4-isopropyl-5-oxo-4,5-dihydro-1,3,4-oxadiazol-2-yl)-4-methyl-1-phenyl-1H-pyrazol-5-ylcarbamate: A solution of 5-(5-amino-4-methyl-1-phenyl-1H-pyrazol-3-yl)-3-isopropyl-1,3,4-oxadiazol-2(3H)-one (30 mg, 0.100 mmol) in EtOAc (1 mL) was cooled to 0° C. NaOH (251 µL, 0.501 mmol) and phenylchloroformate (37.7 µL, 0.301 mmol) were added sequentially and the mixture was stirred for 5 minutes. The ice bath was removed and the mixture stirred at ambient temperature for 16 hours. The mixture was washed with H$_2$O (2×), 1M HCl, H$_2$O and saturated NaCl. The organic layer was diluted with 1 equal volume of hexanes and dried over MgSO$_4$. The solution was eluted through a SiO$_2$ plug eluting with 50% EtOAc-hexanes. The eluent was concentrated and the residual white solid was washed with hexanes (3× with sonication) and dried in vacuum to provide the title compound (28 mg, 67%). MS (apci) m/z=420.1 (M+H).

Step D: 1-((3S,4R)-4-(3,4-difluorophenyl)-1-(2-methoxyethyl)pyrrolidin-3-yl)-3-(3-(4-isopropyl-5-oxo-4,5-dihydro-1,3,4-oxadiazol-2-yl)-4-methyl-1-phenyl-1H-pyrazol-5-yl) urea: To a mixture of phenyl 3-(4-isopropyl-5-oxo-4,5-dihydro-1,3,4-oxadiazol-2-yl)-4-methyl-1-phenyl-1H-pyrazol-5-ylcarbamate (26 mg, 0.0620 mmol) and (3S,4R)-4-(3,4-difluorophenyl)-1-(2-methoxyethyl)pyrrolidin-3-amine dihydrochloride (Preparation F, 26.5 mg, 0.0806 mmol) in CH$_2$Cl$_2$ (1 mL) was added DIEA (54.1 µL, 0.310 mmol). The resulting homogeneous solution was stirred at ambient temperature for 3 hours. The mixture was diluted with CH$_2$Cl$_2$ (2 mL) and was washed with H$_2$O (2×), 1M NaOH (2×) and H$_2$O. The CH$_2$Cl$_2$ solution was dried over Na$_2$SO$_4$, filtered and concentrated. The residue was purified on a SiO$_2$ column with step gradient elution: 50% EtOAc/hexanes, EtOAc then 5% MeOH/EtOAc. The combined product pools were concentrated to give a colorless glass. The glass was dissolved in 1:1 CH$_2$Cl$_2$/hexanes and concentrated to afford the title compound as a white solid, dried in vacuum (20 mg, 56%). MS (apci) m/z=582.2 (M+H).

Example 602

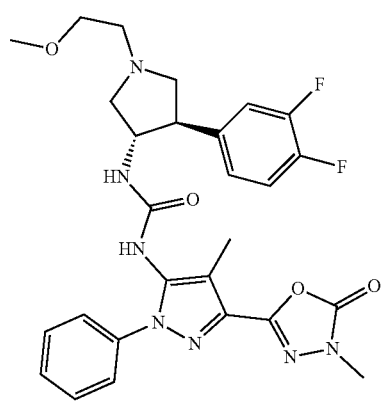 [SMILES: COCCN1C[C@@H](NC(=O)Nc2c(C)c(-c3nn(C)c(=O)o3)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-3-(4-methyl-5-oxo-4,5-dihydro-1,3,4-oxadiazol-2-yl)-1-phenyl-1H-pyrazol-5-yl)urea Step A: tert-butyl 2-(5-amino-4-methyl-1-phenyl-1H-pyrazole-3-carbonyl)-1-methylhydrazinecarboxylate: To a fine suspension of 5-amino-4-methyl-1-phenyl-1H-pyrazole-3-carboxylic acid (Intermediate 171, 0.434 g, 2.00 mmol) in dry CH$_2$Cl$_2$ (5 mL) was added DIEA (0.766 mL, 4.40 mmol) and the mixture was stirred at ambient temperature for 5 minutes. The resulting solution was treated with isobutyl chloroformate (0.292 mL, 2.20 mmol) and the mixture was stirred for 2 hours. Tert-butyl 1-methylhydrazinecarboxylate (0.308 mL, 2.00 mmol) was added and the mixture stirred at ambient temperature for 23 hours. The mixture was washed with H$_2$O (2×), dried over Na$_2$SO$_4$, and the dried CH$_2$Cl$_2$ solution was eluted through a SiO$_2$ plug (50% EtOAc-hexanes for elution). The eluent was concentrated a colorless waxy solid. The solid was treated with 50% Et$_2$O-hexanes and stirred until a granular white suspension formed. The solvent was decanted, the residual solid was washed with 50% Et$_2$O-hexanes and dried in vacuum provide the title compound as a white powder (550 mg, 80%). MS (apci) m/z=346.2 (M+H).

Step B: 5-amino-N',4-dimethyl-1-phenyl-1H-pyrazole-3-carbohydrazide dihydrochloride: To a solution of tert-butyl 2-(5-amino-4-methyl-1-phenyl-1H-pyrazole-3-carbonyl)-1-methylhydrazinecarboxylate (540 mg, 1.56 mmol) in EtOAc (10 mL) was added 4M HCl (7.82 mL, 31.3 mmol) in dioxane and the mixture was stirred at ambient temperature for 17 hours. The resulting white suspension was concentrated and the residual white solid was dried in vacuum to provide the title compound (490 mg, 99%). MS (apci) m/z=246.1 (M+H). $^1$H NMR (DMSO d$_6$) δ 11.6 (br s, 2H), 11.3 (s, 1H), 7.63 (d, 2H), 7.54 (t, 2H), 7.44 (t, 1H), 2.82 (s, 3H), 2.13 (s, 3H).

Step C: 5-(5-amino-4-methyl-1-phenyl-1H-pyrazol-3-yl)-3-methyl-1,3,4-oxadiazol-2(3H)-one: A solution of 5-amino-N',4-dimethyl-1-phenyl-1H-pyrazole-3-carbohydrazide dihydrochloride (484 mg, 1.52 mmol) and DIEA (1.32 mL, 7.61 mmol) in dry CH$_2$Cl$_2$ (10 mL) was cooled to 0° C. and triphosgene (230 mg, 0.761 mmol) was added in one portion. The mixture stirred for 17 hours during which time temperature reached ambient temperature after 2 hours. Additional DIEA (0.40 mL), was added and the mixture was stirred for an 5 hours. The mixture was washed with H₂O (3×), dried over Na₂SO₄ and the dried solution was eluted through a short SiO₂ column eluting 25% EtOAc-hexanes. The eluent was concentrated and the residual waxy solid was treated with 50% Et₂O-hexanes and stirred until a fine, granular suspension formed. The solvent was decanted and the residual solid was washed with 50% Et₂O-hexanes (2×) and dried in vacuum to afford the title compound as a ivory white solid (197 mg, 48%). MS (apci) m/z=272.1 (M+H).

Step D: Phenyl 4-methyl-3-(4-methyl-5-oxo-4,5-dihydro-1,3,4-oxadiazol-2-yl)-1-phenyl-1H-pyrazol-5-ylcarbamate: Using 5-(5-amino-4-methyl-1-phenyl-1H-pyrazol-3-yl)-3-methyl-1,3,4-oxadiazol-2(3H)-one in the procedure described for the preparation of Example 601, Step C provided the title compound as a white solid (80 mg, 59%). MS (apci) m/z=272.1 (aminopyrazole fragment M+H).

Step E: 1-((3S,4R)-4-(3,4-difluorophenyl)-1-(2-methoxyethyl)pyrrolidin-3-yl)-3-(4-methyl-3-(4-methyl-5-oxo-4,5-dihydro-1,3,4-oxadiazol-2-yl)-1-phenyl-1H-pyrazol-5-yl)urea: Prepared according to the method of Example 601, Step D, using Phenyl 4- methyl-3-(4-methyl-5-oxo-4,5-dihydro-1,3,4-oxadiazol-2-yl)-1-phenyl-1H-pyrazol-5-ylcarbamate. The title compound was isolated as a white solid (50 mg, 60%). MS (apci) m/z=554.2 (M+H).

Example 603

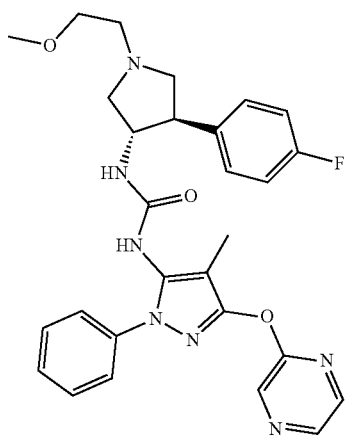 [SMILES: COCCN1C[C@@H](NC(=O)Nc2c(C)c(Oc3cnccn3)nn2-c2ccccc2)[C@H](c2ccc(F)cc2)C1]

1-((3S,4R)-4-(4-fluorophenyl)-1-(2-methoxyethyl)pyrrolidin-3-yl)-3-(4-methyl-1-phenyl-3-(pyrazin-2-yloxy)-1H-pyrazol-5-yl)urea Step A: 4-methyl-1-phenyl-3-(pyrazin-2-yloxy)-1H-pyrazol-5-amine: In a sealed tube were combined 5-amino-4-methyl-1-phenyl-1H-pyrazol-3(2H)-one (Preparation P135, Step A, 300 mg, 1.59 mmol), 2-chloropyrazine (185 mg, 1.59 mmol), CuCN (14.2 mg, 0.159 mmol), cesium carbonate (620 mg, 1.90 mmol) and dry DMF (3.2 mL). Ethylenediamine (23.3 µL, 0.349 mmol) was added and the vessel was flushed with N₂ and sealed. The mixture was stirred at 110° C. for 18 hours and was cooled to ambient temperature. The mixture was added to ice-H₂O (30 mL) and stirred for 10 minutes. The mixture was extracted with EtOAc (3×) and the combined organic fractions were washed with saturated NaCl (2×), dried over MgSO₄ filtered through packed Celite®. The filtrate was concentrated and the residual syrup was purified on a SiO₂ column eluting with 40% EtOAc-hexanes to provide the title compound as a white solid (310 mg, 73%). MS (apci) m/z=268.0 (M+H). ¹H NMR (CDCl₃) δ 8.54 (s, 1H), 8.28 (s, 1H), 8.16 (s, 1H), 7.58 (d, 2H), 7.44 (t, 2H), 7.31 (t, 1H), 3.74 (br s, 2H), 1.81 (s, 3H).

Step B: 1-((3S,4R)-4-(4-fluorophenyl)-1-(2-methoxyethyl)pyrrolidin-3-yl)-3-(4-methyl-1-phenyl-3-(pyrazin-2-yloxy)-1H-pyrazol-5-yl)urea: To a solution of 4-methyl-1-phenyl-3-(pyrazin-2-yloxy)-1H-pyrazol-5-amine (50.0 mg, 0.187 mmol) in dry DMF (1.0 mL) was added CDI (36.4 mg, 0.224 mmol) and DIEA (49.0 µL, 0.281 mmol). The mixture was stirred at ambient temperature for 16 hours. Additional CDI (31 mg) was added and the mixture stirred for 24 hours. To the mixture was added (3S,4R)-4-(4-fluorophenyl)-1-(2-methoxyethyl)pyrrolidin-3-amine (Preparation L1, 98.1 mg, 0.412 mmol) and the mixture was stirred at ambient temperature for 5 hours. The mixture was diluted with chilled H₂O (4 mL) and the resulting milky suspension was treated with 2M HCl to pH=7 (starting pH=1). The mixture was extracted with EtOAc (3×) and the combined EtOAc fractions were washed with saturated NaCl (3×). The EtOAc solution was dried over MgSO₄, filtered through packed Celite® and concentrated. The residual colorless glass was purified on a SiO₂ column with step gradient elution (EtOAc, 5% MeOH/EtOAc, 10% (9:1 CH₃OH/NH₄OH)/EtOAc). The resulting white foam was recrystallized from 50% EtOAc-hexanes to furnish the title compound as white spheres that were crushed and dried in vacuum (44 mg, 44%). MS (apci) m/z=532.2 (M+H).

Example 604

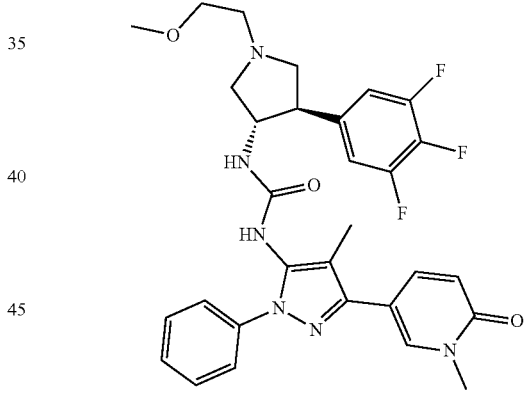

1-((3S,4R)-1-(2-methoxyethyl)-4-(3,4,5-trifluorophenyl)pyrrolidin-3-yl)-3-(4-methyl-3-(1-methyl-6-oxo-1,6-dihydropyridin-3-yl)-1-phenyl-1H-pyrazol-5-yl)urea A solution of triphosgene (23.1 mg, 0.074 mmol) in dry CH₃CN (1 mL) was cooled to 0° C. and a solution of (3S,4R)-1-(2-methoxyethyl)-4-(3,4,5-trifluorophenyl)pyrrolidin-3-amine dihydrochloride (Preparation M, 76.4 mg, 0.220 mmol) and DIEA (115 µL, 0.660 mmol) in dry CH₃CN (0.5 mL) was added over 45 minutes. The mixture was stirred for 1 hour during which time the temperature reached 15° C. 5-(5-Amino-4-methyl-1-phenyl-1H-pyrazol-3-yl)-1-methylpyridin-2(1H)-one (56.1 mg, 0.200 mmol) was added in one portion and the mixture stirred at ambient temperature for 7 hours followed by stirring at 40° C. for 17 hours. The mixture was cooled to ambient temperature and was diluted with chilled H₂O (4 mL). The cold mixture (pH=5) was treated with 2M NaOH to pH=10. The mixture was extracted with EtOAc (3×) and the combined extracts were washed with H₂O and saturated NaCl (2×). The EtOAc solution was dried over MgSO₄ and eluted through a short SiO₂ column eluting with EtOAc, 10% MeOH/EtOAc then 10% (9:1/CH₃OH—NH₄OH)/EtOAc. The combined product pools were concentrated. The residue was treated with Et₂O and agitated until a white suspension formed. The solvent was decanted and the remaining solid was washed with Et₂O (2×) and dried in vacuum to provide the title compound as a white solid (34 mg, 29%). MS (apci) m/z=581.2 (M+H).

Example 605

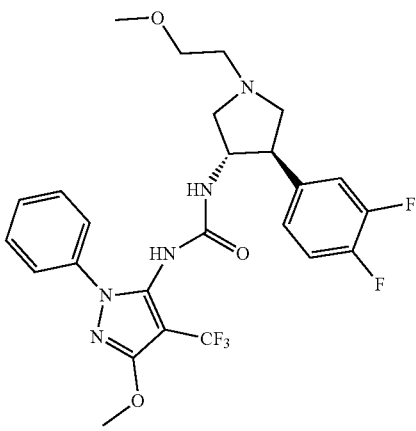 [SMILES: COCCN1C[C@@H](NC(=O)Nc2c(C(F)(F)F)c(OC)nn2-c2ccccc2)[C@H](c2ccc(F)c(F)c2)C1]

1-((3S,4R)-4-(3,4-difluorophenyl)-1-(2-methoxy-ethyl)pyrrolidin-3-yl)-3-(3-methoxy-1-phenyl-4-(trifluoromethyl)-1H-pyrazol-5-yl)urea Step A: Preparation of 5-fluoro-3-methoxy-1-phenyl-4-(trifluoromethyl)-1H-pyrazole. A mixture of NEt₃ (0.657 mL, 4.72 mmol) and phenylhydrazine (0.561 g, 5.19 mmol) in EtOH (2 mL) was added dropwise to a solution of 1,3,3-tetrafluoro-1-methoxy-2-(trifluoromethyl)prop-1-ene (1.00 g, 4.72 mmol) in EtOH (3 mL). After the addition was complete, the reaction was stirred at ambient temperature overnight, concentrated and purified by silica gel column chromatography, eluting with 0-10% EtOAc/hexanes to afford the tile compound (372 mg, 1.43 mmol, 30.3% yield). MS (apci) m/z=261.1 (M+H).

Step B: Preparation of 3-methoxy-1-phenyl-4-(trifluoromethyl)-1H-pyrazol-5-amine. 5-fluoro-3-methoxy-1-phenyl-4-(trifluoromethyl)-1H-pyrazole (400 mg, 1.54 mmol), hydrazine (148 mg, 4.61 mmol) and NEt₃ (643 μL, 4.61 mmol) were combined in DME (3 mL) in a sealed vessel and heated in a 90° C. sand bath for 3 hours. The reaction was cooled and Raney Nickel (132 mg, 1.54 mmol) added. The reaction was stirred at ambient temperature for 3 hours, filtered through Celite®, concentrated and purified by reverse-phase column chromatography, eluting with 0-80% acetonitrile/water, to afford the title compound (322 mg, 1.25 mmol, 81.4% yield). MS (apci) m/z=258.1 (M+H).

Step C: Preparation of 1-((3S,4R)-4-(3,4-difluorophenyl)-1-(2-methoxyethyl)-pyrrolidin-3-yl)-3-(3-methoxy-1-phenyl-4-(trifluoromethyl)-1H-pyrazol-5-yl)urea. 3-methoxy-1-phenyl-4-(trifluoromethyl)-1H-pyrazol-5-amine (77 mg, 0.2994 mmol), CDI (50.97 mg, 0.3143 mmol) and DIEA (521.4 μL, 2.994 mmol) were combined in 0.8 mL of DMF and stirred ambient temperature overnight. 0.6 mL of the resultant solution were then added to (3S,4R)-4-(3,4-difluorophenyl)-1-(2-methoxyethyl)pyrrolidin-3-amine dihydrochloride (60 mg, 0.18 mmol) and the mixture was stirred at ambient temperature for 2 hours, loaded onto a samplet and purified by reverse-phase column chromatography, eluting with 5-80% acetonitrile/water, to afford the title compound (40 mg, 0.074 mmol, 52% yield). (MS (apci) m/z=540.2 (M+H).

Example 606

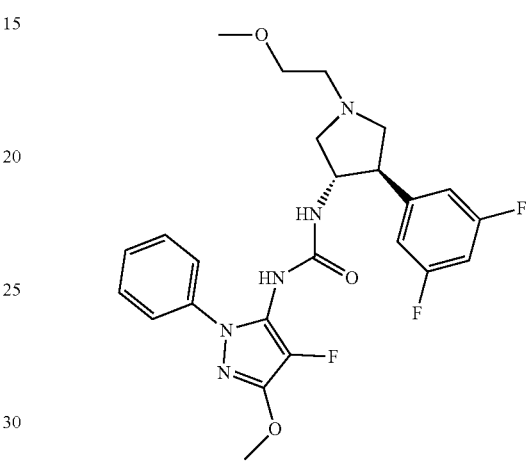

1-((3S,4R)-4-(3,5-difluorophenyl)-1-(2-methoxy-ethyl)pyrrolidin-3-yl)-3-(3-methoxy-1-phenyl-4-(trifluoromethyl)-1H-pyrazol-5-yl)urea Prepared by the method as described in Example 605, Step C, using (3S,4R)-4-(3,5-difluorophenyl)-1-(2-methoxyethyl)pyrrolidin-3-amine dihydrochloride instead of (3S,4R)-4-(3,4-difluorophenyl)-1-(2-methoxyethyl)pyrrolidin-3-amine dihydrochloride. The material was purified by reverse-phase column chromatography using 5-80% acetonitrile/H₂O as the eluent to provide the title compound (11 mg, 0.021 mmol, 30% yield). MS (apci) m/z=540.2 (M+H).

Example 607

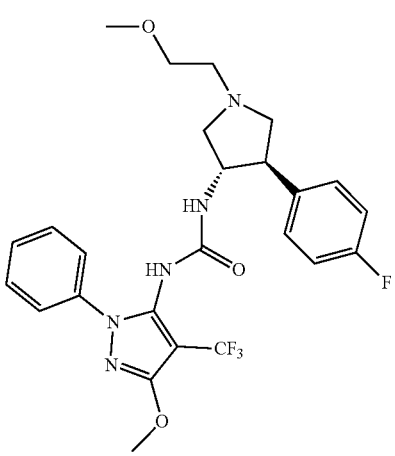 [SMILES: COCCN1C[C@@H](NC(=O)Nc2c(C(F)(F)F)c(OC)nn2-c2ccccc2)[C@H](c2ccc(F)cc2)C1]

1-((3S,4R)-4-(4-fluorophenyl)-1-(2-methoxyethyl) pyrrolidin-3-yl)-3-(3-methoxy-1-phenyl-4-(trifluoromethyl)-1H-pyrazol-5-yl)urea Prepared by the method as described in Example 605, Step C using (3S,4R)-4-(4-fluorophenyl)-1-(2-methoxyethyl)pyrrolidin-3-amine dihydrochloride instead of (3S,4R)-4-(3,4-difluorophenyl)-1-(2-methoxyethyl)pyrrolidin-3-amine dihydrochloride. The material was purified by reverse-phase column chromatography using 5-80% acetonitrile/H$_2$O as the eluent to provide the title compound (22 mg, 0.042 mmol, 60% yield). MS (apci) m/z=522.2 (M+H).

Example 608

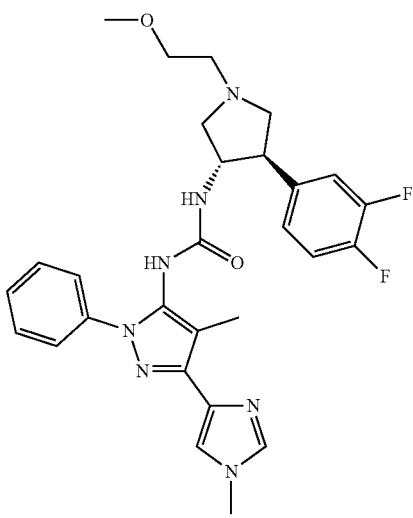 [SMILES: COCCN1C[C@@H](NC(=O)Nc2c(C)c(-c3cn(C)cn3)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-3-(1-methyl-1H-imidazol-4-yl)-1-phenyl-1H-pyrazol-5-yl)urea Step A: Preparation of 2-methyl-3-(1-methyl-1H-imidazol-4-yl)-3-oxopropanenitrile. Propiononitrile (0.893 g, 16.2 mmol) was added dropwise to a 1M solution of LHMDS (13.0 mL, 13.0 mmol) in THF at −78° C. The mixture was stirred for 30 minutes and a solution of ethyl 1-methyl-1H-imidazole-4-carboxylate (1.00 g, 6.49 mmol) in THF (20 mL, heated to dissolve the starting material) was added dropwise. The reaction was allowed to warm to ambient temperature, stirred overnight, poured into ice water (50 mL) and extracted with EtOAc (100 mL). The pH was adjusted to 6.5 using 2N HCl and the mixture was extracted with EtOAc (100 mL). The pH was then adjusted to 6 using 2N HCl and the mixture was extracted with EtOAc (2×100 mL). The combined extracts from the pH 6.5 and pH 6 extractions were dried (MgSO$_4$), filtered and concentrated to provide the title compound (1.02 g, 6.25 mmol, 96.4% yield). MS (apci) m/z=164.2 (M+H).

Step B: Preparation of 4-methyl-3-(1-methyl-1H-imidazol-4-yl)-1-phenyl-1H-pyrazol-5-amine hydrochloride. A pressure vessel was charged with 2-methyl-3-(1-methyl-1H-imidazol-4-yl)-3-oxopropanenitrile (1.00 g, 6.13 mmol), absolute EtOH (12.3 mL, 6.13 mmol) and phenylhydrazine hydrochloride (0.975 g, 6.74 mmol). The reaction was sealed, heated at 80° C. overnight and concentrated to afford the title compound (1.70 g, 5.87 mmol, 95.7% yield). MS (apci) m/z=254.1 (M+H).

Step C: Preparation of 1-((3S,4R)-4-(3,4-difluorophenyl)-1-(2-methoxyethyl) pyrrolidin-3-yl)-3-(4-methyl-3-(1-methyl-1H-imidazol-4-yl)-1-phenyl-1H-pyrazol-5-yl)urea. 4-methyl-3-(1-methyl-1H-imidazol-4-yl)-1-phenyl-1H-pyrazol-5-amine (20 mg, 0.07896 mmol) was dissolved in 2 mL of EtOAc and NaOH (789.6 µL, 0.7896 mmol) was added followed by phenylchloroformate (29.72 µL, 0.2369 mmol). The reaction was stirred at ambient temperature overnight, 10 mL of EtOAc were added and the organic layer was washed with Brine, dried (MgSO$_4$), concentrated and taken up in CH$_2$Cl$_2$ (1 mL). (3S,4R)-4-(3,4-Difluorophenyl)-1-(2-methoxyethyl)pyrrolidin-3-amine dihydrochloride (20 mg, 0.061 mmol) and DIEA (88 µL, 0.51 mmol) were added and the reaction was stirred at ambient temperature overnight, concentrated and purified reverse-phase column chromatography, eluting with 0-70% acetonitrile/water, to afford the title compound (2.4 mg, 0.0045 mmol, 8.9% yield). (MS (apci) m/z=536.2 (M+H).

Example 609

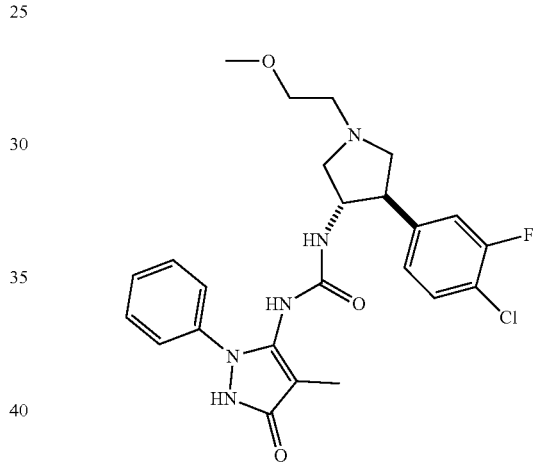

1-((trans)-4-(4-chloro-3-fluorophenyl)-1-(2-methoxyethyl)pyrrolidin-3-yl)-3-(4-methyl-5-oxo-2-phenyl-2,5-dihydro-1H-pyrazol-3-yl)urea CDI (360 mg, 2.22 mmol), 5-amino-4-methyl-1-phenyl-1H-pyrazol-3(2H)-one (350 mg, 1.85 mmol) and DIEA (805 µL, 4.62 mmol) were combined in 3 mL of DMF and stirred at ambient temperature overnight. Additional CDI (360 mg, 2.22 mmol) was added and the reaction stirred at ambient temperature for 24 hours. 0.2 mL of the resultant solution were added to a solution of (trans)-4-(4-chloro-3-fluorophenyl)-1-(2-methoxyethyl)pyrrolidin-3-amine dihydro-chloride (67.5 mg, 0.195 mmol) and DIEA (80.9 µl, 0.465 mmol) in DMF (2 mL) and stirred at ambient temperature for 3 hours. The reaction was loaded onto a samplet and purified reverse-phase column chromatography, eluting with 0-70% acetonitrile/water, to afford the title compound (39 mg, 0.0799 mmol, 86.0% yield). (MS (apci) m/z=488.1 (M+H).

The following compounds were prepared according to the method of Example 609, replacing (3S,4R)-4-(4-chloro-3-fluorophenyl)-1-(2-methoxyethyl)pyrrolidin-3-amine dihydro-chloride with the appropriate pyrrolidine intermediate.

| Ex. # | Structure | Name | MS (apci) m/z |
|---|---|---|---|
| 610 | 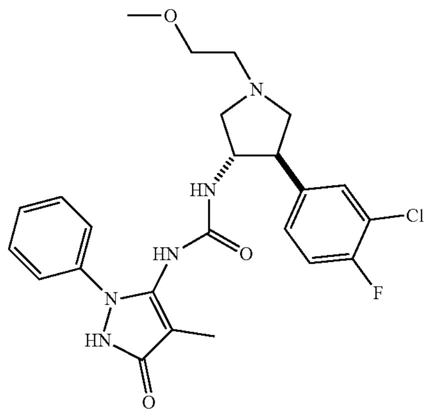 [SMILES: COCCN1C[C@@H](NC(=O)Nc2c(C)c(=O)[nH]n2-c2ccccc2)[C@H](c2ccc(F)c(Cl)c2)C1] | 1-((trans)-4-(3-chloro-4-fluorophenyl)-1-(2-methoxyethyl)pyrrolidin-3-yl)-3-(4-methyl-5-oxo-2-phenyl-2,5-dihydro-1H-pyrazol-3-yl)urea | 488.2 (M + H) |
| 611 | 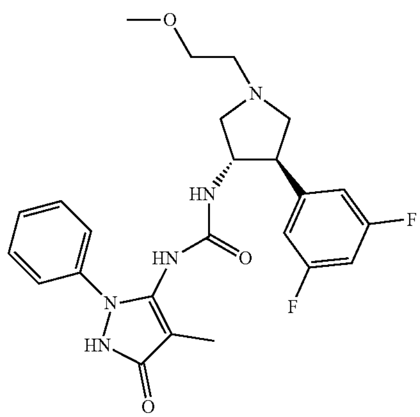 [SMILES: COCCN1C[C@@H](NC(=O)Nc2c(C)c(=O)[nH]n2-c2ccccc2)[C@H](c2cc(F)cc(F)c2)C1] | 1-((3S,4R)-4-(3,5-difluorophenyl)-1-(2-methoxyethyl)pyrrolidin-3-yl)-3-(4-methyl-5-oxo-2-phenyl-2,5-dihydro-1H-pyrazol-3-yl)urea | 472.2 (M + H) |
| 612 | 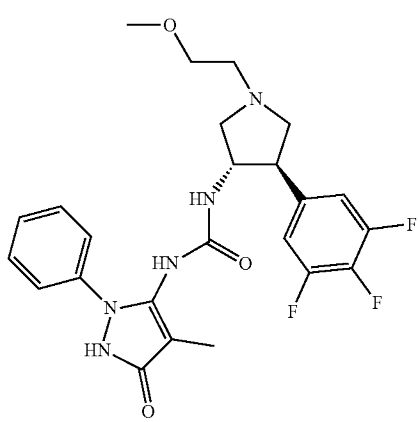 [SMILES: COCCN1C[C@@H](NC(=O)Nc2c(C)c(=O)[nH]n2-c2ccccc2)[C@H](c2cc(F)c(F)c(F)c2)C1] | 1-((3S,4R)-1-(2-methoxyethyl)-4-(3,4,5-trifluorophenyl)pyrrolidin-3-yl)-3-(4-methyl-5-oxo-2-phenyl-2,5-dihydro-1H-pyrazol-3-yl)urea | 490.2 (M + H) |

| Ex. # | Structure | Name | MS (apci) m/z |
|---|---|---|---|
| 613 | 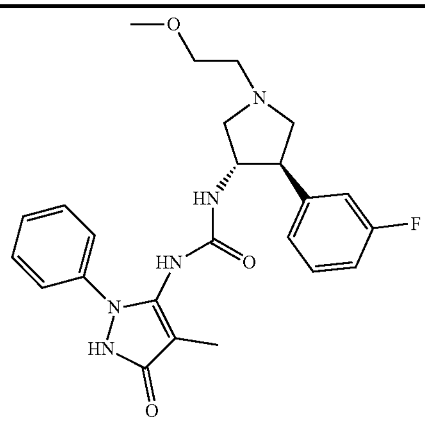 | 1-((3S,4R)-4-(3-fluorophenyl)-1-(2-methoxyethyl)pyrrolidin-3-yl)-3-(4-methyl-5-oxo-2-phenyl-2,5-dihydro-1H-pyrazol-3-yl)urea | 454.2 (M + H) |
| 614 | 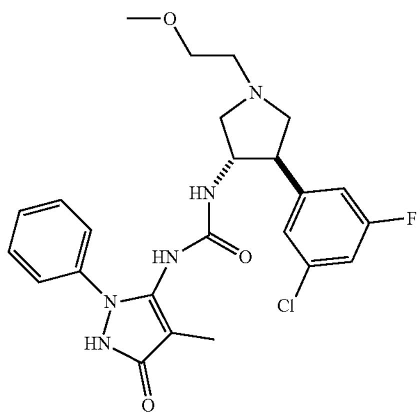 [SMILES: COCCN1C[C@@H](NC(=O)Nc2c(C)c(=O)[nH]n2-c2ccccc2)[C@H](c2cc(F)cc(Cl)c2)C1] | 1-((trans)-4-(3-chloro-5-fluorophenyl)-1-(2-methoxyethyl)pyrrolidin-3-yl)-3-(4-methyl-5-oxo-2-phenyl-2,5-dihydro-1H-pyrazol-3-yl)urea | 488.2 (M + H) |

Example 615

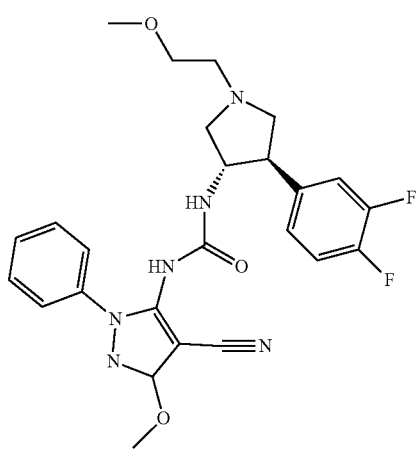

1-(4-cyano-3-methoxy-1-phenyl-1H-pyrazol-5-yl)-3-((3S,4R)-4-(3,4-difluorophenyl)-1-(2-methoxyethyl)pyrrolidin-3-yl)urea Step A: Preparation of 5-amino-3-methoxy-1-phenyl-1H-pyrazole-4-carbonitrile. To a solution of phenylhydrazine (0.783 g, 7.24 mmol) in ethanol (5 mL) in a pressure tube was added 2-(dimethoxymethylene)malononitrile (1.0 g, 7.24 mmol). The mixture was heated to 100° C. for 18 hours. The solvent was evaporated and the crude product was purified by silica gel column chromatography, eluting with 5-35% acetone/hexanes to afford the title compound (708 mg, 45.6% yield). MS (apci) m/z=215.1 (M+H).

Step B: Preparation of 1-(4-cyano-3-methoxy-1-phenyl-1H-pyrazol-5-yl)-3-((3S,4R)-4-(3,4-difluorophenyl)-1-(2-methoxyethyl)pyrrolidin-3-yl)urea. 5-amino-3-methoxy-1-phenyl-1H-pyrazole-4-carbonitrile (160 mg, 0.747 mmol), CDI (133 mg, 0.822 mmol) and DIEA (650 µL, 3.73 mmol) were combined in 5 mL of DMF and stirred at ambient temperature for 3 days. (3S,4R)-4-(3,4-difluorophenyl)-1-(2-methoxyethyl)pyrrolidin-3-amine dihydrochloride (295 mg, 0.896 mmol) was added and the reaction was stirred at ambient temperature for 1 hour, loaded onto a samplet and purified by reverse-phase column chromatography, eluting with 0-70% acetonitrile/water, to afford the title compound (328 mg, 0.661 mmol, 88.4% yield). MS (apci) m/z=497.2 (M+H).

Example 616

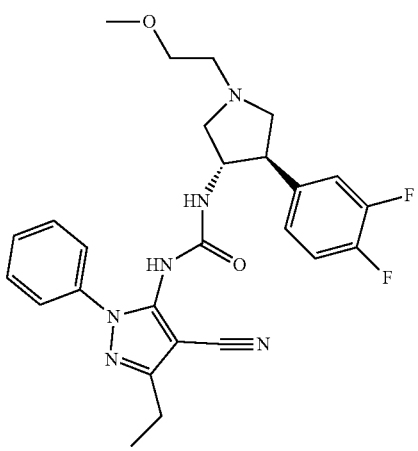 [SMILES: CCc1nn(-c2ccccc2)c(NC(=O)N[C@@H]2CN(CCOC)C[C@H]2c2ccc(F)c(F)c2)c1C#N]

1-(4-cyano-3-ethyl-1-phenyl-1H-pyrazol-5-yl)-3-((3S,4R)-4-(3,4-difluorophenyl)-1-(2-methoxyethyl) pyrrolidin-3-yl)urea.

Prepared as described in Example 615, Step B, substituting 5-amino-3-ethyl-1-phenyl-1H-pyrazole-4-carbonitrile for 5-amino-3-methoxy-1-phenyl-1H-pyrazole-4-carbonitrile. The material was purified by reverse-phase column chromatography using 0-70% acetonitrile/H$_2$O as the eluent to provide the title compound (890 mg, 1.80 mmol, 76.4% yield). MS (apci) m/z=495.2 (M+H).

Example 617

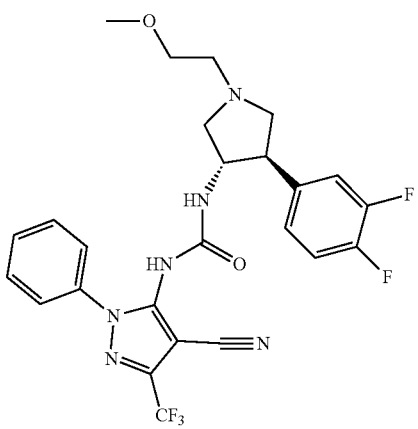 [SMILES: COCCN1C[C@@H](NC(=O)Nc2c(C#N)c(C(F)(F)F)nn2-c2ccccc2)[C@H](c2ccc(F)c(F)c2)C1]

1-(4-cyano-1-phenyl-3-(trifluoromethyl)-1H-pyrazol-5-yl)-3-((3S,4R)-4-(3,4-difluorophenyl)-1-(2-methoxyethyl)pyrrolidin-3-yl)urea Prepared as described in Example 615, Step B, substituting 5-amino-1-phenyl-3-(trifluoromethyl)-1H-pyrazole-4-carbonitrile for 5-amino-3-methoxy-1-phenyl-1H-pyrazole-4-carbonitrile. The material was purified by reverse-phase column chromatography using 0-70% acetonitrile/H$_2$O as the eluent to provide the title compound (0.81 g, 1.52 mmol, 76.4% yield). MS (apci) m/z=535.2 (M+H).

Example 618

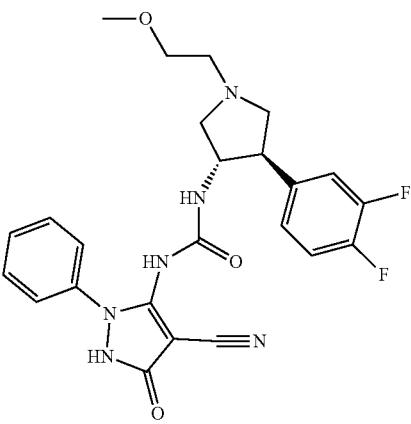 [SMILES: COCCN1C[C@@H](NC(=O)Nc2c(C#N)c(=O)[nH]n2-c2ccccc2)[C@H](c2ccc(F)c(F)c2)C1]

1-(4-cyano-5-oxo-2-phenyl-2,5-dihydro-1H-pyrazol-3-yl)-3-((3S,4R)-4-(3,4-difluorophenyl)-1-(2-methoxyethyl)pyrrolidin-3-yl)urea 1-(4-cyano-3-methoxy-1-phenyl-1H-pyrazol-5-yl)-3-((3S,4R)-4-(3,4-difluorophenyl)-1-(2-methoxyethyl)pyrrolidin-3-yl)urea (30 mg, 0.06042 mmol, prepared as described in Example 615) was taken up in HCl (61.20 mg, 0.6042 mmol) and stirred at ambient temperature for two days. The reaction was poured into 2N NaOH (5 mL) and extracted with EtOAc (2×25 mL). The combined organic extracts were dried (MgSO$_4$), concentrated and purified by reverse-phase column chromatography using 0-70% acetonitrile/H2O as the eluent. Peak 1 was isolated to provide the title compound (11 mg, 0.02280 mmol, 37.73% yield). MS (apci) m/z=483.2 (M+H).

Example 619

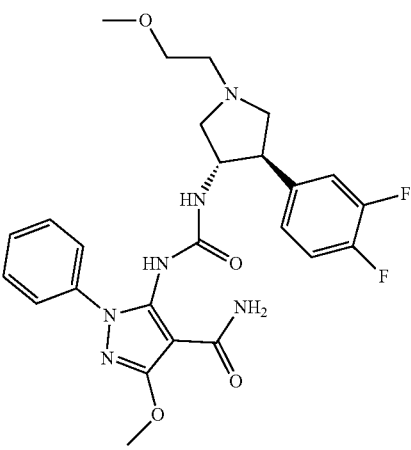 [SMILES: COCCN1C[C@@H](NC(=O)Nc2c(C(N)=O)c(OC)nn2-c2ccccc2)[C@H](c2ccc(F)c(F)c2)C1]

5-(3-((3S,4R)-4-(3,4-difluorophenyl)-1-(2-methoxy-ethyl)pyrrolidin-3-yl)ureido)-3-methoxy-1-phenyl-1H-pyrazole-4-carboxamide Prepared as described in Example 618, isolating peak 2 instead of peak 1 to provide the title compound (1.9 mg, 0.0037 mmol, 6.1% yield). MS (apci) m/z=515.2 (M+H).

The following compounds were prepared according to the method of Example 618, replacing 5-amino-3-methoxy-1-phenyl-1H-pyrazole-4-carbonitrile with the appropriate carbonitrile, and for Examples 623-626, also replacing (3S,4R)-4-(3,4-difluorophenyl)-1-(2-methoxyethyl)pyrrolidin-3-amine dihydrochloride with the appropriate pyrrolidine intermediate.

| Ex. # | Structure | Name | MS (apci) m/z |
|---|---|---|---|
| 620 | 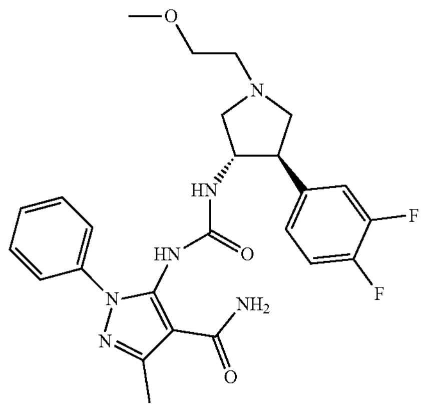 [SMILES: COCCN1C[C@@H](NC(=O)Nc2c(C(N)=O)c(C)nn2-c2ccccc2)[C@H](c2ccc(F)c(F)c2)C1] | 5-(3-((3S,4R)-4-(3,4-difluoro-phenyl)-1-(2-methoxyethyl)pyrrolidin-3-yl)ureido)-3-methyl-1-phenyl-1H-pyrazole-4-carboxamide | 499.2 (M + H) |
| 621 | 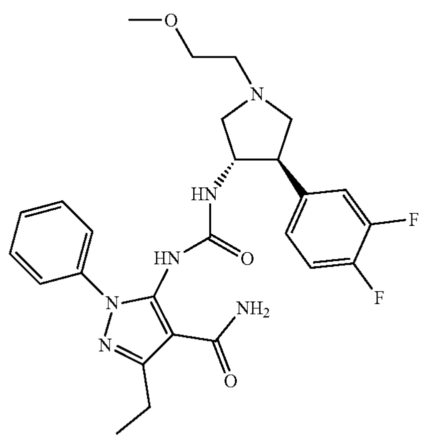 [SMILES: CCc1nn(-c2ccccc2)c(NC(=O)N[C@@H]2CN(CCOC)C[C@H]2c2ccc(F)c(F)c2)c1C(N)=O] | 5-(3-((3S,4R)-4-(3,4-difluorophenyl)-1-(2-methoxyethyl)pyrrolidin-3-yl)ureido)-3-ethyl-1-phenyl-1H-pyrazole-4-carboxamide | 513.2 (M + H) |
| 622 | 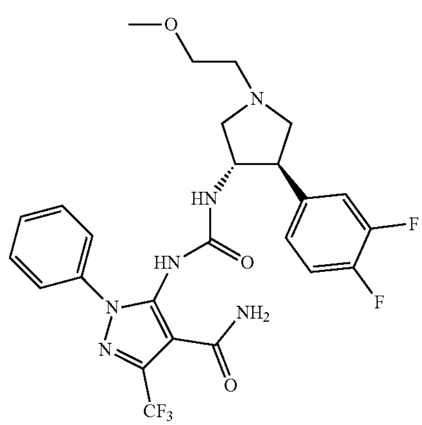 [SMILES: COCCN1C[C@@H](NC(=O)Nc2c(C(N)=O)c(C(F)(F)F)nn2-c2ccccc2)[C@H](c2ccc(F)c(F)c2)C1] | 5-(3-((3S,4R)-4-(3,4-difluorophenyl)-1-(2-methoxyethyl)pyrrolidin-3-yl)ureido)-1-phenyl-3-(trifluoromethyl)-1H-pyrazole-4-carboxamide | 553.2 (M + H) |

-continued

| Ex. # | Structure | Name | MS (apci) m/z |
|---|---|---|---|
| 623 | 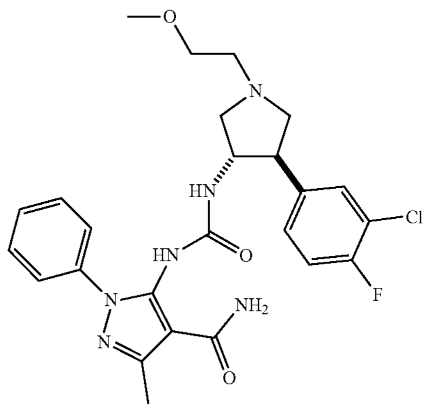 [SMILES: COCCN1C[C@@H](NC(=O)Nc2c(C(N)=O)c(C)nn2-c2ccccc2)[C@H](c2ccc(F)c(Cl)c2)C1] | 5-(3-((trans)-4-(3-chloro-4-fluorophenyl)-1-(2-methoxyethyl)pyrrolidin-3-yl)ureido)-3-methyl-1-phenyl-1H-pyrazole-4-carboxamide | 515.2 (M + H) |
| 624 | 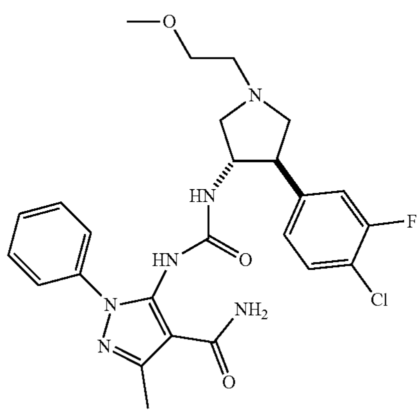 [SMILES: COCCN1C[C@@H](NC(=O)Nc2c(C(N)=O)c(C)nn2-c2ccccc2)[C@H](c2ccc(Cl)c(F)c2)C1] | 5-(3-((trans)-4-(4-chloro-3-fluorophenyl)-1-(2-methoxyethyl)pyrrolidin-3-yl)ureido)-3-methyl-1-phenyl-1H-pyrazole-4-carboxamide | 515.2 (M + H) |
| 625 | 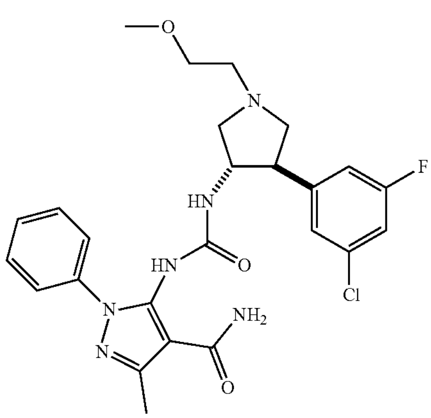 | 5-(3-((trans)-4-(3-chloro-5-fluorophenyl)-1-(2-methoxyethyl)pyrrolidin-3-yl)ureido)-3-methyl-1-phenyl-1H-pyrazole-4-carboxamide | 515.2 (M + H) |

| Ex. # | Structure | Name | MS (apci) m/z |
|---|---|---|---|
| 626 | 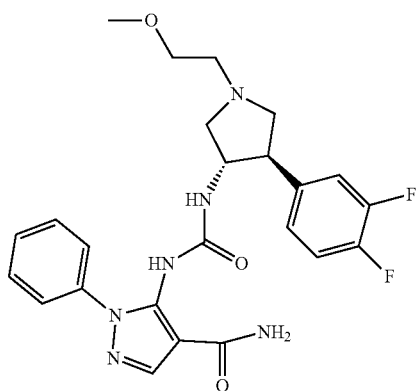 | 5-(3-((3S,4R)-4-(3,5-difluorophenyl)-1-(2-methoxyethyl)pyrrolidin-3-yl)ureido)-3-methyl-1-phenyl-1H-pyrazole-4-carboxamide | 499.2 (M + H) |

Example 627

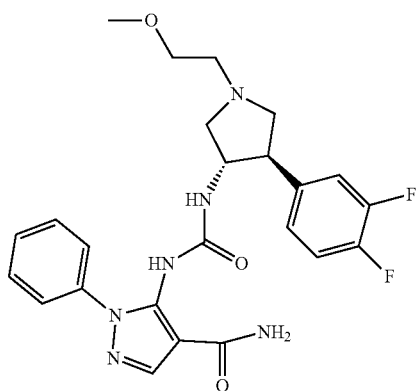 [SMILES: COCCN1C[C@@H](NC(=O)Nc2c(C(N)=O)cnn2-c2ccccc2)[C@H](c2ccc(F)c(F)c2)C1]

5-(3-((3S,4R)-4-(3,4-difluorophenyl)-1-(2-methoxyethyl)pyrrolidin-3-yl)ureido)-1-phenyl-1H-pyrazole-4-carboxamide Step A: Activation of 5-amino-1-phenyl-1H-pyrazole-4-carboxamide. 5-amino-1-phenyl-1H-pyrazole-4-carboxamide (500 mg, 2.47 mmol) was dissolved in 2 mL of CHCl$_3$ and pyridine (600 µL, 7.42 mmol) was added followed by phenylchloroformate (682 µL, 5.44 mmol). The reaction was stirred at ambient temperature for 2 hours and quenched with 2 mL of 2N NaOH. The reaction was extracted with several portions of CH$_2$Cl$_2$ in a phase separator frit and the combined organic extracts were concentrated. The crude material was purified by silica gel column chromatography, eluting with 5-40% acetone/hexanes to afford a bis-phenylcarbamate adduct (191 mg, 0.432 mmol, 17.5% yield). MS (apci) m/z=443.1 (M+H).

Step B: Preparation of 5-(3-((3S,4R)-4-(3,4-difluorophenyl)-1-(2-methoxyethyl) pyrrolidin-3-yl)ureido)-1-phenyl-1H-pyrazole-4-carboxamide. (3S,4R)-4-(3,4-difluorophenyl)-1-(2-methoxyethyl)pyrrolidin-3-amine dihydrochloride (33 mg, 0.099 mmol), the product of step A (20 mg, 0.045 mmol) and DIEA (39 µL, 0.23 mmol) were combined in 0.2 mL of DMF and stirred ambient temperature overnight. The mixture was loaded onto a samplet and purified by reverse-phase column chromatography using 0-70% acetonitrile/H2O as the eluent to provide the title compound (17 mg, 0.035 mmol, 78% yield). MS (apci) m/z=485.2 (M+H).

Example 628

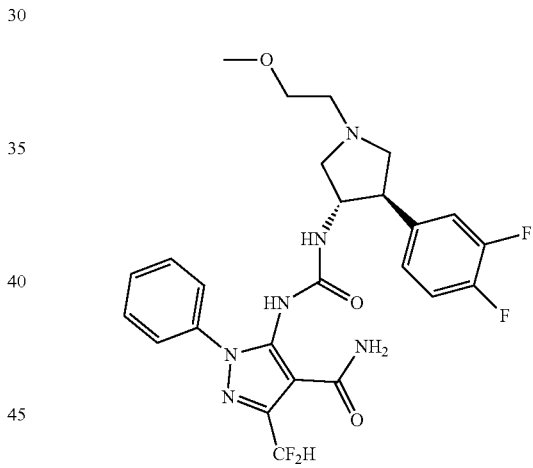

5-(3-((3S,4R)-4-(3,4-difluorophenyl)-1-(2-methoxyethyl)pyrrolidin-3-yl)ureido)-1-phenyl-1H-pyrazole-4-carboxamide Step A: Preparation of 2-(2,2-difluoro-1-hydroxyethylidene)malononitrile. A solution of malononitrile (4 g, 61 mmol) in methanol was charged with sodium methoxide (14 g, 67 mmol) followed by methyl 2,2-difluoroacetate (8.0 g, 73 mmol). The reaction was heated to 60° C. for 4 hours and concentrated in vacuo to afford the title compound (8.7 g, 60 mmol, 100% yield). $^1$H NMR (400 MHz, CDCl$_3$) δ ppm 6.13 (t, J=54 Hz, 1H).

Step B: Preparation of 2-(1-chloro-2,2-difluoroethylidene)malononitrile. To a slurry of 2-(2,2-difluoro-1-hydroxyethylidene)malononitrile (1.9 g, 13 mmol) in CH$_2$Cl$_2$ was added PCl$_5$ (2.7 g, 13 mmol) and the reaction was stirred at ambient temperature for 16 hours. The reaction was diluted with CH$_2$Cl$_2$, washed with water and brine, dried over MgSO₄ and concentrated to provide the title compound (2.3 g, 14 mmol, 107% yield).

Step C: Preparation of 5-amino-3-(difluoromethyl)-1-phenyl-1H-pyrazole-4-carbonitrile. To a solution of 2-(1-chloro-2,2-difluoroethylidene)malononitrile in ethanol was added phenylhydrazine hydrochloride (2.3 g, 16 mmol) and the reaction was heated to 70° C. for 4 hours. The reaction was concentrated in vacuo and the material was partitioned between EtOAc and water. The layers were separated and the organic layer was washed with brine, dried (MgSO₄) and concentrated in vacuo. The crude material was purified by silica gel column chromatography using 5% EtOAc/CH₂Cl₂ as the eluent to provide the title compound (0.25 g, 1.1 mmol, 7.5% yield). MS (apci) m/z=233.1 (M–H).

Step D: Preparation of 3-(difluoromethyl)-5-(3-((3S,4R)-4-(3,4-difluorophenyl)-1-(2-methoxyethyl)pyrrolidin-3-yl)ureido)-1-phenyl-1H-pyrazole-4-carboxamide. 5-amino-3-(difluoromethyl)-1-phenyl-1H-pyrazole-4-carbonitrile was elaborated as described for 5-amino-3-methoxy-1-phenyl-1H-pyrazole-4-carbonitrile in Example 618. The material was purified by reverse-phase column chromatography using 5-80% acetonitrile/H₂O as the eluent followed by Gilson preparative HPLC using a Chiral Technologies OD-H column and hexanes/EtOH 9:1 as the eluent to provide the title compound (1.7 mg, 0.0032 mmol, 0.30% yield for two steps). MS (apci) m/z=533.2 (M–H).

Example 629

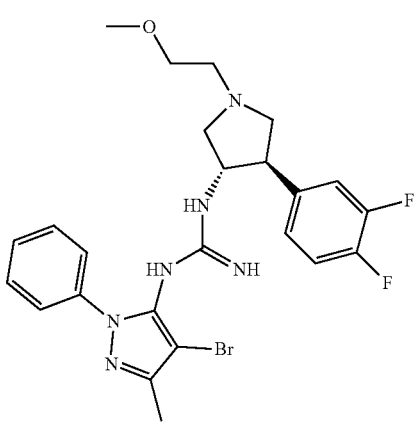 [SMILES: COCCN1C[C@@H](NC(=N)Nc2c(Br)c(C)nn2-c2ccccc2)[C@H](c2ccc(F)c(F)c2)C1]

1-(4-bromo-3-methyl-1-phenyl-1H-pyrazol-5-yl)-3-((3S,4R)-4-(3,4-difluorophenyl)-1-(2-methoxyethyl)pyrrolidin-3-yl)guanidine dihydrochloride 1-(4-bromo-3-methyl-1-phenyl-1H-pyrazol-5-yl)-3-((3S,4R)-4-(3,4-difluorophenyl)-1-(2-methoxyethyl)pyrrolidin-3-yl)thiourea (40 mg, 0.07267 mmol, prepared by the method described in Example 630) and AgOTf (46.68 mg, 0.1817 mmol) were combined in 5 mL of CH₂Cl₂ and cooled in an ice-MeOH bath. Ammonia gas was bubbled through the solution for 1 minute and the reaction was allowed to warm to ambient temperature. HCl (5N in IPA, 60.7 μL, 0.303 mmol) and MeOH (2 mL) were added and the reaction was filtered through Celite®. The solids were washed with several portions of MeOH and the combined filtrate was concentrated and purified by reverse-phase column chromatography using 0-70% acetonitrile/0.1N aqueous HCl as the eluent to provide the title compound (11 mg, 0.01814 mmol, 24.97% yield). MS (apci) m/z=535.1 (M+H).

Example 630

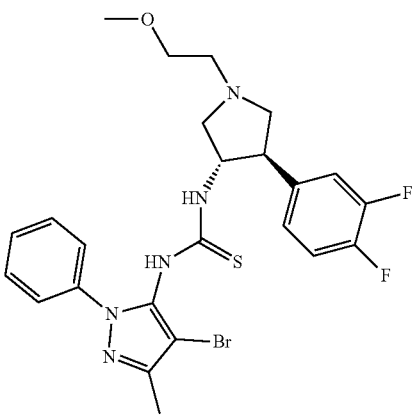 [SMILES: COCCN1C[C@@H](NC(=S)Nc2c(Br)c(C)nn2-c2ccccc2)[C@H](c2ccc(F)c(F)c2)C1]

1-(4-bromo-3-methyl-1-phenyl-1H-pyrazol-5-yl)-3-((3S,4R)-4-(3,4-difluorophenyl)-1-(2-methoxyethyl)pyrrolidin-3-yl)thiourea 4-Bromo-3-methyl-1-phenyl-1H-pyrazol-5-amine (250 mg, 0.992 mmol), DIEA (864 μL, 4.96 mmol) and di(1H-imidazol-1-yl)methanethione (177 mg, 0.992 mmol) were combined in 1 mL of DMF and stirred at ambient temperature for 3 days and then at 70° C. overnight. (3S,4R)-4-(3,4-difluorophenyl)-1-(2-methoxyethyl)pyrrolidin-3-amine dihydrochloride (326 mg, 0.992 mmol) was added and the reaction was stirred at ambient temperature for 24 hours. The mixture was loaded onto a samplet and purified by reverse-phase column chromatography using 5-80% acetonitrile/H₂O as the eluent to provide the title compound (364 mg, 0.661 mmol, 66.7% yield). MS (apci) m/z=550.1 (M+H).

Example 631

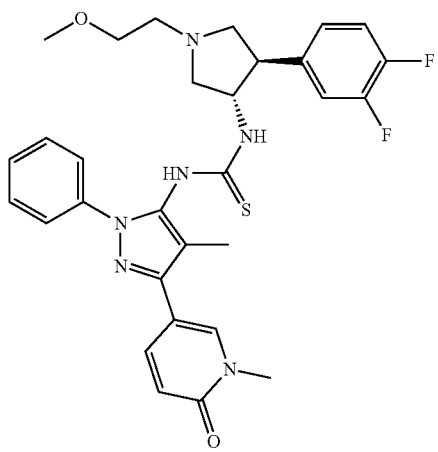 [SMILES: COCCN1C[C@@H](NC(=S)Nc2c(C)c(-c3ccc(=O)n(C)c3)nn2-c2ccccc2)[C@H](c2ccc(F)c(F)c2)C1]

1-((3S,4R)-4-(3,4-difluorophenyl)-1-(2-methoxy-
ethyl)pyrrolidin-3-yl)-3-(4-methyl-3-(1-methyl-6-
oxo-1,6-dihydropyridin-3-yl)-1-phenyl-1H-pyrazol-
5-yl)thiourea Prepared as described for Example 630, substituting 5-(5-amino-4-methyl-1-phenyl-1H-pyrazol-3-yl)-1-methylpyridin-2(1H)-one for 4-bromo-3-methyl-1-phenyl-1H-pyrazol-5-amine. The material was purified by reverse-phase column chromatography using 5-80% acetonitrile/H₂O as the eluent to provide the title compound (4.5 mg, 0.00778 mmol, 12.5% yield). MS (apci) m/z=579.2 (M+H).

Example 632

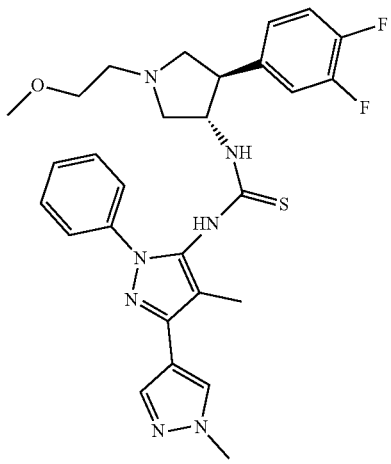 [SMILES: COCCN1C[C@@H](NC(=S)Nc2c(C)c(-c3cnn(C)c3)nn2-c2ccccc2)[C@H](c2ccc(F)c(F)c2)C1]

1-((3S,4R)-4-(3,4-difluorophenyl)-1-(2-methoxy-
ethyl)pyrrolidin-3-yl)-3-(1',4-dimethyl-1-phenyl-1H,
1'H-3,4'-bipyrazol-5-yl)thiourea Prepared as described for Example 630, substituting 1',4-dimethyl-1-phenyl-1H,1'H-3,4'-bipyrazol-5-amine for 4-bromo-3-methyl-1-phenyl-1H-pyrazol-5-amine. The material was purified by reverse-phase column chromatography using 5-80% acetonitrile/H₂O as the eluent to provide the title compound (71 mg, 0.129 mmol, 75.8% yield). MS (apci) m/z=552.2 (M+H).

Example 633

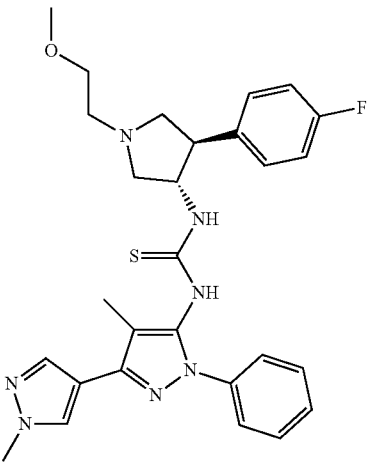 [SMILES: COCCN1C[C@@H](NC(=S)Nc2c(C)c(-c3cnn(C)c3)nn2-c2ccccc2)[C@H](c2ccc(F)cc2)C1]

1-((3S,4R)-4-(4-fluorophenyl)-1-(2-methoxyethyl)
pyrrolidin-3-yl)-3-(1',4-dimethyl-1-phenyl-1H, 1'H-
3,4'-bipyrazol-5-yl)thiourea Prepared as described for Example 630, substituting 1',4-dimethyl-1-phenyl-1H,1'H-3,4'-bipyrazol-5-amine for 4-bromo-3-methyl-1-phenyl-1H-pyrazol-5-amine and (3S,4R)-4-(4-fluorophenyl)-1-(2-methoxyethyl)pyrrolidin-3-amine dihydrochloride for (3S,4R)-4-(3,4-difluorophenyl)-1-(2-methoxyethyl)pyrrolidin-3-amine dihydrochloride. The material was purified by reverse-phase column chromatography using 5-80% acetonitrile/H₂O as the eluent to provide the title compound (50 mg, 0.0937 mmol, 69.0% yield). MS (apci) m/z=534.2 (M+H).

The compounds of were prepared according to the method of Example 52 using the appropriate starting materials in a suitable solvent such as CH₂Cl₂, DMF, DMA or CH₃CN.

| Ex. # | Structure | Name | Data |
|---|---|---|---|
| 634 | ![structure] | Trans-1-(2-methoxyethyl)-4-phenylpyrrolidin-3-yl)-3-(2-phenylpyrazolo[1,5-a]pyridin-3-yl)urea | MS (apci) m/z = 456.3 (M + H) |

-continued

| Ex. # | Structure | Name | Data |
|---|---|---|---|
| 635 | 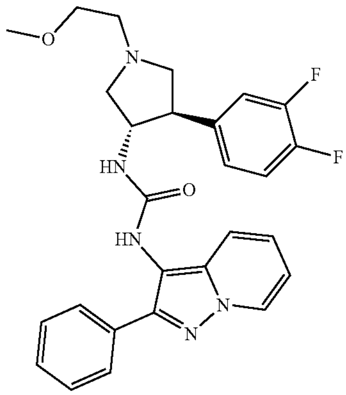 [SMILES: COCCN1C[C@@H](NC(=O)Nc2c(-c3ccccc3)nn3ccccc23)[C@H](c2ccc(F)c(F)c2)C1] | 1-((3S,4R)-4-(3,4-difluorophenyl)-1-(2-methoxyethyl)pyrrolidin-3-yl)-3-(2-phenylpyrazolo[1,5-a]pyridin-3-yl)urea | MS (apci) m/z = 492.0 (M + H) |
| 636 | 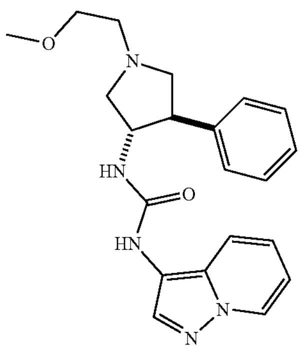 | Trans-1-(2-methoxyethyl)-4-phenylpyrrolidin-3-yl)-3-(pyrazolo[1,5-a]pyridin-3-yl)urea | MS (apci) m/z = 380.2 (M + H) |
| 637 | 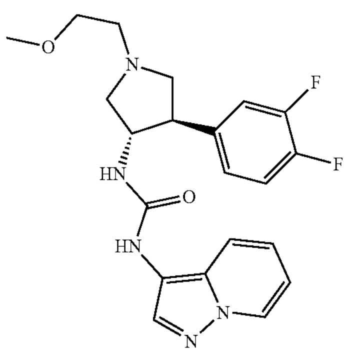 [SMILES: COCCN1C[C@@H](NC(=O)Nc2cnn3ccccc23)[C@H](c2ccc(F)c(F)c2)C1] | 1-((3S,4R)-4-(3,4-difluorophenyl)-1-(2-methoxyethyl)pyrrolidin-3-yl)-3-(pyrazolo[1,5-a]pyridin-3-yl)urea | MS (apci) m/z = 416.1 (M + H) |
| 638 | 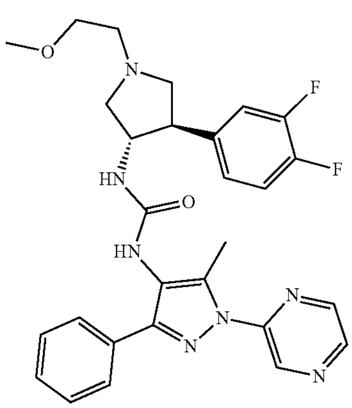 [SMILES: COCCN1C[C@@H](NC(=O)Nc2c(-c3ccccc3)nn(-c3cnccn3)c2C)[C@H](c2ccc(F)c(F)c2)C1] | 1-((3S,4R)-4-(3,4-difluorophenyl)-1-(2-methoxyethyl)pyrrolidin-3-yl)-3-(5-methyl-3-phenyl-1-(pyrazin-2-yl)-1H-pyrazol-4-yl)urea | MS (esi) m/z = 534.2 (M + H) |

The following compounds were prepared according to the method of Example 1 using the appropriate starting materials in a suitable solvent such as CH$_2$Cl$_2$, DMF, DMA or CH$_3$CN.

| Ex. # | Structure | Name | MS (apci) m/z |
|---|---|---|---|
| 639 | 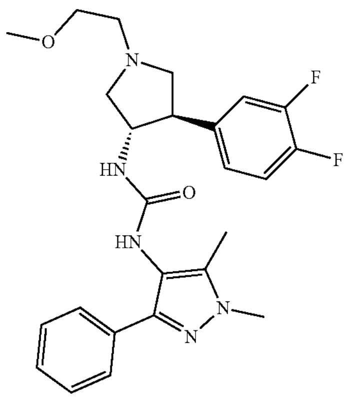 [SMILES: COCCN1C[C@@H](NC(=O)Nc2c(-c3ccccc3)nn(C)c2C)[C@H](c2ccc(F)c(F)c2)C1] | 1-((3S,4R)-4-(3,4-difluorophenyl)-1-(2-methoxyethyl)pyrrolidin-3-yl)-3-(1,5-dimethyl-3-phenyl-1H-pyrazol-4-yl)urea | 470.2 (M + H) |
| 640 | 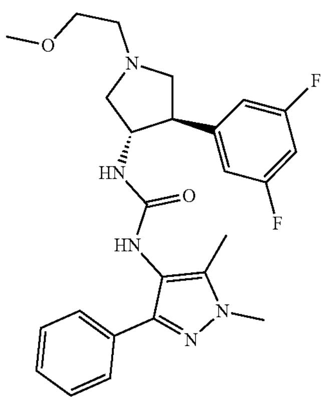 [SMILES: COCCN1C[C@@H](NC(=O)Nc2c(-c3ccccc3)nn(C)c2C)[C@H](c2cc(F)cc(F)c2)C1] | 1-((3S,4R)-4-(3,5-difluorophenyl)-1-(2-methoxyethyl)pyrrolidin-3-yl)-3-(1,5-dimethyl-3-phenyl-1H-pyrazol-4-yl)urea | 470.2 (M + H) |
| 641 | 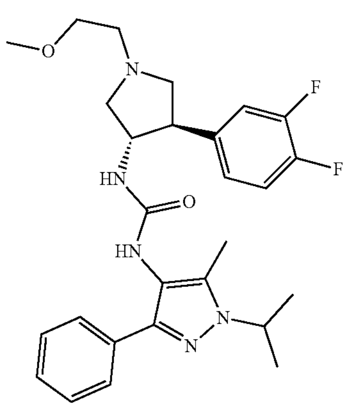 [SMILES: COCCN1C[C@@H](NC(=O)Nc2c(-c3ccccc3)nn(C(C)C)c2C)[C@H](c2ccc(F)c(F)c2)C1] | 1-((3S,4R)-4-(3,4-difluorophenyl)-1-(2-methoxyethyl)pyrrolidin-3-yl)-3-(1-isopropyl-5-methyl-3-phenyl-1H-pyrazol-4-yl)urea | 498.2 (M + H) |

-continued

| Ex. # | Structure | Name | MS (apci) m/z |
|---|---|---|---|
| 642 | 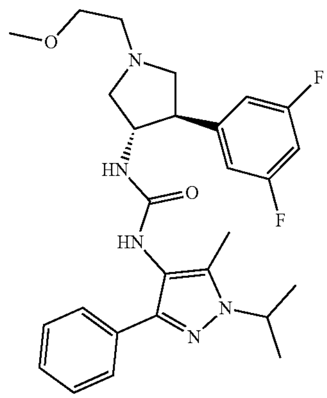 [SMILES: COCCN1C[C@@H](NC(=O)Nc2c(-c3ccccc3)nn(C(C)C)c2C)[C@H](c2cc(F)cc(F)c2)C1] | 1-((3S,4R)-4-(3,5-difluorophenyl)-1-(2-methoxyethyl)pyrrolidin-3-yl)-3-(1-isopropyl-5-methyl-3-phenyl-1H-pyrazol-4-yl)urea | 498.2 (M + H) |
| 643 | 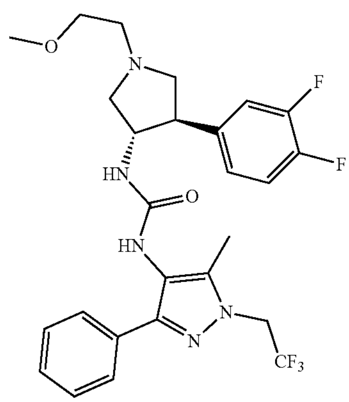 [SMILES: COCCN1C[C@@H](NC(=O)Nc2c(-c3ccccc3)nn(CC(F)(F)F)c2C)[C@H](c2ccc(F)c(F)c2)C1] | 1-((3S,4R)-4-(3,4-difluorophenyl)-1-(2-methoxyethyl)pyrrolidin-3-yl)-3-(5-methyl-3-phenyl-1-(2,2,2-trifluoroethyl)-1H-pyrazol-4-yl)urea | 538.2 (M + H) |
| 644 | 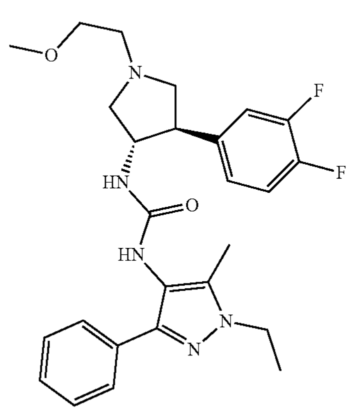 [SMILES: CCn1nc(-c2ccccc2)c(NC(=O)N[C@@H]2CN(CCOC)C[C@H]2c2ccc(F)c(F)c2)c1C] | 1-((3S,4R)-4-(3,4-difluorophenyl)-1-(2-methoxyethyl)pyrrolidin-3-yl)-3-(1-ethyl-5-methyl-3-phenyl-1H-pyrazol-4-yl)urea | 484.2 (M + H) |

| Ex. # | Structure | Name | MS (apci) m/z |
|---|---|---|---|
| 645 | 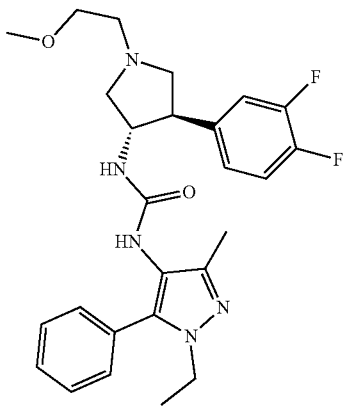 [SMILES: CCn1nc(C)c(NC(=O)N[C@@H]2CN(CCOC)C[C@H]2c2ccc(F)c(F)c2)c1-c1ccccc1] | 1-((3S,4R)-4-(3,4-difluorophenyl)-1-(2-methoxyethyl)pyrrolidin-3-yl)-3-(1-ethyl-3-methyl-5-phenyl-1H-pyrazol-4-yl)urea | 484.3 (M + H) |
| 646 | 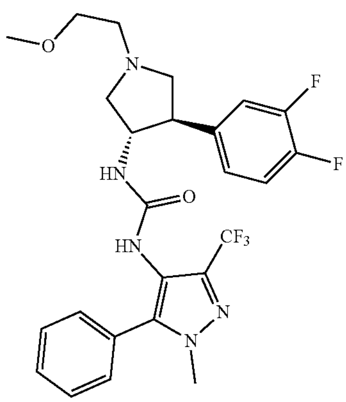 [SMILES: COCCN1C[C@@H](NC(=O)Nc2c(C(F)(F)F)nn(C)c2-c2ccccc2)[C@H](c2ccc(F)c(F)c2)C1] | 1-((3S,4R)-4-(3,4-difluorophenyl)-1-(2-methoxyethyl)pyrrolidin-3-yl)-3-(1-methyl-5-phenyl-3-(trifluoromethyl)-1H-pyrazol-4-yl)urea | 524.2 (M + H) |
| 647 | 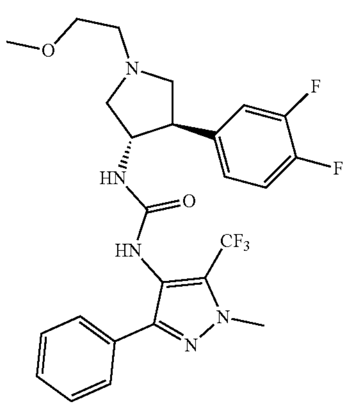 | 1-((3S,4R)-4-(3,4-difluorophenyl)-1-(2-methoxyethyl)pyrrolidin-3-yl)-3-(1-methyl-3-phenyl-5-(trifluoromethyl)-1H-pyrazol-4-yl)urea | 524.2 (M + H) |

Example 648

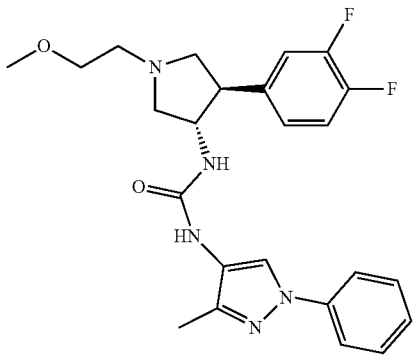 [SMILES: COCCN1C[C@@H](NC(=O)Nc2cn(-c3ccccc3)nc2C)[C@H](c2ccc(F)c(F)c2)C1]

1-((3S,4R)-4-(3,4-difluorophenyl)-1-(2-methoxy-ethyl)pyrrolidin-3-yl)-3-(3-methyl-1-phenyl-1H-pyrazol-4-yl)urea Step A: Preparation of ethyl 3-methyl-1-phenyl-1H-pyrazole-4-carboxylate: A mixture of ethyl 3-methyl-1H-pyrazole-4-carboxylate (0.600 g, 3.89 mmol), phenylboronic acid (0.498 g, 4.09 mmol), Cu(OAc)$_2$ (0.530 g, 2.92 mmol), pyridine (0.630 mL, 7.78 mmol) in dry DMF (39 mL) was stirred at ambient temperature for 3 days. The reaction mixture was partitioned between EtOAc and water and the organic layer was removed. The aqueous layer was extracted with EtOAc (2×) and the combined organic layers were washed with water and saturated NaCl. The EtOAc solution was dried over MgSO$_4$, filtered and concentrated. The residue was purified by flash chromatography on silica gel (4:1 hexanes/EtOAc) to give the title compound (0.428 g, 48%). MS (apci) m/z=231.1 (M+H).

Step B: Preparation of 3-methyl-1-phenyl-1H-pyrazole-4-carboxylic acid. To a solution of ethyl 3-methyl-1-phenyl-1H-pyrazole-4-carboxylate (0.428 g, 1.86 mmol) in 1:1 MeOH/THF (8.0 mL) was added 1M LiOH (3.72 mL, 3.72 mmol) and the mixture was stirred at ambient temperature for 16 hours. The solvents were removed in vacuum, the residue was diluted with water and was extracted with Et$_2$O (2×). The aqueous layer was treated with 1M HCl to pH 4-5 and was extracted with EtOAc (3×). The combined organic fractions were washed with water and saturated NaCl. The EtOAc solution was dried over MgSO$_4$, filtered and concentrated to provide the crude product (0.280 g, 75%) that was used in the next step without further purification. MS (apci) m/z=203.1 (M+H).

Step C: Preparation of 1-((3S,4R)-4-(3,4-difluorophenyl)-1-(2-methoxy-ethyl) pyrrolidin-3-yl)-3-(3-methyl-1-phenyl-1H-pyrazol-4-yl)urea: To a solution of 3-methyl-1-phenyl-1H-pyrazole-4-carboxylic acid (50 mg, 0.25 mmol) and Et$_3$N (0.039 mL, 0.30 mmol) in toluene (2 mL) was added diphenyl phosphorazidate (0.064 mL, 0.30 mmol). The solution was heated at reflux for 1 hour and was cooled to ambient temperature. The mixture was diluted with THF (1 mL) and (3S,4R)-4-(3,4-difluorophenyl)-1-(2-methoxy-ethyl)pyrrolidin-3-amine dihydrochloride (98 mg, 0.30 mmol) was added followed by and Et$_3$N (0.108 mL, 0.90 mmol). The reaction mixture was stirred at ambient temperature for 16 hours. The mixture was partitioned between EtOAc and saturated aqueous NaHCO$_3$. The organic layer was removed and the aqueous layer was extracted with EtOAc (2×). The combined organic layers were washed with saturated NaCl, dried over MgSO$_4$, filtered and concentrated. The residue was purified by flash chromatography on silica gel (5% MeOH/DCM) to give the title compound (66 mg, 59%). MS (apci) m/z=456.2 (M+H).

Example 649

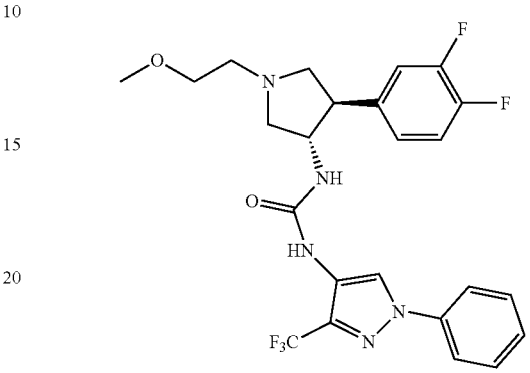

1-((3S,4R)-4-(3,4-difluorophenyvl)-1-(2-methoxy-ethyl)pyrrolidin-3-yl)-3-(1-phenyl-3-(trifluorom-ethyl)-1H-pyrazol-4-yl)urea Prepared according to the procedure described for Example 648, Step C, using 1-phenyl-3-(trifluoromethyl)-1H-pyrazole-4-carboxylic acid as a replacement for 3-methyl-1-phenyl-1H-pyrazole-4-carboxylic. MS (apci) m/z=510.2 (M+H).

What is claimed is:

1. A method for treating pain associated with overexpression of TrkA in a mammal, which comprises administering to said mammal a therapeutically effective amount of a compound of Formula I

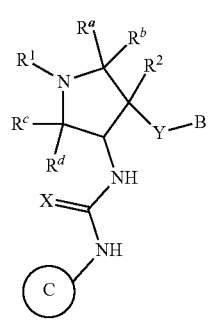

I or stereoisomers, tautomers, or pharmaceutically acceptable salts wherein:
the Y—B moiety and the NH—C(=X)—NH moiety are in the trans configuration;
$R^a$, $R^b$, $R^c$ and $R^d$ are H;
X is O;
$R^1$ is (1-3C alkoxy)(1-6C)alkyl, difluoro(1-6C)alkyl or trifluoro(1-6C)alkyl;
$R^2$ is hydrogen;
Y is a bond;
B is $Ar^1$;

Ar¹ is phenyl optionally substituted with one or more substituents independently selected from halogen, CF₃, CF₃O—, (1-4C)alkoxy, hydroxy(1-4C)alkyl, (1-6C) alkyl and CN;

Ring C is formula C-1

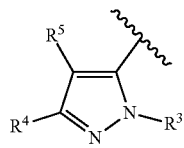

R³ is Ar², hetAr² or (1-6C)alkyl;
Ar² is phenyl optionally substituted with one or more groups independently selected from halogen, (1-6C) alkyl and hydroxymethyl;
hetAr² is a 5-6 membered heteroaryl ring having 1-3 ring heteroatoms independently selected from N, O and S and optionally substituted with one or more groups independently selected from (1-6C)alkyl and halogen;
R⁴ is hetAr⁴ or Ar⁴;
hetAr⁴ is a 5-6 membered heteroaryl ring having 1-3 ring heteroatoms independently selected from N, S and O and optionally substituted with 1-2 substituents independently selected from (1-6C)alkyl, halogen, CN, hydroxy(1-6C)alkyl, trifluoro(1-6C)alkyl, (3-6C)cycloalkyl, (3-6C cycloalkyl)CH₂—, (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), (1-3C)trifluoroalkyl, and methoxybenzyl; or a 9-10 membered bicyclic heteroaryl having 1-3 ring nitrogen atoms;
Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—; and
R⁵ is (1-6C)alkyl.

2. The method of claim 1, where A¹ is phenyl optionally substituted with one or more halogens.

3. The method of claim 2, where hetAr⁴ is a 5-6 membered heteroaryl ring having 1-3 ring heteroatoms independently selected from N, S and O and optionally substituted with 1-2 substituents independently selected from (1-6C)alkyl.

4. The method of claim 3, wherein the Y-B moiety and the —NH—C(=X)—NH— moiety of Formula I are trans in the absolute configuration shown in formula C:

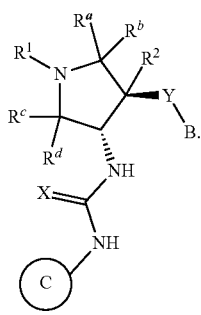

5. The method of claim 4, wherein said compound is selected from:

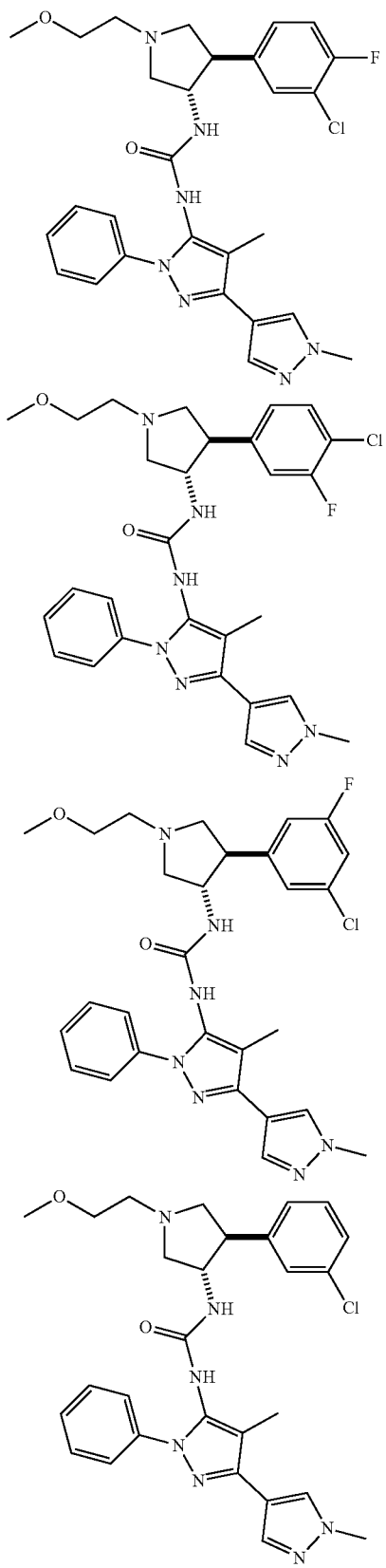

575
-continued
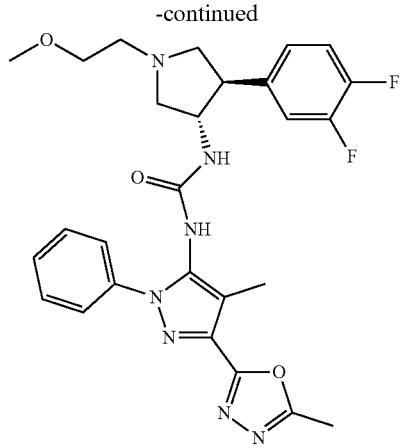
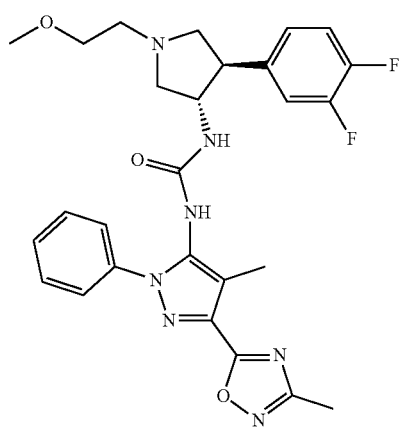
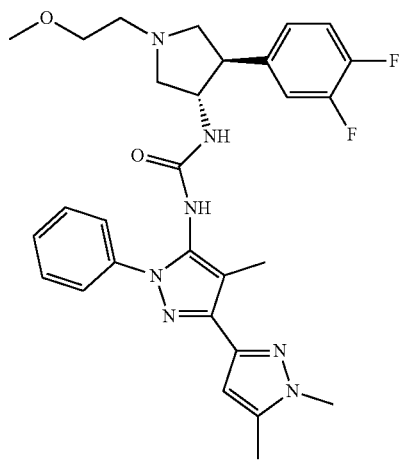
576
-continued
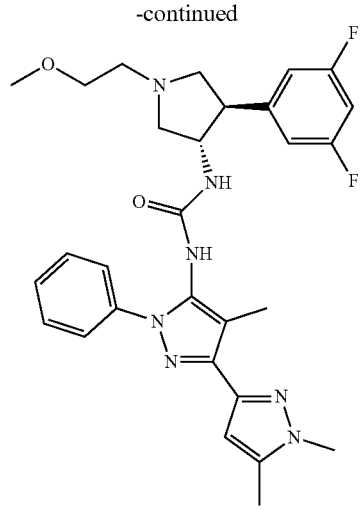
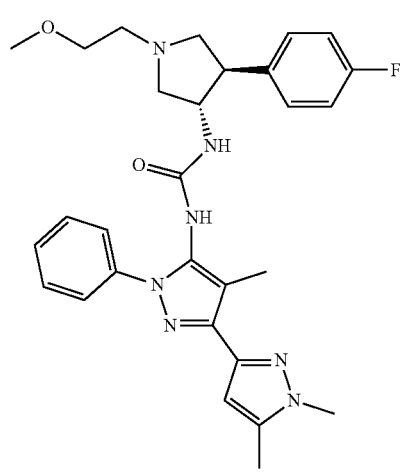
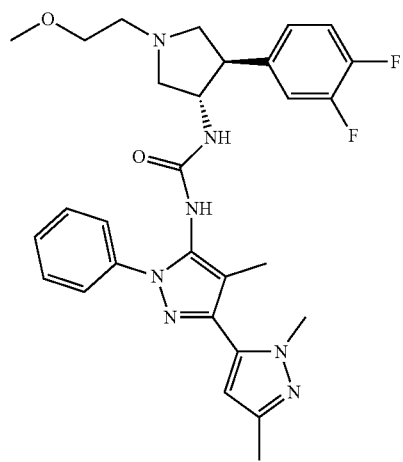

577
-continued
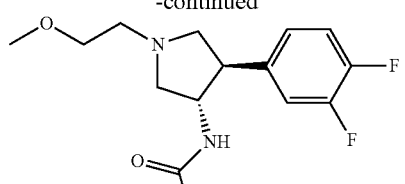
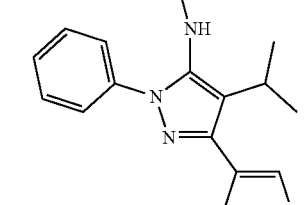
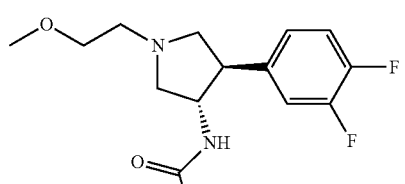
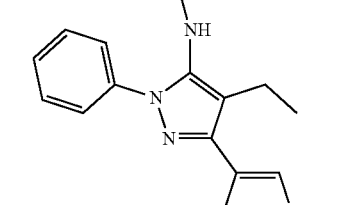
578
-continued
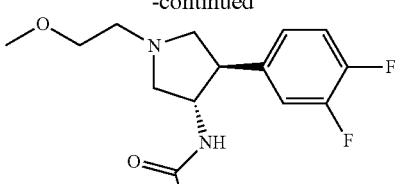
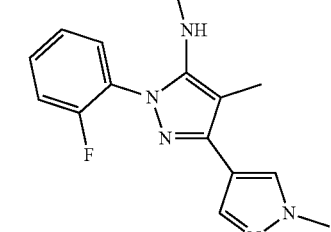
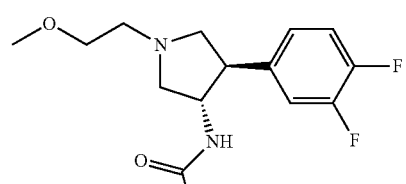
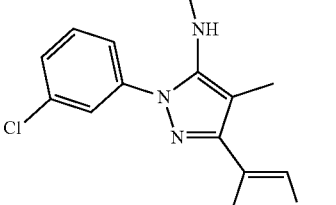
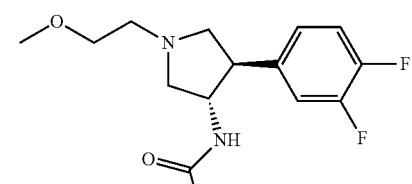
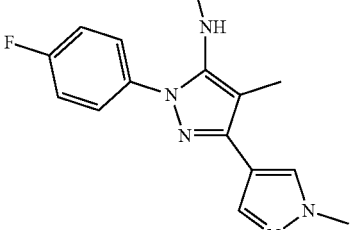
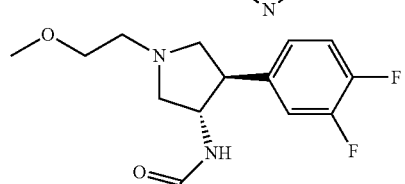
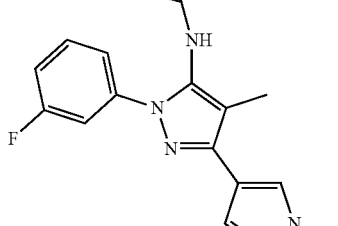
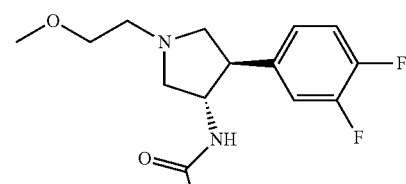
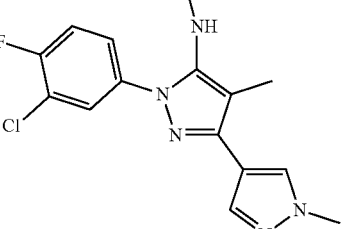
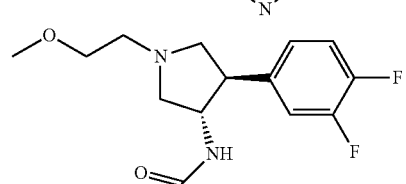
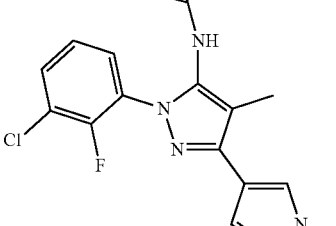

579
-continued
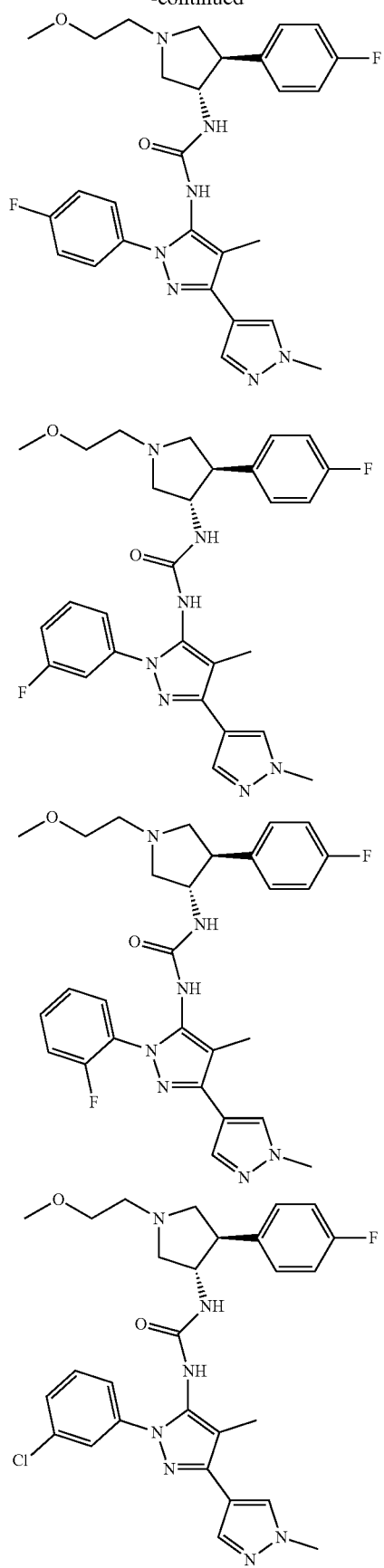
580
-continued
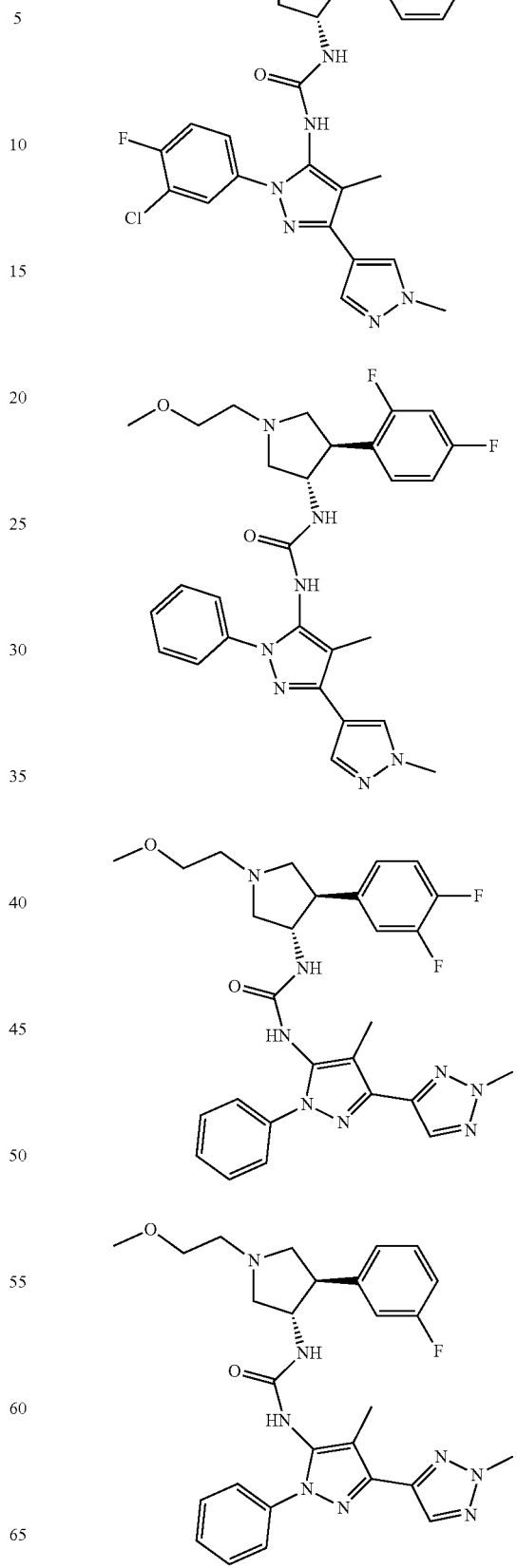

581
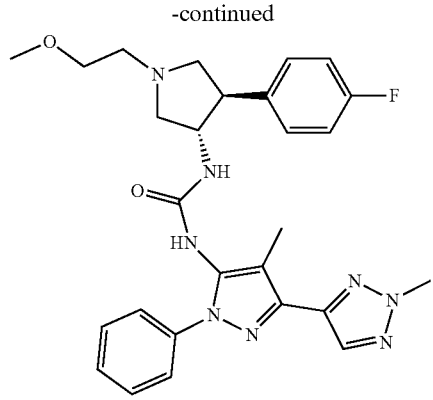
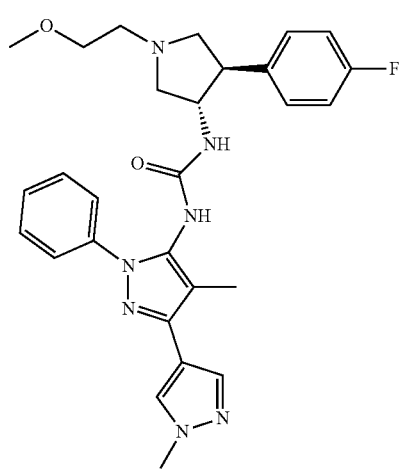
582
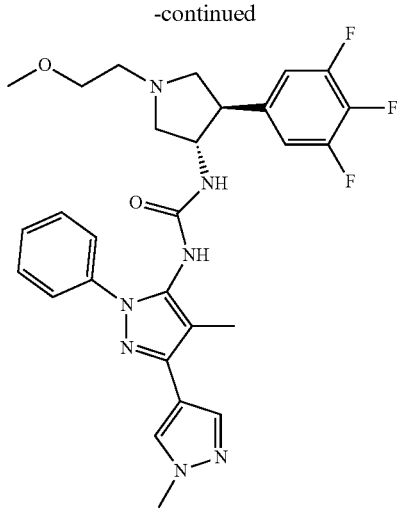
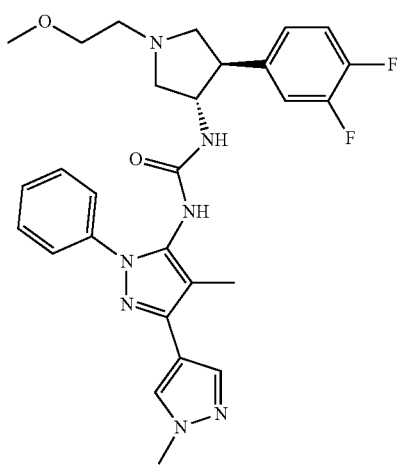
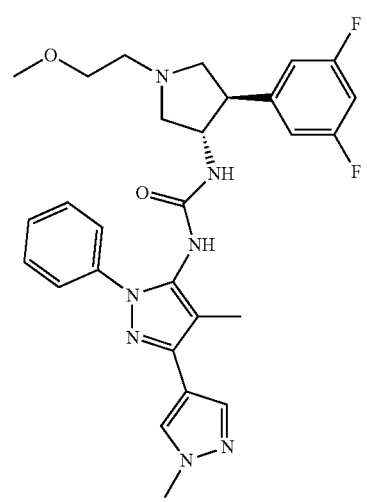
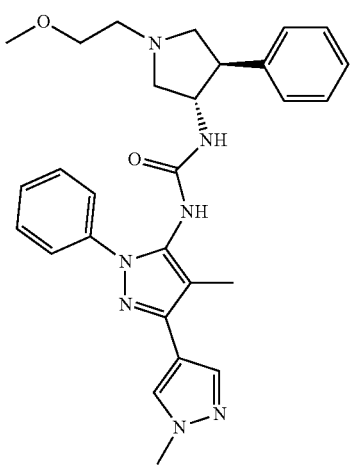

583
-continued
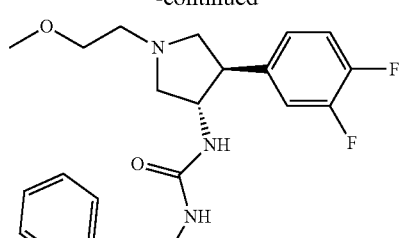
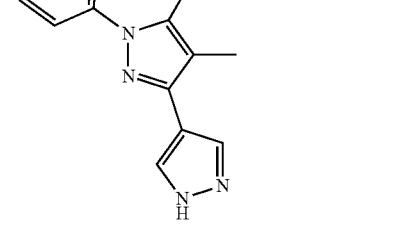
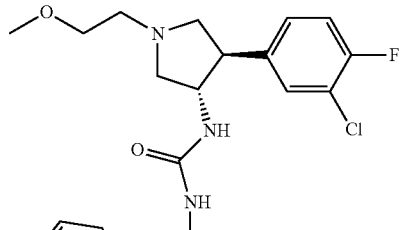
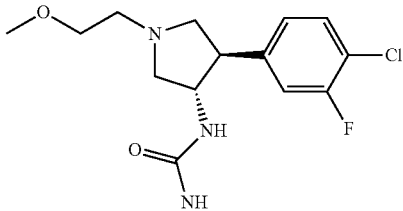
584
-continued
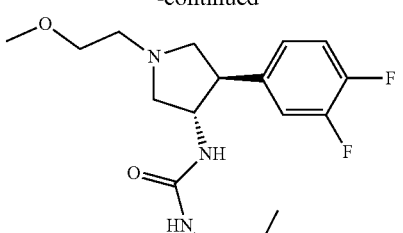
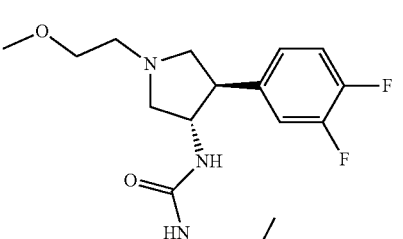
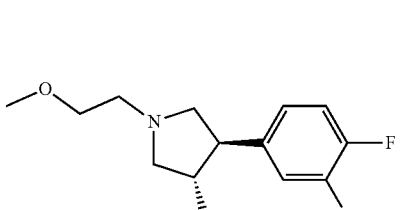
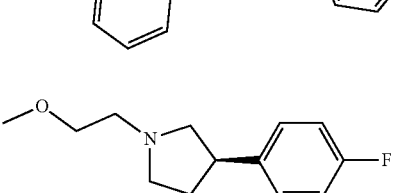

585
-continued
586
-continued
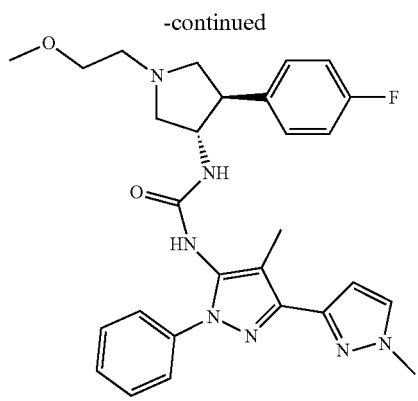
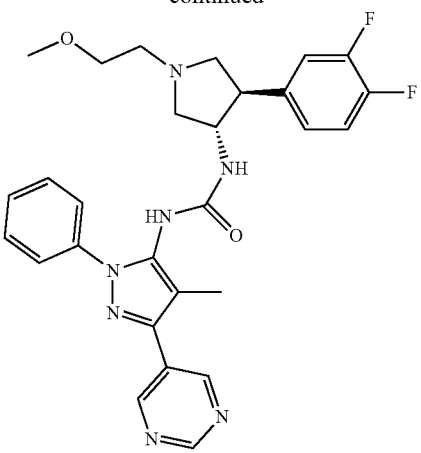

587
-continued
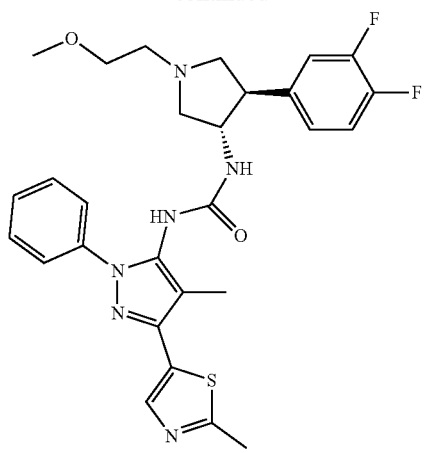
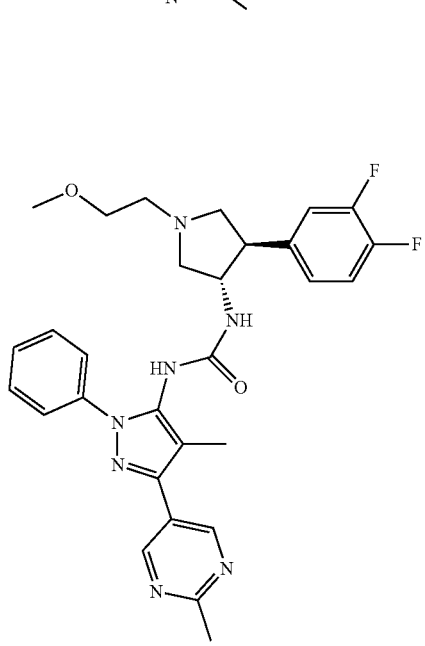
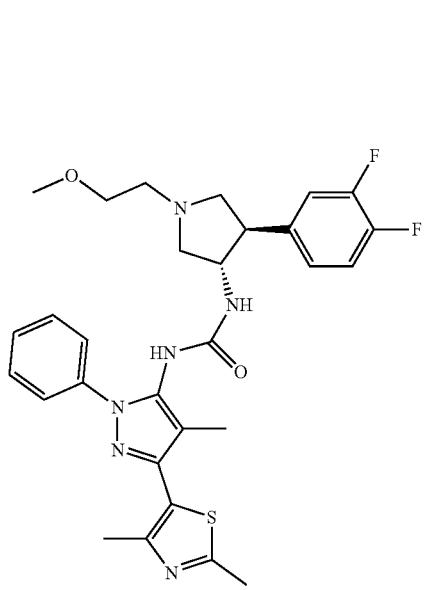
588
-continued
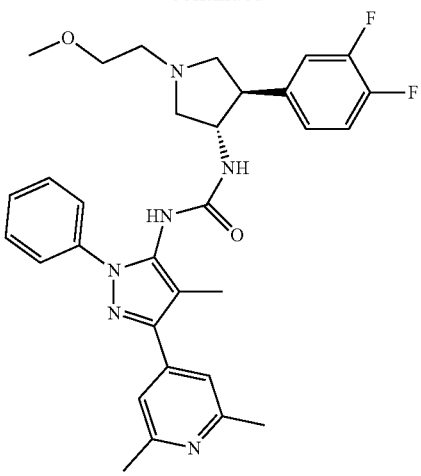
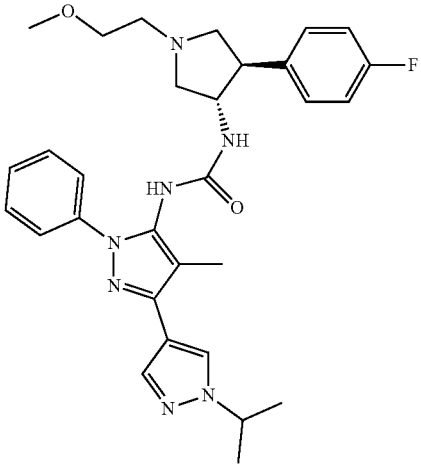
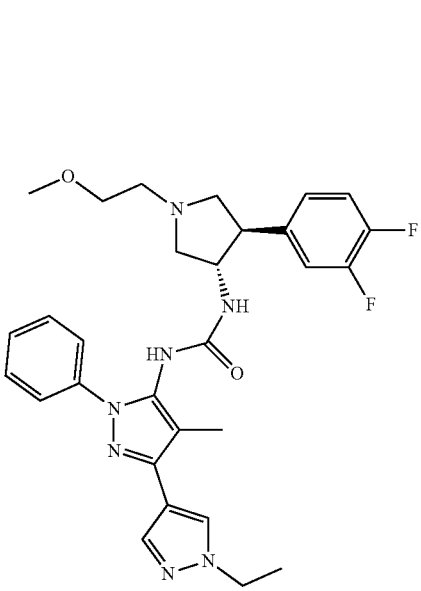

-continued
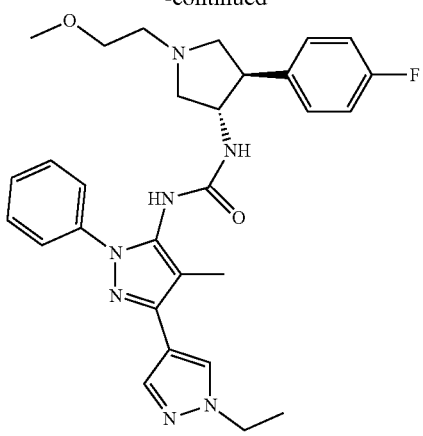
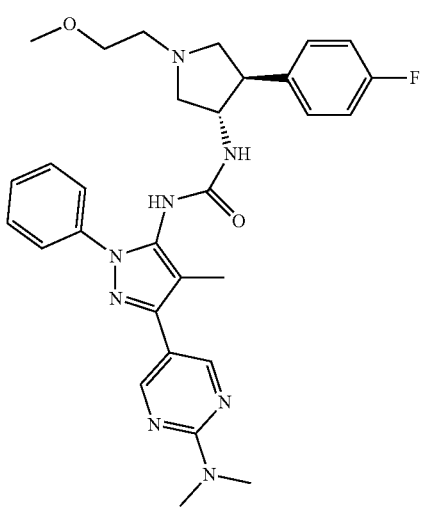
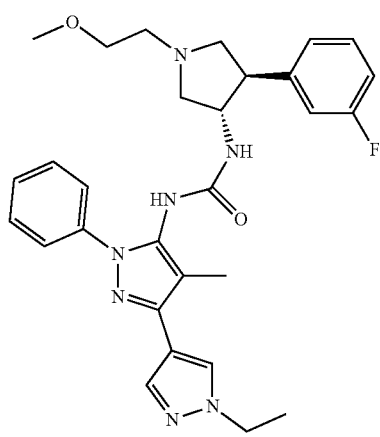
-continued
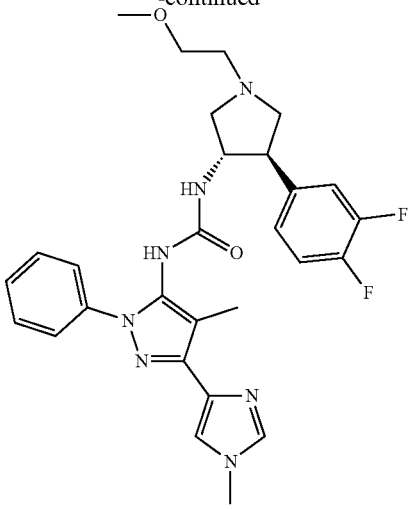
or a pharmaceutically acceptable salt thereof.
6. The method of claim 5, wherein the compound is
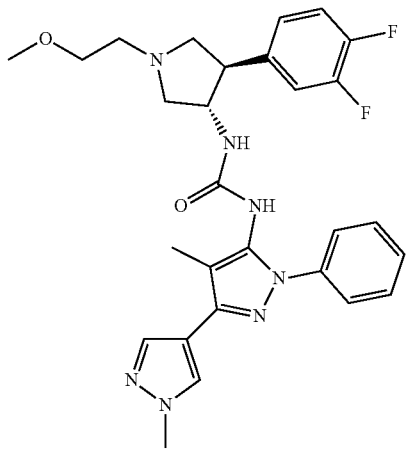 [SMILES: COCCN1C[C@@H](NC(=O)Nc2c(C)c(-c3cnn(C)c3)nn2-c2ccccc2)[C@H](c2ccc(F)c(F)c2)C1]
or a pharmaceutically acceptable salt thereof.
7. The method of claim 5, wherein the compound is
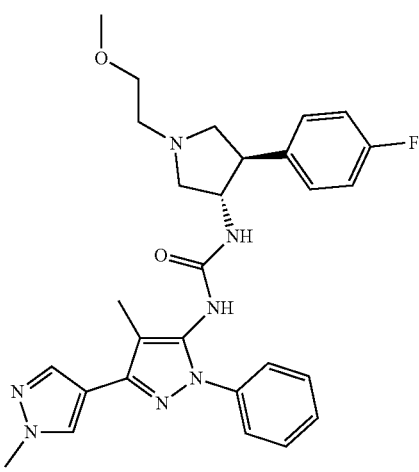 [SMILES: COCCN1C[C@@H](NC(=O)Nc2c(C)c(-c3cnn(C)c3)nn2-c2ccccc2)[C@H](c2ccc(F)cc2)C1]
or a pharmaceutically acceptable salt thereof.

8. The method of claim 5, wherein the compound is

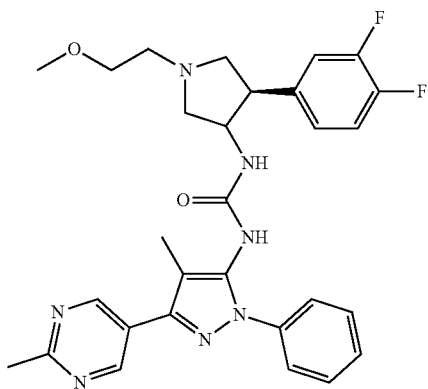 [SMILES: COCCN1CC(NC(=O)Nc2c(C)c(-c3cnc(C)nc3)nn2-c2ccccc2)[C@H](c2ccc(F)c(F)c2)C1]

or a pharmaceutically acceptable salt thereof.

9. The method of claim 5, wherein the compound is

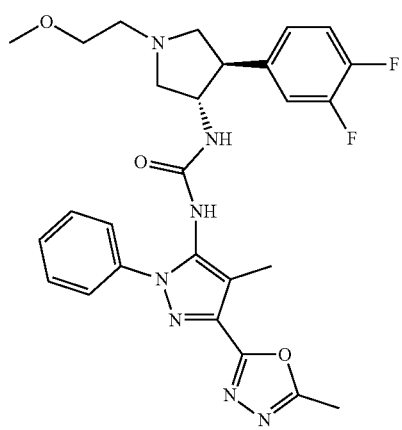 [SMILES: COCCN1C[C@@H](NC(=O)Nc2c(C)c(-c3nnc(C)o3)nn2-c2ccccc2)[C@H](c2ccc(F)c(F)c2)C1]

or a pharmaceutically acceptable salt thereof.

10. The method of claim 5, wherein the compound is

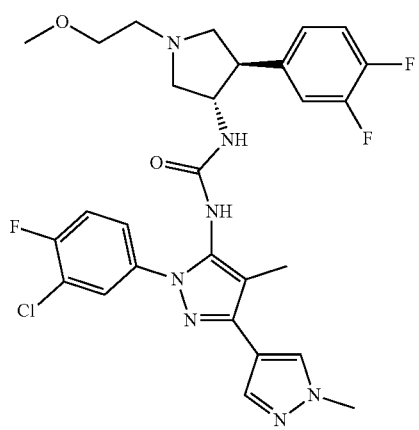 [SMILES: COCCN1C[C@@H](NC(=O)Nc2c(C)c(-c3cnn(C)c3)nn2-c2ccc(F)c(Cl)c2)[C@H](c2ccc(F)c(F)c2)C1]

or a pharmaceutically acceptable salt thereof.

11. The method of claim 5, wherein the compound is

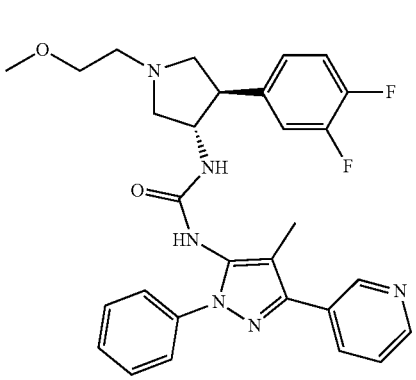 [SMILES: COCCN1C[C@@H](NC(=O)Nc2c(C)c(-c3cccnc3)nn2-c2ccccc2)[C@H](c2ccc(F)c(F)c2)C1]

or a pharmaceutically acceptable salt thereof.

12. The method of claim 5, wherein the compound is

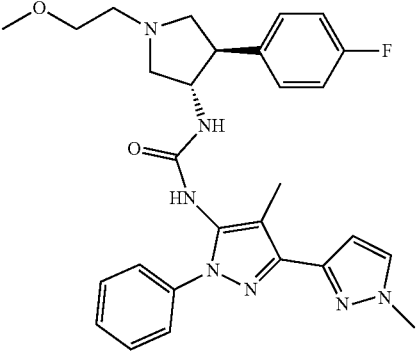

or a pharmaceutically acceptable salt thereof.

13. The method of claim 5, wherein the compound is

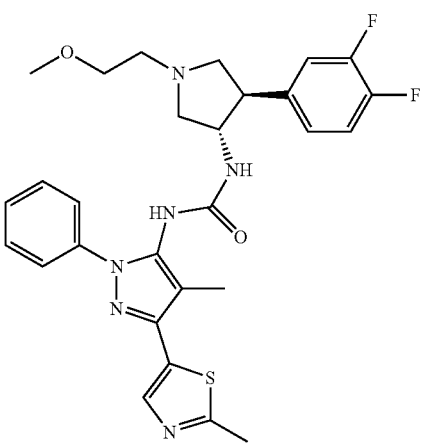 [SMILES: COCCN1C[C@@H](NC(=O)Nc2c(C)c(-c3cnc(C)s3)nn2-c2ccccc2)[C@H](c2ccc(F)c(F)c2)C1]

or a pharmaceutically acceptable salt thereof.

14. The method of claim 5, wherein the compound is

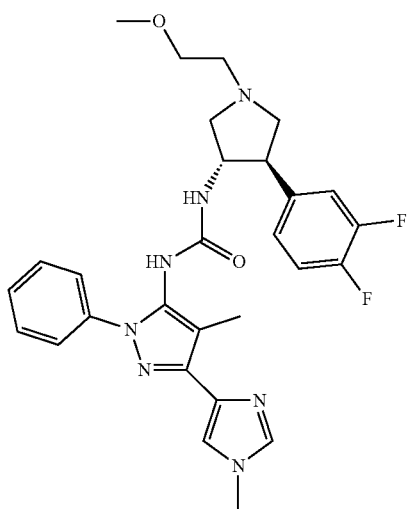 [SMILES: COCCN1C[C@@H](NC(=O)Nc2c(C)c(-c3cn(C)cn3)nn2-c2ccccc2)[C@H](c2ccc(F)c(F)c2)C1]

or a pharmaceutically acceptable salt thereof.

15. The method of claim 1, wherein the pain is chronic pain.
16. The method of claim 1, wherein the pain is acute pain.
17. The method of claim 1, wherein the pain is inflammatory pain.
18. The method of claim 1, wherein the pain is neuropathic pain.
19. The method of claim 1, wherein the pain is pain is associated with cancer.
20. The method of claim 1, wherein the pain is pain is associated with bone fracture.
21. The method of claim 5, wherein the pain is chronic pain.
22. The method of claim 5, wherein the pain is acute pain.
23. The method of claim 5, wherein the pain is inflammatory pain.
24. The method of claim 5, wherein the pain is neuropathic pain.
25. The method of claim 5, wherein the pain is pain is associated with cancer.
26. The method of claim 5, wherein the pain is pain is associated with bone fracture.

* * * * *